United States Patent
Wang et al.

(10) Patent No.: US 11,999,753 B2
(45) Date of Patent: *Jun. 4, 2024

(54) TETRAHYDROPYRIDOPYRIMIDINE PAN-KRAS INHIBITORS

(71) Applicant: Mirati Therapeutics, Inc., San Diego, CA (US)

(72) Inventors: Xiaolun Wang, San Diego, CA (US); Anthony Ivetac, San Diego, CA (US); Svitlana Kulyk, San Diego, CA (US); John David Lawson, Carlsbad, CA (US); Matthew Arnold Marx, San Diego, CA (US); Christopher Ronald Smith, San Diego, CA (US)

(73) Assignee: MIRATI THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/553,224

(22) Filed: Dec. 16, 2021

(65) Prior Publication Data
US 2022/0194961 A1 Jun. 23, 2022

Related U.S. Application Data

(60) Provisional application No. 63/126,350, filed on Dec. 16, 2020, provisional application No. 63/158,119, filed on Mar. 8, 2021, provisional application No. 63/164,345, filed on Mar. 22, 2021.

(51) Int. Cl.
*C07D 471/04* (2006.01)
*A61K 31/519* (2006.01)
*A61P 35/00* (2006.01)
*C07D 519/00* (2006.01)

(52) U.S. Cl.
CPC ............ *C07D 519/00* (2013.01); *A61P 35/00* (2018.01); *C07D 471/04* (2013.01)

(58) Field of Classification Search
CPC ..... C07D 519/00; C07D 471/04; A61P 35/00; A61K 31/519
USPC ....................................... 544/279; 514/264.1
See application file for complete search history.

(56) References Cited

U.S. PATENT DOCUMENTS 10,647,715 B2 * 5/2020 Marx ...................... A61P 35/00
2023/0072276 A1 * 3/2023 Wang ................... C07D 519/00

FOREIGN PATENT DOCUMENTS

WO WO-2020239077 A1 * 12/2020 ............. A61P 35/00

OTHER PUBLICATIONS

English Translation of WO2020239077A1 (Year: 2023).*
RSC Med. Chem., 2020, 11, 760-770 (Year: 2020).*

* cited by examiner

*Primary Examiner* — Charanjit Aulakh
(74) *Attorney, Agent, or Firm* — Wood, Phillips, Katz, Clark & Mortimer

(57) ABSTRACT

The present invention relates to compounds that inhibit at least one of KRas wild type, KRas G12A, KRas G12C, KRas G12D, KRas G12R, KRas G12S, KRas G12V, KRas G13D and KRas Q61H, pharmaceutical compositions comprising the compounds and methods of use therefor.

5 Claims, No Drawings

TETRAHYDROPYRIDOPYRIMIDINE PAN-KRAS INHIBITORS

FIELD OF THE INVENTION

The present invention relates to compounds that inhibit multiple mutated forms of KRas, i.e., pan-KRas inhibitors. In particular, the present invention relates to pan-KRas compounds, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmacol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas. KRas mutations at codons 12, 13, 61 and other positions of the KRas primary amino acid sequence are present in 88% of all pancreatic adenocarcinoma patients, 50% of all colon/rectal adenocarcinoma patients, and 32% lung adenocarcinoma patients (e.g., see Prior et al., (2020) Cancer Res 80:2969-74). A recent publication also suggested wild type Kras inhibition could be a viable therapeutic strategy to treat $KRas^{WT}$ dependent cancers (e.g., see Bery et al., (2020) Nat. Commun. 11: 3233).

The well-known role of KRas in malignancy and the discovery of these frequent mutations in KRas in various tumor types made KRas a highly attractive target of the pharmaceutical industry for cancer therapy. Notwithstanding thirty years of large-scale discovery efforts to develop inhibitors of KRas for treating cancer, no KRas inhibitor has yet demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well recent advances in the covalent targeting of an allosteric pocket of KRas G12C (e.g., see Ostrem et al., (2013) Nature 503:548-551 and Fell et al., (2018) ACS Med. Chem. Lett. 9:1230-1234). Clearly there remains a continued interest and effort to develop inhibitors of KRas, particularly inhibitors of activating KRas mutants.

Thus, there is a need to develop new pan-KRas inhibitors that demonstrate sufficient efficacy for treating KRas-mediated cancers.

SUMMARY OF THE INVENTION

In one aspect of the invention, compounds are provided that inhibit KRas activity.

In another aspect of the invention, compounds of Formula (I):

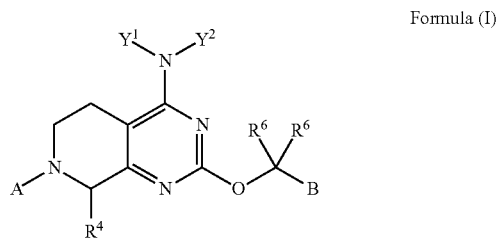

Formula (I)

or a pharmaceutically acceptable salt thereof are provided, wherein:

A is aryl or heteroaryl, wherein the aryl or the heteroaryl is optionally substituted with 1-4 $R^1$;

B is selected from:

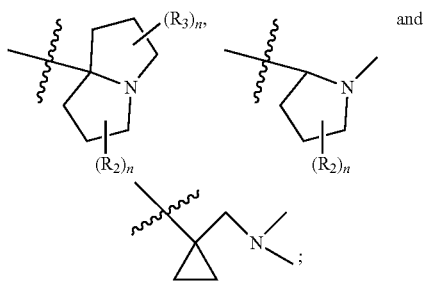

and $Y^1$ is L-hydrogen, hydroxy, halogen, L-C3-C6 cycloalkyl optionally substituted with 1-4 $R^9$, L-S(O)$_2$NH$_2$ optionally substituted with 1-4 $R^9$, L-heteroaryl optionally substituted with 1-4 $R^8$, L-aryl optionally substituted with 1-4 $R^8$, and L-heterocycle substituted with 1-2 oxo (=O) or oxo-containing substituent and optionally further substituted with 1-2 heteroaryl-$R^8$ or $R^8$;

$Y^2$ is hydrogen or C1-C4 alkyl;

or $Y^1$ and $Y^2$ join to form:

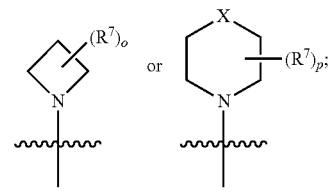

where X is selected from: a bond, —S—, —O—, —N< bound to a fused ring, —CH$_2$—, —CH$_2$—NH—, —CH$_2$—NH—CH$_2$—, —CH$_2$—CH$_2$—CH$_2$—, —CH$_2$—CH$_2$—, —O—CH$_2$— and —S—CH$_2$—;

each $R^1$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —CH₂C(=O)N(R⁵)₂, —C3-C4 alkynyl(NR⁵)₂, —N(R⁵)₂, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl;

each R² is independently hydrogen, hydroxy, halogen, C1-C3 alkyl, C1-C3 cyanoalkyl, C1-C3 hydroxyalkyl, HC(=O)—, —OC(O)N(R⁵)₂, —CO₂R⁵, or —CO₂N(R⁵)₂;

each R³ is independently hydrogen, hydroxy, halogen, C1-C3 alkyl, C1-C3 cyanoalkyl, C1-C3 hydroxyalkyl, HC(=O)—, —OC(O)N(R⁵)₂, —CO₂R⁵, or —CO₂N(R⁵)₂;

R⁴ is hydrogen, halogen or C1-C3 alkyl;

each R⁵ is independently hydrogen or C1-C3 alkyl;

each R⁶ is independently hydrogen, hydroxy, C1-C4 hydroxyalkyl or heteroaryl, or two R⁶ join to form C3-C6 cycloalkyl or heterocycle;

each R⁷ is independently hydrogen, C1-C3 alkyl, hydroxy, halogen, halo-C1-C3 alkyl, —NH₂, —NH(C1-C3 alkyl), —N(C1-C3 alkyl)₂, oxo (=O), —O—(C1-C3 alkyl), —(C1-C3 alkyl)-OH, —C(O)OH, —C(O)O(C1-C3 alkyl), —O—CH₂—C(O)NH₂, L-C(O)NH₂, —C(O)NH(C1-C3 alkyl), —NHC(O)(C1-C3 alkyl), —C(O)N(C1-C3 alkyl)₂, —CN, aryl, dialkylphosphine oxide, —S(O)₂NH(CH₃), sulfone, L-heterocycle optionally substituted with 1-2 substituents selected from oxo (=O), C1-C3 alkyl and C3 cycloalkyl, or L-heteroaryl optionally substituted with 1-2 substituents selected from NH₂, C1-C3 alkyl, C1-C3 haloalkyl, C3 cycloalkyl, —C(O)NH(C3-C4 cycloalkyl) and —NHC(O)(C1-C3 alkyl), two R⁷ on the same atom optionally join to form a spirocyclic ring selected from C3-C6 cycloalkyl and heterocycle, where said spirocyclic ring is optionally substituted with 1-2 substituents selected from oxo (=O), halogen, hydroxy, C1-C3 alkyl and —O—(C1-C3 alkyl), two R⁷ on adjacent atoms optionally join to form a bond or a fused ring selected from C3-C6 cycloalkyl optionally substituted with 1-4 R⁸, heteroaryl optionally substituted with 1-4 R⁸, aryl optionally substituted with 1-4 R⁸, and heterocycle optionally substituted with 1-4 R⁸, and two R⁷ on non-adjacent atoms optionally join to form a 1-2 carbon bridge;

each R⁸ is independently C1-C3 alkyl, hydroxy, halogen, —NH₂, —NH(C1-C3 alkyl), —N(C1-C3 alkyl)₂, oxo (=O), —O—(C1-C3 alkyl), —(C1-C3 alkyl)-OH, —C(O)OH, —C(O)O(C1-C3 alkyl), —C(O)NH₂, —(C1-C3 alkyl)C(O)NH₂, —C(O)NH(C1-C3 alkyl), —C(O)N(C1-C3 alkyl)₂, —C(O)N(R¹⁰)₂, —CN, heteroaryl optionally substituted with C1-C3 alkyl, C1-C3 haloalkyl, —CH₂—S—CH₃, —S(O)₂NH₂ or —S(O)₂(C1-C3 alkyl);

each R⁹ is independently C1-C3 alkyl, hydroxy, halogen, oxo (=O), —O—(C1-C3 alkyl), —(C1-C3 alkyl)-OH, —C(O)OH, —C(O)O(C1-C3 alkyl), —C(O)NH₂, —C(O)NH(C1-C3 alkyl), —C(O)N(C1-C3 alkyl)₂ or —CN, or two R⁹ join to form a bond or —S(O)(CH₃)₂;

each R¹⁰ is independently hydrogen, C1-C3 alkyl, halogen, or joins with R⁷ or another R¹⁰ to form a heterocyclic ring;

L is a bond, —C1-C4 alkyl-, —NH—, —C(O)—, —N(C1-C3 alkyl)- or —(C1-C3 alkyl)NH—;

each n is 0-3;

is 1-6; and p is 1-8.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting the activity of cells containing wild type KRas or one or more KRas mutations, for instance the KRas mutations G12A, G12C, G12D, G12R, G12S, G12V, G13D or Q61H, in a in a cell, comprising contacting the cell with a compound of Formula (I), or a pharmaceutically acceptable salt thereof, or a pharmaceutical composition thereof as defined herein. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (I), or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas wild type-associated or KRas G12A, G12C, G12D, G12R, G12S, G12V, G13D and/or Q61H-associated disease or disorder in a patient in need of such treatment, the method comprising administering to the patient a therapeutically effective amount of a compound of Formula (I), or a pharmaceutically acceptable salt thereof, or a pharmaceutical composition thereof as defined herein.

Also provided herein is a compound of Formula (I), or a pharmaceutically acceptable salt thereof, or a pharmaceutical composition thereof as defined herein for use in therapy.

Also provided herein is a compound of Formula (I), or a pharmaceutically acceptable salt thereof or a pharmaceutical composition thereof as defined herein for use in the treatment of cancer.

Also provided herein is a compound of Formula (I), or a pharmaceutically acceptable salt thereof for use in the inhibition of wild type KRas or multiple types of KRas mutations, for instance KRas G12A, G12C, G12D, G12R, G12S, G12V, G13D and/or Q61H mutations.

Also provided herein is a compound of Formula (I), or a pharmaceutically acceptable salt thereof or a pharmaceutical composition thereof as defined herein, for use in the treatment of wild type KRas or a KRas mutation G12A, G12C, G12D, G12R, G12S, G12V, G13D and/or Q61H-associated disease or disorder.

Also provided herein is the use of a compound of Formula (I), or a pharmaceutically acceptable salt thereof, as defined herein in the manufacture of a medicament for the treatment of cancer.

Also provided herein is a use of a compound of Formula (I), or a pharmaceutically acceptable salt thereof, as defined herein in the manufacture of a medicament for the inhibition of activity of wild type KRas or mutated forms of KRas, including the mutations: G12A, G12C, G12D, G12R, G12S, G12V, G13D and/or Q61H.

Also provided herein is the use of a compound of Formula (I), or a pharmaceutically acceptable salt thereof, as defined herein, in the manufacture of a medicament for the treatment of a wild type KRas-associated or a KRas G12A, G12C, G12D, G12R, G12S, G12V, G13D and/or Q61H-associated disease or disorder.

Also provided herein is a method for treating cancer in a patient in need thereof, the method comprising (a) determining that the cancer is associated with wild type KRas or a KRas G12A, G12C, G12D, G12R, G12S, G12V, G13D and/or Q61H mutation (i.e., a wild type KRas-associated or a KRas G12A, G12C, G12D, G12R, G12S, G12V, G13D and/or Q61HG12X-associated cancer); and (b) administering to the patient a therapeutically effective amount of a compound of Formula (I), or a pharmaceutically acceptable salt thereof, or a pharmaceutical composition thereof.

One potential utility of the herein-described pan-KRas inhibitors, including pan-KRas inhibitors such as (R)-1-(7-(8-ethyl-7-fluoro-3-hydroxynaphthalen-1-yl)-8-fluoro-2-(((2R,7aS)-2-fluorohexahydro-1H-pyrrolizin-7a-yl) methoxy)pyrido[4,3-d]pyrimidin-4-yl)-3-methylpiperidin-3-ol (Example 5 in 63/125,776), is for the treatment of cancers that develop resistance following long-term treatment with KRas G12C inhibitors. Thus, embodiments of the invention include those wherein a patient suffering from cancer is treated with a herein-described pan-KRas inhibitor after treatment with a G12C inhibitor becomes ineffective or less effective due to the emergence of resistance-imparting mutations.

Treatment of KRas G12C mutant cancers with covalent KRas G12C inhibitors such as adagrasib (MRTX849) or sotorasib (AMG510) may result in the incorporation of additional mutations that confer resistance to adagrasib. These mutations could confer resistance through numerous mechanisms.

Mutations that change the mutant cysteine at codon 12 to another amino acid would render the current covalent KRas G12C inhibitors ineffective since current inhibitors make a covalent bond with the mutant cysteine amino acid side chain. Likewise, in patients that have one wild type KRas allele in addition to the KRas G12C-mutant allele, mutations in the wild type codon 12 glycine to another codon would allow bypass signaling in these tumors through the novel mutant protein. The repertoire of codon 12 mutations that can occur with a single nucleotide substitution in the wild type gene (glycine codon) includes mutations commonly observed in cancer such as G12S, G12V, G12R, G12C. The repertoire of codon 12 mutations that can occur with single nucleotide base substitutions of the cysteine codon 12 include mutations not frequently observed in cancer, G12Y, G12F and G12W, in addition to G12S and G12R.

Second-site mutations may also occur in another location in the KRas G12C mutant gene that confers resistance to KRas G12C inhibitor treatment. These mutations may confer resistance through different mechanisms. RAS proteins are small GTPases that normally cycle between an active, GTP-bound state and an inactive, GDP-bound state. RAS proteins are loaded with GTP through guanine nucleotide exchange factors (GEFs; e.g., SOS1) which are activated by upstream receptor tyrosine kinases, triggering subsequent interaction with effector proteins that activate RAS-dependent signaling. RAS proteins hydrolyze GTP to GDP through their intrinsic GTPase activity which is dramatically enhanced by GTPase-activating proteins (GAPs). Mutations at codons 12 and 13 in RAS proteins impair GAP-stimulated GTP hydrolysis leaving RAS predominantly in the GTP-bound, active state. Covalent KRas G12C inhibitors in current clinical development only bind GDP-bound KRas G12C. Mutations such as Q61 codon mutations, which may or may not occur on the same allele as the G12C mutation, reduce the intrinsic GTPase activity of KRas and may represent a mechanism of resistance to KRas G12C inhibitor treatment by shifting KRas into the GTP-loaded state where it is not susceptible to covalent inhibition. Co-mutations such as R68, H95 and Y96 may be present along with the KRas G12C mutation and may diminish the binding affinity of KRas G12C inhibitors to the Switch II binding pocket.

The herein-described pan-KRas inhibitors may demonstrate activity against common as well as uncommon codon 12 mutations or mutations that occur in the KRas protein that diminish binding of KRas G12C inhibitors to the KRas protein.

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

DETAILED DESCRIPTION OF THE INVENTION

The present invention relates to inhibitors of wild type KRas or multiple mutated forms of KRas, for instance KRas G12A, G12C, G12D, G12R, G12S, G12V, G13D and/or Q61H mutations. In particular, the present invention relates to compounds that inhibit the activity of wild type KRas or KRas mutations such as G12A, G12C, G12D, G12R, G12S, G12V, G13D and/or Q61H, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12A" refers to a mutant form of a mammalian KRas protein that contains an amino acid substitution of an alanine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12A inhibitor" refers to compounds of the present invention that are represented by Formula (I), as described herein. These compounds are capable of negatively modulating or inhibiting all or a portion of the enzymatic activity of KRas G12A. A "KRas G12A-associated disease or disorder" as used herein refers to diseases or disorders associated with or mediated by or having a KRas G12A mutation. A non-limiting example of a KRas G12A-associated disease or disorder is a KRas G12A-associated cancer.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12C inhibitor" refers to compounds of the present invention that are represented by Formula (I), as described herein. These compounds are capable of negatively modulating or inhibiting all or a portion of the enzymatic activity of KRas G12C. A "KRas G12C-associated disease or disorder" as used herein refers to diseases or disorders associated with or mediated by or having a KRas G12C mutation. A non-limiting example of a KRas G12C-associated disease or disorder is a KRas G12CD-associated cancer.

As used herein, "KRas G12D" refers to a mutant form of a mammalian KRas protein that contains an amino acid substitution of an aspartic acid for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12D inhibitor" refers to compounds of the present invention that are represented by Formula (I), as described herein. These compounds are capable of negatively modulating or inhibiting all or a portion of the enzymatic activity of KRas G12D. A "KRas G12D-associated disease or disorder" as used herein refers to diseases or disorders associated with or mediated by or having a KRas G12D mutation. A non-limiting example of a KRas G12D-associated disease or disorder is a KRas G12D-associated cancer.

As used herein, "KRas G12R" refers to a mutant form of a mammalian KRas protein that contains an amino acid substitution of an arginine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12R inhibitor" refers to compounds of the present invention that are represented by Formula (I), as described herein. These compounds are capable of negatively modulating or inhibiting all or a portion of the enzymatic activity of KRas G12R. A "KRas G12R-associated disease or disorder" as used herein refers to diseases or disorders associated with or mediated by or having a KRas G12R mutation. A non-limiting example of a KRas G12R-associated disease or disorder is a KRas G12R-associated cancer.

As used herein, "KRas G12S" refers to a mutant form of a mammalian KRas protein that contains an amino acid substitution of a serine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12S inhibitor" refers to compounds of the present invention that are represented by Formula (I), as described herein. These compounds are capable of negatively modulating or inhibiting all or a portion of the enzymatic activity of KRas G12S. A "KRas G12S-associated disease or disorder" as used herein refers to diseases or disorders associated with or mediated by or having a KRas G12S mutation. A non-limiting example of a KRas G12S-associated disease or disorder is a KRas G12S-associated cancer.

As used herein, "KRas G12V" refers to a mutant form of a mammalian KRas protein that contains an amino acid substitution of a valine for a glycine at amino acid position 12. The assignment of amino acid codon and residue positions for human KRas is based on the amino acid sequence identified by UniProtKB/Swiss-Prot P01116: Variantp.Gly12Asp.s used herein, a "KRas G12V inhibitor" refers to compounds of the present invention that are represented by Formula (I), as described herein. These compounds are capable of negatively modulating or inhibiting all or a portion of the enzymatic activity of KRas G12V. A "KRas G12V-associated disease or disorder" as used herein refers to diseases or disorders associated with or mediated by or having a KRas G12V mutation. A non-limiting example of a KRas G12V-associated disease or disorder is a KRas G12V-associated cancer.

As used herein, "KRas G13D" refers to a mutant form of a mammalian KRas protein that contains an amino acid substitution of an aspartic acid for a glycine at amino acid position 13. The assignment of amino acid codon and residue positions for human KRas is based on the amino acid sequence identified by UniProtKB/Swiss-Prot P01116: Variantp.Gly12Asp.s used herein, a "KRas G13D inhibitor" refers to compounds of the present invention that are represented by Formula (I), as described herein. These compounds are capable of negatively modulating or inhibiting all or a portion of the enzymatic activity of KRas G13D. A "KRas G13D-associated disease or disorder" as used herein refers to diseases or disorders associated with or mediated by or having a KRas G13D mutation. A non-limiting example of a KRas G13D-associated disease or disorder is a KRas G13D-associated cancer.

As used herein, "KRas Q61H" refers to a mutant form of a mammalian KRas protein that contains an amino acid substitution of a histidine for a glutamine at amino acid position 61. The assignment of amino acid codon and residue positions for human KRas is based on the amino acid sequence identified by UniProtKB/Swiss-Prot P01116: Variantp.Gly12Asp.s used herein, a "KRas Q61H inhibitor" refers to compounds of the present invention that are represented by Formula (I), as described herein. These compounds are capable of negatively modulating or inhibiting all or a portion of the enzymatic activity of KRas Q61H. A "KRas Q61H-associated disease or disorder" as used herein refers to diseases or disorders associated with or mediated by or having a KRas Q61H mutation. A non-limiting example of a KRas Q61H-associated disease or disorder is a KRas Q61H-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having wild type KRas or a KRas G12A, G12C, G12D, G12R, G12S, G12V, G13D and/or Q61H mutation (e.g., as determined using a regulatory agency-approved, e.g., FDA-approved, assay or kit). In some embodiments, the subject has a tumor that is positive for wild type KRas or a KRas G12A, G12C, G12D, G12R, G12S, G12V, G13D and/or Q61H mutation (e.g., as determined using a regulatory agency-approved assay or kit). The subject can be a subject with a tumor(s) that is positive for wild type KRas or a KRas G12A, G12C, G12D, G12R, G12S, G12V, G13D and/or Q61H mutation (e.g., identified as positive using a regulatory agency-approved, e.g., FDA-approved, assay or kit). The subject can be a subject whose tumors have wild type KRas or a KRas G12A, G12C, G12D, G12R, G12S, G12V, G13D and/or Q61H mutation (e.g., where the tumor is identified as such using a regulatory agency-approved, e.g., FDA-approved, kit or assay). In some embodiments, the subject is suspected of having wild type KRas-associated or a KRas G12A, KRas G12C, KRas G12D, KRas G12R, KRas G12S, KRas G12V, KRas G13D or KRas Q61H gene-associated cancer. In some embodiments, the subject has a clinical record indicating that the subject has a tumor that has wild type KRas or a KRas G12A, G12C, G12D, G12R, G12S, G12V, G13D and/or Q61H mutation (and optionally the clinical record indicates that the subject should be treated with any of the compositions provided herein).

In some embodiments of any of the methods or uses described herein, an assay is used to determine whether the patient has wild type KRas or a KRas G12A, G12C, G12D, G12R, G12S, G12V, G13D and/or Q61H mutation using a sample (e.g., a biological sample or a biopsy sample (e.g., a paraffin-embedded biopsy sample) from a patient (e.g., a patient suspected of having wild type KRas or a KRas G12A, G12C, G12D, G12R, G12S, G12V, G13D and/or Q61H-associated cancer, a patient having one or more symptoms of a wild type KRas-associated or a KRas G12A, G12C, G12D, G12R, G12S, G12V, G13D and/or Q61H-associated cancer, and/or a patient that has an increased risk of developing a wild type KRas-associated or a KRas G12A, G12C, G12D, G12R, G12S, G12V, G13D and/or Q61H-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "acyl" refers to —C(O)CH$_3$.

The terms "C1-C6 alkyl", "C1-C4 alkyl" and "C1-C3 alkyl" as employed herein refers to straight and branched chain aliphatic groups having from 1-6 carbon atoms, or 1-4 carbon atoms, or 1-3 carbon atoms, respectively. Examples of alkyl groups include, without limitation, methyl, ethyl, propyl, isopropyl, butyl, isobutyl, sec-butyl, tert-butyl, pentyl, and hexyl.

The terms "C1-C3 haloalkyl" and "C1-C4 haloalkyl" refer to a C1-C3 alkyl chain or C1-C4 alkyl chain, respectively, as defined herein in which one or more hydrogen has been replaced by a halogen. Examples include trifluoromethyl, difluoromethyl and fluoromethyl.

An "C1-C4 alkylene," group is a C1-C4 alkyl group, as defined hereinabove, that is positioned between and serves to connect two other chemical groups. Exemplary alkylene groups include, without limitation, methylene, ethylene, propylene, and butylene.

The terms "C1-C3 alkoxy" and "C1-C4 alkoxy" refer to —OC1-C3 alkyl and —OC1-C4 alkyl, respectively, wherein the alkyl portion is as defined herein above.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted with one or more R$^8$ or R$^9$ groups as defined herein. Examples of cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkyl" also includes bridged cycloalkyls, such as bicyclo[1.1.1]pentanyl.

As used herein, the terms "C1-C3 hydroxyalkyl" and "C1-C4 hydroxyalkyl" refer to —C1-C3 alkylene-OH and —C1-C4 alkylene-OH, respectively.

As used herein, the term "C2-C4 hydroxyalkynyl" refers to —C2-C4 alkynylene-OH.

An "aryl" group is a C$_6$-C$_{14}$ aromatic moiety comprising one to three aromatic rings, which is optionally substituted with one or more substituents as defined herein and in Formula I. As one embodiment, the aryl group is a C$_6$-C$_{10}$ aryl group. Examples of aryl groups include, without limitation, phenyl, naphthyl, anthracenyl, fluorenyl, and dihydrobenzofuranyl. "Aryl" also refers to bicyclic or tricyclic ring systems in which one or two rings, respectively, of said aryl ring system may be saturated or partially saturated, and wherein if said ring system includes two saturated rings, said saturated rings may be fused or spirocyclic. An example of an aryl ring system comprising two saturated rings wherein the rings are spirocyclic includes the following ring system:

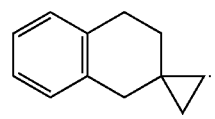

An "araC1-C6 alkyl" or "arylalkyl" group comprises an aryl group covalently linked to an alkyl group, either of which may independently be optionally substituted or unsubstituted. An example of an aralkyl group is (C$_6$-C$_{10}$)aryl(C$_1$-C$_6$)alkyl-, including, without limitation, benzyl, phenethyl, and naphthylmethyl. An example of a substituted araC1-C6 alkyl is wherein the alkyl group is substituted with hydroxyalkyl.

A "heterocyclyl" or "heterocyclic" group is a saturated or partially unsaturated ring structure having from 3 to 12 atoms, for example 4 to 8 atoms, wherein one or more atoms are selected from the group consisting of N, O, and S wherein the ring N atom may be oxidized to N—O, and the ring S atom may be oxidized to SO or SO$_2$, the remainder of the ring atoms being carbon. The heterocyclyl may be a monocyclic, a bicyclic, a spirocyclic or a bridged ring system. The heterocyclic group is optionally substituted on ring carbon or ring nitrogen at one or more positions as defined herein and in Formula I. The heterocyclic group is also independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1 dioxide, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H,3H,5H-oxazolo[3,4-c]oxazolyl, tetrahydro-1'H, 3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabiocycloheptanyls, hexahydropyrrolizinyl 4(1H)-oxide, tetrahydro-2H-thiopyranyl 1-oxide and tetrahydro-2H-thiopyranyl 1,1-dioxide. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring, or from one to three heteroatoms in at least one ring, selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a]imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. "Heteroaryl" also refers to bicyclic ring systems having, in addition to carbon atoms, from one to three heteroatoms per ring selected from the group consisting of N, O, and S in which one ring system may be saturated or partially saturated.

As used herein, "an effective amount" of a compound is an amount that is sufficient to negatively modulate or inhibit the activity of one or more of wild type KRas or a KRas G12A, KRas G12C, KRas G12D, KRas G12R, KRas G12S, KRas G12V, KRas G13D or KRas Q61H. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of wild type KRas or one or more of KRas G12A, KRas G12C, KRas G12D, KRas G12R, KRas G12S, KRas G12V, KRas G13D or KRas Q61H. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In certain embodiments of the invention, compound of Formula (I):

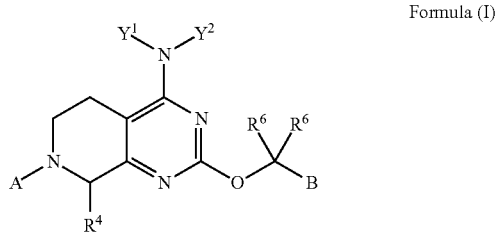

Formula (I)

or a pharmaceutically acceptable salt thereof are provided, wherein:
A is aryl or heteroaryl, wherein the aryl or the heteroaryl is optionally substituted with 1-4 $R^1$;
B is selected from:

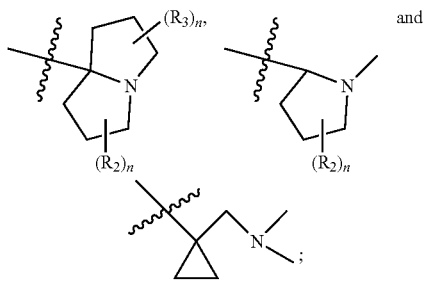

$Y^1$ is L-hydrogen, hydroxy, halogen, L-C3-C6 cycloalkyl optionally substituted with 1-4 $R^9$, L-S(O)$_2$NH$_2$ optionally substituted with 1-4 $R^9$, L-heteroaryl optionally substituted with 1-4 $R^8$, L-aryl optionally substituted with 1-4 $R^8$, and L-heterocycle substituted with 1-2 oxo (=O) or oxo-containing substituent and optionally further substituted with 1-2 heteroaryl-$R^8$ or $R^8$;
$Y^2$ is hydrogen or C1-C4 alkyl;
or $Y^1$ and $Y^2$ join to form:

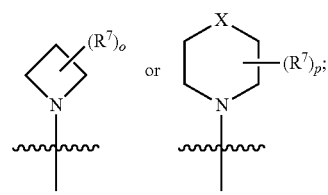

where X is selected from: a bond, —S—, —O—, —N< bound to a fused ring, —CH$_2$—, —CH$_2$—NH—, —CH$_2$—NH—CH$_2$—, —CH$_2$—CH$_2$—CH$_2$—, —CH$_2$—CH$_2$—, —O—CH$_2$— and —S—CH$_2$—;
each $R^1$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, —S—C1-C3 haloalkyl, C1-C3 alkoxy, hydroxyC1-C3 alkyl, —CH$_2$C(=O)N(R$^5$)$_2$, —C3-C4 alkynyl(NR$^5$)$_2$, —N(R$^5$)$_2$, deuteroC2-C4 alkynyl, (C1-C3 alkoxy)haloC1-C3 alkyl-, or C3-C6 cycloalkyl wherein said C3-C6 cycloalkyl is optionally substituted with halogen or C1-C3 alkyl;

each $R^2$ is independently hydrogen, hydroxy, halogen, C1-C3 alkyl, C1-C3 cyanoalkyl, C1-C3 hydroxyalkyl, HC(=O)—, —OC(O)N($R^5$)$_2$, —CO$_2$$R^5$, or —CO$_2$N($R^5$)$_2$;

each $R^3$ is independently hydrogen, hydroxy, halogen, C1-C3 alkyl, C1-C3 cyanoalkyl, C1-C3 hydroxyalkyl, HC(=O)—, —OC(O)N($R^5$)$_2$, —CO$_2$$R^5$, or —CO$_2$N($R^5$)$_2$;

$R^4$ is hydrogen, halogen or C1-C3 alkyl;

each $R^5$ is independently hydrogen or C1-C3 alkyl;

each $R^6$ is independently hydrogen, hydroxy, C1-C4 hydroxyalkyl or heteroaryl, or two $R^6$ join to form C3-C6 cycloalkyl or heterocycle;

each $R^7$ is independently hydrogen, C1-C3 alkyl, hydroxy, halogen, halo-C1-C3 alkyl, —NH$_2$, —NH (C1-C3 alkyl), —N(C1-C3 alkyl)$_2$, oxo (=O), —O—(C1-C3 alkyl), —(C1-C3 alkyl)-OH, —C(O)OH, —C(O)O(C1-C3 alkyl), —O—CH$_2$—C(O)NH$_2$, L-C(O)NH$_2$, —C(O)NH(C1-C3 alkyl), —NHC(O)(C1-C3 alkyl), —C(O)N(C1-C3 alkyl)$_2$, —CN, aryl, dialkylphosphine oxide, —S(O)$_2$NH(CH$_3$), sulfone, L-heterocycle optionally substituted with 1-2 substituents selected from oxo (=O), C1-C3 alkyl and C3 cycloalkyl, or L-heteroaryl optionally substituted with 1-2 substituents selected from NH$_2$, C1-C3 alkyl, C1-C3 haloalkyl, C3 cycloalkyl, —C(O)NH(C3-C4 cycloalkyl) and —NHC(O)(C1-C3 alkyl), two $R^7$ on the same atom optionally join to form a spirocyclic ring selected from C3-C6 cycloalkyl and heterocycle, where said spirocyclic ring is optionally substituted with 1-2 substituents selected from oxo (=O), halogen, hydroxy, C1-C3 alkyl and —O—(C1-C3 alkyl), two $R^7$ on adjacent atoms optionally join to form a bond or a fused ring selected from C3-C6 cycloalkyl optionally substituted with 1-4 $R^8$, heteroaryl optionally substituted with 1-4 $R^8$, aryl optionally substituted with 1-4 $R^8$, and heterocycle optionally substituted with 1-4 $R^8$, and two $R^7$ on non-adjacent atoms optionally join to form a 1-2 carbon bridge;

each $R^8$ is independently C1-C3 alkyl, hydroxy, halogen, —NH$_2$, —NH(C1-C3 alkyl), —N(C1-C3 alkyl)$_2$, oxo (=O), —O—(C1-C3 alkyl), —(C1-C3 alkyl)-OH, —C(O)OH, —C(O)O(C1-C3 alkyl), —C(O)NH$_2$, —(C1-C3 alkyl)C(O)NH$_2$, —C(O)NH(C1-C3 alkyl), —C(O)N(C1-C3 alkyl)$_2$, —C(O)N($R^{10}$)$_2$, —CN, heteroaryl optionally substituted with C1-C3 alkyl, C1-C3 haloalkyl, —CH$_2$—S—CH$_3$, —S(O)$_2$NH$_2$ or —S(O)$_2$(C1-C3 alkyl);

each $R^9$ is independently C1-C3 alkyl, hydroxy, halogen, oxo (=O), —O—(C1-C3 alkyl), —(C1-C3 alkyl)-OH, —C(O)OH, —C(O)O(C1-C3 alkyl), —C(O)NH$_2$, —C(O)NH(C1-C3 alkyl), —C(O)N(C1-C3 alkyl)$_2$ or —CN, or two $R^9$ join to form a bond or —S(O)(CH$_3$)$_2$;

each $R^{10}$ is independently hydrogen, C1-C3 alkyl, halogen, or joins with $R^7$ or another $R^{10}$ to form a heterocyclic ring;

L is a bond, —C1-C4 alkyl-, —NH—, —C(O)—, —N(C1-C3 alkyl)- or —(C1-C3 alkyl)NH—;

each n is 0-3;

is 1-6; and p is 1-8.

In certain other embodiments of the invention, compounds of Formula (I):

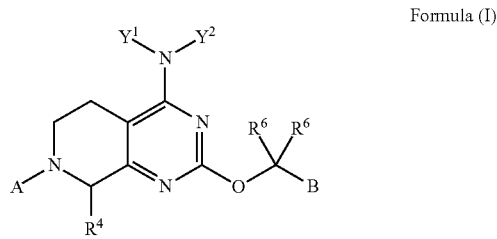

Formula (I)

or a pharmaceutically acceptable salt thereof are provided, wherein:

A is naphthyl, optionally substituted with 1-4 $R^1$;

B is:

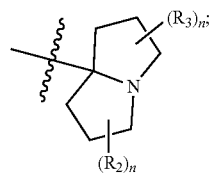

$Y^1$ is hydrogen, hydroxy, halogen or L-heteroaryl optionally substituted with 1-4 $R^8$;

$Y^2$ is hydrogen or C1-C4 alkyl;

or $Y^1$ and $Y^2$ join to form:

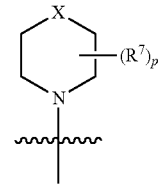

where X is selected from: a bond, —CH—, —CH2-NH—, —CH2-NH—CH2-, —CH2-CH2-CH2-, —CH2-CH2- and —O—CH2-;

each $R^1$ is independently halogen, cyano, hydroxy;

each $R^2$ is independently hydrogen, hydroxy or, halogen;

each $R^3$ is independently hydrogen, hydroxy or halogen;

$R^4$ is hydrogen, halogen or C1-C3 alkyl;

each $R^5$ is independently hydrogen or C1-C3 alkyl;

each $R^6$ is independently hydrogen, hydroxy, C1-C4 hydroxyalkyl or heteroaryl, or two $R^6$ join to form C3-C6 cycloalkyl or heterocycle;

each $R^7$ is independently hydrogen, C1-C3 alkyl, halo-C1-C3 alkyl, hydroxy, —(C1-C3 alkyl)-OH, sulfone, or heteroaryl optionally substituted with NH$_2$;

two $R^7$ on the same atom optionally join to form a spirocyclic ring selected from C3-C6 cycloalkyl and heterocycle, where said spirocyclic ring is optionally substituted with oxo (=O), halogen, hydroxy, C1-C3 alkyl and —O—(C1-C3 alkyl), two $R^7$ on adjacent atoms optionally join to form a bond or a fused ring selected from heteroaryl optionally substituted with 1-4 $R^8$, and heterocycle optionally substituted with 1-4 $R^8$;

each $R^8$ is independently C1-C3 alkyl, hydroxy, halogen, —NH$_2$, —NH(C1-C3 alkyl), —N(C1-C3 alkyl)$_2$, oxo (=O), —O—(C1-C3 alkyl), —(C1-C3 alkyl)-OH, —C(O)OH, —C(O)O(C1-C3 alkyl), —C(O)NH$_2$, —C(O)NH(C1-C3 alkyl), —C(O)N(C1-C3 alkyl)$_2$ or —CN;

each R$^9$ is independently C1-C3 alkyl, hydroxy, halogen, oxo (═O), —O—(C1-C3 alkyl), —(C1-C3 alkyl)-OH, —C(O)OH, —C(O)O(C1-C3 alkyl), —C(O)NH$_2$, —C(O)NH(C1-C3 alkyl), —C(O)N(C1-C3 alkyl)$_2$ or —CN;

L is a bond, —C1-C4 alkyl-, —NH— or —N(C1-C3 alkyl)-;

each n is 0-3;

is 1-6; and p is 1-8.

In certain other embodiments of the invention, compounds or salts of Formula I are provided, wherein:

A is naphthyl;

B is:

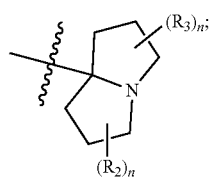

and Y$^1$ and Y$^2$ join to form:

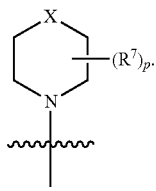

In certain other embodiments of the invention, compounds or salts of Formula I are provided, wherein Y$^1$ is hydrogen, hydroxy, halogen or L-heteroaryl optionally substituted with 1-4 R$^8$, and Y$^2$ is hydrogen or C1-C4 alkyl.

In certain other embodiments of the invention, compounds or salts of Formula I are provided, wherein Y$^1$ and Y$^2$ join to form:

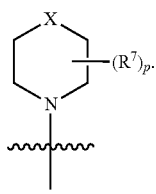

In some embodiments of the invention, compounds or salts of Formula I are provided, wherein X is —CH2-NH—, and two R$^7$ join to form a fused heteroaryl ring substituted with 1-4 R$^8$ where one R$^8$ is —C(O)N(R$^{10}$)$_2$.

In some of these embodiments, the fused heteroaryl ring is pyrazolyl, one R$^8$ is —C(O)N(R$^{10}$)$_2$ and one R$^8$ is halogen or C1-C3 alkyl.

In specific embodiments, compounds or salts of Formula I are provided, wherein the compound has the formula:

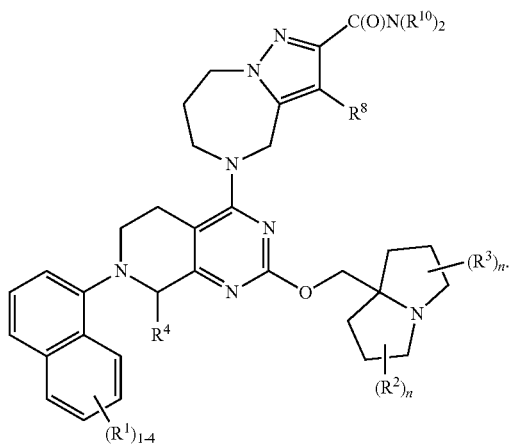

In some embodiments of the invention, compounds or salts of Formula I are provided, wherein X is a bond, and two R$^7$ join to form a fused heterocyclyl ring, optionally substituted with one or two oxo.

In specific embodiments, compounds or salts of Formula I are provided, wherein the compound have the formula:

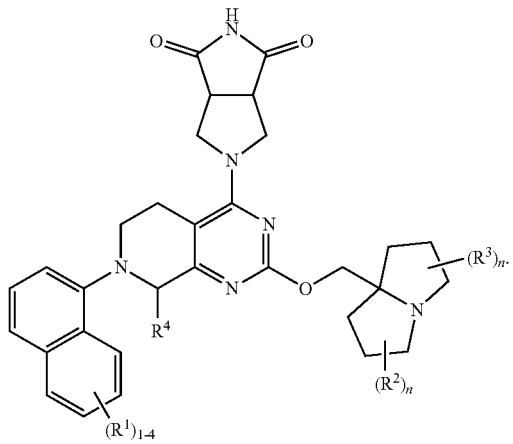

In some embodiments of the invention, compounds or salts of Formula I are provided, wherein X is —CH2-, and two R$^7$ join to form a spirocyclic heterocyclyl ring substituted with one or two oxo.

In specific embodiments, compound or salts of Formula I are provided, wherein the compound has the formula:

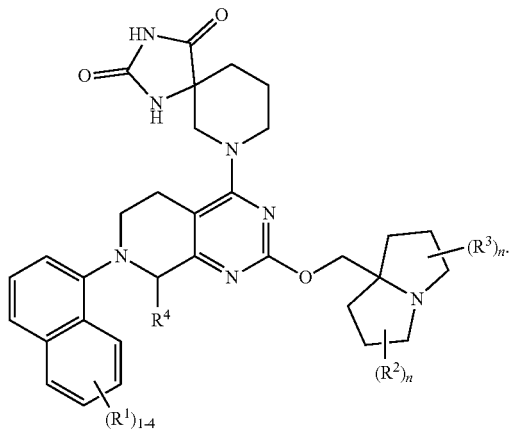

In some embodiments of the invention, compounds or salts of Formula I are provided, wherein at least one $R^1$ is C1-C4 alkyl.

In some embodiments of the invention, compounds or salts of Formula I are provided, wherein at least one $R^1$ is halogen.

In some embodiments of the invention, compounds or salts of Formula I are provided, wherein said $R^1$ halogen is a fluorine.

In some embodiments of the invention, compounds or salts of Formula I are provided, wherein at least one $R^1$ is hydroxy.

In some embodiments of the invention, compounds or salts of Formula I are provided, wherein one $R^2$ is C1-C4 alkyl.

In some embodiments of the invention, compounds or salts of Formula I are provided, wherein at least one $R^2$ is halogen.

In some embodiments of the invention, compounds or salts of Formula I are provided, wherein said $R^2$ halogen is a fluorine.

In some embodiments of the invention, compounds or salts of Formula I are provided, wherein at least one $R^2$ is hydroxy.

In some embodiments of the invention, compounds or salts of Formula I are provided, wherein at least one $R^3$ is C1-C4 alkyl.

In some embodiments of the invention, compounds or salts of Formula I are provided, wherein at least one $R^3$ is halogen.

In some embodiments of the invention, compounds or salts of Formula I are provided, wherein said $R^3$ halogen is fluorine.

In some embodiments of the invention, compounds or salts of Formula I are provided, wherein at least one $R^3$ is hydroxy.

In some embodiments of the invention, compounds or salts of Formula I are provided, wherein $R^4$ is halogen.

In some embodiments of the invention, compounds or salts of Formula I are provided, wherein the $R^4$ halogen is fluorine.

In some embodiments of the invention, compounds or salts of Formula I are provided, wherein at least one $R^5$ is C1-C4 alkyl.

In some embodiments of the invention, compounds or salts of Formula I are provided, wherein at least one $R^5$ is hydrogen.

In some embodiments of the invention, compounds or salts of Formula I are provided, wherein one or both $R^6$ are hydrogen or C1-C4 alkyl.

In some embodiments of the invention, compounds or salts of Formula I are provided, wherein two $R^6$ join to form C3-C6 cycloalkyl or heterocycle.

In some embodiments of the invention, compounds or salts of Formula I are provided, wherein $Y^1$ is L-C3-C6 cycloalkyl, L-heteroaryl, L-aryl, or L-heterocycle, where L is a bond, C1-C4 alkyl, NH or N(C1-C3) alkyl.

In some embodiments of the invention, compounds or salts of Formula I are provided, wherein $Y^1$ is L-heteroaryl.

In some such embodiments the heteroaryl is thietane dioxide, iso-thiazolidine dioxide, imidazopyrazine, pyridine or pyrimidine.

In some embodiments of the invention, compounds or salts of Formula I are provided, wherein $Y^1$ is L-C3-C6 cycloalkyl.

In some such embodiments, the cycloalkyl is cyclobutane, cyclopentane, cyclohexane or cycloheptane.

In some embodiments of the invention, compounds or salts of Formula I are provided, wherein $Y^1$ is L-heterocycle.

In some such embodiments the heterocycle is pyrrolidinone.

In some embodiments of the invention, compounds or salts of Formula I are provided, wherein $Y^2$ is hydrogen.

In some embodiments of the invention, compounds or salts of Formula I are provided, wherein $Y^2$ is C1-C4 alkyl;

In some embodiments of the invention, compounds or salts of Formula I are provided, wherein at least one $R^8$ is C1-C4 alkyl.

In some embodiments of the invention, compounds or salts of Formula I are provided, wherein at least one $R^8$ is hydroxy or C1-C3 alkyl-hydroxy.

In some embodiments of the invention, compounds or salts of Formula I are provided, wherein one or two $R^8$ are oxo (=O).

In some embodiments of the invention, compounds or salts of Formula I are provided, wherein at least one $R^8$ is aryl or heteroaryl.

In some embodiments of the invention, compounds or salts of Formula I are provided, wherein at least one $R^8$ is C(O)OH.

In some embodiments of the invention, compounds or salts of Formula I are provided, wherein at least one $R^8$ is —C(O)NH$_2$, —C(O)NH(C1-C3 alkyl) or —C(O)N(C1-C3 alkyl)$_2$.

In some embodiments of the invention, compounds or salts of Formula I are provided, wherein at least one $R^8$ is —NH$_2$, —NH(C1-C3 alkyl); —N(C1-C3 alkyl)$_2$.

In some embodiments of the invention, compounds or salts of Formula I are provided, wherein at least one $R^9$ is C1-C4 alkyl.

In some embodiments of the invention, compounds or salts of Formula I are provided, wherein at least one $R^9$ is hydroxy or C1-C3 alkyl-hydroxy.

In some embodiments of the invention, compounds or salts of Formula I are provided, wherein one or two $R^9$ is oxo (=O).

In some embodiments of the invention, compounds or salts of Formula I are provided, wherein at least one $R^9$ is aryl or heteroaryl.

In some embodiments of the invention, compounds or salts of Formula I are provided, wherein at least one $R^9$ is C(O)OH.

In some embodiments of the invention, compounds or salts of Formula I are provided, wherein at least one $R^9$ is —C(O)NH$_2$, —C(O)NH(C1-C3 alkyl) or —C(O)N(C1-C3 alkyl)$_2$.

In some embodiments of the invention, compounds or salts of Formula I are provided, wherein $Y^1$ and $Y^2$ join to form piperidine, azepane, azocane, thiazepine, diazepane, oxazepane, azetidine, pyrrolidine, piperazine bound to a fused ring via nitrogen or thiomorpholine.

In some embodiments of the invention, compounds or salts of Formula I are provided, wherein two $R^7$ on the same atom join to form a spirocyclic ring selected from C3-C6 cycloalkyl and heterocycle, where said spirocyclic ring is optionally substituted with one or more substituents selected from oxo (=O), halogen, hydroxy, C1-C3 alkyl and —O—(C1-C3 alkyl).

In some embodiments of the invention, compounds or salts of Formula I are provided, wherein two $R^7$ on adjacent atoms join to form a bond or a fused ring selected from C3-C6 cycloalkyl optionally substituted with 1-4 $R^8$; heteroaryl optionally substituted with 1-4 R⁸; aryl optionally substituted with 1-4 R⁸, and heterocycle optionally substituted with 1-4 R⁸.

In some embodiments of the invention, compounds or salts of Formula I are provided, wherein two $R^7$ on non-adjacent atoms join to form a 1-2 carbon bridge.

In some embodiments of the invention, compounds or salts of Formula I are provided, wherein one $R^{10}$ is hydrogen, C1-C3 alkyl or halogen, and another $R^{10}$ joins with $R^7$ to form a heterocyclic ring.

In some embodiments of the invention, compounds or salts of Formula I are provided, wherein two $R^{10}$ join to form a heterocyclic ring.

In some embodiments of the invention, compounds or salts of Formula I are provided, wherein each $R^{10}$ is independently hydrogen, C1-C3 alkyl or halogen.

Non-limiting examples of compounds of Formula (I) are selected from the group consisting of:

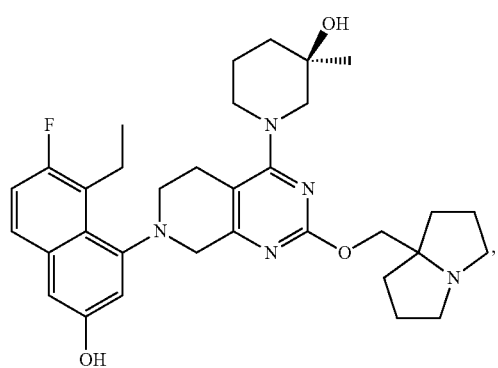

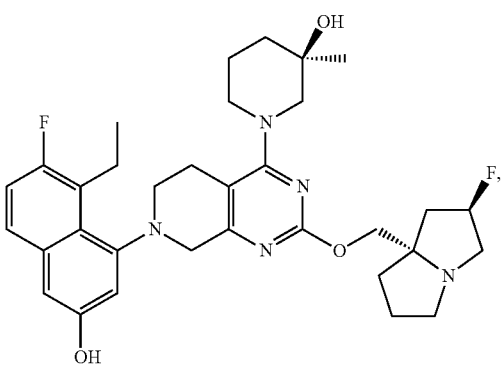

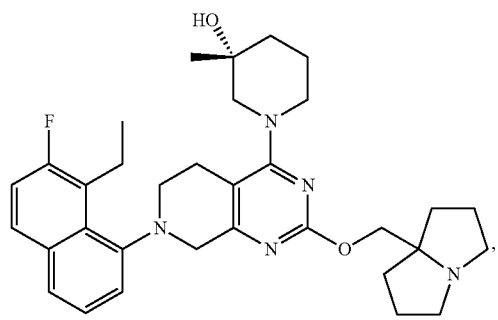

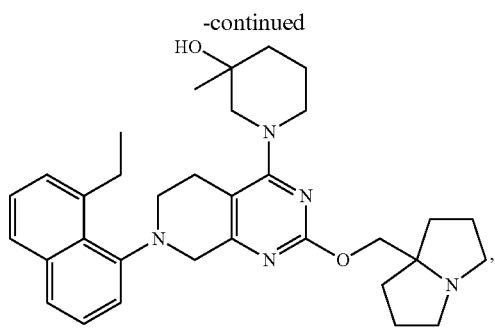

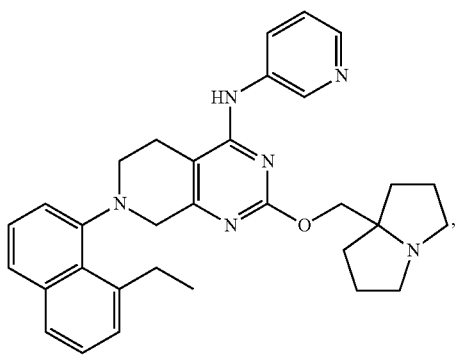

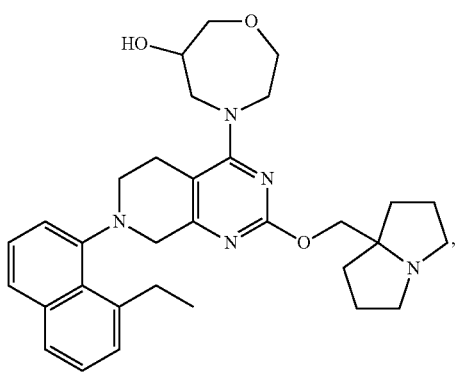

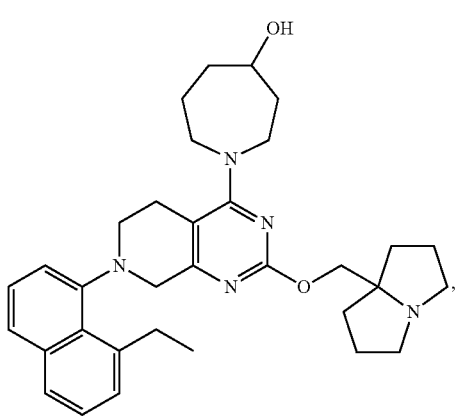

-continued
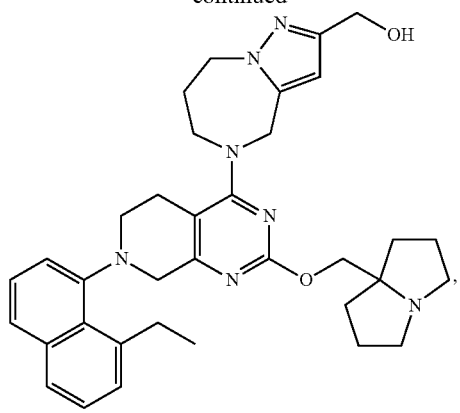
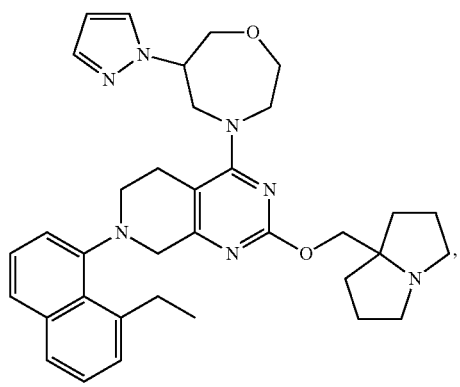
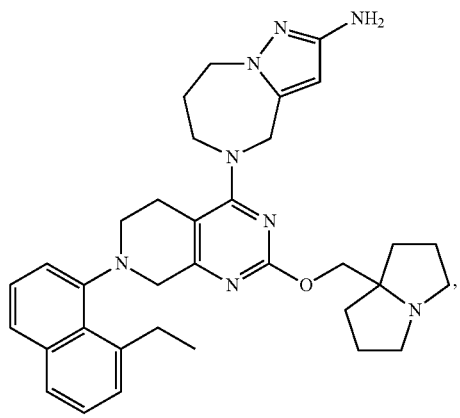
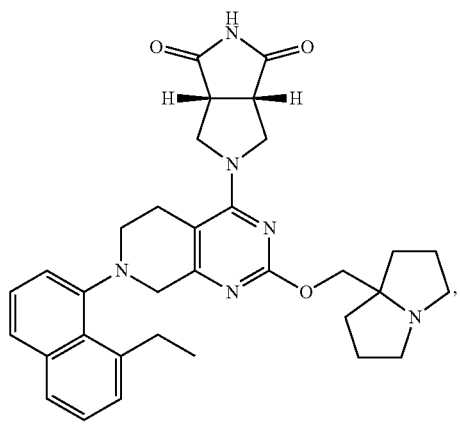
-continued
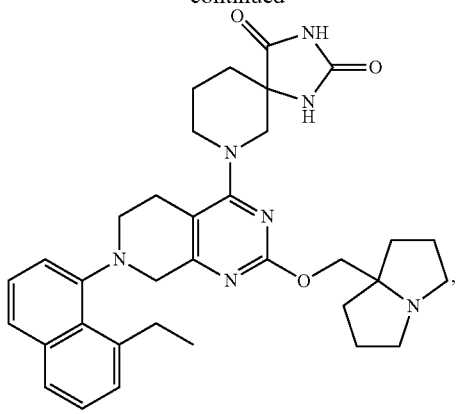
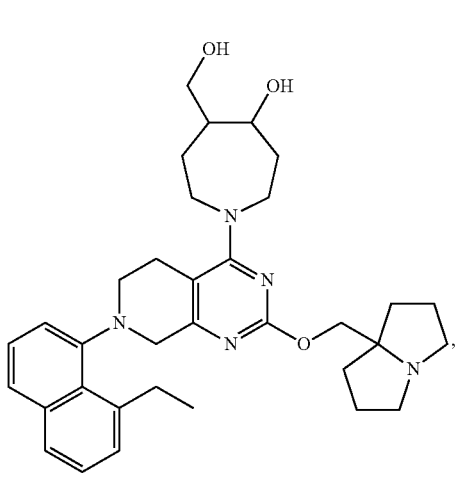
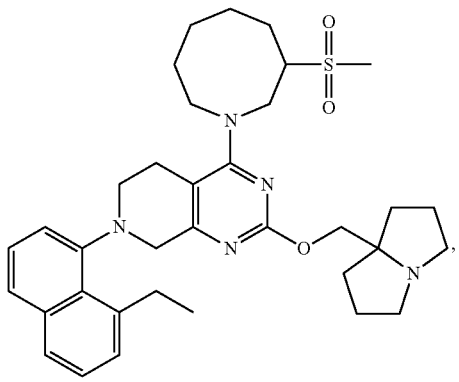
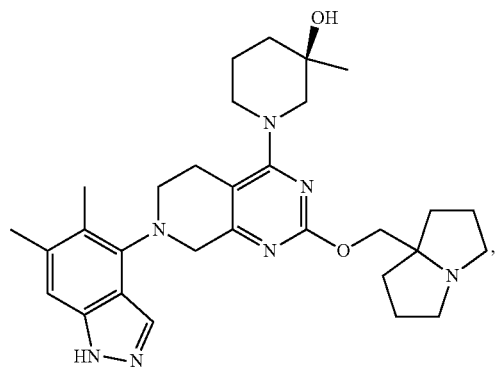

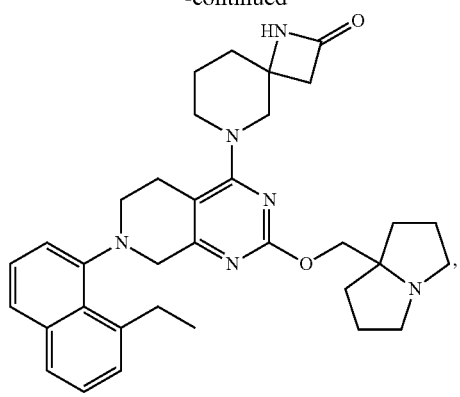
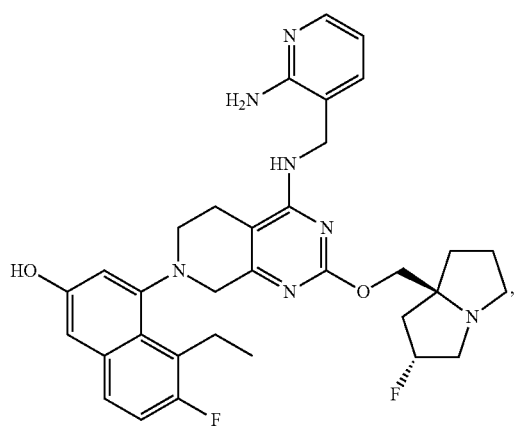
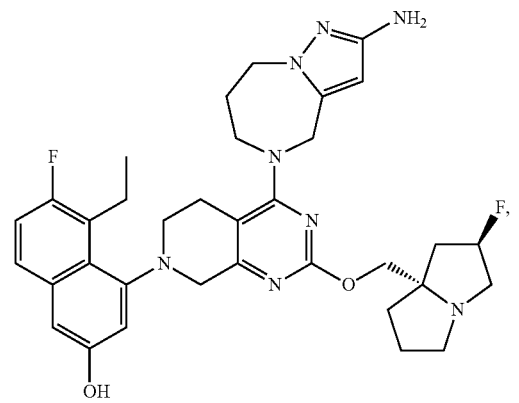
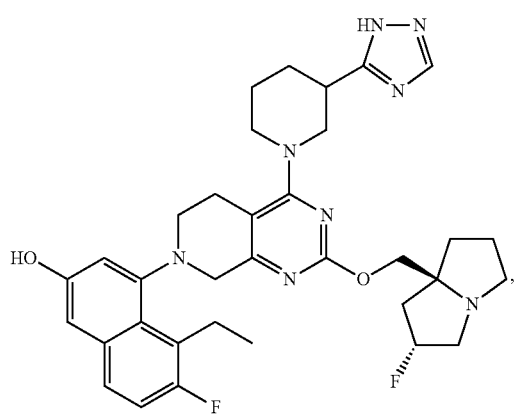
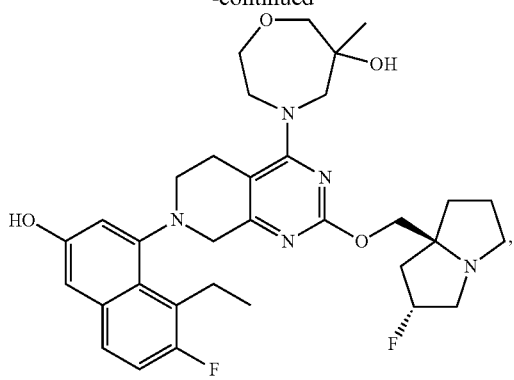
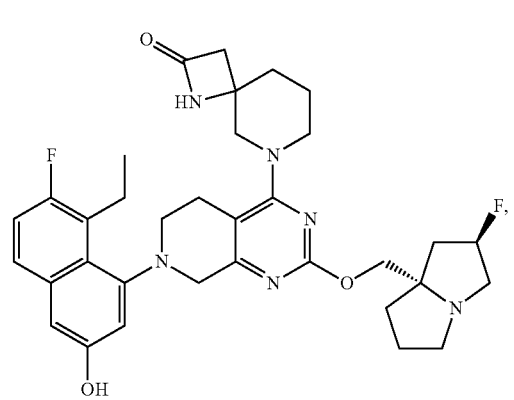
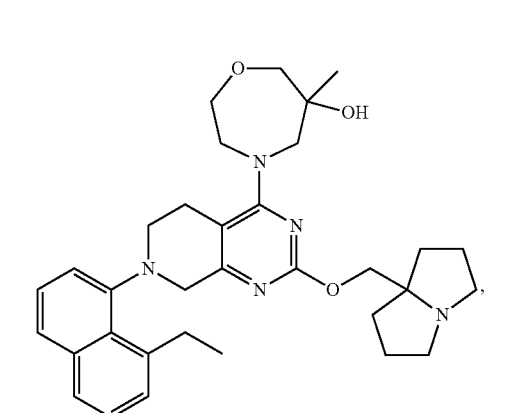
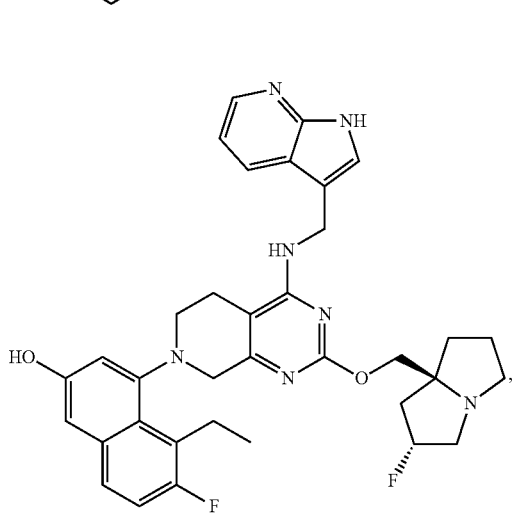

25
-continued
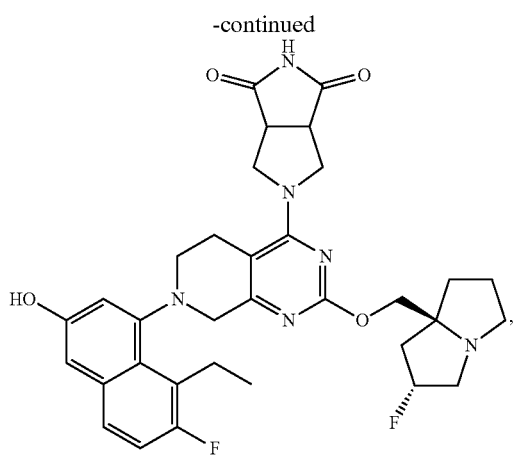
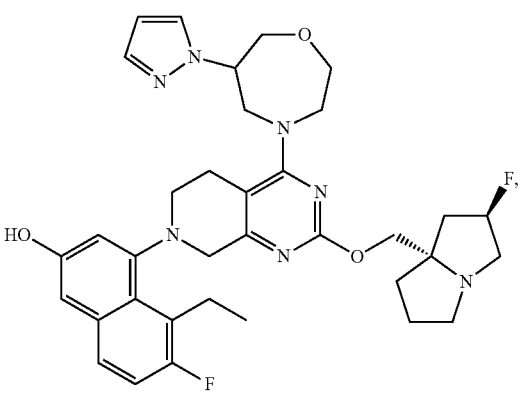
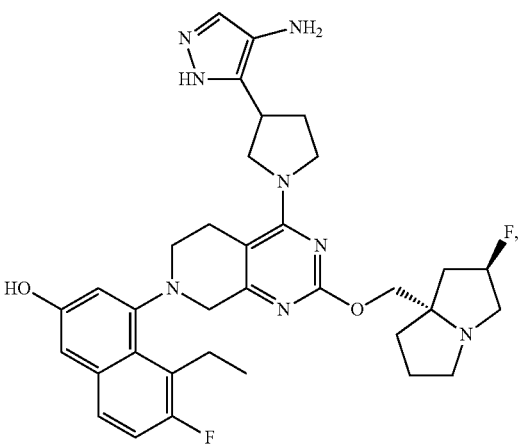
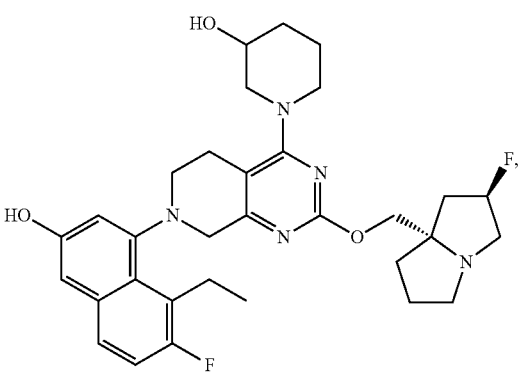
26
-continued
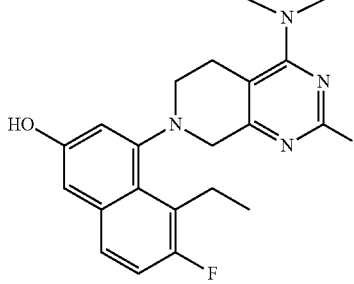
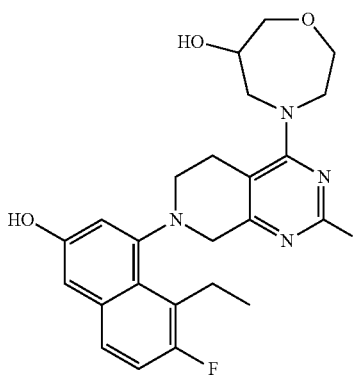
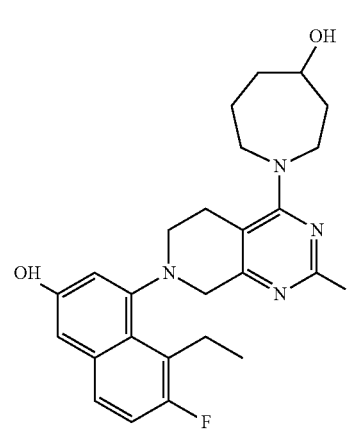
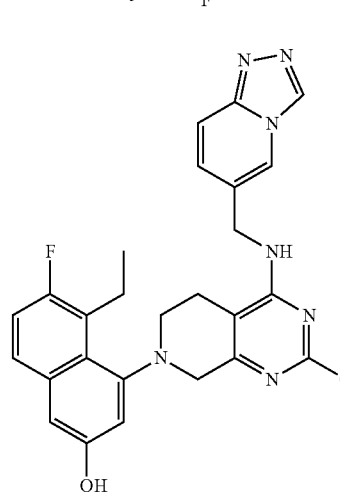

27
-continued
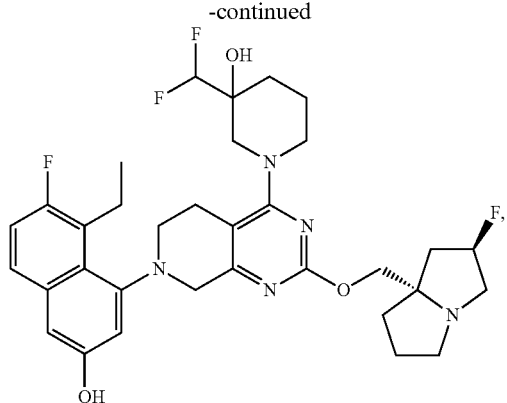
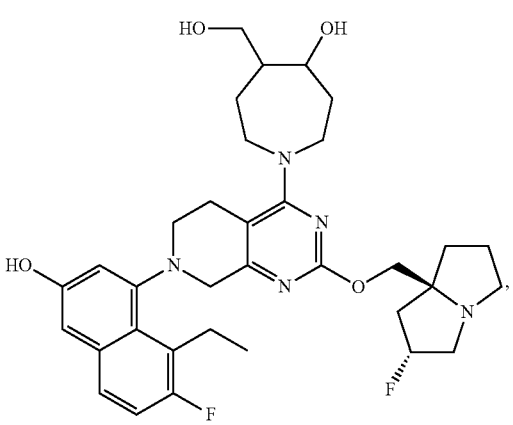
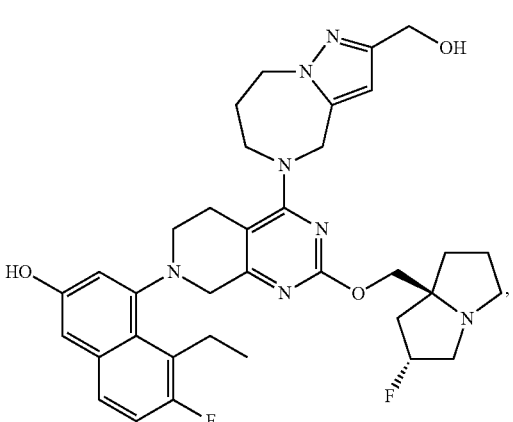
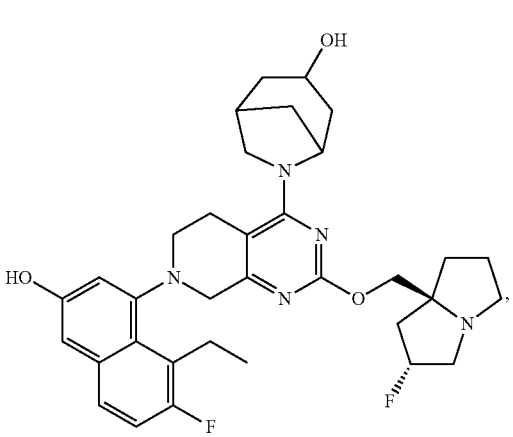
28
-continued
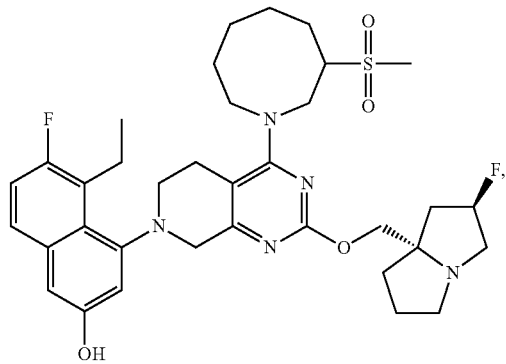
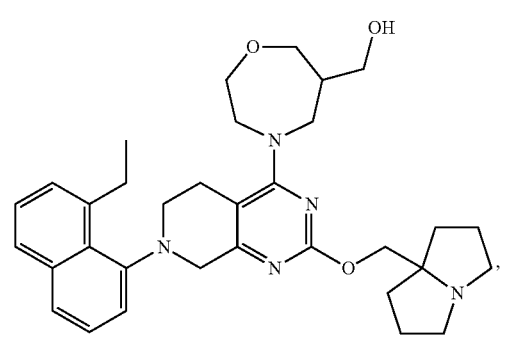
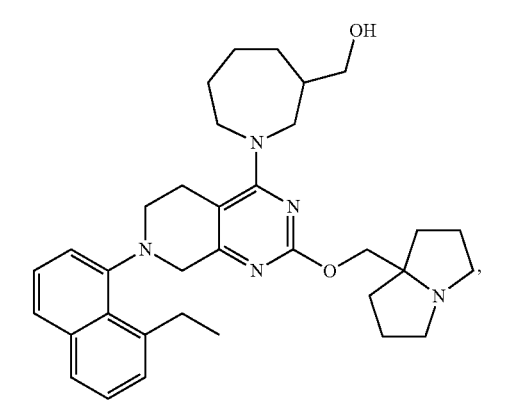
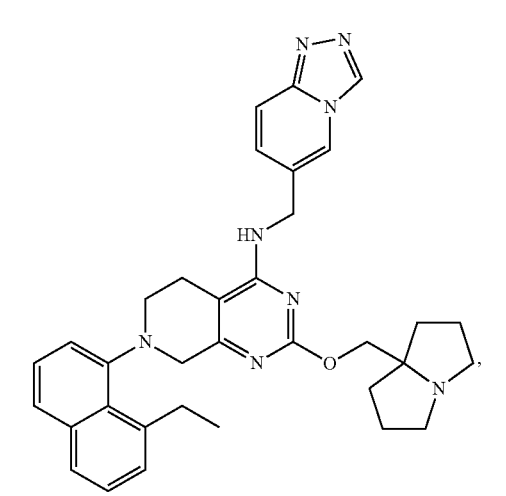

29
-continued
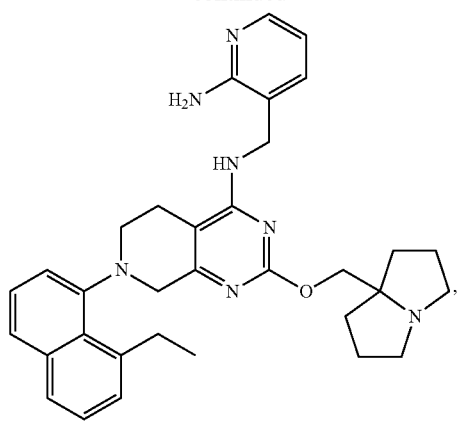
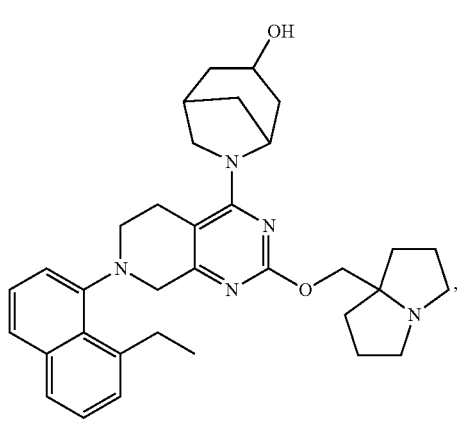
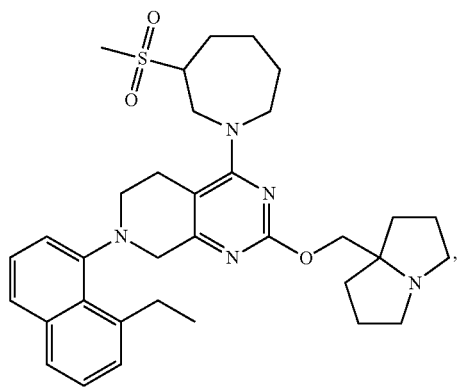
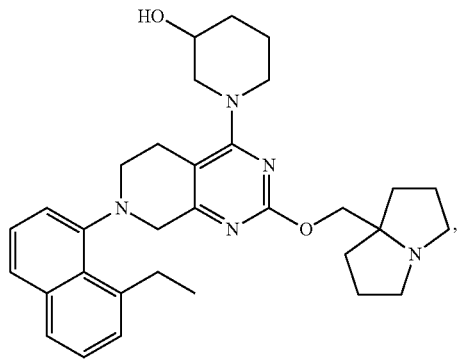
30
-continued
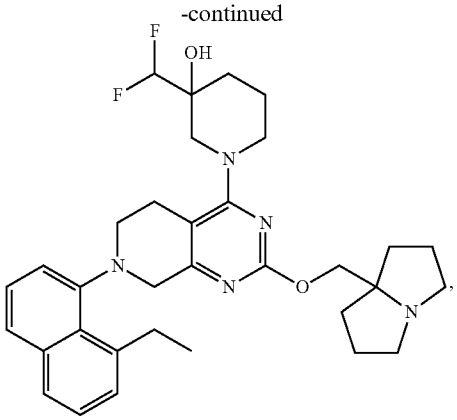
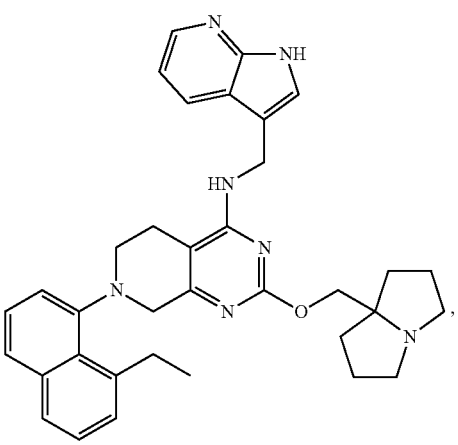
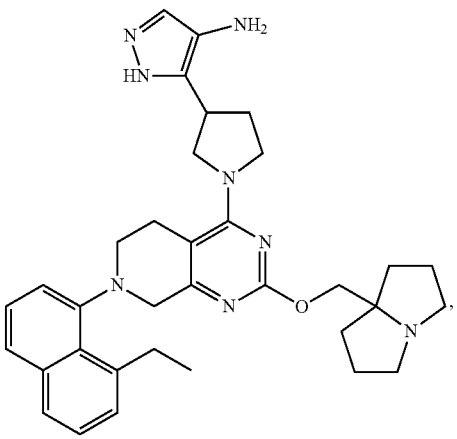
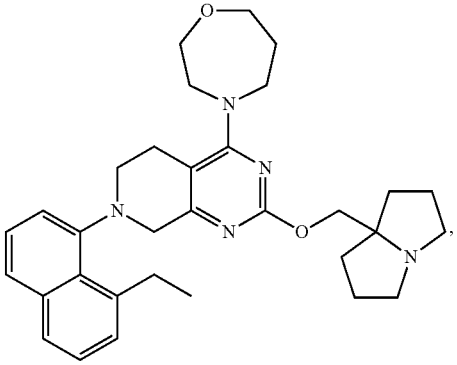

31
-continued
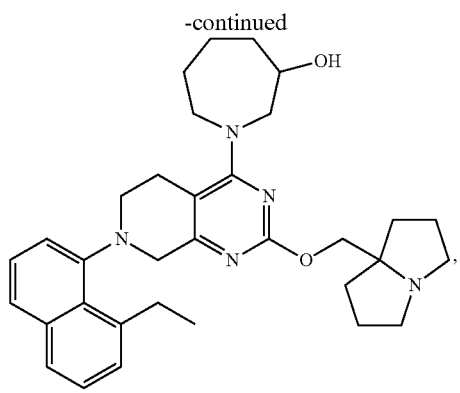
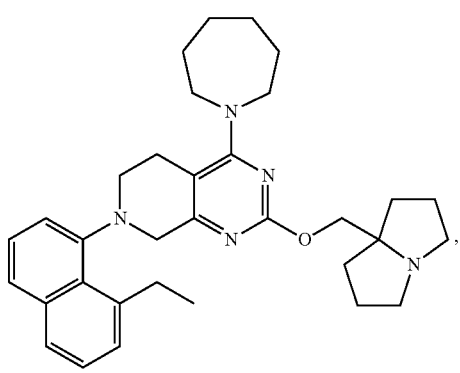
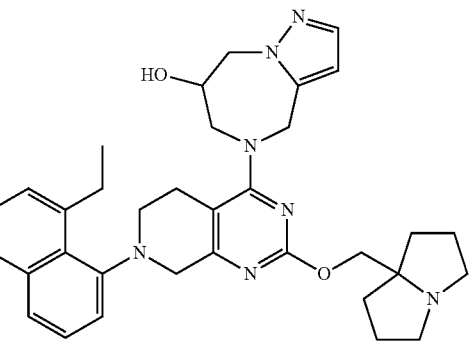
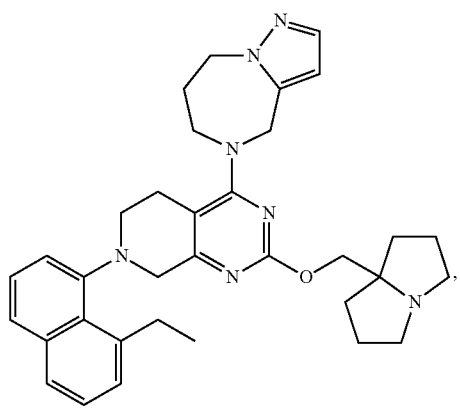
32
-continued
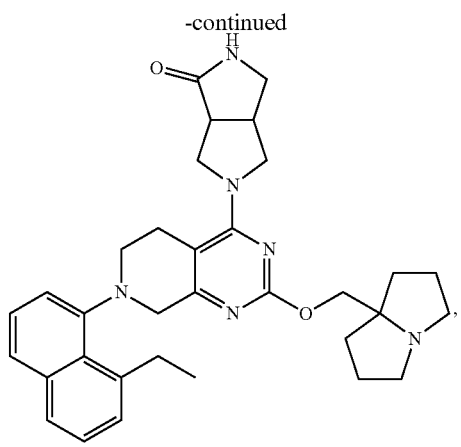
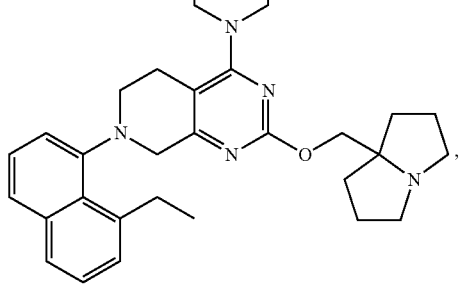
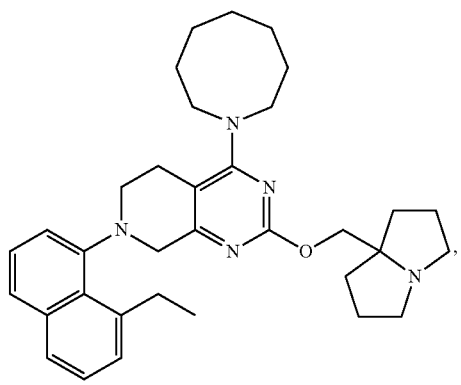
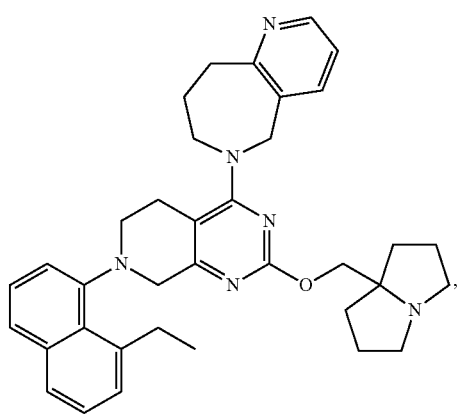

33
-continued
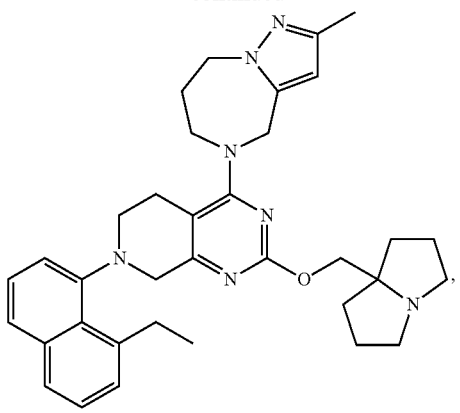
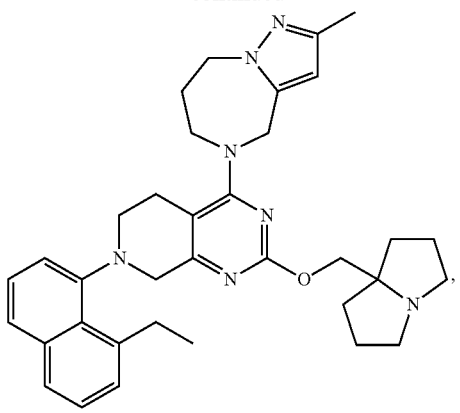
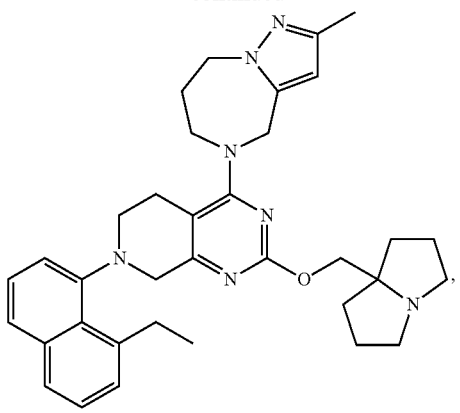
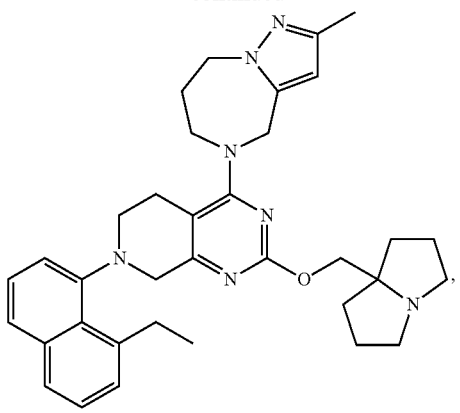
34
-continued
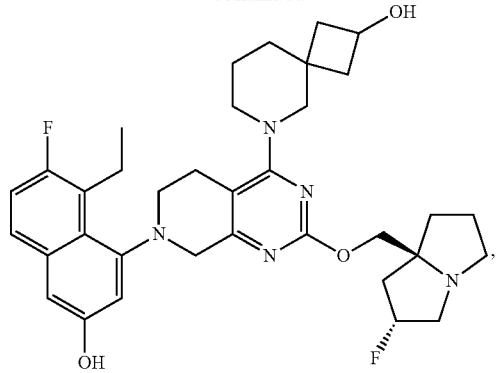
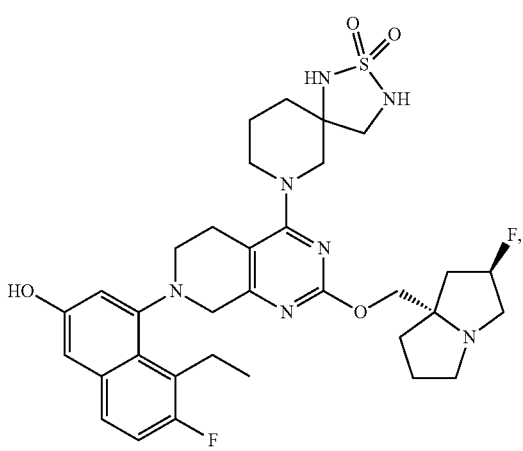
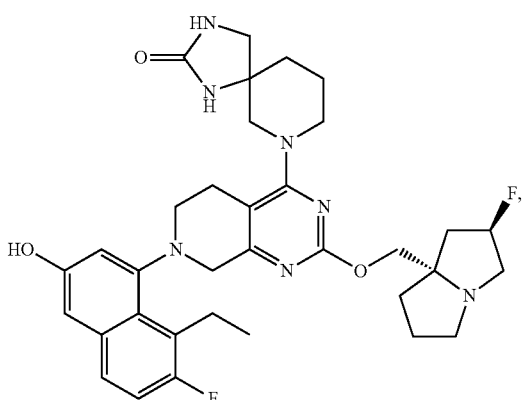
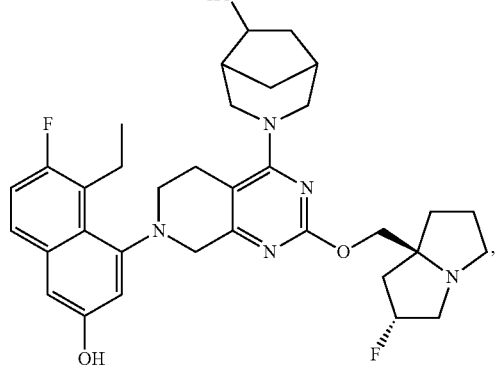

-continued
35
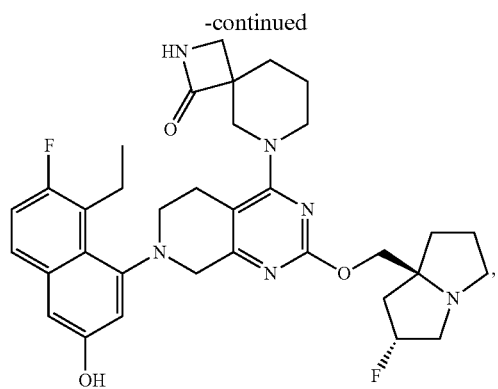
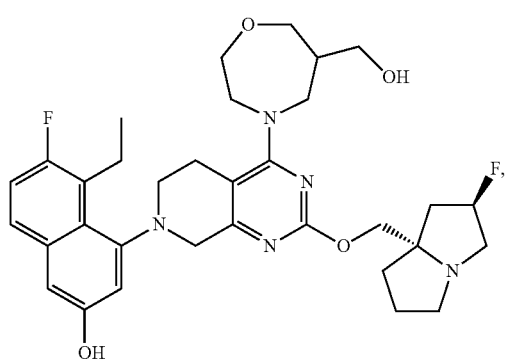
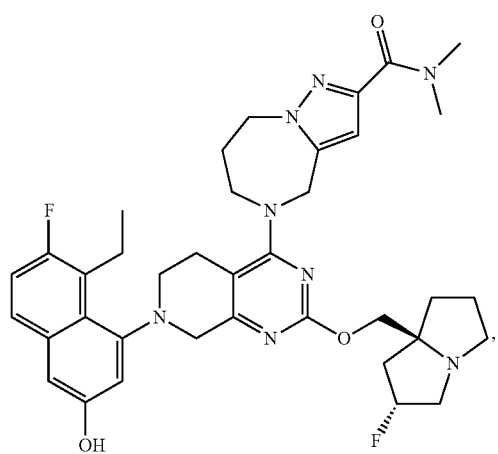
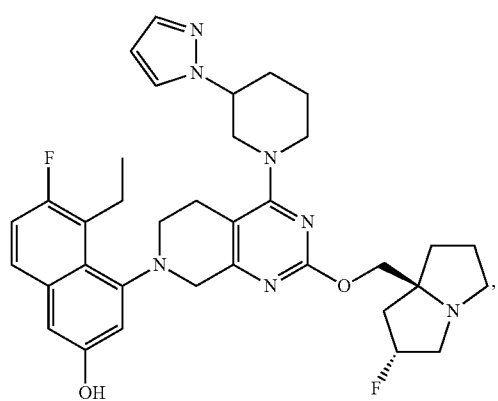
-continued
36
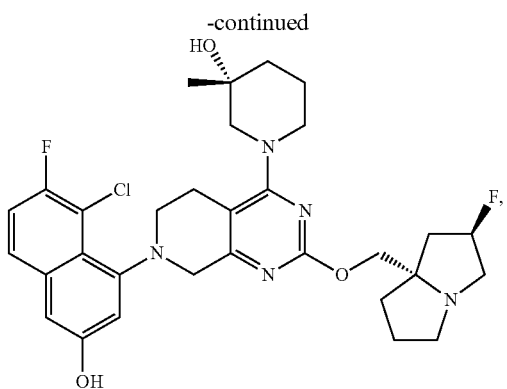
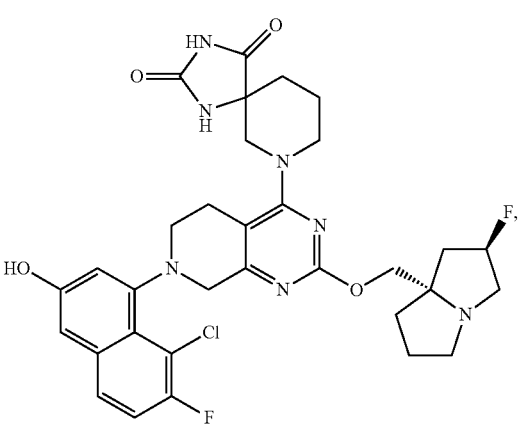
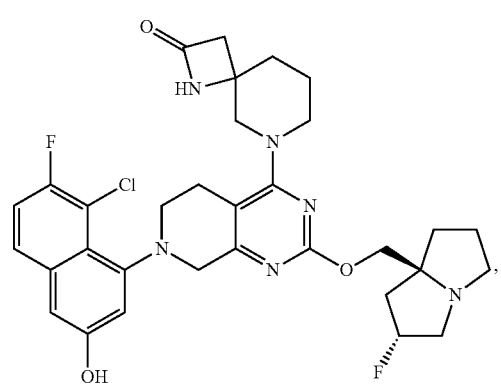
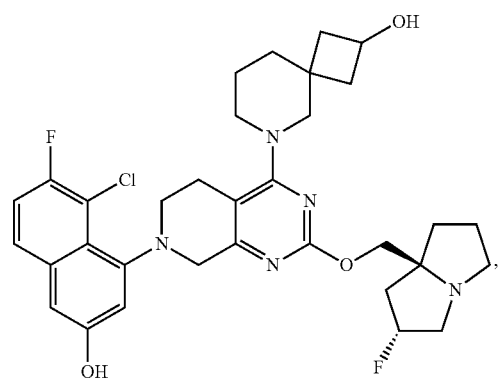

37
-continued
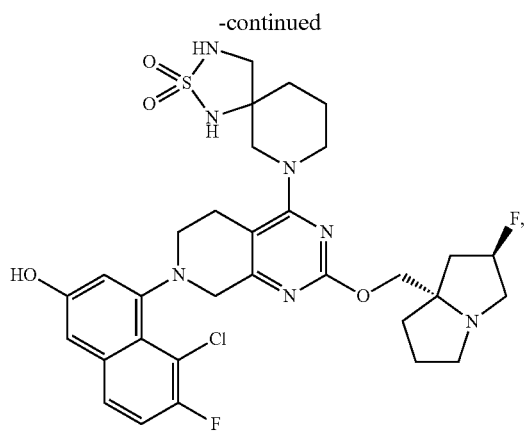
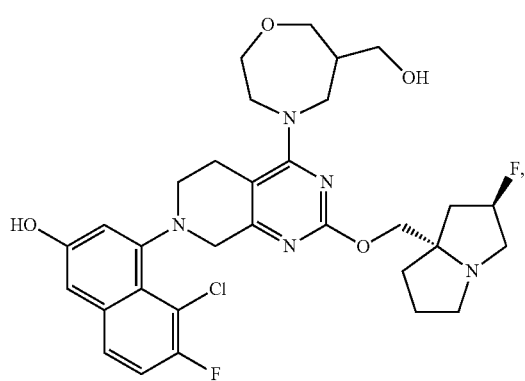
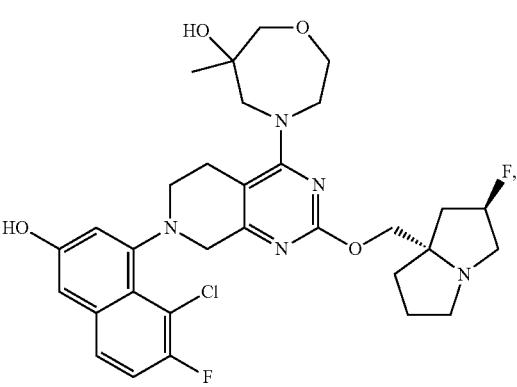
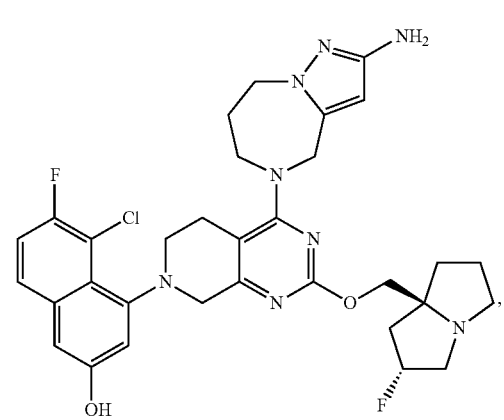
38
-continued
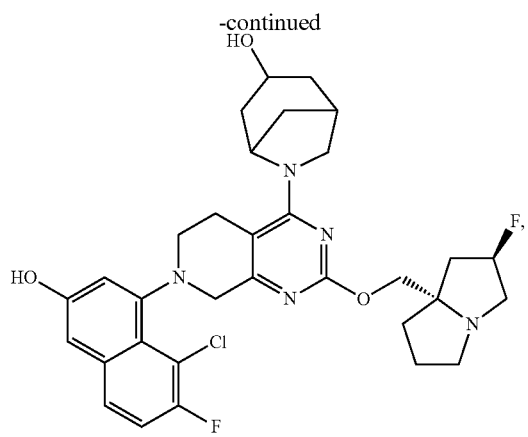
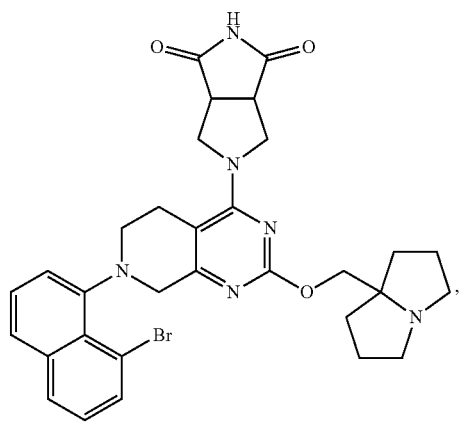
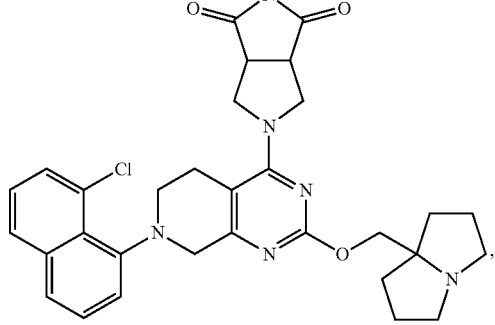
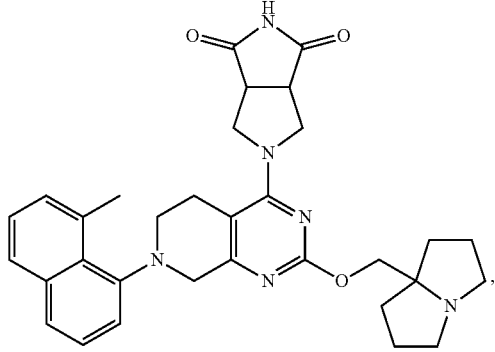

39
-continued
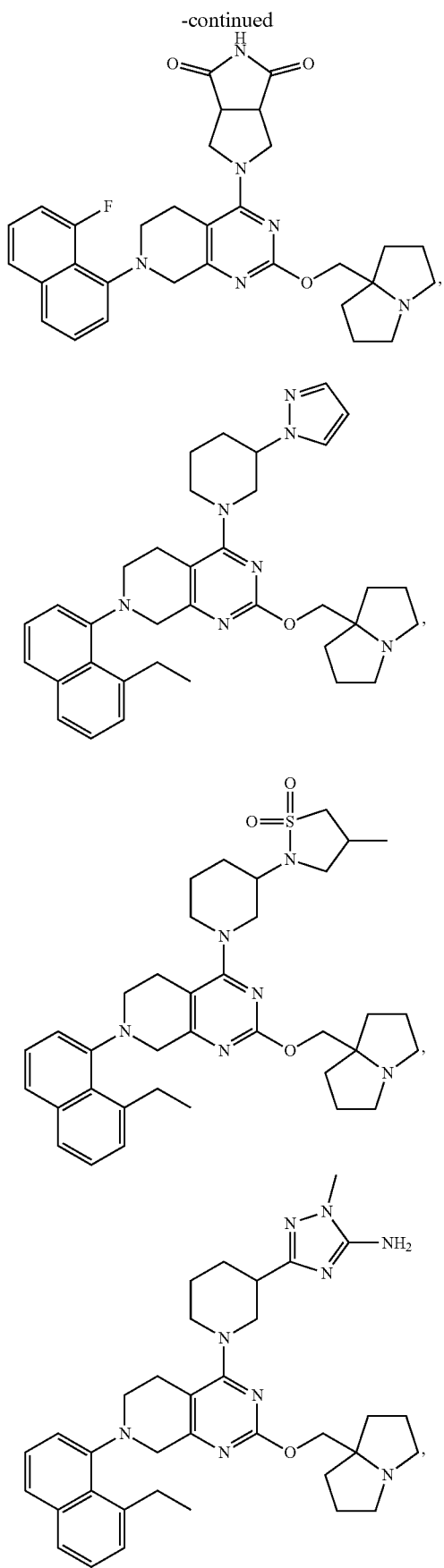
40
-continued
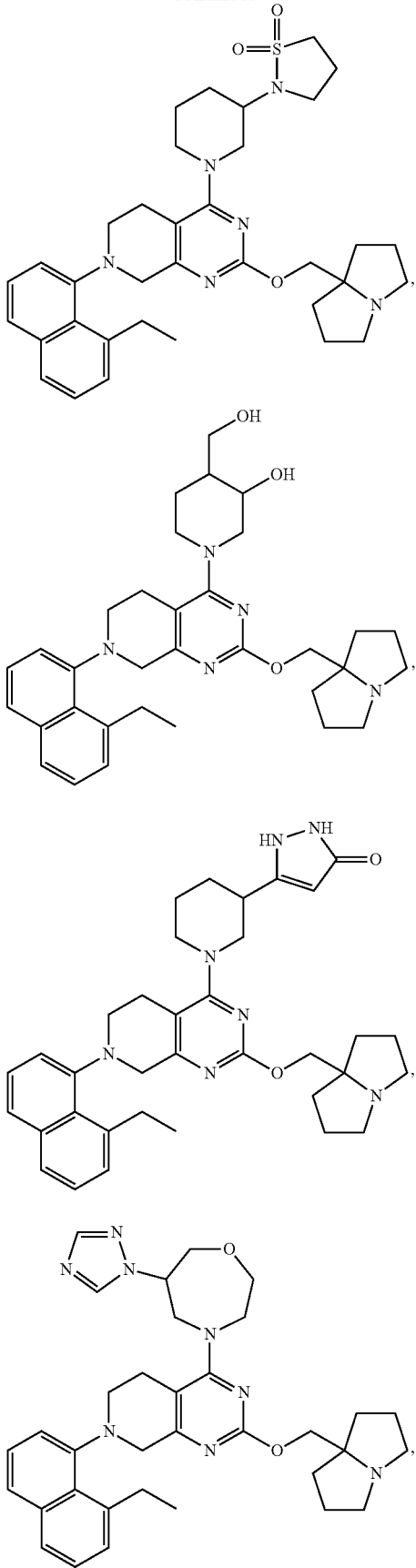

41
-continued
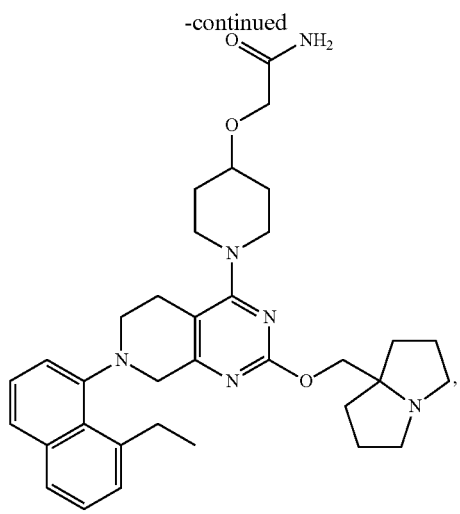
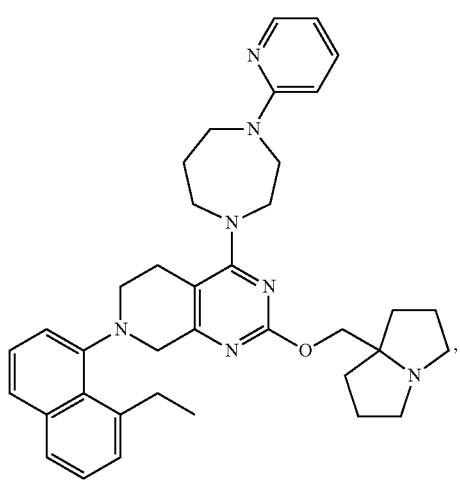
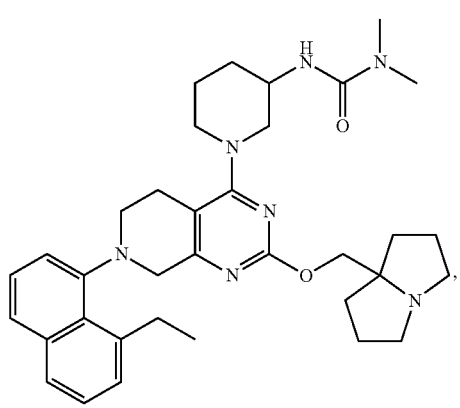
42
-continued
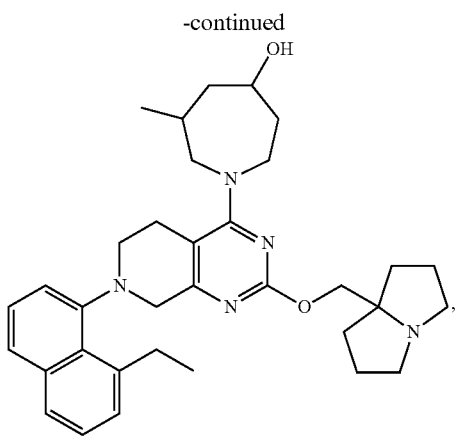
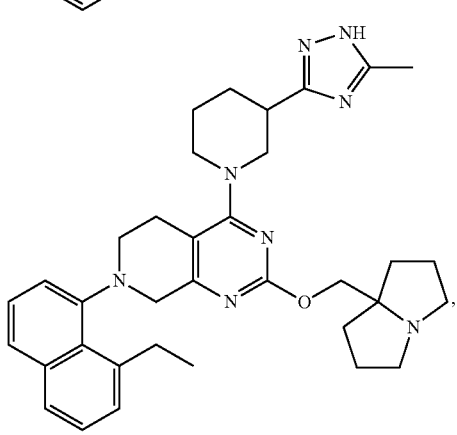
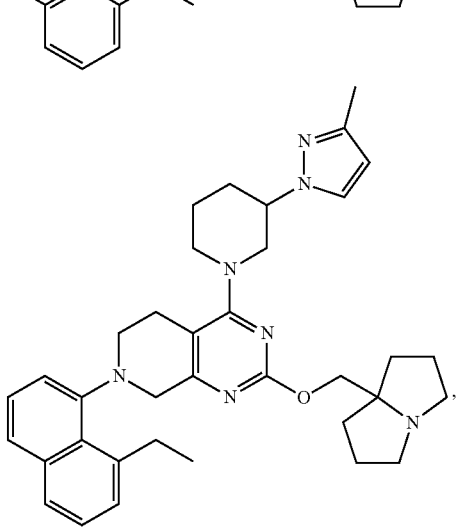
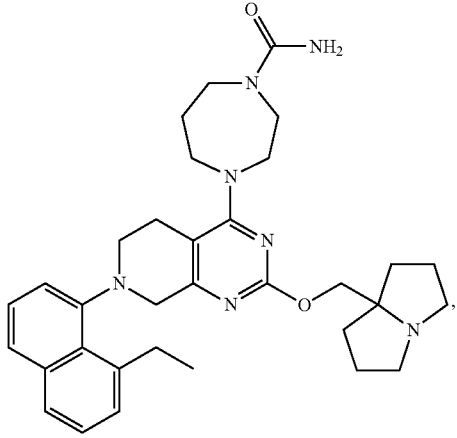

43
-continued
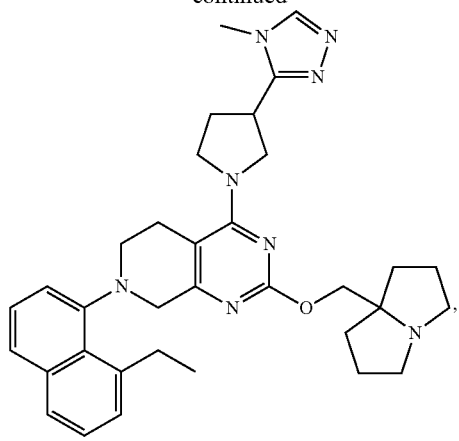
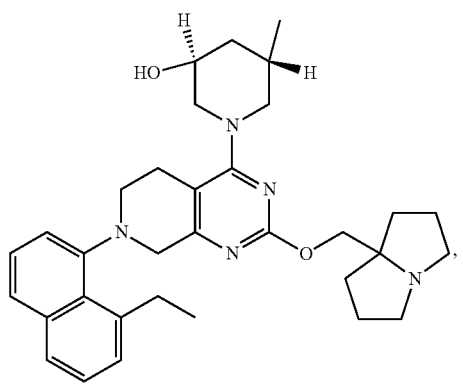
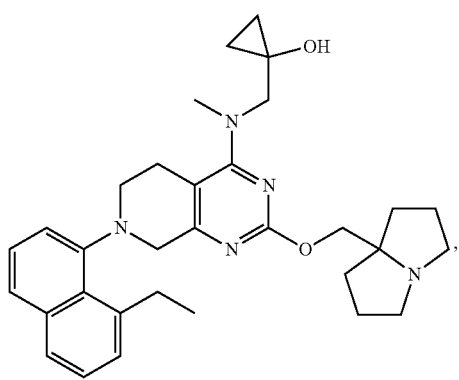
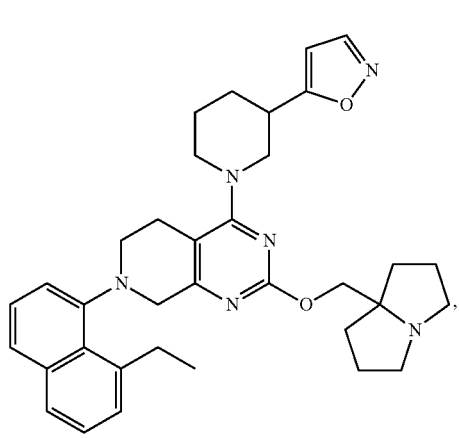
44
-continued
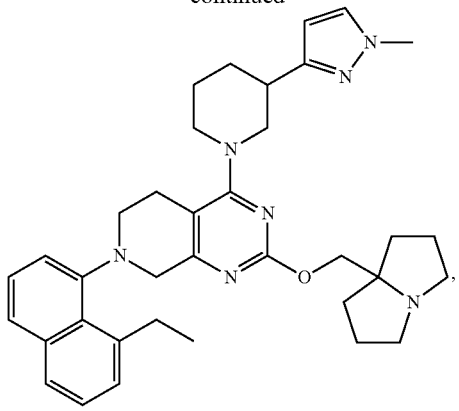
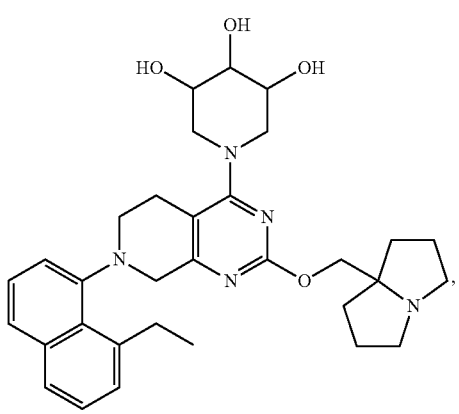
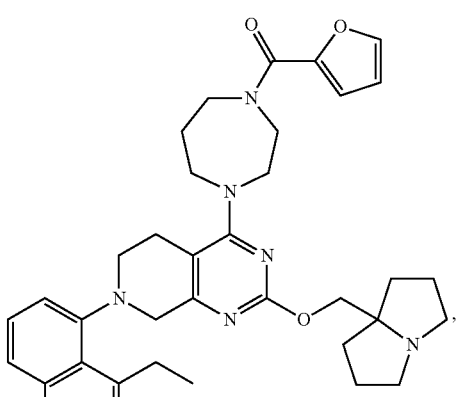
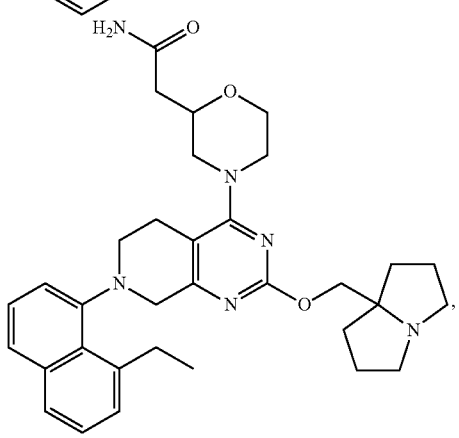

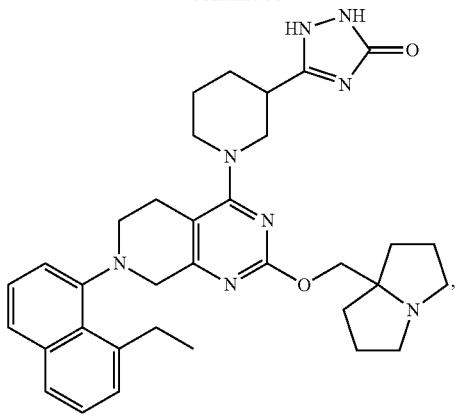
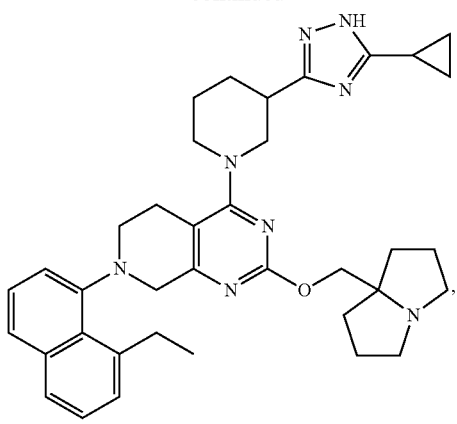
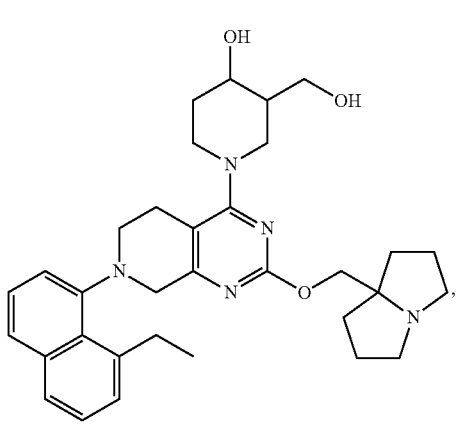
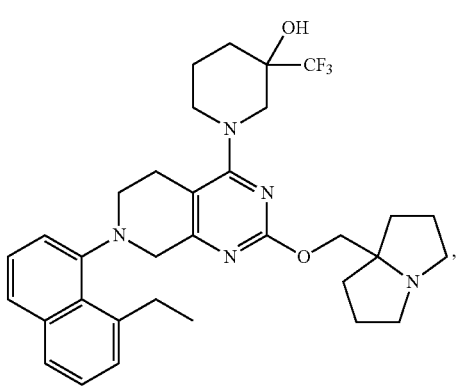
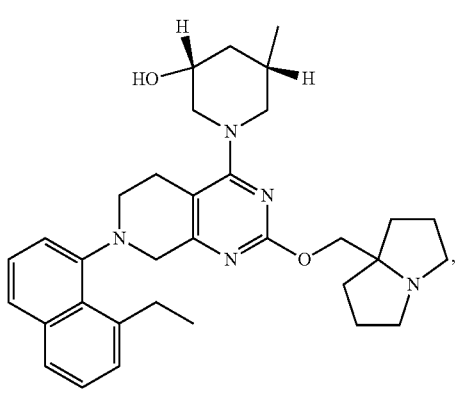

47
-continued
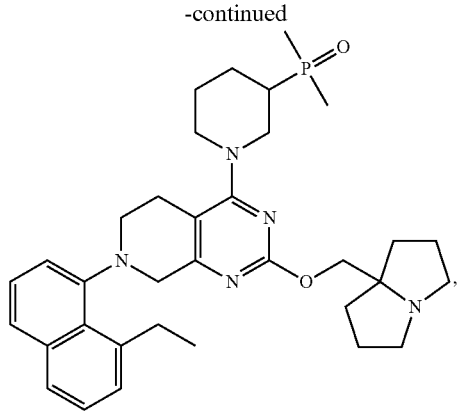
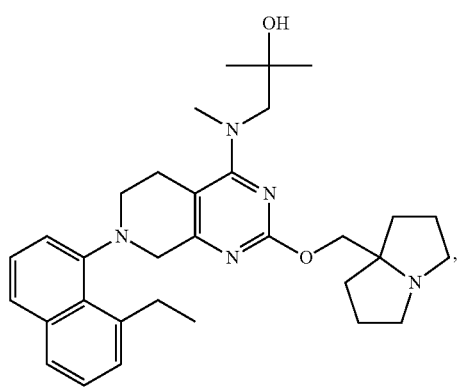
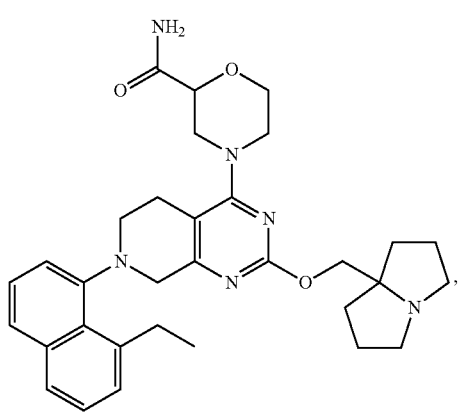
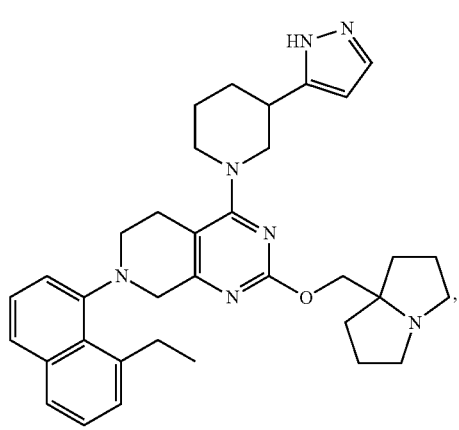
48
-continued
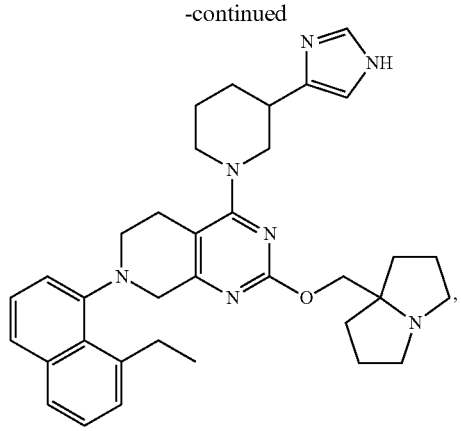
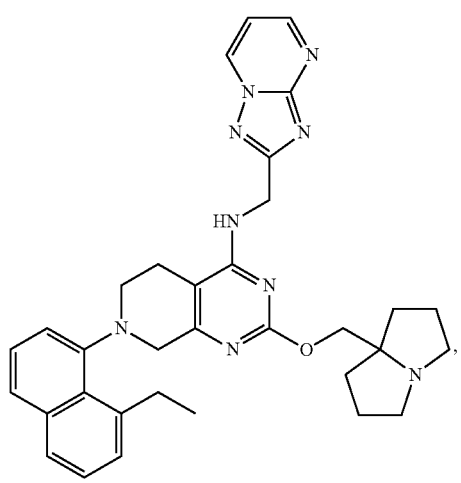
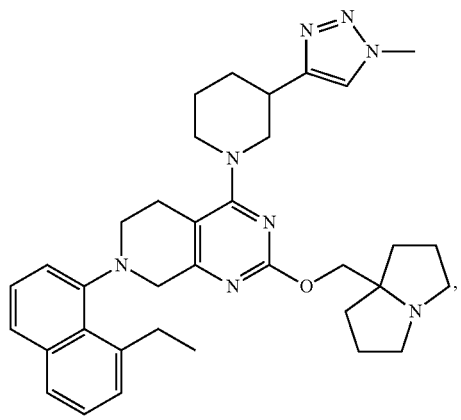
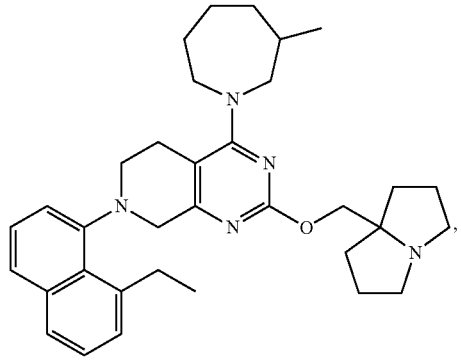

49
-continued
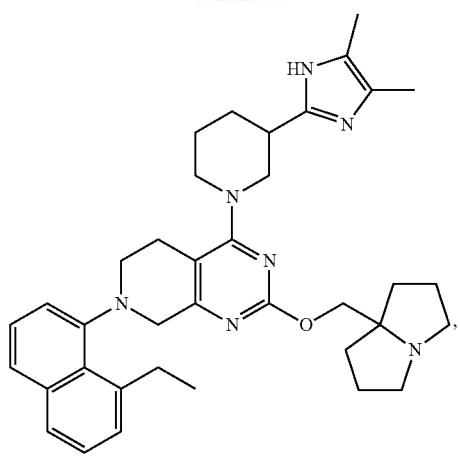
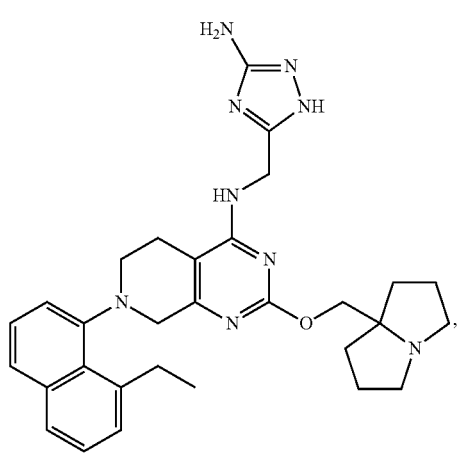
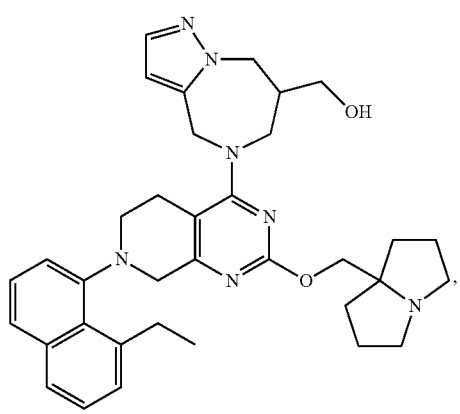
50
-continued
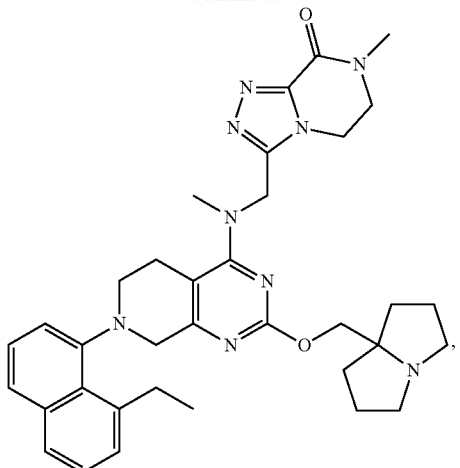
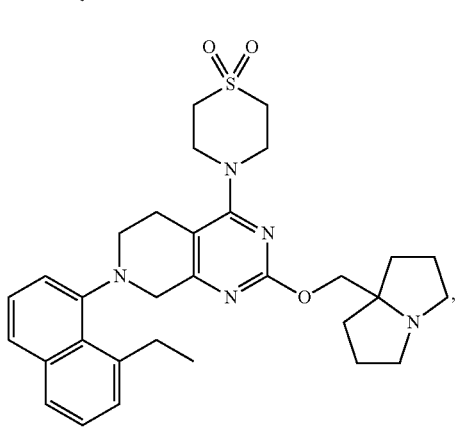
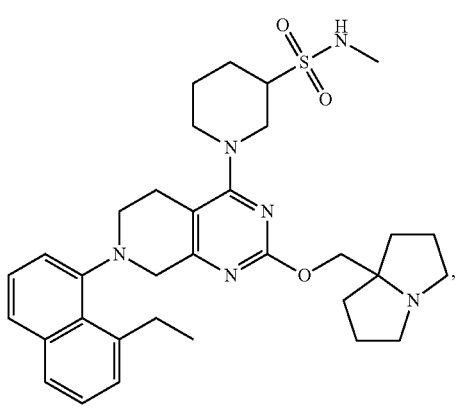
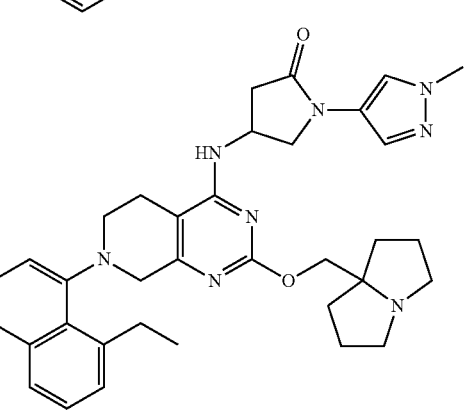

51
-continued
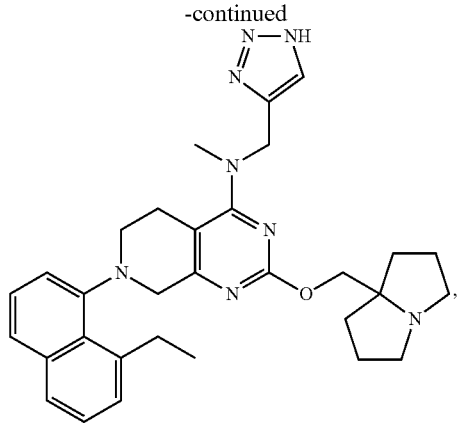
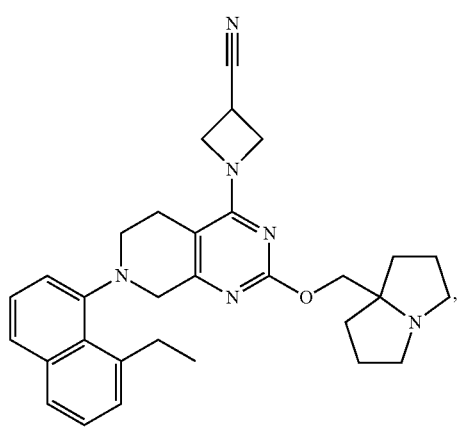
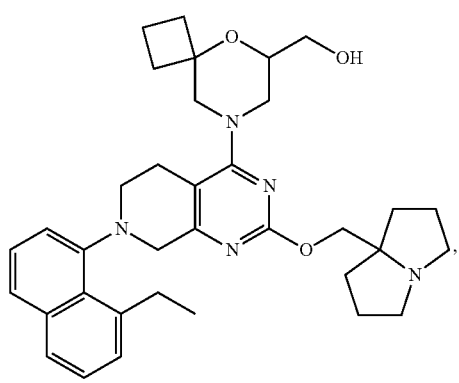
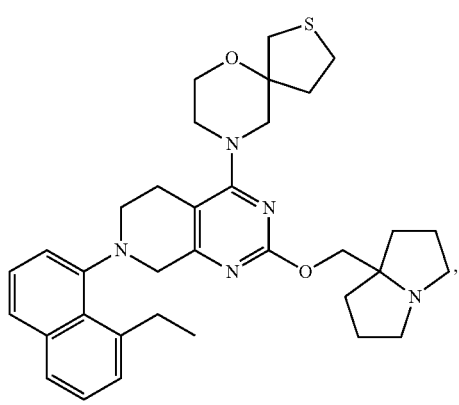
52
-continued
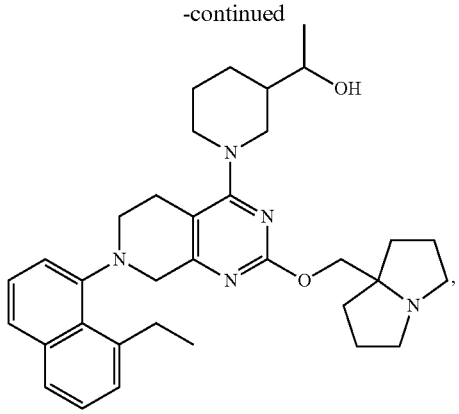
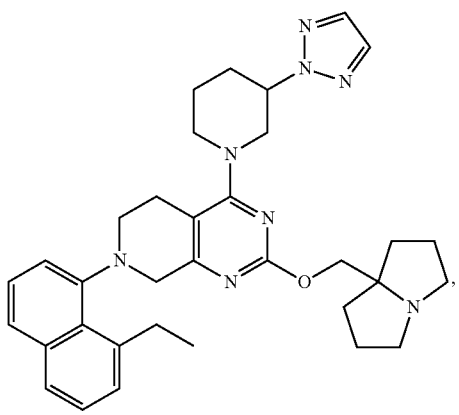
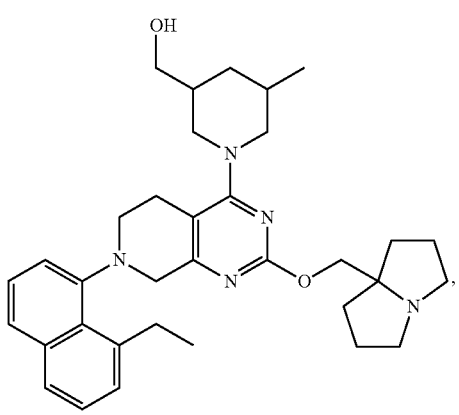
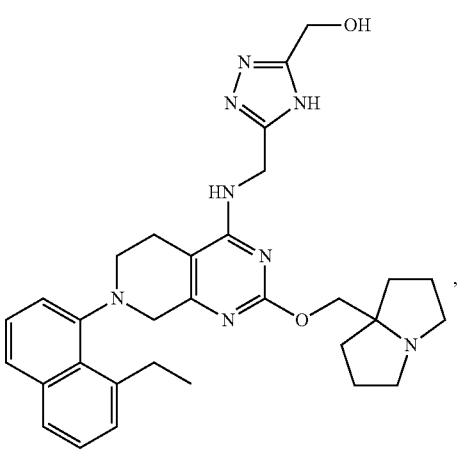

53
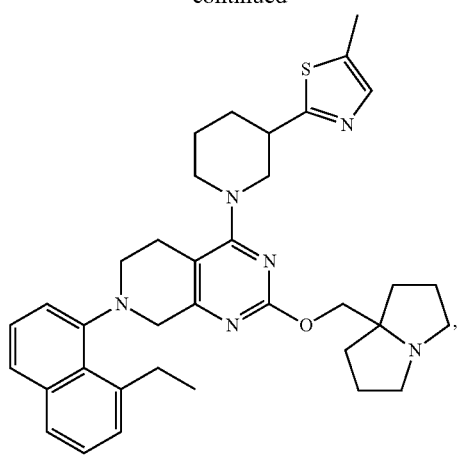
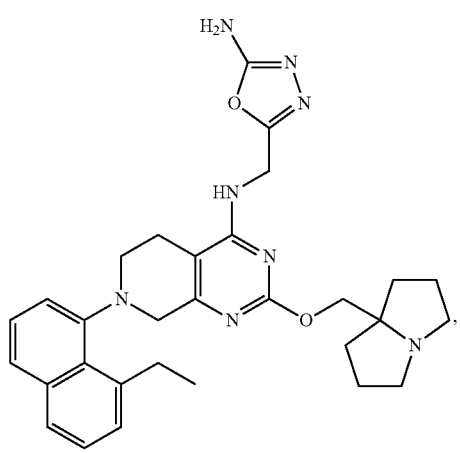
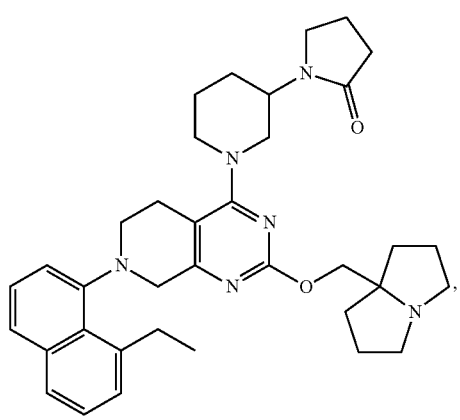
54
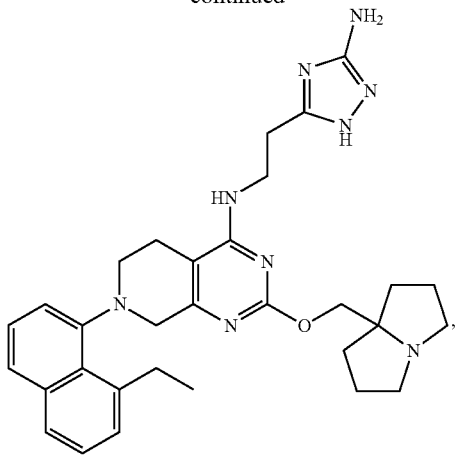
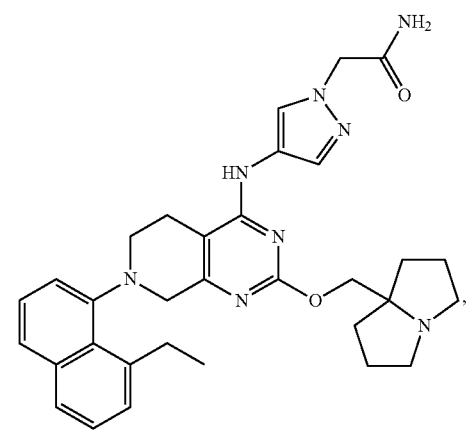
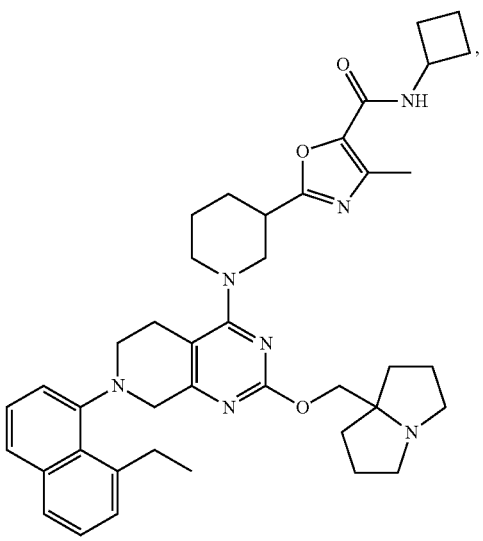

55
-continued
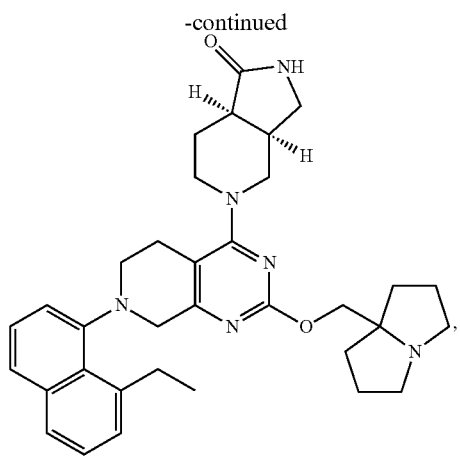
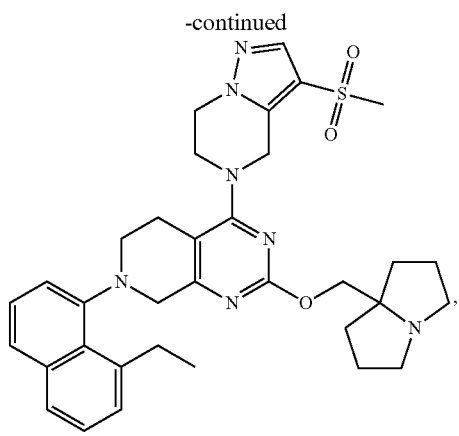
56
-continued
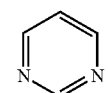
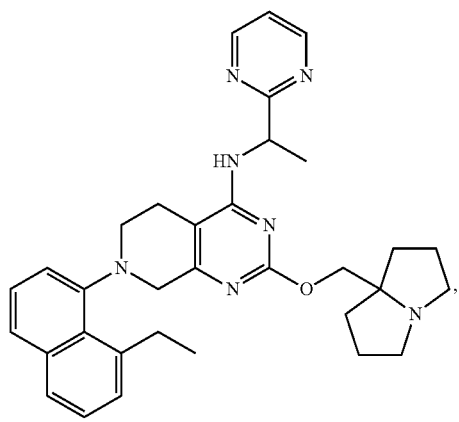
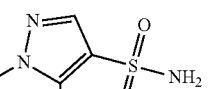
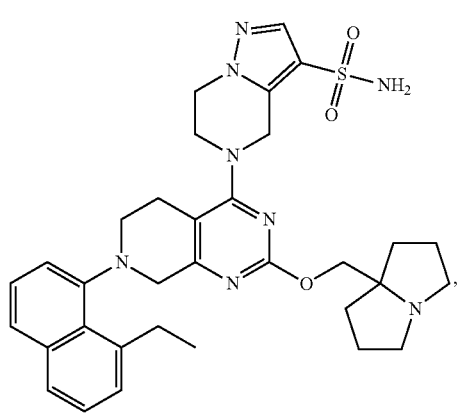
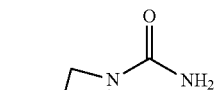
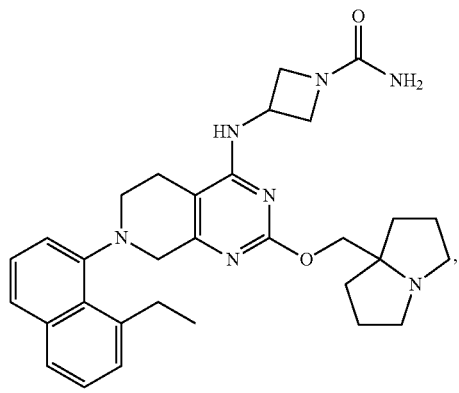

-continued
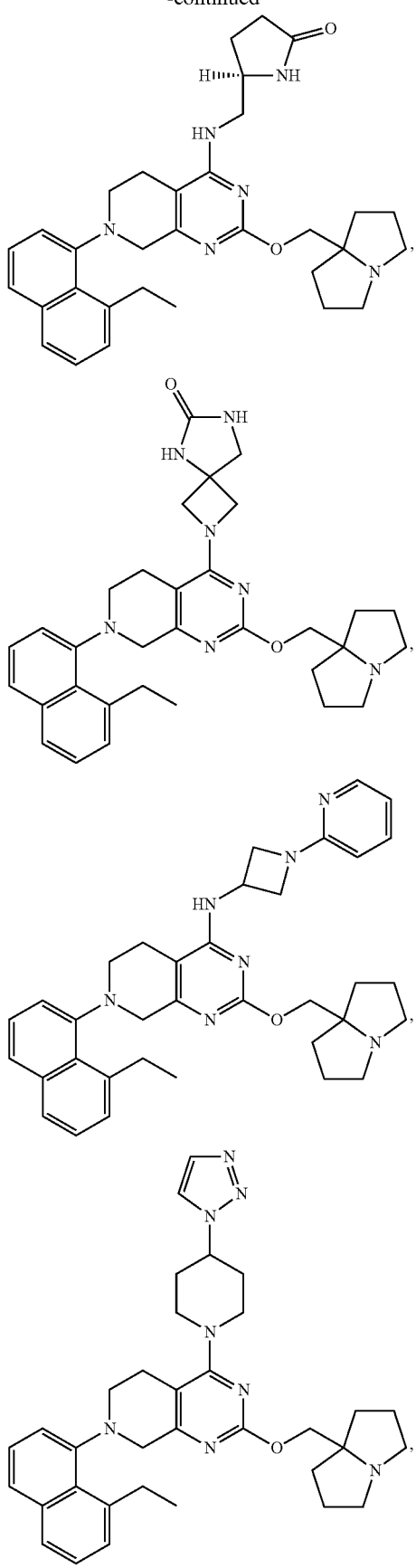
-continued
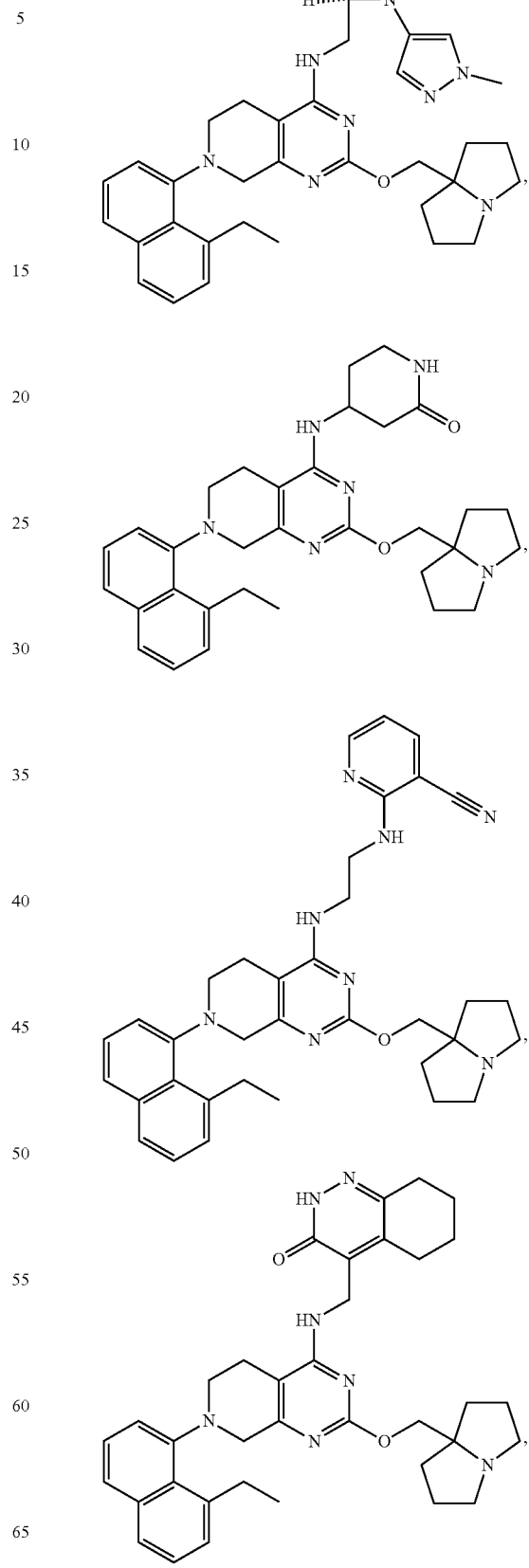

59
-continued
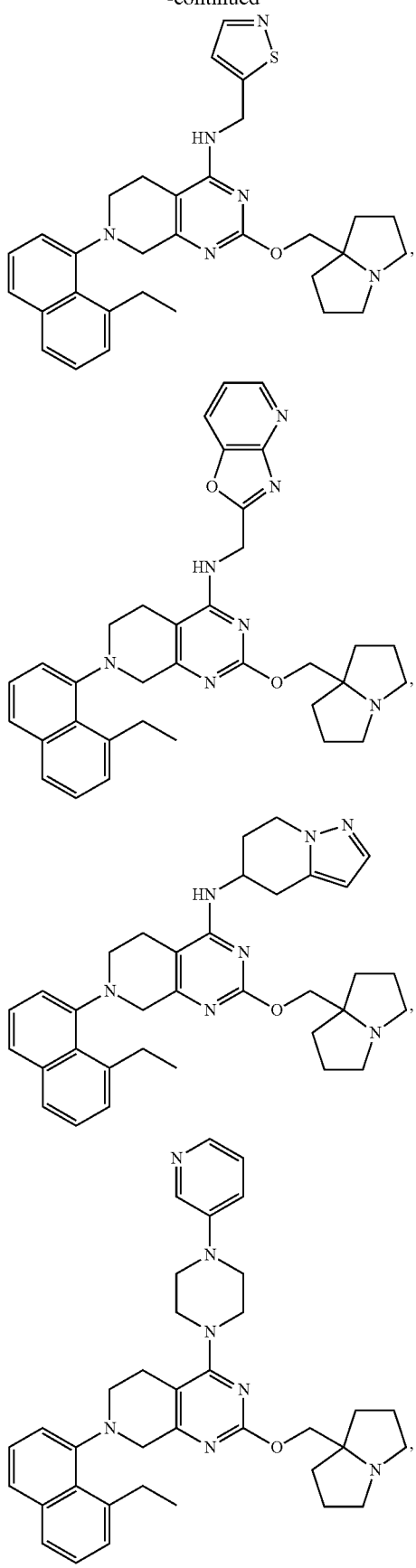
60
-continued
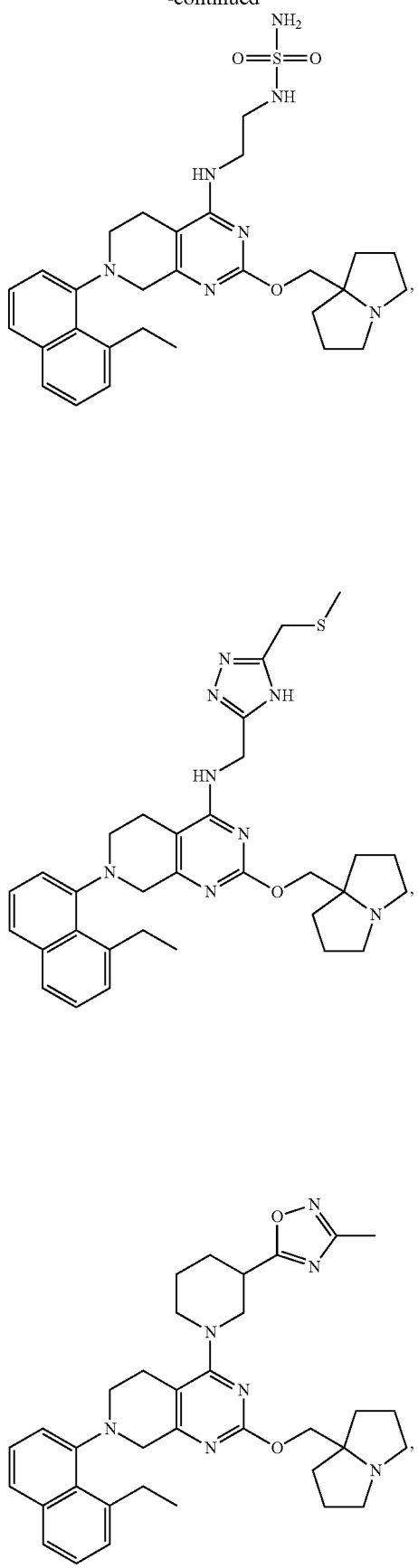

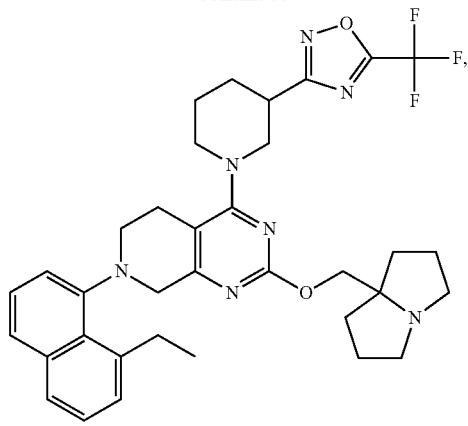
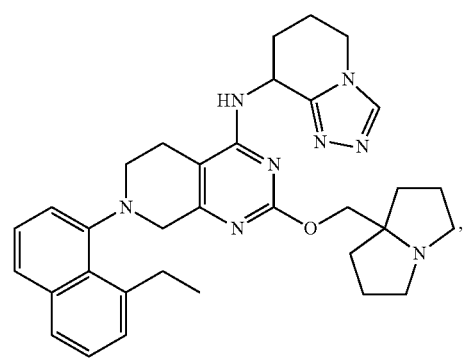
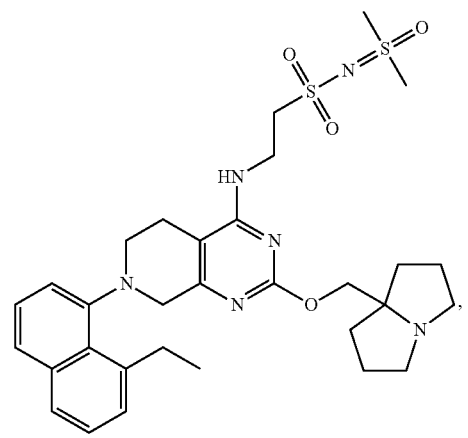
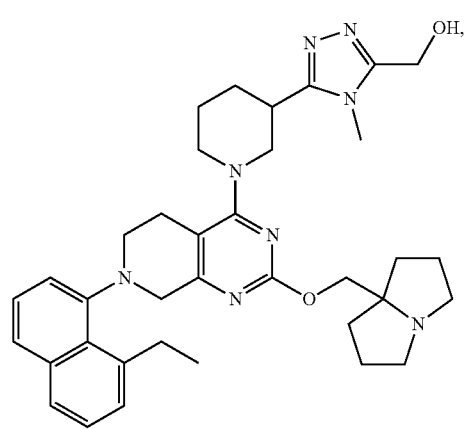
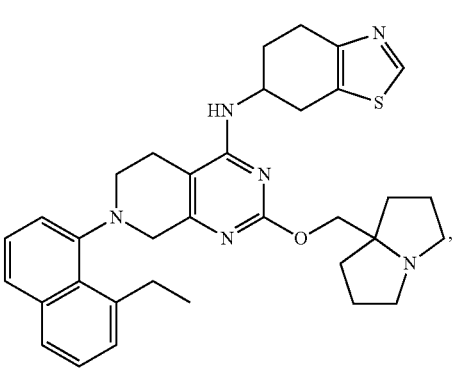
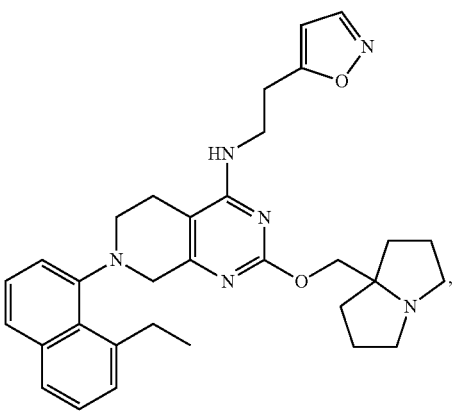
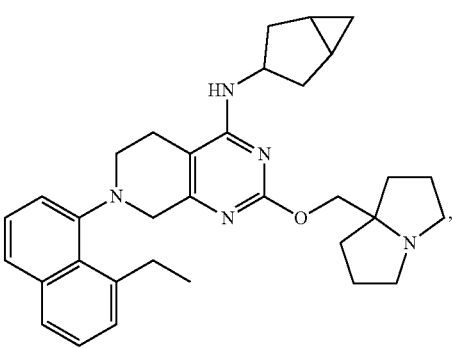
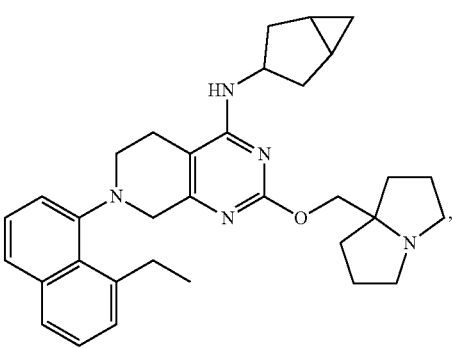

63
-continued
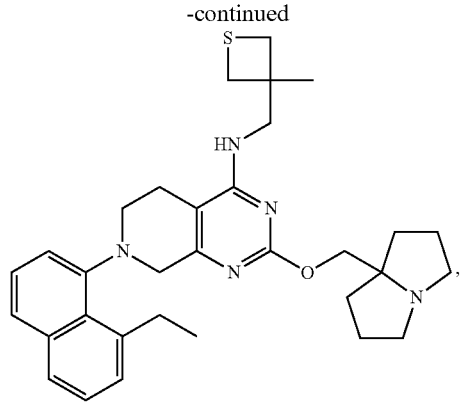
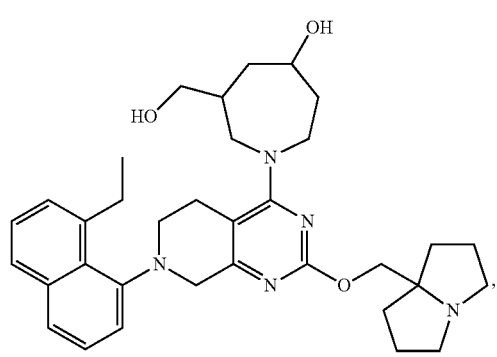
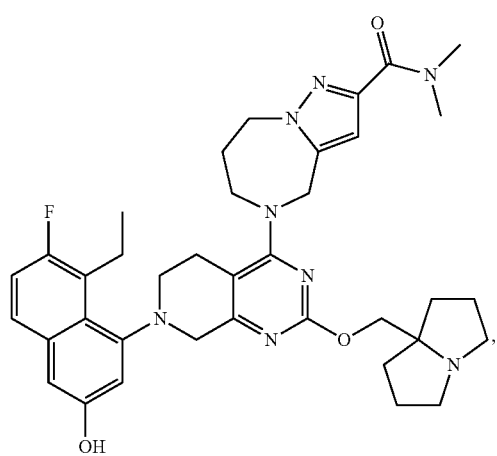
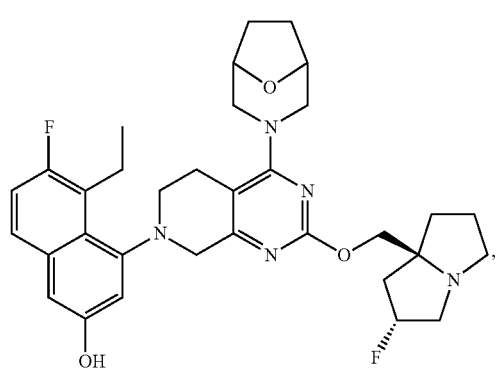
64
-continued
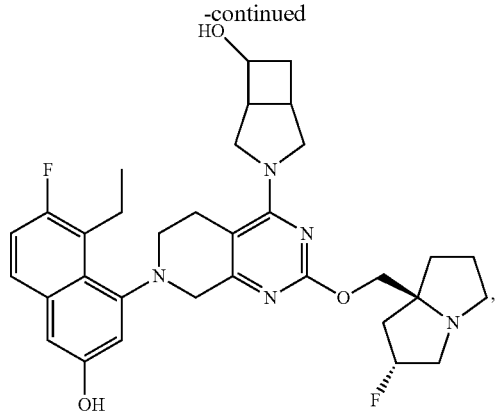
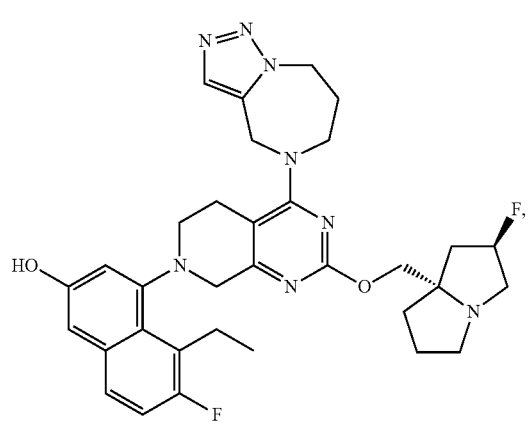
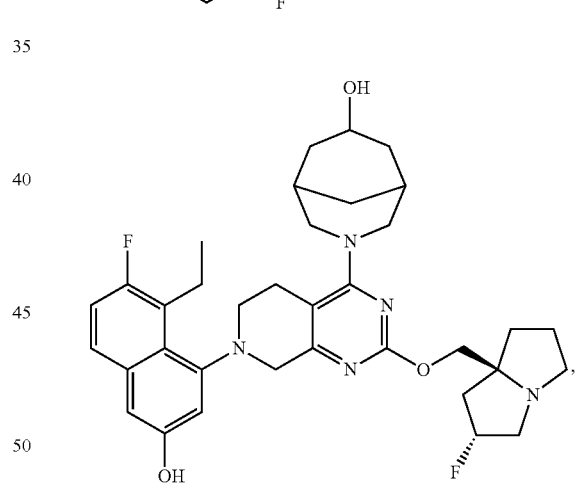
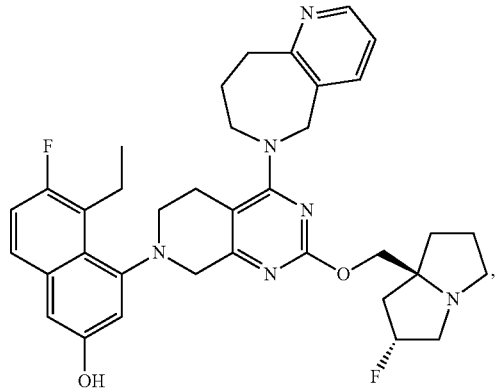

65
-continued
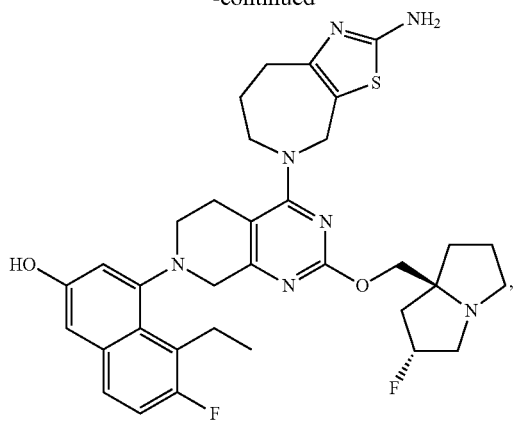
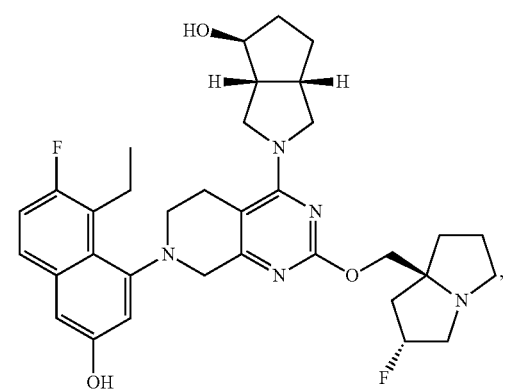
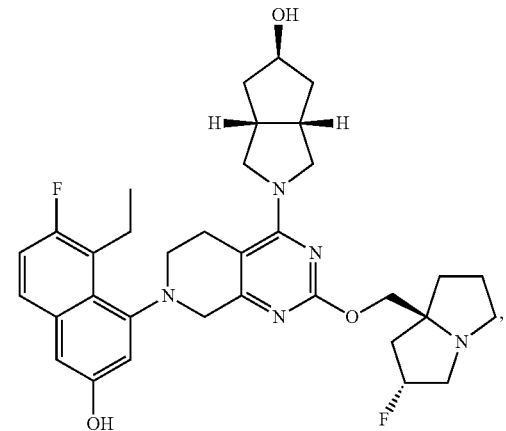
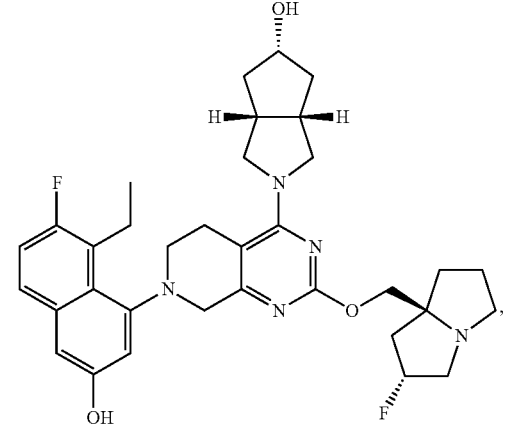
66
-continued
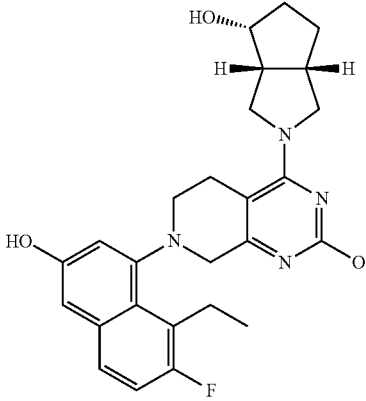
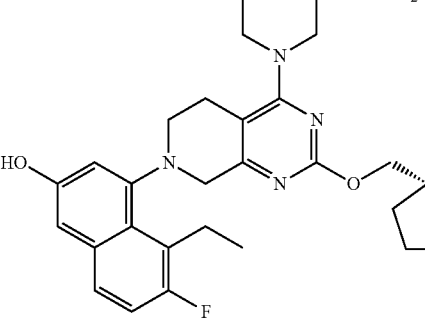
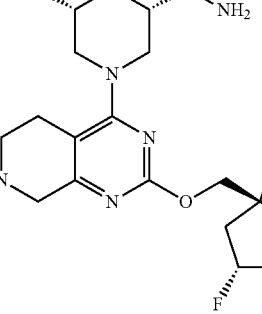
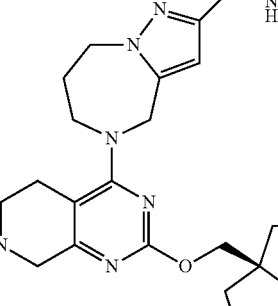

67
-continued
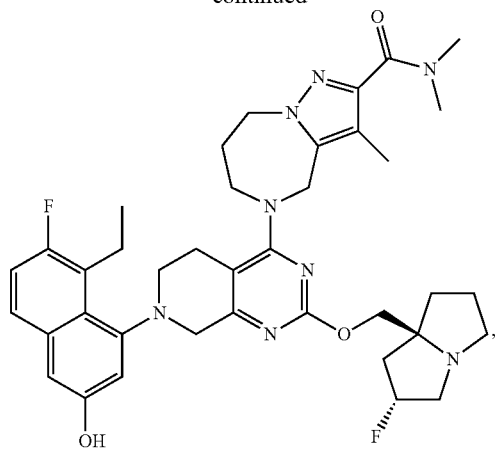
68
-continued
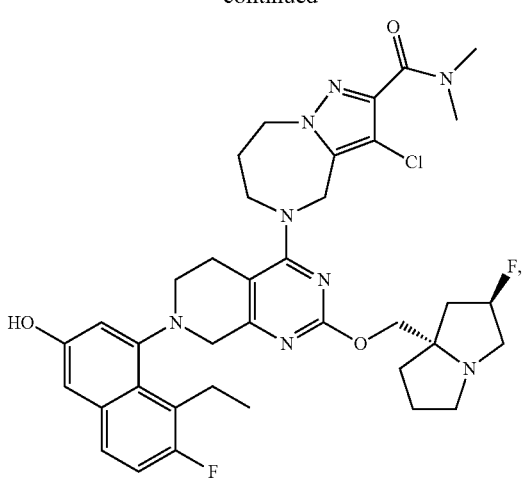
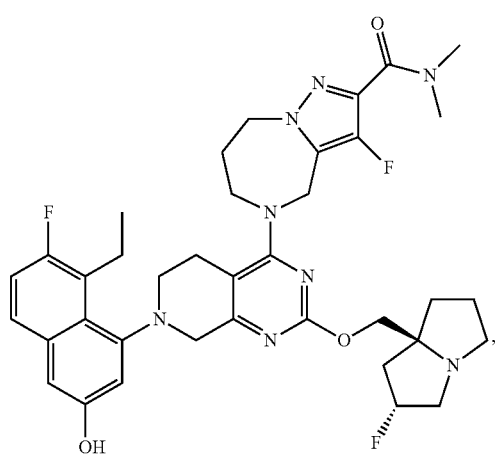
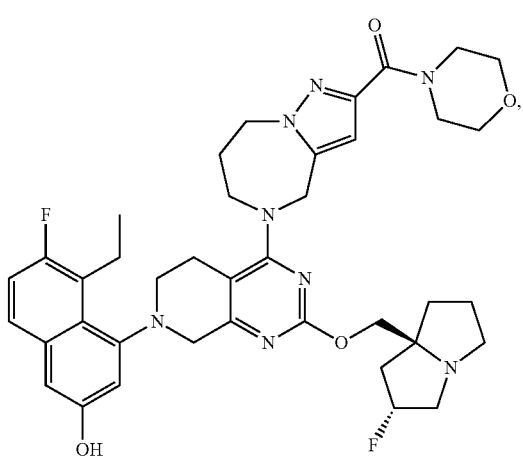
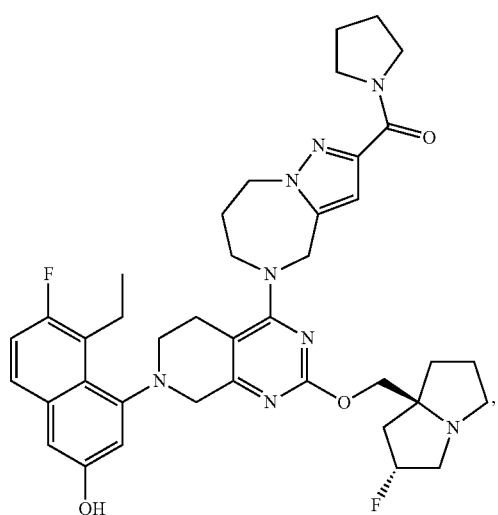
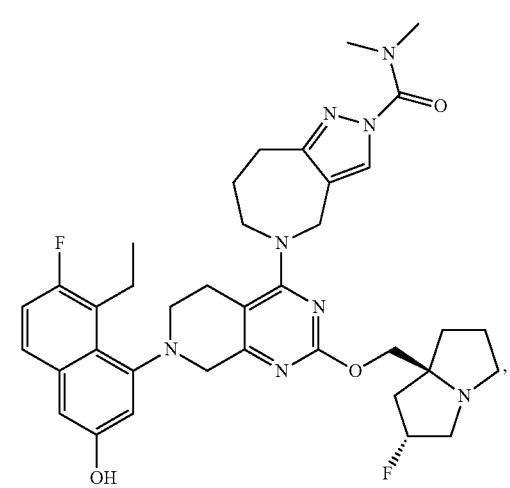

69
-continued
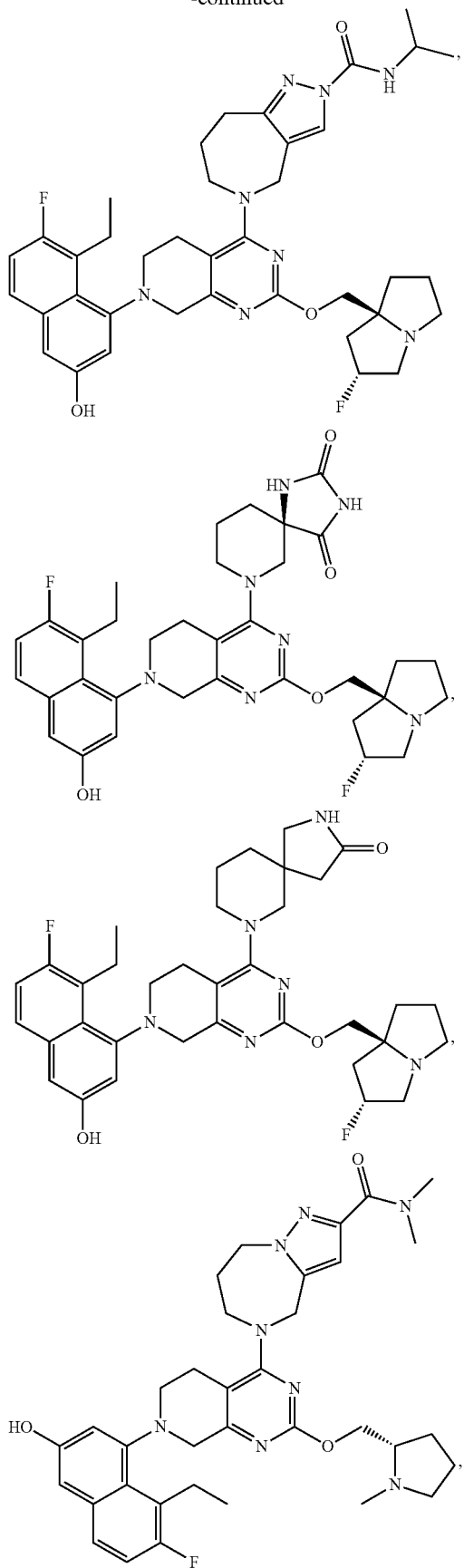
70
-continued
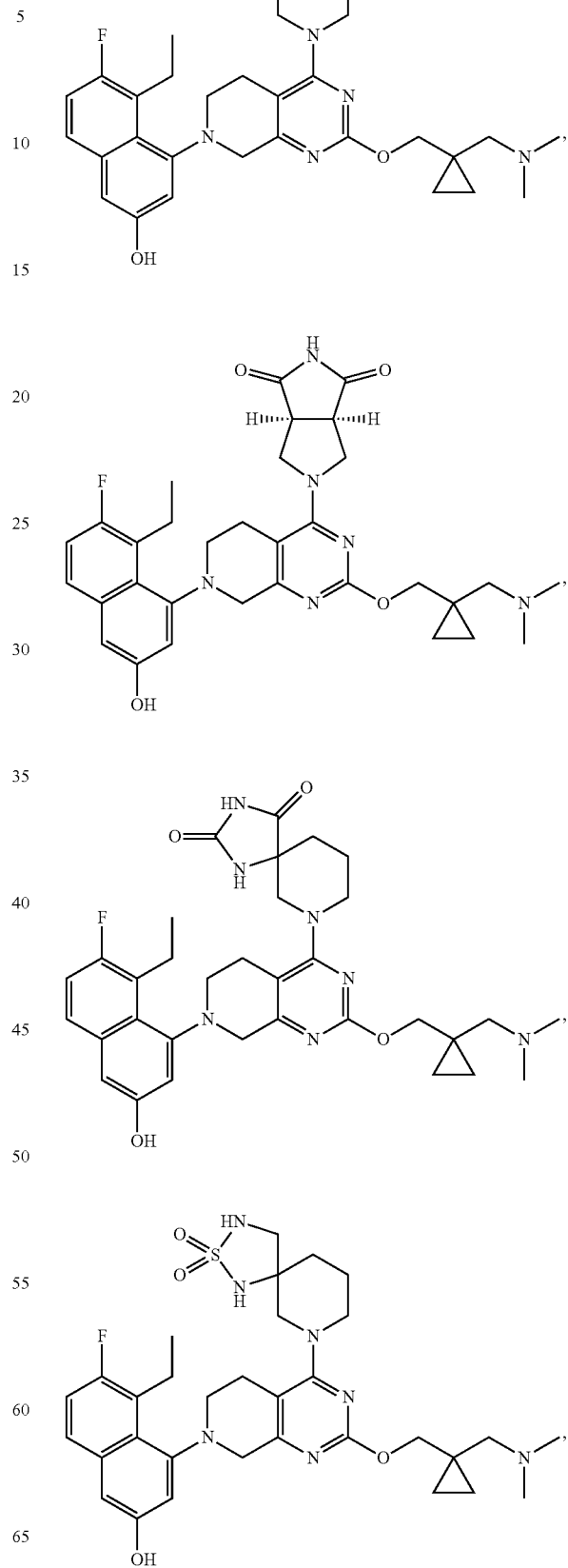

71
-continued
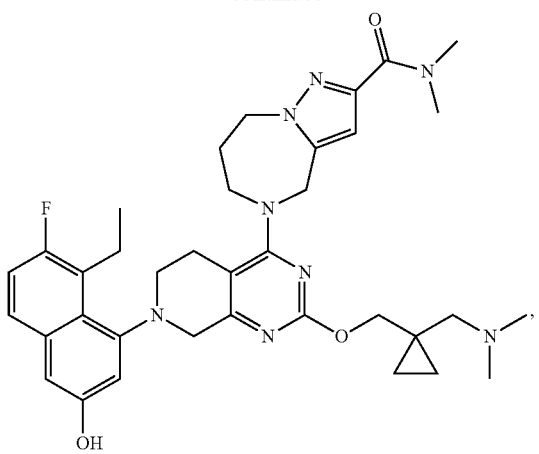
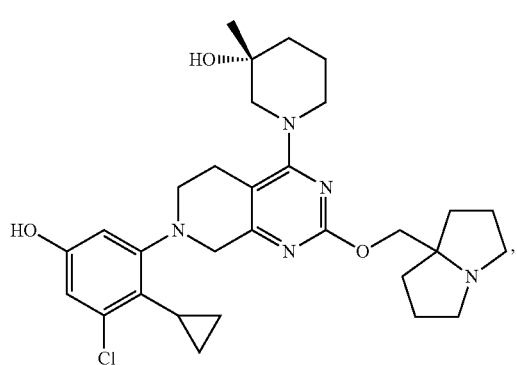
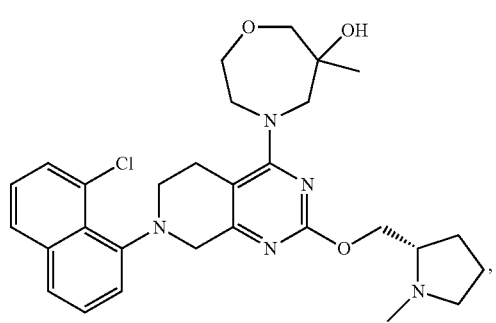
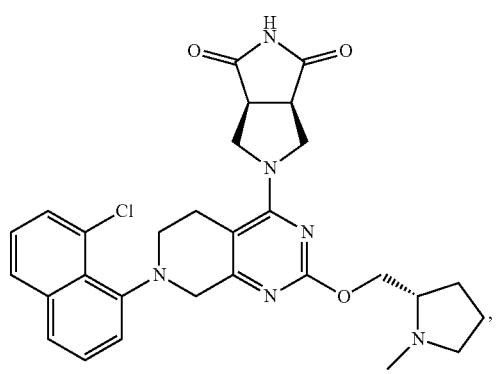
72
-continued
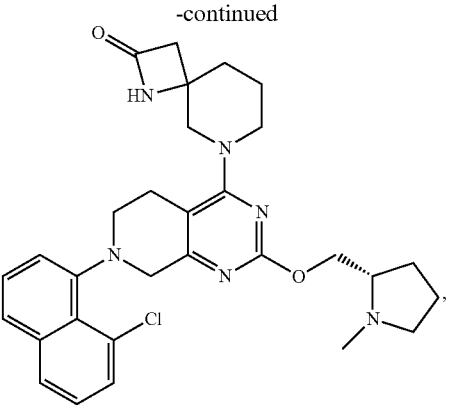
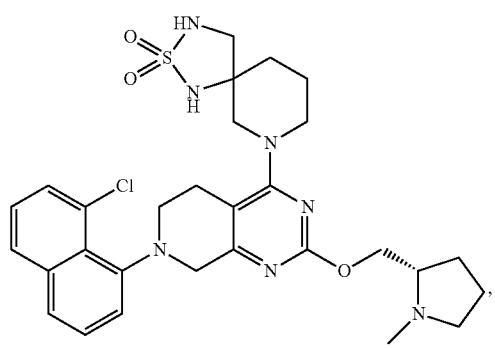
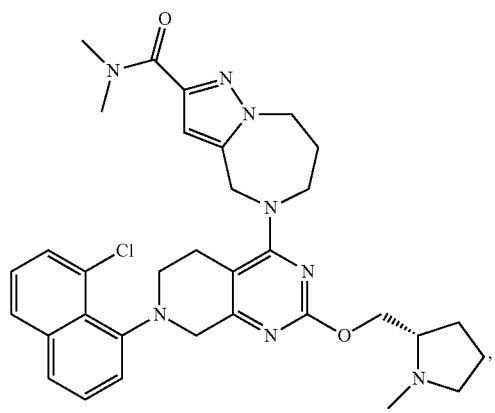
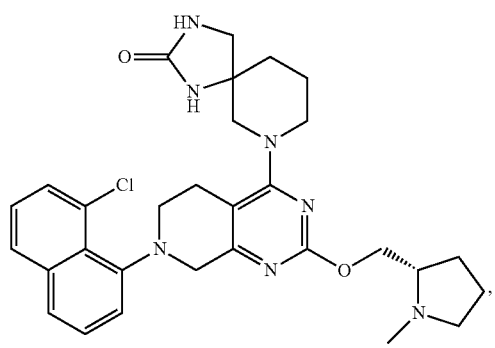

73
-continued
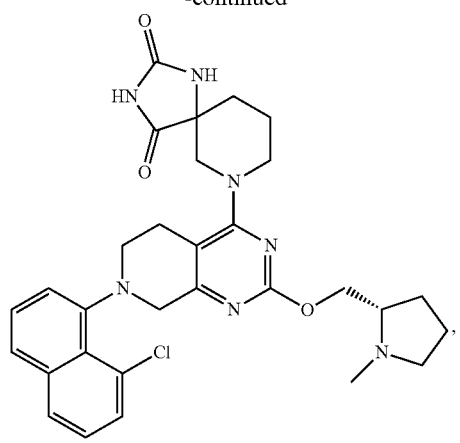
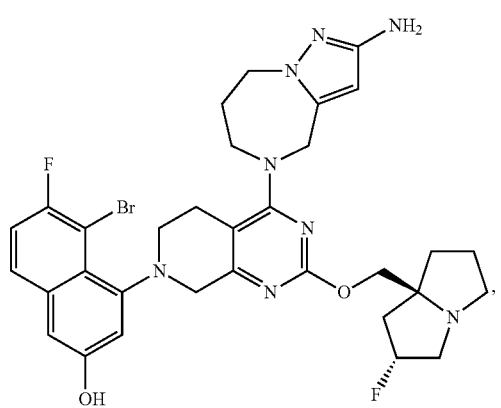
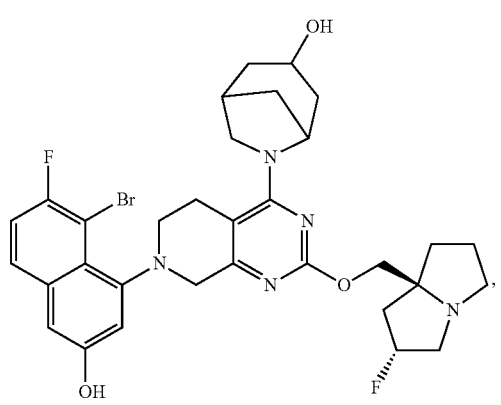
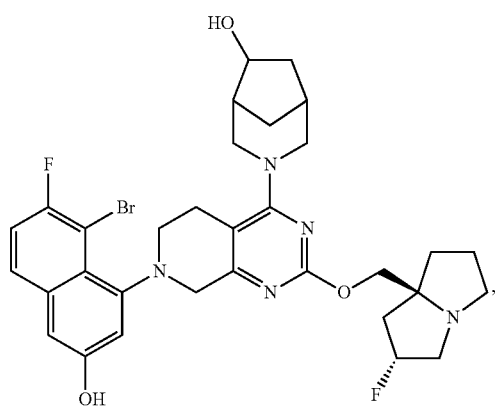
74
-continued
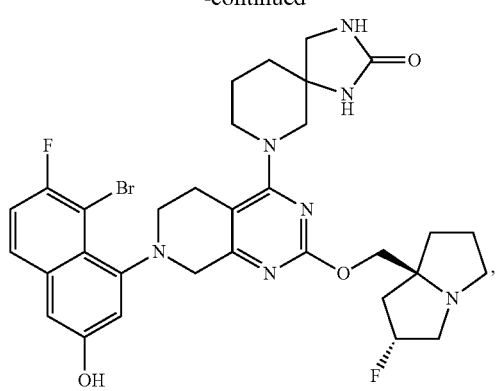
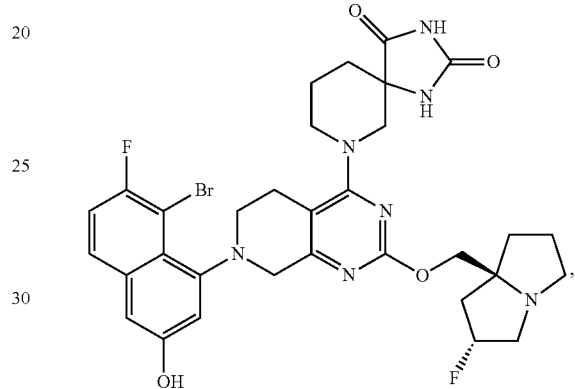
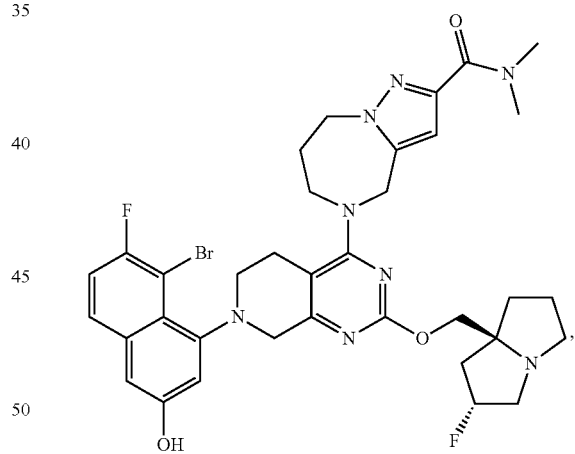
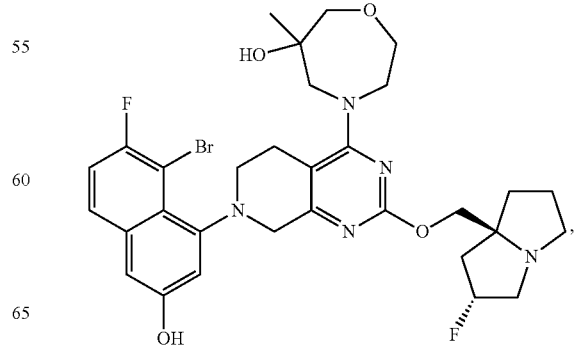

75
-continued
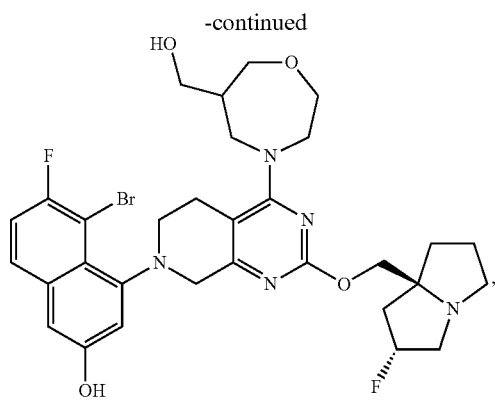
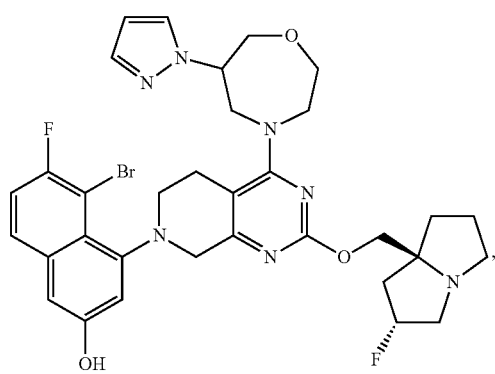
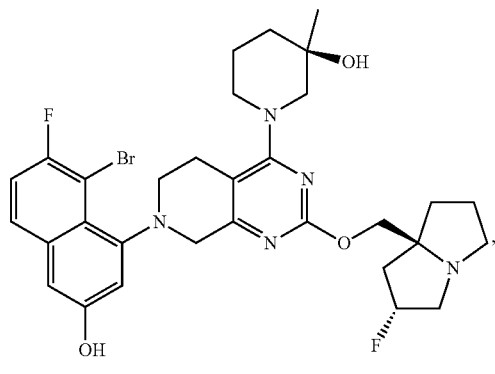
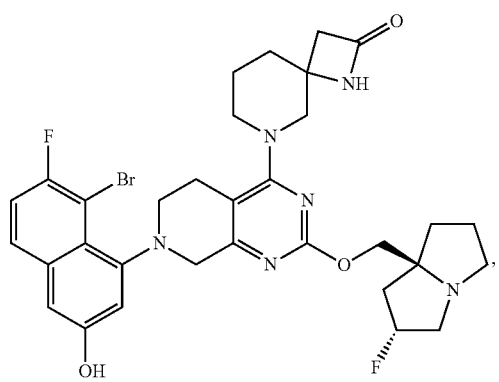
76
-continued
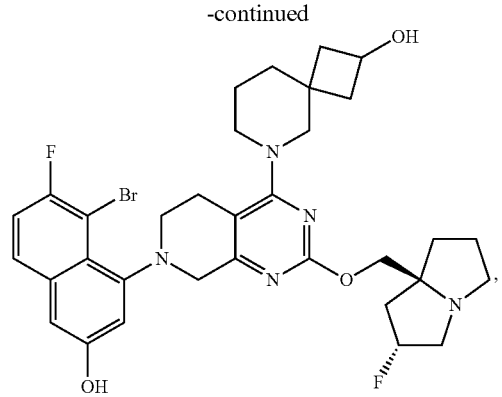
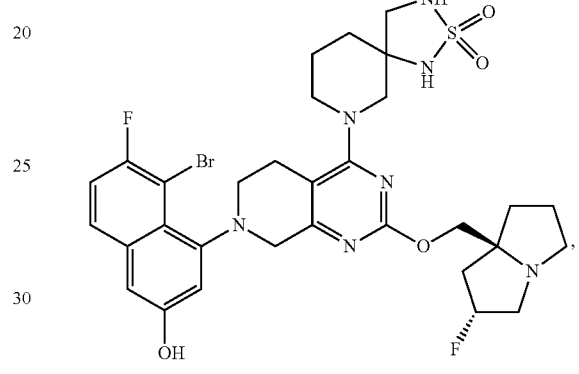
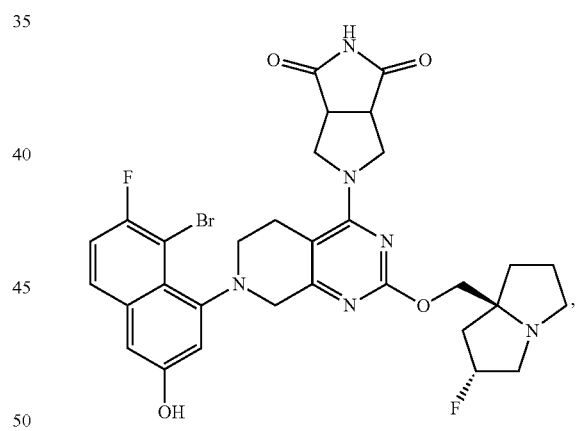
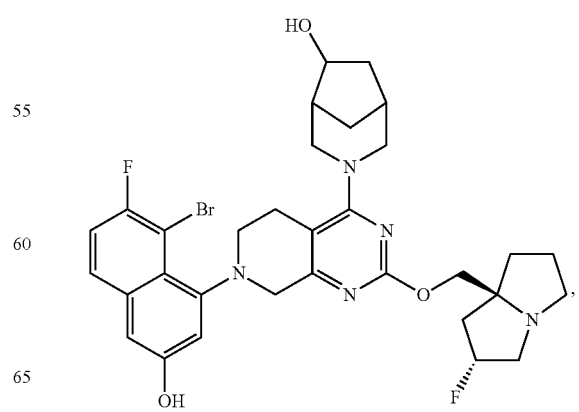

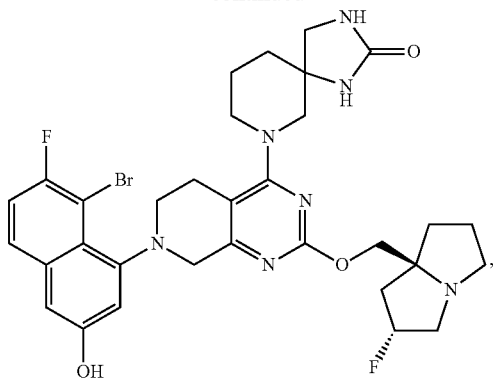

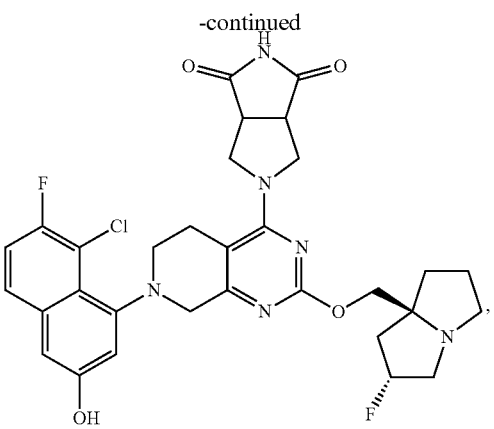

and pharmaceutically acceptable salts thereof.

In one embodiment, the compounds of Formula (I) include bis-hydrochloride, tris-hydrochloride, trifluoroacetic acid, bis-trifluoroacetic acid, and tris-trifluoracetic acid salts of the above compounds. The compounds of Formula (I) or pharmaceutically acceptable salt thereof may be formulated into pharmaceutical compositions.

Pharmaceutical Compositions

In another aspect, the invention provides pharmaceutical compositions comprising a KRas wild type, KRas G12A, KRas G12C, KRas G12D, KRas G12R, KRas G12S, KRas G12V, KRas G13D and/or KRas Q61H inhibitor according to the invention and a pharmaceutically acceptable carrier, excipient, or diluent. Compounds of the invention may be formulated by any method well known in the art and may be prepared for administration by any route, including, without limitation, parenteral, intraperitoneal, intradermal, intracardiac, intraventricular, intracranial, intracerebrospinal, intrasynovial, intrathecal administration, intramuscular injection, intravitreous injection, intravenous injection, intra-arterial injection, oral, buccal, sublingual, transdermal, topical, intranasal, intratracheal, intrarectal, subcutaneous, and topical administration. In certain embodiments, compounds of the invention are administered intravenously in a hospital setting. In one embodiment, administration may be by the oral route. In some embodiments, the provided pharmaceutical compositions may be administered to a subject in need of treatment by injection systemically, such as by intravenous injection; or by injection or application to the relevant site, such as by direct injection via syringe, or direct application to the site when the site is exposed in surgery; or by topical administration.

Parenteral administration can be by bolus injection or continuous infusion. Pharmaceutical compositions for injection may be presented in unit dosage form, e.g., in ampoules or in multi-dose containers, with an added preservative.

The provided pharmaceutical compositions can also be formulated as a depot preparation. Such long-acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or a medical device, including but not limited to a dispenser device which may contain one or more unit dosage forms containing the active ingredient. In one embodiment the dispenser device can comprise a syringe having a single dose of the liquid formulation ready for injection. The syringe can be accompanied by instructions for administration.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting wild type KRas, KRas G12A, KRas G12C, KRas G12D, KRas G12R, KRas G12S, KRas G12V and/or KRas Q61H activity in a cell, comprising contacting the cell in which inhibition of wild type KRas or KRas G12A, KRas G12C, KRas G12D, KRas G12R, KRas G12S, KRas G12V and/or Q61H activity is desired with an effective amount of a compound of Formula (I), pharmaceutically acceptable salts thereof, or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" wild type KRas, KRas G12A, KRas G12C, KRas G12D, KRas G12R, KRas G12S, KRas G12V, KRas G13D and/or KRas Q61H with a compound provided herein includes the administration of a compound provided herein to an individual or patient, such as a human, having wild type KRas or a KRas G12A, KRas G12C, KRas G12D, KRas G12R, KRas G12S, KRas G12V, KRas G13D and/or KRas Q61H mutation, as well as, for example, introducing a compound provided herein into a sample containing a cellular or purified preparation containing wild type KRas or a KRas G12A, KRas G12C, KRas G12D, KRas G12R, KRas G12S, KRas G12V, KRas G13D or KRas Q61H mutation.

In one embodiment, a cell in which inhibition of wild type KRas, KRas G12A, KRas G12C, KRas G12D, KRas G12R, KRas G12S, KRas G12V, KRas G13D and/or KRas Q61H activity is desired is contacted with an effective amount of a compound of Formula (I) or pharmaceutically acceptable salt thereof to negatively modulate the activity of one or more of wild type KRas, KRas G12A, KRas G12C, KRas G12D, KRas G12R, KRas G12S, KRas G12V, KRas G13D and KRas Q61H.

By negatively modulating the activity of one or more of wild type KRas, KRas G12A, KRas G12C, KRas G12D, KRas G12R, KRas G12S, KRas G12V, KRas G13D and KRas Q61H, the methods described herein are designed to inhibit undesired cellular proliferation resulting from enhanced wild type KRas, KRas G12A, KRas G12C, KRas G12D, KRas G12R, KRas G12S, KRas G12V, KRas G13D and/or KRas Q61H activity within the cell. The cells may be contacted in a single dose or multiple doses in accordance with a particular treatment regimen to affect the desired negative modulation of wild type KRas, KRas G12A, KRas G12C, KRas G12D, KRas G12R, KRas G12S, KRas G12V, KRas G13D and/or KRas Q61H. The ability of compounds to bind one or more of wild type KRas, KRas G12A, KRas G12C, KRas G12D, KRas G12R, KRas G12S, KRas G12V, KRas G13D and KRas Q61H may be monitored in vitro using well known methods, including those described in Examples A and B below. In addition, the inhibitory activity of exemplary compounds in cells may be monitored, for example, by measuring the inhibition of one or more of wild type KRas, KRas G12A, KRas G12C, KRas G12D, KRas G12R, KRas G12S, KRas G12V, KRas G13D and/or KRas Q61H activity of the amount of phosphorylated ERK, for example using the method described in Example C below.

In another aspect, methods of treating cancer in a patient in need thereof, comprising administering to said patient a therapeutically effective amount of a compound of Formula (I) or a pharmaceutically acceptable salt thereof, or a pharmaceutical composition comprising the compound or pharmaceutically acceptable salt thereof are provided.

The compositions and methods provided herein may be used for the treatment of a wild type KRas-associated or KRas G12A, KRas G12C, KRas G12D, KRas G12R, KRas G12S, KRas G12V, KRas G13D and/or KRas Q61H-associated cancer in a patient in need thereof, comprising administering to said patient a therapeutically effective amount of a compound of Formula (I), a pharmaceutically acceptable salt thereof, or a pharmaceutical composition comprising the compound or pharmaceutically acceptable salt thereof are provided. In one embodiment, the wild type KRas-associated or KRas G12A, KRas G12C, KRas G12D, KRas G12R, KRas G12S, KRas G12V, KRas G13D and/or KRas Q61H-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer, small cell lung cancer, colorectal cancer, rectal cancer or pancreatic cancer. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

Also provided herein is a compound of Formula (I) or a pharmaceutically acceptable salt thereof, or a pharmaceutical composition thereof as defined herein for use in therapy.

Also provided herein is a compound of Formula (I) or a pharmaceutically acceptable salt thereof, or a pharmaceutical composition thereof as defined herein for use in the treatment of cancer.

Also provided herein is a compound of Formula (I) or a pharmaceutically acceptable salt thereof, or a pharmaceutical composition thereof for use in the inhibition of wild type KRas or KRas G12A, KRas G12C, KRas G12D, KRas G12R, KRas G12S, KRas G12V, KRas G13D and/or KRas Q61H.

Also provided herein is a compound of Formula (I) or a pharmaceutically acceptable salt thereof, or a pharmaceutical composition thereof as defined herein, for use in the treatment of a wild type KRas-associated or a KRas G12A, KRas G12C, KRas G12D, KRas G12R, KRas G12S, KRas G12V, KRas G13D and/or KRas Q61H-associated disease or disorder.

Also provided herein is the use of a compound of Formula (I) or a pharmaceutically acceptable salt thereof, as defined herein in the manufacture of a medicament for the treatment of cancer.

Also provided herein is a use of a compound of Formula (I) or a pharmaceutically acceptable salt thereof, as defined herein in the manufacture of a medicament for the inhibition of activity of wild type KRas, KRas G12A, KRas G12C, KRas G12D, KRas G12R, KRas G12S, KRas G12V, KRas G13D and/or KRas Q61H.

Also provided herein is the use of a compound of Formula (I) or a pharmaceutically acceptable salt thereof, as defined herein, in the manufacture of a medicament for the treatment of a wild type KRas-associated or KRas G12A, KRas G12C, KRas G12D, KRas G12R, KRas G12S, KRas G12V, KRas G13D and/or KRas Q61H-associated disease or disorder.

Also provided herein is a method for treating cancer in a patient in need thereof, the method comprising (a) determining that cancer is associated with wild type KRas or a KRas G12A, KRas G12C, KRas G12D, KRas G12R, KRas G12S, KRas G12V, KRas G13D and/or KRas Q61H mutation (e.g., as determined using a regulatory agency-approved, e.g., FDA-approved, assay or kit); and (b) administering to the patient a therapeutically effective amount of a compound of Formula (I), or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

REACTION SCHEMES AND EXAMPLES

The compounds of the present invention may be prepared from commercially available reagents using the synthetic methods and reaction schemes described herein, or using other reagents and conventional methods well known to those skilled in the art. For instance, compounds of the present invention may be prepared according to the reaction schemes and examples outlines below.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The compounds of the present invention may be in anhydrous, solvated or hydrated forms, and all such forms are included within the scope of the invention.

The following Intermediates are intended to illustrate further certain embodiments of the invention and are not intended to limit the scope of the invention.

Intermediate 1

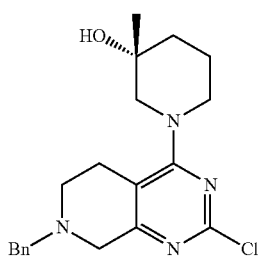 [SMILES: C[C@@]1(O)CCCN(c2nc(Cl)nc3c2CCN(Cc2ccccc2)C3)C1]

(R)-1-(7-benzyl-2-chloro-5,6,7,8-tetrahydropyrido[3,4-d]pyrimidin-4-yl)-3-methylpiperidin-3-ol

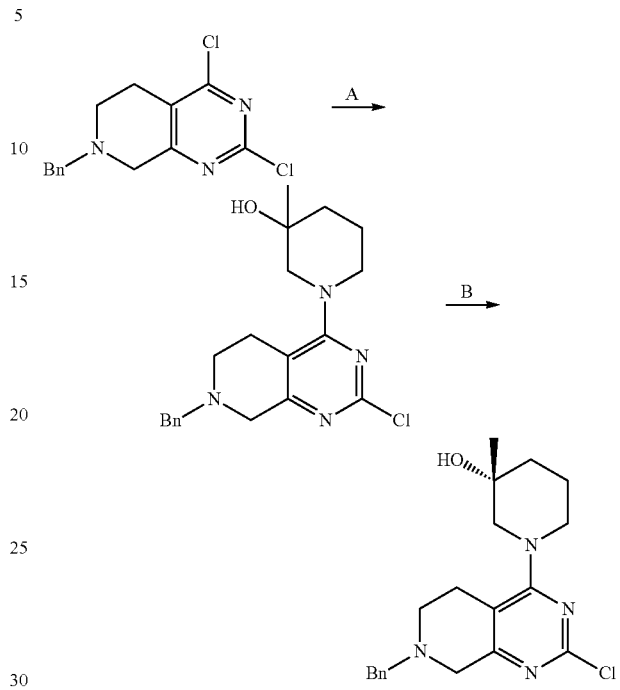

Step A and B. (R)-1-(7-benzyl-2-chloro-5,6,7,8-tetrahydropyrido[3,4-d]pyrimidin-4-yl)-3-methylpiperidin-3-ol: To a solution of 7-benzyl-2,4-dichloro-5,6,7,8-tetrahydropyrido[3,4-d]pyrimidine (5.30 g, 18.0 mmol) in DMA (40.0 mL) were added 3-methylpiperidin-3-ol (3.55 g, 23.42 mmol, HCl) and N-ethyl-N-isopropylpropan-2-amine (6.99 g, 54.0 mmol, 9.41 mL). The mixture was stirred at 20° C. for 1 hour. After completion, the reaction mixture was diluted with $H_2O$ (100 mL) and extracted with ethyl acetate (2×100 mL). The combined organic layers were washed with brine (300 mL) and dried over $Na_2SO_4$. The mixture was filtered and concentrated under reduced pressure to give a residue. The residue was purified by HPLC [C18, 0.1% FA in water, 0-60% MeCN] to give 1-(7-benzyl-2-chloro-5,6,7,8-tetrahydropyrido[3,4-d]pyrimidin-4-yl)-3-methylpiperidin-3-ol (6.0 g) as yellow oil, which was further separated by SFC (column: DAICEL CHIRALPAK AD-H (250 mm×30 mm, 5um); mobile phase: [0.1% $NH_3·H_2O$ EtOH]; B %: 30%-30%, 4.1 min; 600 min) to give (R)-1-(7-benzyl-2-chloro-5,6,7,8-tetrahydropyrido[3,4-d]pyrimidin-4-yl)-3-methylpiperidin-3-ol (2.75 g, 40% yield). Yellow solid. $^1$H NMR (400 MHz, chloroform-d) δ=7.38-7.27 (m, 5H), 3.93-3.80 (m, 2H), 3.68 (s, 3H), 3.53-3.45 (m, 1H), 3.37-3.13 (m, 1H), 3.06-2.91 (m, 2H), 2.85-2.70 (m, 2H), 2.67-2.58 (m, 1H), 2.56-2.47 (m, 1H), 1.92-1.75 (m, 2H), 1.67-1.48 (m, 2H), 1.26 (s, 3H); SFC: 99.7%, $t_R$=1.786 min, Column: Chiralpak AD-3 50×4.6 mm I.D., 3 um Mobile phase: Phase A for $CO_2$, and Phase B for EtOH (0.05% DEA); Gradient elution: EtOH (0.05% DEA) in $CO_2$ from 5% to 40% Flow rate: 3 mL/min; Detector: 220 nm; Column Temp: 35° C.; Back Pressure: 100 Bar; LCMS (ESI, M+1): m/z 373.0.

Intermediate 2

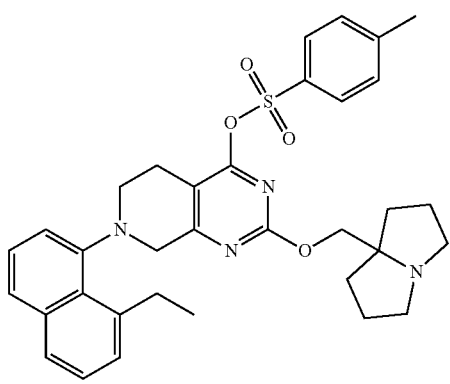 [SMILES: CCc1cccc2cccc(N3CCc4c(nc(OCC56CCCN5CCC6)nc4OS(=O)(=O)c4ccc(C)cc4)C3)c12]

7-(8-ethylnaphthalen-1-yl)-2-((tetrahydro-1H-pyr-rolizin-7a(5H)-yl)methoxy)-5,6,7,8-tetrahydropyrido[3,4-d]pyrimidin-4-yl 4-methylbenzenesulfonate

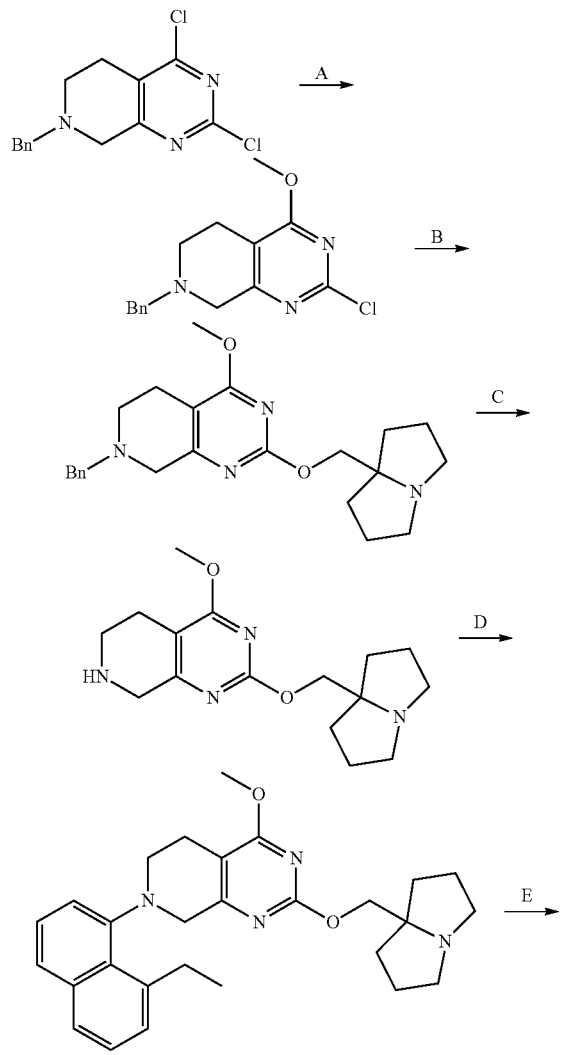

Step A. 7-benzyl-2-chloro-4-methoxy-5,6,7,8-tetrahydropyrido[3,4-d]pyrimidine: To a solution of 7-benzyl-2,4-dichloro-5,6,7,8-tetrahydropyrido[3,4-d]pyrimidine (6.0 g, 20.4 mmol) in MeOH (50 mL) was added NaOMe (2.20 g, 40.8 mmol) at 0° C. The mixture was stirred at 0° C. for 2 hours. The pH of the mixture was adjusted to 7 with aqueous HCl (2 N). Water (100 mL) was added, and the mixture was extracted with DCM (50 mL×3). The combined organic layers were washed with brine (20 mL) and dried over sodium sulfate. The mixture was filtered and concentrated to give a residue. The residue was purified by column chromatography (SiO$_2$, Petroleum ether/Ethyl acetate=1/0 to 10/1) to afford 7-benzyl-2-chloro-4-methoxy-5,6,7,8-tetrahydropyrido[3,4-d]pyrimidine (5.3 g, 90% yield) as yellow oil; $^1$H NMR (400 MHz, CDCl$_3$) δ=7.67 (br d, J=3.7 Hz, 2H), 7.55-7.41 (m, 3H), 5.30 (s, 1H), 4.46 (br s, 1H), 4.24 (br d, J=16.0 Hz, 2H), 4.04 (s, 3H), 3.96-3.67 (m, 2H), 3.49 (br s, 1H), 3.05 (br s, 1H), 2.86 (br d, J=18.6 Hz, 1H). LCMS [ESI, M+1]: m/z 290.1.

Step B. 7-benzyl-2-((hexahydro-1H-pyrrolizin-7a-yl)methoxy)-4-methoxy-5,6,7,8-tetrahydropyrido[3,4-d]pyrimidine: A mixture of 7-benzyl-2-chloro-4-methoxy-5,6,7,8-tetrahydropyrido[3,4-d]pyrimidine (1.30 g, 4.49 mmol), 1,2,3,5,6,7-hexahydropyrrolizin-8-ylmethanol (697 mg, 4.94 mmol), RuPhos (419 mg, 897 μmol), Cs$_2$CO$_3$ (4.39 g, 13.5 mmol) and Pd(OAc)$_2$ (101 mg, 449 μmol) in Toluene (30 mL) was degassed and purged with N$_2$ for 3 times. The mixture was stirred at 110° C. for 8 hours under N$_2$ atmosphere. The reaction mixture was quenched with water 100 mL and extracted with EtOAc (30 mL×3). The combined organic layers were washed with brine (20 mL×2) and dried over Na$_2$SO$_4$. The mixture was filtered and concentrated under reduced pressure to give a residue. The residue was purified by column chromatography (SiO$_2$, DCM/MeOH=1/0 to 5/1) to afford 7-benzyl-2-((hexahydro-1H-pyrrolizin-7a-yl)methoxy)-4-methoxy-5,6,7,8-tetrahydropyrido[3,4-d]pyrimidine (1.2 g, 34% yield). Yellow oil; LCMS [ESI, M+H]: m/z 395.2.

Step C. 2-((hexahydro-1H-pyrrolizin-7a-yl)methoxy)-4-methoxy-5,6,7,8-tetrahydropyrido[3,4-d]pyrimidine: To a solution of 7-benzyl-2-((hexahydro-1H-pyrrolizin-7a-yl)methoxy)-4-methoxy-5,6,7,8-tetrahydropyrido[3,4-d]pyrimidine (3.3 g, 8.36 mmol) in 2-methylpropan-2-ol (200 mL) was added Pd/C (8.0 g, 10% purity) under H2. The suspension was degassed under vacuum and purged with H2 several times. The mixture was stirred under H2 (50 psi) at 40° C. for 30 hours. The reaction mixture was filtered and concentrated under reduced pressure to afford 2-((hexahydro-1H-pyrrolizin-7a-yl)methoxy)-4-methoxy-5,6,7,8-tetrahydropyrido[3,4-d]pyrimidine (2.1 g, crude). Yellow oil; LCMS [ESI, M+H]: m/z 305.2.

Step D. 7-(8-ethylnaphthalen-1-yl)-2-((hexahydro-1H-pyrrolizin-7a-yl)methoxy)-4-methoxy-5,6,7,8-tetrahydropyrido[3,4-d]pyrimidine: A mixture of 1-bromo-8-ethylnaphthalene (1.6 g, 6.81 mmol), 2-((hexahydro-1H-pyrrolizin-7a-yl)methoxy)-4-methoxy-5,6,7,8-tetrahydropyrido[3,4-d]pyrimidine (1.6 g, 5.26 mmol), BINAP (1.31 g, 2.10 mmol), $Cs_2CO_3$ (4.28 g, 13.1 mmol) and $Pd_2(dba)_3$ (962 mg, 1.05 mmol) in toluene (30 mL) was degassed and purged with $N_2$ for 3 times. The mixture was stirred at 90° C. for 8 hours under $N_2$ atmosphere. The reaction mixture was quenched with water (30 mL) and extracted with EtOAc (10 mL×3). The combined organic layers were washed with brine (5 mL×2) and dried over $Na_2SO_4$. The mixture was filtered and concentrated under reduced pressure to give a residue. The residue was purified by prep-TLC ($SiO_2$, EtOAc:MeOH=5:1) to afford 7-(8-ethylnaphthalen-1-yl)-2-((hexahydro-1H-pyrrolizin-7a-yl)methoxy)-4-methoxy-5,6,7,8-tetrahydropyrido[3,4-d]pyrimidine (0.8 g, 1.74 mmol, 33% yield). Brown solid. LCMS [ESI, M+H]: m/z 459.3.

Step E. 7-(8-ethylnaphthalen-1-yl)-2-((hexahydro-1H-pyrrolizin-7a-yl)methoxy)-5,6,7,8-tetrahydropyrido[3,4-d]pyrimidin-4-ol: To a solution of NaH (523 mg, 13.1 mmol, 60% purity) in DMF (10 mL) was added EtSH (1.22 g, 19.6 mmol, 1.45 mL) at 0° C. The mixture was stirred for 30 minutes, and 7-(8-ethylnaphthalen-1-yl)-2-((hexahydro-1H-pyrrolizin-7a-yl)methoxy)-4-methoxy-5,6,7,8-tetrahydropyrido[3,4-d]pyrimidine (600 mg, 1.31 mmol) was added. The mixture was stirred at 60° C. for 1 hour. The reaction mixture was quenched with water (10 mL). The mixture was extracted with EtOAc (5 mL×2). The combined organic layers were washed with brine (3 mL) and dried over $Na_2SO_4$. The mixture was filtered and concentrated under reduced pressure to afford 7-(8-ethylnaphthalen-1-yl)-2-((hexahydro-1H-pyrrolizin-7a-yl)methoxy)-5,6,7,8-tetrahydropyrido[3,4-d]pyrimidin-4-ol (600 mg, crude) as brown solid. LCMS [ESI, M+H]: m/z 445.2.

Step F. 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate: To a solution of 7-(8-ethylnaphthalen-1-yl)-2-((hexahydro-1H-pyrrolizin-7a-yl)methoxy)-5,6,7,8-tetrahydropyrido[3,4-d]pyrimidin-4-ol (600 mg, 1.35 mmol) and TEA (341 mg, 3.37 mmol) in DCM (10 mL) was added TsCl (257 mg, 1.35 mmol). The mixture was stirred at 20° C. for 1 hour. The reaction mixture was quenched with water (30 mL), and then extracted with DCM (10 mL×2). The combined organic layers were washed with saturated $NaHCO_3$ (10 mL×2) and brine (10 mL). The mixture was dried over $Na_2SO_4$ and filtrate. The solvent was removed under reduced pressure to give a residue. The residue was purified by prep-TLC ($SiO_2$, DCM:MeOH=5:1) to afford 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (530 mg, 52% yield) as yellow solid. LCMS [ESI, M+H]: m/z 559.2.

Intermediate 3

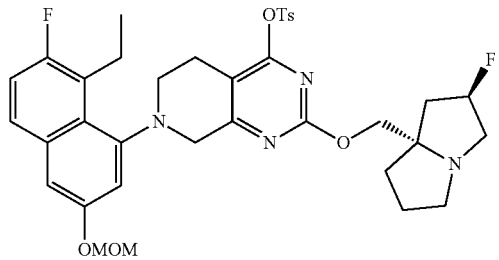

7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl 4-methylbenzenesulfonate

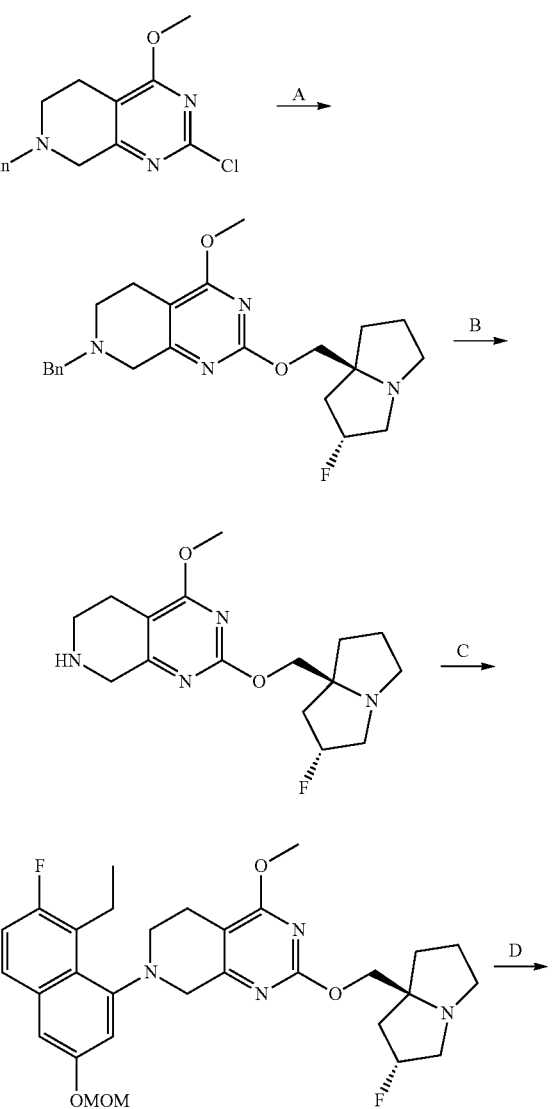

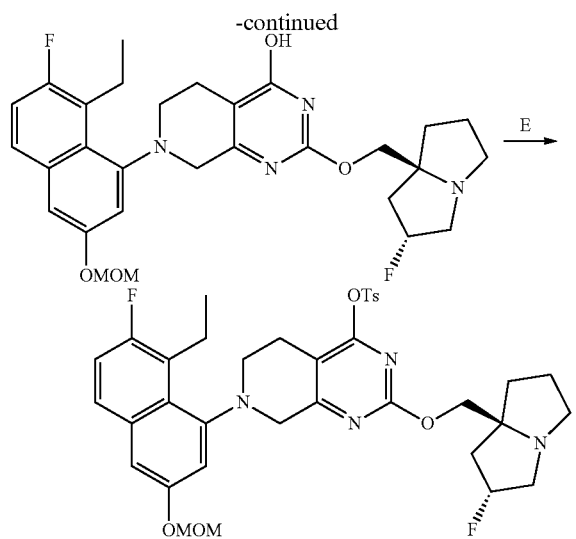

Step A. tert-butyl 2-(((2R,7aS)-2-fluorohexahydro-1H-pyrrolizin-7a-yl)methoxy)-4-methoxy-5,6-dihydropyrido[3,4-d]pyrimidine-7(8H)-carboxylate: To a solution of tert-butyl 2-chloro-4-methoxy-5,6-dihydropyrido[3,4-d]pyrimidine-7(8H)-carboxylate (50 g, 1.0 equiv) and ((2R,7aS)-2-fluorohexahydro-1H-pyrrolizin-7a-yl)methanol (31.9 g, 1.2 equiv) in toluene (500 mL) were added $Cs_2CO_3$ (163 g, 3.0 equiv) and BINAP (20.7 g, 0.2 equiv) at 25° C. The suspension was degassed under vacuum and purged with $N_2$ two times. $Pd(OAc)_2$ (3.74 g, 0.1 equiv) was added. The suspension was degassed under vacuum and purged with $N_2$ three times. Then the reaction was heated to 110° C. and stirred for 12 hours. The mixture was diluted with water (1000 mL) and extracted with ethyl acetate (500 mL×3). The combined organic layers were dried over $Na_2SO_4$ and concentrated under vacuum. The residue was purified by column chromatography ($SiO_2$, DCM/MeOH=10/1) and then by reversed phase flash chromatography [water (FA, 0.1%)/acetonitrile] to afford the title compound (51 g, 72% yield) as yellow oil. LCMS (ESI, M+1): m/z=423.2.

Step B. 2-(((2R,7aS)-2-fluorohexahydro-1H-pyrrolizin-7a-yl)methoxy)-4-methoxy-5,6,7,8-tetrahydropyrido[3,4-d]pyrimidine: To a solution of tert-butyl 2-(((2R,7aS)-2-fluorohexahydro-1H-pyrrolizin-7a-yl)methoxy)-4-methoxy-5,6-dihydropyrido[3,4-d]pyrimidine-7(8H)-carboxylate (50 g, 1.0 equiv) in DCM (200 mL) was added TFA (308 g, 200 mL, 22.8 equiv) dropwise with stirring at 0° C. Then, the reaction was stirred at 25° C. for 2 hours. The mixture was concentrated under vacuum to removed DCM and some TFA. The residue was diluted with ice water (150 mL), and then the pH of the residue was adjusted to 7 with $NaHCO_3$ (30 g). The mixture was concentrated under oil pump to removed water. Then the residue was diluted with saturation $Na_2CO_3$ (500 mL) and extracted with ethyl acetate (200 mL×6). The combined organic layer was dried over $Na_2SO_4$ and concentrated under vacuum to afford the title compound (34.3 g, crude) as white solid. LCMS (ESI, M+1): m/z=323.0.

Step C. 7-(8-ethyl-7-fluoro-3-(methoxymethoxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine: To a solution of 2-(((2R,7aS)-2-fluorohexahydro-1H-pyrrolizin-7a-yl)methoxy)-4-methoxy-5,6,7,8-tetrahydropyrido[3,4-d]pyrimidine (50 g, 1.0 equiv) and 8-ethyl-7-fluoro-3-(methoxymethoxy)naphthalen-1-yl trifluoromethanesulfonate (77.1 g, 1.3 equiv) in toluene (500 mL) were added $Cs_2CO_3$ (152 g, 3.0 equiv) and Xantphos (18.0 g, 0.2 equiv) at 25° C. The suspension was degassed under vacuum and purged with $N_2$ two times. $Pd_2(dba)_3$ (14.2 g, 0.1 equiv) was added. The suspension was degassed under vacuum and purged with $N_2$ three times. The reaction was stirred at 110° C. for 6 hours. Then the mixture was filtered by Celite, and the residue was washed by ethyl acetate (50 mL×3). The combined organic layer was concentrated under vacuum. The residue was purified by column chromatography ($SiO_2$, Petroleum ether/Ethyl acetate=3/1 to DCM/MeOH=5/1) and reversed phase flash chromatography [C18, water (FA, 0.1%)/acetonitrile] to afford the title compound (67 g, two steps 77% yield) as brown oil; LCMS (ESI, M+1): m/z=555.2. $^1H$ NMR (400 MHz, METHANOL-d4) δ=7.59 (dd, J=5.6, 9.2 Hz, 1H), 7.24 (d, J=2.4 Hz, 1H), 7.21-7.11 (m, 2H), 5.33-5.16 (m, 3H), 4.16-4.06 (m, 2H), 4.03 (s, 3H), 3.97 (d, J=17.2 Hz, 1H), 3.72 (d, J=17.2 Hz, 1H), 3.48 (s, 3H), 3.47-3.41 (m, 1H), 3.36-3.30 (m, 2H), 3.25-3.11 (m, 4H), 2.99-2.81 (m, 2H), 2.71-2.64 (m, 1H), 2.31-2.03 (m, 3H), 1.99-1.77 (m, 3H), 1.01 (t, J=7.2 Hz, 3H).

Step D. 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol: To a solution of EtSH (13.4 g, 16.0 mL, 3.0 equiv) in DMAc (400 mL) was added NaH (8.65 g, 60% purity, 3.0 equiv) at 0° C. The mixture was stirred at 0° C. for 0.5 hour. Then 7-(8-ethyl-7-fluoro-3-(methoxymethoxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine (40 g, 1.0 equiv) was added to the mixture. The mixture was stirred at 20° C. for another 1 hour. After completion, water (400 mL) was added, and its pH was adjusted to 6 by 2N HCl. The mixture was extracted with ethyl acetate (400 mL×3). The combined organic layer was washed with brine (400 mL×2), dried over $Na_2SO_4$, filtered, and concentrated under vacuum to afford the title compound (45 g, crude) as yellow solid. LCMS (ESI, M+1):m/z=541.2.

Step E. 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl 4-methylbenzenesulfonate: To a mixture of 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol, N-ethyl-N-isopropylpropan-2-amine (15.1 g, 3 equiv) and DMAP (475 mg, 0.1 equiv) in DCM (200 mL) was added 4-methylbenzene-1-sulfonyl chloride (11.1 g, 1.5 equiv) at 0° C. The mixture was stirred at 25° C. for 0.5 hour. The reaction mixture was concentrated under reduced pressure and purified by column chromatography ($Al_2O_3$, Petroleum ether/Ethyl acetate=10/1 to 0/1) to afford the title compound (22 g, 82% yield two steps) as yellow solid. LCMS (ESI, M+1): m/z=695.8.

Intermediate 4

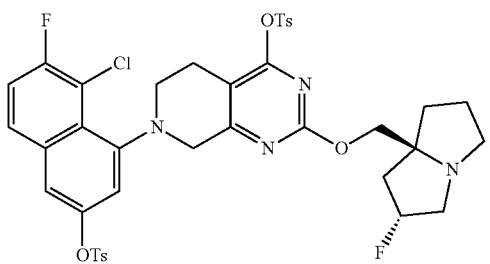 [SMILES: Cc1ccc(S(=O)(=O)Oc2cc(N3CCc4c(nc(OC[C@@]56CCCN5C[C@H](F)C6)nc4OS(=O)(=O)c4ccc(C)cc4)C3)c3c(Cl)c(F)ccc3c2)cc1]

5-chloro-6-fluoro-4-(2-(((2R,7aS)-2-fluorotetra-hydro-1H-pyrrolizin-7a(5H)-yl)methoxy)-4-(tosy-loxy)-5,8-dihydropyrido[3,4-d]pyrimidin-7(6H)-yl)naphthalen-2-yl 4-methylbenzenesulfonate

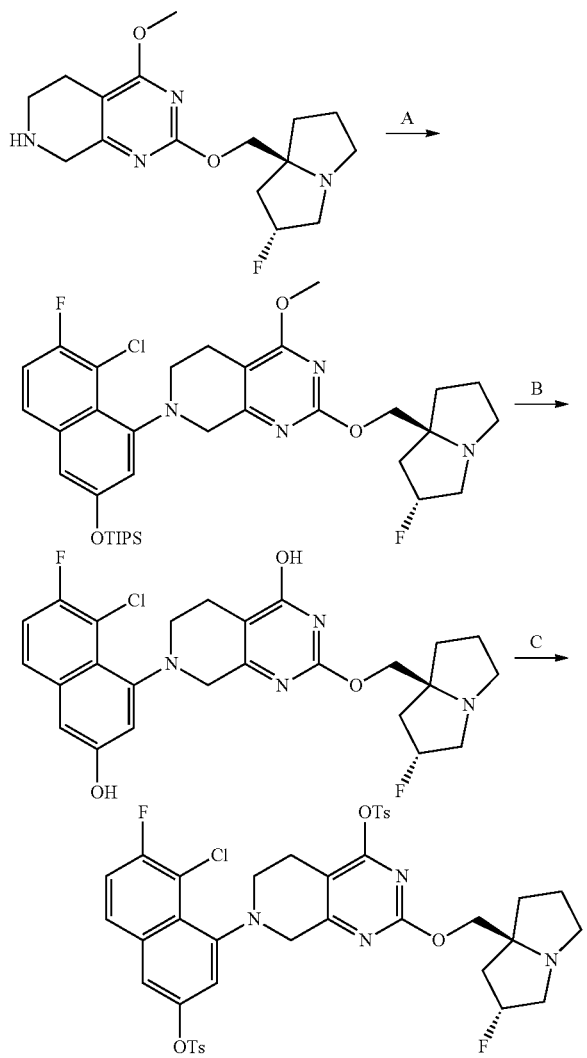

Step A. 7-(8-chloro-7-fluoro-3-((triisopropylsilyl)oxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine: A mixture of 2-(((2R,7aS)-2-fluorohexahydro-1H-pyrrolizin-7a-yl)methoxy)-4-methoxy-5,6,7,8-tetrahydropyrido[3,4-d]pyrimidine (4 g, 1.0 equiv), 8-chloro-7-fluoro-3-((triisopropylsilyl)oxy)naphthalen-1-yl trifluoromethanesulfonate (7.46 g, 1.2 equiv), $Cs_2CO_3$ (12.1 g, 3.0 equiv), RuPhos (1.16 g, 0.2 equiv), and $Pd_2(dba)_3$ (1.14 g, 0.1 equiv) in toluene (80 mL) was degassed and purged with $N_2$ several times. The mixture was stirred at 100° C. for 3 hrs under $N_2$ atmosphere. The mixture was diluted with water (100 mL) and extracted with ethyl acetate (100 mL). The organic layer was dried over sodium sulfate, filtered, and concentrated under vacuum to give a residue and the residue was purified by HPLC [0.1% FA condition] to afford the title compound (3.9 g, 46% yield) as yellow solid. LCMS (ESI, M+1): m/z=673.2.

Step B. 7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol: To a mixture of EtSH (1.99 g, 2.37 mL, 6.0 equiv) in DMAC (30 mL) was added NaH (855 mg, 60% purity, 4.0 equiv) at 0° C. The reaction was stirred at 20° C. for 0.5 hour, and then 7-(8-chloro-7-fluoro-3-((triisopropylsilyl)oxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine (3.6 g, 1 equiv) was added. The mixture was stirred at 60° C. for 1 hours. Water (40 mL) was added to the mixture and the pH was adjusted to 6 with 2N HCl. the mixture was extracted with ethyl acetate (3×40 mL). The organic layer was washed with brine (2×40 mL), dried over $Na_2SO_4$, filtered, and concentrated under vacuum to afford the title compound (4.2 g, crude) as yellow oil; LCMS (ESI, M+1): m/z=503.0.

Step C. 5-chloro-6-fluoro-4-(2-(((2R,7aS)-2-fluorohexahydro-1H-pyrrolizin-7a-yl)methoxy)-4-(tosyloxy)-5,6-dihydropyrido[3,4-d]pyrimidin-7(8H)-yl)naphthalen-2-yl-4-methylbenzenesulfonate: To a mixture of 7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol (2 g, 1 equiv) and N-ethyl-N-isopropylpropan-2-amine (4.11 g, 8.0 equiv), DMAP (48.6 mg, 0.1 equiv) in DCM (20 mL) was added TsCl (3.03 g, 4.0 equiv) at 0° C. The mixture was stirred at 0° C. for 0.25 hour. The mixture was concentrated and purified by prep-HPLC [column: Welch Xtimate C18 250× 50 mm×10 μm; mobile phase: water (FA)-ACN; B %: 31%-61%, 15 minutes] to afford the title compound (3 g, 45% yield) as yellow solid. LCMS (ESI, M+1): m/z=811.1.

Intermediate 5

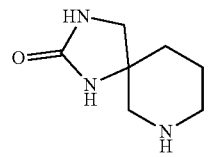 [SMILES: O=C1NCC2(CCCNC2)N1]

1,3,7-triazaspiro[4.5]decan-2-one

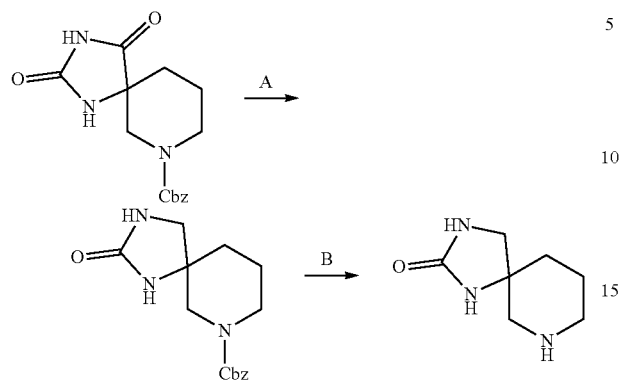

Step A. benzyl 2-oxo-1,3,7-triazaspiro[4.5]decane-7-carboxylate: To a solution of benzyl 2,4-dioxo-1,3,7-triazaspiro[4.5]decane-7-carboxylate (4.0 g, 1.0 equiv) in THF (40 mL) was added BH₃·Me₂S (10 M, 6.59 mL, 5.0 equiv) in one portion at 0° C. under N₂. The reaction was stirred at 10° C. for 0.5 hour. The reaction was stirred at 85° C. for 3 hours. The mixture was quenched with MeOH and stirred at 60° C. for 1 hour. The mixture was diluted with water (20 mL) and extracted with EtOAc (3×20 mL). The combined organic layers were washed with brine (15 mL), dried over anhydrous sodium sulfate, and concentrated. The residue was purified with reversed phase flash chromatography [C18, 0.1% formic acid condition] to afford the title compound (1.40 g, 30.1% yield) as yellow liquid; LCMS (ESI, M+1): m/z=290.1.

Step B. 1,3,7-triazaspiro[4.5]decan-2-one: To a solution of benzyl 2-oxo-1,3,7-triazaspiro[4.5]decane-7-carboxylate (1.40 g, 1.0 equiv) in MeOH (20 mL) was added Pd/C (800 mg, 10% purity) under N₂. The suspension was degassed under vacuum and purged with H₂ several times. The reaction was stirred under H₂ (15 psi) at 20° C. for 2 hours. The mixture was filtered and the solution was concentrated to afford the title compound (800 mg, 87% yield) as yellow solid. LCMS (ESI, M+1): m/z=156.2.

Intermediate 6

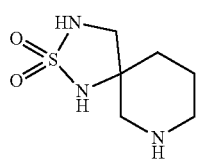 [SMILES: O=S1(=O)NCC2(CCCNC2)N1]

2-thia-1,3,7-triazaspiro[4.5]decane 2,2-dioxide

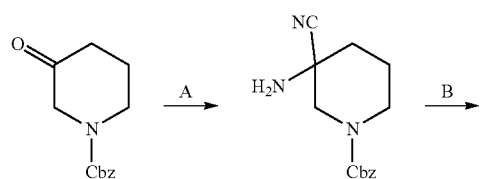

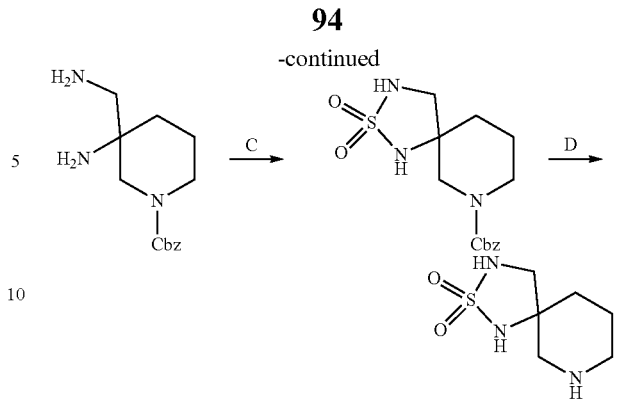

Step A. benzyl 3-amino-3-cyano-piperidine-1-carboxylate: To a mixture of benzyl 3-oxopiperidine-1-carboxylate (10.0 g, 1.0 equiv) and NH₄Cl (9.17 g, 4.0 equiv) in isopropyl alcohol (60 mL) and NH₃·H₂O (120 mL) was added KCN (10.1 g, 3.61 equiv) in one portion at 25° C. under N₂. The mixture was stirred at 25° C. for 12 hours. Water (150 mL) was added to the mixture, and the aqueous phase was extracted with ethyl acetate (3×50 mL). The combined organic phase was washed with brine (100 mL), and dried with anhydrous Na₂SO₄, filtered, and concentrated in vacuum. The residue was purified by column chromatography (SiO₂, Petroleum ether/Ethyl acetate=20/1 to 0/1) to afford the title compound (10.0 g, 89% yield) as yellow oil; LCMS (ESI, 2M+1): m/z=519.2.

Step B. benzyl 3-amino-3-(aminomethyl)piperidine-1-carboxylate: To a mixture of benzyl 3-amino-3-cyano-piperidine-1-carboxylate (200 mg, 1.0 equiv), NH₃·MeOH (1.00 mL, 20% purity, 1.0 equiv) in MeOH (5 mL) was added Raney Ni (30.0 mg) and then the mixture was stirred at 25° C. for 5 hours under H₂ atmosphere (15 psi). The reaction mixture was filtered and concentrated under reduced pressure. The residue was purified by prep-HPLC [Waters Xbridge 150×25 mm×5 μm; A: water (10 mM NH₄HCO₃), B: ACN, B %: 9%-39% over 10 min] to afford the title compound (100 mg, 45% yield) as colorless oil; ¹H NMR (400 MHz, chloroform-d₄) δ=7.38-7.30 (m, 5H), 5.23-5.03 (m, 2H), 3.45 (br s, 3H), 3.19 (br d, J=13.2 Hz, 1H), 2.78-2.63 (m, 1H), 2.49 (d, J=13.2 Hz, 1H), 1.66-1.40 (m, 4H).

Step C. benzyl 2-thia-1,3,7-triazaspiro[4.5]decane-7-carboxylate 2,2-dioxide: To a refluxing solution of sulfamide (109 mg, 10.0 equiv) in Pyridine (2 mL) was added benzyl 3-amino-3-(aminomethyl)piperidine-1-carboxylate (30.0 mg, 1.0 equiv). The resulting mixture was stirred at 120° C. for further 12 hours under nitrogen. The reaction mixture was concentrated under reduced pressure to give a residue. The residue was purified by prep-HPLC [Phenomenex Gemini-NX C18 75×30 mm×3 μm; A: water (0.225% FA), B: ACN, B %: 22%-52% over 7 min] to afford the title compound (15.0 mg, 40% yield) as yellow solid. ¹H NMR (400 MHz, chloroform-d₄) δ=7.35 (s, 5H), 5.62 (br d, J=0.8 Hz, 1H), 5.13 (br s, 2H), 5.03 (br s, 1H), 3.65 (br d, J=12.0 Hz, 1H), 3.58-3.31 (m, 4H), 3.22-3.11 (m, 1H), 1.95-1.84 (m, 1H), 1.81-1.67 (m, 2H), 1.54 (br dd, J=2.8, 7.2 Hz, 1H).

Step D. 2-thia-1,3,7-triazaspiro[4.5]decane 2,2-dioxide: A mixture of benzyl 2-thia-1,3,7-triazaspiro[4.5]decane-7-carboxylate 2,2-dioxide (15.0 mg, 1.0 equiv) in MeOH (2 mL) was added Pd/C (3.00 mg, 10% purity) and then the mixture was stirred at 25° C. for 1 hour under H₂ atmosphere (15 psi). The mixture was filtered and concentrated under reduced pressure to afford the title compound (17.0 mg, crude) as yellow solid.

Intermediate 7

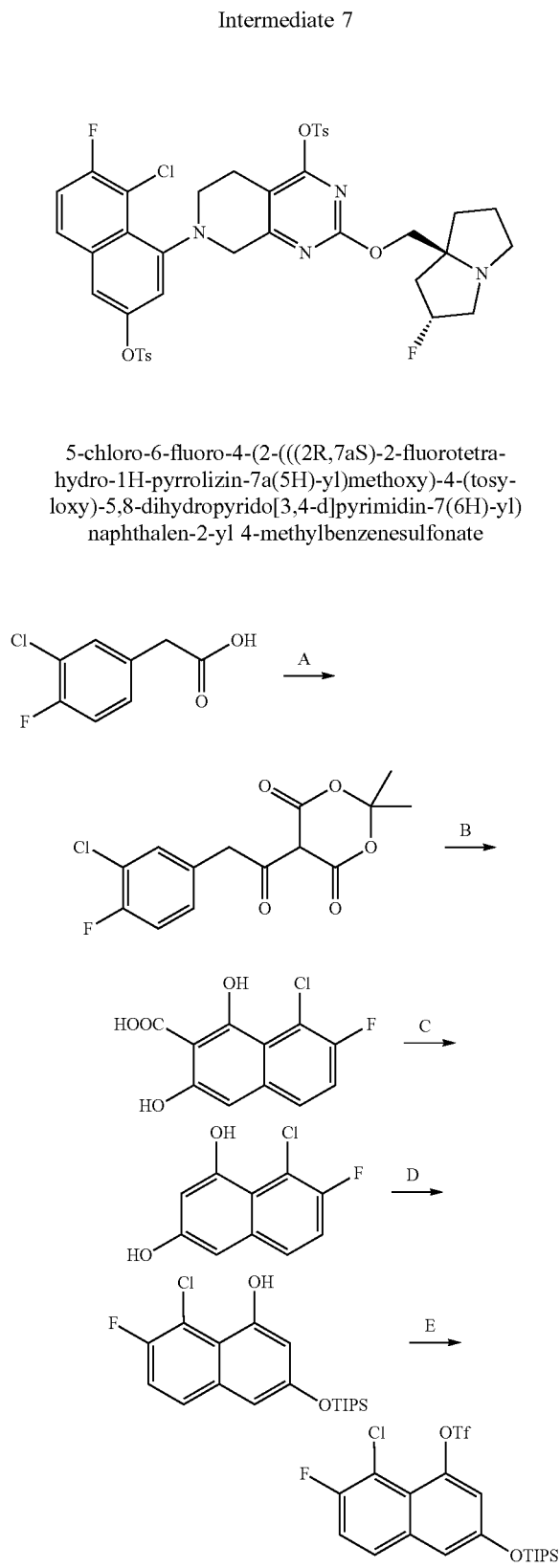

5-chloro-6-fluoro-4-(2-(((2R,7aS)-2-fluorotetra-hydro-1H-pyrrolizin-7a(5H)-yl)methoxy)-4-(tosy-loxy)-5,8-dihydropyrido[3,4-d]pyrimidin-7(6H)-yl)naphthalen-2-yl 4-methylbenzenesulfonate

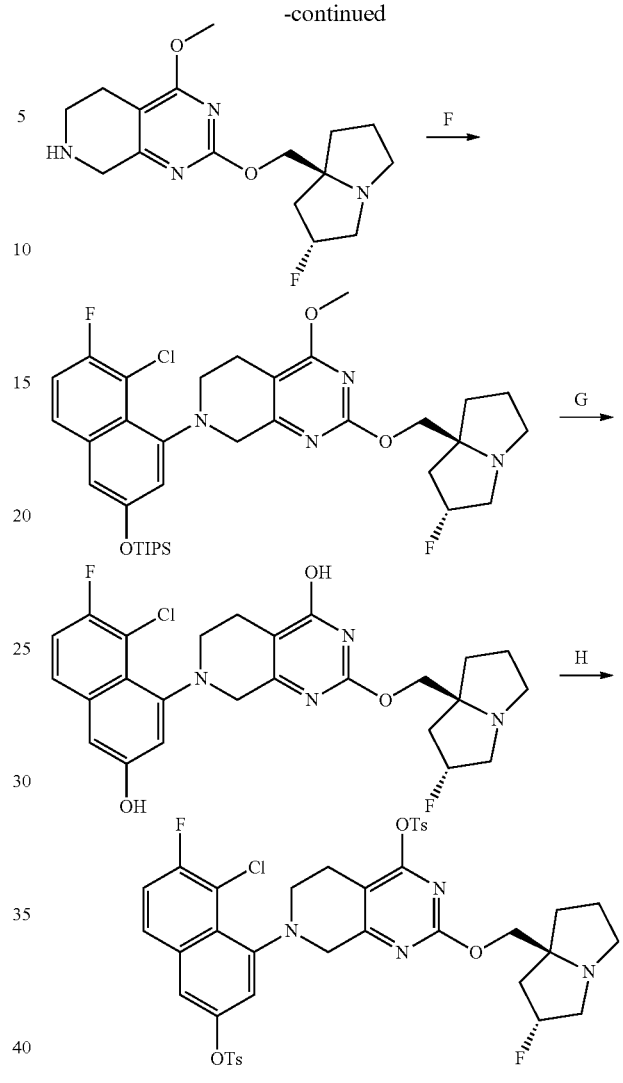

Step A. 5-(2-(3-chloro-4-fluorophenyl)acetyl)-2,2-dimethyl-1,3-dioxane-4,6-dione: To a mixture of 2-(3-chloro-4-fluoro-phenyl)acetic acid (330 g, 1 equiv) and 2,2-dimethyl-1,3-dioxane-4,6-dione (277 g, 1.1 equiv) in MeCN (1500 mL) was added DMAP (18.2 g, 0.09 equiv) at 20° C. N-ethyl-N-isopropylpropan-2-amine (486 g, 2.15 equiv) was added carefully in 1 hour while temperature was controlled between 15 and 30° C. and then 2,2-dimethylpropanoyl chloride (232.10 g, 1.1 equiv) was added during a period of 1 hour. The reaction mixture was stirred at 45° C. for 3 hours. The mixture was cooled to 0° C. and the pH was adjusted to 3 with HCl (4N, ~5 L). The mixture was stirred at 0° C. for 1 hour. The solid was filtered and triturated with MeCN (3 L) to afford the title compound (933 g, 84% yield) as yellow solid, which was used in the next step without further purification. $^{1}$HNMR (400 MHz, CDCl$_3$) δ=7.46 (dd, J=2.0, 6.8 Hz, 1H), 7.30-7.25 (m, 1H), 7.10 (t, J=8.8 Hz, 1H), 4.39-4.34 (m, 2H), 1.74 (s, 6H).

Step B. 8-chloro-7-fluoro-1,3-dihydroxy-2-naphthoic acid: A mixture of 5-(2-(3-chloro-4-fluorophenyl)acetyl)-2,2-dimethyl-1,3-dioxane-4,6-dione (650 g, 1.0 equiv) in CF$_3$SO$_3$H (1300 mL) was stirred at 5-20° C., and then the mixture was stirred at 10° C. for 2 hours. After completion, the mixture was poured into ice water (2 L) and filtered. The solid was washed with water (5 L) and collected to afford the title compound (2000 g, crude) as yellow solid, which was used in the next step without further purification.

Step C. 8-chloro-7-fluoronaphthalene-1,3-diol: A mixture of 8-chloro-7-fluoro-1,3-dihydroxy-2-naphthoic acid (1.2 kg, 1.0 equiv) in MeCN (700 mL) and $H_2O$ (700 mL) was stirred at 85° C. for 12 hours under $N_2$. The mixture was concentrated under vacuum. The residue was extracted with ethyl acetate (2 L×2), dried over $Na_2SO_4$ and concentrated under vacuum. The residue was purified by column chromatography ($SiO_2$, PE/EA=3/1) and prep-HPLC (column: Phenomenex Luna C18 200*40 mm*10 μm; mobile phase: [water (FA)-ACN]; B %: 27%-57%, 10 min). The desired fraction was collected and extracted with ethyl acetate (2 L). The organic combined layers were dried over $Na_2SO_4$ and concentrated under vacuum to afford the title compound (17 g, 16% yield two steps) as yellow solid. $^1H$ NMR (400 MHz, DMSO-d6) δ 10.17 (s, 1H), 9.71 (s, 1H), 7.58 (dd, J=5.6, 8.8 Hz, 1H), 7.32 (t, J=8.8 Hz, 1H), 6.67 (d, J=2.0 Hz, 1H), 6.63 (d, J=2.0 Hz, 1H).

Step D. 8-chloro-7-fluoro-3-((triisopropylsilyl)oxy)naphthalen-1-ol: To a solution of 8-chloro-7-fluoronaphthalene-1,3-diol (10 g, 1 equiv) and N-ethyl-N-isopropylpropan-2-amine (12.2 g, 2.0 equiv) in DCM (150 mL) was added TIPSCl (8.16 g, 0.9 equiv) at 0° C. The reaction was stirred at 0° C. for 0.5 hour. The mixture was concentrated under vacuum to give a residue and the residue was purified by column chromatography ($SiO_2$, PE/EA=10/1) to afford the title compound (15 g, 86% yield) as yellow oil.

Step E. 8-chloro-7-fluoro-3-((triisopropylsilyl)oxy)naphthalen-1-yl trifluoromethanesulfonate: To a mixture of 8-chloro-7-fluoro-3-((triisopropylsilyl)oxy)naphthalen-1-ol (15 g, 1.0 equiv) and N-ethyl-N-isopropylpropan-2-amine (15.8 g, 3.0 equiv) in DCM (150 mL) was added $Tf_2O$ (17.2 g, 1.5 equiv) at −40° C. The reaction was stirred at −40° C. for 0.5 hour. The mixture was concentrated under vacuum and purified by column chromatography ($SiO_2$, PE/EA=10/1) to afford the title compound (19 g, 90% yield) as yellow oil. LCMS (ESI, M+1): m/z=501.0

Step F. 7-(8-chloro-7-fluoro-3-((triisopropylsilyl)oxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine: A mixture of 2-(((2R,7aS)-2-fluorohexahydro-1H-pyrrolizin-7a-yl)methoxy)-4-methoxy-5,6,7,8-tetrahydropyrido[3,4-d]pyrimidine (4 g, 1.0 equiv), 8-chloro-7-fluoro-3-((triisopropylsilyl)oxy)naphthalen-1-yl trifluoromethanesulfonate (7.46 g, 1.2 equiv), $Cs_2CO_3$ (12.1 g, 3.0 equiv), RuPhos (1.16 g, 0.2 equiv) and $Pd_2(dba)_3$ (1.14 g, 0.1 equiv) in toluene (80 mL) was degassed and purged with $N_2$ several times. The mixture was stirred at 100° C. for 3 hours under $N_2$ atmosphere. The mixture was diluted with water (100 mL) and extracted with ethyl acetate (100 mL). The organic layer was dried over sodium sulfate and concentrated under vacuum to give a residue. The residue was purified by HPLC (0.1% FA condition) to afford the title compound (3.9 g, 46% yield) as yellow solid. LCMS (ESI, M+1): m/z=673.2.

Step G. 7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol: To a mixture of EtSH (1.99 g, 2.37 mL, 6.0 equiv) in DMAC (30 mL) was added NaH (855 mg, 60% purity, 4.0 equiv) at 0° C. After the reaction was stirred at 20° C. for 0.5 hour, 7-(8-chloro-7-fluoro-3-((triisopropylsilyl)oxy)naphthalen-1-yl)-2-(((2R,7aS)-2-fluorohexahydro-1H-pyrrolizin-7a-yl)methoxy)-4-methoxy-5,6,7,8-tetrahydropyrido[3,4-d]pyrimidine (3.6 g, 1 equiv) was added. The mixture was stirred at 60° C. for 1 hours. Water (40 mL) was added and the pH of mixture was adjusted to 6 with 2N HCl. The mixture was extracted with ethyl acetate (3×40 mL). The combined organic layers were washed with brine (2×40 mL), dried over $Na_2SO_4$ and concentrated under vacuum to afford the title compound (4.2 g, crude) as yellow oil, which was used in the next step without further purification. LCMS (ESI, M+1): m/z=503.1.

Step H. 5-chloro-6-fluoro-4-(2-(((2R,7aS)-2-fluorohexahydro-1H-pyrrolizin-7a-yl)methoxy)-4-(tosyloxy)-5,6-dihydropyrido[3,4-d]pyrimidin-7(8H)-yl)naphthalen-2-yl 4-methylbenzenesulfonate: To a mixture of 7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol (2 g, 1 equiv), N-ethyl-N-isopropylpropan-2-amine (4.11 g, 5.54 mL, 8.0 equiv), and DMAP (48.6 mg, 0.1 equiv) in DCM (20 mL) was added TsCl (3.03 g, 4.0 equiv) at 0° C. The mixture was stirred at 0° C. for 0.25 hour. The mixture was concentrated under vacuum and purified by prep-HPLC (column: Welch Xtimate C18 250*50 mm*10 μm; mobile phase: [water (FA)-ACN]; B %: 31%-61%, 15 min) to afford the title compound (3 g, 45% yield) as yellow solid. LCMS (ESI, M+1): m/z=811.1.

Intermediate 8

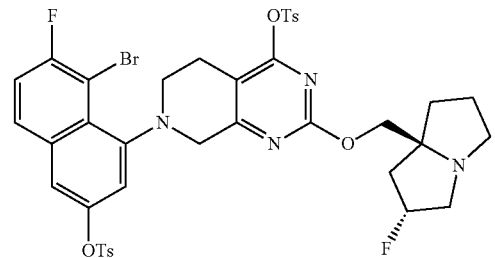 [SMILES: Cc1ccc(S(=O)(=O)Oc2cc(N3CCc4c(nc(OC[C@@]56CCCN5C[C@H](F)C6)nc4OS(=O)(=O)c4ccc(C)cc4)C3)c3c(Br)c(F)ccc3c2)cc1]

5-bromo-6-fluoro-4-(2-(((2R,7aS)-2-fluorotetrahydro-1H-pyrrolizin-7a(5H)-yl)methoxy)-4-(tosyloxy)-5,8-dihydropyrido[3,4-d]pyrimidin-7(6H)-yl)naphthalen-2-yl 4-methylbenzenesulfonate

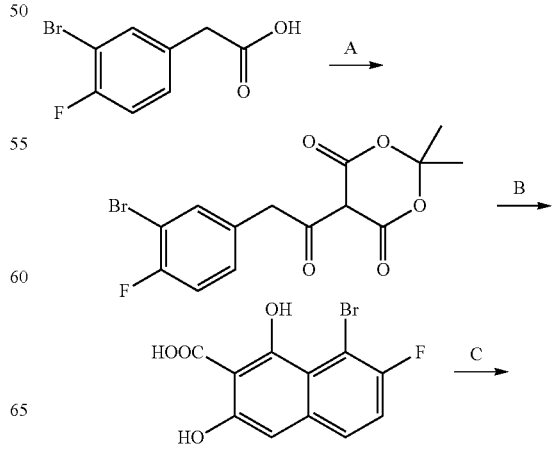

99
-continued

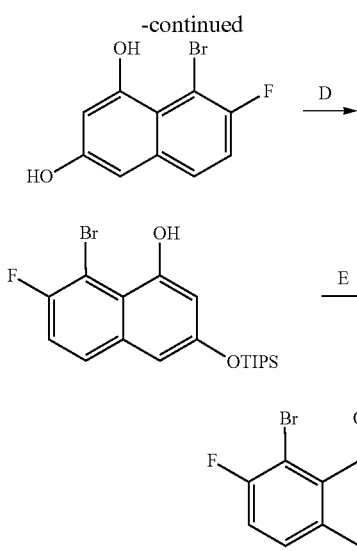

100
Intermediate 9

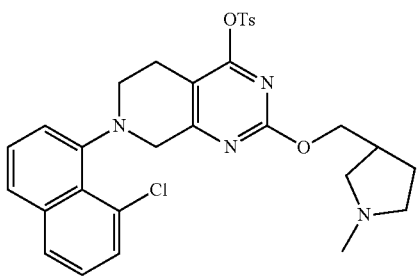 [SMILES: Cc1ccc(S(=O)(=O)Oc2nc(OCC3CCN(C)C3)nc3c2CCN(c2cccc4cccc(Cl)c24)C3)cc1]

(S)-7-(8-chloronaphthalen-1-yl)-2-((1-methylpyrrolidin-2-yl)methoxy)-5,6,7,8-tetrahydropyrido[3,4-d]pyrimidin-4-yl 4-methylbenzenesulfonate

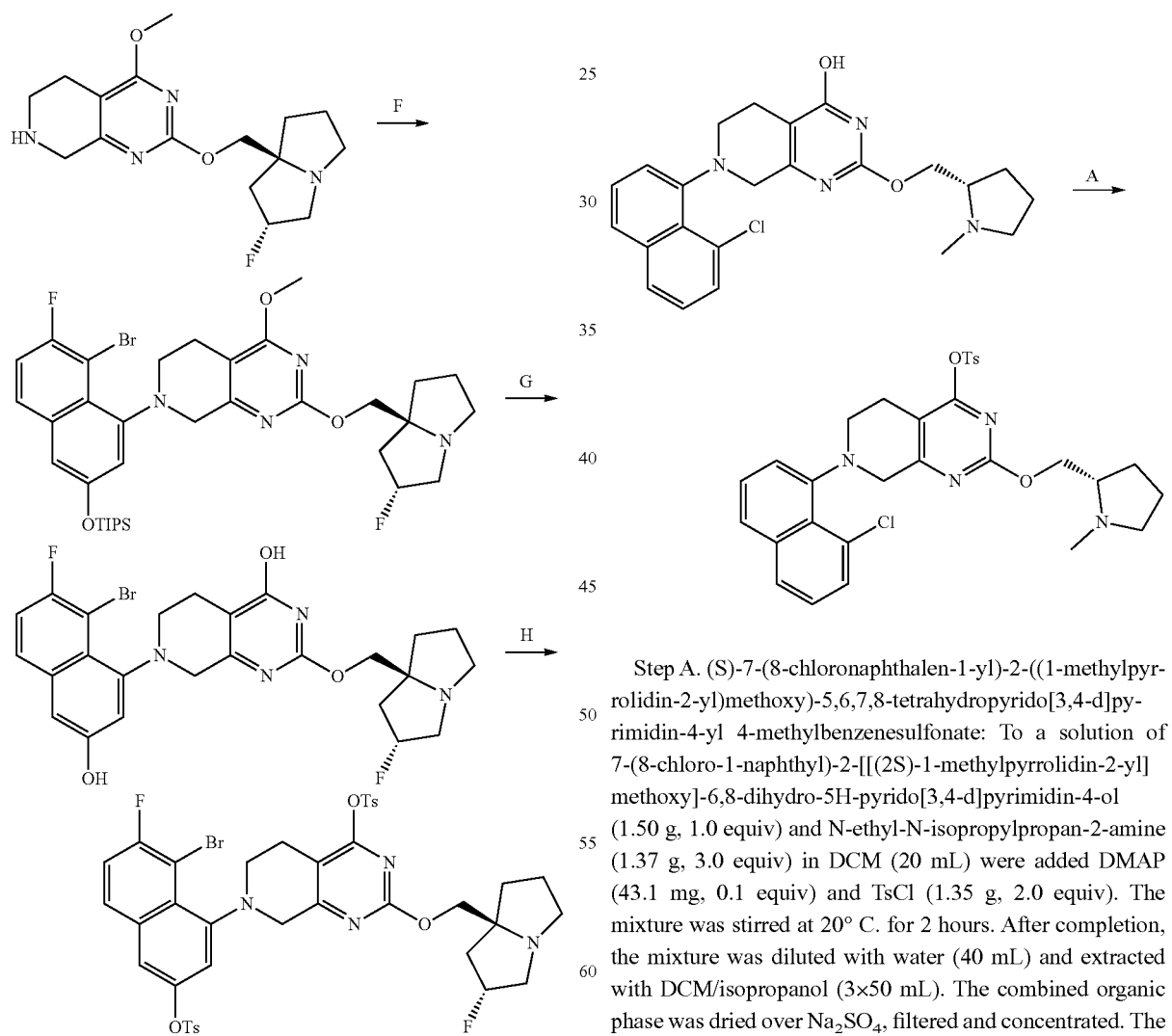

Synthesized according to intermediate 7. The title compound was obtained as yellow solid. LCMS (ESI, M+1): m/z=855.0.

Step A. (S)-7-(8-chloronaphthalen-1-yl)-2-((1-methylpyrrolidin-2-yl)methoxy)-5,6,7,8-tetrahydropyrido[3,4-d]pyrimidin-4-yl 4-methylbenzenesulfonate: To a solution of 7-(8-chloro-1-naphthyl)-2-[[(2S)-1-methylpyrrolidin-2-yl]methoxy]-6,8-dihydro-5H-pyrido[3,4-d]pyrimidin-4-ol (1.50 g, 1.0 equiv) and N-ethyl-N-isopropylpropan-2-amine (1.37 g, 3.0 equiv) in DCM (20 mL) were added DMAP (43.1 mg, 0.1 equiv) and TsCl (1.35 g, 2.0 equiv). The mixture was stirred at 20° C. for 2 hours. After completion, the mixture was diluted with water (40 mL) and extracted with DCM/isopropanol (3×50 mL). The combined organic phase was dried over Na$_2$SO$_4$, filtered and concentrated. The residue was purified by column chromatography (neutral Al$_2$O$_3$, Petroleum ether/Ethyl acetate=10/1 to Ethyl acetate:MeOH=10:1) to afford the title compound (1.0 g, 49% yield) as a brown solid. LCMS (ESI, M+1): m/z=579.2.

Example 1

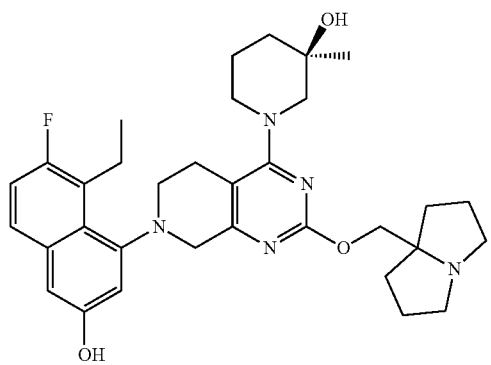 [SMILES: CCc1c(F)ccc2cc(O)cc(N3CCc4c(nc(OCC56CCCN5CCC6)nc4N4CCC[C@@](C)(O)C4)C3)c12]

(R)-1-(7-(8-ethyl-7-fluoro-3-hydroxynaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol

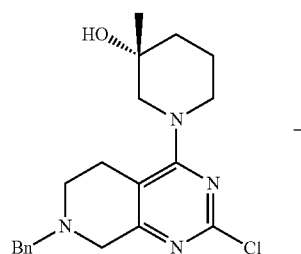

A ⟶

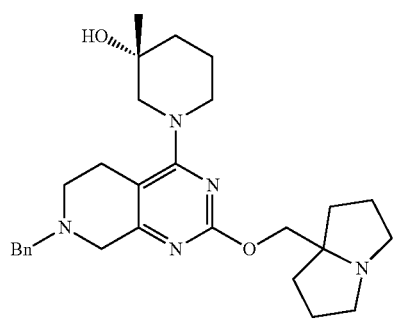

B ⟶

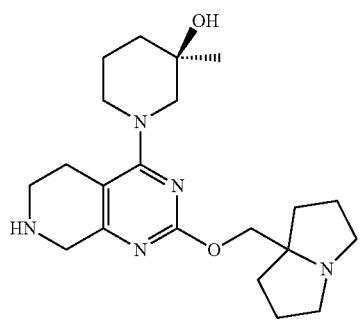

C ⟶

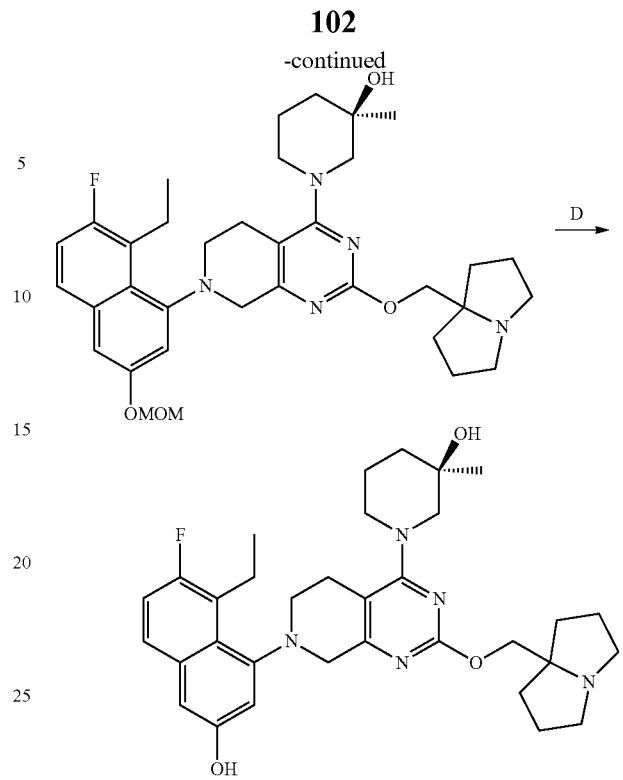

D ⟶

Step A. (R)-1-(7-benzyl-2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-1-(7-benzyl-2-chloro-5,6,7,8-tetrahydropyrido[3,4-d]pyrimidin-4-yl)-3-methylpiperidin-3-ol (1.00 g, 2.68 mmol), (hexahydro-1H-pyrrolizin-7a-yl)methanol (568 mg, 4.02 mmol), BINAP (417 mg, 670 µmol), $Cs_2CO_3$ (2.62 g, 8.05 mmol) and $Pd(OAc)_2$ (120 mg, 536 µmol) in toluene (10 mL) was degassed and purged with $N_2$ for 3 times. The mixture was stirred at 110° C. for 3 hours under $N_2$ atmosphere. After completion, the reaction mixture was diluted with $H_2O$ (10 mL) and extracted with ethyl acetate (2×10 mL). The combined organic layers were washed with brine (2×30 mL), dried over $Na_2SO_4$, filtered, and concentrated under reduced pressure to give a residue. The residue was purified by HPLC [C18, 0.1% FA in water, 0-60% MeCN] to give the title compound (480 mg, 30% yield, 80% purity). Yellow solid. $^1$H NMR (400 MHz, chloroform-d) δ=7.39-7.28 (m, 5H), 4.07-3.96 (m, 2H), 3.96-3.92 (m, 1H), 3.87-3.82 (m, 1H), 3.81-3.74 (m, 1H), 3.71-3.65 (m, 3H), 3.43 (d, J=17.2 Hz, 1H), 3.11-3.04 (m, 2H), 2.98-2.91 (m, 1H), 2.91-2.87 (m, 1H), 2.85-2.77 (m, 1H), 2.76-2.67 (m, 1H), 2.64-2.52 (m, 3H), 2.51-2.43 (m, 1H), 2.07-1.98 (m, 2H), 1.86-1.76 (m, 6H), 1.66-1.57 (m, 3H), 1.26-1.25 (m, 3H); LCMS (ESI, M+1): m/z 478.3.

Step B. (R)-1-(2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-1-(7-benzyl-2-((hexahydro-1H-pyrrolizin-7a-yl)methoxy)-5,6,7,8-tetrahydropyrido[3,4-d]pyrimidin-4-yl)-3-methylpiperidin-3-ol (450 mg, 754 µmol, 80% purity), and $Pd(OH)_2$ (250 mg, 1.78 mmol) in MeOH (5.00 mL) was degassed and purged with $H_2$ for 3 times. The mixture was stirred at 40° C. for 2 hours under $H_2$ (50 psi). After completion, the reaction mixture was filtered through Celite and the filtrate was concentrated. The residue was purified by HPLC [C18, 0.1%

FA in water, 0-40% MeCN] to give the title compound (160 mg, 45% yield). White solid. LCMS (ESI, M+1): m/z 388.1.

Step C. (R)-1-(7-(8-ethyl-7-fluoro-3-(methoxymethoxy)naphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-1-(2-((hexahydro-1H-pyrrolizin-7a-yl)methoxy)-5,6,7,8-tetrahydropyrido[3,4-d]pyrimidin-4-yl)-3-methylpiperidin-3-ol (110 mg, 252 μmol), 8-ethyl-7-fluoro-3-(methoxymethoxy)naphthalen-1-yl trifluoromethanesulfonate (193 mg, 505 μmol), XantPhos Pd G3 (59.9 mg, 63.2 μmol), Xantphos (21.9 mg, 37.9 μmol), Cs$_2$CO$_3$ (247 mg, 758 μmol) and 4 Å MS (50.0 mg) in toluene (2.00 mL) was degassed and purged with N$_2$ for 3 times. The mixture was stirred at 110° C. for 20 hours under N$_2$ atmosphere. After completion, the reaction mixture was diluted with H$_2$O (5 mL) and extracted with ethyl acetate (2×5 mL). The combined organic layers were washed with brine (15 mL), dried over Na$_2$SO$_4$, filtered, and concentrated under reduced pressure to give a residue. The residue was purified by HPLC [C18, 0.1% FA in water, 0-70% MeCN] to give the title compound (48 mg, 29% yield). Yellow solid. LCMS (ESI, M+1): m/z 620.3.

Step D. (R)-1-(7-(8-ethyl-7-fluoro-3-hydroxynaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol: To a solution of (R)-1-(7-(8-ethyl-7-fluoro-3-(methoxymethoxy)naphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol (30.0 mg, 48.4 μmol) in ACN (0.50 mL) was added HCl·MeOH (4.0 M, 1.00 mL) at 0° C. The mixture was stirred at 0° C. for 20 min. After completion, the reaction mixture was diluted with saturated Na$_2$CO$_3$ solution (2 mL) and extracted with ethyl acetate (2×5.00 mL). The combined organic layers were dried over Na$_2$SO$_4$ and filtered. The mixture was concentrated under reduced pressure to give a residue. The residue was purified by prep-HPLC (column: Phenomenex Luna C18 150×25 mm×10 μm; mobile phase: [water (0.225% FA)-ACN]; B %: 21%-51%, 10 min) to give (R)-1-(7-(8-ethyl-7-fluoro-3-hydroxynaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol (8.16 mg, 26.9% yield, FA). Yellow solid. $^1$H NMR (400 MHz, methanol-d$_4$) δ=7.60-7.43 (m, 1H), 7.19-7.10 (t, J=9.6 Hz, 1H), 7.06-6.90 (m, 2H), 4.60 (br s, 2H), 4.47-4.34 (m, 2H), 4.15-4.03 (m, 1H), 3.76-3.62 (m, 2H), 3.59-3.48 (m, 4H), 3.47-3.35 (m, 2H), 3.21-3.11 (m, 4H), 2.82-2.65 (m, 1H), 2.34-1.95 (m, 9H), 1.88-1.63 (m, 3H), 1.24 (d, J=26.4 Hz, 3H), 1.17-1.02 (m, 3H); LCMS (ESI, M+1): m/z 576.3.

Example 2

(R)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol

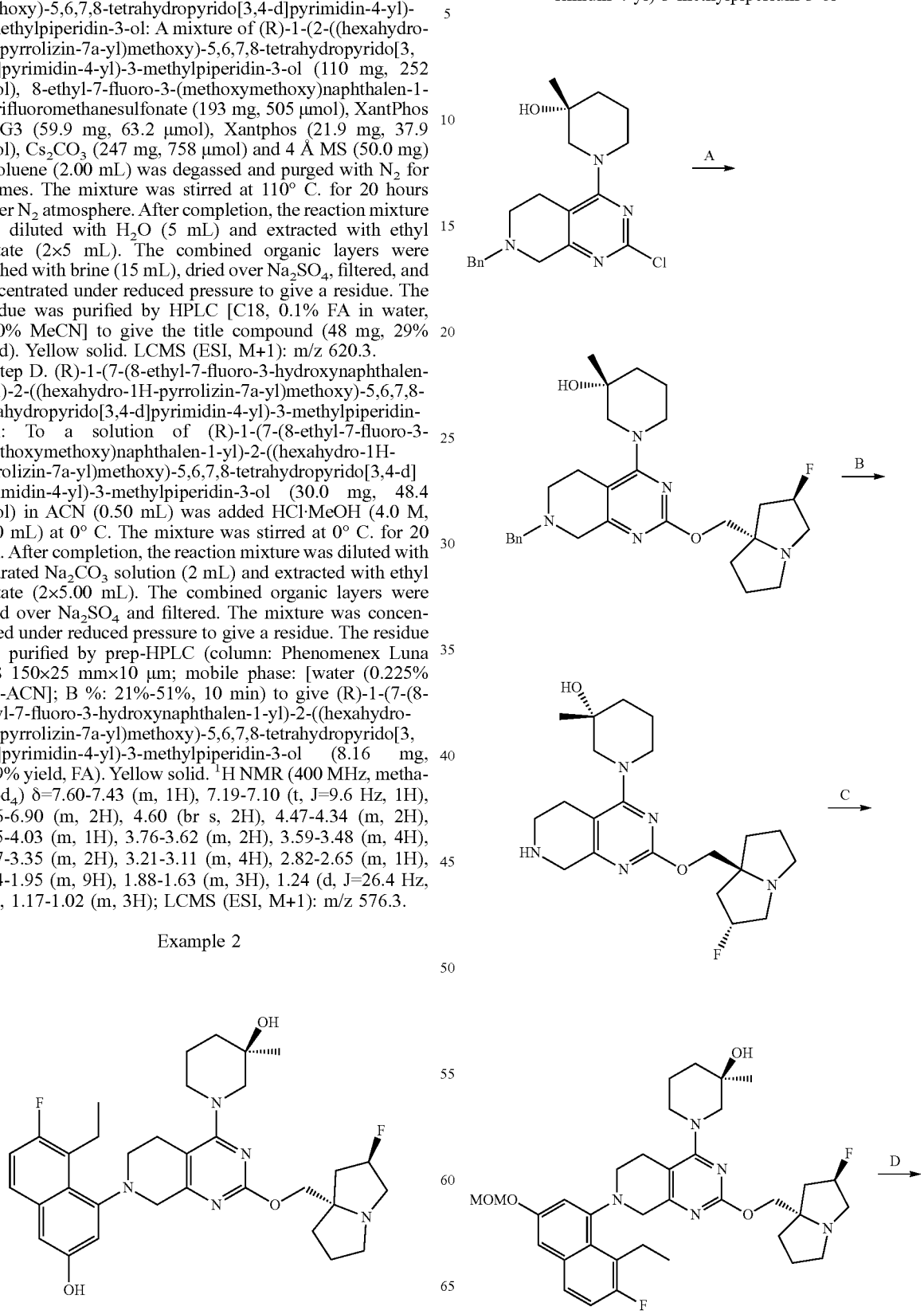

-continued

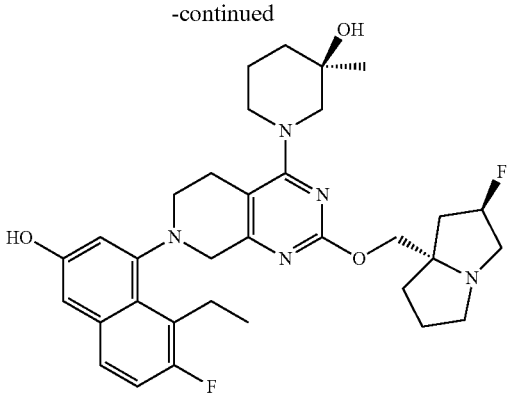

Step A. (R)-1-(7-benzyl-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: To a mixture of ((2R,7aS)-2-fluorohexahydro-1H-pyrrolizin-7a-yl)methanol (80.0 mg, 503 μmol) and THF (2 mL) was added NaH (40.0 mg, 1.00 mmol, 60% purity) at 0° C. The reaction was stirred at 0° C. for 0.5 hour and (R)-1-(7-benzyl-2-chloro-5,6,7,8-tetrahydropyrido[3,4-d]pyrimidin-4-yl)-3-methylpiperidin-3-ol (125 mg, 335 μmol) was added at 20° C. over 0.5 hour. The reaction was stirred at 45° C. for 3 hours. The reaction mixture was quenched with sat. NH$_4$Cl (5 mL), diluted with ethyl acetate (10 mL), and extracted with ethyl acetate (10 mL×2). The combined organic phase was washed with brine (10 mL) and dried over anhydrous sodium sulfate. The mixture was filtered and concentrated to give a residue. The residue was purified by reversed phase flash chromatography [water (FA 0.10%)/acetonitrile] to give the title compound (74.0 mg, 44% yield). Yellow Oil; LCMS (ESI, M+1): m/z 496.4.

Step B. (R)-1-(2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: To a solution of (R)-1-(7-benzyl-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol (72.0 mg, 145 μmol) in MeOH (2 mL) was added Pd(OH)$_2$/C (36.0 mg, 10% purity) under N$_2$. The suspension was degassed under vacuum and purged with H$_2$ several times. The mixture was stirred under H$_2$ (15 psi) at 20° C. for 2 hours. Upon completion, the mixture was filtered and concentrated to give the title compound (50.0 mg, crude). Colorless Oil; LCMS (ESI, M+1): m/z 406.3.

Step C. (R)-1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: To a mixture of (R)-1-(2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol (40.0 mg, 98.6 μmol), 8-ethyl-7-fluoro-3-(methoxymethoxy)naphthalen-1-yl trifluoromethanesulfonate (56.6 mg, 148 μmol), Xantphos (11.4 mg, 19.7 μmol), and Cs$_2$CO$_3$ (96.4 mg, 296 μmol) in toluene (1.5 mL) was added XantPhos Pd G3 (9.35 mg, 9.86 μmol) under N$_2$. The mixture was degassed and purged with N$_2$ for 3 times. The reaction was stirred at 110° C. for 12 hours. Upon completion, the reaction mixture was diluted with ethyl acetate (5 mL) and water (5 mL). The aqueous layer was extracted with ethyl acetate (5 mL). The combined organic phase was washed with brine (5 mL) and dried over anhydrous sodium sulfate. The mixture was filtered and concentrated to give a residue. The residue was purified by reversed phase flash chromatography [water (FA 0.10%)/acetonitrile] to give the title compound (9.00 mg, 14% yield). Yellow Solid. LCMS (ESI, M+1): m/z 638.4.

Step D. (R)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: To a solution of (R)-1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol (8.00 mg, 12.5 μmol) in MeOH (0.5 mL) was added HCl·MeOH (4 M, 0.5 mL) at 0° C. The mixture was stirred at 0° C. for 0.5 hour. Upon completion, the mixture was concentrated to give a residue. The residue was purified by prep-HPLC (column: Phenomenex Luna C18 150×25 mm×10 μm; mobile phase: [water (0.225% FA)-ACN]; B %: 22%-52%, 10 min) to afford the title compound (6.67 mg, 87% yield, 0.16 FA). Off-white Solid. $^1$H NMR (400 MHz, METHANOL-d$_4$) δ=7.56-7.46 (m, 1H), 7.15 (t, J=9.3 Hz, 1H), 7.02-6.92 (m, 2H), 5.48-5.31 (m, 1H), 4.40-3.90 (m, 2H), 4.14-3.88 (m, 1H), 3.75-3.32 (m, 11H), 3.24-3.09 (m, 3H), 2.84-2.64 (m, 1H), 2.54-1.57 (m, 10H), 1.28-1.18 (m, 3H), 1.16-1.08 (m, 3H); LCMS (ESI, M+1): m/z 594.4.

Example 3

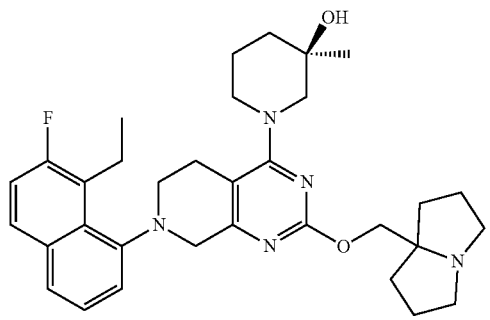 [SMILES: CCc1c(F)ccc2cccc(N3CCc4c(nc(OCC56CCCN5CCC6)nc4N4CCC[C@@](C)(O)C4)C3)c12]

(R)-1-(7-(8-ethyl-7-fluoronaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol

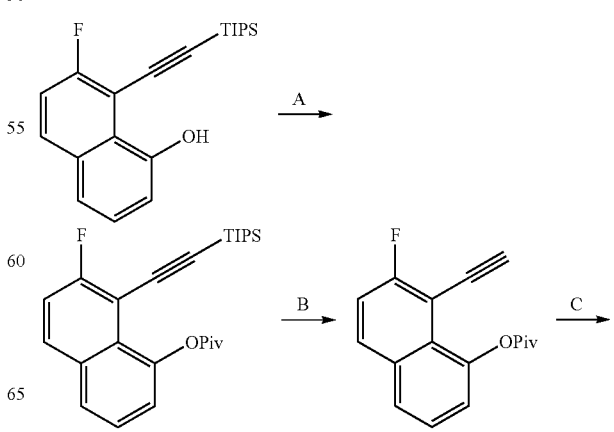

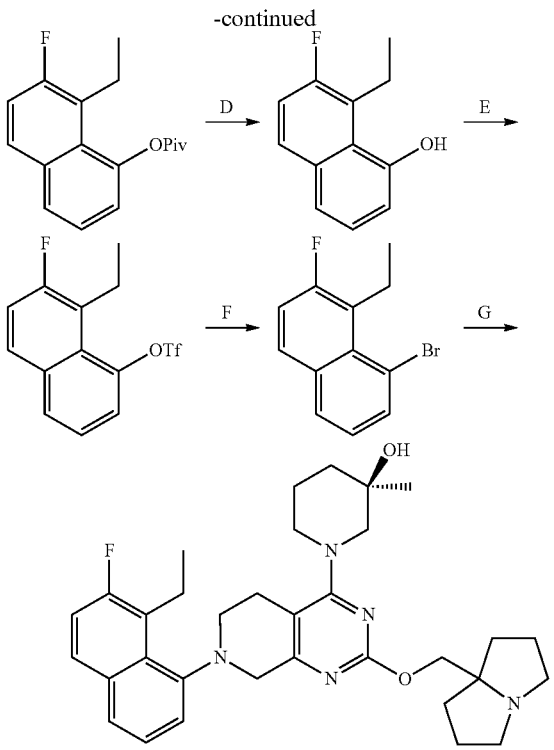

Step A. 7-fluoro-8-((triisopropylsilyl)ethynyl)naphthalen-1-yl pivalate: To a solution of 7-fluoro-8-((triisopropylsilyl)ethynyl)naphthalen-1-ol (5 g, 14.6 mmol) in DCM (50 mL) were added N-ethyl-N-isopropylpropan-2-amine (4.72 g, 36.5 mmol), DMAP (178 mg, 1.46 mmol), and pivaloyl chloride (2.64 g, 21.9 mmol) under $N_2$ atmosphere at 0° C. The mixture was stirred at 0° C. for 0.5 hour. The mixture was diluted with water (50.0 mL) and extracted with DCM (3×25.0 mL). The organic layers were washed with brine, dried over $Na_2SO_4$, and concentrated under reduced pressure to give a residue. The residue was purified by column chromatography ($SiO_2$, Petroleum ether/Ethyl acetate=1/0 to 20/1) to give the title compound (6.00 g, 94% yield) as yellow solid. $^1$H NMR (400 MHz, CHLOROFORM-d) δ 7.84-7.75 (m, 1H), 7.72-7.67 (m, 1H), 7.46-7.40 (t, J=7.6 Hz, 1H), 7.32-7.28 (m, 1H), 7.08 (d, J=8.0 Hz, 1H), 1.51-1.47 (m, 9H), 1.23-1.14 (m, 21H). LCMS (ESI, M+1): m/z 427.2.

Step B. 8-ethynyl-7-fluoronaphthalen-1-yl pivalate: To a solution of 7-fluoro-8-((triisopropylsilyl)ethynyl)naphthalen-1-yl pivalate (5 g, 11.5 mmol) in DMF (50 mL) was added CsF (34.9 g, 220 mmol) under $N_2$ atmosphere. The mixture was stirred at 20° C. for 1 hour. The mixture was diluted with water (150 mL) and extracted with EtOAc (3×50.0 mL). The combined organic layers were washed with brine, dried over $Na_2SO_4$, filtered, and concentrated under reduced pressure. The residue was purified by column chromatography ($SiO_2$, Petroleum ether/Ethyl acetate=100/1 to 20/1) to give the title compound (2.76 g, 87% yield). Yellow solid. $^1$H NMR (400 MHz, CHLOROFORM-d) δ 7.90-7.84 (m, 1H), 7.77-7.71 (m, 1H), 7.46 (t, J=7.6 Hz, 1H), 7.31 (t, J=8.8 Hz, 1H), 7.14-7.09 (m, 1H), 3.63-3.58 (m, 1H), 1.51-1.44 (m, 9H).

Step C. 8-ethyl-7-fluoronaphthalen-1-yl pivalate: To a solution of 8-ethynyl-7-fluoronaphthalen-1-yl pivalate (3.27 g, 11.9 mmol) in MeOH (30.0 mL) was added Pd/C (0.33 g, 10% purity) under $N_2$ atmosphere. The mixture was stirred at 20° C. for 1 hour under $H_2$ (15 psi) atmosphere. The mixture was filtered, and concentrated under reduced pressure to give the title compound (3.23 g, crude). Yellow oil; $^1$H NMR (400 MHz, CHLOROFORM-d) δ 7.76-7.69 (m, 2H), 7.39 (t, J=8.4 Hz, 1H), 7.29-7.23 (m, 1H), 7.05-6.99 (m, 1H), 3.23-3.13 (m, 2H), 1.49-1.45 (m, 9H), 1.25 (t, J=7.2 Hz, 3H). LCMS (ESI, M+1): m/z 275.1.

Step D. 8-ethyl-7-fluoronaphthalen-1-ol: To a solution of 8-ethyl-7-fluoronaphthalen-1-yl pivalate (3.23 g, 11.5 mmol) in MeOH (30.0 mL) was added KOH (2.59 g, 46.2 mmol). The reaction mixture was stirred at 20° C. for 0.5 hour. The mixture was diluted with water (300 mL) and extracted with EtOAc (3×100 mL). The combined organic layers were washed with brine (100 mL) and dried over $Na_2SO_4$. The mixture was filtered and concentrated under reduced pressure to give a residue. The residue was purified by column chromatography ($SiO_2$, Petroleum ether/Ethyl acetate=100/1 to 10/1) to give the title compound (2.11 g, 94% yield). Yellow oil; $^1$H NMR (400 MHz, CHLOROFORM-d) δ 7.66-7.59 (m, 1H), 7.44-7.37 (m, 1H), 7.26-7.19 (m, 2H), 6.79-6.74 (m, 1H), 5.24 (s, 1H), 3.43-3.34 (m, 2H), 1.33 (t, J=7.6 Hz, 3H).

Step E. 8-ethyl-7-fluoronaphthalen-1-yl trifluoromethanesulfonate: To a solution of 8-ethyl-7-fluoronaphthalen-1-ol (1.20 g, 6.31 mmol) and 4 Å molecular sieve (1.00 g) in DCM (12.0 mL) was added dropwise N-ethyl-N-isopropylpropan-2-amine (4.89 g, 37.8 mmol, 6.59 mL) at 20° C. The mixture was stirred at this temperature for 10 min, and then trifluoromethylsulfonyl trifluoromethanesulfonate (2.31 g, 8.20 mmol, 1.35 mL) was added dropwise at −40° C. The resulting mixture was stirred at −40° C. for 20 min. The reaction mixture was diluted with $H_2O$ (20.0 mL) and extracted with ethyl acetate (2×30.0 mL). The combined organic layers were washed with brine (80.0 mL) and dried over $Na_2SO_4$. The mixture was filtered and concentrated under reduced pressure to give a residue. The residue was purified by column chromatography ($SiO_2$, petroleum ether:ethyl acetate=20:1 to 5:1) to give the title compound (1.35 g, 66% yield). Colorless oil, $^1$H NMR (400 MHz, DMSO-$d_6$) δ 8.14-8.09 (m, 1H), 8.08-8.01 (m, 1H), 7.70-7.64 (m, 1H), 7.63-7.52 (m, 2H), 3.22-3.12 (m, 2H), 1.16 (t, J=7.6 Hz, 3H).

Step F. 8-bromo-1-ethyl-2-fluoronaphthalene: A mixture of 8-ethyl-7-fluoronaphthalen-1-yl trifluoromethanesulfonate (500 mg, 1.55 mmol), LiBr (202 mg, 2.33 mmol) and Chloro(pentamethylcyclopentadienyl)ruthenium(II) Tetramer (84.3 mg, 77.6 μmol) in 1,3-dimethylimidazolidin-2-one (4.00 mL) was degassed and purged with $N_2$ for 3 times. The mixture was stirred at 100° C. for 4 hours under $N_2$ atmosphere. After completion, the reaction mixture was diluted with $H_2O$ (5.00 mL) and extracted with ethyl acetate (2×10.0 mL). The combined organic layers were washed with brine (20.0 mL) and dried over $Na_2SO_4$. The mixture was filtered and concentrated under reduced pressure to give a residue. The residue was purified by column chromatography ($SiO_2$, petroleum ether:ethyl acetate=1:0) to give the title compound (300 mg, 76% yield). Colorless oil; $^1$H NMR (400 MHz, chloroform-d) δ 7.95-7.64 (m, 3H), 7.32-7.18 (m, 2H), 3.63-3.50 (m, 2H), 1.42-1.37 (m, 3H).

Step G. (R)-1-(7-(8-ethyl-7-fluoronaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-1-(2-((hexahydro-1H-pyrrolizin-7a-yl)methoxy)-5,6,7,8-tetrahydropyrido[3,4-d]pyrimidin-4-yl)-3-methylpiperidin-3-ol (70 mg, 144 μmol, 80% purity), 8-bromo-1-ethyl-2-fluoronaphthalene (73.1 mg, 289 μmol), $Pd_2(dba)_3$ (26.5 mg, 28.9 μmol), Xantphos (12.5 mg, 21.7

μmol), t-BuONa (41.7 mg, 433 μmol) and 4 Å molecular sieve (70 mg) in toluene (2 mL) was degassed and purged with $N_2$ in the glove box. The mixture was stirred at 70° C. for 15 hours under $N_2$ atmosphere. After completion, the reaction mixture was diluted with $H_2O$ (3.00 mL) and extracted with ethyl acetate (3×5.00 mL). The combined organic layers were washed with brine (20.0 mL), dried over $Na_2SO_4$, filtered, and concentrated under reduced pressure to give a residue. The residue was purified by prep-HPLC (column: Phenomenex Luna C18 150×25 mm×10 μm; mobile phase: [water (0.225% FA)-ACN]; B %: 23%-53%, 10 min) to give the title compound (18.14 mg, 22% yield). Yellow solid. $^1$H NMR (400 MHz, methanol-$d_4$) δ 7.78-7.73 (m, 1H), 7.72-7.65 (m, 1H), 7.44-7.38 (m, 2H), 7.25 (t, J=9.2 Hz, 1H), 4.81-4.44 (m, 2H), 4.28-4.12 (m, 2H), 4.07 (dd, J=3.6 Hz, 17.6 Hz, 1H), 3.74-3.63 (m, 2H), 3.55-3.42 (m, 4H), 3.29-3.08 (m, 5H), 2.85-2.68 (m, 3H), 2.11-1.83 (m, 7H), 1.82-1.61 (m, 5H), 1.27 (s, 3H), 1.17-1.11 (t, J=7.2 Hz, 3H); SFC analysis >99.9%, $t_R$=0.557 min, Column: Chiralcel IC-3 50×4.6 mm I.D., 3 μm Mobile phase: Phase A for $CO_2$, and Phase B for MeOH+ACN (0.05% DEA); Gradient elution: 60% MeOH+ACN (0.05% DEA) in $CO_2$. Flow rate: 3 mL/min; Detector: 220 nm; LCMS (ESI, M+1): m/z 560.4.

Example 4

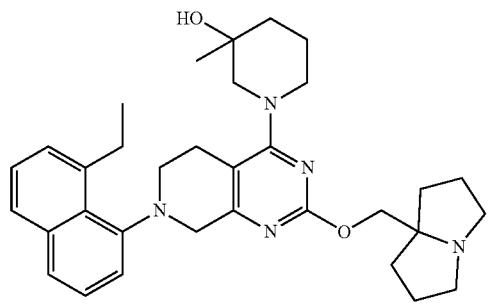 [SMILES: CCc1cccc2cccc(N3CCc4c(nc(OCC56CCCN5CCC6)nc4N4CCCC(C)(O)C4)C3)c12]

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol

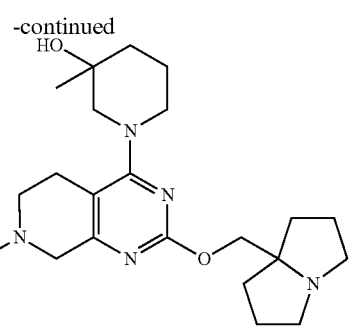

Step A. 1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-3-methylpiperidin-3-ol: To a solution of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (100 mg, 167 μmol), 4A molecular sieve (10 mg) and N-ethyl-N-isopropylpropan-2-amine (108 mg, 835 μmol, 145 μL) in DMF (1 mL) was added 3-methylpiperidin-3-ol (50.7 mg, 334 μmol, HCl). The mixture was stirred at 40° C. for 12 hours. After completion, the mixture was purified by prep-HPLC (column: Phenomenex Luna C18 150×25 mm×10 μm; mobile phase: [water (0.225% FA)-ACN]; B %: 25%-55%, 10 min) to afford the title compound (21.2 mg, 23% yield) as white solid. $^1$H NMR (400 MHz, DMSO-$d_6$) δ=7.76 (d, J=8.0 Hz, 1H), 7.70 (d, J=8.0 Hz, 1H), 7.49-7.42 (m, 1H), 7.41-7.36 (m, 1H), 7.36-7.31 (m, 1H), 7.30 (d, J=6.8 Hz, 1H), 4.02 (s, 2H), 3.75-3.68 (m, 1H), 3.65-3.59 (m, 2H), 3.54-3.45 (m, 4H), 3.27-3.18 (m, 2H), 3.16-2.97 (m, 6H), 2.80-2.70 (m, 2H), 1.99-1.71 (m, 7H), 1.71-1.47 (m, 5H), 1.18-1.05 (m, 6H); LCMS [ESI, M+H]: m/z 542.4.

Example 5

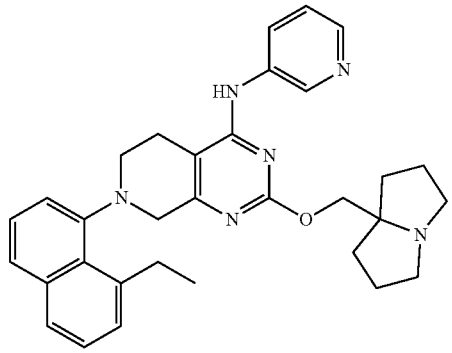 [SMILES: CCc1cccc2cccc(N3CCc4c(nc(OCC56CCCN5CCC6)nc4Nc4cccnc4)C3)c12]

7-(8-ethylnaphthalen-1-yl)-2-((hexahydro-1H-pyrrolizin-7a-yl)methoxy)-N-(pyridin-3-yl)-5,6,7,8-tetrahydropyrido[3,4-d]pyrimidin-4-amine

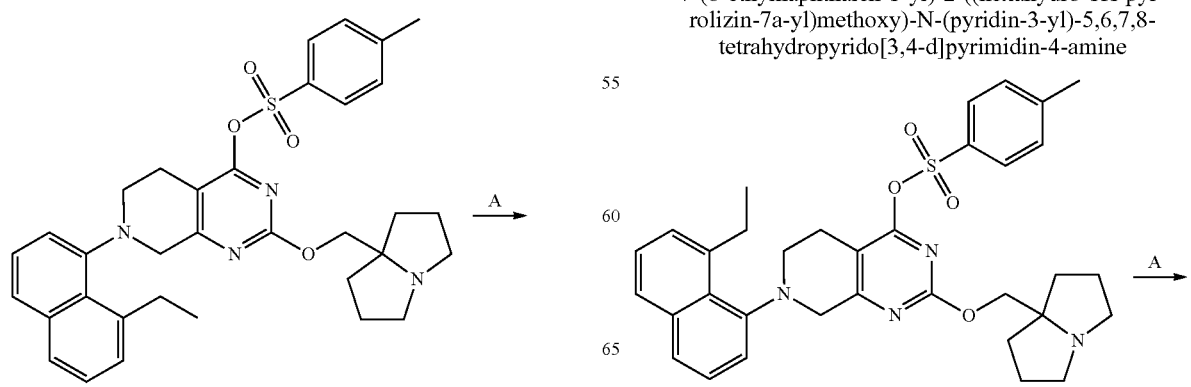

-continued

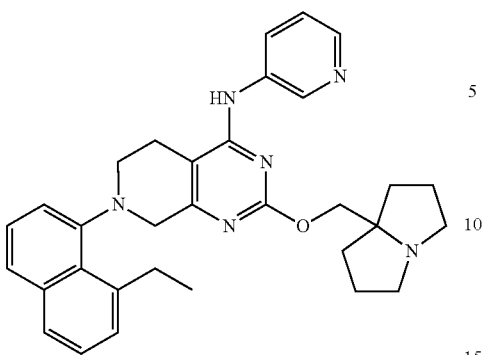

Step A. 7-(8-ethylnaphthalen-1-yl)-2-((hexahydro-1H-pyrrolizin-7a-yl)methoxy)-N-(pyridin-3-yl)-5,6,7,8-tetrahydropyrido[3,4-d]pyrimidin-4-amine: A mixture of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (80.0 mg, 134 μmol), pyridin-3-amine (50.3 mg, 534 μmol, 28.7 μL), BINAP (16.6 mg, 26.7 μmol), Pd(OAc)$_2$ (3.00 mg, 13.4 μmol) and Cs$_2$CO$_3$ (87.1 mg, 267 μmol) in toluene (1 mL) was degassed and purged with N$_2$ for 3 times. The mixture was stirred at 110° C. for 2 hours under N$_2$ atmosphere. The reaction mixture was quenched with water (10 mL) and extracted with EtOAc (5 mL×3). The combined organic layers were washed with brine (5 mL) and dried over Na$_2$SO$_4$. The mixture was filtered and concentrated under reduced pressure to give a residue. The residue was purified by prep-HPLC twice (column: 3_Phenomenex Luna C18 75×30 mm×3 μm; mobile phase: [water (0.2% FA)-ACN]; B %: 20%-50%, 8 min. column: Phenomenex Gemini-NX 80×30 mm×3 μm; mobile phase: [water (10 mM NH$_4$HCO$_3$)-ACN]; B %: 35%-85%, 10 min) to afford the title compound (5.56 mg, 52% yield) as a yellow solid. $^1$H NMR (400 MHz, CDCl$_3$) δ=8.72 (s, 1H), 8.35 (br d, J=4.9 Hz, 2H), 7.69 (dd, J=8.0, 14.8 Hz, 2H), 7.40 (td, J=7.7, 17.7 Hz, 3H), 7.29 (br d, J=4.8 Hz, 2H), 7.31-7.27 (m, 1H), 6.45 (s, 1H), 4.21-4.09 (m, 3H), 3.85 (br d, J=17.4 Hz, 1H), 3.64 (br s, 1H), 3.47-3.33 (m, 2H), 3.22-3.10 (m, 3H), 2.99-2.88 (m, 1H), 2.71-2.54 (m, 3H), 2.11-2.03 (m, 2H), 1.91-1.82 (m, 5H), 1.69-1.62 (m, 1H), 1.13 (t, J=7.3 Hz, 3H). LCMS (ESI, M+1): m/z 521.3.

General Procedure for EXAMPLE 6 to 14.

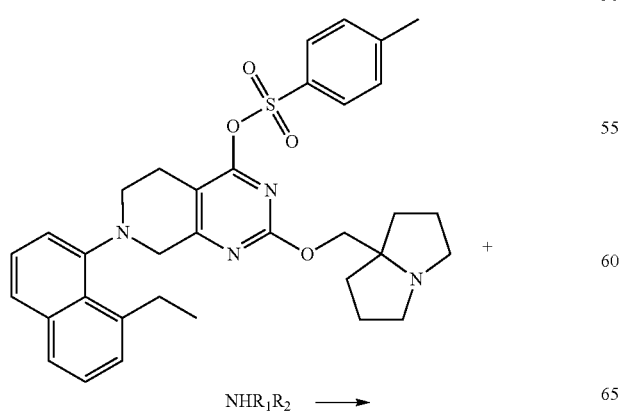

NHR$_1$R$_2$ ⟶

-continued

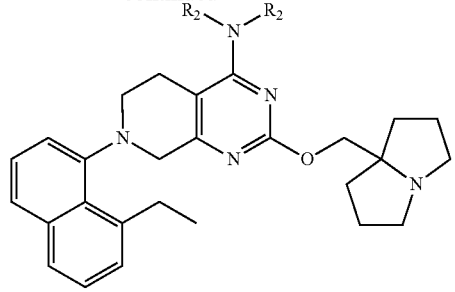

A mixture of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (1 equiv.), amine (2 equiv.), and N-ethyl-N-isopropylpropan-2-amine (3 equiv. or 5/7 equiv. for amine hydro/dihydro chlorides) in DMSO (1 mL) was heated with stirring at 40° C. for 16 hours. The resulting solution was cooled to room temperature and subjected to HPLC purification (deionized water/HPLC-grade methanol, ammonia) to give the product.

Example 6

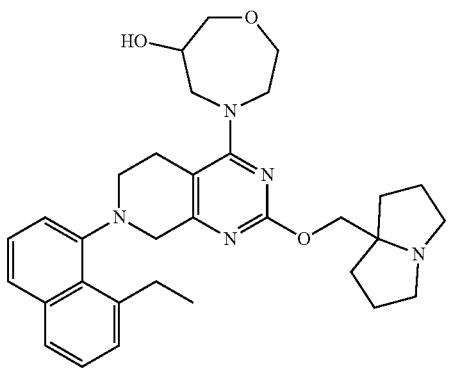 [SMILES: CCc1cccc2cccc(N3CCc4c(nc(OCC56CCCN5CCC6)nc4N4CCOCC(O)C4)C3)c12]

4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-1,4-oxazepan-6-ol LCMS (ESI, M+1): m/z 544.2

Example 7

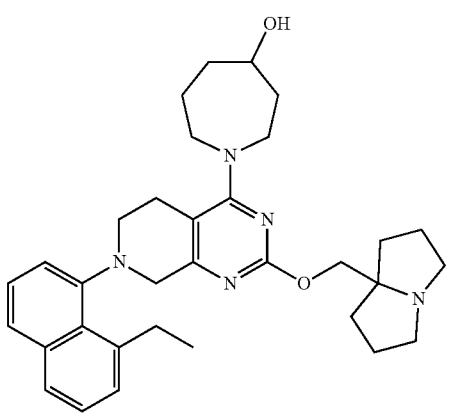 [SMILES: CCc1cccc2cccc(N3CCc4c(nc(OCC56CCCN5CCC6)nc4N4CCCC(O)CC4)C3)c12]

113

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)azepan-4-ol LCMS (ESI, M+1): m/z 542.2

Example 8

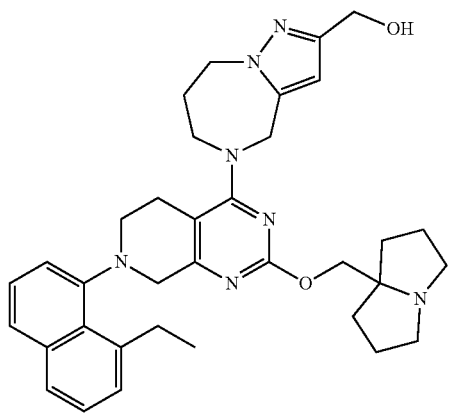 [SMILES: CCc1cccc2cccc(N3CCc4c(nc(OCC56CCCN5CCC6)nc4N4CCCn5nc(CO)cc5C4)C3)c12]

(5-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5,6,7,8-tetrahydro-4H-pyrazolo[1,5-a][1,4]diazepin-2-yl)methanol LCMS (ESI, M+1): m/z 594.2

Example 9

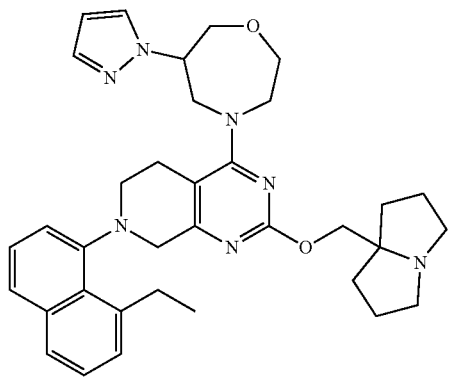 [SMILES: CCc1cccc2cccc(N3CCc4c(nc(OCC56CCCN5CCC6)nc4N4CCOCC(n5cccn5)C4)C3)c12]

114

4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-6-(1H-pyrazol-1-yl)-1,4-oxazepane LCMS (ESI, M+1): m/z 594.4

Example 10

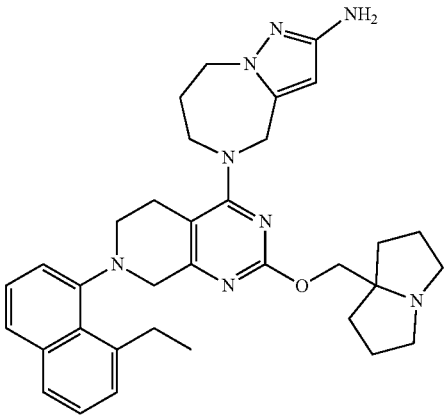 [SMILES: CCc1cccc2cccc(N3CCc4c(nc(OCC56CCCN5CCC6)nc4N4CCCn5nc(N)cc5C4)C3)c12]

5-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5,6,7,8-tetrahydro-4H-pyrazolo[1,5-a][1,4]diazepin-2-amine LCMS (ESI, M+1): m/z 579.4

Example 11

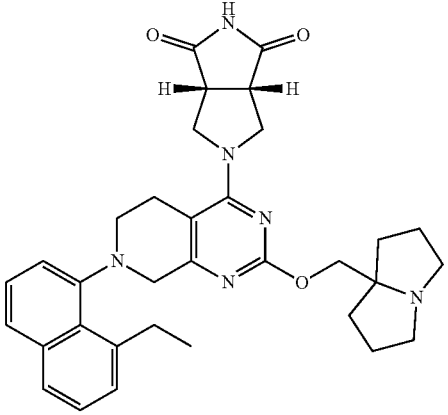 [SMILES: CCc1cccc2cccc(N3CCc4c(nc(OCC56CCCN5CCC6)nc4N4C[C@@H]5C(=O)NC(=O)[C@@H]5C4)C3)c12]

115

(3aR,6aS)-5-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)tetrahydropyrrolo[3,4-c]pyrrole-1,3(2H,3aH)-dione LCMS (ESI, M+1): m/z 567.4

Example 12

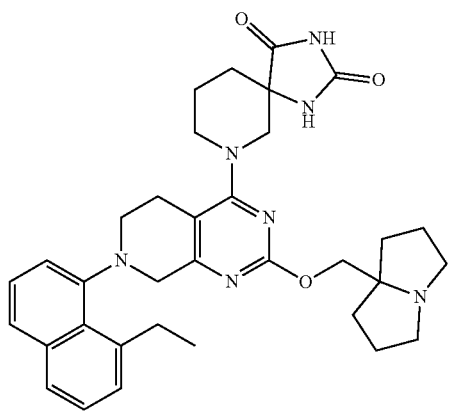 [SMILES: CCc1cccc2cccc(N3CCc4c(nc(OCC56CCCN5CCC6)nc4N4CCCC5(C4)NC(=O)NC5=O)C3)c12]

116

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5-(hydroxymethyl)azepan-4-ol LCMS (ESI, M+1): m/z 572.4

Example 14

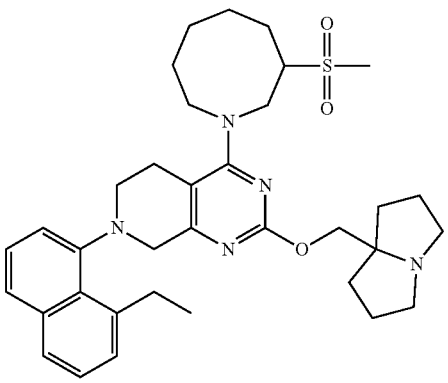

7-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-1,3,7-triazaspiro[4.5]decane-2,4-dione LCMS (ESI, M+1): m/z 596.2

Example 13

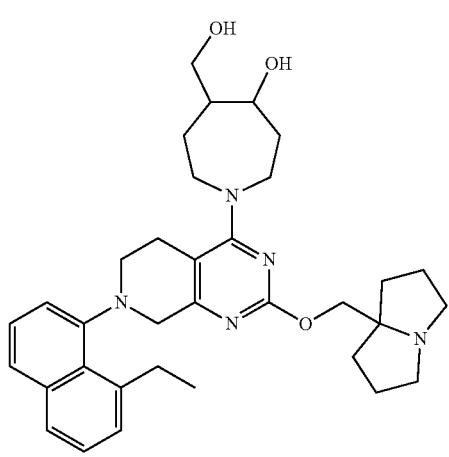 [SMILES: CCc1cccc2cccc(N3CCc4c(nc(OCC56CCCN5CCC6)nc4N4CCC(O)C(CO)CC4)C3)c12]

7-(8-ethylnaphthalen-1-yl)-4-(3-(methylsulfonyl)azocan-1-yl)-2-((tetrahydro-1H-pyrrolizin-7a(5H)-yl)methoxy)-5,6,7,8-tetrahydropyrido[3,4-d]pyrimidine LCMS (ESI, M+1): m/z 618.4

Example 15

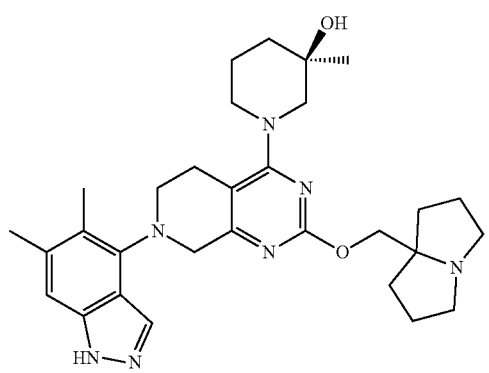 [SMILES: Cc1cc2[nH]ncc2c(N2CCc3c(nc(OCC45CCCN4CCC5)nc3N3CCC[C@@](C)(O)C3)C2)c1C]

(R)-1-(7-(5,6-dimethyl-1H-indazol-4-yl)-2-((hexahydro-1H-pyrrolizin-7a-yl)methoxy)-5,6,7,8-tetrahydropyrido[3,4-d]pyrimidin-4-yl)-3-methylpiperidin-3-ol

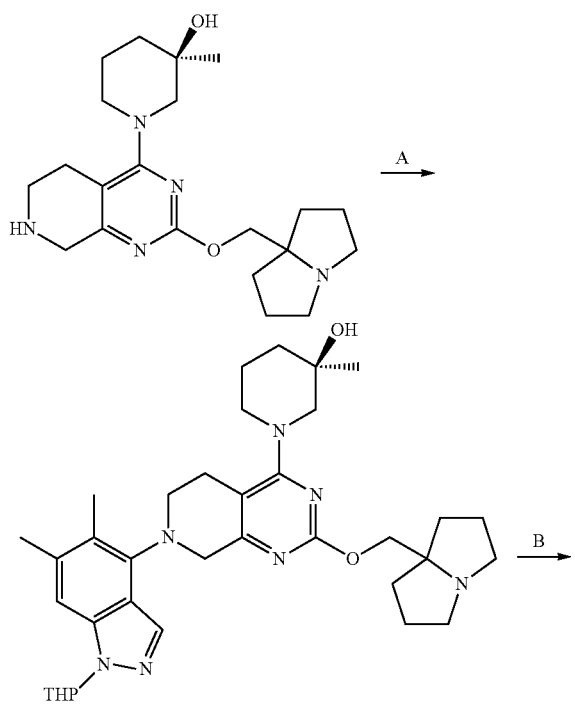

dried over anhydrous sodium sulfate and concentrated under vacuum to afford the title compound (90 mg, 56.3% yield) as a white solid. LCMS (ESI, M+1): m/z=616.5.

Step B. ((R)-1-(7-(5,6-dimethyl-1H-indazol-4-yl)-2-((hexahydro-1H-pyrrolizin-7a-yl)methoxy)-5,6,7,8-tetrahydropyrido[3,4-d]pyrimidin-4-yl)-3-methylpiperidin-3-ol: To a solution of (3R)-1-(7-(5,6-dimethyl-1-(tetrahydro-2H-pyran-2-yl)-1H-indazol-4-yl)-2-((tetrahydro-1H-pyrrolizin-7a(5H)-yl)methoxy)-5,6,7,8-tetrahydropyrido[3,4-d]pyrimidin-4-yl)-3-methylpiperidin-3-ol (85 mg, 138 µmol, 1.0 equiv) in DCM (0.5 mL) was added TFA (770 mg, 6.75 mmol, 0.5 mL). The reaction was stirred at 25° C. for 1 hour. The mixture was added dropwise to ice saturated NaHCO₃ solution (30 mL) and the pH was adjusted to 8. Then the mixture was extracted with dichloromethane (20 mL). The organic layer was washed with brine (20 mL), dried over anhydrous sodium sulfate, filtered, and concentrated to give a residue. The residue was purified by prep-HPLC [column: Unisil 3-100 C18 Ultra 150×50 mm×3 µm; A: water (FA); B: ACN, B %: 6%-36% over 10 min] to afford the title compound (35.7 mg, 47.9% yield, 98.5% purity) as white solid. ¹H NMR (400 MHz, Acetic) δ=8.24 (s, 1H), 8.12 (s, 1H), 7.35 (s, 1H), 4.85-4.73 (m, 2H), 4.48-4.22 (m, 4H), 3.90-3.78 (m, 2H), 3.63-3.51 (m, 3H), 3.49-3.36 (m, 1H), 3.27 (td, J=6.2, 11.9 Hz, 2H), 3.20-2.82 (m, 2H), 2.46-2.42 (m, 3H), 2.42-2.35 (m, 5H), 2.29-2.19 (m, 4H), 2.16-2.09 (m, 3H), 1.97-1.89 (m, 1H), 1.83-1.70 (m, 2H), 1.36 (s, 3H); LCMS (ESI, M+1): m/z=532.4.

Example 16

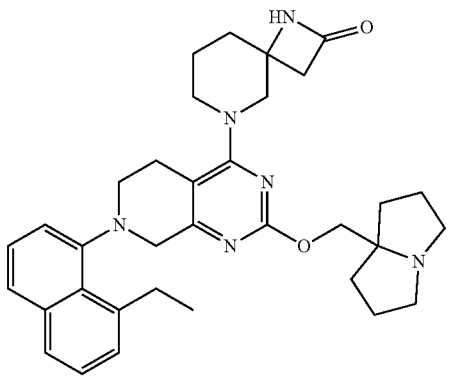 [SMILES: CCc1cccc2cccc(N3CCc4c(nc(OCC56CCCN5CCC6)nc4N4CCCC5(CC(=O)N5)C4)C3)c12]

6-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-1,6-diazaspiro[3.5]nonan-2-one Step A. (3R)-1-(7-(5,6-dimethyl-1-(tetrahydro-2H-pyran-2-yl)-1H-indazol-4-yl)-2-((tetrahydro-1H-pyrrolizin-7a(5H)-yl)methoxy)-5,6,7,8-tetrahydropyrido[3,4-d]pyrimidin-4-yl)-3-methylpiperidin-3-ol: A mixture of (R)-3-methyl-1-(2-((tetrahydro-1H-pyrrolizin-7a(5H)-yl)methoxy)-5,6,7,8-tetrahydropyrido[3,4-d]pyrimidin-4-yl)piperidin-3-ol (100 mg, 1 equiv), 4-bromo-5,6-dimethyl-1-tetrahydropyran-2-yl-indazole (95.8 mg, 1.2 equiv), Cs₂CO₃ (252 mg, 3 equiv), RuPhos (48.2 mg, 0.4 equiv), Pd₂(dba)₃ (47.3 mg, 0.2 equiv) and 4 Å molecular sieve (10 mg) in toluene (2 mL) was degassed and purged with N₂ for 3 times, and then the reaction was stirred at 90° C. for 8 hours under N₂ atmosphere. The mixture was filtered and concentrated under vacuum to give a residue. The residue was purified by reversed phase flash chromatography [water (0.10% FA)/acetonitrile]. The desired fractions were collected, neutralized with solid NaHCO₃, and concentrated under vacuum to remove acetonitrile. The aqueous layer was extracted with ethyl acetate (2×10 mL). The combined organic layers were

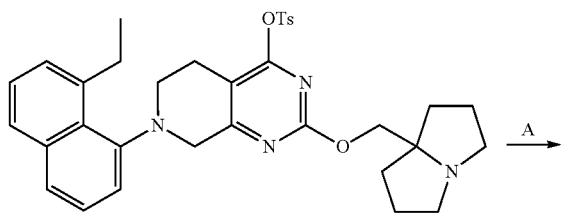

119
-continued

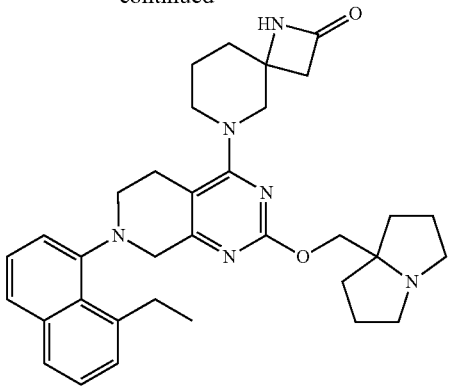

Step A. 6-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-1,6-diazaspiro[3.5]nonan-2-one: To the mixture of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv), 1,6-diazaspiro[3.5]nonan-2-one (32.8 mg, 1.4 equiv) in DMF (1.0 mL) was added N-ethyl-N-isopropylpropan-2-amine (108 mg, 5.0 equiv). The reaction was stirred at 30° C. for 12 hours. The mixture was filtered and purified with prep-HPLC [column: Phenomenex Synergi C18 150×25 mm×10 μm; mobile phase: water (0.225% FA)-ACN; B %: 19%-49%, 10 min] and lyophilized to afford the title compound (53.8 mg, 55% yield) as white solid. $^1$H NMR (400 MHz, methanol-d4): δ=8.53 (s, 1H), 7.74-7.65 (m, 2H), 7.46-7.40 (m, 1H), 7.38-7.27 (m, 3H), 4.45-4.33 (m, 2H), 4.11 (br d, J=18 Hz, 1H), 3.93-3.80 (m, 1H), 3.71-3.66 (m, 1H), 3.65-3.47 (m, 6H), 3.16-3.09 (m, 1H), 3.28-3.08 (m, 1H), 3.07-2.98 (m, 1H), 2.87 (d, J=14.8 Hz, 1H), 2.90-2.65 (m, 1H), 2.26-2.18 (m, 2H), 2.17-2.03 (m, 4H), 1.97 (dt, J=6.8, 12.4 Hz, 4H), 1.90 (br d, J=3.2 Hz, 2H), 1.15 (t, J=7.2 Hz, 3H); LCMS (ESI, M+1): m/z=567.4.

Example 17

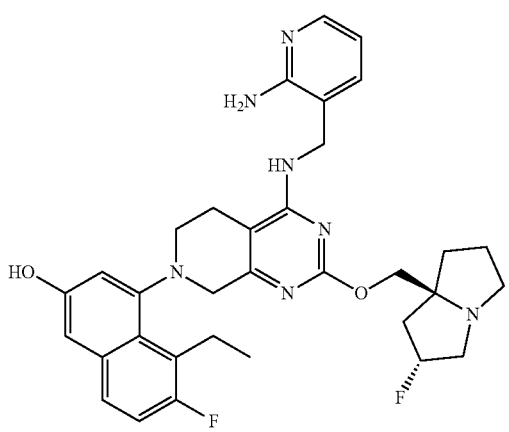 [SMILES: CCc1c(F)ccc2cc(O)cc(N3CCc4c(nc(OC[C@@]56CCCN5C[C@H](F)C6)nc4NCc4cccnc4N)C3)c12]

120
4-(4-(((2-aminopyridin-3-yl)methyl)amino)-2-(((2R,7aS)-2-fluorohexahydro-1H-pyrrolizin-7a-)yl)methoxy)-5,6-dihydropyrido[3,4-d]pyrimidin-7(8H)-yl)-5-ethyl-6-fluoronaphthalen-2-ol

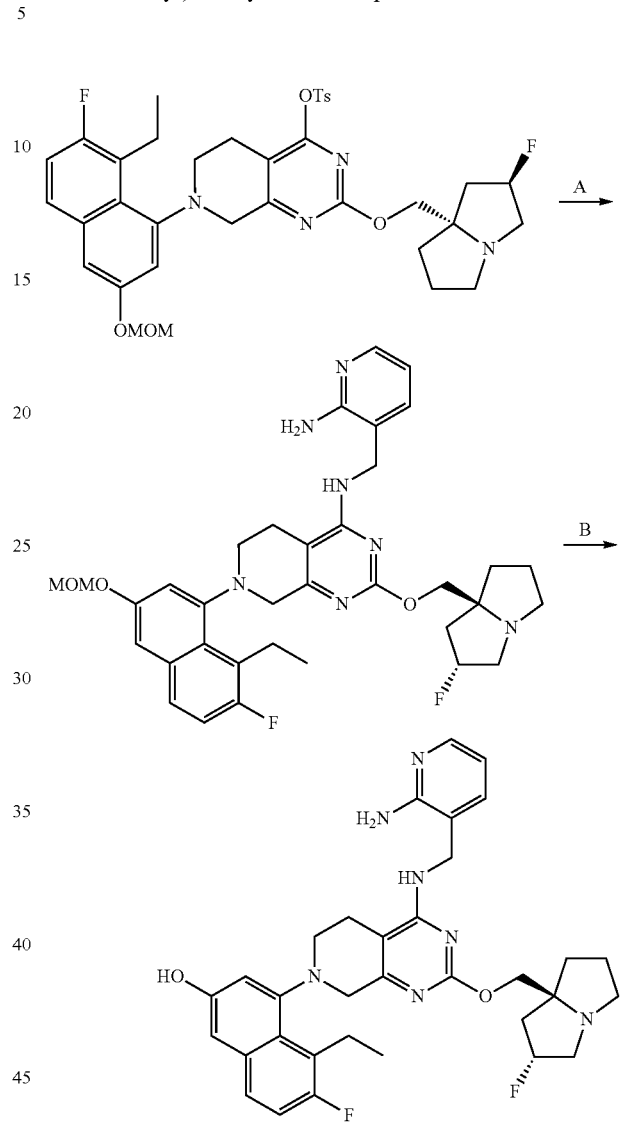

Step A. N-((2-aminopyridin-3-yl)methyl)-7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-amine: To the mixture of 7-(8-ethyl-7-fluoro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl 4-methylbenzenesulfonate (120 mg, 1.0 equiv), 4 Å molecular sieve (10 mg) and N-ethyl-N-isopropylpropan-2-amine (112 mg, 5.0 equiv) in DMAc (2.0 mL) was added 3-(aminomethyl)pyridin-2-amine (31.9 mg, 1.50 equiv). The mixture was stirred at 40° C. until the reaction was completed. The mixture was quenched with water (5 mL) and extracted with ethyl acetate (3×5 mL). The combined organic layers were dried over anhydrous sodium sulfate, concentrated, and purified by reversed phase flash chromatography [C18, 0.1% formic acid condition] to afford the title compound (40 mg, 36% yield) as yellow solid. LCMS (ESI, M+1): m/z=646.4.

Step B. 4-(4-(((2-aminopyridin-3-yl)methyl)amino)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol: To the solution of N-((2-aminopyridin-3-yl)methyl)-7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-amine (35.0 mg, 1.0 equiv) in DCM (1 mL) was added TFA (1.54 g). The mixture was stirred at 20° C. for 0.5 hour. The mixture was treated with saturated NaHCO₃ aqueous solution to adjust pH to ~8 at 0° C. and extracted with dichloromethane (3×5 mL). The organic layer was dried over anhydrous sodium sulfate, concentrated, and purified by prep-HPLC [column: Phenomenex Gemini-NX C18 75×30 mm×3 μm; mobile phase: water (0.225% FA)-ACN; B %: 18%-28%, 7 min] to afford the title compound (6.19 mg, 19% yield) as yellow solid. $^1$H NMR (400 MHz, methanol-d4) δ=8.50 (br s, 1H), 7.87 (dd, J=1.6, 5.2 Hz, 1H), 7.55-7.44 (m, 2H), 7.14 (t, J=9.6 Hz, 1H), 7.02 (d, J=2.4 Hz, 1H), 6.97 (d, J=2.4 Hz, 1H), 6.67 (dd, J=5.2, 7.2 Hz, 1H), 5.54-5.25 (m, 1H), 4.68-4.48 (m, 2H), 4.36-4.15 (m, 2H), 3.90 (br d, J=17.2 Hz, 1H), 3.68 (br d, J=16.8 Hz, 1H), 3.61-3.45 (m, 4H), 3.33 (br s, 2H), 3.26-3.11 (m, 2H), 2.90-2.75 (m, 1H), 2.55 (br d, J=14.4 Hz, 1H), 2.49-2.27 (m, 2H), 2.25-2.06 (m, 3H), 2.05-1.89 (m, 1H), 1.04 (dt, J=1.6, 7.2 Hz, 3H); LCMS (ESI, M+1): m/z=602.3.

Example 18

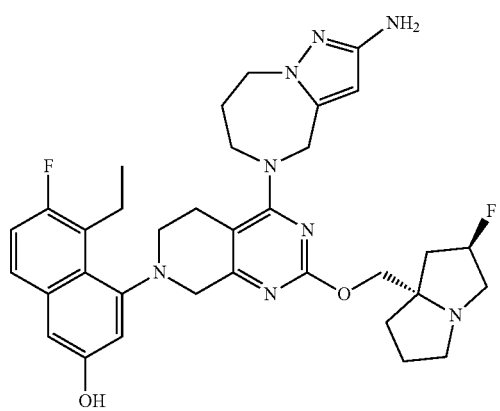 [SMILES: CCc1c(F)ccc2cc(O)cc(N3CCc4c(nc(OC[C@@]56CCCN5C[C@H](F)C6)nc4N4CCCn5nc(N)cc5C4)C3)c12]

4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 17. The title compound was obtained as white solid. $^1$H NMR (400 MHz, methanol-d4) δ=7.42 (dd, J=6.0, 9.2 Hz, 1H), 7.05 (t, J=9.2 Hz, 1H), 6.91-6.78 (m, 2H), 5.46 (d, J=2.4 Hz, 1H), 5.26-5.07 (m, 1H), 4.69 (s, 1H), 4.62-4.55 (m, 1H), 4.17-4.09 (m, 2H), 4.03 (dd, J=3.6, 7.2 Hz, 1H), 4.01-3.92 (m, 3H), 3.91-3.83 (m, 1H), 3.62 (dd, J=3.6, 18.0 Hz, 1H), 3.43-3.37 (m, 1H), 3.36-3.27 (m, 2H), 3.16-3.01 (m, 5H), 2.95-2.85 (m, 1H), 2.60 (br d, J=14.4 Hz, 1H), 2.20-2.03 (m, 3H), 2.01-1.91 (m, 2H), 1.90-1.71 (m, 3H), 1.07-0.99 (m, 3H); LCMS (ESI, M+1): m/z=631.4.

Example 19

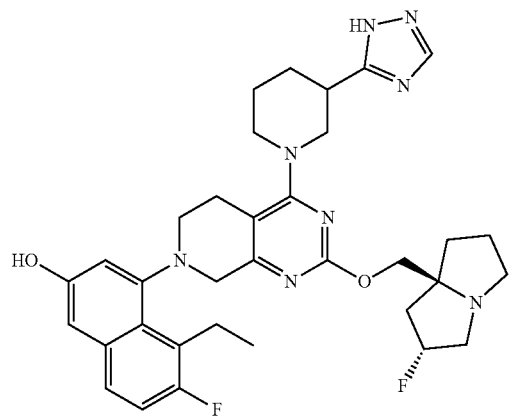 [SMILES: CCc1c(F)ccc2cc(O)cc(N3CCc4c(nc(OC[C@@]56CCCN5C[C@H](F)C6)nc4N4CCCC(c5ncn[nH]5)C4)C3)c12]

4-(4-(3-(1H-1,2,4-triazol-5-yl)piperidin-1-yl)-2-(((2R,7aS)-2-fluorotetrahydro-1H-pyrrolizin-7a(5H)-yl)methoxy)-5,8-dihydropyrido[3,4-d]pyrimidin-7(6H)-yl)-5-ethyl-6-fluoronaphthalen-2-ol Synthesized according to Example 17. The title compound was obtained as yellow solid (TFA). $^1$H NMR (400 MHz, methanol-d4): δ 8.36 (s, 1H), 7.53 (dd, J=5.6, 9.2 Hz, 1H), 7.16 (t, J=9.2 Hz, 1H), 7.05-6.97 (m, 2H), 5.66-5.43 (m, 1H), 4.73-4.53 (m, 3H), 4.38-4.22 (m, 1H), 4.21-4.08 (m, 1H), 4.00-3.83 (m, 3H), 3.82-3.67 (m, 1H), 3.58-3.36 (m, 6H), 3.27-3.12 (m, 3H), 2.80-2.53 (m, 3H), 2.46-2.24 (m, 4H), 2.21-1.69 (m, 4H), 1.12 (t, J=7.2 Hz, 3H); LCMS (ESI, M+1): m/z=631.4.

Example 20

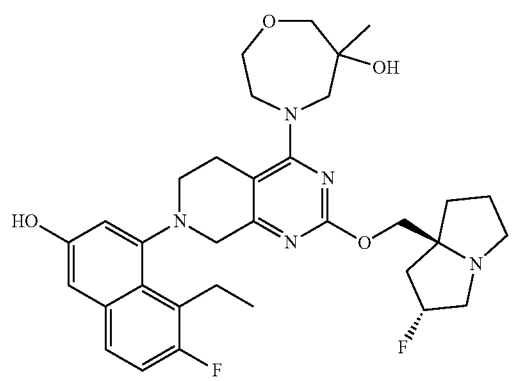 [SMILES: CCc1c(F)ccc2cc(O)cc(N3CCc4c(nc(OC[C@@]56CCCN5C[C@H](F)C6)nc4N4CCOCC(C)(O)C4)C3)c12]

4-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-methyl-1,4-oxazepan-6-ol Synthesized according to Example 17. The title compound was obtained as blue solid. $^1$H NMR (400 MHz, methanol-d4) δ=8.51 (s, 1H), 7.56-7.45 (m, 1H), 7.19-7.08 (m, 1H), 7.05-6.89 (m, 2H), 5.46-5.27 (m, 1H), 4.37-3.91 (m, 6H), 3.90-3.68 (m, 3H), 3.67-3.51 (m, 3H), 3.50-3.35 (m, 6H), 3.26-3.07 (m, 3H), 2.82-2.58 (m, 1H), 2.47-2.25 (m, 2H), 2.23-2.03 (m, 3H), 2.00-1.86 (m, 1H), 1.19 (s, 3H), 1.09 (t, J=7.2 Hz, 3H); LCMS (ESI, M+1): m/z=610.3.

Example 21

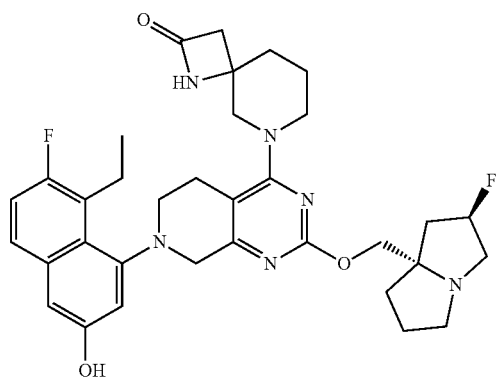 [SMILES: CCc1c(F)ccc2cc(O)cc(N3CCc4c(nc(OC[C@@]56CCCN5C[C@H](F)C6)nc4N4CCCC5(CC(=O)N5)C4)C3)c12]

6-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,6-diazaspiro[3.5]nonan-2-one Synthesized according to Example 17. The title compound was obtained as white solid. ¹H NMR (400 MHz, methanol-d$_4$) δ=7.51 (dd, J=5.6, 8.8 Hz, 1H), 7.14 (t, J=9.6 Hz, 1H), 7.02-6.94 (m, 2H), 5.35-5.17 (m, 1H), 4.20-4.08 (m, 2H), 4.08-3.84 (m, 2H), 3.83-3.57 (m, 3H), 3.56-3.36 (m, 4H), 3.23-3.13 (m, 5H), 3.04-2.92 (m, 1H), 2.88-2.64 (m, 3H), 2.30-2.03 (m, 3H), 2.02-1.88 (m, 5H), 1.87-1.78 (m, 2H), 1.11 (t, J=7.2 Hz, 3H); LCMS (ESI, M+1): m/z=619.3

Example 22

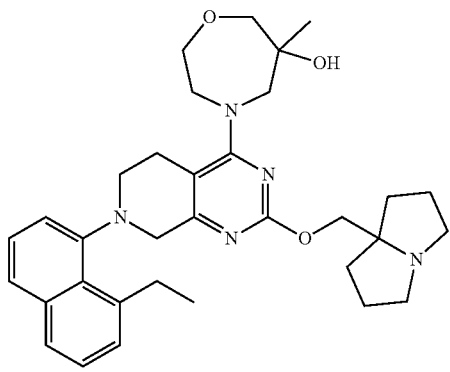 [SMILES: CCc1cccc2cccc(N3CCc4c(nc(OCC56CCCN5CCC6)nc4N4CCOCC(C)(O)C4)C3)c12]

4-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-methyl-1,4-oxazepan-6-ol

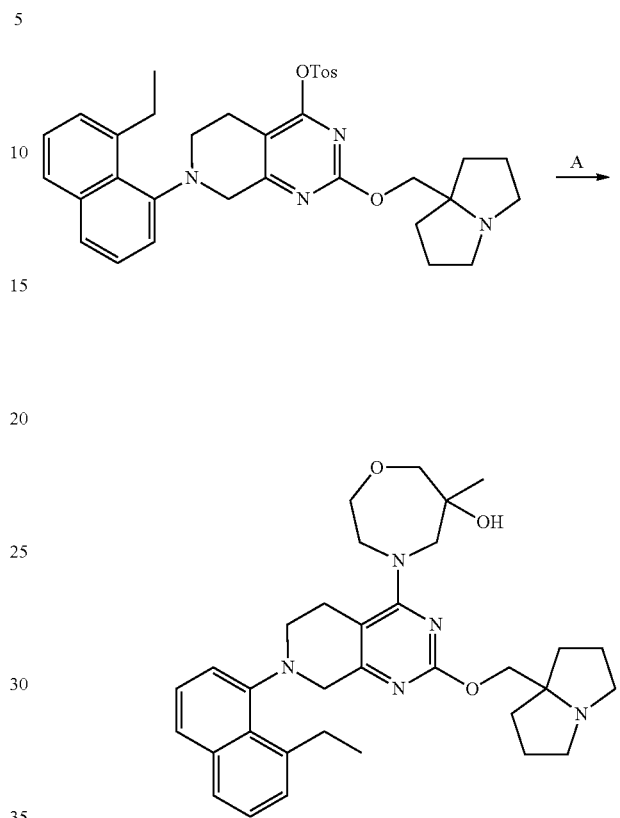

Step A 4-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-methyl-1,4-oxazepan-6-ol: A mixture of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (60 mg, 1.0 equiv), 6-methyl-1,4-oxazepan-6-ol (20 mg, 1.5 equiv), N-ethyl-N-isopropylpropan-2-amine (53 μL, 3.0 equiv) and 4 Å MS (20 mg) in DMF (0.8 mL) was stirred at 40° C. for 15 hours. The reaction mixture was diluted with water (20 mL), and extracted with ethyl acetate (20 mL×4). The combined organic layers were dried over anhydrous sodium sulfate, concentrated, and purified with prep-HPLC [column: Phenomenex Luna C18 150×25 mm×10 μm; mobile phase: water (0.225% FA)-ACN; B %: 20%-50%, 2 min] to afford the title compound (46.5 mg, 77% yield) as yellow solid. ¹H NMR (400 MHz, methanol-d4) δ=7.73-7.63 (m, 2H), 7.46-7.25 (m, 4H), 4.40-4.32 (m, 2H), 4.24-3.98 (m, 3H), 3.96-3.75 (m, 3H), 3.73-3.58 (m, 3H), 3.57-3.42 (m, 5H), 3.28-3.19 (m, 2H), 3.17-2.97 (m, 3H), 2.82-2.60 (m, 1H), 2.26-2.04 (m, 6H), 2.03-1.94 (m, 2H), 1.20 (s, 3H), 1.14 (t, J=7.2 Hz, 3H). LCMS (ESI, M+1): m/z=558.4.

Example 23

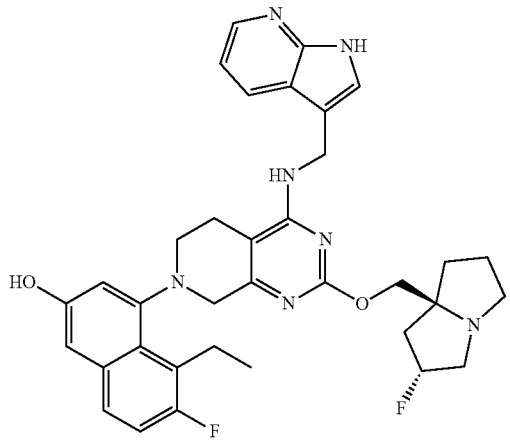 [SMILES: CCc1c(F)ccc2cc(O)cc(N3CCc4c(nc(OC[C@@]56CCCN5C[C@H](F)C6)nc4NCc4c[nH]c5ncccc45)C3)c12]

4-(4-(((1H-pyrrolo[2,3-b]pyridin-3-yl)methyl)amino)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol

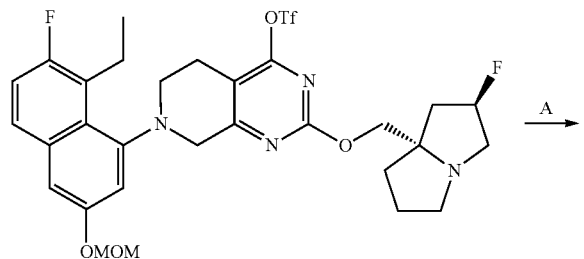

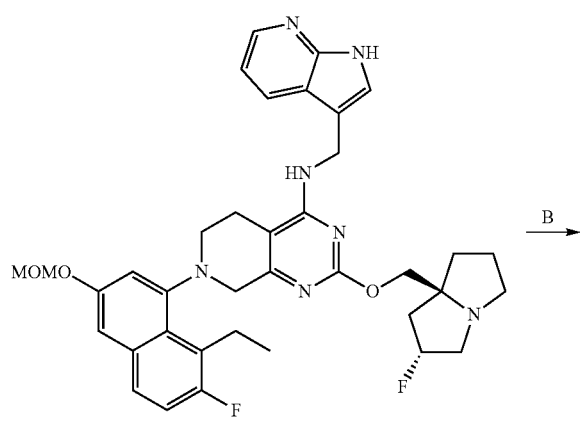

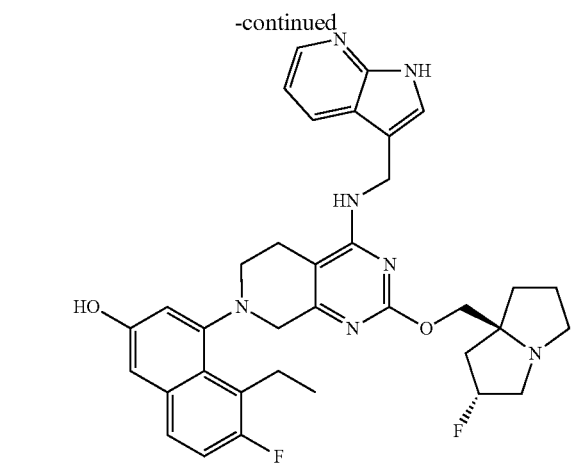

Step A. N-((1H-pyrrolo[2,3-b]pyridin-3-yl)methyl)-7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-amine: To a mixture of 7-(8-ethyl-7-fluoro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl trifluoromethanesulfonate (30.0 mg, 1.0 equiv), 4 Å molecular sieve (10.0 mg) and N-ethyl-N-isopropylpropan-2-amine (28.8 mg, 5.0 equiv) in DMAc (1.0 mL) was added 1H-pyrrolo[2,3-b]pyridin-3-ylmethanamine (13.1 mg, 2.0 equiv). The mixture was stirred at 40° C. until the reaction was completed. The mixture was diluted with water (5 mL) and extracted with ethyl acetate (3×5 mL). The combined organic layers were dried over anhydrous sodium sulfate, concentrated, and purified by reversed phase flash chromatography [C18, 0.1% formic acid condition] to afford the title compound (30 mg, crude) as yellow solid. LCMS (ESI, M+1): m/z=670.4.

Step B. 4-(4-(((1H-pyrrolo[2,3-b]pyridin-3-yl)methyl)amino)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol: To the mixture of N-((1H-pyrrolo[2,3-b]pyridin-3-yl)methyl)-7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-amine (20.0 mg, 1.0 equiv) in MeOH (1.0 mL) was added HCl·MeOH (4 M, 1.5 mL). The mixture was stirred at 0° C. for 1 hour. After completion, the mixture was treated with saturated NaHCO₃ aqueous solution to adjust pH to ~8 at 0° C. and extracted with dichloromethane (3×5 mL). The combined organic layers were dried over anhydrous sodium sulfate, concentrated, and purified by prep-HPLC [column: Phenomenex Luna C18 150×25 mm×10 µm; mobile phase: water (0.225% FA)-ACN; B %: 16%-46%, 10 min] to afford the title compound (5.20 mg, two steps 28% yield) as off-white solid. ¹H NMR (400 MHz, methanol-d4) δ=8.51 (s, 1H), 8.19 (dd, J=1.6, 4.8 Hz, 1H), 8.11 (dd, J=1.6, 8.0 Hz, 1H), 7.50 (dd, J=6.0, 9.2 Hz, 1H), 7.41 (s, 1H), 7.17-7.08 (m, 2H), 7.00 (d, J=2.4 Hz, 1H), 6.96 (d, J=2.4 Hz, 1H), 5.47-5.26 (m, 1H), 4.98-4.89 (m, 2H), 4.37-4.28 (m, 1H), 4.27-4.19 (m, 1H), 3.88 (br d, J=17.2 Hz, 1H), 3.66 (br d, J=16.8 Hz, 1H), 3.59-3.43 (m, 4H), 3.35 (br s, 1H), 3.29-3.24 (m, 1H), 3.21-3.11 (m, 1H), 2.86-2.71 (m, 1H), 2.55-2.27 (m, 3H), 2.26-1.84 (m, 5H), 1.02 (dt, J=2.0, 7.2 Hz, 3H); LCMS (ESI, M+1): m/z=626.4.

Example 24

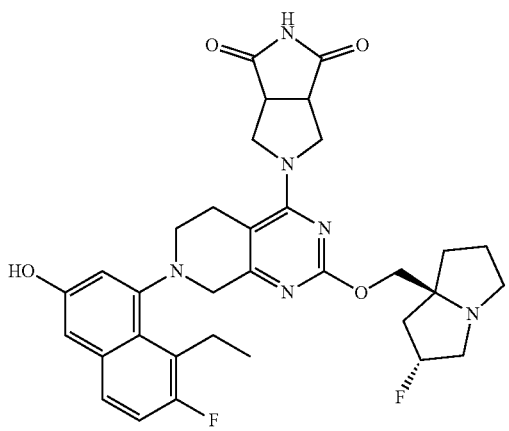 [SMILES: CCc1c(F)ccc2cc(O)cc(N3CCc4c(nc(OC[C@@]56CCCN5C[C@H](F)C6)nc4N4CC5C(=O)NC(=O)C5C4)C3)c12]

5-(7-(8-ethyl-7-fluoro-3-hydroxynaphthalen-1-yl)-2-
(((2R,7aS)-2-fluorohexahydro-1H-pyrrolizin-7a-yl)
methoxy)-5,6,7,8-tetrahydropyrido[3,4-d]pyrimidin-
4-yl)tetrahydropyrrolo[3,4-c]pyrrole-1,3(2H,3aH)-
dione Synthesized according to Example 23. The title compound was obtained as white solid. $^1$H NMR (400 MHz, CDCl$_3$) δ=8.38 (s, 1H), 7.47-7.37 (m, 1H), 7.09 (t, J=8.8 Hz, 1H), 6.93 (dd, J=2.0, 8.4 Hz, 1H), 6.75 (d, J=1.2 Hz, 1H), 5.53-5.26 (m, 1H), 4.65-4.52 (m, 1H), 4.52-4.11 (m, 4H), 3.94-3.63 (m, 3H), 3.52-3.41 (m, 1H), 3.40-3.24 (m, 6H), 3.22-3.08 (m, 2H), 3.06-2.87 (m, 1H), 2.82-2.48 (m, 2H), 2.47-2.19 (m, 4H), 2.17-2.08 (m, 2H), 1.05 (t, J=7.2 Hz, 3H); LCMS (ESI, M+1): m/z=619.4.

Example 25

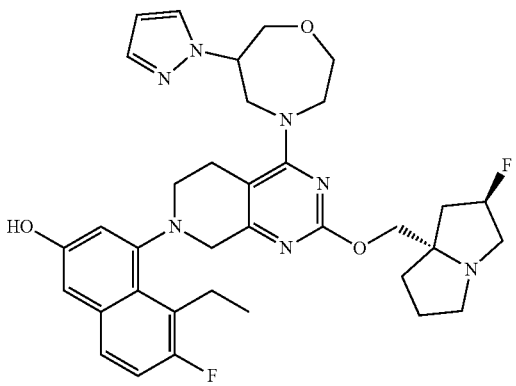 [SMILES: CCc1c(F)ccc2cc(O)cc(N3CCc4c(nc(OC[C@@]56CCCN5C[C@H](F)C6)nc4N4CCOCC(n5cccn5)C4)C3)c12]

4-(4-(6-(1H-pyrazol-1-yl)-1,4-oxazepan-4-yl)-2-
(((2R,7aS)-2-fluorohexahydro-1H-pyrrolizin-7a-yl)
methoxy)-5,6-dihydropyrido[3,4-d]pyrimidin-7(8H)-
yl)-5-ethyl-6-fluoronaphthalen-2-ol Synthesized according to Example 23. The title compound was obtained as yellow solid. $^1$H NMR (400 MHz, methanol-d4) δ=7.86-7.78 (m, 1H), 7.58-7.46 (m, 2H), 7.15 (t, J=9.2 Hz, 1H), 7.03-6.93 (m, 2H), 6.39-6.27 (m, 1H), 5.41-5.22 (m, 1H), 5.19-4.67 (m, 1H), 4.64-4.44 (m, 1H), 4.40-4.26 (m, 1H), 4.24-4.05 (m, 5H), 4.05-3.58 (m, 6H), 3.57-3.47 (m, 1H), 3.44-3.32 (m, 3H), 3.26-3.13 (m, 3H), 3.07-3.00 (m, 1H), 2.80-2.63 (m, 1H), 2.43-2.17 (m, 2H), 2.16-2.07 (m, 1H), 2.04-1.95 (m, 2H), 1.94-1.80 (m, 1H), 1.10 (t, J=7.2 Hz, 3H); LCMS (ESI, M+1): m/z=646.2.

Example 26

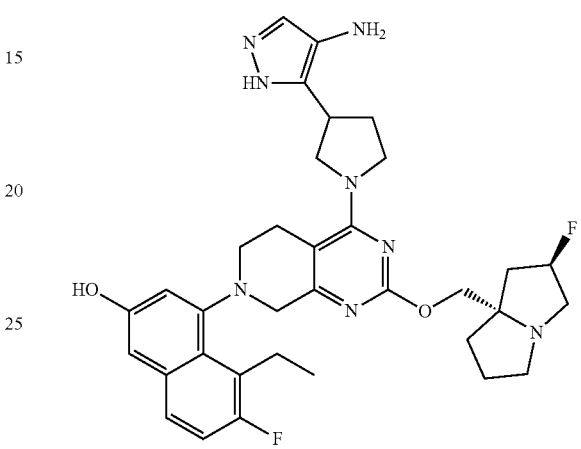

4-(4-(3-(4-amino-1H-pyrazol-5-yl)pyrrolidin-1-yl)-
2-(((2R,7aS)-2-fluorohexahydro-1H-pyrrolizin-7a-
yl)methoxy)-5,6-dihydropyrido[3,4-d]pyrimidin-7
(8H)-yl)-5-ethyl-6-fluoronaphthalen-2-ol Synthesized according to Example 23. The title compound was obtained as yellow solid. $^1$H NMR (400 MHz, methanol-d4) δ=7.54-7.46 (m, 1H), 7.26-7.18 (m, 1H), 7.16-7.09 (m, 1H), 7.04-6.92 (m, 2H), 5.48-5.19 (m, 1H), 4.32-4.12 (m, 3H), 4.10-3.79 (m, 4H), 3.73-3.55 (m, 2H), 3.54-3.32 (m, 7H), 3.21-3.07 (m, 2H), 3.06-2.93 (m, 1H), 2.42-2.12 (m, 5H), 2.08-1.99 (m, 2H), 1.97-1.86 (m, 1H), 1.15-1.04 (m, 3H); LCMS (ESI, M+1): m/z=631.2.

Example 27

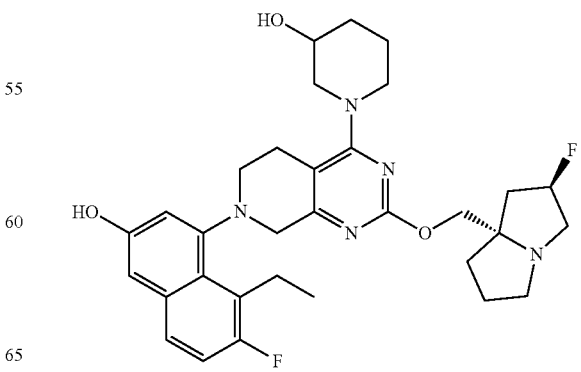

1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol

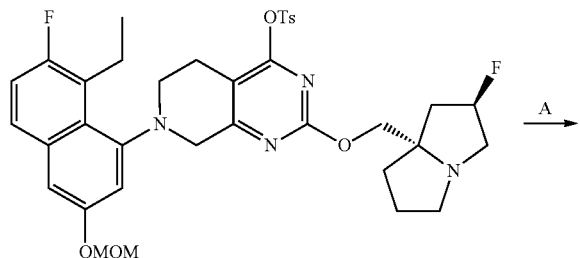

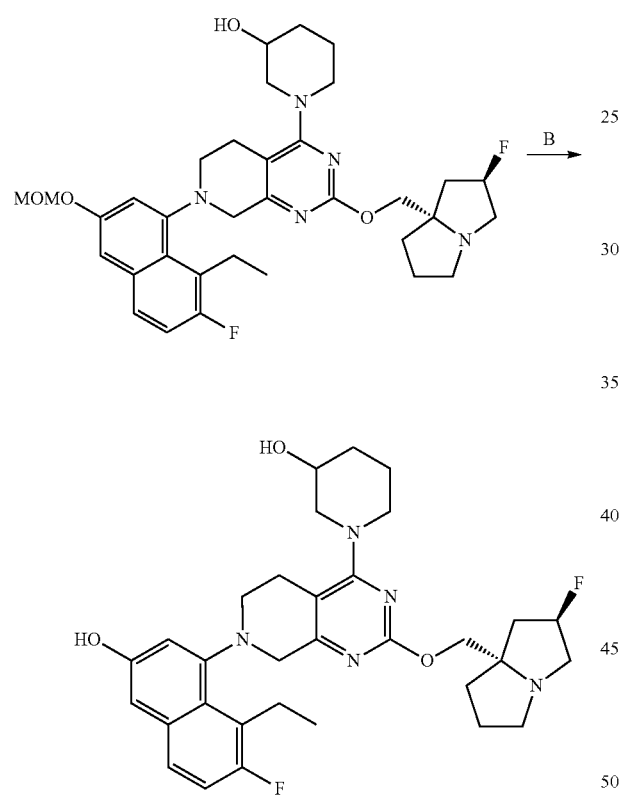

Step A. 1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol: To a mixture of 7-(8-ethyl-7-fluoro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl 4-methylbenzenesulfonate (150 mg, 1.0 equiv) and 4 Å MS (60 mg) in DMF (2.0 mL) were added N-ethyl-N-isopropylpropan-2-amine (112 mg, 4.0 equiv) and piperidin-3-ol (59.4 mg, 2 equiv, HCl). The mixture was stirred at 40° C. until the reaction was completed. The mixture was filtered, concentrated, and purified with reversed phase flash chromatography [C18, 0.1% FA in water, 0-40% ACN] to afford the title compound (80.0 mg, 58% yield) as yellow solid. LCMS (ESI, M+1): m/z=624.4.

Step B. 1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol: To a solution of 1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol (70.0 mg, 1.0 equiv) in DCM (1.0 mL) and MeOH (1.0 mL) was added TsOH (58.0 mg, 3.0 equiv). The mixture was stirred at 10° C. for 12 hours. The pH of reaction mixture was adjusted to 8 with saturated NaHCO$_3$ solution. The mixture was extracted with ethyl acetate (3×5 mL). The combined organic layers were dried over anhydrous sodium sulfate, concentrated, and purified with reversed phase flash chromatography [column: Waters Xbridge 150×25 mm×5 μm; mobile phase: [water (10 mM NH$_4$HCO$_3$)-ACN]; B %: 35%-65%, 9 min] to afford the title compound (37.7 mg, 57% yield) as white solid. $^1$H NMR (400 MHz, methanol-d4) δ=7.51 (dd, J=6.0, 9.2 Hz, 1H), 7.14 (t, J=9.6 Hz, 1H), 7.03-6.90 (m, 2H), 5.37-5.16 (m, 1H), 4.21-3.98 (m, 4H), 3.95-3.84 (m, 1H), 3.82-3.57 (m, 2H), 3.54-3.35 (m, 3H), 3.29-2.94 (m, 8H), 2.73-2.59 (m, 1H), 2.34-2.13 (m, 2H), 2.12-2.01 (m, 2H), 2.00-1.80 (m, 4H), 1.79-1.50 (m, 2H), 1.11 (t, J=7.2 Hz, 3H); LCMS (ESI, M+1): m/z=580.3.

Example 28

5-ethyl-6-fluoro-4-(2-(((2R,7aS)-2-fluorohexahydro-1H-pyrrolizin-7a-yl)methoxy)-4-(3-(methylsulfonyl)azepan-1-yl)-5,6-dihydropyrido[3,4-d]pyrimidin-7(8H)-yl)naphthalen-2-ol

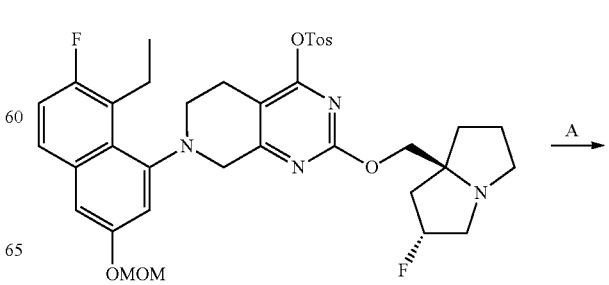

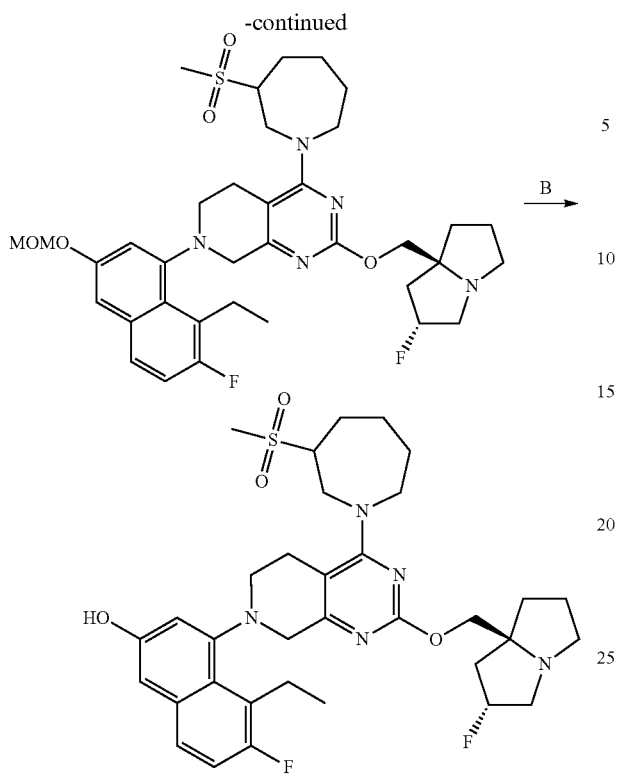

J=963.6 Hz, 1H), 4.78-4.60 (m, 1H), 4.24-4.09 (m, 2H), 4.08-3.97 (m, 2H), 3.96-3.83 (m, 1H), 3.80-3.58 (m, 3H), 3.54-3.45 (m, 1H), 3.42-3.33 (m, 2H), 3.29-3.08 (m, 5H), 3.03-3.00 (m, 3H), 3.00-2.94 (m, 1H), 2.83-2.67 (m, 1H), 2.38-2.03 (m, 5H), 2.00-1.77 (m, 6H), 1.61-1.35 (m, 1H), 1.14-1.06 (m, 3H); LCMS (ESI, M+1): m/z=656.2.

Example 29

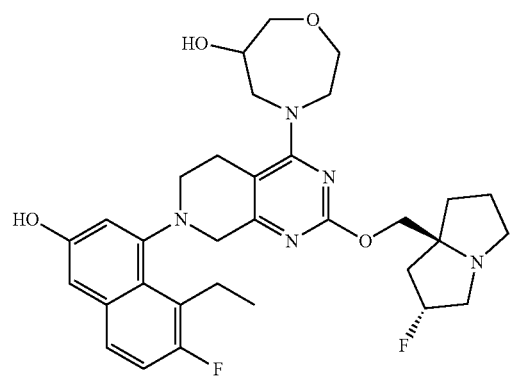 [SMILES: CCc1c(F)ccc2cc(O)cc(N3CCc4c(nc(OC[C@@]56CCCN5C[C@H](F)C6)nc4N4CCOCC(O)C4)C3)c12]

Step A. 7-(8-ethyl-7-fluoro-3-(methoxymethoxy)naphthalen-1-yl)-2-(((2R,7aS)-2-fluorohexahydro-1H-pyrrolizin-7a-yl)methoxy)-4-(3-(methylsulfonyl)azepan-1-yl)-5,6,7,8-tetrahydropyrido[3,4-d]pyrimidine: To a mixture of 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl 4-methylbenzenesulfonate (85 mg, 1 equiv) and 3-(methylsulfonyl)azepane (36.6 mg, 1.4 equiv, HCl) in DMF (1.5 mL) were added 4 Å MS (100 mg) and N-ethyl-N-isopropylpropan-2-amine (79.1 mg, 106 μL, 5.0 equiv). The mixture was stirred at 40° C. until the reaction was completed. The mixture was filtered and purified with HPLC (0.1% FA condition) to afford the title compound (80 mg, 93% yield) as yellow solid. LCMS (ESI, M+1): m/z=700.2.

Step B. 5-ethyl-6-fluoro-4-(2-(((2R,7aS)-2-fluorohexahydro-1H-pyrrolizin-7a-yl)methoxy)-4-(3-(methylsulfonyl)azepan-1-yl)-5,6-dihydropyrido[3,4-d]pyrimidin-7(8H)-yl)naphthalen-2-ol: To a mixture of 7-(8-ethyl-7-fluoro-3-(methoxymethoxy)naphthalen-1-yl)-2-(((2R,7aS)-2-fluorohexahydro-1H-pyrrolizin-7a-yl)methoxy)-4-(3-(methylsulfonyl)azepan-1-yl)-5,6,7,8-tetrahydropyrido[3,4-d]pyrimidine (78 mg, 1 equiv) and ACN (0.5 mL) was added HCl·MeOH (4 M, 279 μL, 10 equiv). The mixture was stirred at 0° C. for 1 hour. The mixture was concentrated under reduced pressure to give a residue. H₂O (10 mL) was added, and the pH of the mixture was adjusted to 8 with solid Na₂CO₃. The mixture was extracted with ethyl acetate (10 mL×3). The combined organic layers were washed with brine (20 mL), dried over anhydrous sodium sulfate, concentrated, and purified by prep-HPLC [column: Phenomenex Gemini-NX C18 75×30 mm×3 μm; mobile phase: water (10 mM NH₄HCO₃)-ACN; B %: 35%-65%, 8 minutes] to give the title compound (30 mg, 40% yield) as white solid. ¹H NMR (400 MHz, CD₃OD) δ 7.54-7.47 (m, 1H), 7.18-7.11 (t, J=9.6 Hz, 1H), 7.03-6.92 (m, 2H), 5.36-5.17 (d, 4-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,4-oxazepan-6-ol Synthesized according to Example 28. The title compound was obtained as off-white solid (TFA). ¹H NMR (400 MHz, methanol-d4) δ=7.53 (dd, J=6.0, 9.2 Hz, 1H), 7.16 (t, J=9.2 Hz, 1H), 7.05-6.98 (m, 2H), 5.65-5.46 (m, 1H), 4.65-4.52 (m, 2H), 4.33-3.71 (m, 14H), 3.69-3.50 (m, 2H), 3.48-3.35 (m, 3H), 3.25-3.14 (m, 1H), 2.98-2.74 (m, 1H), 2.74-2.51 (m, 2H), 2.44-2.27 (m, 3H), 2.24-2.12 (m, 1H), 1.11 (br t, J=7.2 Hz, 3H); LCMS (ESI, M+1, M/2+1): m/z=596.3.

Example 30

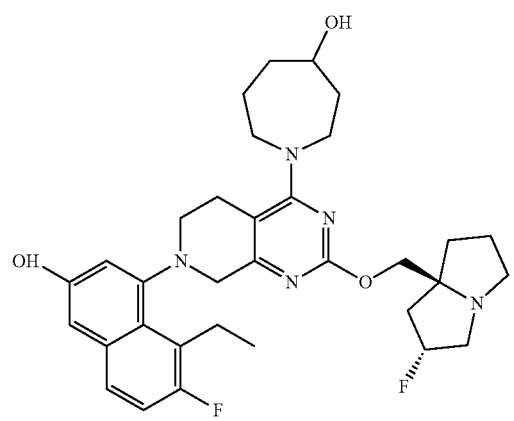 [SMILES: CCc1c(F)ccc2cc(O)cc(N3CCc4c(nc(OC[C@@]56CCCN5C[C@H](F)C6)nc4N4CCCC(O)CC4)C3)c12]

133

1-(7-(8-ethyl-7-fluoro-3-hydroxynaphthalen-1-yl)-2-
(((2R,7aS)-2-fluorohexahydro-1H-pyrrolizin-7a-yl)
methoxy)-5,6,7,8-tetrahydropyrido[3,4-d]pyrimidin-
4-yl)azepan-4-ol Synthesized according to Example 28. The title compound was obtained as white solid. $^1$H NMR (400 MHz, methanol-d4) δ 7.50 (dd, J=5.6, 8.8 Hz, 1H), 7.14 (t, J=9.2 Hz, 1H), 7.01-6.93 (m, 2H), 5.35-5.18 (m, 1H), 4.19-3.98 (m, 3H), 3.96-3.73 (m, 4H), 3.70-3.58 (m, 2H), 3.48 (br d, J=3.2 Hz, 1H), 3.44-3.35 (m, 2H), 3.27-3.09 (m, 5H), 2.98 (m, 1H), 2.79-2.71 (m, 1H), 2.32-1.58 (m, 12H), 1.11 (br t, J=6.8 Hz, 3H); $^{19}$F NMR (400 MHz, methanol-d4) δ=−123.076, −173.617; LCMS (ESI, M+1): m/z=594.3.

Example 31

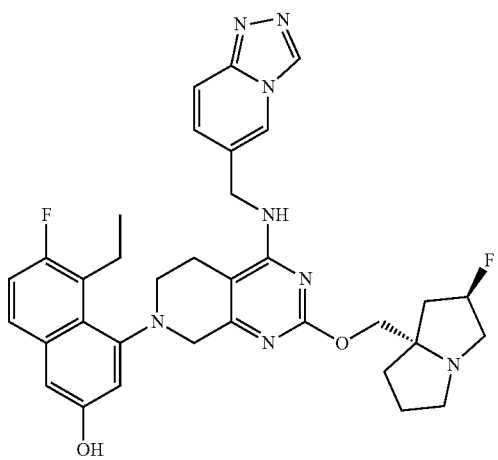 [SMILES: CCc1c(F)ccc2cc(O)cc(N3CCc4c(nc(OC[C@@]56CCCN5C[C@H](F)C6)nc4NCc4ccc5nncn5c4)C3)c12]

4-(4-((([1,2,4]triazolo[4,3-a]pyridin-6-ylmethyl)
amino)-2-(((2R,7aS)-2-fluorohexahydro-1H-pyr-
rolizin-7a-yl)methoxy)-5,6-dihydropyrido[3,4-d]
pyrimidin-7(8H)-yl)-5-ethyl-6-fluoronaphthalen-2-ol Synthesized according to Example 28. The title compound was obtained as off-white solid. $^1$H NMR (400 MHz, methanol-d$_4$) δ=9.15 (s, 1H), 8.51 (s, 1H), 7.75 (d, J=9.6 Hz, 1H), 7.68-7.43 (m, 2H), 7.14 (t, J=9.6 Hz, 1H), 7.06-6.89 (m, 2H), 5.42-5.16 (m, 1H), 4.85-4.78 (m, 2H), 4.77-4.63 (m, 1H), 4.22-4.00 (m, 2H), 3.91 (br d, J=16.8 Hz, 1H), 3.67 (br d, J=16.8 Hz, 1H), 3.56 (br dd, J=5.6, 11.2 Hz, 1H), 3.34 (br dd, J=2.4, 4.0 Hz, 4H), 3.28 (br d, J=4.0 Hz, 1H), 3.06 (dt, J=5.2, 9.2 Hz, 1H), 2.85 (ddd, J=6.8, 10.0, 16.0 Hz, 1H), 2.58 (br d, J=15.6 Hz, 1H), 2.36-2.14 (m, 2H), 2.12-1.91 (m, 3H), 1.87-1.69 (m, 1H), 1.05 (dt, J=1.6, 7.2 Hz, 3H); LCMS (ESI, M+1): m/z=627.3.

134

Example 32

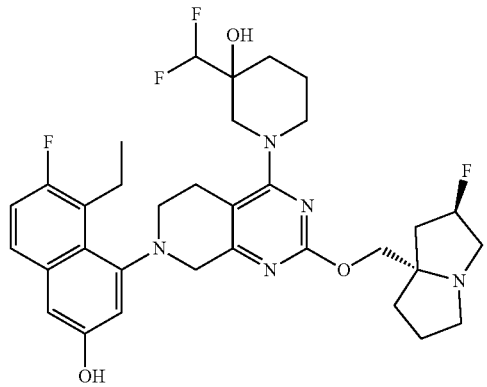 [SMILES: CCc1c(F)ccc2cc(O)cc(N3CCc4c(nc(OC[C@@]56CCCN5C[C@H](F)C6)nc4N4CCCC(O)(C(F)F)C4)C3)c12]

3-(difluoromethyl)-1-(7-(8-ethyl-7-fluoro-3-hy-
droxynaphthalen-1-yl)-2-(((2R,7aS)-2-fluorohexa-
hydro-1H-pyrrolizin-7a-yl)methoxy)-5,6,7,8-tetrahy-
dropyrido[3,4-d]pyrimidin-4-yl)piperidin-3-ol

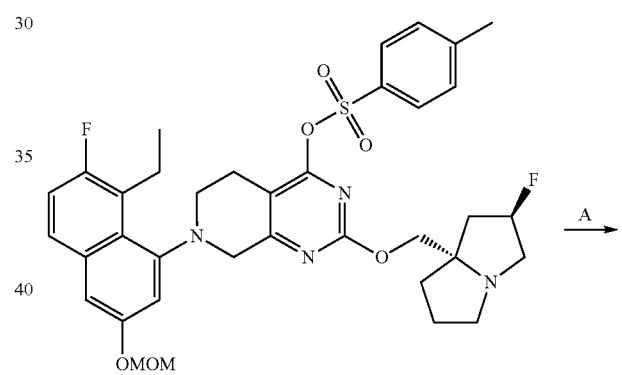

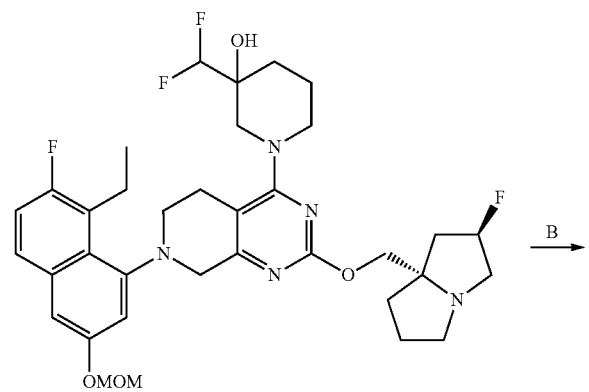

-continued

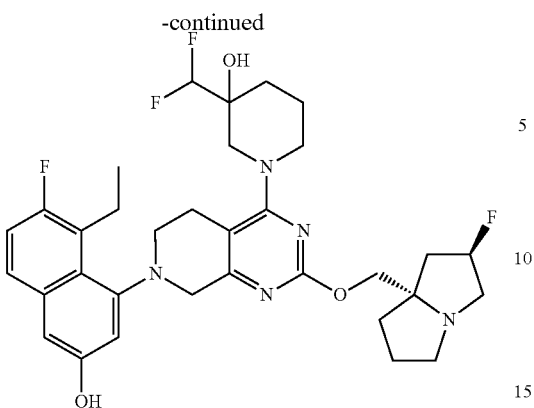

Step A. 3-(difluoromethyl)-1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol: To a mixture of 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv), 3-(difluoromethyl)piperidin-3-ol (54.0 mg, 2.0 equiv, HCl) and 4 Å molecular sieve (20 mg) in DMF (1 mL) was added N-ethyl-N-isopropylpropan-2-amine (74.4 mg, 4.0 equiv). The reaction was stirred at 40-60° C. until the reaction was completed. The mixture was filtered and washed with DMF (1 mL). The reaction was purified with reversed phase flash chromatography [C18, 0.1% formic acid condition] to afford the title compound (85.0 mg, 86% yield) as white solid. LCMS (ESI, M+1): m/z=674.4.

Step B. 3-(difluoromethyl)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol: To a solution of 3-(difluoromethyl)-1-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)piperidin-3-ol (80.0 mg, 1.0 equiv) in MeOH (1.5 mL) was added HCl·MeOH (4 M, 57.7 equiv). The mixture was stirred at 0° C. for 0.5 and then its pH was adjusted to 8 with saturated NaHCO₃ aqueous solution (3 mL). The mixture was extracted with EtOAc (3×5 mL). The combined organic layer was dried over anhydrous sodium sulfate, concentrated and purified with prep-HPLC [Phenomenex Synergi C18 150×25 mm×10 μm; A: water (0.225% FA), B: ACN; B %: 17%-47% over 10 min] and lyophilized to afford the title compound (44.1 mg, 59% yield) as off-white solid. $^1$H NMR (400 MHz, methanol-d$_4$) δ=8.50 (s, 1H), 7.51 (dd, J=6.0, 9.2 Hz, 1H), 7.14 (t, J=9.6 Hz, 1H), 7.06-6.91 (m, 2H), 5.97-5.54 (m, 1H), 5.50-5.27 (m, 1H), 4.38-4.20 (m, 2H), 4.18-3.97 (m, 2H), 3.91-3.76 (m, 1H), 3.73-3.60 (m, 1H), 3.59-3.43 (m, 5H), 3.42-3.33 (m, 2H), 3.30-3.11 (m, 3H), 3.11-2.97 (m, 1H), 2.83-2.62 (m, 1H), 2.50-2.26 (m, 2H), 2.24-1.90 (m, 5H), 1.90-1.68 (m, 3H), 1.20-1.04 (m, 3H); LCMS (ESI, M+1): m/z=630.3.

Example 33

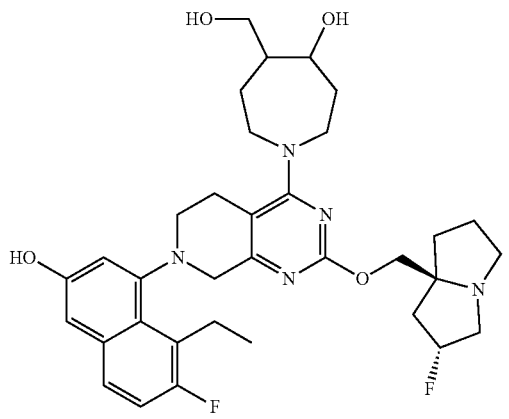 [SMILES: CCc1c(F)ccc2cc(O)cc(N3CCc4c(nc(OC[C@@]56CCCN5C[C@H](F)C6)nc4N4CCC(O)C(CO)CC4)C3)c12]

1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-5-(hydroxymethyl)azepan-4-ol Synthesized according to Example 28. The title compound was obtained as yellow solid. $^1$H NMR (400 MHz, methanol-d4) δ 7.56-7.50 (m, 1H), 7.17 (t, J=9.2 Hz, 1H), 7.07-6.98 (m, 2H), 5.55 (d, J=51.6 Hz, 1H), 4.72-4.57 (m, 2H), 4.27-3.99 (m, 4H), 3.98-3.73 (m, 6H), 3.72-3.35 (m, 7H), 3.25-3.12 (m, 1H), 2.96-2.81 (m, 1H), 2.73-2.52 (m, 2H), 2.49-2.29 (m, 3H), 2.24-1.77 (m, 5H), 1.72-1.61 (m, 1H), 1.18-1.09 (m, 3H). LCMS (ESI, M+1, M/2+1): m/z=624.3.

Example 34

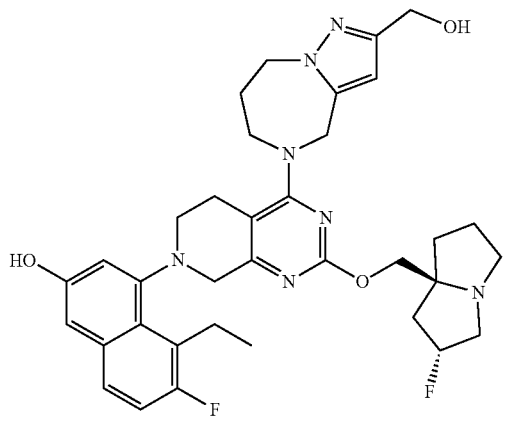 [SMILES: CCc1c(F)ccc2cc(O)cc(N3CCc4c(nc(OC[C@@]56CCCN5C[C@H](F)C6)nc4N4CCCn5nc(CO)cc5C4)C3)c12]

5-ethyl-6-fluoro-4-(2-(((2R,7aS)-2-fluorohexahydro-1H-pyrrolizin-7a-yl)methoxy)-4-(2-(hydroxymethyl)-7,8-dihydro-4H-pyrazolo[1,5-a][1,4]diazepin-5(6H)-yl)-5,6-dihydropyrido[3,4-d]pyrimidin-7(8H)-yl)naphthalen-2-ol Synthesized according to Example 28. The title compound was obtained as white solid. 1H NMR (400 MHz, methanol-d4) δ=7.51 (dd, J=5.6, 8.8 Hz, 1H), 7.18-7.12 (m, 1H), 6.96 (s, 2H), 6.26 (s, 1H), 5.35-5.17 (m, 1H), 4.95 (br d, J=6.0 Hz, 1H), 4.82-4.76 (m, 1H), 4.50 (s, 2H), 4.44 (br d, J=4.4 Hz, 2H), 4.23-4.14 (m, 1H), 4.12-3.92 (m, 4H), 3.72-3.64 (m, 1H), 3.56-3.47 (m, 1H), 3.45-3.39 (m, 2H), 3.26-3.12 (m, 5H), 3.03-2.94 (m, 1H), 2.78-2.69 (m, 1H), 2.32-2.18 (m, 2H), 2.16-2.02 (m, 3H), 2.00-1.81 (m, 3H), 1.18-1.08 (m, 3H); 19F NMR (400 MHz, methanol-d4) δ=−122.947, −173.640; SFC: >99% ee, Chiralpak AD-3 50×4.6 mm I.D., 3 μm column A: 60% MeOH+40% ACN (w/0.05% DEA), B: CO2, 3 mL/min, 220 nm, tR: 0.559 min; LCMS (ESI, M+1): m/z=646.4.

Example 35

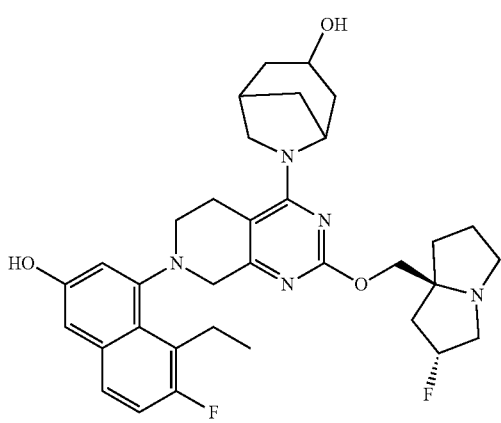 [SMILES: CCc1c(F)ccc2cc(O)cc(N3CCc4c(nc(OC[C@@]56CCCN5C[C@H](F)C6)nc4N4CC5CC(O)CC4C5)C3)c12]

6-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-azabicyclo[3.2.1]octan-3-ol Synthesized according to Example 23. The title compound was obtained as off-white solid. ¹H NMR (400 MHz, methanol-d4) δ=8.48 (s, 1H), 7.56-7.45 (m, 1H), 7.13 (t, J=9.2 Hz, 1H), 7.03-6.92 (m, 2H), 5.57-5.35 (m, 1H), 4.84-4.59 (m, 1H), 4.50-4.28 (m, 2H), 4.23-4.09 (m, 1H), 4.05-3.87 (m, 2H), 3.82-3.55 (m, 5H), 3.54-3.45 (m, 1H), 3.43-3.33 (m, 2H), 3.29-2.94 (m, 3H), 2.75-2.35 (m, 4H), 2.33-1.90 (m, 7H), 1.79-1.36 (m, 2H), 1.14-1.05 (m, 3H); LCMS (ESI, M+1): m/z=606.4.

Example 36

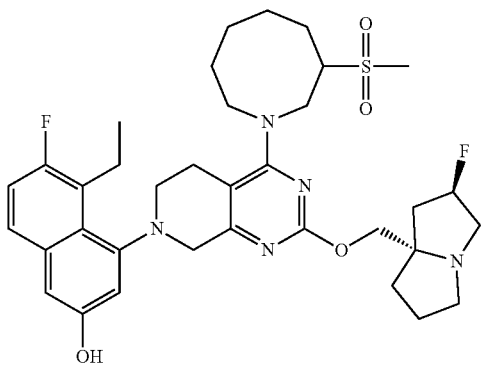 [SMILES: CCc1c(F)ccc2cc(O)cc(N3CCc4c(nc(OC[C@@]56CCCN5C[C@H](F)C6)nc4N4CCCCCC(S(C)(=O)=O)C4)C3)c12]

5-ethyl-6-fluoro-4-(2-(((2R,7aS)-2-fluorotetrahydro-1H-pyrrolizin-7a(5H)-yl)methoxy)-4-(3-(methylsulfonyl)azocan-1-yl)-5,8-dihydropyrido[3,4-d]pyrimidin-7(6H)-yl)naphthalen-2-ol Synthesized according to Example 23. The title compound was obtained as off-white solid. ¹H NMR (400 MHz, methanol-d4) δ=8.52 (s, 1H), 7.60-7.45 (m, 1H), 7.14 (t, J=9.2 Hz, 1H), 7.03-6.90 (m, 2H), 5.50-5.26 (m, 1H), 4.89-4.85 (m, 1H), 4.43-4.14 (m, 3H), 4.14-3.96 (m, 1H), 3.86-3.65 (m, 2H), 3.65-3.49 (m, 3H), 3.49-3.39 (m, 3H), 3.39-3.32 (m, 2H), 3.27-3.08 (m, 3H), 3.04-2.94 (m, 3H), 2.81-2.67 (m, 1H), 2.57-2.46 (m, 1H), 2.45-2.16 (m, 3H), 2.14-1.93 (m, 4H), 1.92-1.79 (m, 2H), 1.78-1.55 (m, 3H), 1.46-1.19 (m, 1H), 1.14-1.02 (m, 3H); LCMS (ESI, M+1): m/z=670.4.

Example 37

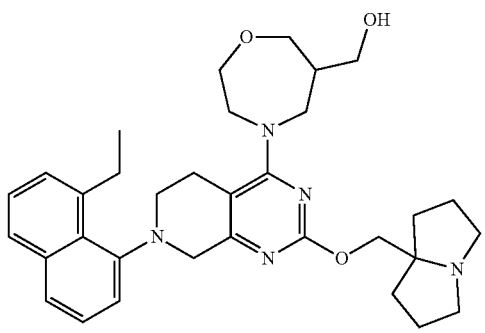 [SMILES: CCc1cccc2cccc(N3CCc4c(nc(OCC56CCCN5CCC6)nc4N4CCOCC(CO)C4)C3)c12]

(4-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-1,4-oxazepan-6-yl)methanol

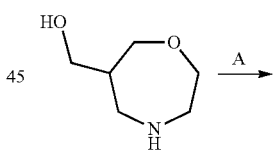

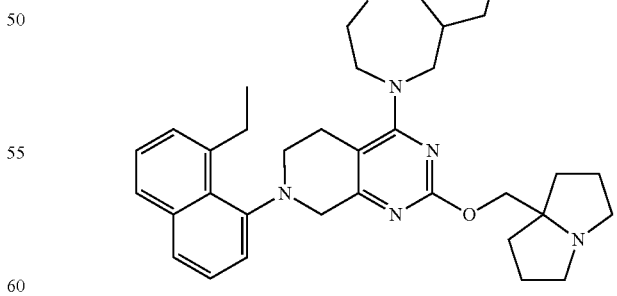

Step A. (4-(7-(8-ethylnaphthalen-1-yl)-2-((hexahydro-1H-pyrrolizin-7a-yl)methoxy)-5,6,7,8-tetrahydropyrido[3, 4-d]pyrimidin-4-yl)-1,4-oxazepan-6-yl)methanol: To a solution of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv), 1,4-oxazepan-6-ylmethanol (56.0 mg, 2.0 equiv, HCl) and 4 Å molecular sieve (10 mg) in DMF (1 mL) was added N-ethyl-N-isopropylpropan-2-amine (108 mg, 5.0 equiv). The reaction was stirred at 40° C. until the reaction was completed. The residue was filtered and washed with DMF (1 mL), and purified with prep-HPLC [Phenomenex Luna C18 150×25 mm×10 μm; A: water (FA), B: ACN; B %: 25%-55% over 7 min] to afford the title compound (14.1 mg, 14% yield) as yellow gum; $^1$H NMR (400 MHz, methanol-$d_4$) δ=7.74-7.64 (m, 2H), 7.43 (dt, J=5.6, 7.6 Hz, 1H), 7.39-7.29 (m, 2H), 7.29-7.21 (m, 1H), 4.57 (br s, 2H), 4.39-4.30 (m, 2H), 4.29-4.14 (m, 1H), 4.12-3.97 (m, 1H), 3.97-3.88 (m, 1H), 3.85-3.72 (m, 2H), 3.72-3.62 (m, 2H), 3.61-3.49 (m, 4H), 3.49-3.41 (m, 2H), 3.40-3.32 (m, 2H), 3.30-3.19 (m, 2H), 3.19-3.10 (m, 1H), 3.10-2.98 (m, 2H), 2.77 (br d, J=14.4 Hz, 1H), 2.56-2.34 (m, 1H), 2.24-2.16 (m, 2H), 2.15-2.07 (m, 2H), 2.06-1.97 (m, 2H), 1.97-1.90 (m, 1H), 1.24-1.03 (m, 3H); LCMS (ESI, M+1): m/z=558.5.

Example 38

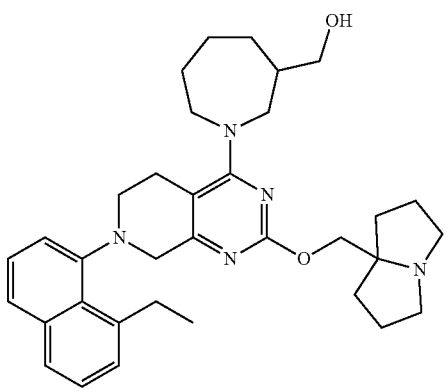 [SMILES: CCc1cccc2cccc(N3CCc4c(nc(OCC56CCCN5CCC6)nc4N4CCCCC(CO)C4)C3)c12]

(1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)azepan-3-yl)methanol Synthesized according to Example 37. The title compound was obtained as yellow solid. $^1$H NMR (400 MHz, METHANOL-$d_4$) δ=7.77-7.58 (m, 2H), 7.46-7.37 (m, 1H), 7.37-7.20 (m, 3H), 4.48-4.23 (m, 1H), 4.22-4.13 (m, 2H), 4.12-4.02 (m, 1H), 4.02-3.74 (m, 1H), 3.70-3.57 (m, 2H), 3.56-3.40 (m, 4H), 3.25-3.12 (m, 4H), 3.11-2.98 (m, 1H), 2.86-2.63 (m, 3H), 2.40-2.12 (m, 1H), 2.10-1.99 (m, 3H), 1.98-1.81 (m, 6H), 1.80-1.61 (m, 4H), 1.50-1.32 (m, 2H), 1.21-1.05 (m, 3H); LCMS (ESI, M+1): m/z=556.3.

Example 39

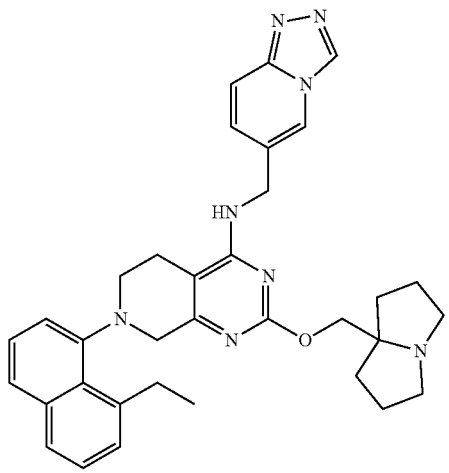 [SMILES: CCc1cccc2cccc(N3CCc4c(nc(OCC56CCCN5CCC6)nc4NCc4ccc5nncn5c4)C3)c12]

N-([1,2,4]triazolo[4,3-a]pyridin-6-ylmethyl)-7-(8-ethylnaphthalen-1-yl)-2-((hexahydro-1H-pyrrolizin-7a-yl)methoxy)-5,6,7,8-tetrahydropyrido[3,4-d]pyrimidin-4-amine Synthesized according to Example 37. The title compound was obtained as yellow solid. $^1$H NMR (400 MHz, METHANOL-$d_4$) δ=9.28 (s, 1H), 8.71 (s, 1H), 7.90 (d, J=9.6 Hz, 1H), 7.80 (dd, J=1.2, 9.6 Hz, 1H), 7.72 (dd, J=4.0, 7.2 Hz, 2H), 7.45 (t, J=7.6 Hz, 1H), 7.40-7.37 (m, 2H), 7.31 (d, J=6.4 Hz, 1H), 4.95 (t, J=15.2 Hz, 2H), 4.64 (q, J=11.6 Hz, 2H), 4.05 (d, J=17.6 Hz, 1H), 3.84 (d, J=17.6 Hz, 1H), 3.66-3.62 (m, 3H), 3.46-3.41 (m, 2H), 3.28-3.23 (m, 2H), 3.15-3.07 (m, 1H), 2.90-2.83 (m, 1H), 2.64 (br d, J=16.0 Hz, 1H), 2.28-2.09 (m, 8H), 1.11 (t, J=7.2 Hz, 3H); LCMS (ESI, M+1): m/z=575.4.

Example 40

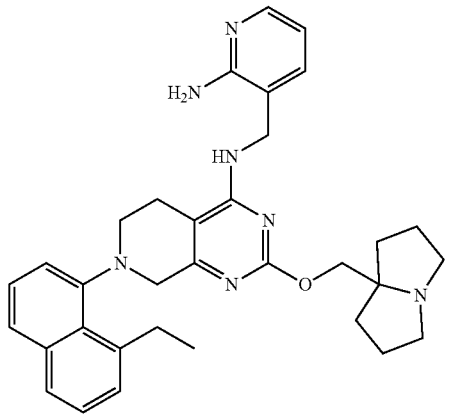 [SMILES: CCc1cccc2cccc(N3CCc4c(nc(OCC56CCCN5CCC6)nc4NCc4cccnc4N)C3)c12]

N-((2-aminopyridin-3-yl)methyl)-7-(8-ethylnaphthalen-1-yl)-2-((hexahydro-1H-pyrrolizin-7a-yl)methoxy)-5,6,7,8-tetrahydropyrido[3,4-d]pyrimidin-4-amine Synthesized according to Example 37. The title compound was obtained as white solid. $^1$H NMR (400 MHz, METHANOL-d₄) δ=7.87 (dd, J=1.6, 5.2 Hz, 1H), 7.69 (ddd, J=0.8, 8.0, 14.4 Hz, 2H), 7.52 (dd, J=1.6, 7.2 Hz, 1H), 7.43-7.41 (m, 1H), 7.37-7.35 (m, 2H), 7.33-7.28 (m, 1H), 6.67 (dd, J=5.2, 7.2 Hz, 1H), 4.58 (q, J=15.6 Hz, 2H), 4.39 (s, 2H), 3.92 (br d, J=17.2 Hz, 1H), 3.68 (br d, J=17.2 Hz, 1H), 3.60-3.55 (m, 4H), 3.37 (br dd, J=7.2, 11.2 Hz, 1H), 3.20 (td, J=6.0, 11.6 Hz, 2H), 3.05 (br dd, J=7.2, 13.2 Hz, 1H), 2.93-2.79 (m, 1H), 2.57 (br d, J=16.0 Hz, 1H), 2.21-2.01 (m, 8H), 1.09 (t, J=7.2 Hz, 3H); LCMS (ESI, M+1): m/z=550.4.

Example 41

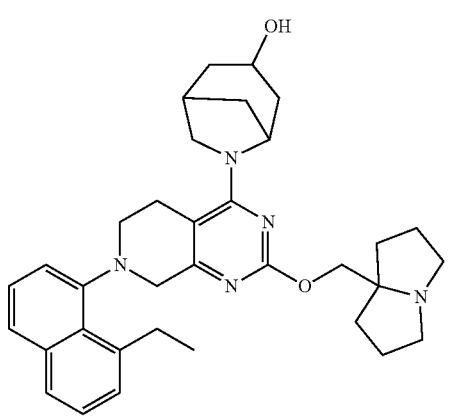 [SMILES: CCc1cccc2cccc(N3CCc4c(nc(OCC56CCCN5CCC6)nc4N4CC5CC(O)CC4C5)C3)c12]

6-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-azabicyclo[3.2.1]octan-3-ol Synthesized according to Example 37. The title compound was obtained as off-white solid (TFA); ¹H NMR (400 MHz, METHANOL-d₄) δ=7.71-7.65 (m, 2H), 7.43-7.41 (m, 1H), 7.35-7.34 (m, 2H), 7.28-7.26 (m, 1H), 4.67-4.64 (m, 1H), 4.34-4.29 (m, 2H), 4.21-4.13 (m, 1H), 4.06-3.87 (m, 2H), 3.83-3.48 (m, 4H), 3.43-3.35 (m, 2H), 3.22-2.97 (m, 6H), 2.77-2.37 (m, 2H), 2.20-2.17 (m, 2H), 2.15-1.99 (m, 8H), 1.87-1.63 (m, 2H), 1.61-1.22 (m, 1H), 1.16-1.11 (m, 3H); LCMS (ESI, M+1): m/z=554.5.

Example 42

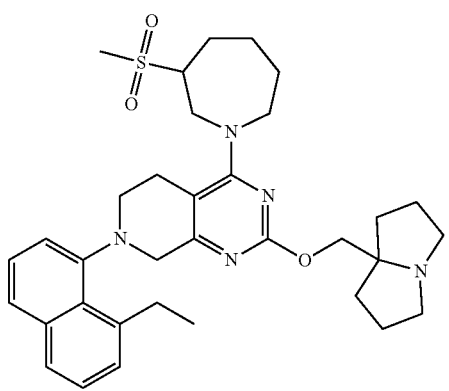 [SMILES: CCc1cccc2cccc(N3CCc4c(nc(OCC56CCCN5CCC6)nc4N4CCCCC(S(C)(=O)=O)C4)C3)c12]

7-(8-ethylnaphthalen-1-yl)-2-((hexahydro-1H-pyrrolizin-7a-yl)methoxy)-4-(3-(methylsulfonyl)azepan-1-yl)-5,6,7,8-tetrahydropyrido[3,4-d]pyrimidine Synthesized according to Example 37. The title compound was obtained as off-white solid (0.44 equiv formic acid). 1H NMR (400 MHz, METHANOL-d4): δ=7.73-7.63 (m, 2H), 7.46-7.25 (m, 4H), 4.70-4.62 (m, 1H), 4.42-4.26 (m, 2H), 4.12-3.94 (m, 2H), 3.91-3.43 (m, 6H), 3.38-3.32 (m, 2H), 3.29-3.08 (m, 2H), 3.08-2.91 (m, 6H), 2.86-2.71 (m, 1H), 2.08-2.06 (m, 1H), 2.34-2.06 (m, 3H), 2.06-2.06 (m, 1H), 2.06-1.82 (m, 8H), 1.58-1.35 (m, 1H), 1.18-1.09 (m, 3H); LCMS (ESI, M+1): m/z=604.3.

Example 43

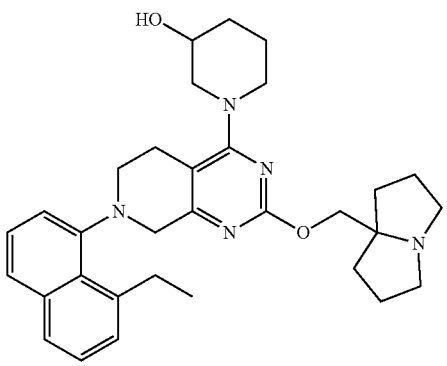 [SMILES: CCc1cccc2cccc(N3CCc4c(nc(OCC56CCCN5CCC6)nc4N4CCCC(O)C4)C3)c12]

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)piperidin-3-ol Synthesized according to Example 37. The title compound was obtained as off-white solid. ¹H NMR (400 MHz, DMSO+D₂O) δ=7.77-7.66 (m, 2H), 7.51-7.23 (m, 4H), 4.12 (s, 2H), 4.00-3.74 (m, 3H), 3.65-3.36 (m, 4H), 3.26-3.08 (m, 4H), 3.04-2.81 (m, 5H), 2.62-2.53 (m, 1H), 2.01-1.71 (m, 10H), 1.62-1.31 (m, 2H), 1.07 (dt, J=1.6, 7.2 Hz, 3H); LCMS (ESI, M+1): m/z=528.4.

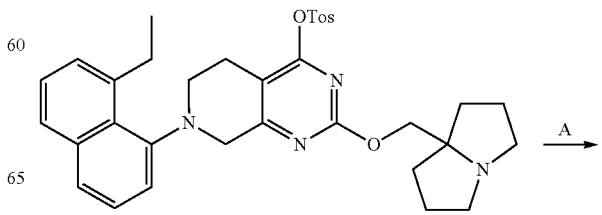

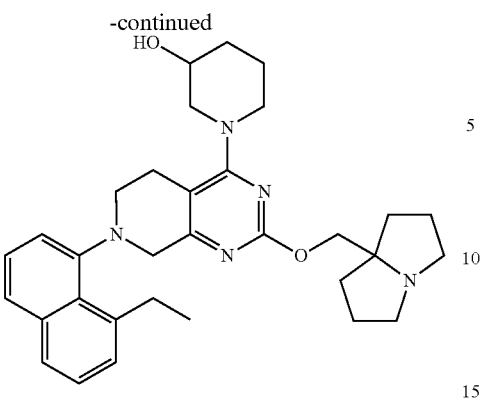

Step A. 1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)piperidin-3-ol: To a mixture of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (90 mg, 1.0 equiv), piperidin-3-ol (31 mg, 2.04 equiv) and 4 Å molecular sieve (20 mg) in DMF (1.0 mL) was added N-ethyl-N-isopropylpropan-2-amine (83.1 mg, 112 μL, 4.28 equiv). The mixture was stirred at 40° C. for 15 hours. The reaction mixture was diluted with water (20 mL) and extracted with ethyl acetate (20 mL×4). The combined organic phase was dried over anh Na$_2$SO$_4$, concentrated and purified with prep-HPLC [Phenomenex Luna C18 150×25 mm×10 μm; A: water (0.2% FA), B: ACN, B %: 17%-47% over 10 min] to afford the title compound (26.2 mg, 33% yield) as off-white solid. $^1$H NMR (400 MHz, DMSO+D$_2$O) δ=7.77-7.66 (m, 2H), 7.51-7.23 (m, 4H), 4.12 (s, 2H), 4.00-3.74 (m, 3H), 3.65-3.36 (m, 4H), 3.26-3.08 (m, 4H), 3.04-2.81 (m, 5H), 2.62-2.53 (m, 1H), 2.01-1.71 (m, 10H), 1.62-1.31 (m, 2H), 1.07 (dt, J=1.6, 7.2 Hz, 3H); LCMS (ESI, M+1): m/z=528.4.

Example 44

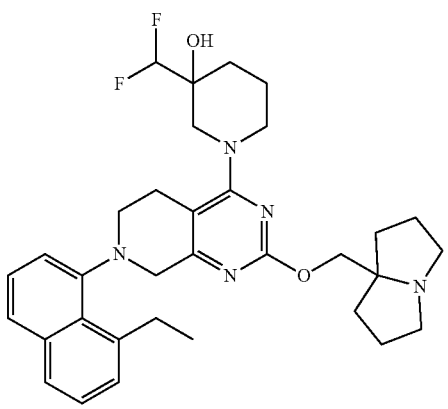 [SMILES: CCc1cccc2cccc(N3CCc4c(nc(OCC56CCCN5CCC6)nc4N4CCCC(O)(C(F)F)C4)C3)c12]

3-(difluoromethyl)-1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)piperidin-3-ol Synthesized according to Example 37. The title compound was obtained as white solid. $^1$H NMR (400 MHz, METHANOL-d$_4$) δ=7.75-7.63 (m, 2H), 7.47-7.24 (m, 4H), 5.92-5.57 (m, 1H), 4.40-4.29 (m, 2H), 4.20-3.98 (m, 2H), 3.93-3.76 (m, 1H), 3.72-3.51 (m, 3H), 3.48-3.33 (m, 3H), 3.27-3.14 (m, 2H), 3.14-2.95 (m, 4H), 2.84-2.63 (m, 1H), 2.23-2.02 (m, 6H), 2.00-1.66 (m, 6H), 1.15 (dt, J=4.4, 7.2 Hz, 3H). LCMS (ESI, M+1): m/z=578.4.

Example 45

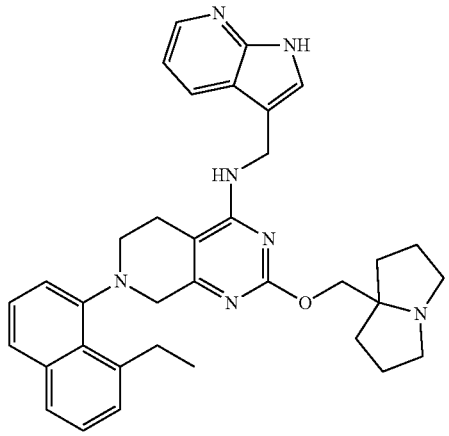 [SMILES: CCc1cccc2cccc(N3CCc4c(nc(OCC56CCCN5CCC6)nc4NCc4c[nH]c5ncccc45)C3)c12]

N-((1H-pyrrolo[2,3-b]pyridin-3-yl)methyl)-7-(8-ethylnaphthalen-1-yl)-2-((hexahydro-1H-pyrrolizin-7a-yl)methoxy)-5,6,7,8-tetrahydropyrido[3,4-d]pyrimidin-4-amine Synthesized according to Example 37. The title compound was obtained as off-white solid. $^1$H NMR (400 MHz, METHANOL-d$_4$) δ=8.47 (dd, J=1.2, 8.0 Hz, 1H), 8.35 (d, J=4.8 Hz, 1H), 7.72-7.71 (m, 2H), 7.67 (s, 1H), 7.44 (t, J=7.6 Hz, 1H), 7.39-7.38 (m, 3H), 7.37-7.31 (m, 1H), 5.07 (q, J=15.2 Hz, 2H), 4.70 (q, J=11.6 Hz, 2H), 4.04 (d, J=18.0 Hz, 1H), 3.84 (d, J=17.6 Hz, 1H), 3.68-3.58 (m, 3H), 3.44-3.40 (m, 2H), 3.29-3.26 (m, 2H), 3.11 (dd, J=7.2, 13.2 Hz, 1H), 2.84-2.80 (m, 1H), 2.56 (br d, J=16.4 Hz, 1H), 2.27-2.10 (m, 8H), 1.10 (t, J=7.2 Hz, 3H); LCMS (ESI, M+1): m/z=574.5.

Example 46

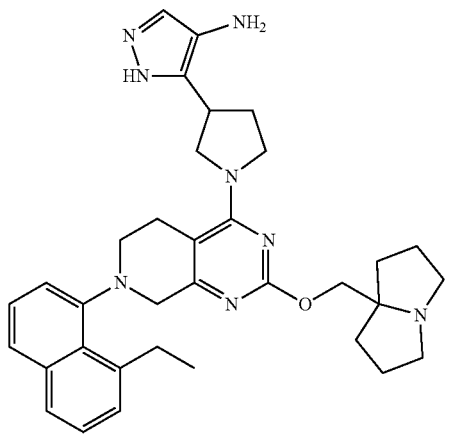 [SMILES: CCc1cccc2cccc(N3CCc4c(nc(OCC56CCCN5CCC6)nc4N4CCC(c5[nH]ncc5N)C4)C3)c12]

5-(1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)pyrrolidin-3-yl)-1H-pyrazol-4-amine Synthesized according to Example 37. The title compound was obtained as gray solid. ¹H NMR (400 MHz, METHANOL-d₄) δ=7.73-7.63 (m, 2H), 7.46-7.39 (m, 1H), 7.38-7.30 (m, 2H), 7.30-7.25 (m, 1H), 7.25-7.20 (m, 1H), 4.52-4.40 (m, 2H), 4.33-4.14 (m, 1H), 4.12-3.82 (m, 4H), 3.74-3.51 (m, 6H), 3.50-3.37 (m, 1H), 3.27-3.17 (m, 3H), 3.14 (br s, 2H), 2.36 (s, 1H), 2.29-2.08 (m, 7H), 2.04 (br dd, J=6.5, 12.0 Hz, 2H), 1.19-1.09 (m, 3H). LCMS (ESI, M+1): m/z=579.4

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)azepan-3-ol Synthesized according to Example 37. The title compound was obtained as light yellow solid. ¹H NMR (400 MHz, METHANOL-d₄): δ=8.54 (s, 1H), 7.69 (dd, J=8.0, 16.4 Hz, 2H), 7.42 (dt, J=2.8, 7.6 Hz, 1H), 7.37-7.26 (m, 3H), 4.35 (d, J=5.6 Hz, 2H), 4.29-3.98 (m, 4H), 3.72-3.54 (m, 4H), 3.53-3.36 (m, 3H), 3.29-3.15 (m, 2H), 3.12-2.98 (m, 3H), 2.83-2.75 (m, 1H), 2.19 (td, J=6.0, 12.4 Hz, 2H), 2.15-2.00 (m, 4H), 1.99-1.90 (m, 3H), 1.89-1.72 (m, 3H), 1.69-1.58 (m, 1H), 1.52-1.28 (m, 1H), 1.14 (t, J=7.2 Hz, 3H); LCMS (ESI, M+1): m/z=542.3.

Example 47

Example 49

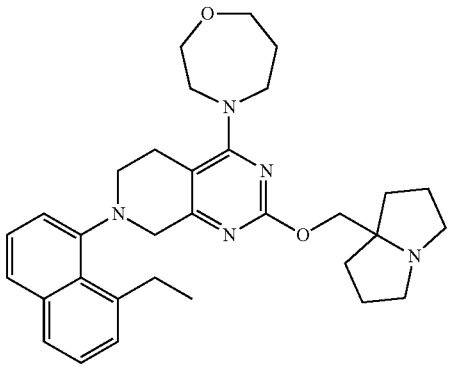 [SMILES: CCc1cccc2cccc(N3CCc4c(nc(OCC56CCCN5CCC6)nc4N4CCCOCC4)C3)c12]

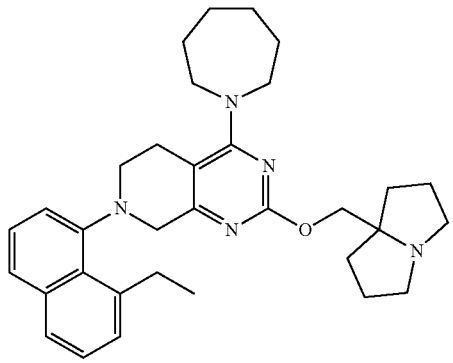

4-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-1,4-oxazepane Synthesized according to Example 37. The title compound was obtained as yellow solid. ¹H NMR (400 MHz, METHANOL-d₄): δ=7.76-7.70 (m, 2H), 7.45 (t, J=7.6 Hz, 1H), 7.40-7.30 (m, 3H), 4.63 (d, J=1.2 Hz, 2H), 4.19-4.06 (m, 4H), 4.05-3.98 (m, 1H), 3.96-3.85 (m, 3H), 3.84-3.73 (m, 2H), 3.70-3.50 (m, 4H), 3.30-3.21 (m, 4H), 3.16-3.05 (m, 1H), 2.90-2.82 (m, 1H), 2.34-2.25 (m, 2H), 2.25-2.06 (m, 7H), 2.04-1.95 (m, 1H), 1.17 (t, J=7.2 Hz, 3H); LCMS (ESI, M+1): m/z=528.3.

4-(azepan-1-yl)-7-(8-ethylnaphthalen-1-yl)-2-((hexahydro-1H-pyrrolizin-7a-yl)methoxy)-5,6,7,8-tetrahydropyrido[3,4-d]pyrimidine Synthesized according to Example 37. The title compound was obtained as yellow solid. ¹H NMR (400 MHz, METHANOL-d₄) δ=7.69 (ddd, J=0.8, 8.0, 17.2 Hz, 2H), 7.43 (t, J=7.6 Hz, 1H), 7.38-7.30 (m, 2H), 7.30-7.26 (m, 1H), 4.41-4.31 (m, 2H), 4.02 (d, J=17.2 Hz, 1H), 3.94-3.85 (m, 2H), 3.82-3.73 (m, 2H), 3.67-3.54 (m, 3H), 3.53-3.44 (m, 2H), 3.29-3.17 (m, 2H), 3.14-2.99 (m, 3H), 2.84-2.73 (m, 1H), 2.25-2.16 (m, 2H), 2.16-2.02 (m, 4H), 2.01-1.79 (m, 6H), 1.69 (br dd, J=4.8, 7.2 Hz, 2H), 1.62-1.51 (m, 2H), 1.14 (t, J=7.2 Hz, 3H); LCMS (ESI, M+1): m/z=526.5.

Example 48

Example 50

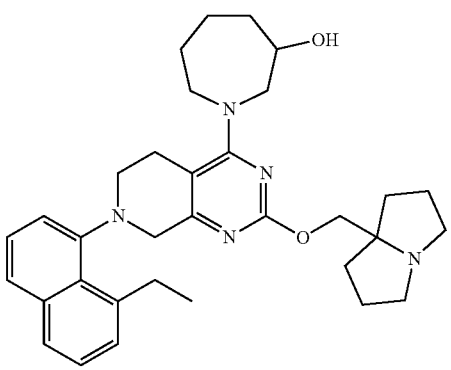 [SMILES: CCc1cccc2cccc(N3CCc4c(nc(OCC56CCCN5CCC6)nc4N4CCCCC(O)C4)C3)c12]

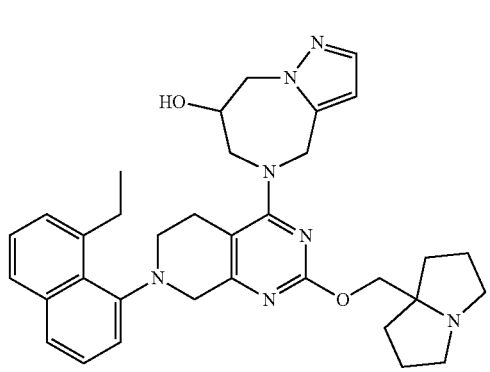 [SMILES: CCc1cccc2cccc(N3CCc4c(nc(OCC56CCCN5CCC6)nc4N4Cc5ccnn5CC(O)C4)C3)c12]

5-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-5,6,7,8-tetrahydro-4H-pyrazolo[1,5-a][1,4]diazepin-7-ol Synthesized according to Example 37. The title compound was obtained as white solid. $^1$H NMR (400 MHz, METHANOL-d$_4$) δ=7.69 (dd, J=8.0, 16.0 Hz, 2H), 7.46-7.36 (m, 1H), 7.36-7.22 (m, 4H), 6.30-6.19 (m, 1H), 5.16-4.91 (m, 1H), 4.79 (br d, J=16.4 Hz, 1H), 4.62-4.50 (m, 1H), 4.47-4.40 (m, 1H), 4.39-4.17 (m, 4H), 4.15-3.87 (m, 2H), 3.82-3.72 (m, 1H), 3.67-3.54 (m, 2H), 3.51-3.34 (m, 1H), 3.29-3.01 (m, 4H), 2.97-2.86 (m, 2H), 2.85-2.72 (m, 1H), 2.15-2.06 (m, 2H), 2.05-1.90 (m, 4H), 1.88-1.78 (m, 2H), 1.17 (t, J=7.2 Hz, 3H); LCMS (ESI, M+1): m/z=580.5.

Example 51

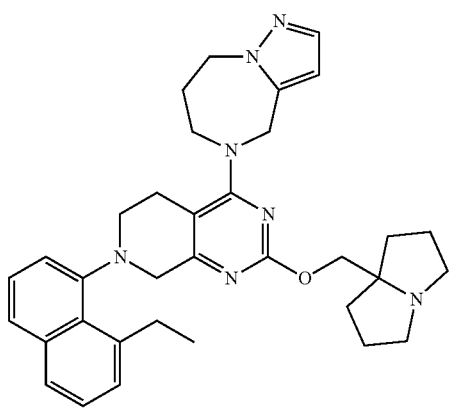 [SMILES: CCc1cccc2cccc(N3CCc4c(nc(OCC56CCCN5CCC6)nc4N4CCCn5nccc5C4)C3)c12]

4-(7,8-dihydro-4H-pyrazolo[1,5-a][1,4]diazepin-5(6H)-yl)-7-(8-ethylnaphthalen-1-yl)-2-((hexahydro-1H-pyrrolizin-7a-yl)methoxy)-5,6,7,8-tetrahydropyrido[3,4-d]pyrimidine Synthesized according to Example 37. The title compound was obtained as light yellow solid. $^1$H NMR (400 MHz, METHANOL-d$_4$) δ=7.68 (br dd, J=8.0, 16.4 Hz, 2H), 7.44-7.36 (m, 1H), 7.35-7.26 (m, 4H), 6.25 (s, 1H), 5.04 (br d, J=16.4 Hz, 1H), 4.78 (br s, 1H), 4.56-4.42 (m, 2H), 4.19 (s, 3H), 4.07 (br d, J=17.6 Hz, 1H), 4.00-3.91 (m, 1H), 3.66 (br d, J=17.6 Hz, 1H), 3.61-3.50 (m, 2H), 3.29-3.18 (m, 4H), 3.12 (br dd, J=7.1, 13.3 Hz, 1H), 2.93-2.83 (m, 2H), 2.73 (br d, J=12.0 Hz, 1H), 2.35-2.23 (m, 1H), 2.11-2.03 (m, 3H), 1.97 (ddd, J=6.4, 13.4, 20.0 Hz, 4H), 1.85-1.76 (m, 2H), 1.16 (br t, J=7.2 Hz, 3H); LCMS (ESI, M+1): m/z=564.4.

Example 52

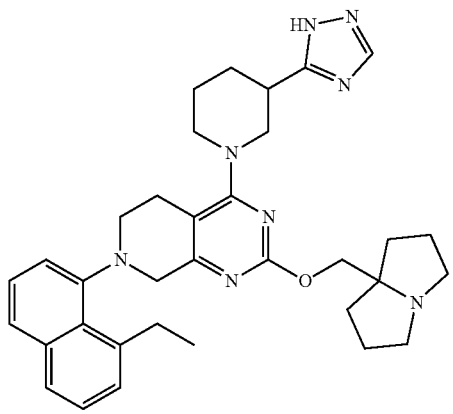 [SMILES: CCc1cccc2cccc(N3CCc4c(nc(OCC56CCCN5CCC6)nc4N4CCCC(c5ncn[nH]5)C4)C3)c12]

5-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)hexahydropyrrolo[3,4-c]pyrrol-1(2H)-one Synthesized according to Example 37. The title compound was obtained as white solid. $^1$H NMR (400 MHz, METHANOL-d$_4$) δ=7.71-7.65 (m, 2H), 7.42 (q, J=7.2 Hz, 1H), 7.36-7.26 (m, 3H), 4.39-4.24 (m, 3H), 4.12-3.96 (m, 3H), 3.80-3.73 (m, 1H), 3.68-3.58 (m, 5H), 3.43-3.42 (m, 2H), 3.22-3.16 (m, 4H), 3.06-3.04 (m, 4H), 2.18-2.16 (m, 2H), 2.09-2.04 (m, 4H), 2.03-1.94 (m, 2H), 1.16-1.10 (m, 3H); LCMS (ESI, M+1): m/z=553.4.

Example 53

4-(3-(1H-1,2,4-triazol-5-yl)piperidin-1-yl)-7-(8-ethylnaphthalen-1-yl)-2-((hexahydro-1H-pyrrolizin-7a-yl)methoxy)-5,6,7,8-tetrahydropyrido[3,4-d]pyrimidine Synthesized according to Example 37. The title compound was obtained as yellow solid. $^1$H NMR (400 MHz, METHANOL-d$_4$) δ=8.43 (d, J=2.8 Hz, 1H), 7.75-7.69 (m, 2H), 7.48-7.42 (m, 1H), 7.40-7.31 (m, 3H), 4.81-4.61 (m, 3H), 4.52-4.33 (m, 1H), 4.27-4.13 (m, 1H), 3.90-3.75 (m, 1H), 3.71-3.62 (m, 3H), 3.62-3.47 (m, 3H), 3.44-3.35 (m, 1H), 3.29-3.23 (m, 3H), 3.23-3.04 (m, 2H), 2.81-2.72 (m, 1H), 2.35-2.26 (m, 3H), 2.25-2.14 (m, 4H), 2.13-1.99 (m, 4H), 1.97-1.72 (m, 1H), 1.17 (t, J=7.2 Hz, 3H); LCMS (ESI, M+1): m/z=579.4.

Example 54

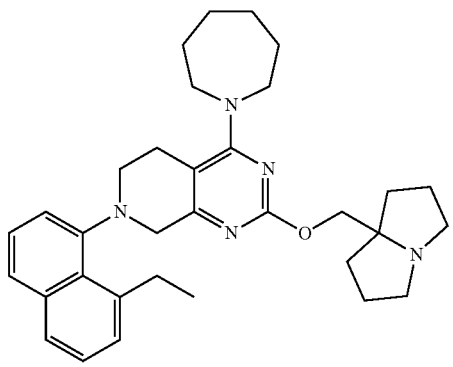 [SMILES: CCc1cccc2cccc(N3CCc4c(nc(OCC56CCCN5CCC6)nc4N4CCCCCC4)C3)c12]

4-(azocan-1-yl)-7-(8-ethylnaphthalen-1-yl)-2-((hexahydro-1H-pyrrolizin-7a-yl)methoxy)-5,6,7,8-tetrahydropyrido[3,4-d]pyrimidine Synthesized according to Example 37. The title compound was obtained as yellow solid. ¹H NMR (400 MHz, METHANOL-d₄) δ=7.73-7.63 (m, 2H), 7.41 (t, J=7.6 Hz, 1H), 7.37-7.25 (m, 3H), 4.22-4.11 (m, 2H), 4.02 (br d, J=17.6 Hz, 2H), 3.93-3.84 (m, 2H), 3.82-3.73 (m, 2H), 3.66-3.51 (m, 3H), 3.23-3.11 (m, 4H), 3.07 (dd, J=7.2, 13.2 Hz, 1H), 2.83-2.68 (m, 3H), 2.10-2.01 (m, 2H), 1.99-1.80 (m, 8H), 1.79-1.65 (m, 4H), 1.58 (br s, 4H), 1.14 (t, J=7.2 Hz, 3H); LCMS (ESI, M+1): m/z=540.5.

Example 55

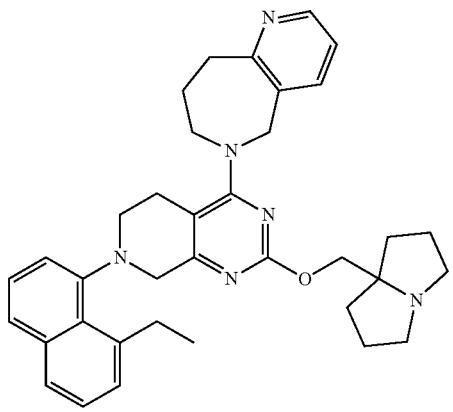 [SMILES: CCc1cccc2cccc(N3CCc4c(nc(OCC56CCCN5CCC6)nc4N4CCCc5ncccc5C4)C3)c12]

6-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6,7,8,9-tetrahydro-5H-pyrido[3,2-c]azepine Synthesized according to Example 37. The title compound was obtained as yellow solid. ¹H NMR (400 MHz, METHANOL-d₄) δ=8.31 (dd, J=1.2, 4.8 Hz, 1H), 7.78 (dd, J=1.2, 7.6 Hz, 1H), 7.69 (dd, J=7.2, 16.0 Hz, 2H), 7.42 (t, J=7.6 Hz, 1H), 7.38-7.33 (m, 1H), 7.32-7.23 (m, 3H), 5.03-4.96 (m, 1H), 4.90-4.79 (m, 1H), 4.41-4.32 (m, 1H), 4.27-4.15 (m, 2H), 4.11-3.97 (m, 2H), 3.65 (br d, J=18.0 Hz, 1H), 3.62-3.52 (m, 4H), 3.27-3.23 (m, 2H), 3.23-3.17 (m, 3H), 3.11 (dd, J=7.6, 13.6 Hz, 1H), 2.73 (br d, J=14.8 Hz, 1H), 2.30-1.97 (m, 11H), 1.16 (t, J=7.6 Hz, 3H); LCMS (ESI, M+1): m/z=575.4.

Example 56

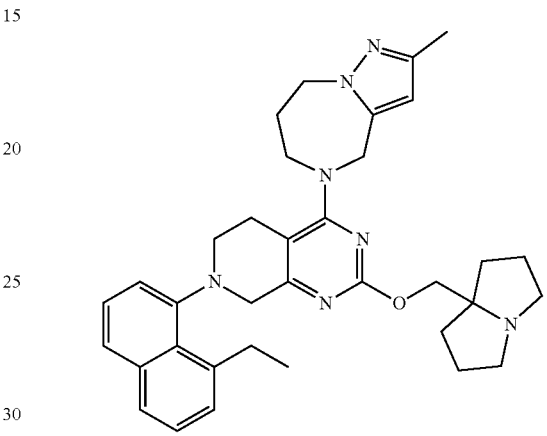

7-(8-ethylnaphthalen-1-yl)-2-((hexahydro-1H-pyrrolizin-7a-yl)methoxy)-4-(2-methyl-7,8-dihydro-4H-pyrazolo[1,5-a][1,4]diazepin-5(6H)-yl)-5,6,7,8-tetrahydropyrido[3,4-d]pyrimidine Synthesized according to Example 37. The title compound was obtained as yellow solid. ¹H NMR (400 MHz, methanol-d₄) δ=7.77-7.63 (m, 2H), 7.43 (t, J=7.6 Hz, 1H), 7.39-7.33 (m, 1H), 7.32-7.20 (m, 2H), 6.03 (s, 1H), 5.01 (d, J=16.4 Hz, 1H), 4.75 (d, J=16.4 Hz, 1H), 4.47-4.34 (m, 4H), 4.31-4.21 (m, 1H), 4.08 (d, J=17.6 Hz, 1H), 3.97-3.86 (m, 1H), 3.73-3.50 (m, 5H), 3.30-3.19 (m, 4H), 3.18-3.09 (m, 1H), 2.81-2.70 (m, 1H), 2.32-2.24 (m, 2H), 2.23-1.98 (m, 11H), 1.17 (t, J=7.2 Hz, 3H); LCMS (ESI, M+1): m/z=578.5.

Example 57

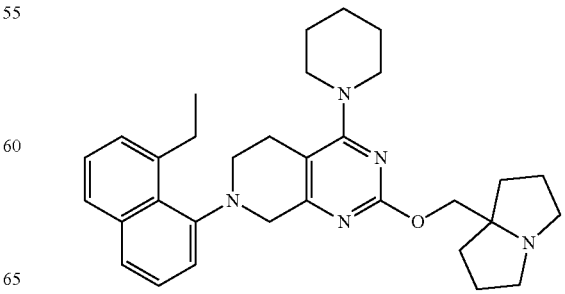

7-(8-ethylnaphthalen-1-yl)-2-((hexahydro-1H-pyr-rolizin-7a-yl)methoxy)-4-(piperidin-1-yl)-5,6,7,8-tetrahydropyrido[3,4-d]pyrimidine Synthesized according to Example 37. The title compound was obtained as white solid. ¹H NMR (400 MHz, METHANOL-d4) δ=7.68 (dd, J=7.6, 17.6 Hz, 2H), 7.42 (t, J=7.7 Hz, 1H), 7.37-7.25 (m, 3H), 4.27-4.15 (m, 2H), 4.09 (d, J=17.6 Hz, 1H), 3.68-3.57 (m, 4H), 3.56-3.48 (m, 3H), 3.27-3.11 (m, 4H), 3.06 (dd, J=7.2, 13.2 Hz, 1H), 2.90-2.79 (m, 2H), 2.69-2.58 (m, 1H), 2.15-2.04 (m, 2H), 2.03-1.86 (m, 4H), 1.85-1.62 (m, 8H), 1.15 (t, J=7.2 Hz, 3H); LCMS (ESI, M+1): m/z=512.4.

Example 58

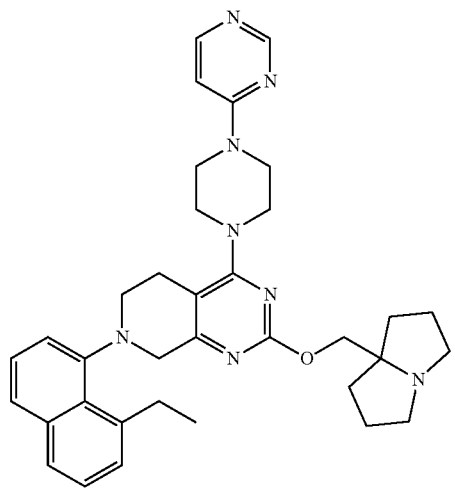 [SMILES: CCc1cccc2cccc(N3CCc4c(nc(OCC56CCCN5CCC6)nc4N4CCN(c5ccncn5)CC4)C3)c12]

7-(8-ethylnaphthalen-1-yl)-2-((hexahydro-1H-pyr-rolizin-7a-yl)methoxy)-4-(4-(pyrimidin-4-yl)piper-azin-1-yl)-5,6,7,8-tetrahydropyrido[3,4-d]pyrimidine Synthesized according to Example 37. The title compound was obtained as pink solid. ¹H NMR (400 MHz, METHANOL-d₄) δ=8.55 (s, 1H), 8.18 (d, J=6.4 Hz, 1H), 7.71 (dd, J=7.2, 16.4 Hz, 2H), 7.44 (t, J=7.6 Hz, 1H), 7.40-7.28 (m, 3H), 6.84 (d, J=6.4 Hz, 1H), 4.41-4.31 (m, 2H), 4.14 (d, J=17.6 Hz, 1H), 4.01-3.92 (m, 2H), 3.89-3.79 (m, 4H), 3.73-3.55 (m, 5H), 3.48-3.38 (m, 2H), 3.28-3.18 (m, 2H), 3.14-3.01 (m, 3H), 2.82-2.71 (m, 1H), 2.24-2.15 (m, 2H), 2.14-1.99 (m, 4H), 1.99-1.90 (m, 2H), 1.17 (t, J=7.2 Hz, 3H); LCMS (ESI, M+1): m/z=591.4.

Example 59

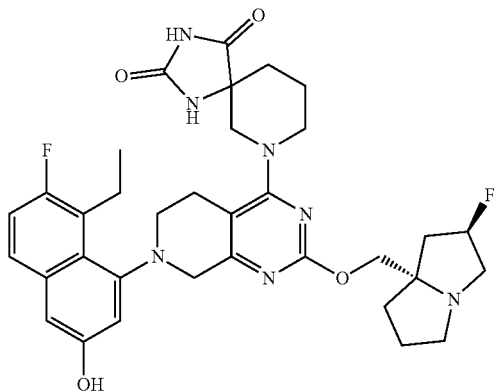 [SMILES: CCc1c(F)ccc2cc(O)cc(N3CCc4c(nc(OC[C@@]56CCCN5C[C@H](F)C6)nc4N4CCCC5(C4)NC(=O)NC5=O)C3)c12]

7-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decane-2,4-dione Synthesized according to Example 32. The title compound was obtained as orange solid. ¹H NMR (400 MHz, METHANOL-d₄) δ=7.52 (dd, J=6.0, 8.8 Hz, 1H), 7.15 (t, J=9.6 Hz, 1H), 7.04-6.93 (m, 2H), 5.61-5.30 (m, 1H), 4.49-4.28 (m, 2H), 4.27-4.14 (m, 1H), 4.14-3.93 (m, 2H), 3.80-3.56 (m, 4H), 3.56-3.32 (m, 5H), 3.29-3.20 (m, 1H), 3.20-3.01 (m, 2H), 2.86-2.68 (m, 1H), 2.61-2.33 (m, 2H), 2.32-2.03 (m, 5H), 2.02-1.72 (m, 3H), 1.10 (t, J=7.2 Hz, 3H); LCMS (ESI, M+1): m/z=648.3.

Example 60

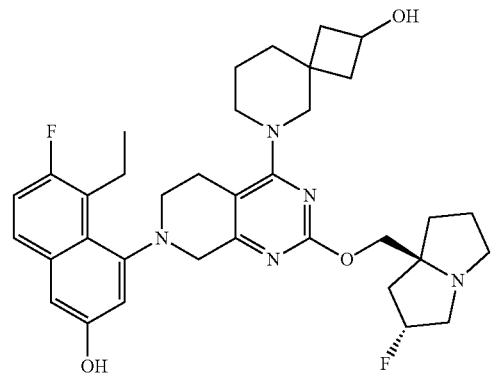 [SMILES: CCc1c(F)ccc2cc(O)cc(N3CCc4c(nc(OC[C@@]56CCCN5C[C@H](F)C6)nc4N4CCCC5(CC(O)C5)C4)C3)c12]

6-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-azaspiro[3.5]nonan-2-ol Synthesized according to Example 28. The title compound was obtained as yellow solid. ¹H NMR (400 MHz, METHANOL-d4) δ=7.51 (dd, J=5.6, 8.8 Hz, 1H), 7.14 (t, J=9.2 Hz, 1H), 6.98 (m, 2H), 5.47-5.22 (m, 1H), 4.33-4.13 (m, 3H), 4.07 (d, J=17.6 Hz, 1H), 3.90-3.72 (m, 1H), 3.70-3.59 (m, 2H), 3.58-3.48 (m, 1H), 3.47-3.35 (m, 1H), 3.45-3.33 (m, 5H), 3.28-3.07 (m, 4H), 2.75-2.55 (m, 1H), 2.46-2.12 (m, 5H), 2.11-2.01 (m, 2H), 2.00-1.90 (m, 1H), 1.89-1.55 (m, 6H), 1.21-1.04 (m, 3H); LCMS (ESI, M+1): m/z=620.1.

Example 61

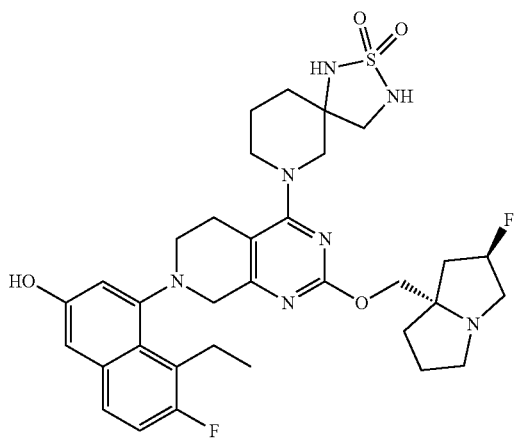 [SMILES: CCc1c(F)ccc2cc(O)cc(N3CCc4c(nc(OC[C@@]56CCCN5C[C@H](F)C6)nc4N4CCCC5(CNS(=O)(=O)N5)C4)C3)c12]

7-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-2-thia-1,3,7-triazaspiro[4.5]decane 2,2-dioxide Synthesized according to Example 32. The title compound was obtained as white solid. $^1$H NMR (400 MHz, METHANOL-d4) δ=8.50 (br s, 1H), 7.60-7.43 (m, 1H), 7.15 (dt, J=2.8, 9.4 Hz, 1H), 7.06-6.88 (m, 2H), 5.53-5.31 (m, 1H), 4.41-4.25 (m, 2H), 4.17-3.97 (m, 2H), 3.72-3.48 (m, 7H), 3.45-3.33 (m, 3H), 3.25-3.14 (m, 4H), 2.76-2.44 (m, 2H), 2.43-2.26 (m, 2H), 2.24-1.92 (m, 5H), 1.90-1.65 (m, 3H), 1.16-1.06 (m, 3H); LCMS (ESI, M+1): m/z=670.3.

Example 62

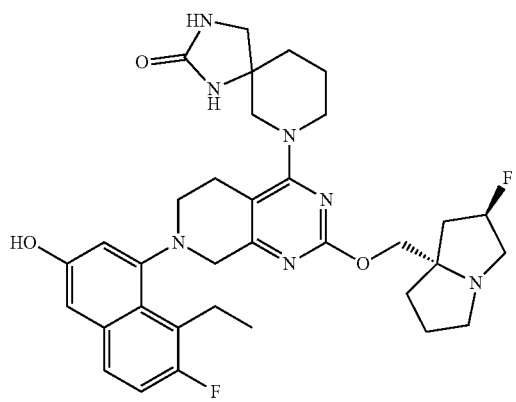 [SMILES: CCc1c(F)ccc2cc(O)cc(N3CCc4c(nc(OC[C@@]56CCCN5C[C@H](F)C6)nc4N4CCCC5(CNC(=O)N5)C4)C3)c12]

7-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decan-2-one Synthesized according to Example 32. The title compound was obtained as yellow solid. $^1$H NMR (400 MHz, METHANOL-d4) δ=8.50 (br s, 1H), 7.52 (dd, J=6.0, 8.8 Hz, 1H), 7.15 (t, J=9.6 Hz, 1H), 7.02-6.95 (m, 2H), 5.49-5.29 (m, 1H), 4.67-4.49 (m, 1H), 4.39-4.19 (m, 2H), 4.16-4.04 (m, 1H), 3.76-3.60 (m, 4H), 3.59-3.34 (m, 8H), 3.25-3.14 (m, 3H), 2.79-2.65 (m, 1H), 2.47-2.27 (m, 2H), 2.25-2.17 (m, 1H), 2.15-2.05 (m, 2H), 2.04-1.95 (m, 1H), 1.94-1.67 (m, 4H), 1.11 (dt, J=2.8, 7.2 Hz, 3H). LCMS (ESI, M+1): m/z=634.3.

Example 63

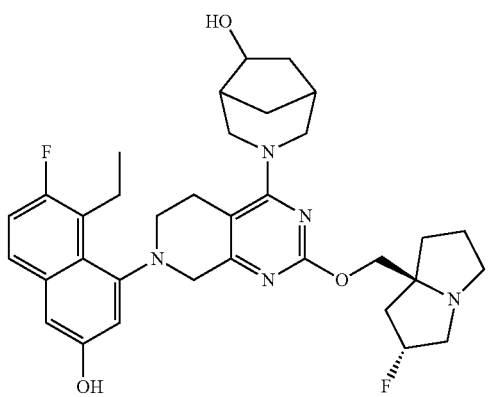 [SMILES: CCc1c(F)ccc2cc(O)cc(N3CCc4c(nc(OC[C@@]56CCCN5C[C@H](F)C6)nc4N4CC5CC(O)C(C5)C4)C3)c12]

3-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.2.1]octan-6-ol Synthesized according to Example 32. The title compound was obtained as white solid. $^1$H NMR (400 MHz, METHANOL-d$_4$) δ=7.57-7.46 (m, 1H), 7.21-7.09 (m, 1H), 7.03-6.92 (m, 2H), 5.45-5.25 (m, 1H), 4.66-4.47 (m, 1H), 4.36-4.23 (m, 2H), 4.23-4.02 (m, 2H), 4.07 (br d, J=17.6 Hz, 1H), 3.85-3.74 (m, 1H), 3.68-3.58 (m, 1H), 3.51-3.34 (m, 7H), 3.23-3.07 (m, 3H), 3.06-2.99 (m, 1H), 3.06-2.69 (m, 1H), 2.45-2.25 (m, 3H), 2.24-2.12 (m, 3H), 2.12-2.00 (m, 2H), 1.99-1.87 (m, 1H), 1.82-1.69 (m, 2H), 1.61-1.24 (m, 1H), 1.15-1.05 (m, 3H); LCMS (ESI, M+1): m/z=606.3.

Example 64

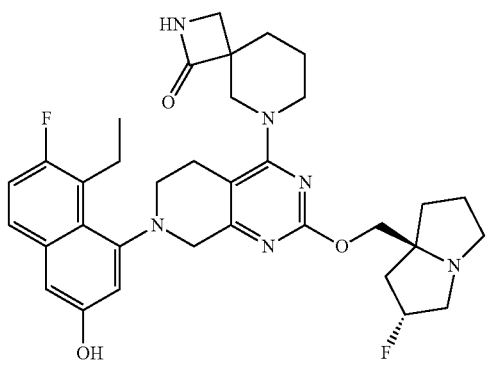 [SMILES: CCc1c(F)ccc2cc(O)cc(N3CCc4c(nc(OC[C@@]56CCCN5C[C@H](F)C6)nc4N4CCCC5(CNC5=O)C4)C3)c12]

155

6-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-2,6-diazaspiro[3.5]nonan-1-one Synthesized according to Example 27. The title compound was obtained as pink solid. ¹HNMR (400 MHz, METHANOL-d4) δ=7.52-7.49 (m, 1H), 7.15 (t, J=9.2 Hz, 1H), 7.04-6.93 (m, 2H), 5.40 (d, J=53.2 Hz, 1H), 4.69-4.53 (m, 1H), 4.51-4.32 (m, 2H), 4.16-4.03 (m, 1H), 4.03-3.77 (m, 3H), 3.76-3.62 (m, 4H), 3.57-3.47 (m, 1H), 3.46-3.33 (m, 3H), 3.27-3.08 (m, 4H), 2.74-2.41 (m, 3H), 2.36-2.17 (m, 3H), 2.16-1.76 (m, 5H), 1.11 (m, 3H); LCMS (ESI, M+1): m/z=619.4.

Example 65

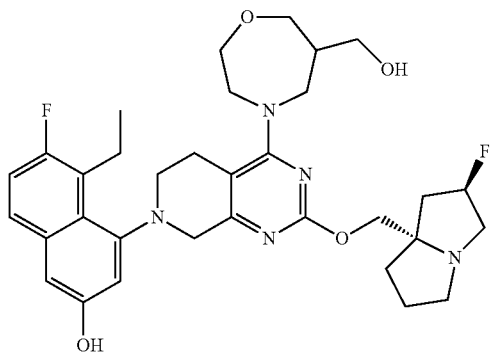 [SMILES: CCc1c(F)ccc2cc(O)cc(N3CCc4c(nc(OC[C@@]56CCCN5C[C@H](F)C6)nc4N4CCOCC(CO)C4)C3)c12]

5-ethyl-6-fluoro-4-(2-(((2R,7aS)-2-fluorohexahydro-1H-pyrrolizin-7a-yl)methoxy)-4-(6-(hydroxymethyl)-1,4-oxazepan-4-yl)-5,6-dihydropyrido[3,4-d]pyrimidin-7(8H)-yl)naphthalen-2-ol Synthesized according to Example 32. The title compound was obtained as yellow solid. 1H NMR (400 MHz, METHANOL-d4) δ=8.52 (s, 1H), 7.68-7.46 (m, 1H), 7.21-7.10 (m, 1H), 7.09-6.90 (m, 2H), 6.90-6.87 (m, 1H), 5.48-5.23 (m, 1H), 4.49-4.14 (m, 4H), 4.11-3.77 (m, 4H), 3.75-3.36 (m, 12H), 3.28-3.08 (m, 3H), 2.81-2.70 (m, 1H), 2.52-1.89 (m, 4H), 2.14-1.82 (m, 3H), 1.26-1.05 (m, 3H); LCMS (ESI, M+1): m/z=610.5.

Example 66

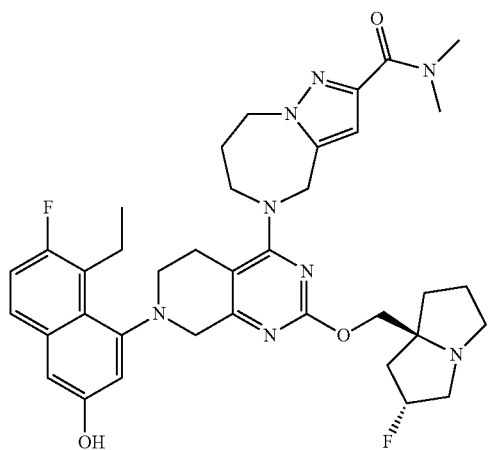 [SMILES: CCc1c(F)ccc2cc(O)cc(N3CCc4c(nc(OC[C@@]56CCCN5C[C@H](F)C6)nc4N4CCCn5nc(C(=O)N(C)C)cc5C4)C3)c12]

156

5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide

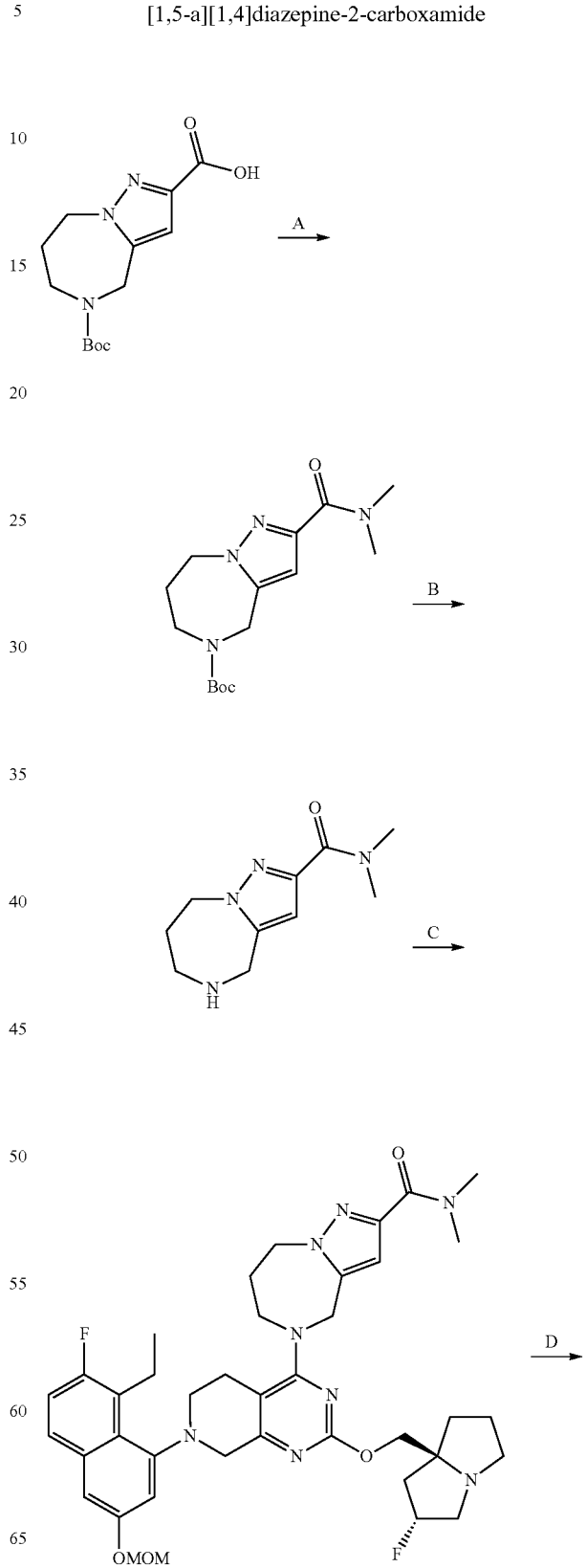

157
-continued

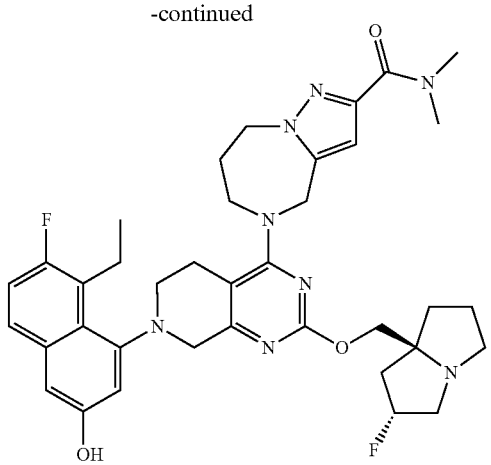

Step A. tert-butyl 2-(dimethylcarbamoyl)-7,8-dihydro-4H-pyrazolo[1,5-a][1,4]diazepine-5(6H)-carboxylate: To a solution of 5-(tert-butoxycarbonyl)-5,6,7,8-tetrahydro-4H-pyrazolo[1,5-a][1,4]diazepine-2-carboxylic acid (1.0 g, 1.0 equiv) and N-methylmethanamine (3.55 mL, 2.0 equiv) in DCM (10 mL) was added HATU (2.03 g, 1.5 equiv) and N-ethyl-N-isopropylpropan-2-amine (1.38 g, 1.86 mL, 3.0 equiv). The mixture was stirred at 20° C. for 1 hr. The mixture was concentrated under vacuum. The residue was purified by reversed phase flash chromatography [water (FA, 0.1%)/acetonitrile]. The desire fractions were combined. Its pH was adjusted to 8 by NaHCO$_3$ (4.0 g) and solvent was removed to afford the title compound (1.0 g, 91% yield) as yellow solid. LCMS [ESI, M+1]: m/z=309.2.

Step B. N,N-dimethyl-5,6,7,8-tetrahydro-4H-pyrazolo[1,5-a][1,4]diazepine-2-carboxamide: A mixture of tert-butyl 2-(dimethylcarbamoyl)-7,8-dihydro-4H-pyrazolo[1,5-a][1,4]diazepine-5(6H)-carboxylate and HCl/dioxane (9.50 mL, 12.3 equiv) in MeCN (9.5 mL) was stirred at 0° C. for 1 hour. The mixture was concentrated under vacuum. The pH of the residue was adjusted to 8 with saturated sodium bicarbonate (4 mL). The residue was purified by prep HPLC [column: YMC Triart C18 250×50 mm×7 μm; mobile phase: water (ammonia hydroxide v/v)-ACN; B %: 2%-32%, 8 minutes] to afford the title compound (0.50 g, 77% yield) as yellow solid. LCMS [ESI, M+1]: m/z=209.2.

Step C. 5-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide: A mixture of 7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv), N,N-dimethyl-5,6,7,8-tetrahydro-4H-pyrazolo[1,5-a][1,4]diazepine-2-carboxamide (60.0 mg, 2.0 equiv), 4 Å molecular sieve (10.0 mg) and N-ethyl-N-isopropylpropan-2-amine (74.4 mg, 4.0 equiv) in DMF (0.3 mL) was stirred at 40° C. for 12 hours. The reaction mixture was filtered and purified with prep-HPLC column: Phenomenex Luna C18 100×30 mm×5 μm; mobile phase: water (FA)-ACN; B %: 19%-49%, 8 minutes]. The desire fractions were combined, and solvents were removed. The pH of the residue was adjusted to 8 with saturated sodium bicarbonate. The residue was extracted with ethyl acetate (0.1 ml×3), dried over Na$_2$SO$_4$ and con-

158 centrated under vacuum to afford the title compound (71.0 mg, 67% yield) as yellow solid. LCMS (ESI, M+1): m/z=731.4.

Step D. 5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide: A mixture of 5-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide (80.0 mg, 1.0 equiv) and HCl·MeOH (2.00 mL, 73 equiv) was stirred at 0° C. for 1 hours. The mixture was concentrated under vacuum. The pH of the residue was adjusted to 8 with saturated sodium bicarbonate solution. The mixture was diluted with ethyl acetate (3×1 mL), dried over Na$_2$SO$_4$, concentrated and purified by prep-HPLC [column: Waters xbridge 150×25 mm×10 μm; mobile phase: water (NH$_4$HCO$_3$)-ACN; B %: 35%-65%, 11 minutes] to afford the title compound (27.0 mg, 34% yield) as yellow solid. $^1$H NMR (400 MHz, METHANOL-d4) δ=9.18 (s, 1H), 8.58-8.43 (m, 1H), 7.81 (dd, J=5.2, 9.2 Hz, 1H), 7.43-7.35 (m, 2H), 7.21 (d, J=2.4 Hz, 1H), 6.76 (s, 1H), 5.48-5.18 (m, 3H), 4.54 (br d, J=6.4 Hz, 2H), 4.48-4.36 (m, 4H), 3.63-3.41 (m, 3H), 3.33 (s, 3H), 3.23-3.16 (m, 1H), 3.08 (s, 3H), 2.47-2.23 (m, 5H), 2.18-1.98 (m, 3H); LCMS (ESI, M+1): m/z=687.3.

Example 67

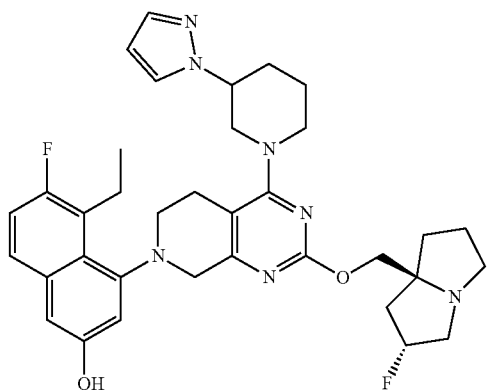 [SMILES: CCc1c(F)ccc2cc(O)cc(N3CCc4c(nc(OC[C@@]56CCCN5C[C@H](F)C6)nc4N4CCCC(n5cccn5)C4)C3)c12]

4-(4-(3-(1H-pyrazol-1-yl)piperidin-1-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 28. The title compound was obtained as off-white solid. $^1$H NMR (400 MHz, methanol-d$_4$) δ=7.78-7.73 (m, 1H), 7.56-7.47 (m, 2H), 7.14 (t, J=9.4 Hz, 1H), 7.02-6.94 (m, 2H), 6.32 (td, J=2.0, 4.0 Hz, 1H), 5.45-5.14 (m, 1H), 4.66-4.64 (m, 1H), 4.74-4.55 (m, 1H), 4.51-4.25 (m, 2H), 4.24-3.94 (m, 4H), 3.66 (dd, J=11.2, 17.6 Hz, 1H), 3.55-3.46 (m, 1H), 3.43-3.33 (m, 3H), 3.26 (br d, J=9.2 Hz, 2H), 3.22-3.14 (m, 2H), 3.13-2.94 (m, 2H), 2.74-2.57 (m, 1H), 2.41-2.15 (m, 4H), 2.14-2.07 (m, 1H), 2.05-1.97 (m, 3H), 1.96-1.87 (m, 1H), 1.87-1.63 (m, 1H), 1.17-1.02 (m, 3H); LCMS (ESI, M+1): m/z=630.4.

Example 68

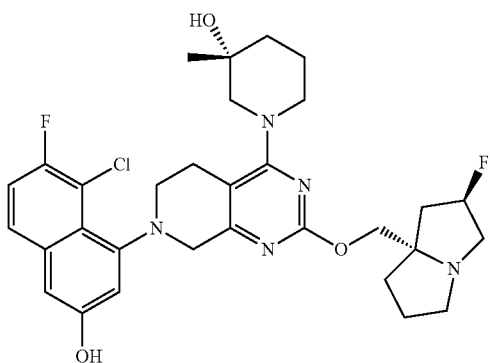 [SMILES: C[C@@]1(O)CCCN(c2nc(OC[C@@]34CCCN3C[C@H](F)C4)nc3c2CCN(c2cc(O)cc4ccc(F)c(Cl)c24)C3)C1]

(R)-1-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol

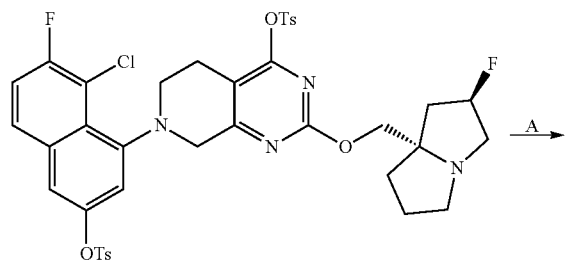

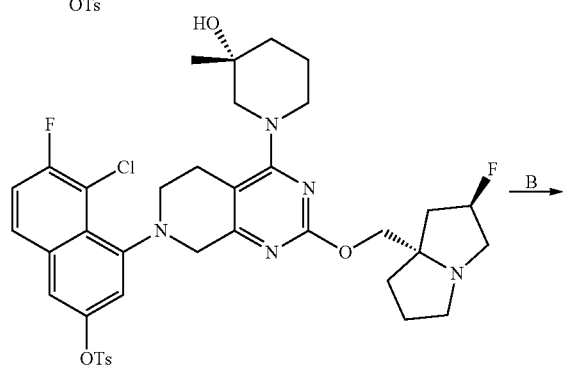

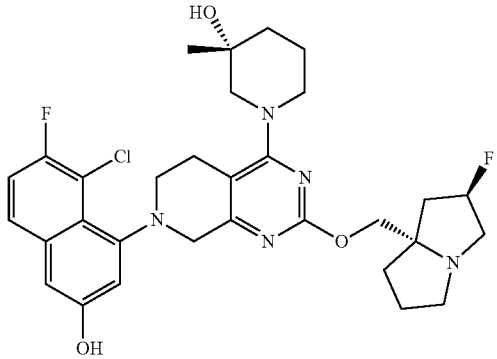

Step A. 5-chloro-6-fluoro-4-(2-(((2R,7aS)-2-fluorotetrahydro-1H-pyrrolizin-7a(5H)-yl)methoxy)-4-((R)-3-hydroxy-3-methylpiperidin-1-yl)-5,8-dihydropyrido[3,4-d]pyrimidin-7(6H)-yl)naphthalen-2-yl 4-methylbenzenesulfonate: To a mixture of 5-chloro-6-fluoro-4-(2-(((2R,7aS)-2-fluorotetrahydro-1H-pyrrolizin-7a(5H)-yl)methoxy)-4-(tosyloxy)-5,8-dihydropyrido[3,4-d]pyrimidin-7(6H)-yl)naphthalen-2-yl 4-methylbenzenesulfonate (100 mg, 1.0 equiv) and (3R)-3-methylpiperidin-3-ol (28.4 mg, 2.0 equiv) in DMF (1 mL) were added N-ethyl-N-isopropylpropan-2-amine (63.7 mg, 4.0 equiv) and 4 Å molecular sieve (10.0 mg). The mixture was stirred at 40-60° C. until the reaction was completed. The mixture was diluted with ethyl acetate (10 mL) and washed with water (5 mL×3). The organic layers were washed with saturated brine (5 mL), dried over anhydrous sodium sulfate, and concentrated to afford the title compound (81.0 mg, crude) as yellow oil; LCMS (ESI, M−1): m/z=754.3.

Step B. (R)-1-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-methylpiperidin-3-ol: A mixture of 5-chloro-6-fluoro-4-(2-(((2R,7aS)-2-fluorotetrahydro-1H-pyrrolizin-7a(5H)-yl)methoxy)-4-((R)-3-hydroxy-3-methylpiperidin-1-yl)-5,8-dihydropyrido[3,4-d]pyrimidin-7(6H)-yl)naphthalen-2-yl 4-methylbenzenesulfonate (70 mg, 1.0 equiv) and NaOH (371 mg, 100 equiv) in MeOH (2 mL) was stirred at 25° C. for 1 hour. The reaction mixture was diluted with water (3 mL), concentrated under vacuum to remove MeOH, extracted with ethyl acetate (5 mL×3). The combined organic layers were washed with brine (3×5 mL), dried over anhydrous sodium sulfate, concentrated, and purified with prep-HPLC [column: Phenomenex Luna C18 150×25 mm×10 μm; mobile phase: water (FA)-ACN; B %: 14%-44%, 8 minutes] to afford the title compound (8.71 mg, 15% yield) as off-white solid. $^1$H NMR (400 MHz, METHANOL-$d_4$) δ=7.62 (dd, J=5.6, 8.8 Hz, 1H), 7.28 (t, J=8.8 Hz, 1H), 6.95 (d, J=2.0 Hz, 2H), 5.55-5.32 (m, 1H), 4.41-4.16 (m, 3H), 4.03-3.37 (m, 8H), 3.28-3.02 (m, 4H), 2.77-2.59 (m, 1H), 2.54-2.30 (m, 2H), 1.89-1.62 (m, 3H), 2.25-1.60 (m, 5H), 1.30-1.18 (m, 3H); LCMS (ESI, M+1): m/z=600.5.

Example 69

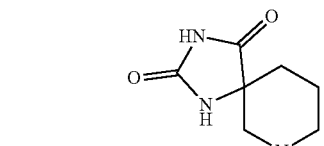
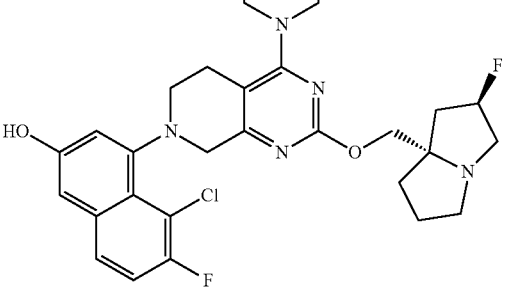

7-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decane-2,4-dione Synthesized according to Example 68. The title compound was obtained as pink solid. $^1$H NMR (400 MHz, METHANOL-d₄) δ=7.62 (dd, J=5.6, 9.2 Hz, 1H), 7.28 (t, J=8.8 Hz, 1H), 6.98-6.92 (m, 2H), 5.55-5.30 (m, 1H), 4.44-4.29 (m, 2H), 4.25-3.98 (m, 2H), 3.71-3.64 (m, 1H), 3.61-3.52 (m, 3H), 3.45-3.35 (m, 2H), 3.27-3.00 (m, 4H), 2.80-2.64 (m, 1H), 2.56-2.33 (m, 2H), 2.32-2.22 (m, 1H), 2.19-1.76 (m, 8H). LCMS (ESI, M+1): m/z=654.2.

Example 70

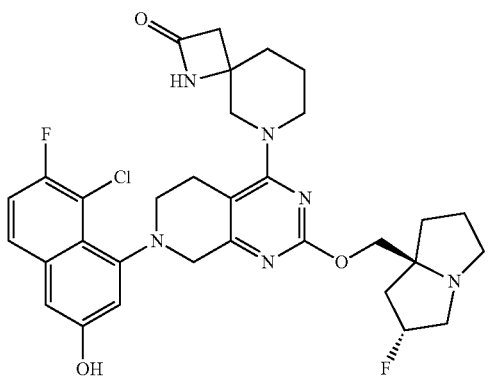 [SMILES: O=C1CC2(CCCN(c3nc(OC[C@@]45CCCN4C[C@H](F)C5)nc4c3CCN(c3cc(O)cc5ccc(F)c(Cl)c35)C4)C2)N1]

6-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,6-diazaspiro[3.5]nonan-2-one Synthesized according to Example 68. The title compound was obtained as pink solid. ¹H NMR (400 MHz, METHANOL-d4) δ=7.62 (dd, J=5.6, 9.2 Hz, 1H), 7.27 (t, J=8.8 Hz, 1H), 6.95 (d, J=2.0 Hz, 2H), 5.36-5.19 (m, 1H), 4.27 (br d, J=17.6 Hz, 1H), 4.22-4.03 (m, 2H), 3.92-3.48 (m, 6H), 3.26-3.10 (m, 5H), 3.00 (dt, J=5.6, 9.2 Hz, 1H), 2.88-2.59 (m, 3H), 2.34-2.04 (m, 3H), 2.03-1.78 (m, 7H); LCMS (ESI, M+1): m/z=625.3.

Example 71

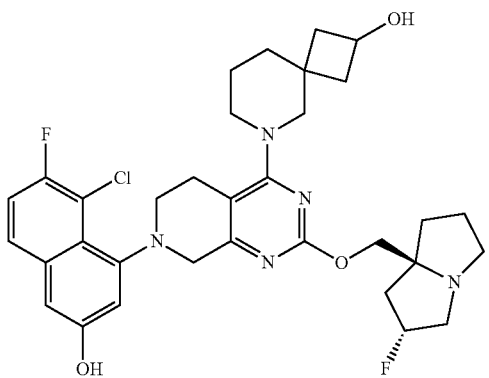 [SMILES: Oc1cc(N2CCc3c(nc(OC[C@@]45CCCN4C[C@H](F)C5)nc3N3CCCC4(CC(O)C4)C3)C2)c2c(Cl)c(F)ccc2c1]

6-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-azaspiro[3.5]nonan-2-ol Synthesized according to Example 68. The title compound was obtained as pink solid. ¹H NMR (400 MHz, METHANOL-d₄) δ=8.64-8.48 (m, 1H), 7.62 (dd, J=5.6, 9.2 Hz, 1H), 7.27 (t, J=8.8 Hz, 1H), 6.95 (s, 2H), 5.45-5.13 (m, 1H), 4.32-4.06 (m, 4H), 3.79-3.39 (m, 5H), 3.30-2.97 (m, 7H), 2.66-2.55 (m, 1H), 2.38-2.08 (m, 5H), 2.04-1.59 (m, 9H); LCMS (ESI, M+1): m/z=626.3.

Example 72

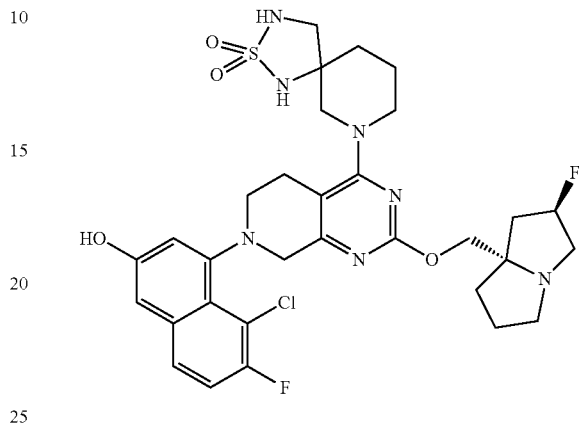

7-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-2-thia-1,3,7-triazaspiro[4.5]decane 2,2-dioxide Synthesized according to Example 68. The title compound was obtained as off-white solid. ¹H NMR (400 MHz, METHANOL-d4) δ=7.67-7.60 (m, 1H), 7.29 (dt, J=3.2, 8.8 Hz, 1H), 7.01-6.93 (m, 2H), 5.40-5.20 (m, 1H), 4.29 (d, J=17.6 Hz, 1H), 4.22-4.09 (m, 2H), 3.98-3.80 (m, 1H), 3.75-3.35 (m, 6H), 3.29-3.23 (m, 2H), 3.23-3.17 (m, 3H), 3.16-2.96 (m, 2H), 2.74-2.59 (m, 1H), 2.39-2.11 (m, 3H), 2.08-1.92 (m, 4H), 1.91-1.68 (m, 3H); LCMS (ESI, M+1): m/z=676.3.

Example 73

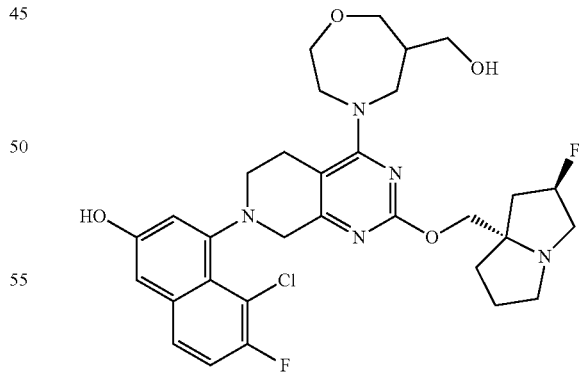

5-chloro-6-fluoro-4-(2-(((2R,7aS)-2-fluorohexahydro-1H-pyrrolizin-7a-yl)methoxy)-4-(6-(hydroxymethyl)-1,4-oxazepan-4-yl)-5,6-dihydropyrido[3,4-d]pyrimidin-7(8H)-yl)naphthalen-2-ol Synthesized according to Example 68. The title compound was obtained as white solid. ¹H NMR (400 MHz, METHANOL-d4) δ=7.70-7.53 (m, 1H), 7.27 (t, J=8.8 Hz, 1H), 6.95 (dd, J=2.8, 5.1 Hz, 2H), 5.39-5.16 (m, 1H), 4.46-4.26 (m, 1H), 4.26-4.15 (m, 2H), 4.15-4.02 (m, 2H), 3.98-3.76 (m, 3H), 3.76-3.64 (m, 2H), 3.60 (br s, 1H), 3.57-3.37 (m, 4H), 3.28-3.20 (m, 2H), 3.20-2.95 (m, 4H), 2.75-2.64 (m, 1H), 2.53-2.32 (m, 1H), 2.26-2.05 (m, 3H), 2.02-1.80 (m, 3H); LCMS (ESI, M+1): m/z=616.3.

Example 74

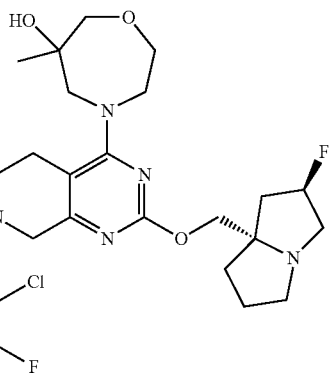

4-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-methyl-1,4-oxazepan-6-ol Synthesized according to Example 68. The title compound was obtained as yellow solid. $^1$H NMR (400 MHz, METHANOL-d4) δ=7.62 (td, J=6.4, 8.8 Hz, 1H), 7.31-7.24 (m, 1H), 6.99-6.87 (m, 2H), 5.50-5.31 (m, 1H), 4.35-4.29 (m, 1H), 4.28-4.17 (m, 2H), 4.10-4.00 (m, 1H), 4.00-3.92 (m, 1H), 3.91-3.85 (m, 1H), 3.84-3.73 (m, 2H), 3.69-3.59 (m, 2H), 3.58-3.49 (m, 4H), 3.49-3.41 (m, 2H), 3.26-3.17 (m, 2H), 3.16-3.04 (m, 1H), 2.76-2.56 (m, 1H), 2.53-2.31 (m, 2H), 2.26-2.07 (m, 3H), 2.06-1.90 (m, 2H), 1.24-1.14 (m, 3H); LCMS (ESI, M+1): m/z=616.3.

Example 75

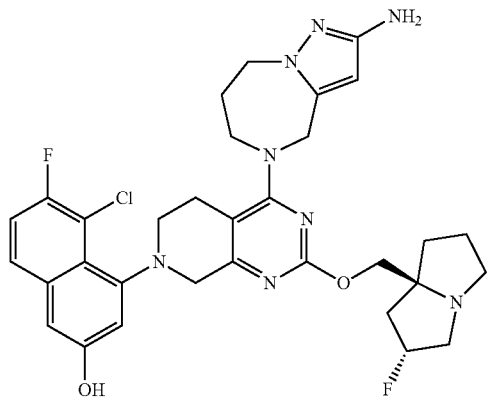 [SMILES: Nc1cc2n(n1)CCCN(c1nc(OC[C@@]34CCCN3C[C@H](F)C4)nc3c1CCN(c1cc(O)cc4ccc(F)c(Cl)c14)C3)C2]

4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-chloro-6-fluoronaphthalen-2-ol Synthesized according to Example 68. The title compound was obtained as white solid. $^1$H NMR (400 MHz, METHANOL-d$_4$) δ=7.62 (dd, J=5.6, 9.1 Hz, 1H), 7.27 (t, J=8.8 Hz, 1H), 6.96 (d, J=2.0 Hz, 1H), 6.91 (s, 1H), 5.55 (s, 1H), 5.40-5.26 (m, 1H), 4.75 (br d, J=2.4 Hz, 1H), 4.70-4.63 (m, 2H), 4.27 (s, 1H), 4.29-4.16 (m, 3H), 4.15-4.09 (m, 1H), 4.08-3.91 (m, 2H), 3.72 (br d, J=17.2 Hz, 1H), 3.57-3.48 (m, 1H), 3.35 (br d, J=1.2 Hz, 2H), 3.23-3.12 (m, 2H), 3.12-3.02 (m, 1H), 2.71-2.59 (m, 1H), 2.40-2.27 (m, 1H), 2.27-2.11 (m, 3H), 2.10-1.97 (m, 3H), 1.97-1.84 (m, 1H); LCMS (ESI, M+1): m/z=637.2.

Example 76 and Example 77

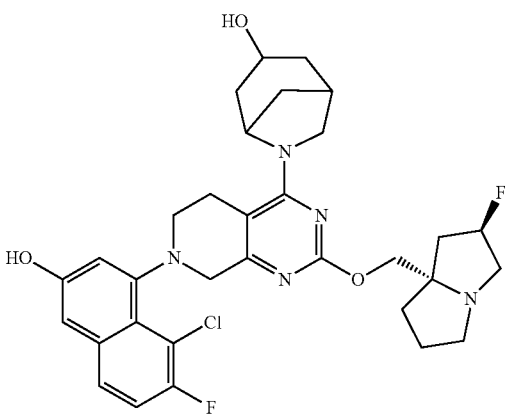 [SMILES: Oc1cc(N2CCc3c(nc(OC[C@@]45CCCN4C[C@H](F)C5)nc3N3CC4CC(O)CC3C4)C2)c2c(Cl)c(F)ccc2c1]

6-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-azabicyclo[3.2.1]octan-3-ol Synthesized according to Example 68. Two isomers of the title compounds were separated with HPLC in the final step. Isomer 1: yellow solid. 1H NMR (400 MHz, METHANOL-d4) δ=7.58 (br dd, J=6.0, 8.8 Hz, 1H), 7.26-7.20 (m, 1H), 6.98-6.87 (m, 1H), 5.39-5.17 (m, 1H), 4.19-4.15 (m, 1H), 4.13-4.07 (m, 3H), 4.03-3.74 (m, 2H), 3.72-3.56 (m, 1H), 3.55-3.43 (m, 2H), 3.24-3.13 (m, 4H), 3.09-2.93 (m, 4H), 2.70-2.48 (m, 2H), 2.23-2.05 (m, 3H), 2.00-1.91 (m, 5H), 1.76-1.63 (m, 2H), 1.35-1.28 (m, 1H); LCMS (ESI, M+1): m/z=612.5. Isomer 2: yellow oil; 1H NMR (400 MHz, METHANOL-d4) δ=7.57 (dd, J=6.0, 8.8 Hz, 1H), 7.22 (t, J=8.8 Hz, 1H), 6.98-6.84 (m, 2H), 5.40-5.17 (m, 1H), 4.87 (br s, 1H), 4.19-4.11 (m, 2H), 4.08-4.02 (m, 1H), 4.00-3.90 (m, 1H), 3.81-3.58 (m, 3H), 3.57-3.34 (m, 2H), 3.26-3.13 (m, 4H), 3.02-2.87 (m, 2H), 2.80-2.52 (m, 2H), 2.50-2.16 (m, 2H), 2.13-2.05 (m, 2H), 2.01-1.91 (m, 3H), 1.89-1.80 (m, 1H), 1.71 (br d, J=11.2 Hz, 1H), 1.55-1.46 (m, 1H), 1.44-1.35 (m, 1H); LCMS (ESI, M+1): m/z=612.5.

Example 78

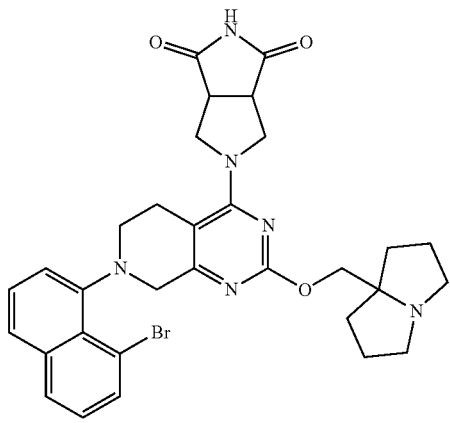 [SMILES: O=C1NC(=O)C2CN(c3nc(OCC45CCCN4CCC5)nc4c3CCN(c3cccc5cccc(Br)c35)C4)CC12]

5-(7-(8-bromonaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione

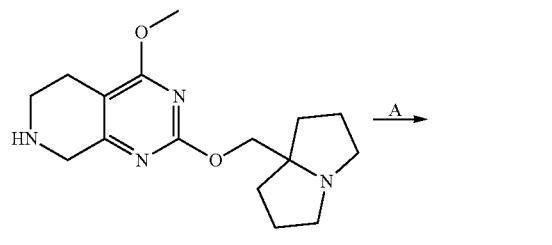

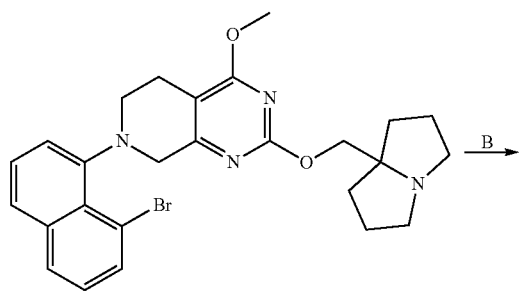

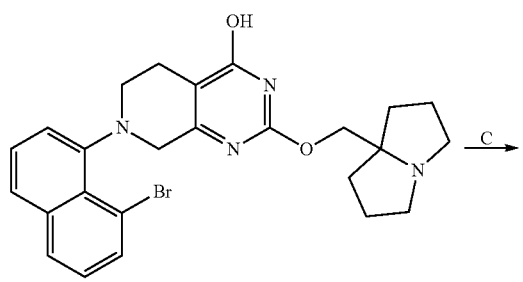

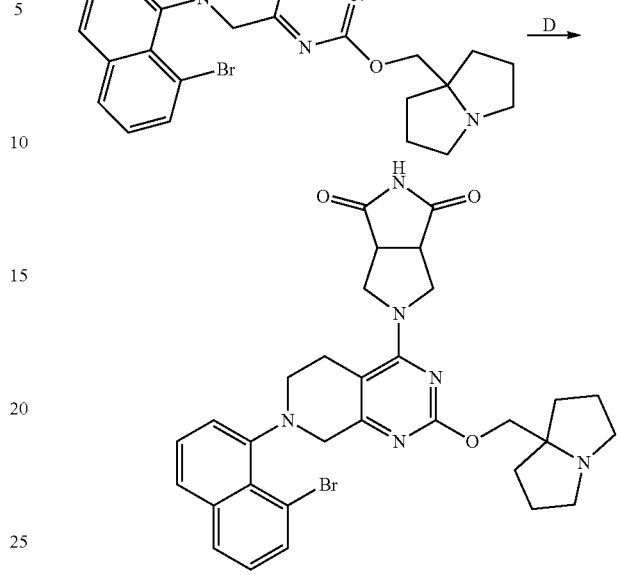

Step A. 7-(8-bromonaphthalen-1-yl)-2-((hexahydro-1H-pyrrolizin-7a-yl)methoxy)-4-methoxy-5,6,7,8-tetrahydropyrido[3,4-d]pyrimidine: A mixture of 2-((hexahydro-1H-pyrrolizin-7a-yl)methoxy)-4-methoxy-5,6,7,8-tetrahydropyrido[3,4-d]pyrimidine (500 mg, 1.0 equiv), 1,8-dibromonaphthalene (1.41 g, 3.0 equiv), BINAP (306 mg, 0.3 equiv), t-BuONa (237 mg, 1.5 equiv) and $Pd_2(dba)_3$ (150 mg, 0.1 equiv) in toluene (20 mL) was degassed and purged with $N_2$ for 3 times, and then the mixture was stirred at 90° C. for 3 hours under $N_2$ atmosphere. The mixture was diluted with $H_2O$ (10 mL) and extracted with ethyl acetate (3×10 mL). The combined organic layers were dried over anhydrous sodium sulfate, concentrated, and purified by reversed phase flash chromatography [C18, 0.1% formic acid condition] to afford the tittle compound (400 mg, 41% yield) as yellow solid. LCMS (ESI, M+1): m/z=511.2.

Step B. 7-(8-bromonaphthalen-1-yl)-2-((hexahydro-1H-pyrrolizin-7a-yl)methoxy)-5,6,7,8-tetrahydropyrido[3,4-d]pyrimidin-4-ol: To a solution of NaH (47.1 mg, 60% purity, 2.0 equiv) in DMAC (1 mL) was added EtSH (256 mg, 7.0 equiv) at 0° C. under $N_2$ atmosphere. The mixture was stirred at 0° C. for 10 minutes, and then 7-(8-bromonaphthalen-1-yl)-2-((hexahydro-1H-pyrrolizin-7a-yl)methoxy)-4-methoxy-5,6,7,8-tetrahydropyrido[3,4-d]pyrimidine (300 mg, 1.0 equiv) in DMAC (2 mL) was added. The mixture was stirred at 60° C. for 1 hour. The mixture was quenched with saturated $NH_4Cl$ (20 mL) at 0° C., and extracted with ethyl acetate (3×10 mL). The combined organic layers were dried over anhydrous $Na_2SO_4$, concentrated, and purified by reversed phase flash chromatography [C18, 0.1% formic acid condition] to afford the title compound (125 mg, 82% yield) as yellow solid. LCMS (ESI, M+1): m/z=495.1.

Step C. 7-(8-bromonaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate: To a solution of 7-(8-bromonaphthalen-1-yl)-2-((hexahydro-1H-pyrrolizin-7a-yl)methoxy)-5,6,7,8-tetrahydropyrido[3,4-d]pyrimidin-4-ol (120 mg, 1.0 equiv) in THF (3 mL) were added N-ethyl-N-isopropylpropan-2-amine (78.26 mg, 2.5 equiv)

and DMAP (2.96 mg, 0.1 equiv). Then 4-methylbenzene-1-sulfonyl chloride (60.0 mg, 1.3 equiv) was added at 0° C. The solution was stirred at 20° C. for 2 hours. The mixture was diluted with H₂O (10 mL) at 0° C. and extracted with ethyl acetate (3×10 mL). The combined organic layers were dried over anhydrous sodium sulfate, concentrated, and purified by reversed phase flash chromatography [C18, 0.1% formic acid condition] to afford the title compound (120 mg, 76% yield) as yellow solid.

Step D. 5-(7-(8-bromonaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione: To a solution of 7-(8-bromonaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (100 mg, 1.0 equiv) and tetrahydropyrrolo[3,4-c]pyrrole-1,3(2H,3aH)-dione (28.5 mg, 1.3 equiv) in DMF (1 mL) were added N-ethyl-N-isopropylpropan-2-amine (59.7 mg, 3 equiv), and 4 Å molecular sieve (30 mg). The reaction mixture was stirred at 40° C. for 12 hours. The mixture was filtered and purified with prep-HPLC [Waters Xbridge 150×25 mm×5 μm; A: water (10 mM NH₄HCO₃), B: ACN, B %: 40%-70%, 10 minutes] to afford the title compound (24 mg, 22% yield,) as yellow solid. ¹H NMR (400 MHz, METHANOL-d₄) δ=7.88-7.85 (m, 1H), 7.79 (dd, J=0.8, 7.6 Hz, 1H), 7.73-7.66 (m, 1H), 7.50 (t, J=8.0 Hz, 1H), 7.39-7.32 (m, 1H), 7.31-7.25 (m, 1H), 4.62 (d, J=10.4 Hz, 1H), 4.40-4.15 (m, 4H), 3.80-3.74 (m, 1H), 3.66-3.55 (m, 2H), 3.54-3.44 (m, 3H), 3.43-3.35 (m, 2H), 3.29-3.12 (m, 2H), 3.07-2.96 (m, 2H), 2.74-2.65 (m, 1H), 2.23-2.13 (m, 2H), 2.12-1.97 (m, 4H), 1.95-1.82 (m, 2H); LCMS (ESI, M+1): m/z=617.2.

Example 79

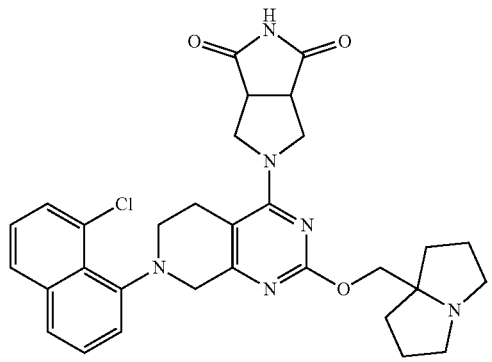 [SMILES: O=C1NC(=O)C2CN(c3nc(OCC45CCCN4CCC5)nc4c3CCN(c3cccc5cccc(Cl)c35)C4)CC12]

5-(7-(8-chloronaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione

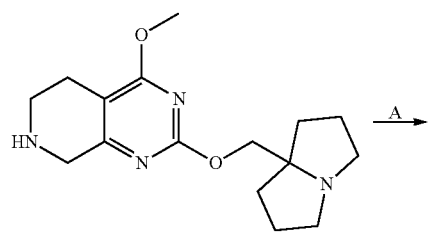

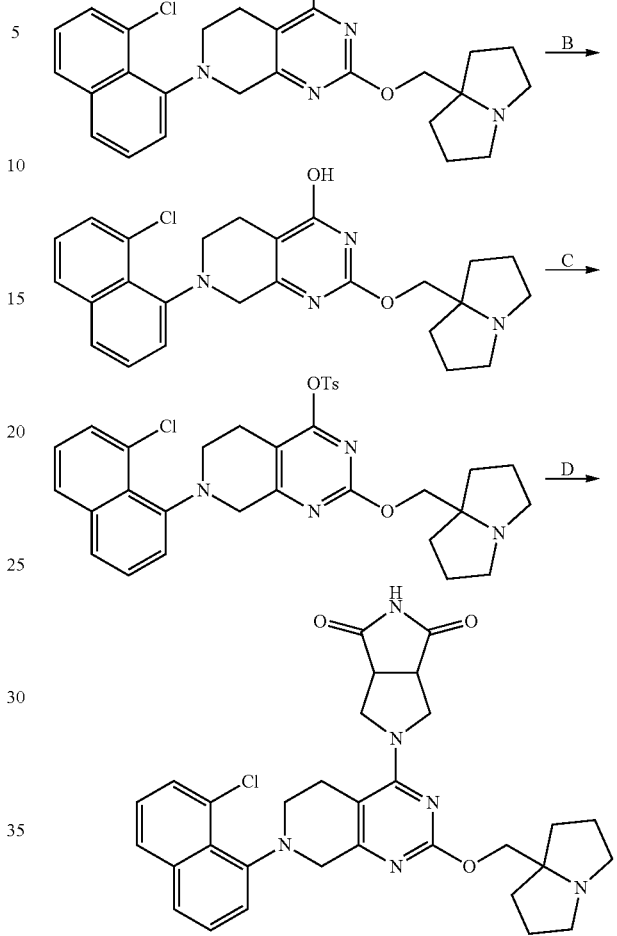

Step A. 7-(8-chloronaphthalen-1-yl)-2-((hexahydro-1H-pyrrolizin-7a-yl)methoxy)-4-methoxy-5,6,7,8-tetrahydropyrido[3,4-d]pyrimidine: To a mixture of 1-bromo-8-chloronaphthalene (600 mg, 1.0 equiv), 2-((hexahydro-1H-pyrrolizin-7a-yl)methoxy)-4-methoxy-5,6,7,8-tetrahydropyrido[3,4-d]pyrimidine (832 mg, 1.1 equiv), Cs₂CO₃ (2.43 g, 3.0 equiv), Xantphos (287 mg, 0.2 equiv) in toluene (12 mL) was added Pd₂(dba)₃ (227 mg, 0.1 equiv) under N₂. The mixture was stirred at 110° C. for 10 hours. The reaction mixture was filtered. The mixture was diluted with water (10 mL) and extracted with ethyl acetate (3×15 mL). The combined organic phase was washed with brine (30 mL), dried over anhydrous sodium sulfate, concentrated, and purified with reversed phase flash chromatography [C18, 0.1% formic acid condition] to afford the title compound (760 mg, 56% yield) as yellow oil; LCMS (ESI, M+1): m/z=465.1.

Step B. 7-(8-chloronaphthalen-1-yl)-2-((hexahydro-1H-pyrrolizin-7a-yl)methoxy)-5,6,7,8-tetrahydropyrido[3,4-d]pyrimidin-4-ol: To a mixture of NaH (120 mg, 60% purity, 2.0 equiv) in DMAc (7 mL) was added EtSH (654 mg, 7.0 equiv) at 0° C. and the mixture was stirred at 0° C. for minutes. 7-(8-chloronaphthalen-1-yl)-2-((hexahydro-1H-pyrrolizin-7a-yl)methoxy)-4-methoxy-5,6,7,8-tetrahydropyrido[3,4-d]pyrimidine (700 mg, 1.0 equiv) in DMAc (7 mL) was added at 0° C. and the mixture was stirred at 60°

C. for 1 hour. The reaction mixture was quenched with saturated NH₄Cl aqueous (50 mL) at 0° C. and extracted with ethyl acetate (3×50 mL). The combined organic layers were dried over anhydrous Na₂SO₄, concentrated, and purified with reversed phase flash chromatography [C18, 0.1% formic acid condition] to afford the title compound (420 mg, 57% yield) as yellow solid. LCMS (ESI, M+1): m/z=451.1.

Step C. 7-(8-chloronaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate: To a solution of 7-(8-chloronaphthalen-1-yl)-2-((hexahydro-1H-pyrrolizin-7a-yl)methoxy)-5,6,7,8-tetrahydropyrido[3,4-d]pyrimidin-4-ol (150 mg, 1.0 equiv), DMAP (4.06 mg, 0.1 equiv), N-ethyl-N-isopropylpropan-2-amine (129 mg, 3.0 equiv) in dichloromethane (3 mL) was added TsCl (88.8 mg, 1.4 equiv) at 0° C. The mixture was stirred at 15° C. for 1 hour. The reaction mixture was quenched with water (5 mL) and extracted with dichloromethane (10 mL). The organic phase was washed with brine (10 mL), dried over anhydrous sodium sulfate, concentrated, and purified by column chromatography [Al₂O₃, petroleum ether/ethyl acetate=20/1 to 0/1] to afford the title compound (120 mg, 57% yield) as yellow solid. LCMS (ESI, M+1): m/z=605.1.

Step D. 5-(7-(8-chloronaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione: A mixture of 7-(8-chloronaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (110 mg, 1.0 equiv), tetrahydropyrrolo[3,4-c]pyrrole-1,3(2H,3aH)-dione (50.9 mg, 2.0 equiv), N-ethyl-N-isopropylpropan-2-amine (70.5 mg, 3.0 equiv), and 4 Å molecular sieve (30 mg) in DMF (1 mL) was stirred at 40° C. for 10 hours. The reaction was filtered and purified with prep-HPLC [column: Phenomenex Synergi C18 150×25 mm×10 μm; mobile phase: water (0.225% FA)-ACN; B %: 11%-41%, 10 minutes] to afford the title compound (64.5 mg, 56% yield, FA) as light yellow solid. ¹H NMR (400 MHz, methanol-d₄) δ=7.82 (dd, J=0.8, 8.0 Hz, 1H), 7.68 (d, J=7.6 Hz, 1H), 7.58-7.44 (m, 2H), 7.40-7.34 (m, 1H), 7.31 (dd, J=0.8, 7.6 Hz, 1H), 4.64-4.56 (m, 1H), 4.53-4.39 (m, 2H), 4.30-4.19 (m, 2H), 3.84-3.57 (m, 5H), 3.55-3.45 (m, 3H), 3.29-3.09 (m, 4H), 2.69 (br d, J=14.8 Hz, 1H), 2.35-2.23 (m, 2H), 2.23-2.11 (m, 4H), 2.10-1.98 (m, 2H); LCMS (ESI, M+1): m/z=573.2.

Example 80

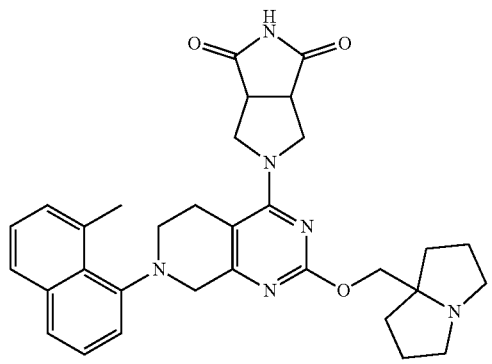 [SMILES: Cc1cccc2cccc(N3CCc4c(nc(OCC56CCCN5CCC6)nc4N4CC5C(=O)NC(=O)C5C4)C3)c12]

5-(2-((hexahydro-1H-pyrrolizin-7a-yl)methoxy)-7-(8-methylnaphthalen-1-yl)-5,6,7,8-tetrahydropyrido[3,4-d]pyrimidin-4-yl)tetrahydropyrrolo[3,4-c]pyrrole-1,3(2H,3aH)-dione

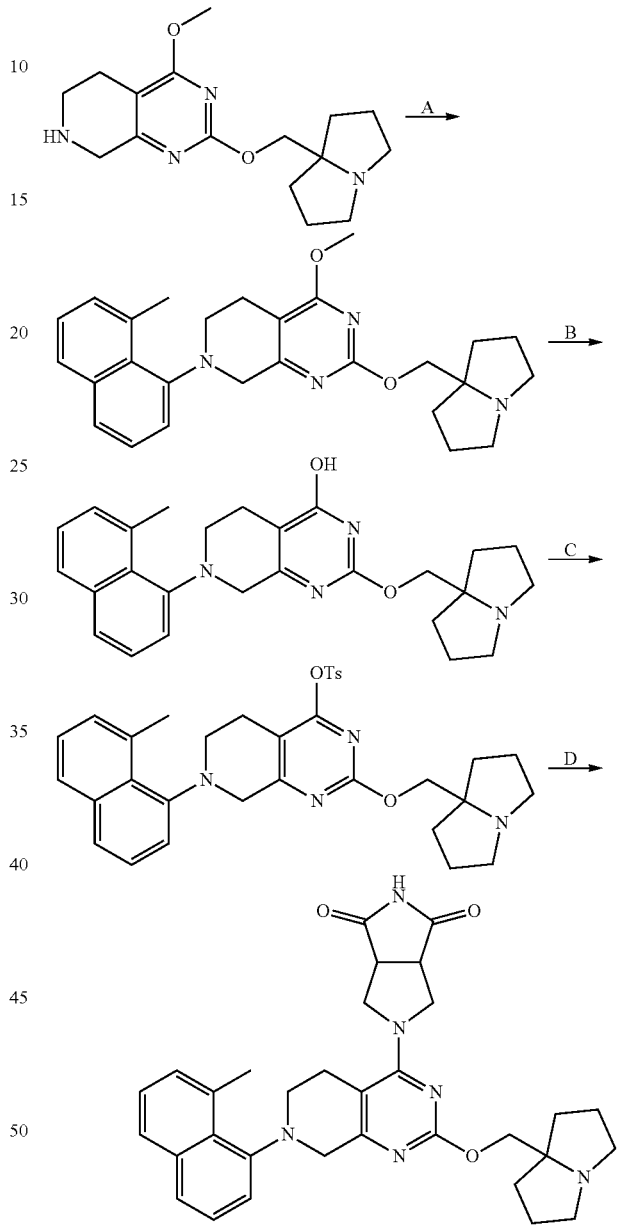

Step A. 2-((hexahydro-1H-pyrrolizin-7a-yl)methoxy)-4-methoxy-7-(8-methylnaphthalen-1-yl)-5,6,7,8-tetrahydropyrido[3,4-d]pyrimidine: To a mixture of 4-methoxy-2-((tetrahydro-1H-pyrrolizin-7a(5H)-yl)methoxy)-5,6,7,8-tetrahydropyrido[3,4-d]pyrimidine (500 mg, 1.0 equiv), 1-bromo-8-methyl-naphthalene (436 mg, 1.2 equiv), Cs₂CO₃ (1.61 g, 3.0 equiv), Xantphos (190 mg, 0.2 equiv) in toluene (10 mL) was added Pd₂(dba)₃ (150 mg, 0.1 equiv) under N₂. The reaction was stirred at 110° C. for 8 hours. The mixture was filtered and diluted with water (15 mL). The mixture was extracted with ethyl acetate (2×30 mL). The combined organic phase was washed with brine (50 mL), dried over anhydrous Na$_2$SO$_4$, concentrated and purified with reversed phase flash chromatography [C18, 0.1% formic acid condition] to afford the title compound (490 mg, 60% yield) as yellow oil; LCMS (ESI, M+1): m/z=445.1.

Step B. 2-((hexahydro-1H-pyrrolizin-7a-yl)methoxy)-7-(8-methylnaphthalen-1-yl)-5,6,7,8-tetrahydropyrido[3,4-d]pyrimidin-4-ol: To the mixture of NaH (86.0 mg, 60% purity, 2.0 equiv) in DMAC (5 mL) was added EtSH (467 mg, 7.0 equiv) at 0° C. for 5 minutes and the mixture was stirred at 0° C. for 10 minutes. 2-((hexahydro-1H-pyrrolizin-7a-yl)methoxy)-4-methoxy-7-(8-methylnaphthalen-1-yl)-5,6,7,8-tetrahydropyrido[3,4-d]pyrimidine (478 mg, 1.0 equiv) in DMAC (5 mL) was added at 0° C. The mixture was stirred at 60° C. for 1 hour. The reaction was quenched with saturated NH$_4$Cl aqueous (20 mL) at 0° C. The mixture was diluted with H$_2$O (60 mL) and extracted with ethyl acetate (3×20 mL). The combined organic layers were dried over anhydrous Na$_2$SO$_4$, concentrated and purified with reversed phase flash chromatography [C18, 0.1% formic acid condition] to afford the title compound (100 mg, 17% yield) as yellow solid. LCMS (ESI, M+1): m/z=431.2.

Step C. 2-((hexahydro-1H-pyrrolizin-7a-yl)methoxy)-7-(8-methylnaphthalen-1-yl)-5,6,7,8-tetrahydropyrido[3,4-d]pyrimidin-4-yl 4-methylbenzenesulfonate: To a solution of 2-((hexahydro-1H-pyrrolizin-7a-yl)methoxy)-7-(8-methylnaphthalen-1-yl)-5,6,7,8-tetrahydropyrido[3,4-d]pyrimidin-4-ol (100 mg, 1.0 equiv), DMAP (2.84 mg, 0.1 equiv), N-ethyl-N-isopropylpropan-2-amine (90.0 mg, 3.0 equiv) in DCM (3 mL) was added TsCl (62.0 mg, 1.4 equiv) at 0° C. The mixture was stirred at 15° C. for 1 hour. The reaction mixture was quenched with water (5 mL) and extracted with DCM (10 mL). The combined organic phase was washed with brine (10 mL), dried over anhydrous Na$_2$SO$_4$, concentrated, and purified with column chromatography [Al$_2$O$_3$, petroleum ether/ethyl acetate=20/1 to 0/1] to afford the title compound (90.0 mg, 61% yield) as yellow oil; LCMS (ESI, M+1): m/z=585.2.

Step D. 5-(2-((hexahydro-1H-pyrrolizin-7a-yl)methoxy)-7-(8-methylnaphthalen-1-yl)-5,6,7,8-tetrahydropyrido[3,4-d]pyrimidin-4-yl)tetrahydropyrrolo[3,4-c]pyrrole-1,3(2H,3aH)-dione: A mixture of 2-((hexahydro-1H-pyrrolizin-7a-yl)methoxy)-7-(8-methylnaphthalen-1-yl)-5,6,7,8-tetrahydropyrido[3,4-d]pyrimidin-4-yl 4-methylbenzenesulfonate (90.0 mg, 1.0 equiv), 2,3,3a,6a-tetrahydro-1H-pyrrolo[3,4-c]pyrrole-4,6-dione (43.1 mg, 2.0 equiv), N-ethyl-N-isopropylpropan-2-amine (59.7 mg, 3.0 equiv) and 4 Å molecular sieve (30.0 mg) in DMF (1 mL) was stirred at 40° C. for 10 hours. The mixture was filtered and purified with prep-HPLC [column: Phenomenex Synergi C18 150×25 mm×10 μm; mobile phase: water (0.225% FA)-ACN; B %: 11%-44%, 11 minutes] to afford the title compound (36.6 mg, 39% yield, 0.67FA) as white solid. $^1$H NMR (400 MHz, methanol-d$_4$) δ=7.67 (dd, J=8.0, 16.4 Hz, 2H), 7.41 (t, J=7.6 Hz, 1H), 7.35-7.25 (m, 2H), 7.23 (d, J=7.2 Hz, 1H), 4.65-4.54 (m, 1H), 4.44-4.30 (m, 2H), 4.26 (d, J=12.0 Hz, 1H), 4.02 (d, J=17.6 Hz, 1H), 3.78 (dd, J=8.0, 11.6 Hz, 1H), 3.67 (d, J=17.6 Hz, 1H), 3.58-3.39 (m, 6H), 3.23-3.14 (m, 2H), 3.12-3.03 (m, 2H), 2.87 (s, 3H), 2.76-2.62 (m, 1H), 2.26-2.16 (m, 2H), 2.15-2.01 (m, 4H), 2.00-1.90 (m, 2H); LCMS (ESI, M+1): m/z=553.2.

Example 81

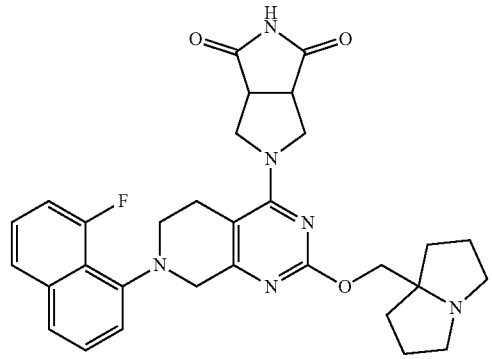 [SMILES: O=C1NC(=O)C2CN(c3nc(OCC45CCCN4CCC5)nc4c3CCN(c3cccc5cccc(F)c35)C4)CC12]

5-(7-(8-fluoronaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione

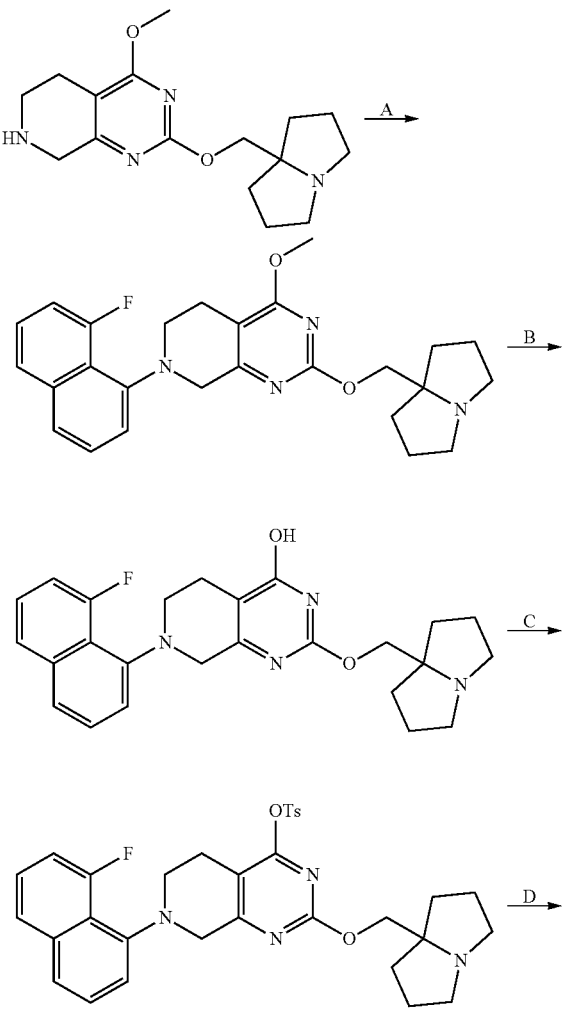

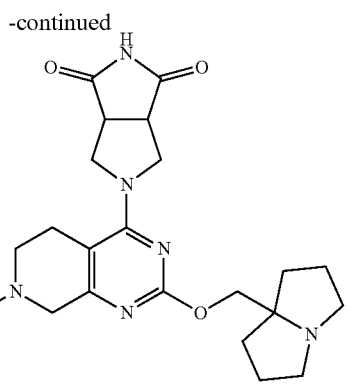

Step A. 7-(8-fluoronaphthalen-1-yl)-2-((hexahydro-1H-pyrrolizin-7a-yl)methoxy)-4-methoxy-5,6,7,8-tetrahydropyrido[3,4-d]pyrimidine: To a solution of 4-methoxy-2-((tetrahydro-1H-pyrrolizin-7a(5H)-yl)methoxy)-5,6,7,8-tetrahydropyrido[3,4-d]pyrimidine (200 mg, 1.0 equiv), 1-bromo-8-fluoro-naphthalene (148 mg, 1.0 equiv), RuPhos (61.3 mg, 0.2 equiv) and Cs₂CO₃ (642 mg, 3.0 equiv) in toluene (2 mL) was added Pd₂(dba)₃ (60.2 mg, 0.1 equiv). The mixture was stirred at 110° C. for 12 hours. The mixture was diluted with water (10 mL) and extracted with ethyl acetate (3×10 mL). The combined organic layers were dried over anhydrous sodium sulfate, concentrated, and purified by reversed phase flash chromatography [C18, 0.1% formic acid condition] to afford the title compound (110 mg, 34% yield) as yellow liquid; LCMS (ESI, M+1): m/z=449.2.

Step B. 7-(8-fluoronaphthalen-1-yl)-2-((hexahydro-1H-pyrrolizin-7a-yl)methoxy)-5,6,7,8-tetrahydropyrido[3,4-d]pyrimidin-4-ol: To a solution of NaH (44.6 mg, 60% purity, 2.0 equiv) in DMAC (3 mL) was added EtSH (200 mg, 5.8 equiv) at 10° C. The mixture was stirred at 10° C. for 0.5 hour. Then 7-(8-fluoronaphthalen-1-yl)-2-((hexahydro-1H-pyrrolizin-7a-yl)methoxy)-4-methoxy-5,6,7,8-tetrahydropyrido[3,4-d]pyrimidine (250 mg, 1.0 equiv) was added to the reaction. The reaction was stirred at 60° C. for 1 hour. The mixture was diluted with water (10 mL) and extracted with ethyl acetate (3×10 mL). The combined organic layers were dried over anhydrous sodium sulfate, concentrated to afford the title compound (270 mg, crude) as yellow liquid; LCMS (ESI, M+1): m/z=435.1.

Step C. 7-(8-fluoronaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate: To a solution of 7-(8-fluoronaphthalen-1-yl)-2-((hexahydro-1H-pyrrolizin-7a-yl)methoxy)-5,6,7,8-tetrahydropyrido[3,4-d]pyrimidin-4-ol (270 mg, 1 equiv), N-ethyl-N-isopropylpropan-2-amine (241 mg, 3.0 equiv) and DMAP (7.59 mg, 0.1 equiv) in DCM (4 mL) was added TsCl (178 mg, 1.5 equiv) at 0° C. The mixture was stirred at 20° C. for 12 hours. The mixture was diluted with water (10 mL) and extracted with ethyl acetate (3×10 mL). The combined organic layers were dried over anhydrous sodium sulfate, concentrated and purified by column chromatography [Al₂O₃, Petroleum ether/Ethyl acetate=10/1 to 1/1] to afford the title compound (120 mg, 33% yield) as yellow liquid; LCMS (ESI, M+1): m/z=589.2.

Step D. 5-(7-(8-fluoronaphthalen-1-yl)-2-((hexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione: To a solution of 7-(8-fluoronaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (110 mg, 1.0 equiv), 2,3,3a,6a-tetrahydro-1H-pyrrolo[3,4-c]pyrrole-4,6-dione (78.6 mg, 3.0 equiv) and 4 Å molecular sieve (10 mg) in DMF (1 mL) was added N-ethyl-N-isopropylpropan-2-amine (72.4 mg, 3.0 equiv). The mixture was stirred at 40° C. for 12 hours. The residue was filtered and washed with DMF (1 mL), and purified with prep-HPLC [Waters Xbridge 150×25 mm×5 μm; A: water (10 mM NH₄HCO₃), B: ACN; B %: 25%-55% over 9 min] to give a crude product. The crude product was purified with prep-HPLC [Phenomenex Gemini-NX C18 75×30 mm×3 μm; A: water (0.225% FA), B: ACN; B %: 12%-42%, 7 minutes] to afford the title compound (11.0 mg, 10% yield) as yellow solid. ¹H NMR (400 MHz, METHANOL-d₄) δ=7.69 (d, J=7.8 Hz, 1H), 7.61 (d, J=8.4 Hz, 1H), 7.49-7.39 (m, 2H), 7.23-7.12 (m, 2H), 4.67-4.54 (m, 1H), 4.41 (br d, J=1.6 Hz, 2H), 4.35-4.11 (m, 2H), 4.09-3.92 (m, 1H), 3.86-3.63 (m, 2H), 3.61-3.46 (m, 5H), 3.30-3.22 (m, 1H), 3.19-3.10 (m, 2H), 3.05-2.83 (m, 1H), 2.67 (br dd, J=5.6, 10.4 Hz, 1H), 2.29-2.20 (m, 2H), 2.20-2.06 (m, 4H), 2.05-1.96 (m, 2H); LCMS (ESI, M+1): m/z=557.1.

General procedure for the preparation of EXAMPLE 82 to 171: A mixture of 7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl 4-methylbenzenesulfonate (33 μmol, 1 equiv), amine (2 equiv), and N-ethyl-N-isopropylpropan-2-amine (5 equiv) in NMP (1 mL) was stirred at 120° C. for 16 hours. Then the mixture was cooled to room temperature, the solvent was evaporated under reduced pressure, and the residue was dissolved in the DMSO (1 mL). DMSO solution was filtered, analyzed by LCMS and subjected to HPLC purification (acetonitrile/methanol, ammonia) to give the product.

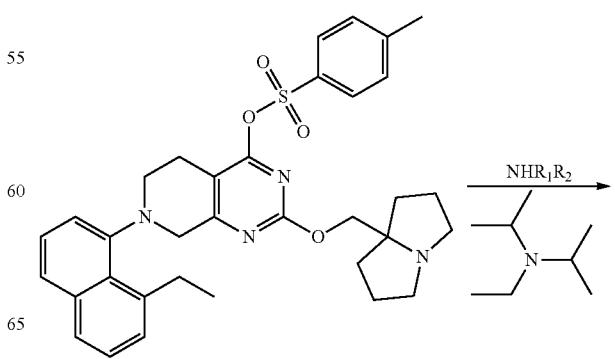

-continued

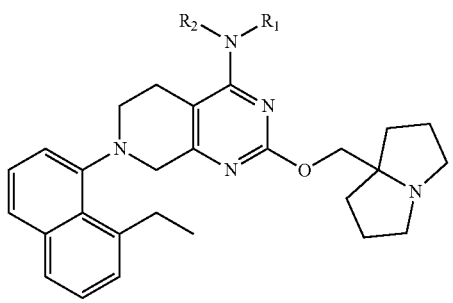

TABLE 1

MS for EXAMPLE 82 to 171.

| EXAMPLE No. | Obs. M + 1 | EXAMPLE No. | Obs. M + 1 | EXAMPLE No. | Obs. M + 1 |
|---|---|---|---|---|---|
| 82 | 578.4 | 112 | 588.4 | 142 | 602.2 |
| 83 | 645.2 | 113 | 530.4 | 143 | 635.4 |
| 84 | 608.2 | 114 | 557.4 | 144 | 628.4 |
| 85 | 631.4 | 115 | 578.4 | 145 | 550.4 |
| 86 | 558.4 | 116 | 578.4 | 146 | 629.4 |
| 87 | 594.2 | 117 | 576.2 | 147 | 542.4 |
| 88 | 595.4 | 118 | 593.4 | 148 | 541.6 |
| 89 | 585.2 | 119 | 540.4 | 149 | 554.2 |
| 90 | 604.4 | 120 | 606.4 | 150 | 576.2 |
| 91 | 598.4 | 121 | 540.4 | 151 | 579.4 |
| 92 | 556.4 | 122 | 594.4 | 152 | 607.2 |
| 93 | 593.6 | 123 | 622.2 | 153 | 541.2 |
| 94 | 592.4 | 124 | 562.2 | 154 | 589.4 |
| 95 | 570.4 | 125 | 605.2 | 155 | 606.4 |
| 96 | 579.4 | 126 | 607.4 | 156 | 541.4 |
| 97 | 542.4 | 127 | 539.2 | 157 | 576.2 |
| 98 | 528.4 | 128 | 509.4 | 158 | 564.2 |
| 99 | 579.4 | 129 | 584.4 | 159 | 590.2 |
| 100 | 592.4 | 130 | 586.4 | 160 | 566.4 |
| 101 | 560.4 | 131 | 556.4 | 161 | 585.3 |
| 102 | 621.4 | 132 | 579.2 | 162 | 594.4 |
| 103 | 571.2 | 133 | 556.4 | 163 | 648.2 |
| 104 | 595.2 | 134 | 555.2 | 164 | 565.2 |
| 105 | 569.4 | 135 | 609.2 | 165 | 627.2 |
| 106 | 619.2 | 136 | 541.4 | 166 | 623.2 |
| 107 | 556.6 | 137 | 595.4 | 167 | 542.2 |
| 108 | 619.2 | 138 | 554.2 | 168 | 581.2 |
| 109 | 558.4 | 139 | 567.2 | 169 | 539.2 |
| 110 | 596.2 | 140 | 690.2 | 170 | 524.3 |
| 111 | 542.4 | 141 | 567.4 | 171 | 544.2 |

EXAMPLE 82

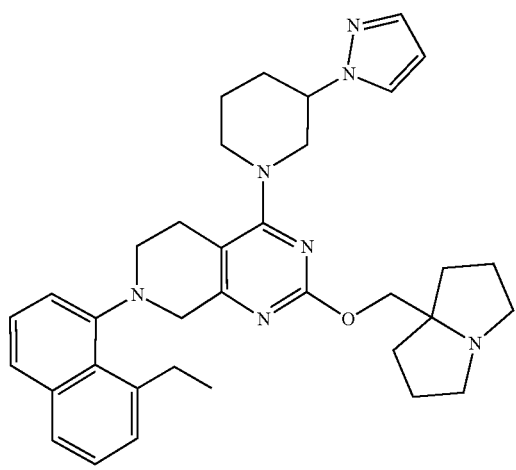

TABLE 1-continued 4-(3-(1H-pyrazol-1-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine
EXAMPLE 83

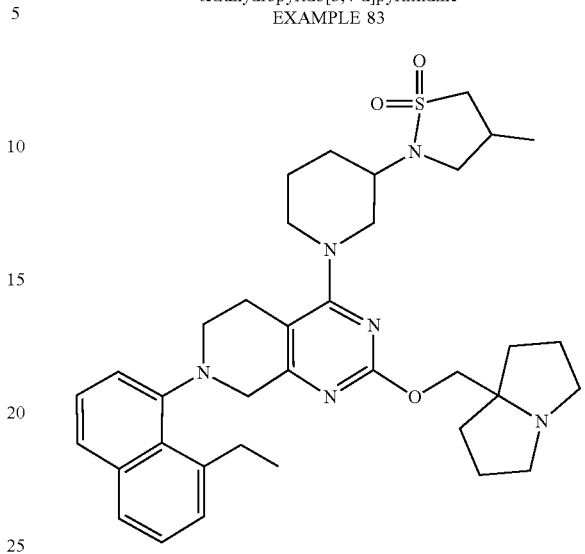

2-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-4-methylisothiazolidine 1,1-dioxide
EXAMPLE 84

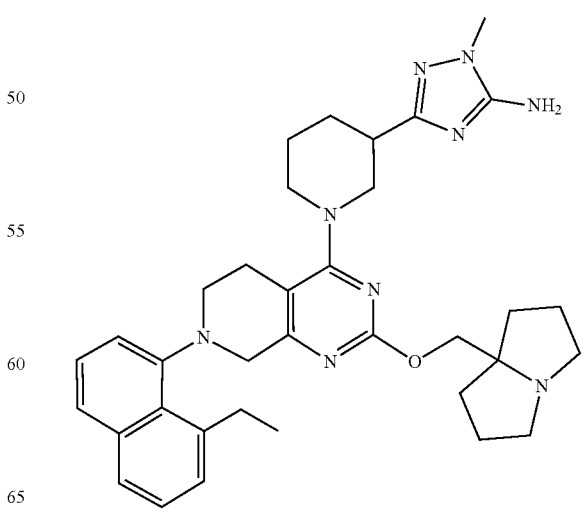

TABLE 1-continued 3-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-1-methyl-1H-1,2,4-triazol-5-amine
EXAMPLE 85

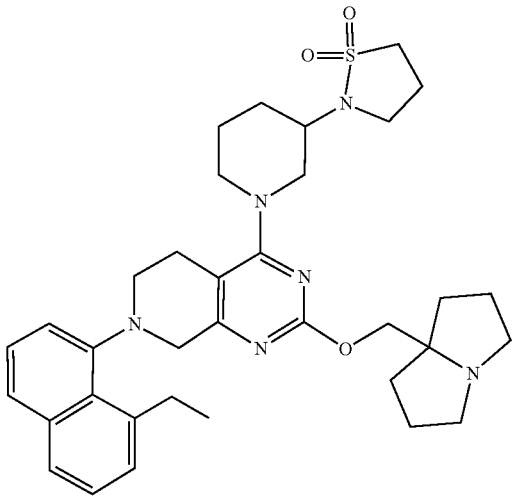

2-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)isothiazolidine 1,1-dioxide
EXAMPLE 86

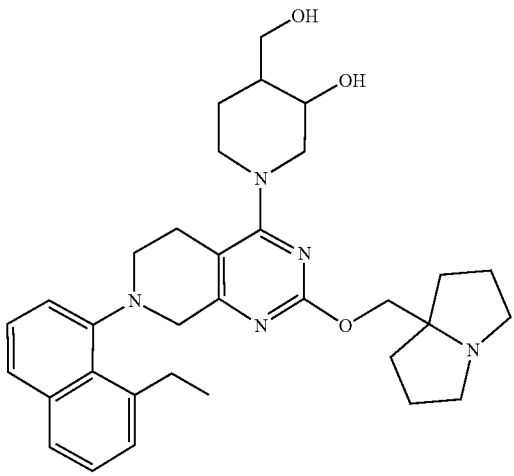 [SMILES: CCc1cccc2cccc(N3CCc4c(nc(OCC56CCCN5CCC6)nc4N4CCC(CO)C(O)C4)C3)c12]

TABLE 1-continued 1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-4-(hydroxymethyl)piperidin-3-ol
EXAMPLE 87

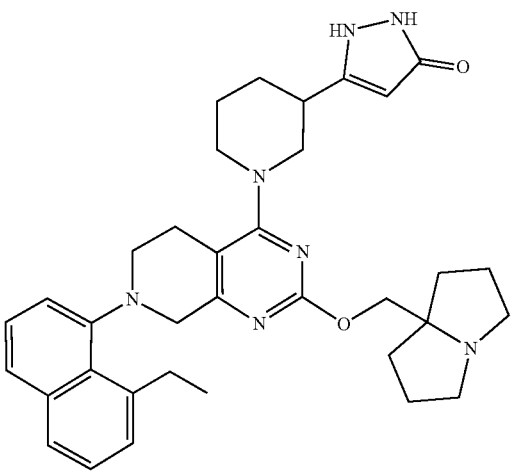 [SMILES: CCc1cccc2cccc(N3CCc4c(nc(OCC56CCCN5CCC6)nc4N4CCCC(c5cc(=O)[nH][nH]5)C4)C3)c12]

5-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-1,2-dihydro-3H-pyrazol-3-one
EXAMPLE 88

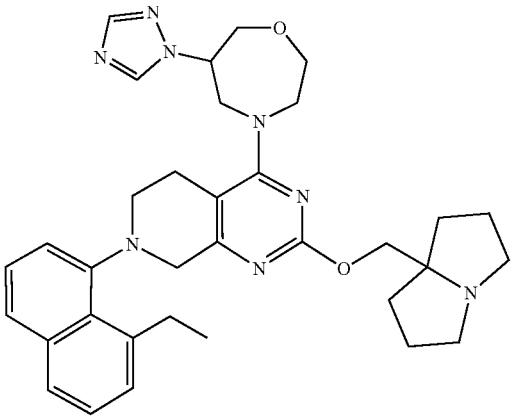 [SMILES: CCc1cccc2cccc(N3CCc4c(nc(OCC56CCCN5CCC6)nc4N4CCOCC(n5cncn5)C4)C3)c12]

4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-6-(1H-1,2,4-triazol-1-yl)-1,4-oxazepane
EXAMPLE 89

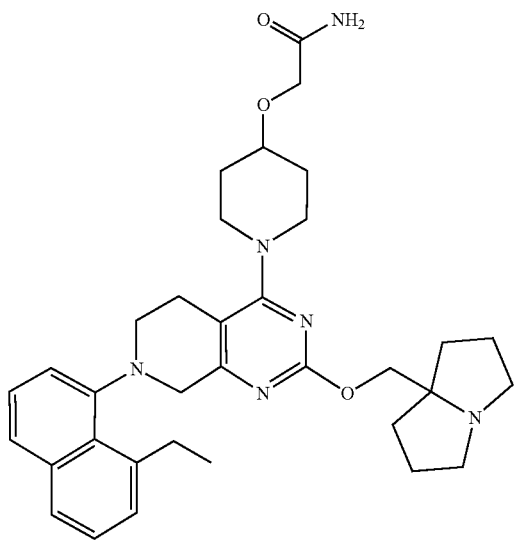 [SMILES: CCc1cccc2cccc(N3CCc4c(nc(OCC56CCCN5CCC6)nc4N4CCC(OCC(N)=O)CC4)C3)c12]

2-((1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-4-yl)oxy)acetamide
EXAMPLE 90

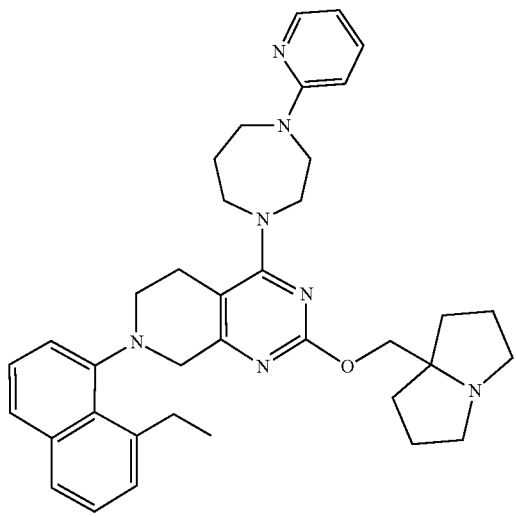 [SMILES: CCc1cccc2cccc(N3CCc4c(nc(OCC56CCCN5CCC6)nc4N4CCCN(c5ccccn5)CC4)C3)c12]

7-(8-ethylnaphthalen-1-yl)-4-(4-(pyridin-2-yl)-1,4-diazepan-1-yl)-2-((tetrahydro-1H-pyrrolizin-7a(5H)-yl)methoxy)-5,6,7,8-tetrahydropyrido[3,4-d]pyrimidine
EXAMPLE 91

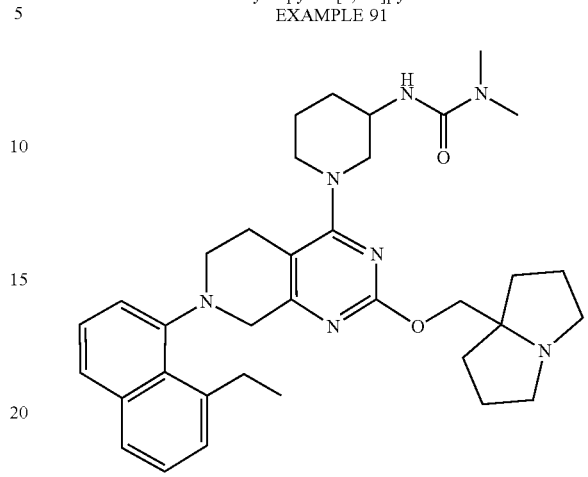

3-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-1,1-dimethylurea
EXAMPLE 92

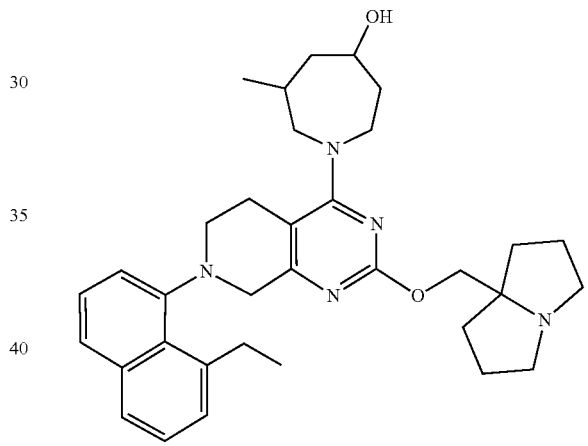

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-6-methylazepan-4-ol
EXAMPLE 93

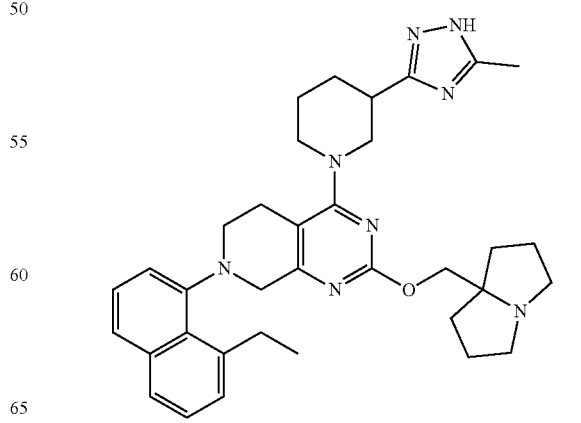

TABLE 1-continued 7-(8-ethylnaphthalen-1-yl)-4-(3-(5-methyl-1H-1,2,4-triazol-
3-yl)piperidin-1-yl)-2-((tetrahydro-1H-pyrrolizin-7a(5H)-yl)
methoxy)-5,6,7,8-tetrahydropyrido[3,4-d]pyrimidine
EXAMPLE 94

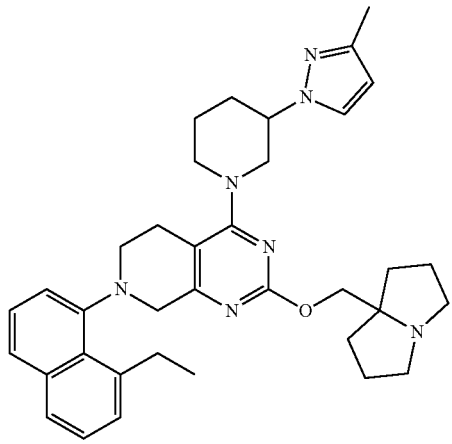 [SMILES: CCc1cccc2cccc(N3CCc4c(nc(OCC56CCCN5CCC6)nc4N4CCCC(n5ccc(C)n5)C4)C3)c12]

7-(8-ethylnaphthalen-1-yl)-4-(3-(3-methyl-1H-pyrazol-1-yl)
piperidin-1-yl)-2-((tetrahydro-1H-pyrrolizin-7a(5H)-yl)methoxy)-
5,6,7,8-tetrahydropyrido[3,4-d]pyrimidine
EXAMPLE 95

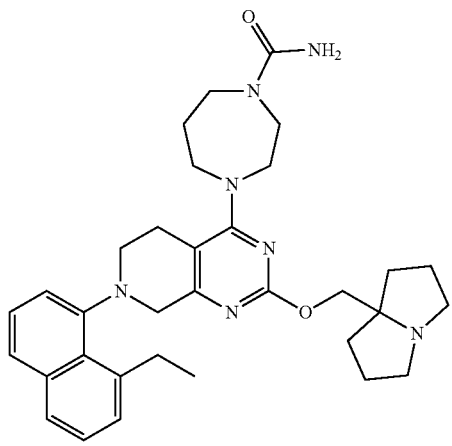 [SMILES: CCc1cccc2cccc(N3CCc4c(nc(OCC56CCCN5CCC6)nc4N4CCCN(C(N)=O)CC4)C3)c12]

4-(7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)-1,4-diazepane-1-carboxamide
EXAMPLE 96

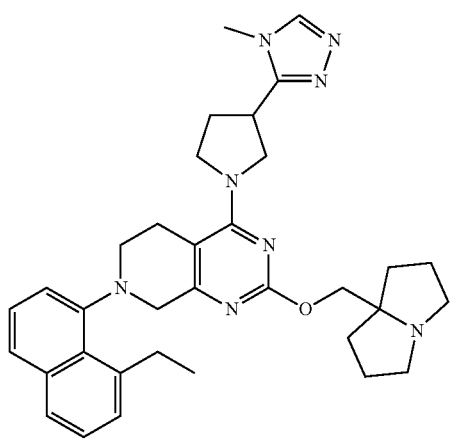 [SMILES: CCc1cccc2cccc(N3CCc4c(nc(OCC56CCCN5CCC6)nc4N4CCC(c5nncn5C)C4)C3)c12]

TABLE 1-continued 7-(8-ethylnaphthalen-1-yl)-4-(3-(4-methyl-4H-1,2,4-triazol-
3-yl)pyrrolidin-1-yl)-2-((tetrahydro-1H-pyrrolizin-7a(5H)-
yl)methoxy)-5,6,7,8-tetrahydropyrido[3,4-d]pyrimidine
EXAMPLE 97

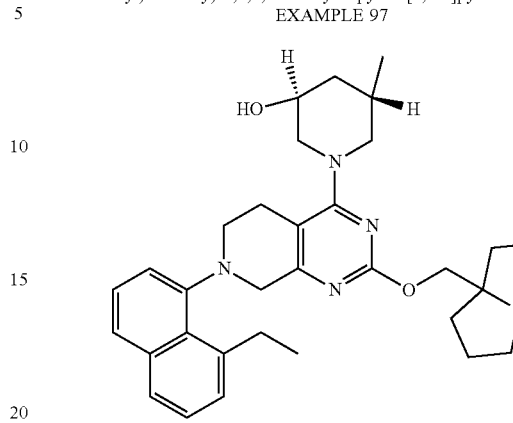

(3S, 5S)-1-(7-(8-ethylnaphthalen-1-yl)-2-((tetrahydro-1H-
pyrrolizin-7a(5H)-yl)methoxy)-5,6,7,8-tetrahydropyrido
[3,4-d]pyrimidin-4-yl)-5-methylpiperidin-3-ol
EXAMPLE 98

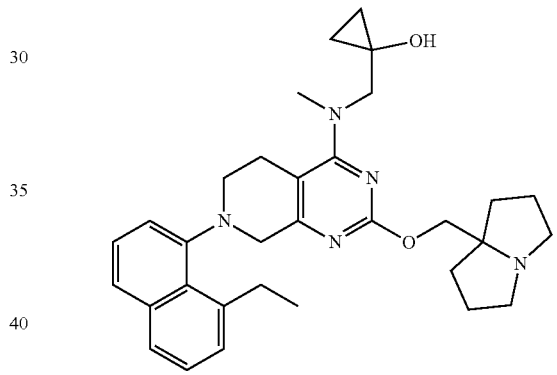

1-(((7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)(methyl)amino)methyl)cyclopropan-1-ol
EXAMPLE 99

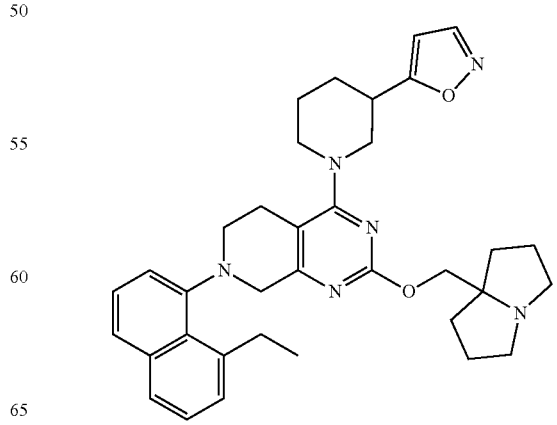

5-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)isoxazole
EXAMPLE 100

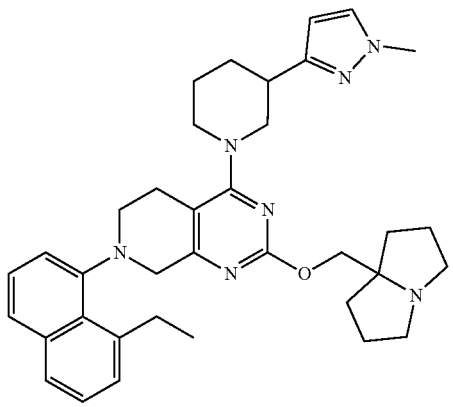 [SMILES: CCc1cccc2cccc(N3CCc4c(nc(OCC56CCCN5CCC6)nc4N4CCCC(c5ccn(C)n5)C4)C3)c12]

7-(8-ethylnaphthalen-1-yl)-4-(3-(1-methyl-1H-pyrazol-3-yl)piperidin-1-yl)-2-((tetrahydro-1H-pyrrolizin-7a(5H)-yl)methoxy)-5,6,7,8-tetrahydropyrido[3,4-d]pyrimidine
EXAMPLE 101

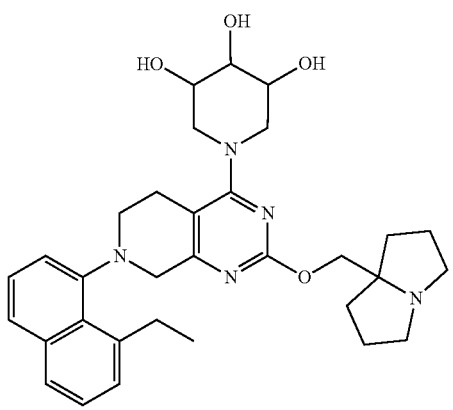 [SMILES: CCc1cccc2cccc(N3CCc4c(nc(OCC56CCCN5CCC6)nc4N4CC(O)C(O)C(O)C4)C3)c12]

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidine-3,4,5-triol
EXAMPLE 102

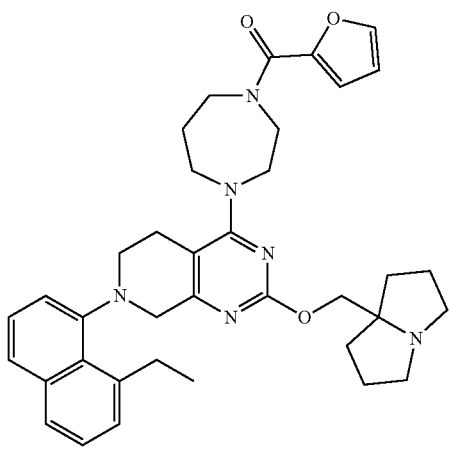 [SMILES: CCc1cccc2cccc(N3CCc4c(nc(OCC56CCCN5CCC6)nc4N4CCCN(C(=O)c5ccco5)CC4)C3)c12]

(4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-1,4-diazepan-1-yl)(furan-2-yl)methanone
EXAMPLE 103

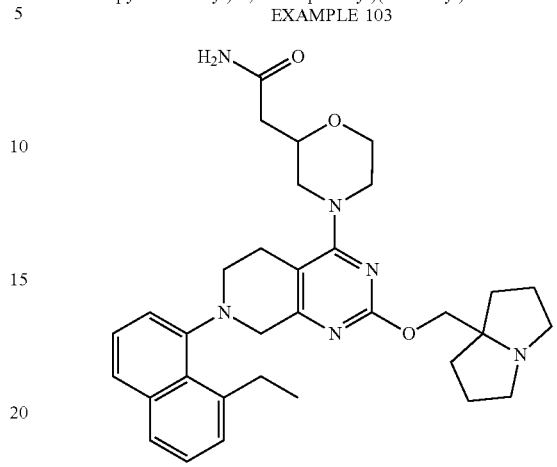

2-(4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)morpholin-2-yl)acetamide
EXAMPLE 104

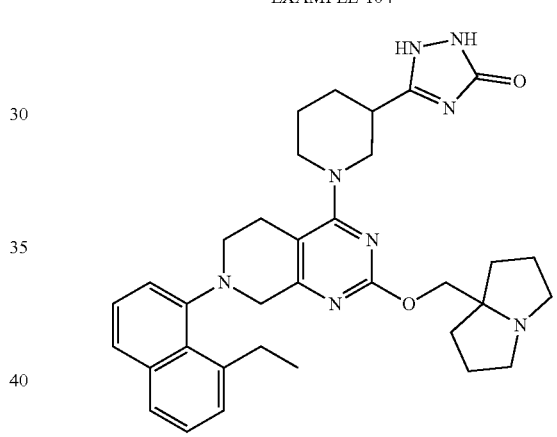

5-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-1,2-dihydro-3H-1,2,4-triazol-3-one
EXAMPLE 105

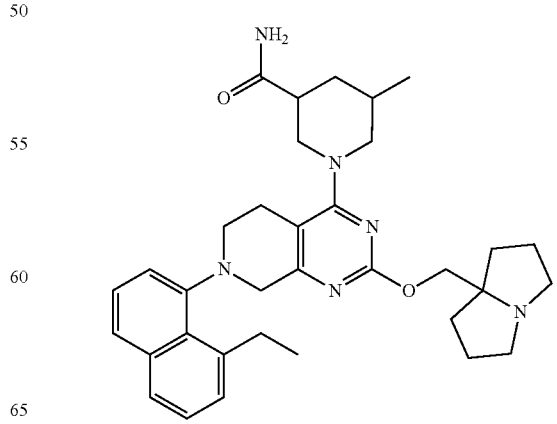

TABLE 1-continued 1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5-methylpiperidine-3-carboxamide
EXAMPLE 106

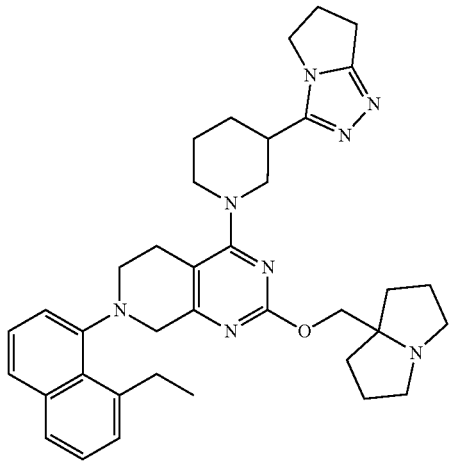 [SMILES: CCc1cccc2cccc(N3CCc4c(nc(OCC56CCCN5CCC6)nc4N4CCCC(c5nnc6n5CCC6)C4)C3)c12]

4-(3-(6,7-dihydro-5H-pyrrolo[2,1-c][1,2,4]triazol-3-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine
EXAMPLE 107

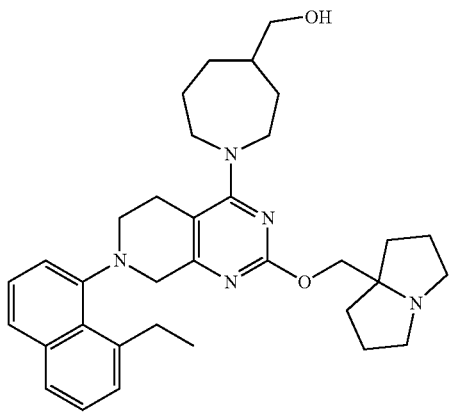 [SMILES: CCc1cccc2cccc(N3CCc4c(nc(OCC56CCCN5CCC6)nc4N4CCCC(CO)CC4)C3)c12]

(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)azepan-4-yl)methanol
EXAMPLE 108

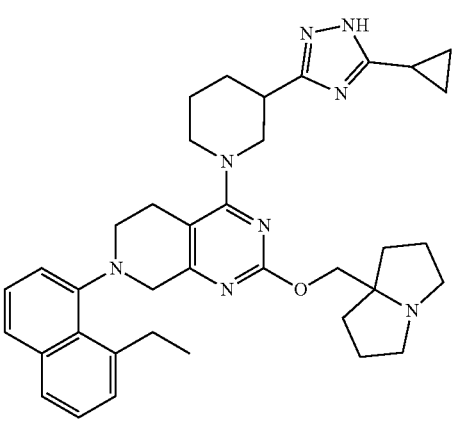 [SMILES: CCc1cccc2cccc(N3CCc4c(nc(OCC56CCCN5CCC6)nc4N4CCCC(c5n[nH]c(C6CC6)n5)C4)C3)c12]

TABLE 1-continued 4-(3-(5-cyclopropyl-1H-1,2,4-triazol-3-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine
EXAMPLE 109

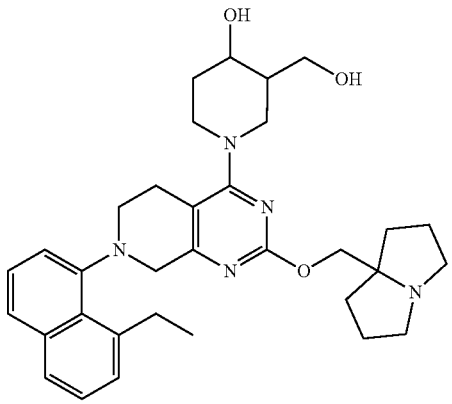 [SMILES: CCc1cccc2cccc(N3CCc4c(nc(OCC56CCCN5CCC6)nc4N4CCC(O)C(CO)C4)C3)c12]

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-3-(hydroxymethyl)piperidin-4-ol
EXAMPLE 110

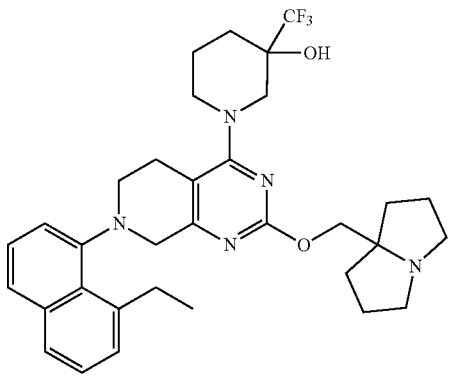 [SMILES: CCc1cccc2cccc(N3CCc4c(nc(OCC56CCCN5CCC6)nc4N4CCCC(O)(C(F)(F)F)C4)C3)c12]

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-3-(trifluoromethyl)piperidin-3-ol
EXAMPLE 111

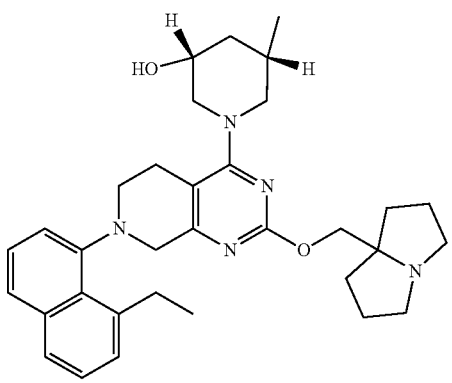 [SMILES: CCc1cccc2cccc(N3CCc4c(nc(OCC56CCCN5CCC6)nc4N4C[C@@H](C)C[C@@H](O)C4)C3)c12]

TABLE 1-continued (3R,5S)-1-(7-(8-ethylnaphthalen-1-yl)-2-((tetrahydro-
1H-pyrrolizin-7a(5H)-yl)methoxy)-5,6,7,8-
tetrahydropyrido[3,4-d]pyrimidin-4-yl)-5-methylpiperidin-3-ol
EXAMPLE 112

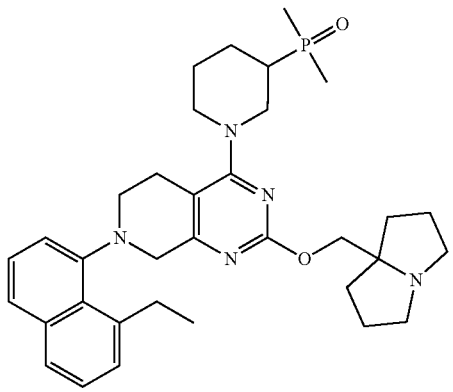 [SMILES: CCc1cccc2cccc(N3CCc4c(nc(OCC56CCCN5CCC6)nc4N4CCCC(P(C)(C)=O)C4)C3)c12]

(1-(7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)piperidin-3-yl)dimethylphosphine oxide
EXAMPLE 113

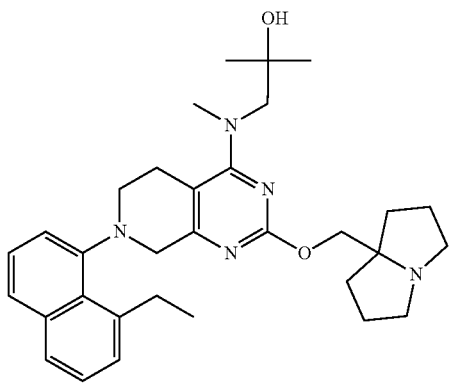 [SMILES: CCc1cccc2cccc(N3CCc4c(nc(OCC56CCCN5CCC6)nc4N(C)CC(C)(C)O)C3)c12]

1-((7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)(methyl)amino)-2-methylpropan-2-ol
EXAMPLE 114

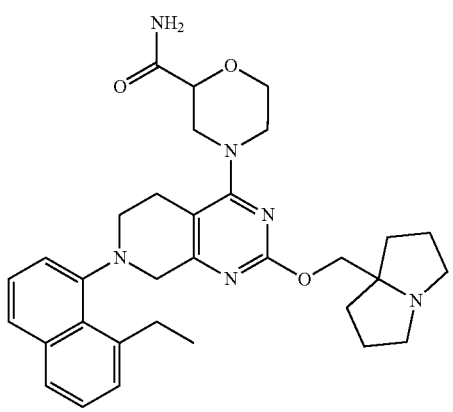 [SMILES: CCc1cccc2cccc(N3CCc4c(nc(OCC56CCCN5CCC6)nc4N4CCOC(C(N)=O)C4)C3)c12]

TABLE 1-continued 4-(7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)morpholine-2-carboxamide
EXAMPLE 115

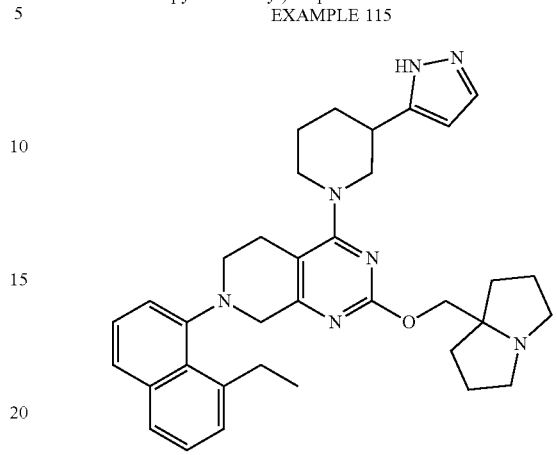

4-(3-(1H-pyrazol-5-yl)piperidin-1-yl)-7-(8-ethylnaphthalen-
1-yl)-2-((tetrahydro-1H-pyrrolizin-7a(5H)-yl)methoxy)-
5,6,7,8-tetrahydropyrido[3,4-d]pyrimidine
EXAMPLE 116

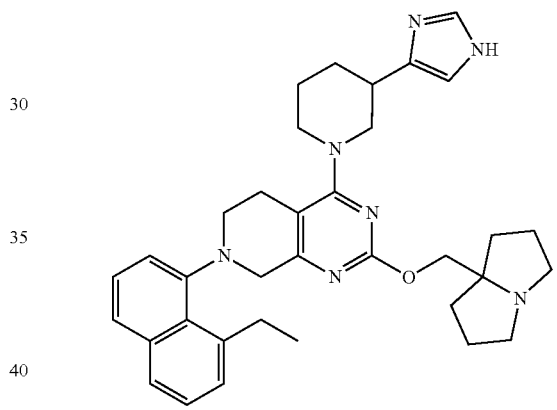

4-(3-(1H-imidazol-4-yl)piperidin-1-yl)-7-(8-ethylnaphthalen-
1-yl)-2-((tetrahydro-1H-pyrrolizin-7a(5H)-yl)methoxy)-
5,6,7,8-tetrahydropyrido[3,4-d]pyrimidine
EXAMPLE 117

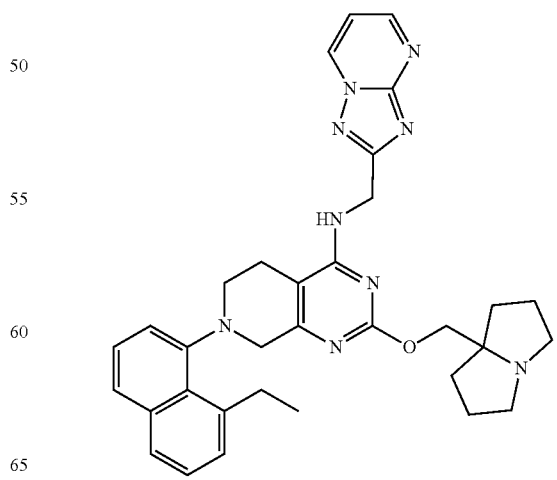

TABLE 1-continued

N-([1,2,4]triazolo[1,5-a]pyrimidin-2-ylmethyl)-
7-(8-ethylnaphthalen-1-yl)-2-((tetrahydro-1H-pyrrolizin-7a(5H)-
yl)methoxy)-5,6,7,8-tetrahydropyrido[3,4-d]
pyrimidin-4-amine
EXAMPLE 118

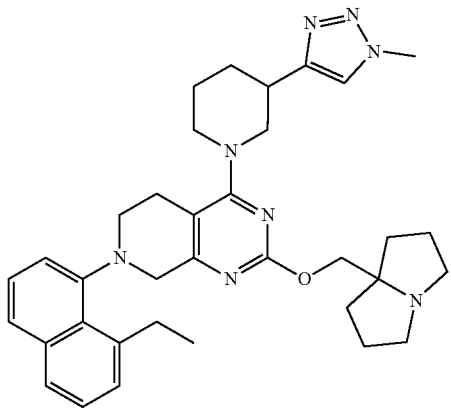 [SMILES: CCc1cccc2cccc(N3CCc4c(nc(OCC56CCCN5CCC6)nc4N4CCCC(c5cn(C)nn5)C4)C3)c12]

7-(8-ethylnaphthalen-1-yl)-4-(3-(1-methyl-1H-1,2,3-triazol-
4-yl)piperidin-1-yl)-2-((tetrahydro-1H-pyrrolizin-7a(5H)-
yl)methoxy)-5,6,7,8-tetrahydropyrido[3,4-d]pyrimidine
EXAMPLE 119

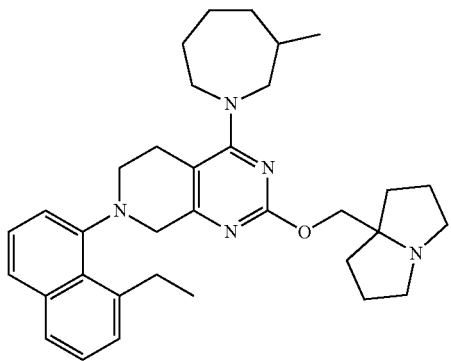 [SMILES: CCc1cccc2cccc(N3CCc4c(nc(OCC56CCCN5CCC6)nc4N4CCCCC(C)C4)C3)c12]

7-(8-ethylnaphthalen-1-yl)-4-(3-(1-methyl-1H-1,2,3-triazol-
4-yl)piperidin-1-yl)-2-((tetrahydro-1H-pyrrolizin-7a(5H)-yl)
methoxy)-5,6,7,8-tetrahydropyrido[3,4-d]pyrimidine
EXAMPLE 120

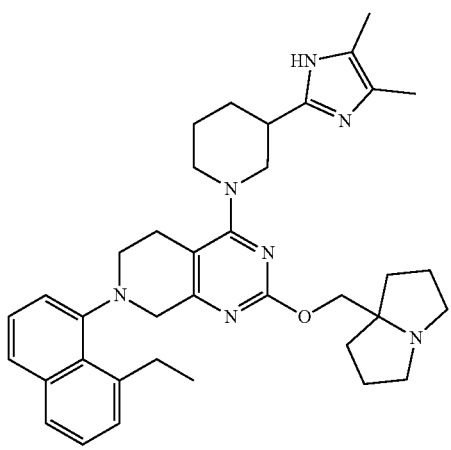 [SMILES: CCc1cccc2cccc(N3CCc4c(nc(OCC56CCCN5CCC6)nc4N4CCCC(c5nc(C)c(C)[nH]5)C4)C3)c12]

TABLE 1-continued 4-(3-(4,5-dimethyl-1H-imidazol-2-yl)piperidin-1-yl)-7-(8-
ethylnaphthalen-1-yl)-2-((tetrahydro-1H-pyrrolizin-7a(5H)-
yl)methoxy)-5,6,7,8-tetrahydropyrido[3,4-d]pyrimidine
EXAMPLE 121

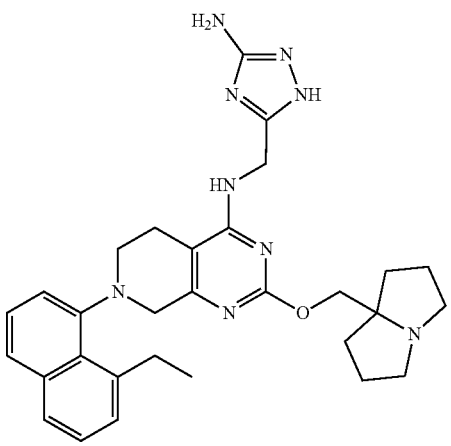 [SMILES: CCc1cccc2cccc(N3CCc4c(nc(OCC56CCCN5CCC6)nc4NCc4nc(N)n[nH]4)C3)c12]

N-((3-amino-1H-1,2,4-triazol-5-yl)methyl)-7-(8-ethylnaphthalen-
1-yl)-2-((tetrahydro-1H-pyrrolizin-7a(5H)-yl)methoxy)-5,6,7,8-
tetrahydropyrido[3,4-d]pyrimidin-4-amine
EXAMPLE 122

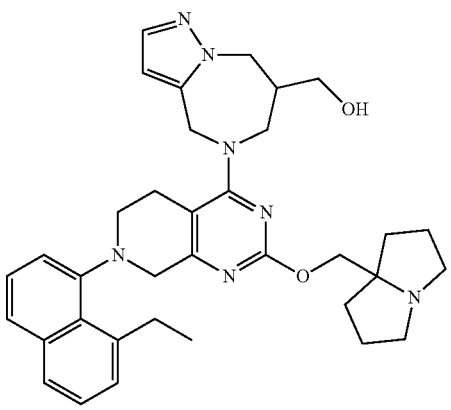 [SMILES: CCc1cccc2cccc(N3CCc4c(nc(OCC56CCCN5CCC6)nc4N4Cc5ccnn5CC(CO)C4)C3)c12]

(5-(7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)-5,6,7,8-tetrahydro-4H-pyrazolo[1,5-a]
[1,4]diazepin-7-yl)methanol
EXAMPLE 123

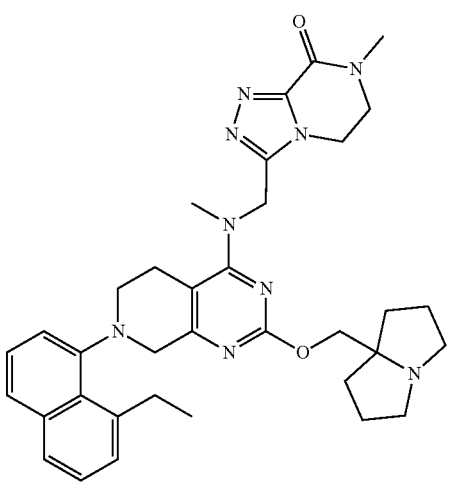 [SMILES: CCc1cccc2cccc(N3CCc4c(nc(OCC56CCCN5CCC6)nc4N(C)Cc4nnc5n4CCN(C)C5=O)C3)c12]

3-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)methyl)-7-methyl-6,7-dihydro-[1,2,4]triazolo[4,3-a]pyrazin-8(5H)-one
EXAMPLE 124

4-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)-1-(1-methyl-1H-pyrazol-4-yl)pyrrolidin-2-one
EXAMPLE 127

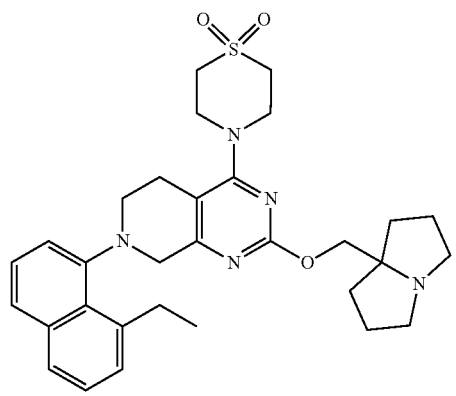 [SMILES: CCc1cccc2cccc(N3CCc4c(nc(OCC56CCCN5CCC6)nc4N4CCS(=O)(=O)CC4)C3)c12]

4-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)thiomorpholine 1,1-dioxide
EXAMPLE 125

N-((1H-1,2,3-triazol-4-yl)methyl)-7-(8-ethylnaphthalen-1-yl)-N-methyl-2-((tetrahydro-1H-pyrrolizin-7a(5H)-yl)methoxy)-5,6,7,8-tetrahydropyrido[3,4-d]pyrimidin-4-amine
EXAMPLE 128

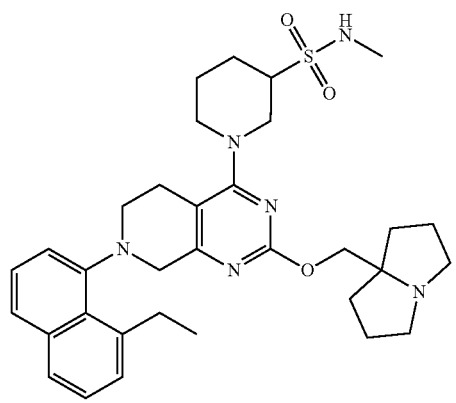 [SMILES: CCc1cccc2cccc(N3CCc4c(nc(OCC56CCCN5CCC6)nc4N4CCCC(S(=O)(=O)NC)C4)C3)c12]

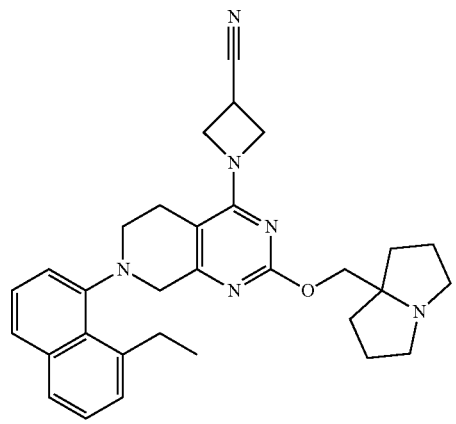

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-N-methylpiperidine-3-sulfonamide
EXAMPLE 126

1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)azetidine-3-carbonitrile
EXAMPLE 129

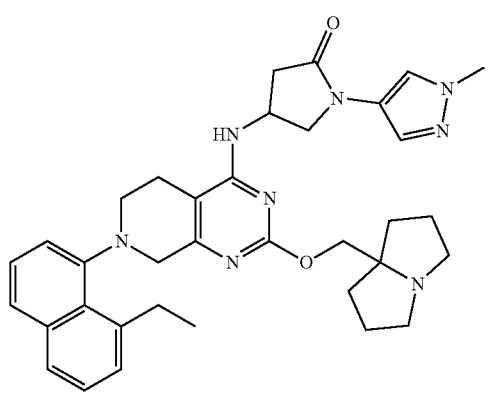 [SMILES: CCc1cccc2cccc(N3CCc4c(nc(OCC56CCCN5CCC6)nc4NC4CC(=O)N(c5cnn(C)c5)C4)C3)c12]

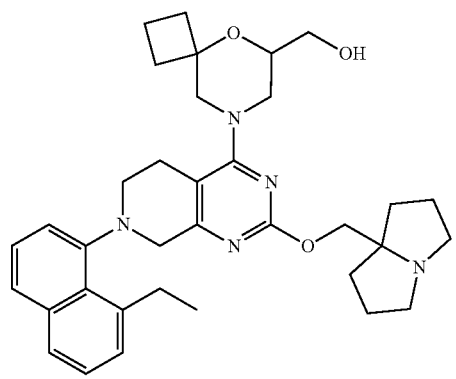 [SMILES: CCc1cccc2cccc(N3CCc4c(nc(OCC56CCCN5CCC6)nc4N4CC(CO)OC5(CCC5)C4)C3)c12]

TABLE 1-continued (8-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5-oxa-8-azaspiro[3.5]nonan-6-yl)methanol
EXAMPLE 130

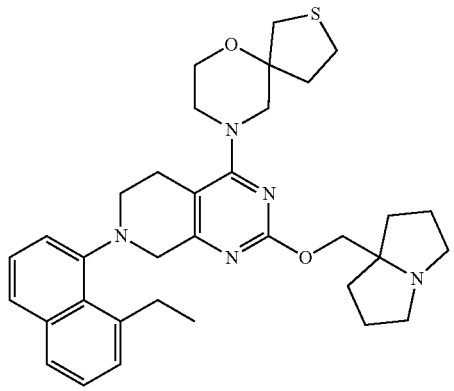 [SMILES: CCc1cccc2cccc(N3CCc4c(nc(OCC56CCCN5CCC6)nc4N4CCOC5(CCSC5)C4)C3)c12]

9-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-6-oxa-2-thia-9-azaspiro[4.5]decane
EXAMPLE 131

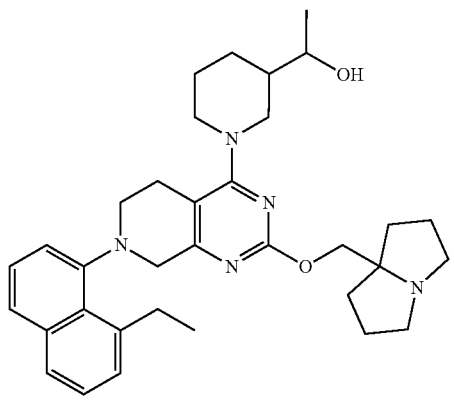 [SMILES: CCc1cccc2cccc(N3CCc4c(nc(OCC56CCCN5CCC6)nc4N4CCCC(C(C)O)C4)C3)c12]

1-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)ethan-1-ol
EXAMPLE 132

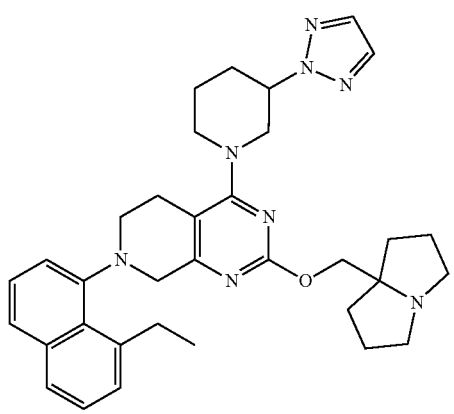 [SMILES: CCc1cccc2cccc(N3CCc4c(nc(OCC56CCCN5CCC6)nc4N4CCCC(n5nccn5)C4)C3)c12]

4-(3-(2H-1,2,3-triazol-2-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine
EXAMPLE 133

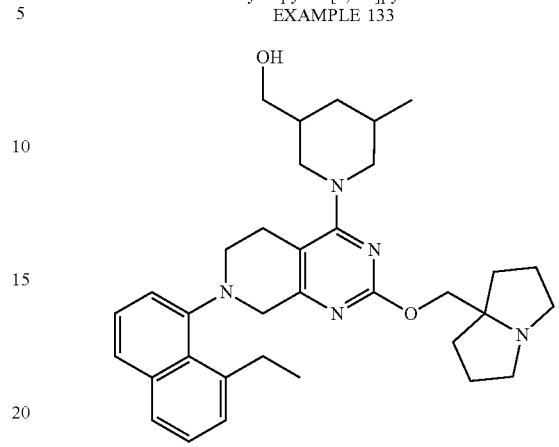

(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-5-methylpiperidin-3-yl)methanol
EXAMPLE 134

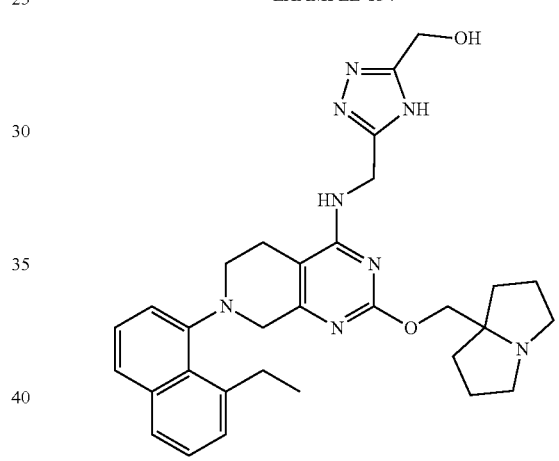

(5-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)methyl)-4H-1,2,4-triazol-3-yl)methanol
EXAMPLE 135

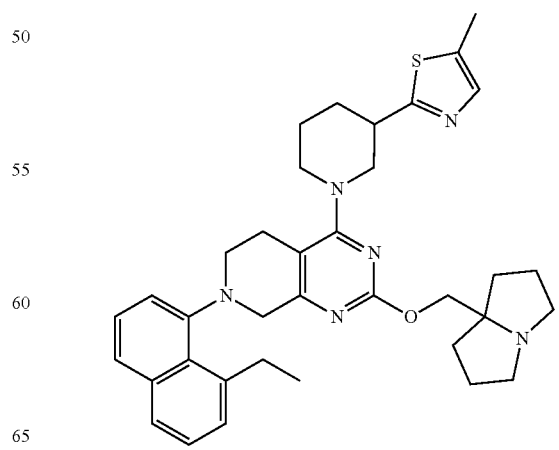

TABLE 1-continued 2-(1-(7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)piperidin-3-yl)-5-methylthiazole
EXAMPLE 136

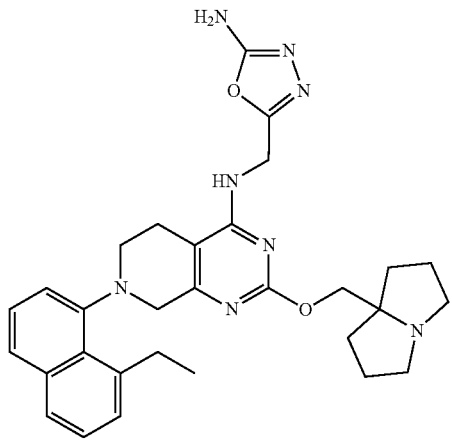 [SMILES: CCc1cccc2cccc(N3CCc4c(nc(OCC56CCCN5CCC6)nc4NCc4nnc(N)o4)C3)c12]

5-(((7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)amino)methyl)-1,3,4-oxadiazol-2-amine
EXAMPLE 137

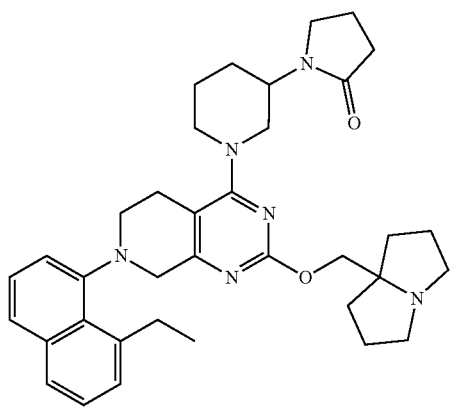 [SMILES: CCc1cccc2cccc(N3CCc4c(nc(OCC56CCCN5CCC6)nc4N4CCCC(N5CCCC5=O)C4)C3)c12]

1-(1-(7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)piperidin-3-yl)pyrrolidin-2-one
EXAMPLE 138

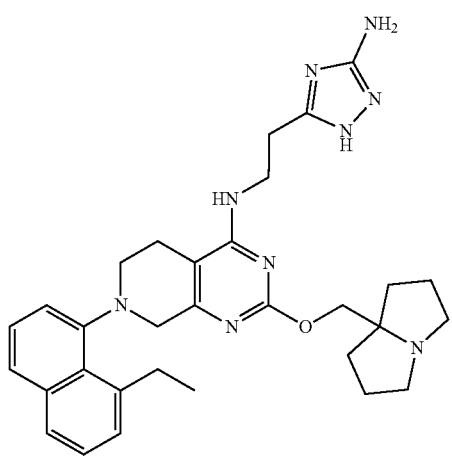 [SMILES: CCc1cccc2cccc(N3CCc4c(nc(OCC56CCCN5CCC6)nc4NCCc4nc(N)n[nH]4)C3)c12]

TABLE 1-continued

N-(2-(3-amino-1H-1,2,4-triazol-5-yl)ethyl)-7-(8-ethylnaphthalen-
1-yl)-2-((tetrahydro-1H-pyrrolizin-7a(5H)-yl)methoxy)-5,6,7,8-
tetrahydropyrido[3,4-d]pyrimidin-4-amine
EXAMPLE 139

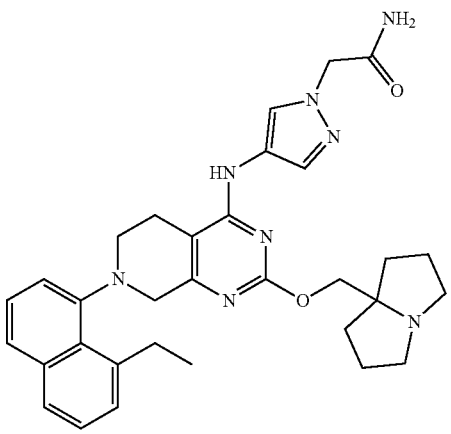 [SMILES: CCc1cccc2cccc(N3CCc4c(nc(OCC56CCCN5CCC6)nc4Nc4cnn(CC(N)=O)c4)C3)c12]

2-(4-((7-(8-ethylnaphthalen-1-yl)-2-((tetrahydro-1H-pyrrolizin-
7a(5H)-yl)methoxy)-5,6,7,8-tetrahydropyrido[3,4-d]
pyrimidin-4-yl)amino)-1H-pyrazol-1-yl)acetamide
EXAMPLE 140

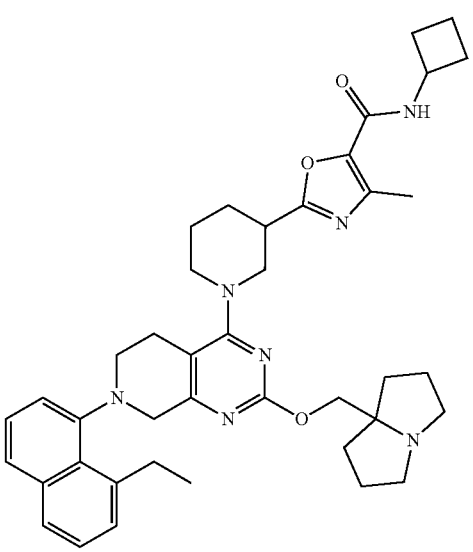 [SMILES: CCc1cccc2cccc(N3CCc4c(nc(OCC56CCCN5CCC6)nc4N4CCCC(c5nc(C)c(C(=O)NC6CCC6)o5)C4)C3)c12]

TABLE 1-continued

N-cyclobutyl-2-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-4-methyloxazole-5-carboxamide
EXAMPLE 141

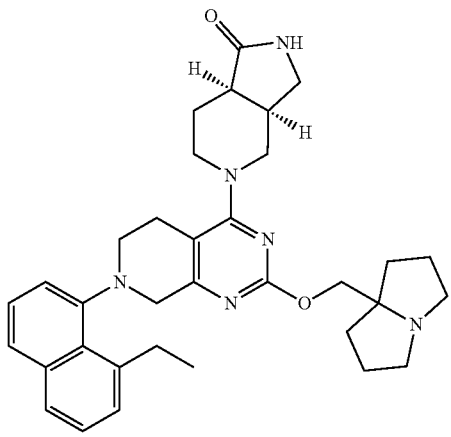 [SMILES: CCc1cccc2cccc(N3CCc4c(nc(OCC56CCCN5CCC6)nc4N4CC[C@H]5C(=O)NC[C@H]5C4)C3)c12]

(3aS,7aR)-5-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)octahydro-1H-pyrrolo[3,4-c]pyridin-1-one
EXAMPLE 142

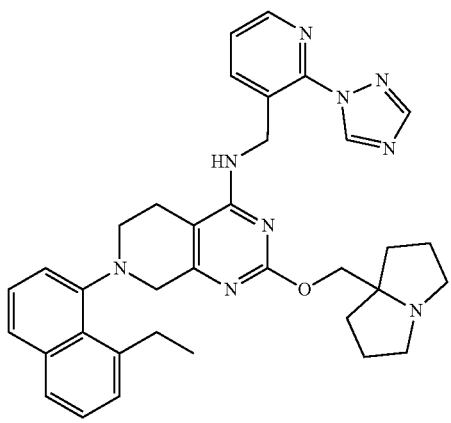 [SMILES: CCc1cccc2cccc(N3CCc4c(nc(OCC56CCCN5CCC6)nc4NCc4cccnc4-n4cncn4)C3)c12]

N-((2-(1H-1,2,4-triazol-1-yl)pyridin-3-yl)methyl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-amine
EXAMPLE 143

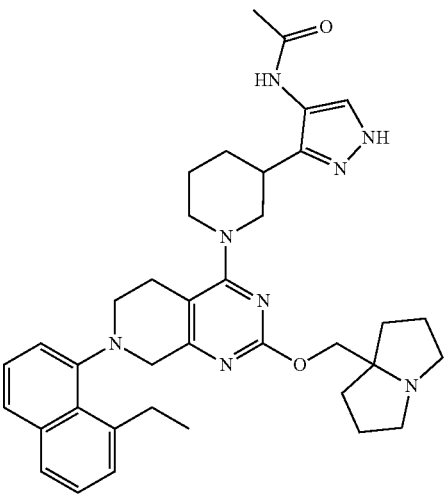 [SMILES: CCc1cccc2cccc(N3CCc4c(nc(OCC56CCCN5CCC6)nc4N4CCCC(c5n[nH]cc5NC(C)=O)C4)C3)c12]

N-(3-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-1H-pyrazol-4-yl)acetamide
EXAMPLE 144

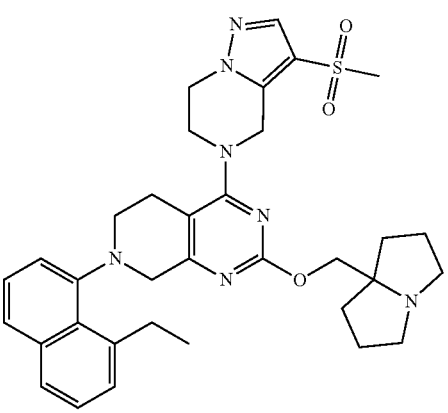 [SMILES: CCc1cccc2cccc(N3CCc4c(nc(OCC56CCCN5CCC6)nc4N4CCn5ncc(S(C)(=O)=O)c5C4)C3)c12]

TABLE 1-continued 7-(8-ethylnaphthalen-1-yl)-4-(3-(methylsulfonyl)-6,7-dihydropyrazolo[1,5-a]pyrazin-5(4H)-yl)-2-((tetrahydro-1H-pyrrolizin-7a(5H)-yl)methoxy)-5,6,7,8-tetrahydropyrido[3,4-d]pyrimidine
EXAMPLE 145

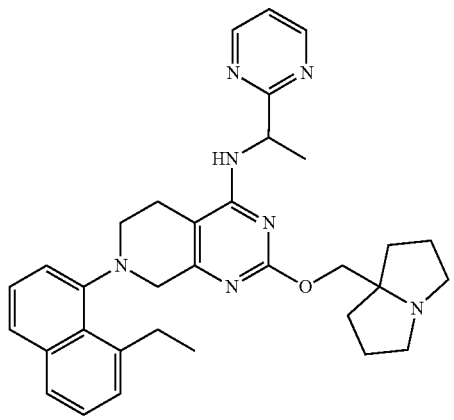 [SMILES: CCc1cccc2cccc(N3CCc4c(nc(OCC56CCCN5CCC6)nc4NC(C)c4ncccn4)C3)c12]

7-(8-ethylnaphthalen-1-yl)-N-(1-(pyrimidin-2-yl)ethyl)-2-((tetrahydro-1H-pyrrolizin-7a(5H)-yl)methoxy)-5,6,7,8-tetrahydropyrido[3,4-d]pyrimidin-4-amine
EXAMPLE 146

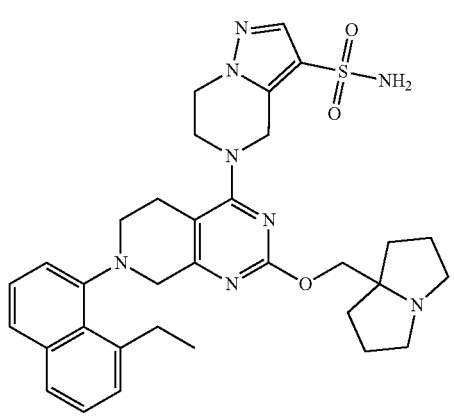 [SMILES: CCc1cccc2cccc(N3CCc4c(nc(OCC56CCCN5CCC6)nc4N4CCn5ncc(S(N)(=O)=O)c5C4)C3)c12]

5-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-4,5,6,7-tetrahydropyrazolo[1,5-a]pyrazine-3-sulfonamide
EXAMPLE 147

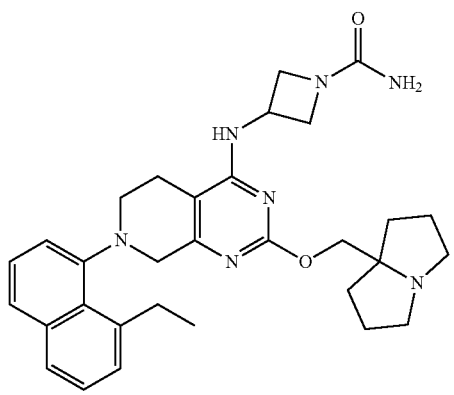 [SMILES: CCc1cccc2cccc(N3CCc4c(nc(OCC56CCCN5CCC6)nc4NC4CN(C(N)=O)C4)C3)c12]

3-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)azetidine-1-carboxamide
EXAMPLE 148

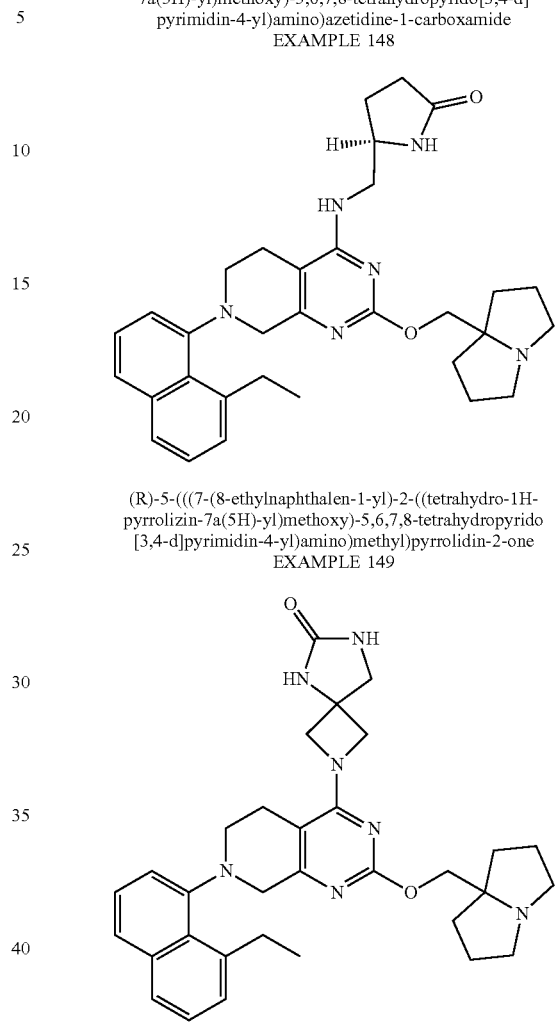

(R)-5-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)methyl)pyrrolidin-2-one
EXAMPLE 149

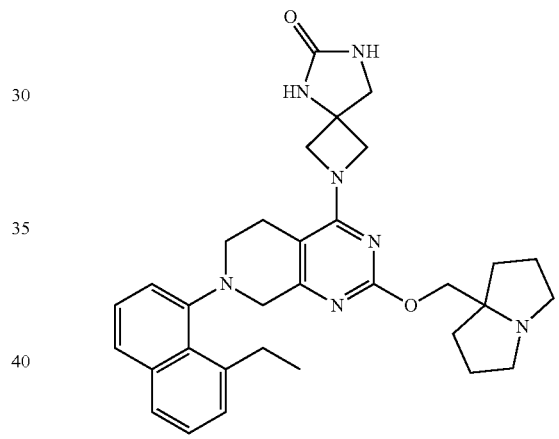

2-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-2,5,7-triazaspiro[3.4]octan-6-one
EXAMPLE 150

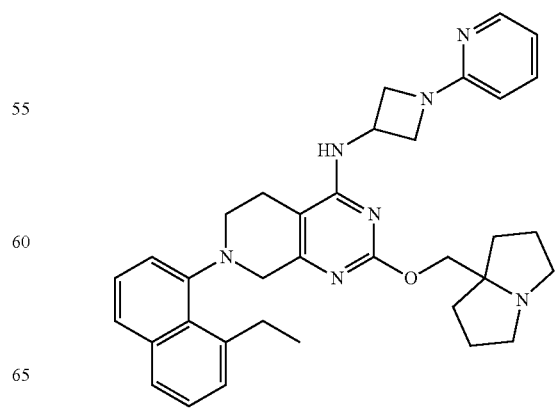

7-(8-ethylnaphthalen-1-yl)-N-(1-(pyridin-2-yl)azetidin-3-yl)-2-((tetrahydro-1H-pyrrolizin-7a(5H)-yl)methoxy)-5,6,7,8-tetrahydropyrido[3,4-d]pyrimidin-4-amine
EXAMPLE 151

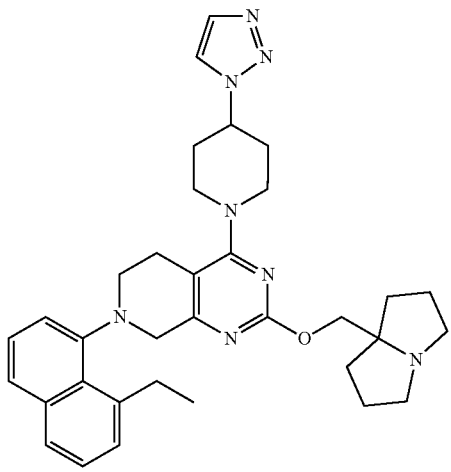 [SMILES: CCc1cccc2cccc(N3CCc4c(nc(OCC56CCCN5CCC6)nc4N4CCC(n5ccnn5)CC4)C3)c12]

4-(4-(1H-1,2,3-triazol-1-yl)piperidin-1-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine
EXAMPLE 152

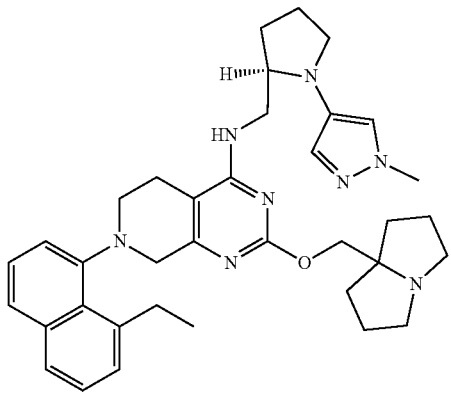 [SMILES: CCc1cccc2cccc(N3CCc4c(nc(OCC56CCCN5CCC6)nc4NC[C@H]4CCCN4c4cnn(C)c4)C3)c12]

(R)-7-(8-ethylnaphthalen-1-yl)-N-((1-(1-methyl-1H-pyrazol-4-yl)pyrrolidin-2-yl)methyl)-2-((tetrahydro-1H-pyrrolizin-7a(5H)-yl)methoxy)-5,6,7,8-tetrahydropyrido[3,4-d]pyrimidin-4-amine
EXAMPLE 153

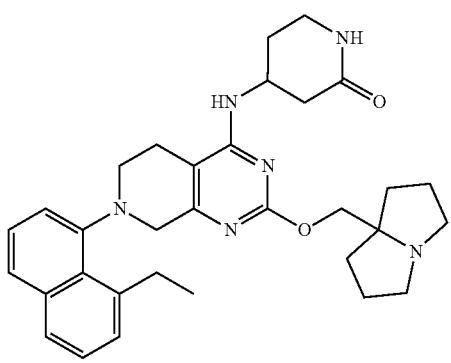 [SMILES: CCc1cccc2cccc(N3CCc4c(nc(OCC56CCCN5CCC6)nc4NC4CCNC(=O)C4)C3)c12]

4-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)piperidin-2-one
EXAMPLE 154

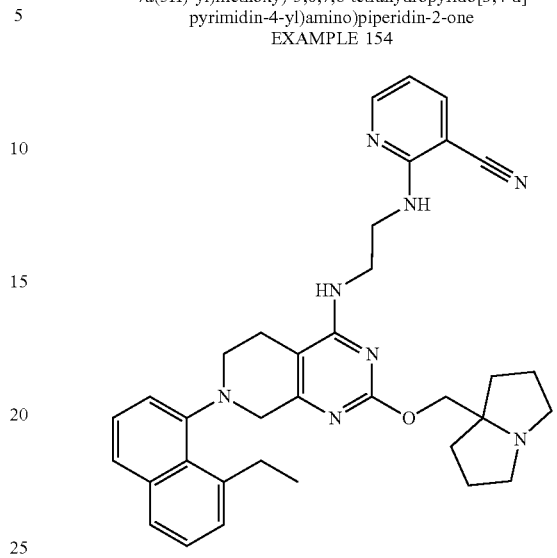

2-((2-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)ethyl)amino)nicotinonitrile
EXAMPLE 155

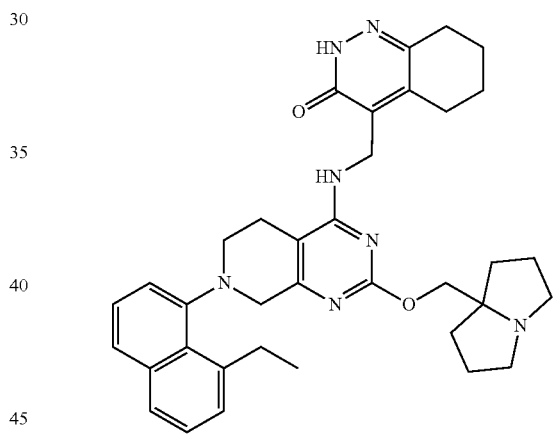

4-(((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)methyl)-5,6,7,8-tetrahydrocinnolin-3(2H)-one
EXAMPLE 156

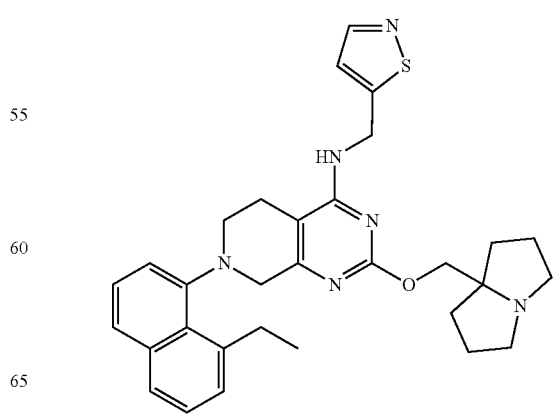

TABLE 1-continued 7-(8-ethylnaphthalen-1-yl)-N-(isothiazol-5-ylmethyl)-2-((tetrahydro-1H-pyrrolizin-7a(5H)-yl)methoxy)-5,6,7,8-tetrahydropyrido[3,4-d]pyrimidin-4-amine
EXAMPLE 157

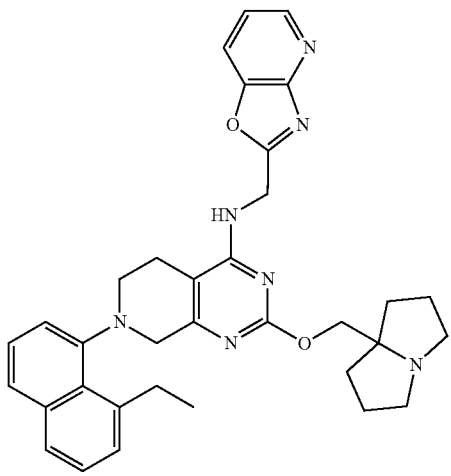 [SMILES: CCc1cccc2cccc(N3CCc4c(nc(OCC56CCCN5CCC6)nc4NCc4nc5ncccc5o4)C3)c12]

7-(8-ethylnaphthalen-1-yl)-N-(oxazolo[4,5-b]pyridin-2-ylmethyl)-2-((tetrahydro-1H-pyrrolizin-7a(5H)-yl)methoxy)-5,6,7,8-tetrahydropyrido[3,4-d]pyrimidin-4-amine
EXAMPLE 158

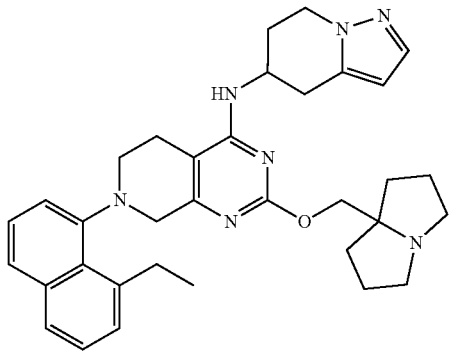 [SMILES: CCc1cccc2cccc(N3CCc4c(nc(OCC56CCCN5CCC6)nc4NC4CCn5nccc5C4)C3)c12]

7-(8-ethylnaphthalen-1-yl)-2-((tetrahydro-1H-pyrrolizin-7a(5H)-yl)methoxy)-N-(4,5,6,7-tetrahydropyrazolo[1,5-a]pyridin-5-yl)-5,6,7,8-tetrahydropyrido[3,4-d]pyrimidin-4-amine
EXAMPLE 159

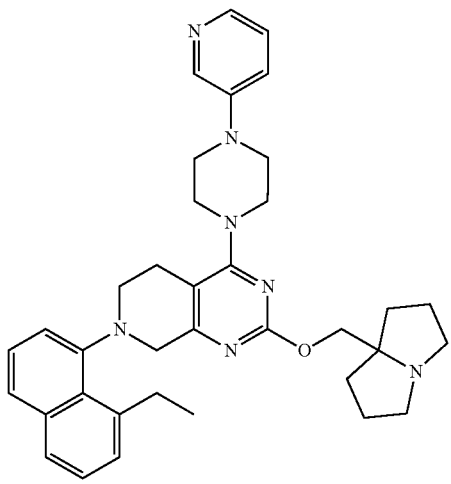 [SMILES: CCc1cccc2cccc(N3CCc4c(nc(OCC56CCCN5CCC6)nc4N4CCN(c5cccnc5)CC4)C3)c12]

TABLE 1-continued 7-(8-ethylnaphthalen-1-yl)-4-(4-(pyridin-3-yl)piperazin-1-yl)-2-((tetrahydro-1H-pyrrolizin-7a(5H)-yl)methoxy)-5,6,7,8-tetrahydropyrido[3,4-d]pyrimidine
EXAMPLE 160

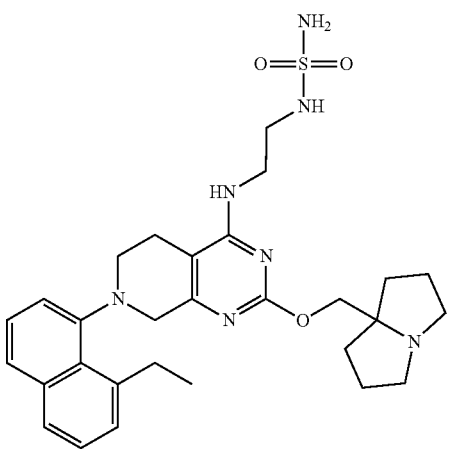 [SMILES: CCc1cccc2cccc(N3CCc4c(nc(OCC56CCCN5CCC6)nc4NCCNS(N)(=O)=O)C3)c12]

N-(2-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)ethyl)sulfamide
EXAMPLE 161

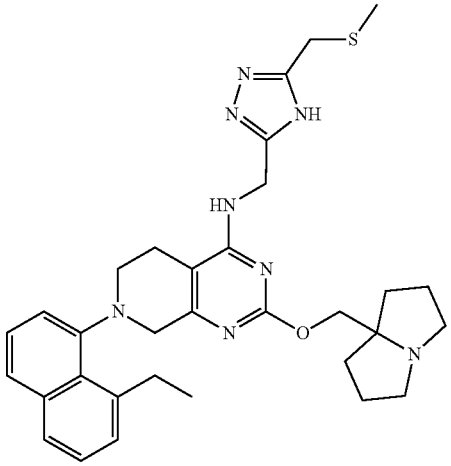 [SMILES: CCc1cccc2cccc(N3CCc4c(nc(OCC56CCCN5CCC6)nc4NCc4nnc(CSC)[nH]4)C3)c12]

TABLE 1-continued 7-(8-ethylnaphthalen-1-yl)-N-((5-((methylthio)methyl)-4H-1,2,4-triazol-3-yl)methyl)-2-((tetrahydro-1H-pyrrolizin-7a(5H)-yl)methoxy)-5,6,7,8-tetrahydropyrido[3,4-d]pyrimidin-4-amine
EXAMPLE 162

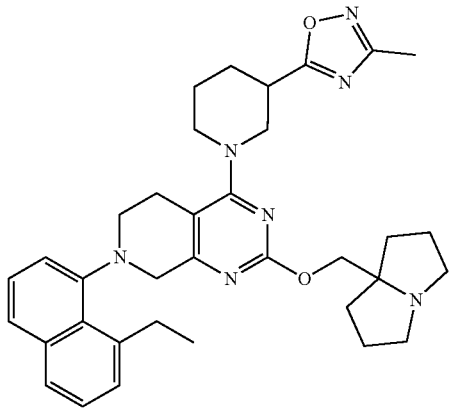 [SMILES: CCc1cccc2cccc(N3CCc4c(nc(OCC56CCCN5CCC6)nc4N4CCCC(c5nc(C)no5)C4)C3)c12]

5-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-3-methyl-1,2,4-oxadiazole
EXAMPLE 163

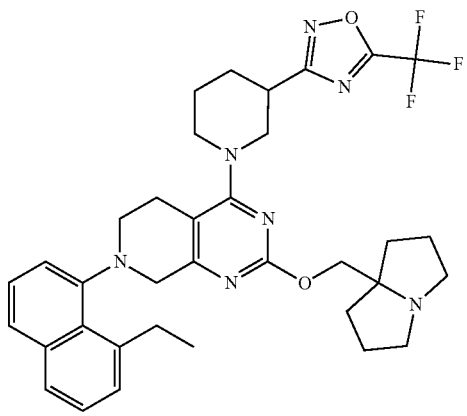 [SMILES: CCc1cccc2cccc(N3CCc4c(nc(OCC56CCCN5CCC6)nc4N4CCCC(c5noc(C(F)(F)F)n5)C4)C3)c12]

3-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-5-(trifluoromethyl)-1,2,4-oxadiazole
EXAMPLE 164

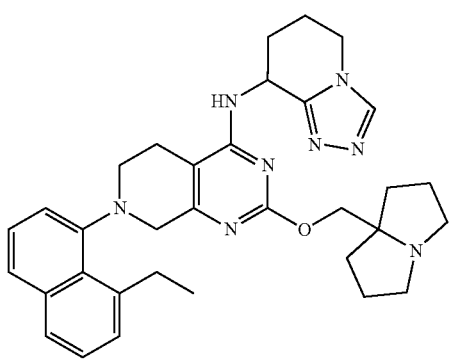 [SMILES: CCc1cccc2cccc(N3CCc4c(nc(OCC56CCCN5CCC6)nc4NC4CCCn5cnnc54)C3)c12]

7-(8-ethylnaphthalen-1-yl)-2-((tetrahydro-1H-pyrrolizin-7a(5H)-yl)methoxy)-N-(5,6,7,8-tetrahydro-[1,2,4]triazolo[4,3-a]pyridin-8-yl)-5,6,7,8-tetrahydropyrido[3,4-d]pyrimidin-4-amine
EXAMPLE 165

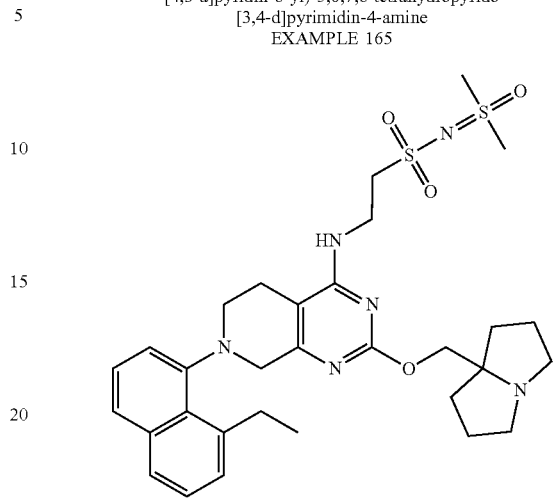

N-(dimethyl(oxo)-l6-sulfaneylidene)-2-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)amino)ethane-1-sulfonamide
EXAMPLE 166

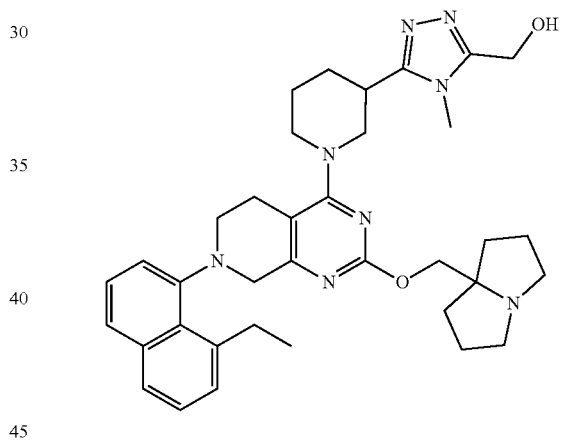

(5-(1-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)piperidin-3-yl)-4-methyl-4H-1,2,4-triazol-3-yl)methanol
EXAMPLE 167

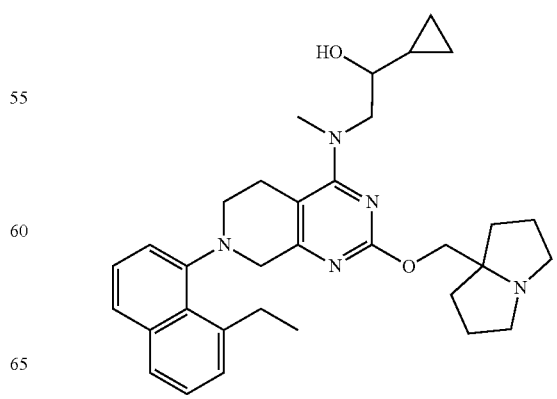

TABLE 1-continued 1-cyclopropyl-2-((7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)ethan-1-ol
EXAMPLE 168

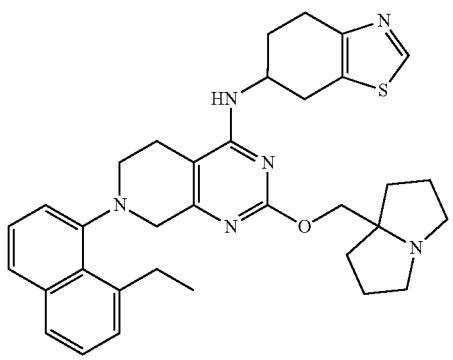 [SMILES: CCc1cccc2cccc(N3CCc4c(nc(OCC56CCCN5CCC6)nc4NC4CCc5ncsc5C4)C3)c12]

N-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-4,5,6,7-tetrahydrobenzo[d]thiazol-6-amine
EXAMPLE 169

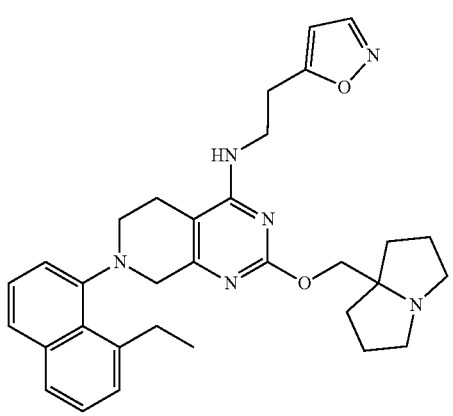 [SMILES: CCc1cccc2cccc(N3CCc4c(nc(OCC56CCCN5CCC6)nc4NCCc4ccno4)C3)c12]

7-(8-ethylnaphthalen-1-yl)-N-(2-(isoxazol-5-yl)ethyl)-2-((tetrahydro-1H-pyrrolizin-7a(5H)-yl)methoxy)-5,6,7,8-tetrahydropyrido[3,4-d]pyrimidin-4-amine
EXAMPLE 170

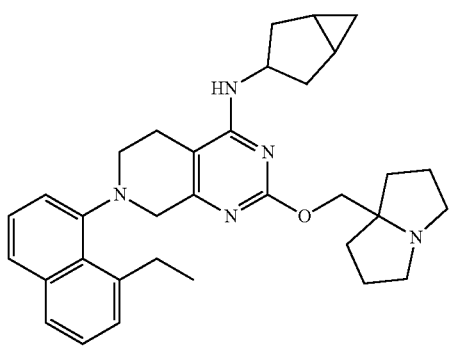 [SMILES: CCc1cccc2cccc(N3CCc4c(nc(OCC56CCCN5CCC6)nc4NC4CC5CC5C4)C3)c12]

TABLE 1-continued

N-(bicyclo[3.1.0]hexan-3-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-amine
EXAMPLE 171

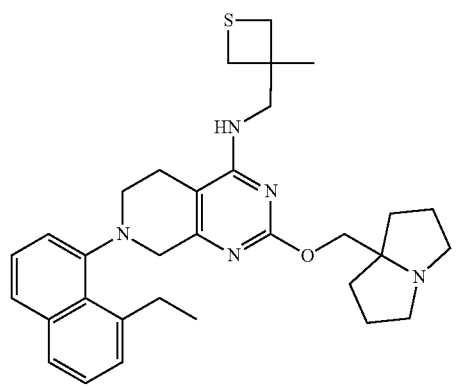 [SMILES: CCc1cccc2cccc(N3CCc4c(nc(OCC56CCCN5CCC6)nc4NCC4(C)CSC4)C3)c12]

7-(8-ethylnaphthalen-1-yl)-N-((3-methylthietan-3-yl)methyl)-2-((tetrahydro-1H-pyrrolizin-7a(5H)-yl)methoxy)-5,6,7,8-tetrahydropyrido[3,4-d]pyrimidin-4-amine
EXAMPLE 172

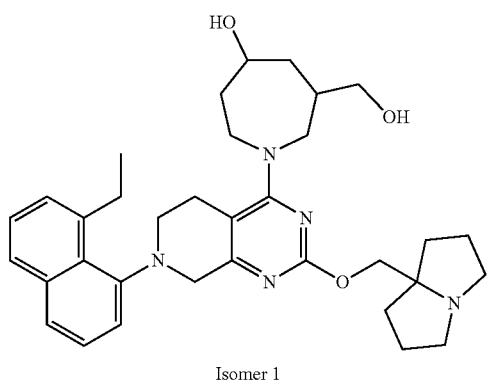 [SMILES: CCc1cccc2cccc(N3CCc4c(nc(OCC56CCCN5CCC6)nc4N4CCC(O)CC(CO)C4)C3)c12]

Isomer 1

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-(hydroxymethyl)azepan-4-ol

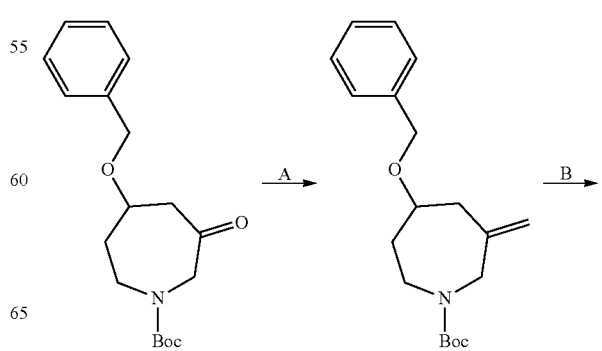

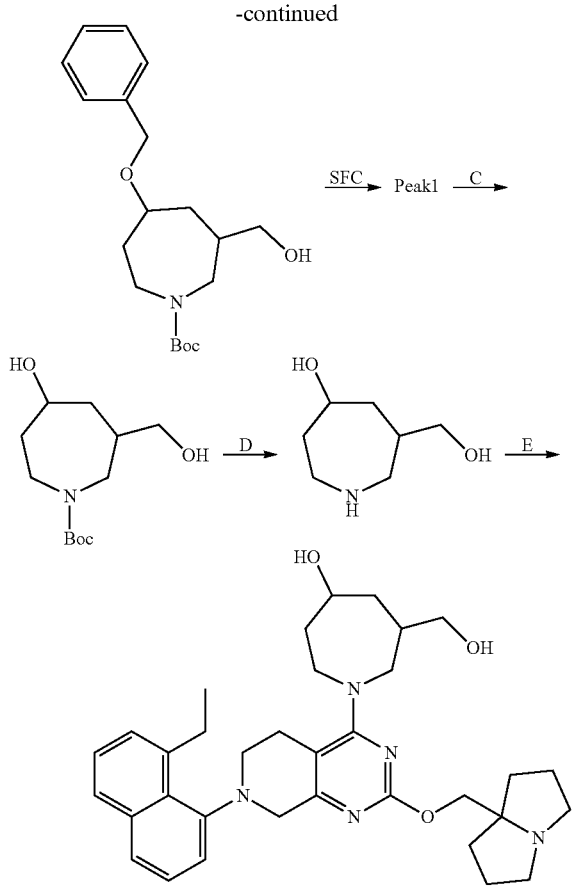

Step A. tert-butyl 5-(benzyloxy)-3-methyleneazepane-1-carboxylate: To a mixture of methyl(triphenyl)phosphonium; bromide (8.39 g, 2.5 equiv) in THF (15 mL) was added n-BuLi (2.5 M, 10.5 mL, 2.8 equiv) at 0° C. The reaction was stirred at 0° C. for 0.5 hours, and then tert-butyl 5-(benzyloxy)-3-oxoazepane-1-carboxylate (3.00 g, 1.0 equiv) was added at 0° C. The reaction was stirred at 0° C. for 1 hour. The mixture was quenched with sat. NH$_4$Cl (10 mL) and extracted with ethyl acetate (10 ml×2). The combined organic layers were dried over Na$_2$SO$_4$ and concentrated. The residue was purified by column chromatography (SiO$_2$, Petroleum ether/Ethyl acetate=50/1 to 2/1) to afford the title compound (1.4 g, 37% yield) as yellow oil; $^1$H NMR (400 MHz, METHANOL-d$_4$) δ=7.44-7.26 (m, 4H), 5.08-4.91 (m, 2H), 4.84-4.42 (m, 3H), 4.23-4.08 (m, 1H), 4.04-3.84 (m, 1H), 3.67-3.38 (m, 2H), 3.22-3.05 (m, 1H), 2.61-2.25 (m, 2H), 2.03-1.67 (m, 2H), 1.46 (d, J=6.8 Hz, 9H); LCMS (ESI, M−99): m/z=218.2.

Step B. tert-butyl 5-(benzyloxy)-3-(hydroxymethyl)azepane-1-carboxylate: To a solution of tert-butyl 5-(benzyloxy)-3-methyleneazepane-1-carboxylate (600 mg, 1.0 equiv) in THF (5 mL) was added BH$_3$·Me$_2$S (10 M, 567 μL, 3.0 equiv) at 0° C., and the mixture was stirred at 0° C. for 1.5 hours. NaOH (3 M, 2.52 mL, 4.0 equiv) and H$_2$O$_2$ (7.94 g, 6.73 mL, 30% purity, 37 equiv) were added and the reaction was stirred at 0° C. for 1.5 hours. The reaction was quenched with sat. Na$_2$SO$_3$, and extracted with ethyl acetate (10 mL×2). The combined organic layers were dried over Na$_2$SO$_4$, concentrated, and purified with reversed phase flash chromatography [C18, 0.1% formic acid condition] to give mixture of stereoisomers (280 mg) which was separated by SFC (column: DAICEL CHIRALCEL OJ (250 mm×30 mm, 10 μm); mobile phase: [0.1% NH$_3$H$_2$O MEOH]; B %: 15%-15%,2.2 min) to afford three peaks. Peak 1 (95 mg, 15% yield) as yellow oil; $^1$H NMR (400 MHz, METHANOL-d$_4$) δ=7.44-7.17 (m, 5H), 4.62-4.39 (m, 2H), 3.88-3.75 (m, 1H), 3.56-3.34 (m, 5H), 3.30-3.15 (m, 1H), 2.30 (td, J=3.0, 5.6 Hz, 1H), 2.13-1.93 (m, 2H), 1.80 (br dd, J=4.4, 9.2 Hz, 1H), 1.51-1.46 (m, 1H), 1.44 (d, J=4.4 Hz, 9H); LCMS (ESI, M+1): m/z=336.1. Peak 2 (35 mg, 4.7% yield) as yellow oil; $^1$H NMR (400 MHz, METHANOL-d$_4$) δ=7.39-7.19 (m, 5H), 4.63-4.47 (m, 2H), 3.63-3.33 (m, 6H), 3.14 (s, 1H), 2.23-1.96 (m, 2H), 1.92-1.77 (m, 1H), 1.74-1.58 (m, 1H), 1.44 (d, J=6.0 Hz, 9H), 1.29 (br s, 1H); LCMS (ESI, M−99): m/z=236.1. Peak 3 (40 mg, 6% yield) as yellow oil; $^1$H NMR (400 MHz, METHANOL-d$_4$) δ=7.42-7.15 (m, 4H), 4.64-4.45 (m, 2H), 3.64-3.40 (m, 5H), 3.34 (br d, J=5.2 Hz, 1H), 3.27 (br s, 1H), 3.20-3.04 (m, 1H), 2.23-2.04 (m, 2H), 1.85 (br dd, J=4.8, 8.4 Hz, 1H), 1.68 (dt, J=4.4, 9.2 Hz, 1H), 1.44 (d, J=6.0 Hz, 9H), 1.40-1.25 (m, 1H); LCMS (ESI, M−99): m/z=236.1.

Step C. tert-butyl 5-hydroxy-3-(hydroxymethyl)azepane-1-carboxylate: To a solution of tert-butyl 5-(benzyloxy)-3-(hydroxymethyl)azepane-1-carboxylate (peak 1, 400 mg, 1.0 equiv) in MeOH (10 mL) was added Pd/C (100 mg, 10% purity) under N$_2$. The suspension was degassed under vacuum and purged with H$_2$ several times and the mixture was stirred under H$_2$ (15 psi) at 50° C. for 2 hours. The mixture was filtered and concentrated to afford the title compound (303 mg, crude) as yellow oil; $^1$H NMR (400 MHz, METHANOL-d$_4$) δ=4.04 (td, J=1.6, 3.2 Hz, 1H), 3.57-3.43 (m, 3H), 3.35 (s, 1H), 3.43-3.34 (m, 1H), 3.30-3.10 (m, 1H), 2.29 (br s, 1H), 1.92-1.69 (m, 3H), 1.63-1.52 (m, 1H), 1.46 (s, 9H).

Step D. 6-(hydroxymethyl)azepan-4-ol: To a solution of tert-butyl 5-hydroxy-3-(hydroxymethyl)azepane-1-carboxylate (150 mg, 1.0 equiv) in DCM (0.8 mL) was added HCl·dioxane (4 M, 153 μL, 1.0 equiv) at 0° C. The mixture was stirred at 0° C. for 30 minutes. After completion, the reaction mixture was concentrated under reduced pressure to afford the title compound (110 mg, crude) as colorless oil.

Step E. 1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-(hydroxymethyl)azepan-4-ol: To a solution of 7-(8-ethylnaphthalen-1-yl)-2-((hexahydro-1H-pyrrolizin-7a-yl)methoxy)-5,6,7,8-tetrahydropyrido[3,4-d]pyrimidin-4-yl 4-methylbenzenesulfonate (120 mg, 1.0 equiv) and N-ethyl-N-isopropylpropan-2-amine (77.7 mg, 105 μL, 3.0 equiv) in DMF (1 mL) was added 6-(hydroxymethyl)azepan-4-ol (100 mg, 3.4 equiv) and 4 Å molecular sieve (30.0 mg, 1.0 equiv). The reaction mixture was degassed and purged with N$_2$ for three times. The reaction mixture was stirred at 40° C. for 12 hours. The mixture was filtered and the filtrate was purified by prep-HPLC [column: Phenomenex C18 150×25 mm×10 μm; mobile phase: water (FA)-ACN; B %: 11%-41%, 10 minutes] to afford the title compound (25.9 mg, 21% yield) as yellow gum; $^1$H NMR (400 MHz, METHANOL-d$_4$) δ=7.69 (dd, J=7.6, 16.7 Hz, 2H), 7.43 (dt, J=3.2, 7.6 Hz, 1H), 7.38-7.30 (m, 2H), 7.29-7.26 (m, 1H), 4.51-4.37 (m, 2H), 4.26-3.90 (m, 4H), 3.78-3.35 (m, 10H), 3.27-3.15 (m, 3H), 3.11-2.94 (m, 1H), 2.91-2.71 (m, 1H), 2.61-2.31 (m, 1H), 2.29-1.97 (m, 9H), 1.96-1.56 (m, 3H), 1.15 (q, J=7.6 Hz, 3H); LCMS (ESI, M+1): m/z=572.5.

Example 173

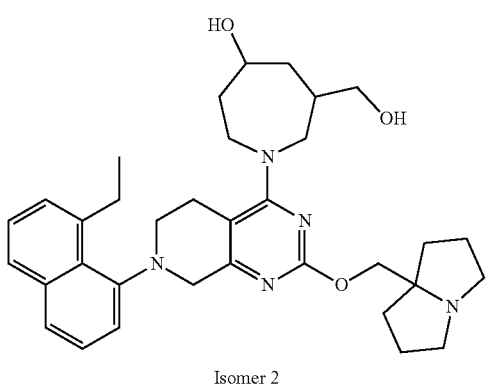 [SMILES: CCc1cccc2cccc(N3CCc4c(nc(OCC56CCCN5CCC6)nc4N4CCC(O)CC(CO)C4)C3)c12]

Isomer 2

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-(hydroxymethyl)azepan-4-ol Synthesized according to Example 172 (step C-E, peak 2 of tert-butyl 5-(benzyloxy)-3-(hydroxymethyl)azepane-1-carboxylate was used). The title compound was obtained as yellow solid. $^1$H NMR (400 MHz, METHANOL-$d_4$) δ=7.78-7.59 (m, 2H), 7.46-7.39 (m, 1H), 7.38-7.31 (m, 2H), 7.31-7.26 (m, 1H), 4.42 (br d, J=2.8 Hz, 2H), 4.22-3.98 (m, 2H), 3.85-3.46 (m, 10H), 3.37 (br dd, J=10.4, 13.6 Hz, 2H), 3.23-3.11 (m, 3H), 3.10-2.97 (m, 1H), 2.88-2.71 (m, 1H), 2.38-1.84 (m, 12H), 1.59-1.47 (m, 1H), 1.23-1.07 (m, 3H). LCMS (ESI, M+1): m/z=572.4.

Example 174

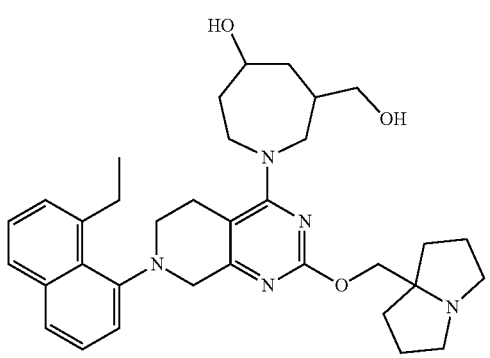

Isomer 3

1-(7-(8-ethylnaphthalen-1-yl)-2-((hexahydro-1H-pyrrolizin-7a-yl)methoxy)-5,6,7,8-tetrahydropyrido[3,4-d]pyrimidin-4-yl)-6-(hydroxymethyl)azepan-4-ol Synthesized according to Example 172 (step C-E, peak 3 of tert-butyl 5-(benzyloxy)-3-(hydroxymethyl)azepane-1-carboxylate was used). The title compound was obtained as yellow solid. $^1$H NMR (400 MHz, METHANOL-$d_4$) δ=7.69 (br dd, J=8.0, 15.6 Hz, 2H), 7.48-7.39 (m, 1H), 7.39-7.31 (m, 2H), 7.31-7.26 (m, 1H), 4.43 (br d, J=3.2 Hz, 2H), 4.22-3.97 (m, 2H), 3.91-3.48 (m, 10H), 3.37 (br dd, J=10.4, 13.6 Hz, 2H), 3.27-3.13 (m, 3H), 3.10-2.95 (m, 1H), 2.91-2.69 (m, 1H), 2.38-1.66 (m, 12H), 1.60-1.42 (m, 1H), 1.23-1.06 (m, 3H); LCMS (ESI, M+1): m/z=572.5.

Example 175

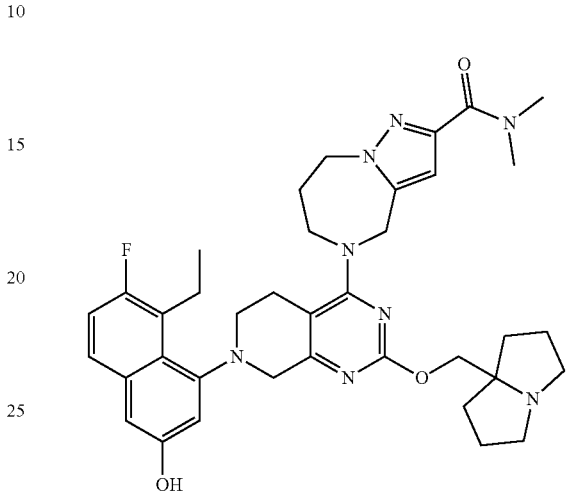

5-[7-(8-ethyl-7-fluoro-3-hydroxy-1-naphthyl)-2-(1,2,3,5,6,7-hexahydropyrrolizin-8-ylmethoxy)-6,8-dihydro-5H-pyrido[3,4-d]pyrimidin-4-yl]-N,N-dimethyl-4,6,7,8-tetrahydropyrazolo[1,5-a][1,4]diazepine-2-carboxamide

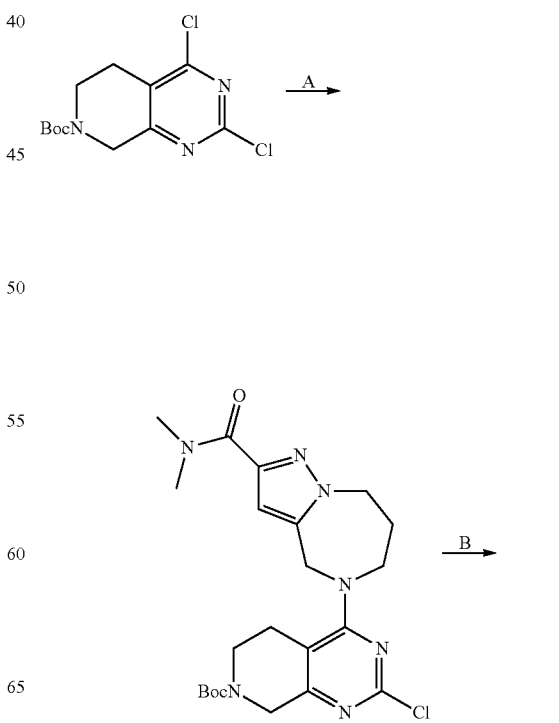

213
-continued

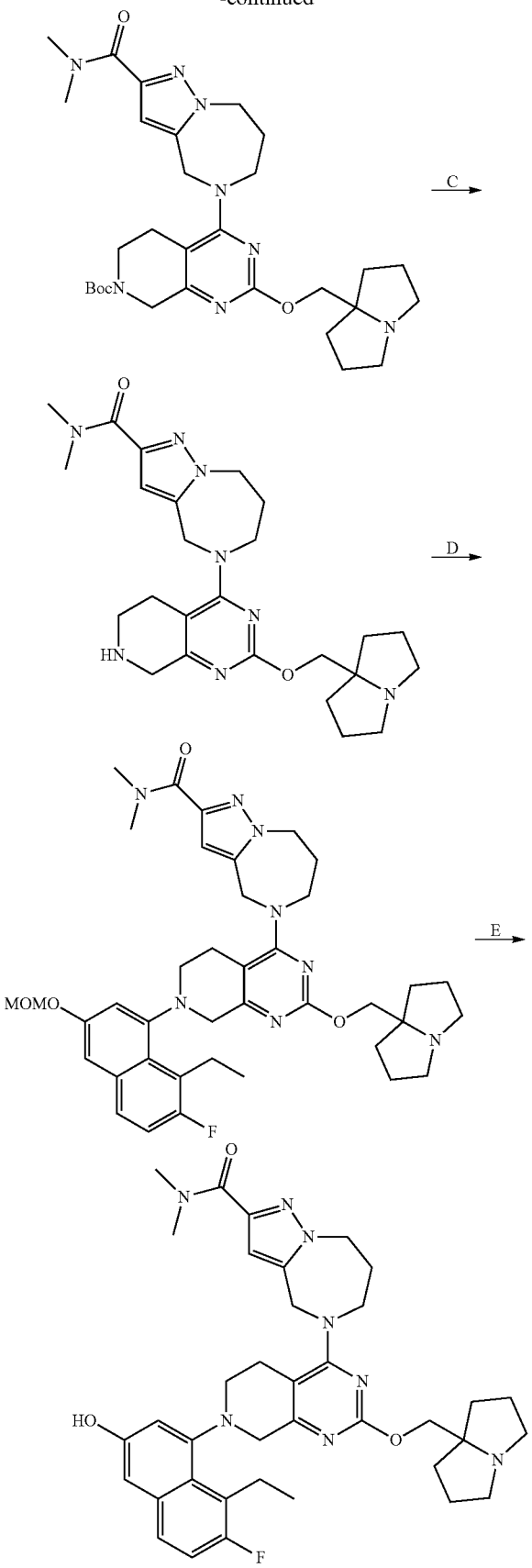

Step A tert-butyl 2-chloro-4-(2-(dimethylcarbamoyl)-7,8-dihydro-4H-pyrazolo[1,5-a][1,4]diazepin-5(6H)-yl)-5,6-dihydropyrido[3,4-d]pyrimidine-7(8H)-carboxylate: To a solution of N,N-dimethyl-5,6,7,8-tetrahydro-4H-pyrazolo[1,5-a][1,4]diazepine-2-carboxamide (1.4 g, 1.09 equiv) in DMSO (30 mL) were added N-ethyl-N-isopropylpropan-2-amine (3.40 g, 5 equiv) and tert-butyl 2,4-dichloro-6,8-dihydro-5H-pyrido[3,4-d]pyrimidine-7-carboxylate (1.6 g, 1 equiv). The mixture was stirred at 60° C. for 12 hours. The reaction mixture was diluted with water (150 mL) and extracted with EtOAc (3×100 mL). The combined organic layers were washed with brine (3×20 mL), dried over anhydrous sodium sulfate, concentrated and purified with column chromatography (SiO$_2$, Petroleum ether/Ethyl acetate=1/1 to 1/2) to afford the title compound as a yellow oil; $^1$H NMR (400 MHz, CHLOROFORM-d) δ=6.61 (s, 1H), 4.71 (br s, 2H), 4.61-4.44 (m, 4H), 3.92 (br d, J=4.4 Hz, 2H), 3.58 (br s, 2H), 3.34 (br s, 3H), 3.10 (br s, 3H), 2.71 (br s, 2H), 2.18 (br s, 2H), 1.51 (s, 9H); LCMS (ESI, M+1): m/z=476.3.

Step B. tert-butyl 4-(2-(dimethylcarbamoyl)-7,8-dihydro-4H-pyrazolo[1,5-a][1,4]diazepin-5(6H)-yl)-2-((tetrahydro-1H-pyrrolizin-7a(5H)-yl)methoxy)-5,8-dihydropyrido[3,4-d]pyrimidine-7(6H)-carboxylate: A mixture of tert-butyl 2-chloro-4-[2-(dimethylcarbamoyl)-4,6,7,8-tetrahydropyrazolo[1,5-a][1,4]diazepin-5-yl]-6,8-dihydro-5H-pyrido[3,4-d]pyrimidine-7-carboxylate (400 mg, 1.0 equiv), 1,2,3,5,6,7-hexahydropyrrolizin-8-ylmethanol (142 mg, 1.2 equiv), BINAP (131 mg, 0.3 equiv), Pd(OAc)$_2$ (37.7 mg, 0.2 equiv) and Cs$_2$CO$_3$ (685 mg, 2.5 equiv) in toluene (7 mL) was degassed and purged with N$_2$ for 3 times, and then the reaction was stirred at 110° C. for 8 hours under N$_2$ atmosphere. The reaction was quenched with water (15 mL) at 25° C. and extracted with ethyl acetate (10 mL×3). The combined organic layers were washed with saturated salt solution (5 mL), dried over anhydrous sodium sulfate, and concentrated under reduced pressure. The residue was purified by prep-HPLC (column: Phenomenex luna C18 150×40 mm×15 μm; mobile phase: [water (FA)-ACN]; B %: 20%-50%, 10 min) to afford the title compound (223 mg, 45% yield) as a yellow solid. LCMS (ESI, M+1): m/z=581.2.

Step C. N,N-dimethyl-5-(2-((tetrahydro-1H-pyrrolizin-7a(5H)-yl)methoxy)-5,6,7,8-tetrahydropyrido[3,4-d]pyrimidin-4-yl)-5,6,7,8-tetrahydro-4H-pyrazolo[1,5-a][1,4]diazepine-2-carboxamide: To a solution of tert-butyl 4-(2-(dimethylcarbamoyl)-7,8-dihydro-4H-pyrazolo[1,5-a][1,4]diazepin-5(6H)-yl)-2-((tetrahydro-1H-pyrrolizin-7a(5H)-yl)methoxy)-5,8-dihydropyrido[3,4-d]pyrimidine-7(6H)-carboxylate (200 mg, 1.0 equiv) in dioxane (0.5 mL) was added HCl/dioxane (2 M, 5.00 mL). The mixture was stirred at 0° C. at 25° C. for 1 hour. The reaction mixture was concentrated under reduced pressure. The residue was dissolved in MeOH (3 mL), and its pH was adjusted to 9 with NaHCO$_3$. The mixture was stirred for 0.3 hour. The reaction mixture was filtered and concentrated under reduced pressure to afford the title compound (185 mg, 90% yield) as a yellow oil; LCMS (ESI, M+1): m/z=481.3.

Step D. 5-(7-(8-ethyl-7-fluoro-3-(methoxymethoxy)naphthalen-1-yl)-2-((tetrahydro-1H-pyrrolizin-7a(5H)-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide: A mixture of N,N-dimethyl-5-(2-((tetrahydro-1H-pyrrolizin-7a(5H)-yl)methoxy)-5,6,7,8-tetrahydropyrido[3,4-d]pyrimidin-4-yl)-5,6,7,8-tetrahydro-4H-pyrazolo[1,5-a][1,4]diazepine-2-carboxamide (160 mg, 1.0 equiv), [8-ethyl-7-fluoro-3-(methoxymethoxy)-1-naphthyl]trifluoromethanesulfonate (140 mg, 1.1 equiv), Pd$_2$ (dba)₃ (45.7 mg, 0.2 equiv), Xantphos (48.2 mg, 0.3 equiv) and Cs₂CO₃ (325 mg, 3 equiv) in toluene (1 mL) was degassed and purged with N₂ for 3 times. The mixture was stirred at 110° C. for 14 hours under N₂ atmosphere. The mixture was concentrated in vacuum to give a residue. The residue was purified by prep-HPLC (column: Phenomenex luna C18 150×40 mm×15 μm; mobile phase: [water (FA)-ACN]; B %: 23%-53%, 10 min) to afford the title compound (30 mg, 12.51% yield) as a yellow solid.

Step E. 5-(7-(8-ethyl-7-fluoro-3-hydroxynaphthalen-1-yl)-2-((tetrahydro-1H-pyrrolizin-7a(5H)-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide: To a solution of 5-(7-(8-ethyl-7-fluoro-3-(methoxymethoxy)naphthalen-1-yl)-2-((tetrahydro-1H-pyrrolizin-7a(5H)-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide (27.0 mg, 1.0 equiv) in MeOH (3 mL) was added HCl/MeOH (4 M, 3 mL). The mixture was stirred at 0° C. for 0.5 hours. The reaction mixture was adjusted pH to 9 with NaHCO₃ and stirred at 0° C. for 0.3 hours. The reaction mixture was filtered and concentrated under reduced pressure. The residue was purified by prep-HPLC (FA condition; column: Phenomenex Luna C18 150×25 mm×10 μm; mobile phase: [water (FA)-ACN]; B %: 17%-47%,10 min) to afford the title compound (11.2 mg, 44% yield) as an off-white solid. $^1$H NMR (400 MHz, METHANOL-d4) δ=8.66-8.37 (m, 1H), 7.54 (dd, J=5.6, 8.8 Hz, 1H), 7.17 (t, J=9.6 Hz, 1H), 7.00 (s, 2H), 6.65 (s, 1H), 4.95 (br s, 2H), 4.59-4.50 (m, 2H), 4.48-4.36 (m, 2H), 4.23-4.12 (m, 2H), 4.09 (br d, J=17.6 Hz, 1H), 3.71 (br d, J=17.6 Hz, 1H), 3.67-3.60 (m, 2H), 3.60-3.53 (m, 1H), 3.44-3.34 (m, 5H), 3.31-3.17 (m, 5H), 3.10 (s, 3H), 2.78 (br d, J=14.4 Hz, 1H), 2.37-2.26 (m, 3H), 2.25-2.13 (m, 4H), 2.12-2.04 (m, 3H), 1.12 (t, J=7.2 Hz, 3H); $^{19}$F NMR (377 MHz, METHANOL-d4) δ=−122.91 (s, 1F); LCMS (ESI, M+1): m/z=669.4.

Example 176

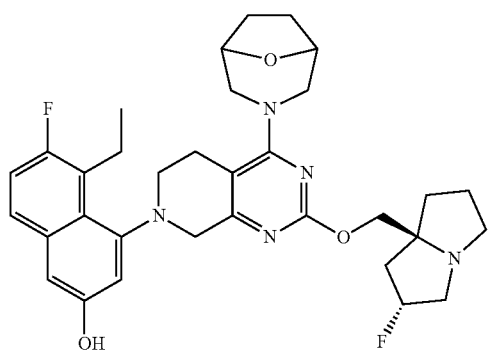 [SMILES: CCc1c(F)ccc2cc(O)cc(N3CCc4c(nc(OC[C@@]56CCCN5C[C@H](F)C6)nc4N4CC5CCC(C4)O5)C3)c12]

4-(4-(8-oxa-3-azabicyclo[3.2.1]octan-3-yl)-2-(((2R,7aS)-2-fluorotetrahydro-1H-pyrrolizin-7a(5H)-yl)methoxy)-5,8-dihydropyrido[3,4-d]pyrimidin-7(6H)-yl)-5-ethyl-6-fluoronaphthalen-2-ol Synthesized according to Example 32. The title compound was obtained as white solid. $^1$H NMR (400 MHz, METHANOL-d₄) δ=7.53-7.58 (m, 1H), 7.14 (t, J=9.2 Hz, 1H), 7.00-6.93 (m, 2H), 5.37-5.17 (m, 1H), 4.42 (s, 2H), 4.26-4.00 (m, 4H), 3.69 (d, J=10.0 Hz, 2H), 3.50-3.35 (m, 4H), 3.26-3.09 (m, 6H), 2.99 (dt, J=5.6, 9.4 Hz, 1H), 2.70-2.60 (m, 1H), 2.10 (d, J=8.0 Hz, 4H), 2.01-1.79 (m, 6H), 1.10 (t, J=7.2 Hz, 3H); LCMS (ESI, M+1): m/z=592.3.

Example 177

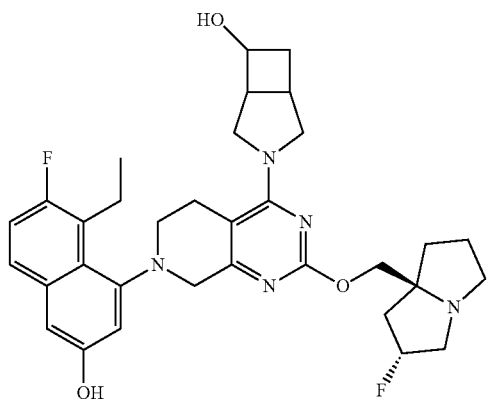 [SMILES: CCc1c(F)ccc2cc(O)cc(N3CCc4c(nc(OC[C@@]56CCCN5C[C@H](F)C6)nc4N4CC5CC(O)C5C4)C3)c12]

3-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.2.0]heptan-6-ol Synthesized according to Example 32. The title compound was obtained as white solid. $^1$H NMR (400 MHz, METHANOL-d4) δ=7.54-7.46 (m, 1H), 7.16-7.01 (m, 1H), 7.00-6.99 (m, 1H), 6.98-6.94 (m, 1H), 5.35-5.16 (m, 1H), 4.69-4.41 (m, 1H), 4.35-4.27 (m, 1H), 4.25-4.07 (m, 2H), 4.07-3.80 (m, 2H), 3.70-3.55 (m, 2H), 3.54-3.46 (m, 1H), 3.44-3.32 (m, 4H), 3.25-3.11 (m, 5H), 3.06-2.92 (m, 2H), 2.72-2.63 (m, 1H), 2.63-2.54 (m, 1H), 2.33-2.13 (m, 2H), 2.12-2.04 (m, 1H), 2.00-1.89 (m, 2H), 1.88-1.80 (m, 1H), 1.77-1.68 (m, 1H), 1.12-1.08 (m, 3H); LCMS (ESI, M+1): m/z=592.4.

Example 178

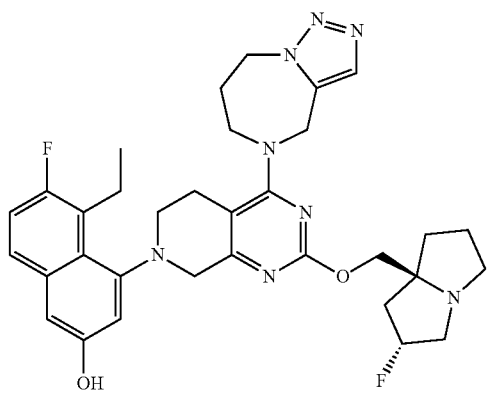 [SMILES: CCc1c(F)ccc2cc(O)cc(N3CCc4c(nc(OC[C@@]56CCCN5C[C@H](F)C6)nc4N4CCCn5nncc5C4)C3)c12]

4-(4-(7,8-dihydro-4H-[1,2,3]triazolo[1,5-a][1,4]diaz-epin-5(6H)-yl)-2-(((2R,7aS)-2-fluorotetrahydro-1H-pyrrolizin-7a(5H)-yl)methoxy)-5,8-dihydropyrido[3,4-d]pyrimidin-7(6H)-yl)-5-ethyl-6-fluoronaphthalen-2-ol Synthesized according to Example 32. The title compound was obtained as light yellow solid. ¹H NMR (400 MHz, METHANOL-d₄) δ=7.71 (s, 1H), 7.51 (dd, J=5.6, 8.8 Hz, 1H), 7.14 (t, J=9.2 Hz, 1H), 6.97 (s, 2H), 5.20 (br s, 1H), 5.09-4.95 (m, 2H), 4.79-4.53 (m, 2H), 4.26-3.94 (m, 5H), 3.67 (br d, J=18.0 Hz, 1H), 3.53 (br s, 1H), 3.39 (br dd, J=2.4, 7.2 Hz, 2H), 3.28-3.14 (m, 5H), 3.00 (dt, J=6.0, 9.2 Hz, 1H), 2.72 (br d, J=11.2 Hz, 1H), 2.35-2.04 (m, 5H), 2.01-1.79 (m, 3H), 1.11 (br t, J=7.2 Hz, 3H); LCMS (M+1): m/z=617.5.

Example 179

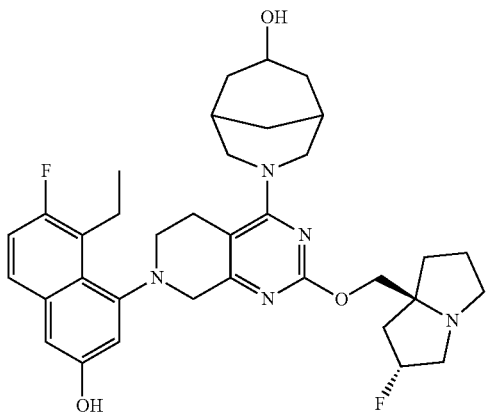 [SMILES: CCc1c(F)ccc2cc(O)cc(N3CCc4c(nc(OC[C@@]56CCCN5C[C@H](F)C6)nc4N4CC5CC(O)CC(C5)C4)C3)c12]

3-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.3.1]nonan-7-ol Synthesized according to Example 32. The title compound was obtained as yellow solid. ¹H NMR (400 MHz, DMSO-d₆) δ=9.70 (s, 1H), 7.59 (dd, J=6.0, 8.8 Hz, 1H), 7.24 (t, J=9.2 Hz, 1H), 6.99 (s, 2H), 5.37-5.11 (m, 1H), 4.67 (d, J=8.0 Hz, 1H), 4.03-3.95 (m, 2H), 3.95-3.91 (m, 1H), 3.85 (dd, J=7.2, 10.0 Hz, 1H), 3.77-3.70 (m, 1H), 3.70-3.66 (m, 1H), 3.64 (s, 1H), 3.16-3.09 (m, 2H), 3.06 (br d, J=5.6 Hz, 3H), 2.98 (br s, 1H), 2.86-2.74 (m, 3H), 2.67 (br d, J=1.6 Hz, 1H), 2.13 (br s, 2H), 2.09-2.02 (m, 2H), 2.02-1.97 (m, 2H), 1.95 (br s, 1H), 1.83 (br s, 1H), 1.78-1.71 (m, 2H), 1.71-1.61 (m, 2H), 1.42 (br d, J=12.0 Hz, 2H), 1.05 (t, J=7.2 Hz, 3H); LCMS (ESI, M+1): m/z=620.5.

Example 180

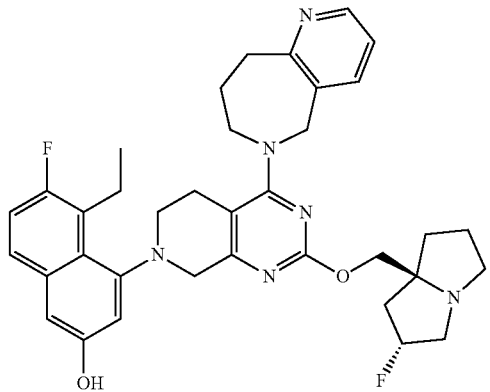 [SMILES: CCc1c(F)ccc2cc(O)cc(N3CCc4c(nc(OC[C@@]56CCCN5C[C@H](F)C6)nc4N4CCCc5ncccc5C4)C3)c12]

4-(4-(8,9-dihydro-5H-pyrido[3,2-c]azepin-6(7H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 32. The title compound was obtained as white solid. ¹H NMR (400 MHz, METHANOL-d₄) δ=8.51 (d, J=5.6 Hz, 1H), 8.36 (br s, 1H), 7.78-7.63 (m, 1H), 7.59-7.47 (m, 1H), 7.15 (t, J=9.6 Hz, 1H), 7.06-6.92 (m, 2H), 5.74-5.42 (m, 1H), 5.11-4.98 (m, 2H), 4.43 (t, J=11.6 Hz, 1H), 4.33-4.21 (m, 1H), 4.20-4.04 (m, 3H), 3.96-3.80 (m, 3H), 3.69 (br dd, J=6.6, 17.6 Hz, 1H), 3.58-3.49 (m, 1H), 3.47-3.35 (m, 5H), 3.28-3.15 (m, 2H), 2.81-2.73 (m, 1H), 2.66-2.48 (m, 2H), 2.39-2.27 (m, 4H), 2.22-2.06 (m, 2H), 1.11 (t, J=7.2 Hz, 3H); LCMS (ESI, M+1): m/z=627.5.

Example 181

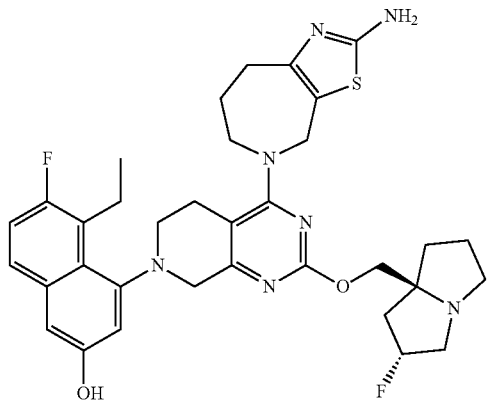 [SMILES: CCc1c(F)ccc2cc(O)cc(N3CCc4c(nc(OC[C@@]56CCCN5C[C@H](F)C6)nc4N4CCCc5nc(N)sc5C4)C3)c12]

4-(4-(2-amino-7,8-dihydro-4H-thiazolo[5,4-c]azepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol Synthesized according to Example 32. The title compound was obtained as white solid. ¹H NMR (400 MHz, METHANOL-d4) δ=7.52-7.48 (m, 1H), 7.14 (t, J=9.6 Hz, 1H), 7.00-6.93 (m, 2H), 5.37-5.15 (m, 1H), 4.77-4.71 (m, 1H), 4.65-4.57 (m, 1H), 4.21-4.04 (m, 3H), 4.04-3.99 (m, 2H), 3.67-3.63 (m, 1H), 3.53-3.46 (m, 1H), 3.44-3.37 (m, 2H), 3.24-3.09 (m, 5H), 3.13-2.96 (m, 1H), 2.89-2.77 (m, 1H), 2.76-2.65 (m, 2H), 2.31-2.17 (m, 1H), 2.17-2.04 (m, 3H), 2.01-1.83 (m, 4H), 1.11 (t, J=7.2 Hz, 3H); LCMS (ESI, M+1): m/z=648.4.

Example 182

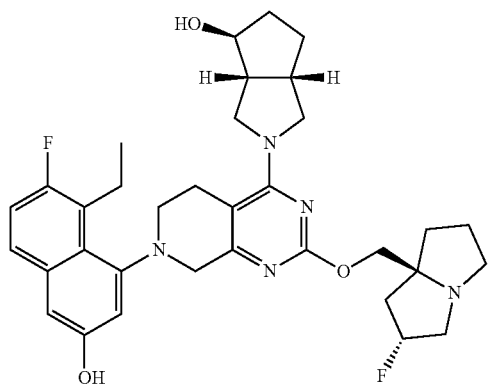 [SMILES: CCc1c(F)ccc2cc(O)cc(N3CCc4c(nc(OC[C@@]56CCCN5C[C@H](F)C6)nc4N4C[C@H]5CC[C@H](O)[C@H]5C4)C3)c12]

(3aR,4S,6aS)-2-(7-(8-ethyl-7-fluoro-3-hydroxynaph-thalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)octahydrocyclopenta[c]pyrrol-4-ol Synthesized according to Example 32. The title compound was obtained as light-yellow solid. $^1$H NMR (400 MHz, METHANOL-d) δ=7.53-7.47 (m, 1H), 7.17-7.10 (m, 1H), 7.00-6.97 (m, 1H), 6.95 (d, J=2.4 Hz, 1H), 5.19 (br s, 1H), 4.07 (s, 2H), 4.05-3.94 (m, 3H), 3.78-3.70 (m, 2H), 3.68-3.62 (m, 1H), 3.61-3.54 (m, 1H), 3.52-3.45 (m, 1H), 3.42-3.32 (m, 3H), 3.27-3.13 (m, 5H), 3.02-2.86 (m, 3H), 2.68-2.53 (m, 1H), 2.32-2.11 (m, 3H), 2.11-2.01 (m, 2H), 1.86 (br d, J=7.8 Hz, 1H), 1.74-1.63 (m, 1H), 1.48 (br d, J=6.0 Hz, 1H), 1.30 (br d, J=4.3 Hz, 1H), 1.12-1.07 (m, 3H); LCMS[ESI, M+1]: m/z=606.3.

Example 183

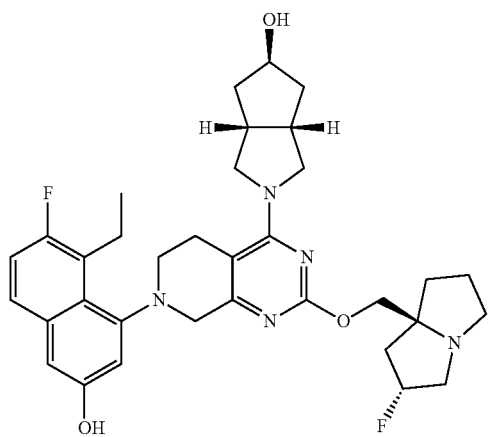 [SMILES: CCc1c(F)ccc2cc(O)cc(N3CCc4c(nc(OC[C@@]56CCCN5C[C@H](F)C6)nc4N4C[C@H]5C[C@H](O)C[C@H]5C4)C3)c12]

(3aR,5R,6aS)-2-(7-(8-ethyl-7-fluoro-3-hydroxynaph-thalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)octahydrocyclopenta[c]pyrrol-5-ol Synthesized according to Example 32. The title compound was obtained as yellow solid. $^1$H NMR (400 MHz, METHANOL-d$_4$) δ=7.53-7.48 (m, 1H), 7.14 (t, J=9.6 Hz, 1H), 7.01-6.94 (m, 2H), 5.36-5.17 (m, 1H), 4.44 (s, 1H), 4.14 (d, J=12.0 Hz, 1H), 4.09-3.92 (m, 3H), 3.82-3.69 (m, 2H), 3.67-3.54 (m, 2H), 3.50-3.34 (m, 3H), 3.29-3.11 (m, 5H), 3.03-2.83 (m, 4H), 2.15 (s, 2H), 2.13-2.04 (m, 1H), 2.01-1.79 (m, 6H), 1.75-1.64 (m, 1H), 1.14-1.05 (m, 3H); LCMS (ESI, M+1): m/z=606.3.

Example 184

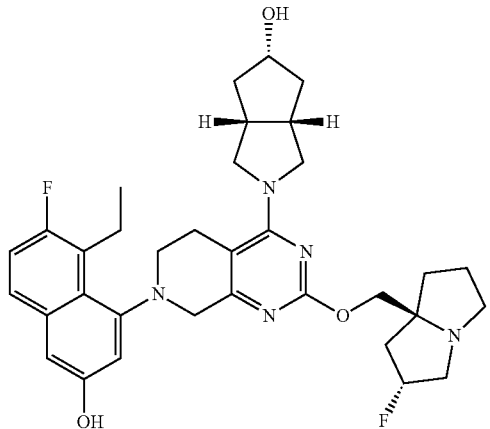 [SMILES: CCc1c(F)ccc2cc(O)cc(N3CCc4c(nc(OC[C@@]56CCCN5C[C@H](F)C6)nc4N4C[C@H]5C[C@@H](O)C[C@H]5C4)C3)c12]

(3aR,5S,6aS)-2-(7-(8-ethyl-7-fluoro-3-hydroxynaph-thalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)octahydrocyclopenta[c]pyrrol-5-ol Synthesized according to Example 28. The title compound was obtained as yellow solid. $^1$H NMR (400 MHz, METHANOL-d4) δ=7.50 (dd, J=6.0, 9.2 Hz, 1H), 7.13 (t, J=9.2 Hz, 1H), 7.02-6.93 (m, 2H), 5.36-5.17 (m, 1H), 4.30 (m, 1H), 4.21-3.91 (m, 5H), 3.84-3.75 (m, 1H), 3.71 (dd, J=2.4, 12.0 Hz, 1H), 3.62 (br d, J=17.6 Hz, 1H), 3.53-3.34 (m, 3H), 3.28-3.10 (m, 5H), 3.03-2.87 (m, 2H), 2.78-2.66 (m, 2H), 2.34-2.04 (m, 5H), 2.02-1.79 (m, 3H), 1.63-1.45 (m, 2H), 1.10 (m, 3H); LCMS (ESI, M+1): m/z=606.5.

Example 185

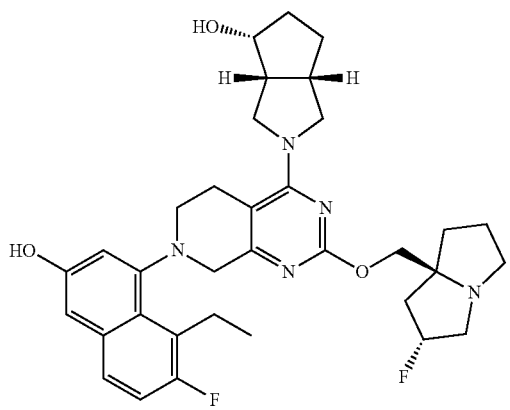 [SMILES: CCc1c(F)ccc2cc(O)cc(N3CCc4c(nc(OC[C@@]56CCCN5C[C@H](F)C6)nc4N4C[C@H]5CC[C@@H](O)[C@H]5C4)C3)c12]

(3aR,4R,6aS)-2-(7-(8-ethyl-7-fluoro-3-hydroxynaph-thalen-1-yl)-2-(((2R,7aS)-2-fluorotetrahydro-1H-pyrrolizin-7a(5H)-yl)methoxy)-5,6,7,8-tetrahydro-pyrido[3,4-d]pyrimidin-4-yl)octahydrocyclopenta[c]pyrrol-4-ol Synthesized according to Example 32. The title compound was obtained as yellow solid. $^1$H NMR (400 MHz, METHANOL-$d_4$) δ=7.53-7.48 (m, 1H), 7.14 (t, J=9.6 Hz, 1H), 7.01-6.94 (m, 2H), 5.36-5.17 (m, 1H), 4.38-4.00 (m, 5H), 3.98-3.72 (m, 2H), 3.65-3.54 (m, 2H), 3.55-3.35 (m, 3H), 3.24-3.14 (m, 5H), 3.12-2.95 (m, 2H), 2.90-2.65 (m, 2H), 1.99-1.94 (m, 3H), 1.93-1.76 (m, 7H), 1.21-1.11 (m, 3H); LCMS (ESI, M+1): m/z=606.3.

Example 186

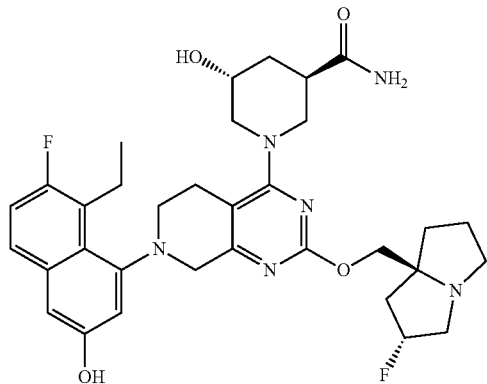 [SMILES: CCc1c(F)ccc2cc(O)cc(N3CCc4c(nc(OC[C@@]56CCCN5C[C@H](F)C6)nc4N4C[C@H](O)C[C@@H](C(N)=O)C4)C3)c12]

(3R,5R)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-5-hydroxypiperidine-3-carboxamide

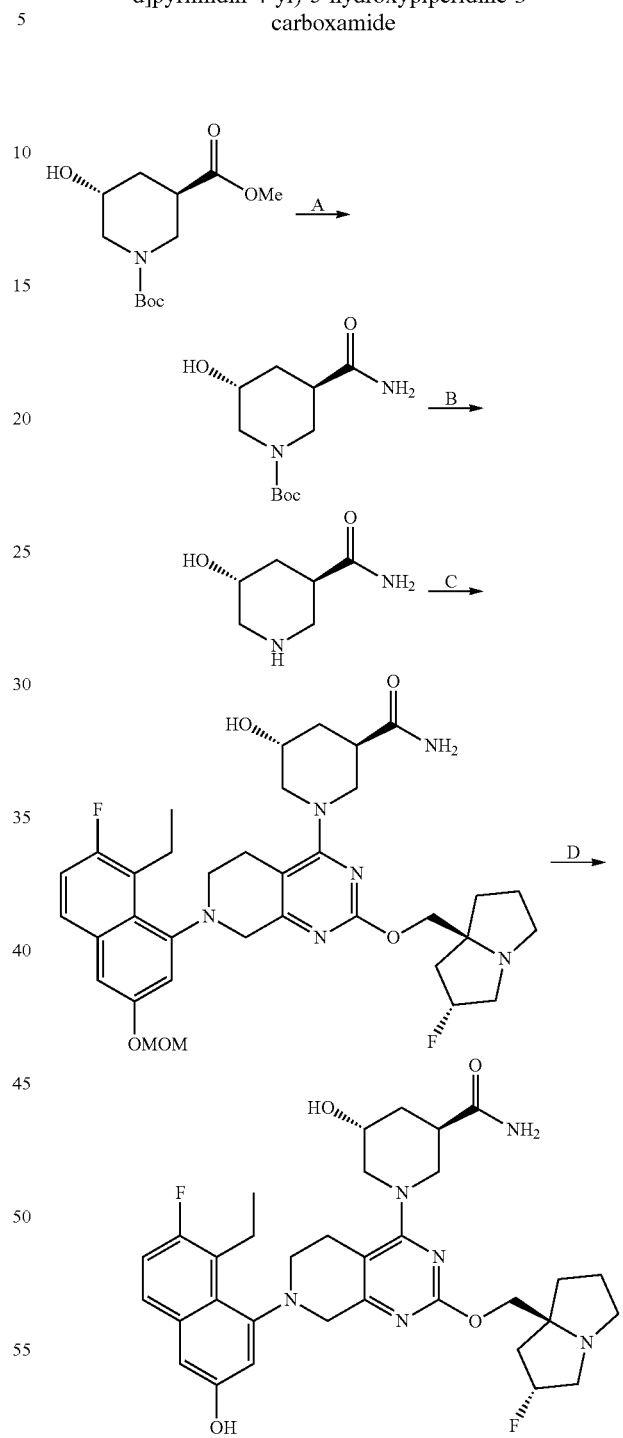

Step A. trans-tert-butyl 3-carbamoyl-5-hydroxypiperidine-1-carboxylate: A solution of O1-tert-butyl O3-methyl trans-5-hydroxypiperidine-1,3-dicarboxylate (200 mg, 1.0 equiv) in NH$_3$·MeOH (5 mL) was stirred in a sealed tube at 60° C. for 96 hours. The residue was concentrated to afford the title compound (180 mg, crude) as white solid. $^1$H NMR (400 MHz, DMSO-$d_6$) δ=7.47-7.28 (m, 1H), 6.94-6.71 (m, 1H), 4.66 (br s, 1H), 4.05-3.47 (m, 3H), 3.13-2.54 (m, 3H), 1.82-1.47 (m, 2H), 1.43-1.34 (m, 9H); LCMS (ESI, M+1): m/z=245.3.

Step B. trans-5-hydroxypiperidine-3-carboxamide: To a solution of tert-butyl trans-3-carbamoyl-5-hydroxy-piperidine-1-carboxylate (160 mg, 1.0 equiv) in MeCN (1 mL) was added HCl·dioxane (4 M, 2 mL, 12.2 equiv). The mixture was stirred at 0° C. for 0.5 hour. The residue was concentrated to afford the title compound (190 mg, HCl, crude) as colorless liquid.

Step C and D: Synthesized according to Example 32. The title compound was obtained as yellow solid. $^1$H NMR (400 MHz, METHANOL-d$_4$) δ=7.51 (dd, J=6.0, 9.2 Hz, 1H), 7.14 (t, J=9.6 Hz, 1H), 7.06-6.92 (m, 2H), 5.50-5.34 (m, 1H), 4.47-4.23 (m, 3H), 4.22-3.86 (m, 4H), 3.79-3.60 (m, 2H), 3.59-3.47 (m, 4H), 3.43-3.35 (m, 2H), 3.25-3.12 (m, 3H), 3.00-2.84 (m, 1H), 2.66 (br d, J=14.4 Hz, 1H), 2.53-2.33 (m, 2H), 2.23 (br d, J=9.6 Hz, 1H), 2.20-1.95 (m, 5H), 1.17-1.06 (m, 3H); LCMS (ESI, M+1): m/z=623.5.

Example 187

(3S,5R)-1-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-5-hydroxypiperidine-3-carboxamide

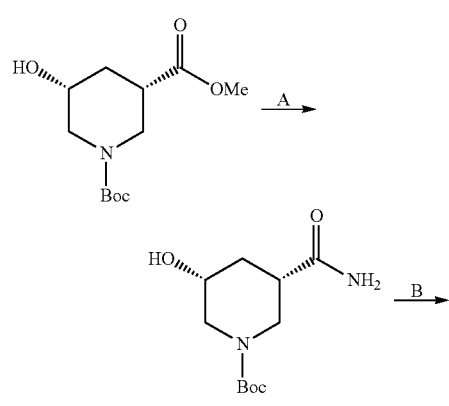

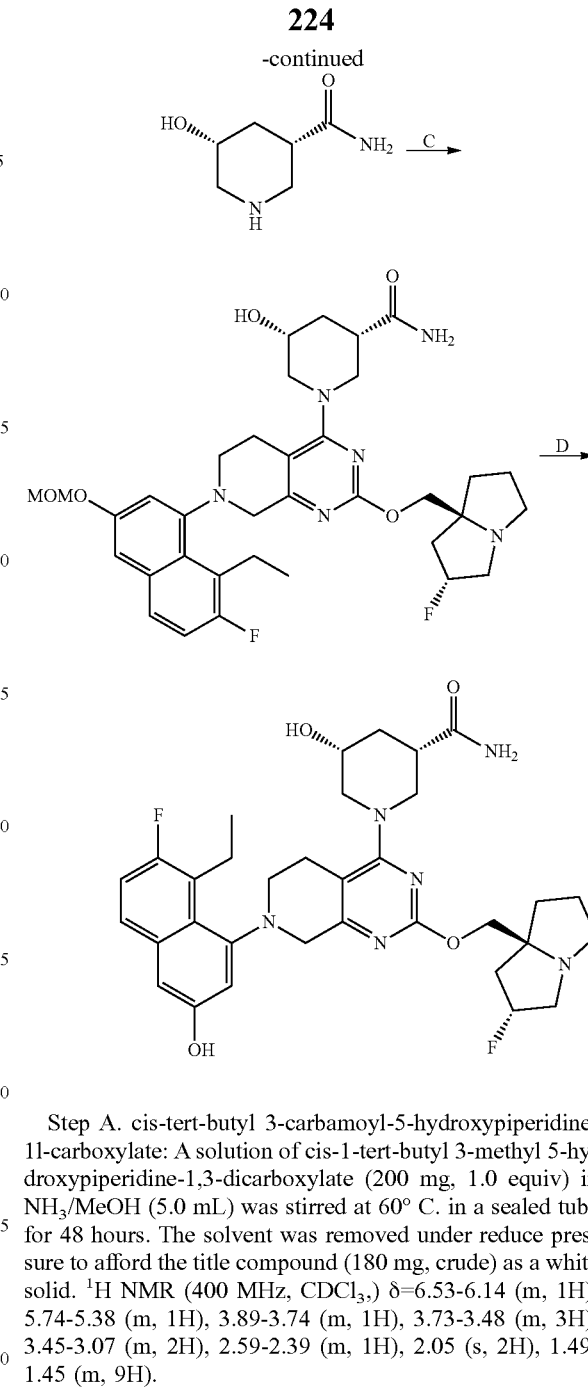

Step A. cis-tert-butyl 3-carbamoyl-5-hydroxypiperidine-1l-carboxylate: A solution of cis-1-tert-butyl 3-methyl 5-hydroxypiperidine-1,3-dicarboxylate (200 mg, 1.0 equiv) in NH$_3$/MeOH (5.0 mL) was stirred at 60° C. in a sealed tube for 48 hours. The solvent was removed under reduce pressure to afford the title compound (180 mg, crude) as a white solid. $^1$H NMR (400 MHz, CDCl$_3$,) δ=6.53-6.14 (m, 1H), 5.74-5.38 (m, 1H), 3.89-3.74 (m, 1H), 3.73-3.48 (m, 3H), 3.45-3.07 (m, 2H), 2.59-2.39 (m, 1H), 2.05 (s, 2H), 1.49-1.45 (m, 9H).

Step B. cis-5-hydroxypiperidine-3-carboxamide: To a solution of tert-butyl cis-3-carbamoyl-5-hydroxy-piperidine-1-carboxylate (180 mg, 1 equiv) in MeOH (1 mL) was added HCl/MeOH (4 M, 1.71 mL, 6.98 equiv) at 25° C. The mixture was stirred at 25° C. for 2 hours. The reaction mixture was concentrated under reduce pressure to afford the title compound (140 mg, crude, HCl) as a white solid.

Step C-D: Synthesized according to Example 32. The title compound was obtained as white solid. $^1$H NMR (400 MHz, METHANOL-d4) δ=7.53-7.47 (m, 1H), 7.17-7.10 (m, 1H), 7.00-6.93 (m, 2H), 5.35-5.16 (m, 1H), 4.25-4.03 (m, 5H), 3.97-3.56 (m, 2H), 3.53-3.33 (m, 3H), 3.24-3.12 (m, 5H), 3.10-2.90 (m, 2H), 2.90-2.52 (m, 3H), 2.32-2.04 (m, 4H), 1.69 (q, J=11.8 Hz, 4H), 1.15-1.07 (m, 3H); LCMS (ESI, M+1): m/z=623.3.

Example 188

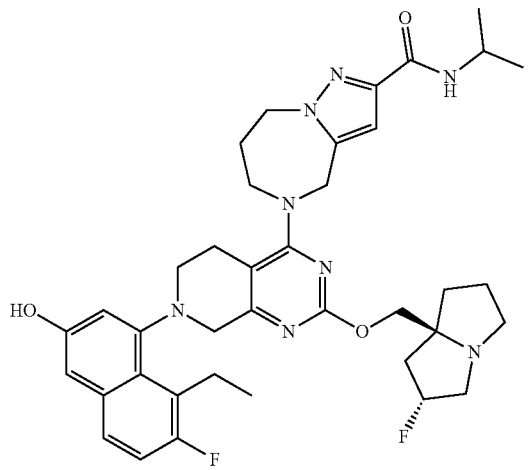 [SMILES: CCc1c(F)ccc2cc(O)cc(N3CCc4c(nc(OC[C@@]56CCCN5C[C@H](F)C6)nc4N4CCCn5nc(C(=O)NC(C)C)cc5C4)C3)c12]

5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-N-isopropyl-5,6,7,8-tetrahydro-4H-pyrazolo[1,5-a][1,4]diazepine-2-carboxamide

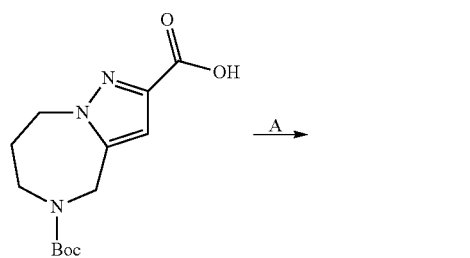

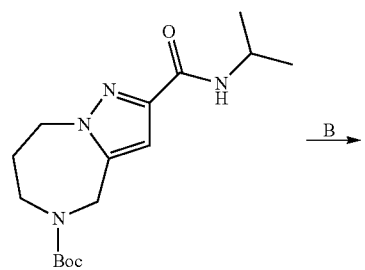

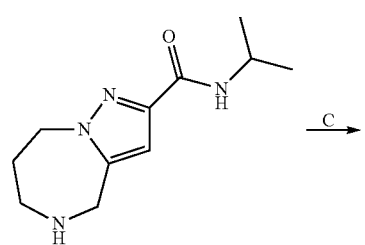

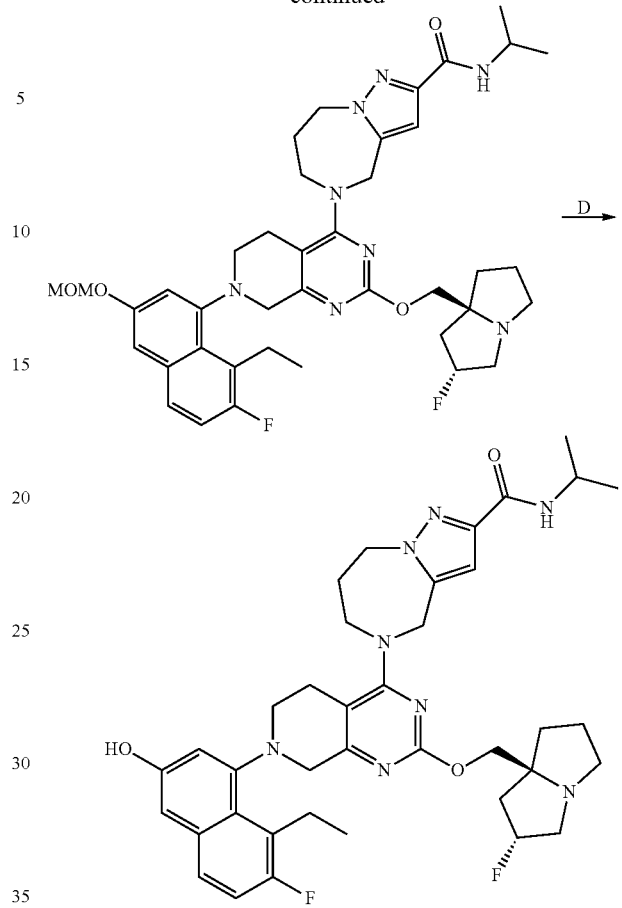

Step A. tert-butyl 2-(isopropylcarbamoyl)-4,6,7,8-tetrahydropyrazolo[1,5-a][1,4]diazepine-5-carboxylate: To a solution of 5-tert-butoxycarbonyl-4,6,7,8-tetrahydropyrazolo[1,5-a][1,4]diazepine-2-carboxylic acid (150 mg, 1.0 equiv) and propan-2-amine (63.0 mg, 2.0 equiv) in DMF (3 mL) were added HATU (304 mg, 1.5 equiv) and N-ethyl-N-isopropylpropan-2-amine (207 mg, 3.0 equiv) at 0° C. The mixture was stirred at 25° C. for 0.5 hour. The reaction mixture was diluted with water (50 mL) and extracted with ethyl acetate (30 mL×3). The combined organic layers were washed with brine (50 mL×3), dried over sodium sulfate, and concentrated under reduced pressure. The residue was purified by column chromatography (SiO$_2$, Petroleum ether/Ethyl acetate=3/1 to 1/2) to afford the title compound (135 mg, 78% yield) as a white solid. LCMS (ESI, M+1): m/z=323.2.

Step B. N-isopropyl-5,6,7,8-tetrahydro-4H-pyrazolo[1,5-a][1,4]diazepine-2-carboxamide: To a solution of tert-butyl 2-(isopropylcarbamoyl)-4,6,7,8-tetrahydropyrazolo[1,5-a][1,4]diazepine-5-carboxylate (160 mg, 1.0 equiv) in DCM (2 mL) was added TFA (0.8 mL). The reaction was stirred at 25° C. for 0.5 hour. The mixture was concentrated and then dissolved in MeOH (5 mL). NaHCO$_3$ was added to neutralize the mixture and then it was stirred at 25° C. for 0.5 hour. MeOH was removed through evaporation. The residue was taken up with ethyl acetate (10 mL), filtered, and concentrated under reduced pressure to afford the title compound (110 mg, 97.72% yield) as a white solid. LCMS (ESI, M+1): m/z=223.1

Step C-D: Synthesized according to Example 32. The title compound was obtained as pink solid. $^1$H NMR (400 MHz, methanol-d4) δ=7.56-7.43 (m, 1H), 7.19-7.08 (m, 1H), 7.01-6.93 (m, 2H), 6.69 (s, 1H), 5.34-5.16 (m, 1H), 5.01-4.95 (m, 1H), 4.79 (br s, 1H), 4.66-4.45 (m, 3H), 4.27-4.11 (m, 2H), 4.10-3.93 (m, 4H), 3.65 (br d, J=18.0 Hz, 1H), 3.54 (br d, J=9.2 Hz, 1H), 3.47-3.34 (m, 2H), 3.19 (br t, J=8.0 Hz, 3H), 3.15-3.11 (m, 1H), 3.03-2.93 (m, 1H), 2.72 (br d, J=14.0 Hz, 1H), 2.40-2.27 (m, 1H), 2.27-2.01 (m, 4H), 2.00-1.89 (m, 2H), 1.89-1.76 (m, 1H), 1.23 (d, J=6.4 Hz, 6H), 1.11 (br t, J=7.2 Hz, 3H); $^{19}$F NMR (377 MHz, METHANOL-d4) δ=−122.86 (br s, 1F), −170.30−−181.06 (m, 1F); LCMS (ESI, M+1): m/z=701

Example 189

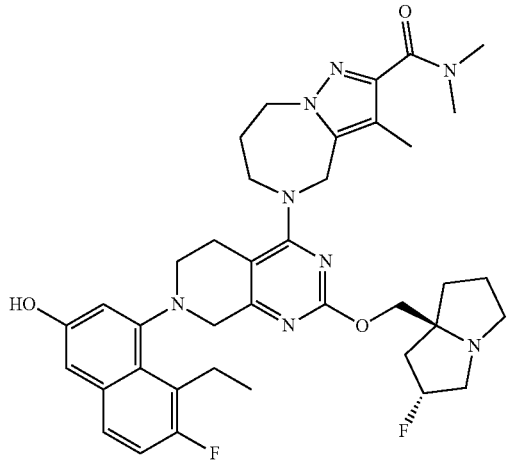

5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-N,N,3-trimethyl-5,6,7,8-tetrahydro-4H-pyrazolo[1,5-a][1,4]diazepine-2-carboxamide

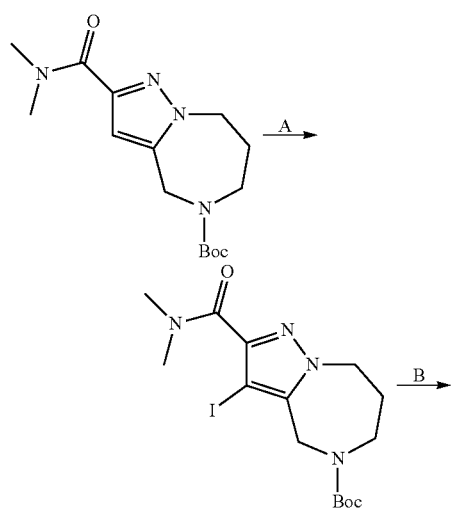

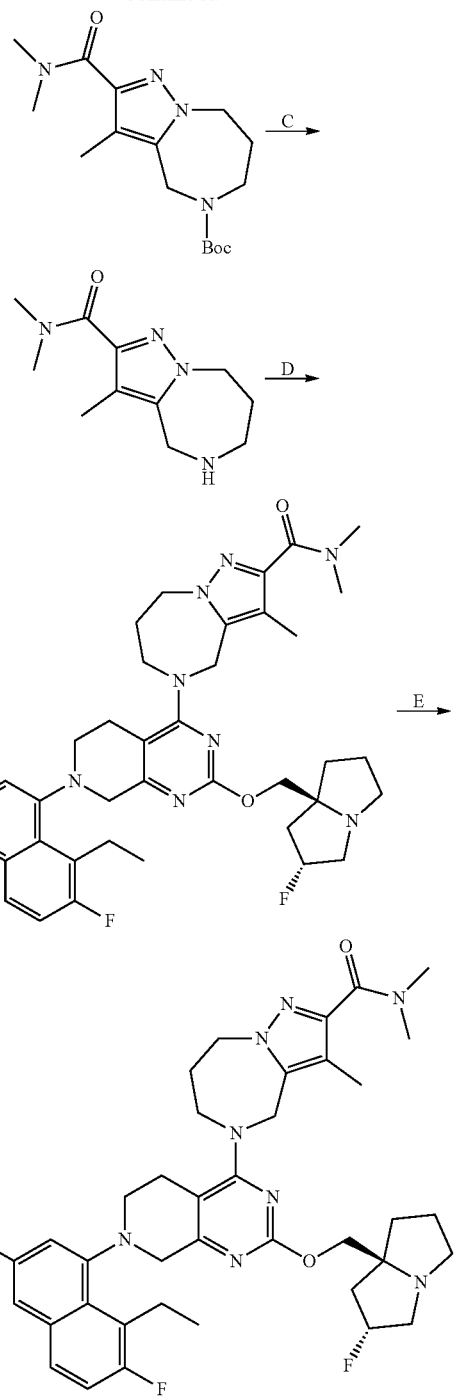

Step A. tert-butyl 2-(dimethylcarbamoyl)-3-iodo-7,8-dihydro-4H-pyrazolo[1,5-a][1,4]diazepine-5(6H)-carboxylate: To a solution of tert-butyl 2-(dimethylcarbamoyl)-4,6,7,8-tetrahydropyrazolo[1,5-a][1,4]diazepine-5-carboxylate (500 mg, 1.0 equiv) in AcOH (5 mL) was added NIS (720 mg, 2.0 equiv). The reaction was stirred at 80° C. for 2 hours. The reaction mixture was diluted with EtOAc (40 mL). The mixture was washed with saturated salt solution (3×20 mL), dried over anhydrous sodium sulfate, filtered, and concentrated under reduced pressure to give a residue. The residue was purified by column chromatography (SiO$_2$, Petroleum ether/Ethyl acetate=1/1 to 0/1) to afford the title compound (560 mg, 79% yield) as a brown solid. LCMS (ESI, M+1): m/z=435.1.

Step B. tert-butyl 2-(dimethylcarbamoyl)-3-methyl-7,8-dihydro-4H-pyrazolo[1,5-a][1,4]diazepine-5(6H)-carboxylate: A mixture of tert-butyl 2-(dimethylcarbamoyl)-3-iodo-4,6,7,8-tetrahydropyrazolo[1,5-a][1,4]diazepine-5-carboxylate (200 mg, 1.0 equiv), methylboronic acid (55.1 mg, 2.0 equiv), Ad$_2$nBuP Pd G$_3$ (cataCXium® A Pd G$_3$) (33.5 mg, 0.1 equiv), and K$_3$PO$_4$ (195 mg, 2.0 equiv) in dioxane (3 mL) and H$_2$O (1 mL) was degassed and purged with N$_2$ for 3 times. The reaction was stirred at 80° C. for 2 hours under N$_2$ atmosphere. The reaction mixture was filtered and concentrated under reduced pressure. The residue was purified by prep-HPLC (column: Waters Xbridge C18 150×50 mm×10 μm; mobile phase: [water (NH$_4$HCO$_3$)-ACN]; B %: 22%-52%, 10 minutes) to afford the title compound (50.0 mg, 34% yield) as a white solid. LCMS (ESI, M+1): m/z=323.1.

Step C. N,N,3-trimethyl-5,6,7,8-tetrahydro-4H-pyrazolo[1,5-a][1,4]diazepine-2-carboxamide: To a solution of tert-butyl 2-(dimethylcarbamoyl)-3-methyl-4,6,7,8-tetrahydropyrazolo[1,5-a][1,4]diazepine-5-carboxylate (50.0 mg, 1.0 equiv) in dioxane (1 mL) was added HCl/dioxane (4 M, 1 mL). The mixture was stirred at 25° C. for 1 hour. The reaction mixture was filtered and concentrated under reduced pressure to afford the title compound (28.0 mg, 81% yield) as yellow oil, which was used in the next step without further purification; LCMS (ESI, M+1): m/z=223.2.

Step D-E: Synthesized according to Example 32. The title compound was obtained as a white solid. $^1$H NMR (400 MHz, METHANOL-d$_4$) δ=7.51 (dd, J=6.0, 8.8 Hz, 1H), 7.19-7.09 (m, 1H), 6.96 (s, 2H), 5.35 (br s, 1H), 5.02-5.00 (m, 1H), 4.71 (br dd, J=3.2, 16.4 Hz, 1H), 4.58 (br s, 1H), 4.53-4.37 (m, 2H), 4.14-4.01 (m, 4H), 4.00-3.90 (m, 1H), 3.67 (br d, J=18.0 Hz, 1H), 3.50 (br d, J=10.4 Hz, 1H), 3.41 (br d, J=7.2 Hz, 2H), 3.29-3.22 (m, 3H), 3.21-3.17 (m, 2H), 3.13 (s, 3H), 3.08 (s, 3H), 3.06-2.97 (m, 1H), 2.70 (br d, J=14.0 Hz, 1H), 2.38-2.25 (m, 2H), 2.23-2.05 (m, 5H), 2.02-1.92 (m, 2H), 1.91-1.78 (m, 1H), 1.10 (br t, J=7.2 Hz, 3H); $^{19}$F NMR (377 MHz, METHANOL-d4) δ=−123.04 (br s, 1F), −171.19−−176.12 (m, 1F); LCMS (ESI, M+1): m/z=701.5.

Example 190

5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3-fluoro-N,N-dimethyl-5,6,7,8-tetrahydro-4H-pyrazolo[1,5-a][1,4]diazepine-2-carboxamide

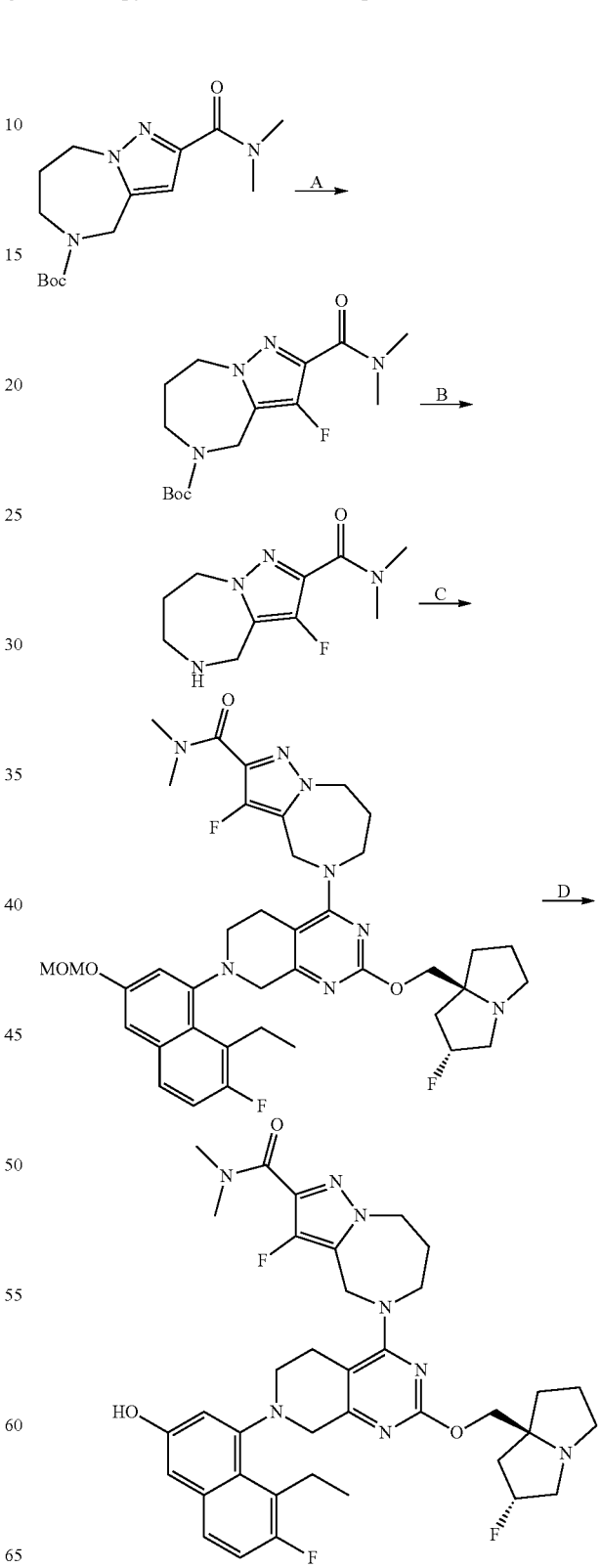

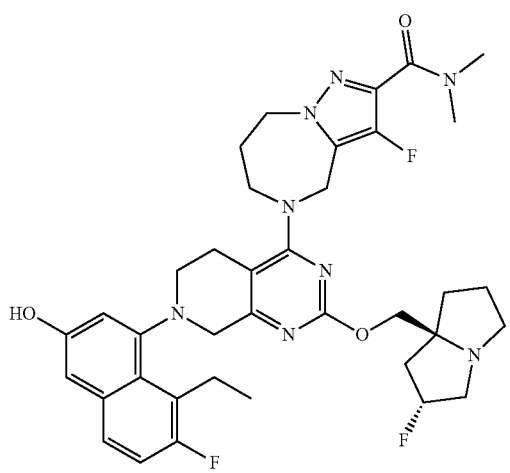 [SMILES: CCc1c(F)ccc2cc(O)cc(N3CCc4c(nc(OC[C@@]56CCCN5C[C@H](F)C6)nc4N4CCCn5nc(C(=O)N(C)C)c(F)c5C4)C3)c12]

Step A. tert-butyl 2-(dimethylcarbamoyl)-3-fluoro-7,8-dihydro-4H-pyrazolo[1,5-a][1,4]diazepine-5(6H)-carboxylate: To a solution of tert-butyl 2-(dimethylcarbamoyl)-4,6,7,8-tetrahydropyrazolo[1,5-a][1,4]diazepine-5-carboxylate (760 mg, 1 equiv) in ACN (10 mL) was added 1-(chloromethyl)-4-fluoro-1,4-diazoniabicyclo[2.2.2]octane; ditetrafluoroborate (4.37 g, 5 equiv). The reaction was stirred at 25° C. for 16 hours. After completion, the reaction mixture was concentrated and purified with prep-HPLC (column: Phenomenex luna C18 200×40 mm×10 μm; mobile phase: [water (FA)-MeCN]; B %: 25%-55%, 10 min) to afford the title compound (107 mg, 13.17% yield) as a yellow oil; LCMS (ESI, M+1): m/z=326.9.

Step B. 3-fluoro-N,N-dimethyl-5,6,7,8-tetrahydro-4H-pyrazolo[1,5-a][1,4]diazepine-2-carboxamide: To a solution of tert-butyl 2-(dimethylcarbamoyl)-3-fluoro-4,6,7,8-tetrahydropyrazolo[1,5-a][1,4]diazepine-5-carboxylate (56 mg, 1 equiv) in DCM (0.25 mL) was added TFA (0.25 mL). The reaction was stirred at 25° C. for 1 hour. The reaction was concentrated under the reduced pressure and filtered to afford the title compound (91 mg, crude, TFA) as a yellow oil; LCMS (ESI, M+1): m/z=226.9.

Step C-D: Synthesized according to Example 32. The title compound was obtained as white solid. $^1$H NMR (400 MHz, DMSO-$d_6$) δ=9.68 (s, 1H), 8.16 (s, 1H), 7.67-7.51 (m, 1H), 7.24 (s, 1H), 6.98 (s, 2H), 5.17 (s, 1H), 4.94 (d, J=16.0 Hz, 1H), 4.73 (d, J=16.0 Hz, 1H), 4.44 (t, J=6.8 Hz, 2H), 4.15-4.00 (m, 1H), 3.98-3.76 (m, 4H), 3.62 (d, J=16.8 Hz, 1H), 3.40 (s, 2H), 3.28-3.21 (m, 2H), 3.10 (s, 3H), 3.04 (s, 2H), 3.01-2.91 (m, 4H), 2.80 (s, 1H), 2.62 (s, 1H), 2.24-1.57 (m, 9H), 1.04 (t, J=7.2 Hz, 3H); LCMS (ESI, M+1): m/z=705.5.

Example 191

(5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-5,6,7,8-tetrahydro-4H-pyrazolo[1,5-a][1,4]diazepin-2-yl)(pyrrolidin-1-yl)methanone

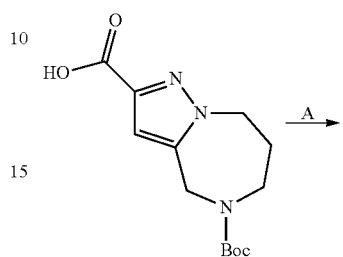

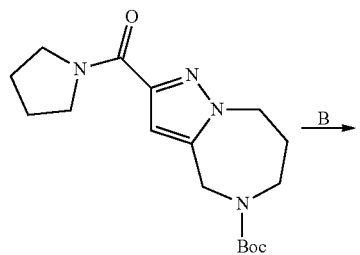

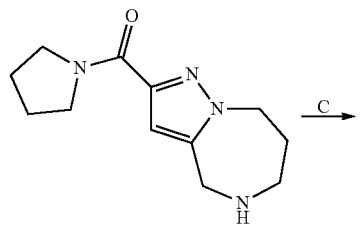

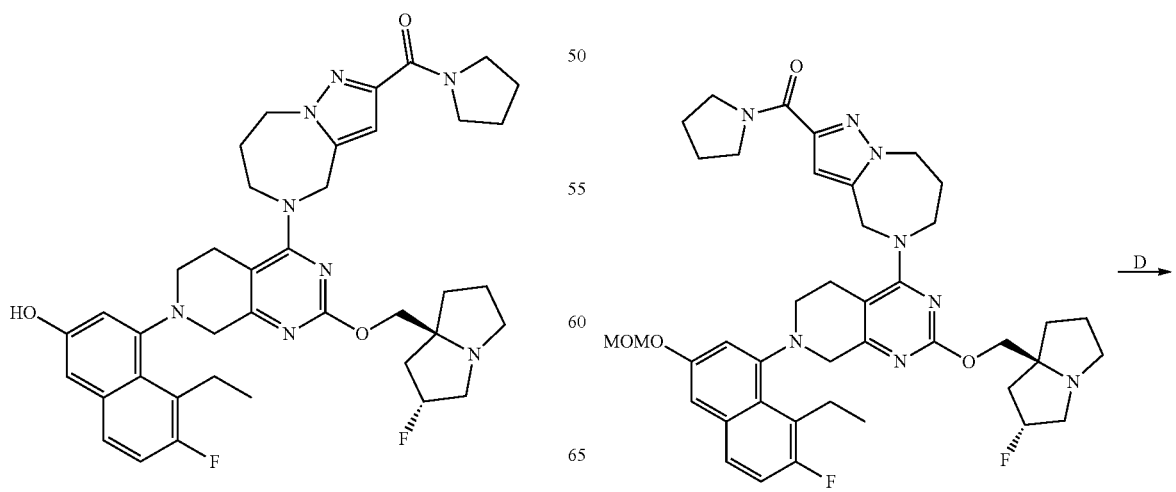

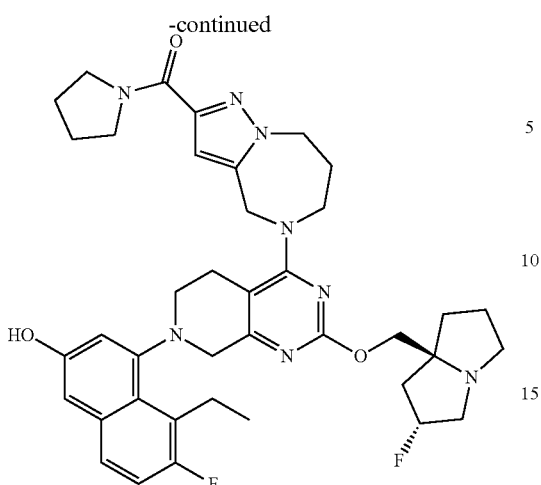

Step A. tert-butyl 2-(pyrrolidine-1-carbonyl)-4,6,7,8-tetrahydropyrazolo[1,5-a][1,4]diazepine-5-carboxylate: To a solution of 5-tert-butoxycarbonyl-4,6,7,8-tetrahydropyrazolo[1,5-a][1,4]diazepine-2-carboxylic acid (200 mg, 1.0 equiv), pyrrolidine (101 mg, 2.0 equiv) and N-ethyl-N-isopropylpropan-2-amine (276 mg, 3.0 equiv) in DMF (1 mL) was added HATU (405 mg, 1.5 equiv) at 0° C. The mixture was stirred at 25° C. for 1 hour. The reaction mixture was quenched with water (5 mL) at 25° C., diluted with water (20 mL) and extracted with ethyl acetate (30 mL×2). The combined organic layers were washed with brine (5 mL), dried over anhydrous sodium sulfate, filtered, and concentrated under reduced pressure. The residue was purified by column chromatography (SiO$_2$, Petroleum ether/Ethyl acetate=10/1 to 0/1) to afford the title compound (240 mg, 99% yield) as a yellow solid. LCMS (ESI, M+1): m/z=335.2.

Step B. pyrrolidin-1-yl(5,6,7,8-tetrahydro-4H-pyrazolo[1,5-a][1,4]diazepin-2-yl)methanone: To a solution of tert-butyl 2-(pyrrolidine-1-carbonyl)-4,6,7,8-tetrahydropyrazolo[1,5-a][1,4]diazepine-5-carboxylate (240 mg, 1.0 equiv) in DCM (1 mL) was added TFA (3 mL). The mixture was stirred at 25° C. for 0.5 hour. The reaction mixture was concentrated under reduced pressure to remove solvent. The residue was dissolved with MeOH (10 mL), and pH was adjusted to 9 with NH$_3$·H$_2$O (4 mL). The mixture was stirred for 0.3 hours. The reaction mixture was diluted with water (10 mL) and extracted with trichloromethane:isopropanol=4:1 (10 mL×3). The organic layer was separated, washed with brine (10 mL×2), dried over anhydrous sodium sulfate, filtered and concentrated under reduced pressure to afford the title compound (160 mg, 95% yield) as a yellow oil; $^1$H NMR (400 MHz, DMSO-d$_6$) δ=6.44 (s, 1H), 4.37-4.31 (m, 2H), 3.81 (s, 2H), 3.80-3.77 (m, 2H), 3.43 (t, J=6.4 Hz, 2H), 3.06-2.99 (m, 2H), 1.89-1.67 (m, 6H).

Step C-D: Synthesized according to Example 32. The title compound was obtained as yellow solid. $^1$H NMR (400 MHz, METHANOL-d4) δ=7.51 (dd, J=5.6, 9.0 Hz, 1H), 7.14 (t, J=9.2 Hz, 1H), 6.97 (s, 2H), 6.68 (s, 1H), 5.37-5.15 (m, 1H), 5.03-4.97 (m, 1H), 4.64-4.51 (m, 3H), 4.25-4.15 (m, 1H), 4.13-3.96 (m, 4H), 3.90 (t, J=6.4 Hz, 2H), 3.66 (d, J=17.6 Hz, 1H), 3.62-3.50 (m, 3H), 3.39 (br dd, J=2.0, 5.9 Hz, 1H), 3.26-3.13 (m, 5H), 3.03-2.95 (m, 1H), 2.72 (br d, J=13.6 Hz, 1H), 2.37-2.12 (m, 3H), 2.11-2.03 (m, 2H), 2.00-1.90 (m, 6H), 1.89-1.81 (m, 1H), 1.38-1.27 (m, 1H), 1.15-1.07 (m, 3H); $^{19}$F NMR (377 MHz, METHANOL-d4) δ=−122.92 (br s, 1F), −173.58 (br d, J=22.9 Hz, 1F); LCMS [ESI, M+1]: m/z=713.4.

Example 192

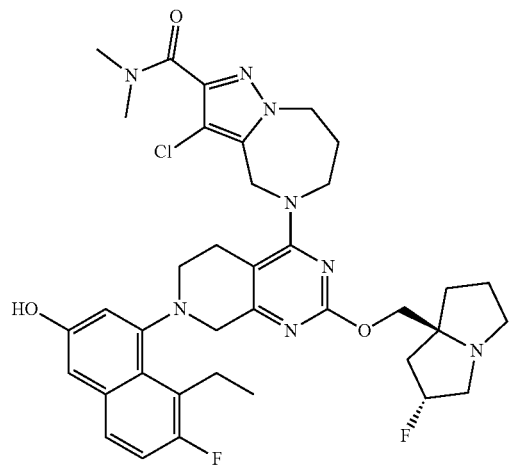 [SMILES: CCc1c(F)ccc2cc(O)cc(N3CCc4c(nc(OC[C@@]56CCCN5C[C@H](F)C6)nc4N4CCCn5nc(C(=O)N(C)C)c(Cl)c5C4)C3)c12]

3-chloro-5-(7-(8-ethyl-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide

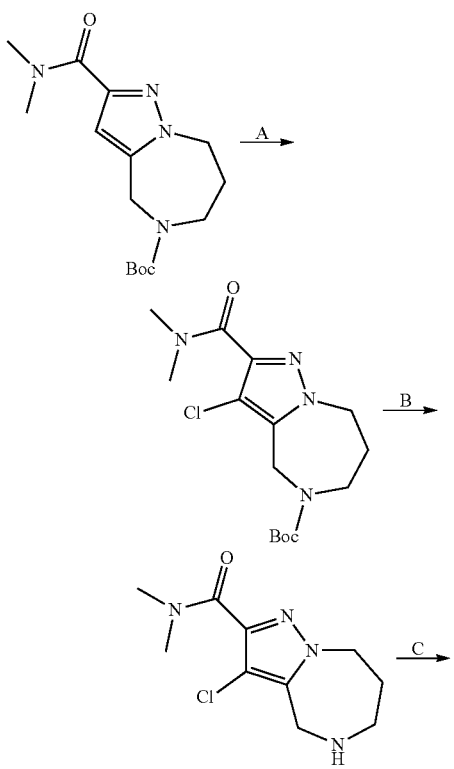

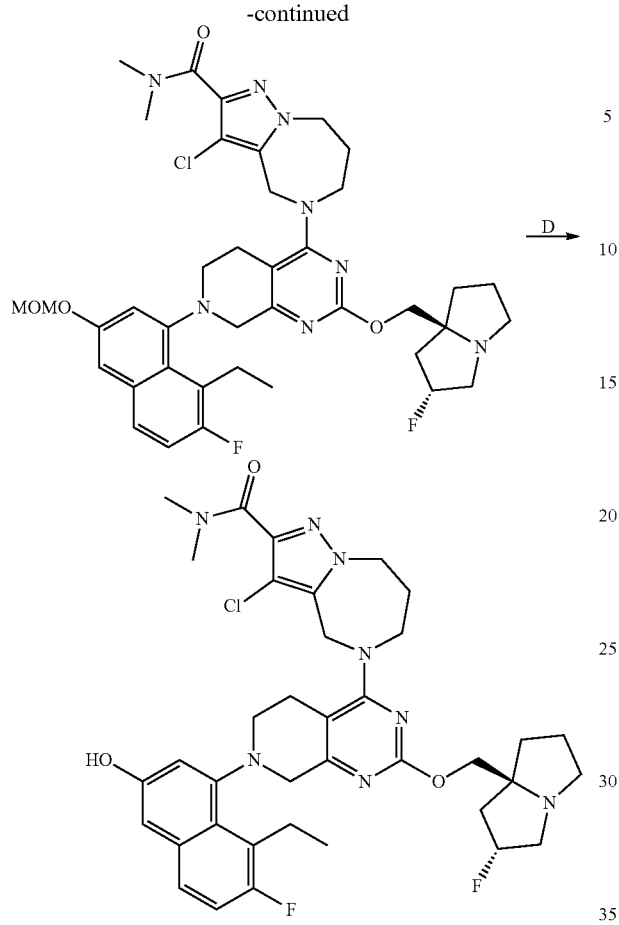

3.08 (m, 1H), 2.99 (d, J=16.0 Hz, 6H), 2.79-2.64 (m, 2H), 2.44-2.38 (m, 1H), 2.35-1.96 (m, 8H), 1.10-0.98 (m, 3H); LCMS (ESI, M+1): m/z=721.3.

Example 193

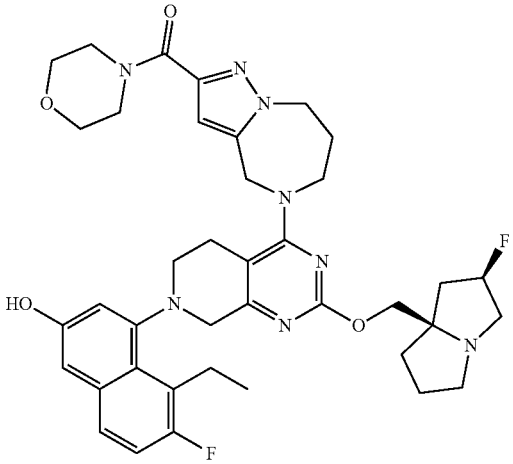 [SMILES: CCc1c(F)ccc2cc(O)cc(N3CCc4c(nc(OC[C@]56CCCN5C[C@H](F)C6)nc4N4CCCn5nc(C(=O)N6CCOCC6)cc5C4)C3)c12]

(5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-5,6,7,8-tetrahydro-4H-pyrazolo[1,5-a][1,4]diazepin-2-yl)(morpholino)methanone

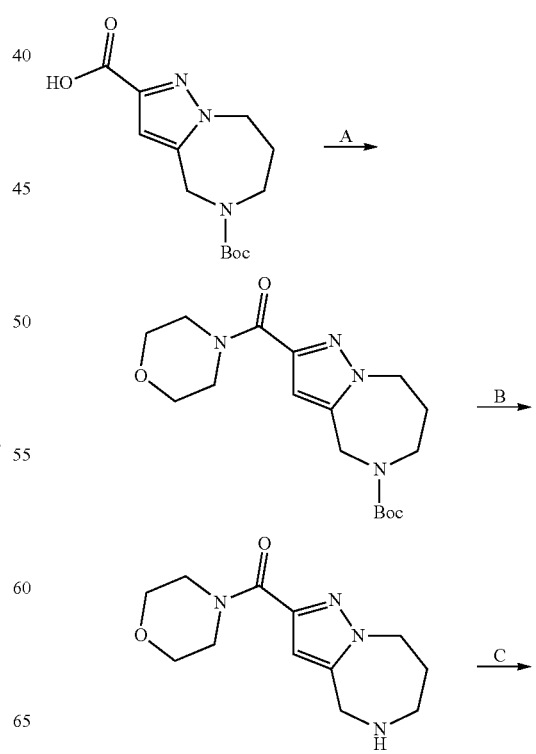

Step A. tert-butyl 3-chloro-2-(dimethylcarbamoyl)-7,8-dihydro-4H-pyrazolo[1,5-a][1,4]diazepine-5(6H)-carboxylate: To a mixture of tert-butyl 2-(dimethylcarbamoyl)-4, 6, 7, 8-tetrahydropyrazolo[1, 5-a][1, 4]diazepine-5-carboxylate (1.2 g, 1 equiv) in DMF (12 mL) was added NCS (779.44 mg, 1.5 equiv) at 0° C. The reaction was stirred at 55° C. for 1 hour. The reaction mixture was diluted with H$_2$O (10 mL×3) and extracted with EtOAc (10 mL×3), the combined organic layers were washed with brine (10 mL×3), dried, filtered, and concentrated to give a residue, which was purified by column chromatography (SiO$_2$, Petroleum ether/Ethyl acetate=10/1 to 1/1) to afford the title compound (740 mg, 51.59% yield) as a light yellow oil; $^1$H NMR (400 MHz, CDCl$_3$) δ=4.50 (s, 2H), 4.45-4.35 (m, 2H), 3.75 (s, 2H), 3.10 (s, 6H), 1.97 (s, 2H), 1.44 (s, 9H); LCMS (ESI, M+1): m/z=343.4.

Step B. 3-chloro-N,N-dimethyl-5,6,7,8-tetrahydro-4H-pyrazolo[1,5-a][1,4]diazepine-2-carboxamide: A mixture of tert-butyl 3-chloro-2-(dimethylcarbamoyl)-4,6,7,8-tetrahydropyrazolo[1,5-a][1,4]diazepine-5-carboxylate (170 mg, 1 equiv) and HCl/dioxane (1 mL) was stirred at 20° C. for 1 hour. The mixture was concentrated to afford the title compound (115 mg, crude) as light-yellow solid.

Step C-D: Synthesized according to Example 32. The title compound was obtained as yellow gum; $^1$H NMR (400 MHz, DMSO-d$_6$) δ=11.23-10.98 (m, 1H), 7.60 (dd, J=6.0 Hz, 8.8 Hz, 1H), 7.30-7.20 (m, 1H), 7.08-6.97 (m, 2H), 5.67-5.46 (m, 1H), 5.05 (d, J=16.0 Hz, 1H), 4.92-4.77 (m, 1H), 4.50-4.35 (m, 4H), 4.19-4.13 (m, 1H), 4.03 (d, J=17.2 Hz, 3H), 3.43 (d, J=8.0 Hz, 2H), 3.33-3.21 (m, 4H), 3.16-

237

-continued

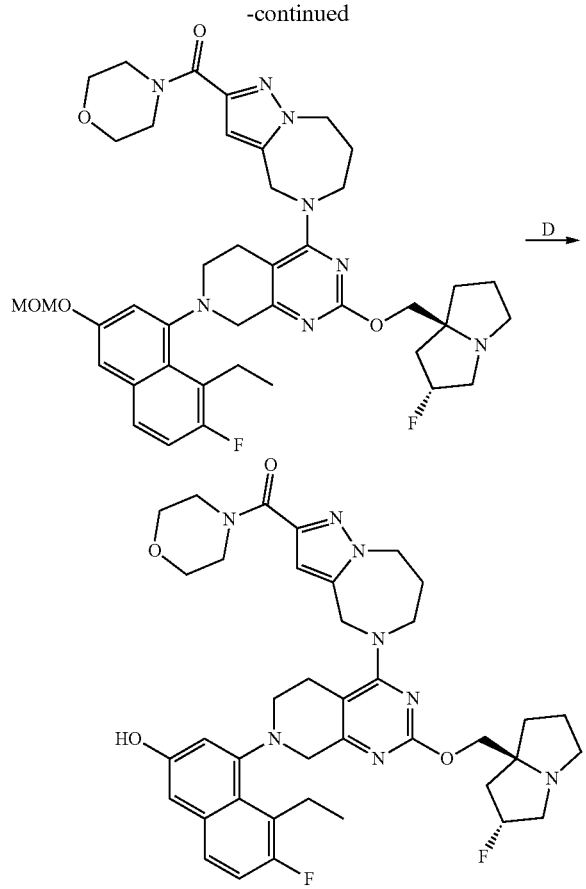

Synthesized according to Example 191. The title compound was obtained as off-white solid. $^1$H NMR (400 MHz, methanol-$d_4$) δ=7.51 (dd, J=5.6, 8.8 Hz, 1H), 7.14 (t, J=9.2 Hz, 1H), 6.96 (s, 2H), 6.62 (s, 1H), 5.38-5.14 (m, 1H), 5.04-4.98 (m, 1H), 4.86-4.80 (m, 1H), 4.69-4.57 (m, 1H), 4.56-4.50 (m, 2H), 4.27-4.15 (m, 1H), 4.12-4.08 (m, 1H), 4.08-3.94 (m, 5H), 3.73 (br s, 3H), 3.70-3.63 (m, 3H), 3.57-3.48 (m, 1H), 3.45-3.35 (m, 2H), 3.26-3.18 (m, 3H), 3.18-3.11 (m, 2H), 2.98 (dt, J=5.2, 9.2 Hz, 1H), 2.72 (br d, J=13.6 Hz, 1H), 2.34-2.11 (m, 3H), 2.11-2.02 (m, 2H), 2.00-1.91 (m, 2H), 1.90-1.79 (m, 1H), 1.15-1.07 (m, 3H); $^{19}$F NMR (377 MHz, methanol-$d_4$) δ=−123, −173; LCMS (ESI, M+1): m/z=729.5.

Example 194

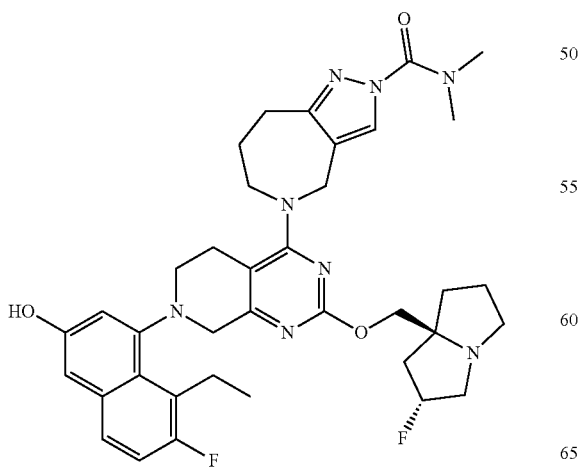

238

5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N,N-dimethyl-5,6,7,8-tetrahydropyrazolo[4,3-c]azepine-2(4H)-carboxamide

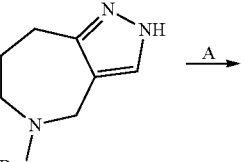

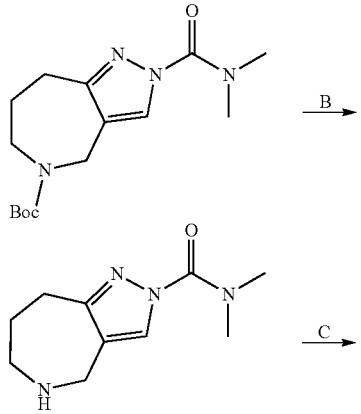

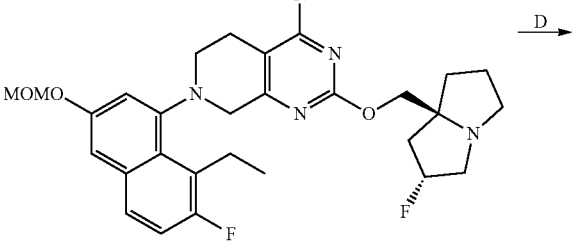

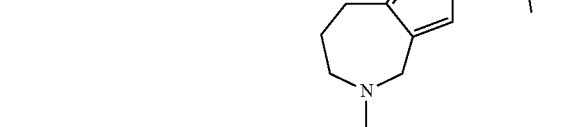

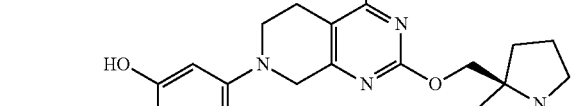

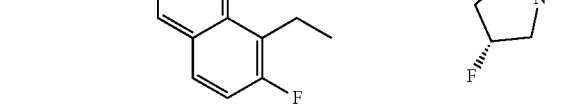

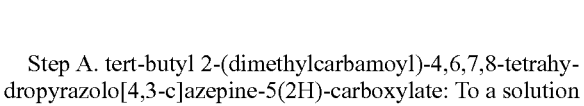

Step A. tert-butyl 2-(dimethylcarbamoyl)-4,6,7,8-tetrahydropyrazolo[4,3-c]azepine-5(2H)-carboxylate: To a solution of tert-butyl 4,6,7,8-tetrahydro-2H-pyrazolo[4,3-c]azepine-5-carboxylate (1.00 g, 1.0 equiv) in THF (10 mL) were added sodium amide (843 mg, 5.0 equiv) and N,N-dimethylcarbamoyl chloride (906 mg, 2.0 equiv) at 0° C. The mixture was stirred at 25° C. for 2 hours. The reaction mixture was quenched with water (20 mL) at 0° C., and then extracted with ethyl acetate (3×30 mL). The combined organic layers were washed with brine (30 mL), dried over Na$_2$SO$_4$, filtered, and concentrated under reduced pressure to afford the title compound (1.10 g, 85% yield) as a white solid. LCMS (ESI, M+1): m/z=309.3.

Step B. N,N-dimethyl-5,6,7,8-tetrahydropyrazolo[4,3-c]azepine-2(4H)-carboxamide: To a solution of tert-butyl 2-(dimethylcarbamoyl)-4,6,7,8-tetrahydropyrazolo[4,3-c]azepine-5-carboxylate (780 mg, 1.0 equiv) in DCM (5 mL) was added TFA (3.16 g, 11 equiv). The mixture was stirred at 25° C. for 0.5 hour. The reaction mixture was concentrated under reduced pressure to afford the title compound (200 mg, 38% yield) as a white solid. LCMS (ESI, M+1): m/z=209.1.

Step C-D: Synthesized according to Example 32. The title compound was obtained as white solid. $^1$H NMR (400 MHz, methanol-d4) δ=8.05 (br d, J=3.2 Hz, 1H), 7.50 (br dd, J=6.0, 8.8 Hz, 1H), 7.13 (br t, J=9.2 Hz, 1H), 6.95 (s, 2H), 5.36-5.16 (m, 1H), 4.76-4.71 (m, 1H), 4.66-4.50 (m, 1H), 4.20-4.12 (m, 1H), 4.12-4.02 (m, 3H), 4.00 (br d, J=8.4 Hz, 1H), 3.65 (br d, J=17.2 Hz, 1H), 3.50 (br d, J=6.4 Hz, 1H), 3.36 (br d, J=7.2 Hz, 2H), 3.18 (br s, 11H), 2.97 (br d, J=3.2 Hz, 3H), 2.72 (br d, J=12.4 Hz, 1H), 2.27-2.05 (m, 4H), 1.99-1.82 (m, 4H), 1.09 (br t, J=6.4 Hz, 3H); $^{19}$F NMR (377 MHz, METHANOL-d4) δ=−123, −173; LCMS (ESI, M+1): m/z=687.6.

Example 195

5-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-N-isopropyl-5,6,7,8-tetrahydropyrazolo[4,3-c]azepine-2(4H)-carboxamide

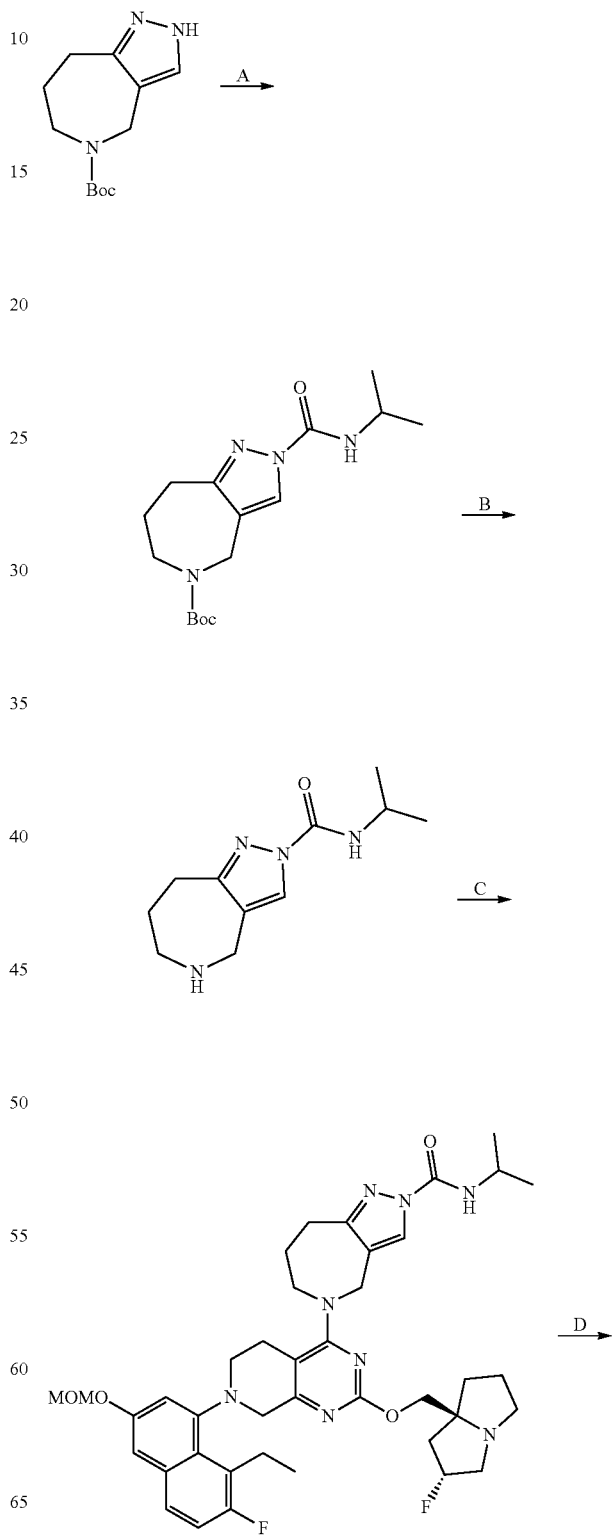

241
-continued

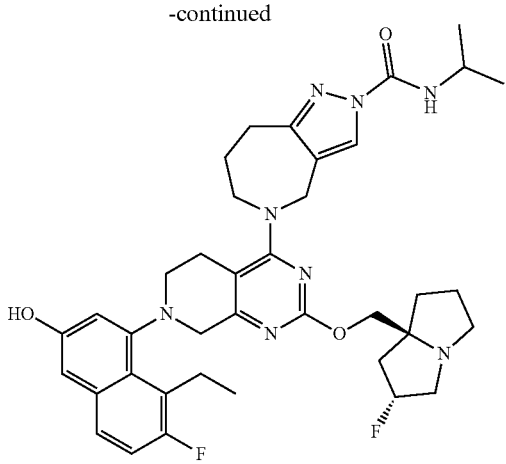

Step A. tert-butyl 2-(isopropylcarbamoyl)-4,6,7,8-tetrahydropyrazolo[4,3-c]azepine-5-carboxylate: To a solution of tert-butyl 4,6,7,8-tetrahydro-2H-pyrazolo[4,3-c]azepine-5-carboxylate (4.0 g, 1.0 equiv) in THF (20 mL) was added CDI (2.73 g, 1 equiv) dropwise at 25° C. for 1 hour. Then isopropyl amine (1.1 g, 1.1 equiv) was added dropwise at 25° C. The mixture was concentrated and purified with column chromatography [SiO$_2$, petroleum ether/ethyl acetate=3/1 to 0/1] to afford the title compound (4.5 g, 82% yield) as white solid. LCMS (ESI, M+1): m/z=323.2.

Step B. N-isopropyl-5,6,7,8-tetrahydropyrazolo[4,3-c]azepine-2(4H)-carboxamide: A solution of tert-butyl 2-(isopropylcarbamoyl)-4,6,7,8-tetrahydropyrazolo[4,3-c]azepine-5-carboxylate (6.0 g, 1 equiv) in HCl/MeOH (30 mL) was stirred at 25° C. for 0.5 hour. The mixture was concentrated to afford the title compound (3.2 g, 77% yield) as white solid. LCMS (ESI, M+1): m/z=223.2.

Step C-D: Synthesized according to Example 32. The title compound was obtained as yellow solid. 1H NMR (400 MHz, DMSO-d6) δ=8.21 (d, J=1.6 Hz, 1H), 7.99 (dd, J=2.0, 8.4 Hz, 1H), 7.59 (dd, J=6.0, 9.1 Hz, 1H), 7.24 (t, J=9.6 Hz, 1H), 7.05-6.95 (m, 2H), 5.66-5.44 (m, 1H), 4.86-4.61 (m, 2H), 4.44-4.21 (m, 2H), 4.07 (br d, J=4.0 Hz, 2H), 3.97-3.79 (m, 3H), 3.75-3.66 (m, 2H), 3.28-3.03 (m, 7H), 2.92 (br t, J=5.6 Hz, 2H), 2.75-2.57 (m, 2H), 2.45-2.40 (m, 1H), 2.37-2.22 (m, 2H), 2.18-1.95 (m, 4H), 1.76-1.66 (m, 1H), 1.17 (d, J=6.8 Hz, 6H), 1.02 (t, J=7.2 Hz, 3H); LCMS (ESI, M+1): m/z=701.5.

Example 196

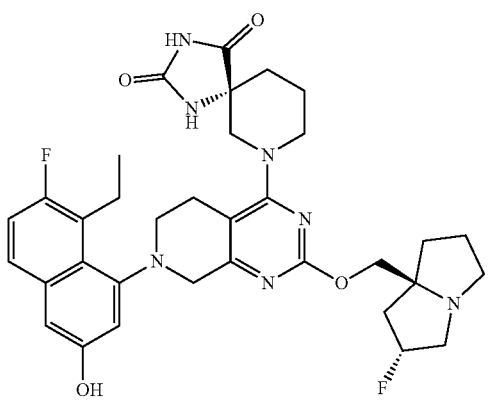 [SMILES: CCc1c(F)ccc2cc(O)cc(N3CCc4c(nc(OC[C@@]56CCCN5C[C@H](F)C6)nc4N4CCC[C@]5(C4)NC(=O)NC5=O)C3)c12]

242

(R)-7-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decane-2,4-dione

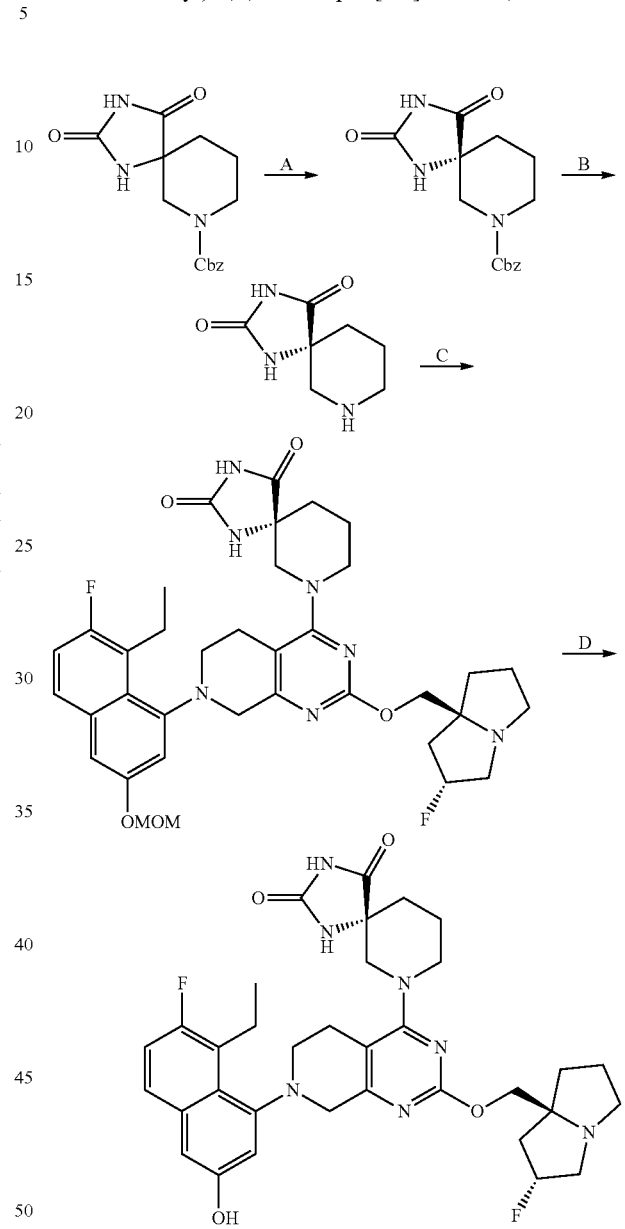

Step A. (R)-benzyl 2,4-dioxo-1,3,7-triazaspiro[4.5]decane-7-carboxylate: Benzyl 2,4-dioxo-1,3,7-triazaspiro[4.5]decane-7-carboxylate (30 g, 1 equiv) was purified with SFC [DAICEL CHIRALPAK AS (250 mm×30 mm, 10 μm); A: 0.1% NH$_3$·H$_2$O, B: MeOH; B %: 27%-27%, 3.4 over 918 minutes]. The first peak was collected and concentrated to afford the title compound (14.5 g, 48% yield) as white solid. SFC: >99% ee, Chiralpak IG-3 50×4.6 mm I.D., 3 μm, Mobile phase: Phase A for CO$_2$, and Phase B for MeOH (0.05% DEA); Gradient elution: 40% MeOH (0.05% DEA) in CO$_2$, 3 mL/min, 220 nm, t$_R$: 1.640 min; LCMS (ESI, M+1): m/z=304.1.

Step B. (R)-1,3,7-triazaspiro[4.5]decane-2,4-dione: To a solution of (R)-benzyl 2,4-dioxo-1,3,7-triazaspiro[4.5]decane-7-carboxylate (14 g, 1.0 equiv) in MeOH (700 mL)

was added Pd/C (1.4 g, 10% purity) under N₂. The suspension was degassed and purged with H₂ several times. The mixture was stirred at 25° C. for 1 hour under H₂ (15 psi) atmosphere. The mixture was filtered, and concentrated to afford the title compound (7.63 g, 88% yield) as white solid. LCMS (ESI, M+1): m/z=170.1.

Step C-D: Synthesized according to Example 32. The title compound was obtained as yellow solid. ¹H NMR (400 MHz, METHANOL-d₄) δ=7.55-7.46 (m, 1H), 7.18-7.10 (m, 1H), 7.02-6.93 (m, 2H), 5.36-5.15 (m, 1H), 4.22-4.09 (m, 3H), 4.08-4.04 (m, 1H), 4.04-3.93 (m, 1H), 3.69-3.61 (m, 1H), 3.54-3.34 (m, 4H), 3.27-3.11 (m, 5H), 3.10-2.93 (m, 2H), 2.83-2.68 (m, 1H), 2.34-2.19 (m, 1H), 2.17-2.05 (m, 3H), 2.01-1.80 (m, 6H), 1.15-1.08 (m, 7.2 Hz, 3H); ¹⁹F NMR (400 MHz, METHANOL-d₄) δ=−123, −173; LCMS (ESI, M+1): m/z=648.4.

Example 197

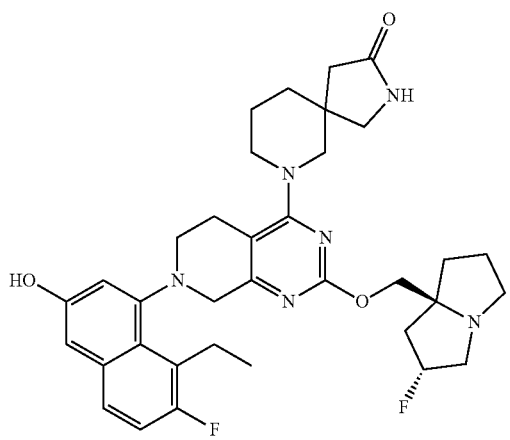 [SMILES: CCc1c(F)ccc2cc(O)cc(N3CCc4c(nc(OC[C@@]56CCCN5C[C@H](F)C6)nc4N4CCCC5(CNC(=O)C5)C4)C3)c12]

7-(7-(8-ethyl-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-2,7-diazaspiro[4.5]decan-3-one Synthesized according to Example 32. The title compound was obtained as white solid. ¹H NMR (400 MHz, METHANOL-d₄) δ=7.52 (dd, J=5.8, 8.9 Hz, 1H), 7.15 (t, J=9.4 Hz, 1H), 7.03-6.91 (m, 2H), 5.55-5.27 (m, 1H), 4.39-4.16 (m, 2H), 4.09 (dd, J=10.0, 17.8 Hz, 1H), 3.89-3.75 (m, 1H), 3.74-3.63 (m, 2H), 3.62-3.34 (m, 9H), 3.29-3.04 (m, 5H), 2.67 (br d, J=12.1 Hz, 1H), 2.47 (br d, J=3.3 Hz, 1H), 2.39-2.15 (m, 4H), 2.11 (br dd, J=5.7, 10.8 Hz, 2H), 1.89-1.65 (m, 4H), 1.16-1.05 (m, 3H); LCMS (ESI, M+1): m/z=633.5.

Example 198

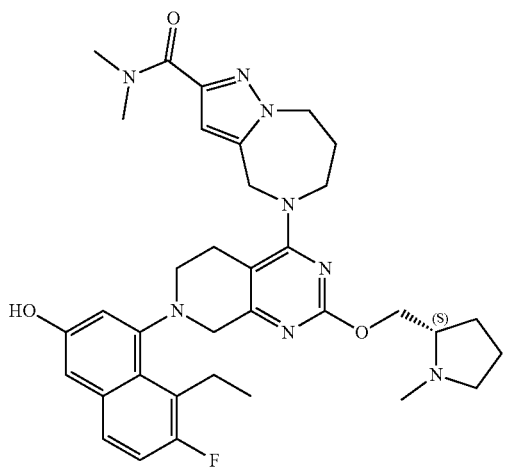

5-[7-(8-ethyl-7-fluoro-3-hydroxy-1-naphthyl)-2-[[(2S)-1-methylpyrrolidin-2-yl]methoxy]-6,8-dihydro-5H-pyrido[3,4-d]pyrimidin-4-yl]-N,N-dimethyl-4,6,7,8-tetrahydropyrazolo[1,5-a][1,4]diazepine-2-carboxamide

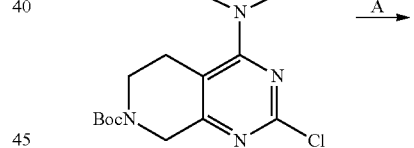

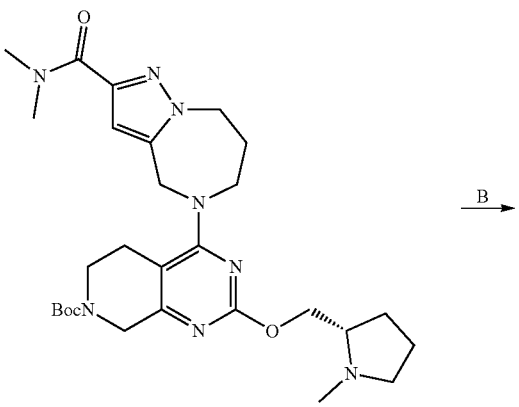

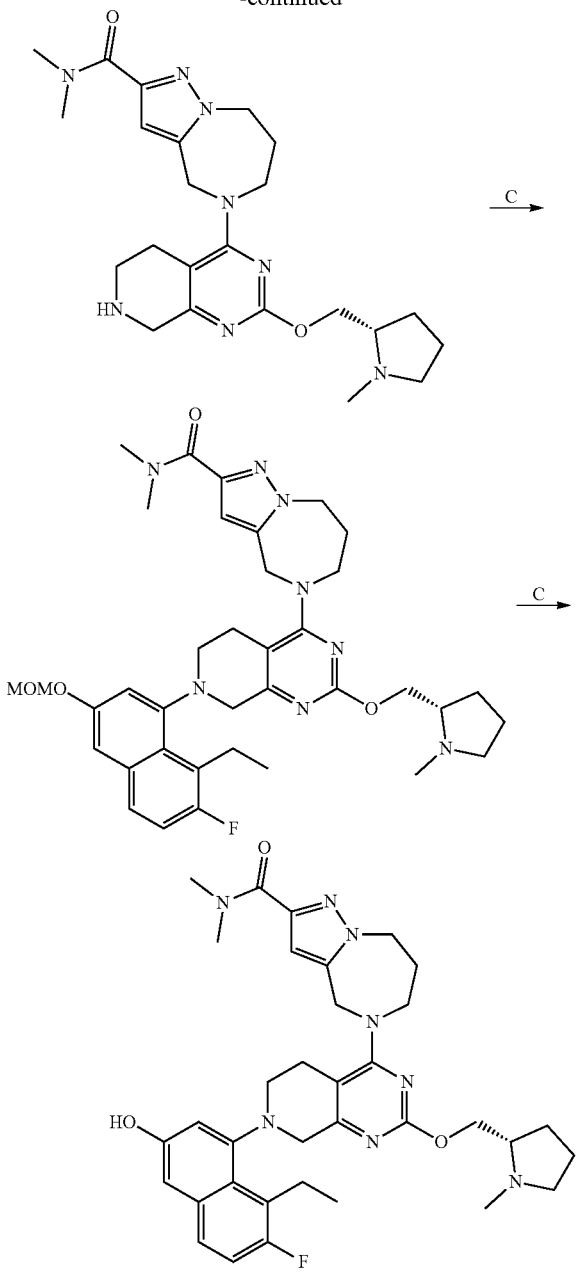

Step A. tert-butyl 4-[2-(dimethylcarbamoyl)-4,6,7,8-tetrahydropyrazolo[1,5-a][1,4]diazepin-5-yl]-2-[[(2S)-1-methylpyrrolidin-2-yl]methoxy]-6,8-dihydro-5H-pyrido[3,4-d]pyrimidine-7-carboxylate: A mixture of tert-butyl 2-chloro-4-[2-(dimethylcarbamoyl)-4,6,7,8-tetrahydropyrazolo[1,5-a][1,4]diazepin-5-yl]-6,8-dihydro-5H-pyrido[3,4-d]pyrimidine-7-carboxylate (560 mg, 1.0 equiv), [(2S)-1-methylpyrrolidin-2-yl]methanol (163 mg, 1.2 equiv), Pd(OAc)$_2$ (52.8 mg, 0.2 equiv), 2,2'-bis(diphenylphosphino)-1,1'-binaphthalene (183 mg, 0.3 equiv) and Cs$_2$CO$_3$ (767 mg, 2.0 equiv) in toluene (12 mL) was degassed and purged with nitrogen for 3 times. The mixture was stirred at 110° C. for 3 hours under nitrogen atmosphere. The mixture was concentrated to remove the solvent. The residue was diluted with water (10 mL) and extracted with dichloromethane:methanol=10:1 (2×10 mL). The combined organic layer was washed with brine (10 mL), dried over anhydrous sodium sulfate, concentrated, and purified with prep-HPLC [column: Phenomenex luna C18 150×25 mm×10 μm; mobile phase: water (FA)-ACN; B %: 28%-58%, 10 minutes] to afford the title compound (222 mg, 34.0% yield) as yellow solid. LCMS (ESI, M+1): m/z=555.5.

Step B. N,N-dimethyl-5-[2-[[(2S)-1-methylpyrrolidin-2-yl]methoxy]-5,6,7,8-tetrahydropyrido [3,4-d]pyrimidin-4-yl]-4,6,7,8-tetrahydropyrazolo[1,5-a][1,4]diazepine-2-carboxamide: To a solution of tert-butyl 4-[2-(dimethylcarbamoyl)-4,6,7,8-tetrahydropyrazolo[1,5-a][1,4]diazepin-5-yl]-2-[[(2S)-1-methylpyrrolidin-2-yl]methoxy]-6,8-dihydro-5H-pyrido[3,4-d]pyrimidine-7-carboxylate (200 mg, 1.0 equiv) in dioxane (6 mL) was added HCl/dioxane (4.0 M, 6.00 mL). The mixture was stirred at 0° C. for 1 hour. The mixture was concentrated. The residue was dissolved in methanol (3 mL) and basified (pH ~8) with NaHCO$_3$ solid. The mixture was stirred for 0.3 hour, filtered, and concentrated to afford the title compound (156 mg, 95.2% yield) as white solid.

Step C. 5-[7-[8-ethyl-7-fluoro-3-(methoxymethoxy)-1-naphthyl]-2-[[(2S)-1-methylpyrrolidin-2-yl]methoxy]-6,8-dihydro-5H-pyrido[3,4-d]pyrimidin-4-yl]-N,N-dimethyl-4,6,7,8-tetrahydropyrazolo[1,5-a][1,4]diazepine-2-carboxamide: A mixture of N,N-dimethyl-5-[2-[[(2S)-1-methylpyrrolidin-2-yl]methoxy]-5,6,7,8-tetrahydropyrido[3,4-d]pyrimidin-4-yl]-4,6,7,8-tetrahydropyrazolo[1,5-a][1,4]diazepine-2-carboxamide (156 mg 1.0 equiv), [8-ethyl-7-fluoro-3-(methoxymethoxy)-1-naphthyl] trifluoromethanesulfonate (144 mg, 1.1 equiv), tris(dibenzylideneacetone)dipalladium(0) (47.1 mg, 0.2 equiv), (5-diphenylphosphanyl-9,9-dimethylxanthen-4-yl)-diphenylphosphane (49.6 mg, 0.3 equiv) and Cs$_2$CO$_3$ (335 mg, 3.0 equiv) in toluene (1 mL) was degassed and purged with N$_2$ for 3 times. The mixture was stirred at 110° C. for 14 hours under N$_2$ atmosphere. The mixture was diluted with water (20 mL) and extracted with ethyl acetate (2×15 mL). The combined organic layers were washed with brine (20 mL), dried over anhydrous sodium sulfate, concentrated and purified with prep-HPLC [column: Phenomenex luna C18 150×40 mm×15 μm; mobile phase: water (FA)-ACN; B %: 23%-53%, 10 minutes] to afford the title compound (45.0 mg, 18.7% yield) as white solid.

Step D. 5-[7-(8-ethyl-7-fluoro-3-hydroxy-1-naphthyl)-2-[[(2S)-1-methylpyrrolidin-2-yl]methoxy]-6,8-dihydro-5H-pyrido[3,4-d]pyrimidin-4-yl]-N,N-dimethyl-4,6,7,8-tetrahydropyrazolo[1,5-a][1,4]diazepine-2-carboxamide: To a solution of 5-[7-[8-ethyl-7-fluoro-3-(methoxymethoxy)-1-naphthyl]-2-[[(2S)-1-methylpyrrolidin-2-yl]methoxy]-6,8-dihydro-5H-pyrido[3,4-d]pyrimidin-4-yl]-N,N-dimethyl-4,6,7,8-tetrahydropyrazolo[1,5-a][1,4]diazepine-2-carboxamide (38.0 mg, 1.0 equiv) in methanol (3 mL) was added HCl/MeOH (4.00 M, 3 mL). The mixture was stirred at 0° C. for 1 hour. The mixture was diluted with methanol (4 mL) and basified (pH ~8) with NaHCO$_3$ solid. The mixture was stirred at 0° C. for 0.3 hour, filtered, concentrated, and purified with prep-HPLC [column: Phenomenex luna C18 150×25 mm×10 μm; mobile phase: water (FA)-ACN; B %: 15%-45%, 10 minutes] to afford the title compound (15.3 mg, 42.9% yield) as white solid. $^1$H NMR (400 MHz, METHANOL-d4) δ=7.51 (dd, J=6.0, 8.8 Hz, 1H), 7.15 (t, J=9.6 Hz, 1H), 6.97 (s, 2H), 6.60 (d, J=0.8 Hz, 1H), 5.05-4.96 (m, 1H), 4.66-4.46 (m, 4H), 4.44-4.34 (m, 1H), 4.25-4.15 (m, 1H), 4.06 (br d, J=17.6 Hz, 2H), 3.68 (br d, J=17.6 Hz, 1H), 3.54 (br d, J=10.4 Hz, 1H), 3.51-3.43 (m, 2H), 3.42-3.35 (m, 2H), 3.33-3.32 (m, 3H), 3.28-3.14 (m, 2H), 3.08 (s, 3H), 2.98-2.89 (m, 1H), 2.84 (d, J=3.6 Hz, 3H), 2.74 (br d, J=13.6 Hz, 1H), 2.38-2.19 (m, 2H), 2.13-1.87 (m, 4H), 1.11 (t, J=7.2 Hz, 3H); ¹⁹F NMR (377 MHz, METHA-NOL-d₄) δ=−122; LCMS (ESI, M+1): m/z=643.5.

Example 199

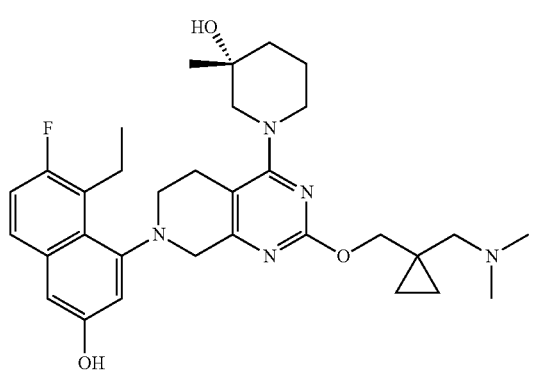 [SMILES: CCc1c(F)ccc2cc(O)cc(N3CCc4c(nc(OCC5(CN(C)C)CC5)nc4N4CCC[C@@](C)(O)C4)C3)c12]

(R)-1-(2-((1-((dimethylamino)methyl)cyclopropyl)
methoxy)-7-(8-ethyl-7-fluoro-3-hydroxynaphthalen-
1-yl)-5,6,7,8-tetrahydropyrido[3,4-d]pyrimidin-4-
yl)-3-methylpiperidin-3-ol

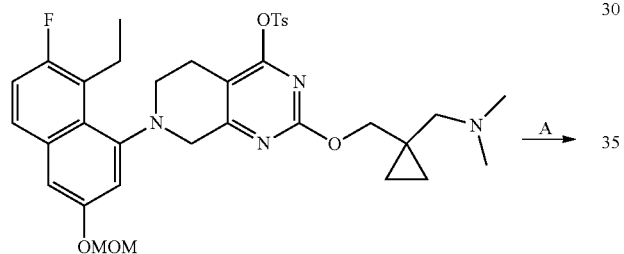

Synthesized according to Example 32. The title compound was obtained as white solid. ¹H NMR (400 MHz, METHANOL-d₄) δ=7.53-7.48 (m, 1H), 7.14 (t, J=9.6 Hz, 1H), 7.05-6.94 (m, 2H), 4.26-4.15 (m, 2H), 4.12-4.00 (m, 2H), 3.90-3.65 (m, 1H), 3.64-3.58 (m, 1H), 3.55-3.85 (m, 5H), 3.24-3.05 (m, 2H), 2.85-2.70 (m, 1H), 2.65-3.51 (m, 2H), 2.49-2.30 (m, 6H), 2.08-1.60 (m, 4H), 1.33-1.15 (m, 3H), 1.13-1.01 (m, 3H), 0.77-0.65 (m, 2H), 0.61-0.48 (m, 2H); LCMS (ESI, M+1): m/z=564.3.

Example 200

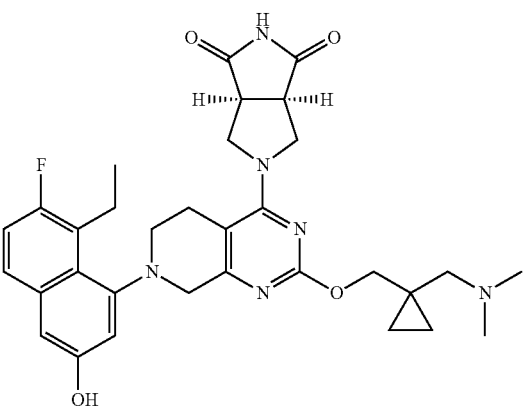 [SMILES: CCc1c(F)ccc2cc(O)cc(N3CCc4c(nc(OCC5(CN(C)C)CC5)nc4N4C[C@@H]5C(=O)NC(=O)[C@@H]5C4)C3)c12]

(3aS,6aR)-5-[2-[[1-[(dimethylamino)methyl]cyclo-
propyl]methoxy]-7-(8-ethyl-7-fluoro-3-hydroxy-1-
naphthyl)-6,8-dihydro-5H-pyrido[3,4-d]pyrimidin-4-
yl]-3a,4,6,6a-tetrahydropyrrolo[3,4-c]pyrrole-1,3-
dione

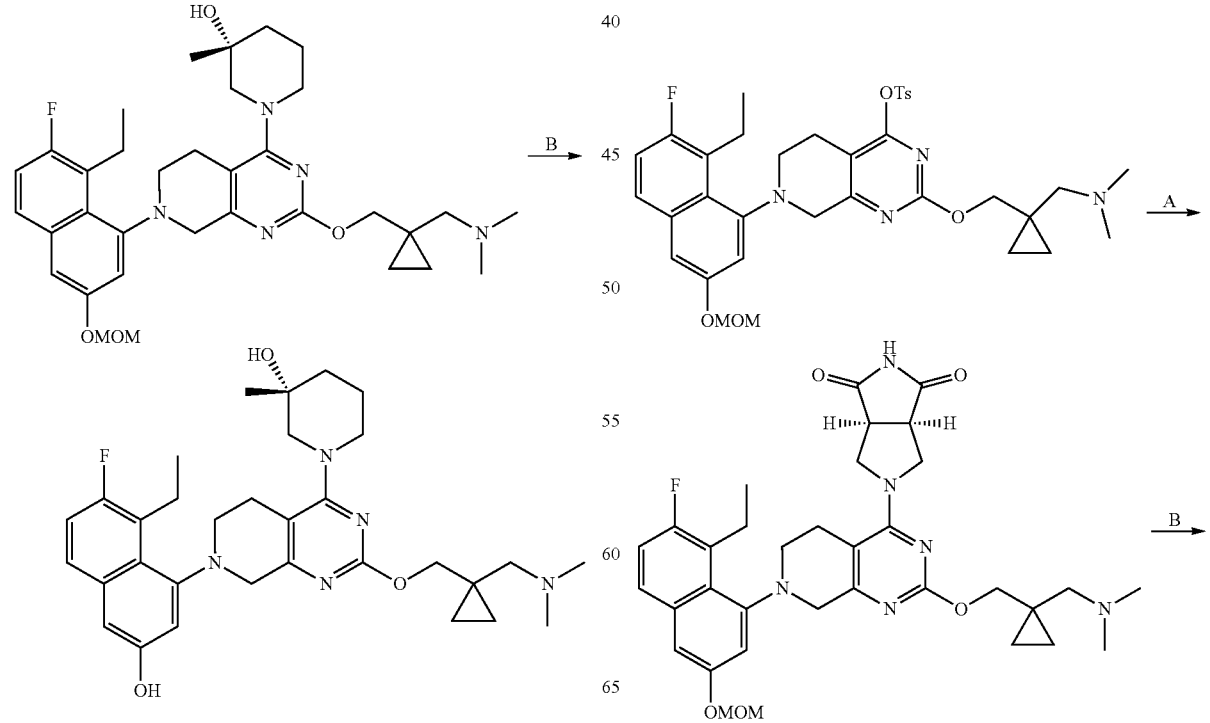

249
-continued

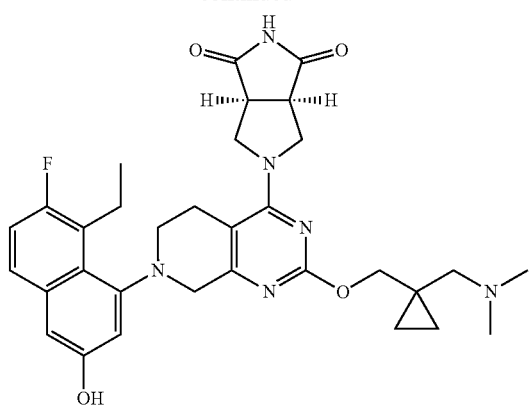

Synthesized according to Example 32. The title compound was obtained as white solid. ¹H NMR (400 MHz, METHANOL-d₄) δ=7.51 (dd, J=6.0, 9.2 Hz, 1H), 7.14 (t, J=9.2 Hz, 1H), 7.04-6.93 (m, 2H), 4.61 (br d, J=10.8 Hz, 2H), 4.31-4.17 (m, 3H), 4.01 (d, J=17.2 Hz, 1H), 3.77 (br s, 1H), 3.66 (d, J=17.6 Hz, 1H), 3.55-3.45 (m, 4H), 3.34 (br d, J=2.8 Hz, 1H), 3.23-3.15 (m, 2H), 2.85 (br s, 2H), 2.76-2.69 (m, 1H), 2.62 (s, 6H), 1.10 (t, J=7.2 Hz, 3H), 0.83-0.76 (m, 2H), 0.66 (s, 2H); LCMS (ESI, M+1): m/z=589.1.

Example 201

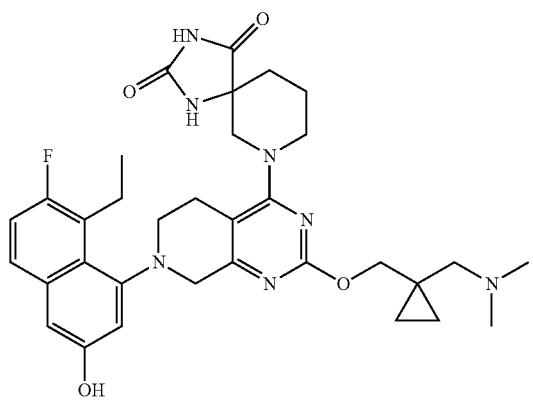 [SMILES: CCc1c(F)ccc2cc(O)cc(N3CCc4c(nc(OCC5(CN(C)C)CC5)nc4N4CCCC5(C4)NC(=O)NC5=O)C3)c12]

7-(2-((1-(((dimethylamino)methyl)cyclopropyl)methoxy)-7-(8-ethyl-7-fluoro-3-hydroxynaphthalen-1-yl)-5,6,7,8-tetrahydropyrido[3,4-d]pyrimidin-4-yl)-1,3,7-triazaspiro[4.5]decane-2,4-dione

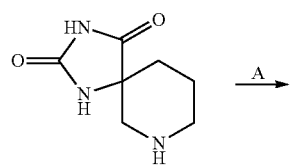

250
-continued

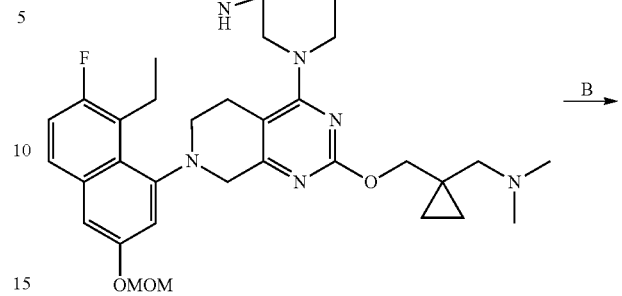

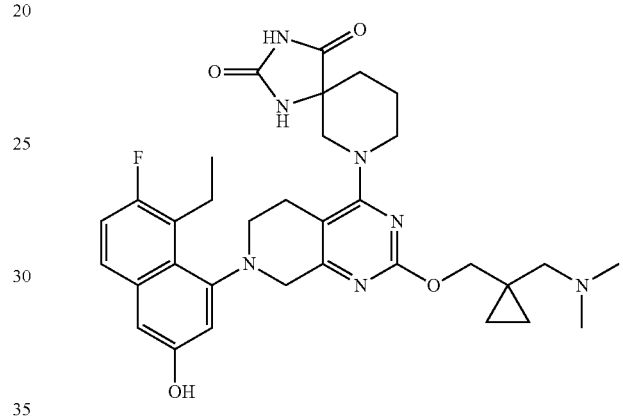

Synthesized according to Example 32. The title compound was obtained as yellow solid. ¹H NMR (400 MHz, METHANOL-d₄) δ=7.51 (dd, J=6.0, 8.98 Hz, 1H), 7.15 (t, J=9.6 Hz, 1H), 7.07-6.91 (m, 2H), 4.27-3.92 (m, 5H), 3.66 (dd, J=6.8, 17.6 Hz, 1H), 3.58-3.32 (m, 5H), 3.24-3.10 (m, 2H), 3.05-2.93 (m, 2H), 2.85-2.75 (m, 1H), 2.72 (br d, J=13.2 Hz, 6H), 2.20-2.07 (m, 1H), 2.05-1.77 (m, 3H), 1.10 (t, J=7.2 Hz, 3H), 0.89-0.78 (m, 2H), 0.73-0.62 (m, 2H); LCMS (ESI, M+1): m/z=618.4.

Example 202

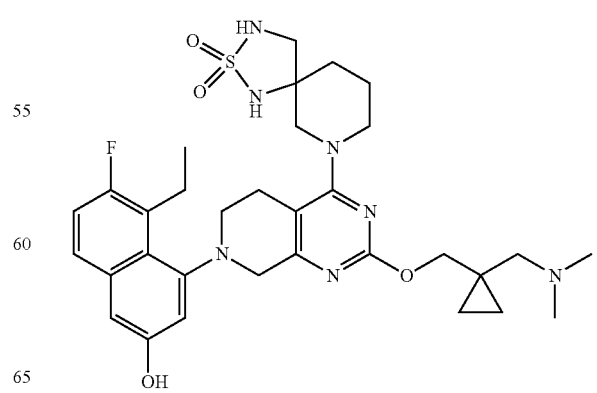

251

7-(2-((1-((dimethylamino)methyl)cyclopropyl)
methoxy)-7-(8-ethyl-7-fluoro-3-hydroxynaphthalen-
1-yl)-5,6,7,8-tetrahydropyrido[3,4-d]pyrimidin-4-
yl)-2-thia-1,3,7-triazaspiro[4.5]decane 2,2-dioxide

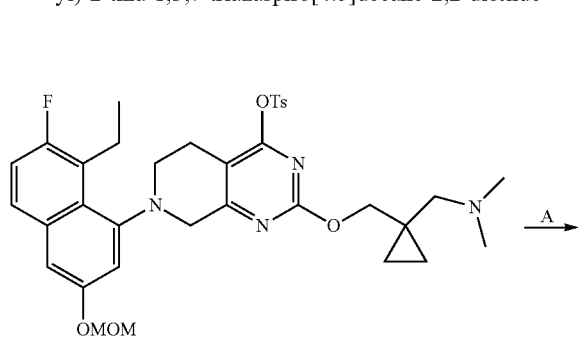

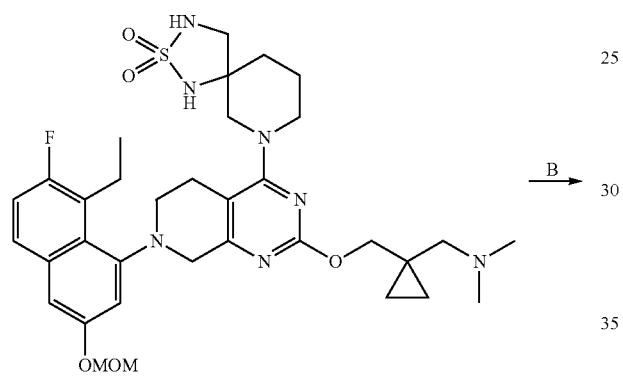

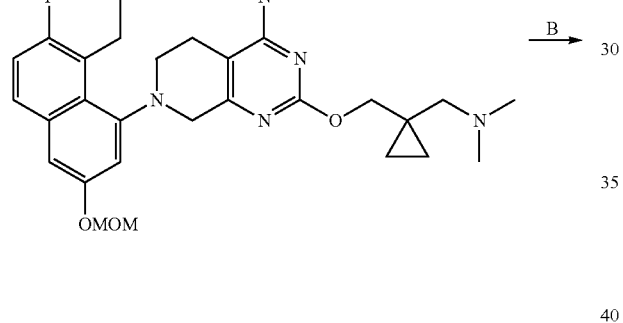

Synthesized according to Example 32. The title compound was obtained as yellow solid. $^1$H NMR (400 MHz, METHANOL-d4) δ=7.56-7.47 (m, 1H), 7.20-7.08 (m, 1H), 7.05-6.92 (m, 2H), 4.31-4.19 (m, 2H), 4.13-4.06 (m, 1H), 3.99-3.87 (m, 1H), 3.70-3.47 (m, 4H), 3.46-3.33 (m, 3H), 3.30-3.08 (m, 4H), 3.18-3.01 (m, 2H), 2.79-2.61 (m, 7H), 1.82 (br s, 4H), 1.17-1.04 (m, 3H), 0.85 (br s, 2H), 0.78-0.67 (m, 2H); LCMS (ESI, M+1): m/z=640.4.

Example 203

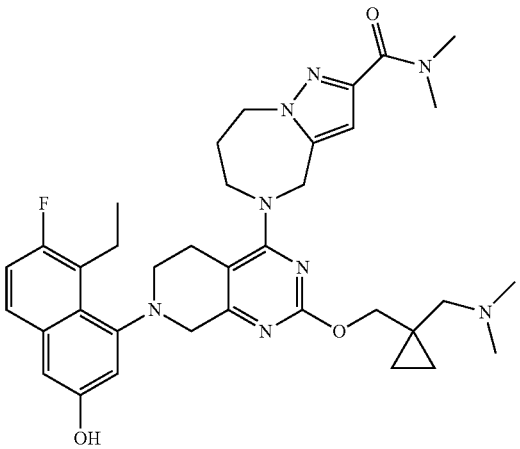 [SMILES: CCc1c(F)ccc2cc(O)cc(N3CCc4c(nc(OCC5(CN(C)C)CC5)nc4N4CCCn5nc(C(=O)N(C)C)cc5C4)C3)c12]

5-(2-((1-((dimethylamino)methyl)cyclopropyl)
methoxy)-7-(8-ethyl-7-fluoro-3-hydroxynaphthalen-
1-yl)-5,6,7,8-tetrahydropyrido[3,4-d]pyrimidin-4-
yl)-N,N-dimethyl-5,6,7,8-tetrahydro-4H-pyrazolo[1,
5-a][1,4]diazepine-2-carboxamide

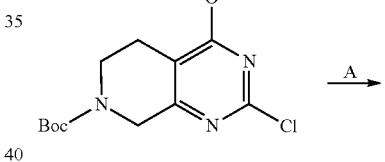

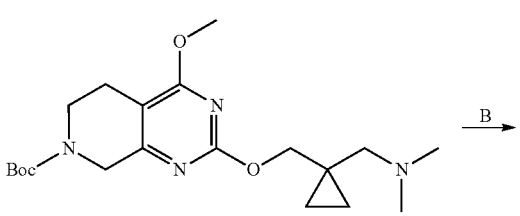

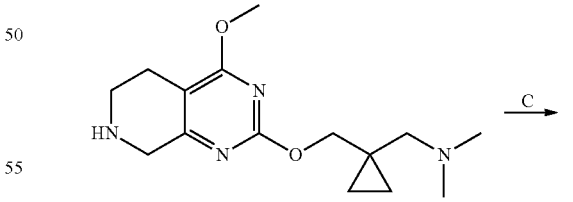

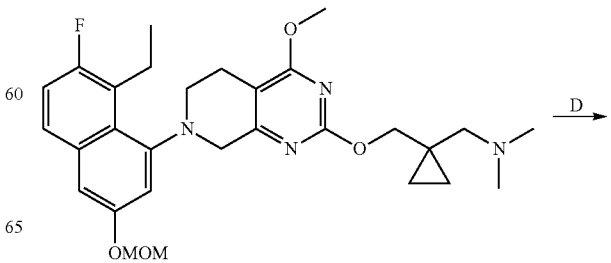

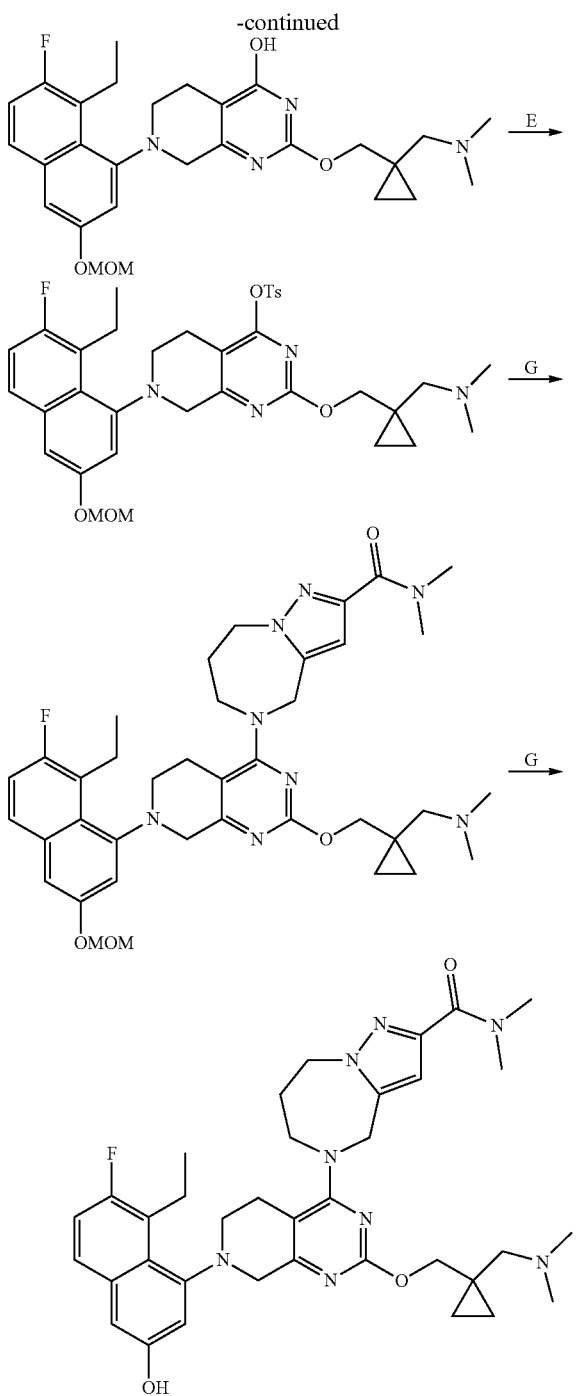

Step A. tert-butyl 2-((1-((dimethylamino)methyl)cyclopropyl)methoxy)-4-methoxy-5,6-dihydropyrido[3,4-d]pyrimidine-7(8H)-carboxylate: To a solution of tert-butyl 2-chloro-4-methoxy-6,8-dihydro-5H-pyrido[3,4-d]pyrimidine-7-carboxylate (20.0 g, 1.0 equiv), [1-[(dimethylamino)methyl]cyclopropyl]methanol (12.9 g, 1.5 equiv), BINAP (8.31 g, 0.2 equiv) and $Cs_2CO_3$ (65.2 g, 3.0 equiv) in toluene (200 mL) was added $Pd(OAc)_2$ (1.50 g, 0.1 equiv) under nitrogen atmosphere. The mixture was stirred at 110° C. for 12 hours. The mixture was diluted with water (30 mL) and extracted with ethyl acetate (3×20 mL). The combined organic layers were dried over anhydrous sodium sulfate, concentrated, and purified by column chromatography [$SiO_2$, Petroleum ether/Ethyl acetate=20/1 to Ethyl acetate/MeOH=5/1] to give a crude product. The crude product was purified by reversed phase flash chromatography [C18, 0.1% formic acid condition] to afford the title compound (17.0 g, 64% yield) as yellow liquid. $^1$H NMR (400 MHz, CHLOROFORM-d) δ=4.41 (s, 2H), 4.20 (s, 2H), 3.98-3.94 (m, 3H), 3.60 (br t, J=5.6 Hz, 2H), 2.55 (br t, J=5.2 Hz, 2H), 2.33 (s, 2H), 2.24 (s, 6H), 1.46 (s, 9H), 0.67-0.56 (m, 2H), 0.48-0.37 (m, 2H); LCMS (ESI, M+1): m/z=393.3.

Step B. 1-(1-(((4-methoxy-5,6,7,8-tetrahydropyrido[3,4-d]pyrimidin-2-yl)oxy)methyl)cyclopropyl)-N,N-dimethyl-methanamine: To a solution of tert-butyl 2-[[1-[(dimethylamino)methyl]cyclopropyl]methoxy]-4-methoxy-6,8-dihydro-5H-pyrido[3,4-d]pyrimidine-7-carboxylate (17.0 g, 1.0 equiv) in DCM (90 mL) was added TFA (92.4 g, 19 equiv). The reaction was stirred at 20° C. for 1 hour. The mixture was concentrated to dryness and dissolved in ethyl acetate (50 mL). The mixture was basified to pH 8 with $Na_2CO_3$ and the aqueous solution was extracted with ethyl acetate (2×50 mL). The combined organic layers were dried over anhydrous sodium sulfate and concentrated to afford the title compound (7.00 g, crude) as yellow liquid; LCMS (ESI, M+1): m/z=293.4.

Step C. 1-(1-(((7-(8-ethyl-7-fluoro-3-(methoxymethoxy)naphthalen-1-yl)-4-methoxy-5,6,7,8-tetrahydropyrido[3,4-d]pyrimidin-2-yl)oxy)methyl)cyclopropyl)-N,N-dimethyl-methanamine: To a solution of 1-[1-[(4-methoxy-5,6,7,8-tetrahydropyrido[3,4-d]pyrimidin-2-yl)oxymethyl]cyclopropyl]-N,N-dimethyl-methanamine (7.00 g, 1.0 equiv), [8-ethyl-7-fluoro-3-(methoxymethoxy)-1-naphthyl] trifluoromethanesulfonate (13.7 g, 1.5 equiv), $Cs_2CO_3$ (23.4 g, 3.0 equiv) and Xantphos (3.46 g, 0.25 equiv) in toluene (70 mL) was added $Pd_2(dba)_3$ (3.29 g, 0.15 equiv). The suspension was degassed under vacuum and purged with $N_2$ several times. The mixture was stirred at 110° C. for 14 hours. The reaction was stirred at 20° C. for 12 hours. The mixture was diluted with water (30 mL) and extracted with ethyl acetate (3×20 mL). The combined organic layers were dried over anhydrous sodium sulfate, concentrated, and purified by reversed phase flash chromatography [C18, 0.1% formic acid condition] to afford the title compound (6.00 g, 48% yield) as yellow liquid; $^1$H NMR (400 MHz, CHLOROFORM-d) δ=7.54 (dd, J=6.0, 8.8 Hz, 1H), 7.22-7.14 (m, 2H), 7.06 (d, J=2.4 Hz, 1H), 5.27 (s, 2H), 4.25-4.17 (m, 2H), 4.03 (s, 3H), 3.75 (br d, J=17.2 Hz, 1H), 3.58-3.43 (m, 4H), 3.33 (dq, J=2.8, 7.2 Hz, 2H), 3.19 (dt, J=4.0, 11.2 Hz, 1H), 2.87 (ddd, J=6.0, 10.4, 16.4 Hz, 1H), 2.68 (br d, J=16.4 Hz, 1H), 2.39-2.30 (m, 2H), 2.24 (s, 6H), 2.00 (br d, J=4.4 Hz, 1H), 1.26 (t, J=7.2 Hz, 3H), 0.70-0.59 (m, 2H), 0.48-0.39 (m, 2H); LCMS (ESI, M+1): m/z=525.4.

Step D. 2-((1-((dimethylamino)methyl)cyclopropyl)methoxy)-7-(8-ethyl-7-fluoro-3-(methoxymethoxy)naphthalen-1-yl)-5,6,7,8-tetrahydropyrido[3,4-d]pyrimidin-4-ol: To a solution of EtSH (2.86 g, 4.0 equiv) in DMAc (60 mL) was added NaH (915 mg, 60% purity, 2.0 equiv) at 10° C. The mixture was stirred at 10° C. for 0.5 hour. 1-[1-[[7-[8-ethyl-7-fluoro-3-(methoxymethoxy)-1-naphthyl]-4-methoxy-6,8-dihydro-5H-pyrido[3,4-d]pyrimidin-2-yl]oxymethyl]cyclopropyl]-N,N-dimethyl-methanamine (6.00 g, 1.0 equiv) was added and the reaction mixture was stirred at 60° C. for 1 hour. The mixture was diluted with water (30 mL) and extracted with ethyl acetate (3×20 mL). The combined organic layers were dried over anhydrous sodium sulfate, filtered, and concentrated to afford the title compound (7.00 g, crude) as yellow liquid; LCMS (ESI, M+1): m/z=511.3.

Step E. 2-((1-((dimethylamino)methyl)cyclopropyl)methoxy)-7-(8-ethyl-7-fluoro-3-(methoxymethoxy)naphthalen-1-yl)-5,6,7,8-tetrahydropyrido[3,4-d]pyrimidin-4-yl 4-methylbenzenesulfonate: To a solution of 2-[[1-[(dimethylamino)methyl]cyclopropyl]methoxy]-7-[8-ethyl-7-fluoro-3-(methoxymethoxy)-1-naphthyl]-6,8-dihydro-5H-pyrido[3,4-d]pyrimidin-4-ol (7.00 g, 1.0 equiv) and DMAP (167 mg, 0.1 equiv) and N-ethyl-N-isopropylpropan-2-amine (5.32 g, 3.0 equiv) in DCM (70 mL) was added TsCl (3.92 g, 1.5 equiv) at 0° C. The mixture was stirred at 20° C. for 2 hours. The mixture was diluted with water (30 mL) and extracted with ethyl acetate (3×20 mL). The combined organic layers were dried over anhydrous sodium sulfate, filtered, concentrated, and purified by column chromatography [Al$_2$O$_3$, Petroleum ether/Ethyl acetate=10/1 to Ethyl acetate] to afford the title compound (2.00 g, 22% yield) as yellow liquid; $^1$H NMR (400 MHz, CHLOROFORM-d) δ=8.02 (d, J=8.4 Hz, 2H), 7.55 (dd, J=6.0, 8.8 Hz, 1H), 7.39 (d, J=8.0 Hz, 2H), 7.24-7.16 (m, 2H), 7.04 (d, J=2.4 Hz, 1H), 5.30-5.24 (m, 2H), 3.97 (s, 2H), 3.80 (br d, J=18.0 Hz, 1H), 3.54-3.47 (m, 4H), 3.31-3.18 (m, 3H), 3.02-2.99 (m, 1H), 2.88-2.80 (m, 1H), 2.48 (s, 3H), 2.33 (br s, 2H), 2.26 (s, 6H), 2.05 (s, 1H), 1.04 (t, J=7.2 Hz, 3H), 0.61-0.56 (m, 2H), 0.46 (br s, 2H); LCMS (ESI, M+1): m/z=665.4.

Step F-G: Synthesized according to Example 32. The title compound was obtained as white solid. $^1$H NMR (400 MHz, METHANOL-d$_4$) δ=7.51 (dd, J=5.6, 8.8 Hz, 1H), 7.14 (t, J=9.6 Hz, 1H), 6.96 (s, 2H), 6.57 (s, 1H), 5.03-4.95 (m, 2H), 4.59-4.49 (m, 2H), 4.22-4.12 (m, 3H), 4.10-3.95 (m, 2H), 3.66 (br d, J=17.6 Hz, 1H), 3.52 (br d, J=10.4 Hz, 1H), 3.38 (td, J=3.2, 7.2 Hz, 2H), 3.32 (br s, 3H), 3.26-3.06 (m, 5H), 2.76-2.63 (m, 3H), 2.49 (s, 6H), 2.35-2.01 (m, 2H), 1.10 (t, J=7.2 Hz, 3H), 0.72 (br s, 2H), 0.58 (s, 2H); LCMS (ESI, M+1): m/z=657.5.

Example 204

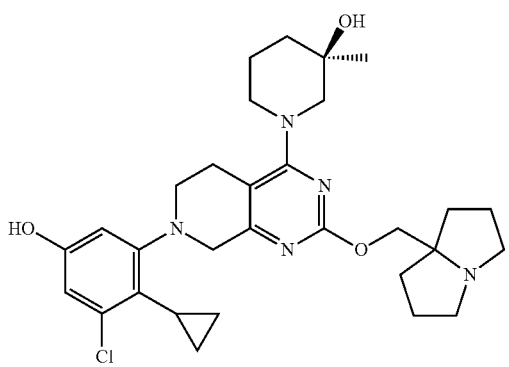 [SMILES: C[C@@]1(O)CCCN(c2nc(OCC34CCCN3CCC4)nc3c2CCN(c2cc(O)cc(Cl)c2C2CC2)C3)C1]

(R)-1-(7-(3-chloro-2-cyclopropyl-5-hydroxyphenyl)-2-((hexahydro-1H-pyrrolizin-7a-yl)methoxy)-5,6,7,8-tetrahydropyrido[3,4-d]pyrimidin-4-yl)-3-methylpiperidin-3-ol

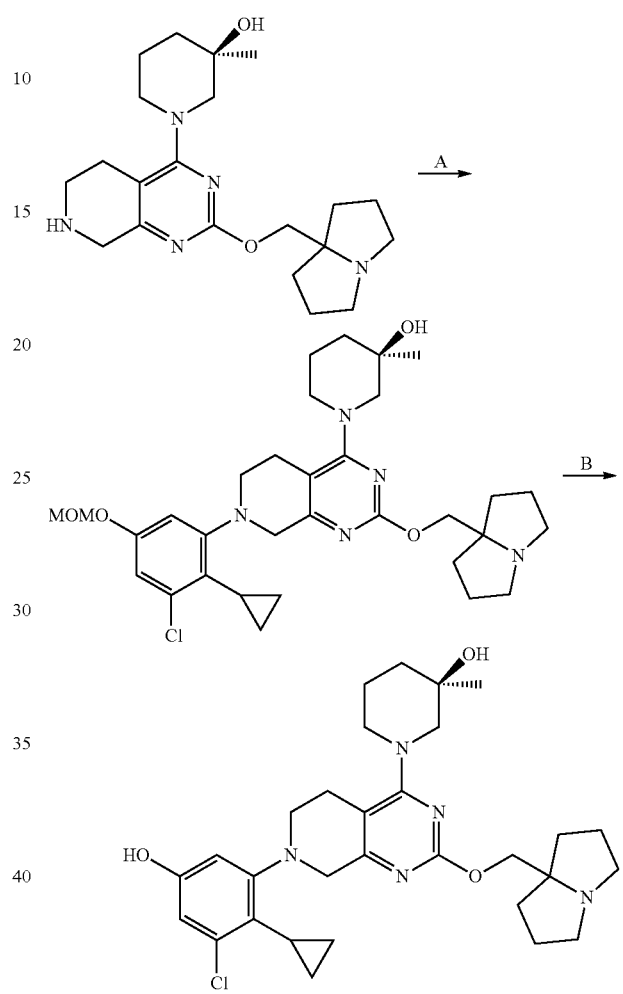

Step A. (R)-1-(7-(3-chloro-2-cyclopropyl-5-(methoxymethoxy)phenyl)-2-((hexahydro-1H-pyrrolizin-7a-yl)methoxy)-5,6,7,8-tetrahydropyrido[3,4-d]pyrimidin-4-yl)-3-methylpiperidin-3-ol: A mixture of (R)-3-methyl-1-(2-((tetrahydro-1H-pyrrolizin-7a(5H)-yl)methoxy)-5,6,7,8-tetrahydropyrido[3,4-d]pyrimidin-4-yl)piperidin-3-ol (100 mg, 258 μmol, 1.0 equiv), 1-bromo-3-chloro-2-cyclopropyl-5-(methoxymethoxy)benzene (90.3 mg, 310 μmol, 1.2 equiv), RuPhos (48.2 mg, 103 μmol, 0.4 equiv), 4 Å molecular sieve (10 mg), Cs$_2$CO$_3$ (252 mg, 774 μmol, 3.0 equiv) and Pd$_2$(dba)$_3$ (47.3 mg, 51.6 μmol, 0.2 equiv) in toluene (2 mL) was degassed and purged with N$_2$ for 3 times, and then the mixture was stirred at 90° C. for 8 hours under N$_2$ atmosphere. The mixture was filtered, and the filtrate was concentrated under vacuum to give a residue. The residue was purified by reversed phase flash chromatography [water (0.10% FA)/acetonitrile]. The desired fractions were collected, neutralized with solid NaHCO$_3$, and concentrated under vacuum to remove acetonitrile. The resulting mixture was extracted with ethyl acetate (2×5 mL). The combined organic layers were dried over anhydrous sodium sulfate and concentrated under vacuum to afford the title compound (27 mg, 16.7% yield, 95.5% purity) as yellow solid. LCMS (ESI, M+1): m/z=598.4.

Step B. (R)-1-(7-(3-chloro-2-cyclopropyl-5-hydroxyphenyl)-2-((hexahydro-1H-pyrrolizin-7a-yl)methoxy)-5,6,7,8-tetrahydropyrido[3,4-d]pyrimidin-4-yl)-3-methylpiperidin-3-ol: To a solution of (R)-1-(7-(3-chloro-2-cyclopropyl-5-(methoxymethoxy)phenyl)-2-((hexahydro-1H-pyrrolizin-7a-yl)methoxy)-5,6,7,8-tetrahydropyrido[3,4-d]pyrimidin-4-yl)-3-methylpiperidin-3-ol (45.0 mg, 75.2 µmol, 1.0 equiv) in MeCN (0.5 mL) was added HCl·MeOH (4 M, 1 mL). The reaction mixture was stirred at 0° C. for 1 hour. The mixture was added dropwise into ice-cold saturated NaHCO₃ solution (20 mL). Then the mixture was extracted with ethyl acetate (2×8 mL). The combined organic layers were washed with saturated brine (10 mL), dried over anhydrous sodium sulfate, and concentrated under vacuum to give a residue. The residue was purified by prep-HPLC [column: Phenomenex luna C18 150×25 mm×10 µm; A: water (FA); B: ACN, B %: 14%-44% over 10 min] to afford the title compound (28.3 mg, 66.2% yield, 97.4% purity) as yellow solid. $^1$H NMR (400 MHz, METHANOL-d4) δ=8.53 (s, 1H), 6.53 (s, 1H), 6.39 (s, 1H), 4.44-4.32 (m, 2H), 4.15-3.98 (m, 2H), 3.83-3.72 (m, 1H), 3.63 (br d, J=13.2 Hz, 1H), 3.55-3.44 (m, 2H), 3.35 (s, 1H), 3.24 (br s, 1H), 3.16-3.04 (m, 2H), 2.97-2.76 (m, 2H), 2.29-1.87 (m, 10H), 1.82-1.55 (m, 4H), 1.22 (s, 3H), 1.04-0.94 (m, 2H), 0.71-0.62 (m, 2H); LCMS [ESI, M+1]: 554.4;

Example 205

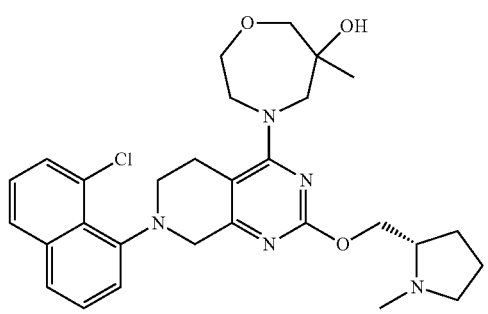 [SMILES: CN1CCC[C@H]1COc1nc2c(c(N3CCOCC(C)(O)C3)n1)CCN(c1cccc3cccc(Cl)c13)C2]

4-[7-(8-chloro-1-naphthyl)-2-[[(2S)-1-methylpyrrolidin-2-yl]methoxy]-6,8-dihydro-5H-pyrido[3,4-d]pyrimidin-4-yl]-6-methyl-1,4-oxazepan-6-ol

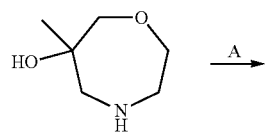

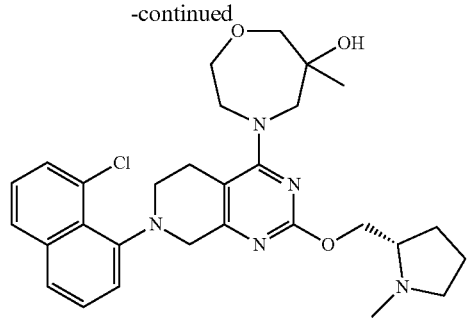

Step A. 4-[7-(8-chloro-1-naphthyl)-2-[[(2S)-1-methylpyrrolidin-2-yl]methoxy]-6,8-dihydro-5H-pyrido[3,4-d]pyrimidin-4-yl]-6-methyl-1,4-oxazepan-6-ol: A mixture of (S)-7-(8-chloronaphthalen-1-yl)-2-((1-methylpyrrolidin-2-yl)methoxy)-5,6,7,8-tetrahydropyrido[3,4-d]pyrimidin-4-yl 4-methylbenzenesulfonate (70 mg, 1.0 equiv), 6-methyl-1,4-oxazepan-6-ol (19.03 mg, 1.2 equiv), N-ethyl-N-isopropylpropan-2-amine (46.87 mg, 3.0 equiv), 4 Å molecular sieve (20 mg) in DMF (2 mL) was degassed and purged with N₂ for 3 times. The reaction was stirred at 60° C. under N₂ atmosphere until the reaction was completed. The mixture was concentrated and purified by prep-HPLC (column: Waters Xbridge 150×25 mm×5 µm; mobile phase: [water (NH₄HCO₃)-ACN]; B %: 54%-84%, 10 minutes) to afford the title compound (21.61 mg, 32% yield) as a yellow solid. $^1$H NMR (400 MHz, methanol-d4) δ=7.85-7.79 (m, 1H), 7.71-7.63 (m, 1H), 7.55-7.43 (m, 2H), 7.40-7.24 (m, 2H), 4.37-4.26 (m, 3H), 4.25-3.89 (m, 3H), 3.88-3.75 (m, 3H), 3.71-3.41 (m, 5H), 3.24-3.12 (m, 1H), 3.07 (dt, J=5.4, 9.8 Hz, 1H), 2.80-2.57 (m, 2H), 2.52-2.47 (m, 3H), 2.43-2.28 (m, 1H), 2.14-2.01 (m, 1H), 1.87-1.76 (m, 2H), 1.75-1.61 (m, 1H), 1.20-1.16 (m, 3H); LCMS (ESI, M): m/z=538.2.

Example 206

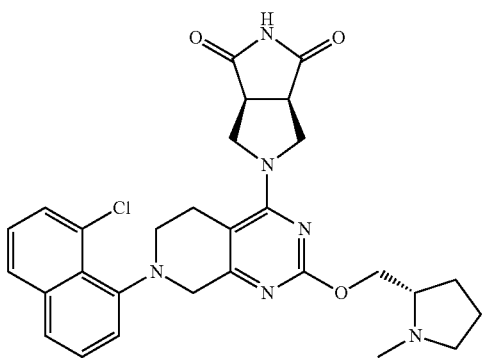 [SMILES: CN1CCC[C@H]1COc1nc2c(c(N3C[C@@H]4C(=O)NC(=O)[C@@H]4C3)n1)CCN(c1cccc3cccc(Cl)c13)C2]

(3aS,6aR)-5-[7-(8-chloro-1-naphthyl)-2-[[(2S)-1-methylpyrrolidin-2-yl]methoxy]-6,8-dihydro-5H-pyrido[3,4-d]pyrimidin-4-yl]-3a,4,6,6a-tetrahydropyrrolo[3,4-c]pyrrole-1,3-dione Synthesized according to Example 205. The title compound was obtained as yellow solid $^1$H NMR (400 MHz, methanol-d4) δ=8.56 (s, 1H), 7.84 (d, J=8.0 Hz, 1H), 7.69 (d, J=8.0 Hz, 1H), 7.54 (d, J=7.6 Hz, 1H), 7.52-7.46 (m, 1H), 7.38 (t, J=7.6 Hz, 1H), 7.32 (d, J=7.6 Hz, 1H), 4.61 (br dd, J=4.8, 10.4 Hz, 1H), 4.56-4.48 (m, 1H), 4.48-4.40 (m, 1H), 4.27 (br d, J=3.2 Hz, 1H), 4.24 (br d, J=9.2 Hz, 1H), 3.78 (br dd, J=8.0, 11.6 Hz, 1H), 3.70 (br d, J=17.2 Hz, 1H), 3.64-3.56 (m, 1H), 3.56-3.45 (m, 3H), 3.44-3.36 (m, 1H), 3.31-3.21 (m, 2H), 3.20-3.10 (m, 1H), 2.84-2.79 (m, 1H), 2.78 (s, 3H), 2.68 (br d, J=14.4 Hz, 1H), 2.32-2.19 (m, 1H), 2.06-1.93 (m, 2H), 1.92-1.82 (m, 1H); LCMS (ESI, M): m/z=547.2.

Example 207

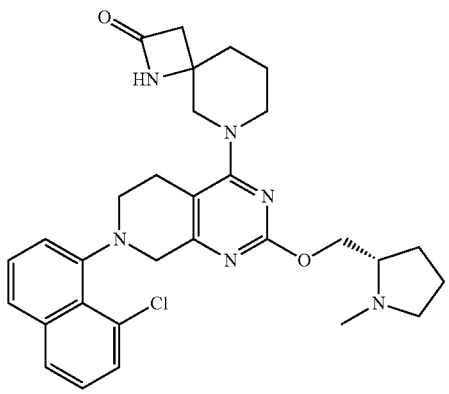 [SMILES: CN1CCC[C@H]1COc1nc2c(c(N3CCCC4(CC(=O)N4)C3)n1)CCN(c1cccc3cccc(Cl)c13)C2]

8-[7-(8-chloro-1-naphthyl)-2-[[(2S)-1-methylpyrrolidin-2-yl]methoxy]-6,8-dihydro-5H-pyrido[3,4-d]pyrimidin-4-yl]-1,8-diazaspiro[3.5]nonan-2-one Synthesized according to Example 205 except using $K_3PO_4$ as the base. The title compound was obtained as yellow solid. $^1$H NMR (400 MHz, METHANOL-$d_4$) δ=7.84 (dd, J=0.8, 8.0 Hz, 1H), 7.69 (d, J=7.6 Hz, 1H), 7.55 (dd, J=1.2, 7.6 Hz, 1H), 7.50 (t, J=7.6 Hz, 1H), 7.42-7.36 (m, 1H), 7.33 (d, J=7.2 Hz, 1H), 4.44-4.36 (m, 1H), 4.35-4.26 (m, 2H), 3.95-3.81 (m, 1H), 3.80-3.62 (m, 2H), 3.62-3.54 (m, 2H), 3.27-3.13 (m, 3H), 3.09 (td, J=4.8, 9.6 Hz, 1H), 2.91-2.61 (m, 4H), 2.51 (s, 3H), 2.36 (q, J=8.8 Hz, 1H), 2.16-2.05 (m, 1H), 2.04-1.77 (m, 6H), 1.77-1.66; LCMS (ESI, M+1): m/z=547.3.

Example 208

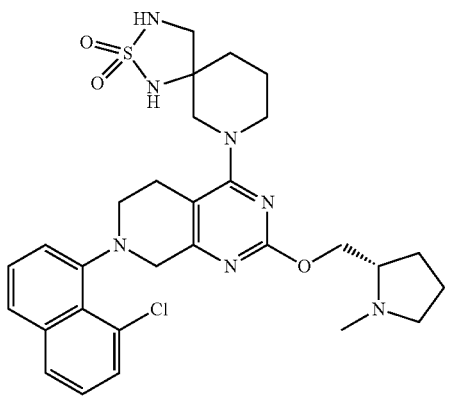 [SMILES: CN1CCC[C@H]1COc1nc2c(c(N3CCCC4(CNS(=O)(=O)N4)C3)n1)CCN(c1cccc3cccc(Cl)c13)C2]

9-[7-(8-chloro-1-naphthyl)-2-[[(2S)-1-methylpyrrolidin-2-yl]methoxy]-6,8-dihydro-5H-pyrido[3,4-d]pyrimidin-4-yl]-2λ6-thia-1,3,9-triazaspiro[4.5]decane 2,2-dioxide Synthesized according to Example 205 except using $K_3PO_4$ as the base. The title compound was obtained as yellow solid. $^1$H NMR (400 MHz, methanol-d4) δ=7.83 (dd, J=3.6, 8.0 Hz, 1H), 7.68 (dd, J=3.6, 8.0 Hz, 1H), 7.57-7.52 (m, 1H), 7.50 (td, J=4.0, 7.6 Hz, 1H), 7.38 (dt, J=2.4, 7.6 Hz, 1H), 7.36-7.30 (m, 1H), 4.45-4.38 (m, 1H), 4.38-4.28 (m, 2H), 3.97-3.83 (m, 1H), 3.78-3.69 (m, 1H), 3.69-3.63 (m, 1H), 3.62-3.53 (m, 2H), 3.53-3.36 (m, 2H), 3.27-3.15 (m, 3H), 3.11 (td, J=4.4, 9.6 Hz, 1H), 2.85-2.76 (m, 1H), 2.75-2.61 (m, 1H), 2.53 (s, 3H), 2.39 (q, J=8.8 Hz, 1H), 2.18-2.04 (m, 1H), 2.04-1.89 (m, 2H), 1.88-1.67 (m, 5H); LCMS (ESI, M+1): m/z=598.2.

Example 209

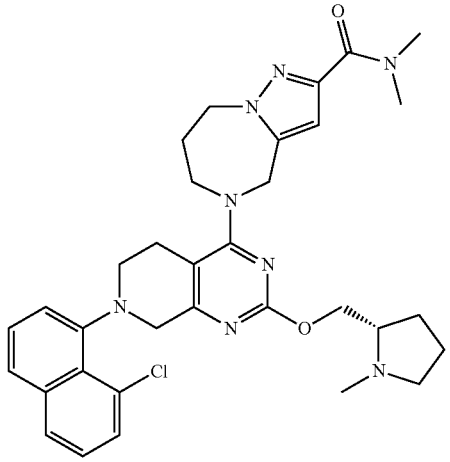 [SMILES: CN(C)C(=O)c1cc2n(n1)CCCN(c1nc(OC[C@@H]3CCCN3C)nc3c1CCN(c1cccc4cccc(Cl)c14)C3)C2]

(S)-5-(7-(8-chloronaphthalen-1-yl)-2-((1-methylpyrrolidin-2-yl)methoxy)-5,6,7,8-tetrahydropyrido[3,4-d]pyrimidin-4-yl)-N,N-dimethyl-5,6,7,8-tetrahydro-4H-pyrazolo[1,5-a][1,4]diazepine-2-carboxamide Synthesized according to Example 205 except using $K_3PO_4$ as the base. The title compound was obtained as yellow solid. $^1$H NMR (400 MHz, METHANOL-$d_4$) δ=8.48 (br s, 1H), 7.82 (br d, J=8.0 Hz, 1H), 7.68 (br d, J=8.0 Hz, 1H), 7.55-7.45 (m, 2H), 7.37 (br t, J=7.6 Hz, 1H), 7.29 (br d, J=7.2 Hz, 1H), 6.58 (s, 1H), 5.00-4.89 (m, 3H), 4.72-4.39 (m, 5H), 4.26 (br d, J=17.6 Hz, 1H), 4.19-4.02 (m, 2H), 3.84-3.49 (m, 5H), 3.18 (br d, J=10.8 Hz, 2H), 3.08 (s, 3H), 2.98 (br d, J=3.2 Hz, 3H), 2.69 (br d, J=14.4 Hz, 1H), 2.38-1.92 (m, 3H), 2.20-1.91 (m, 4H); LCMS (ESI, M+1): m/z=615.4.

Example 210

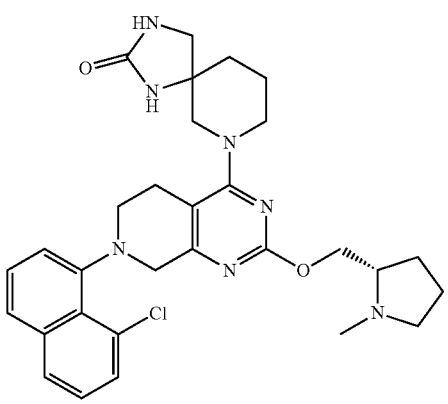 [SMILES: CN1CCC[C@H]1COc1nc2c(c(N3CCCC4(CNC(=O)N4)C3)n1)CCN(c1cccc3cccc(Cl)c13)C2]

7-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1,3,7-triazaspiro[4.5]decan-2-one Synthesized according to Example 205. The title compound was obtained as yellow solid. $^1$H NMR (400 MHz, methanol-d4) δ=7.82 (d, J=8.0 Hz, 1H), 7.67 (dd, J=2.0, 8.0 Hz, 1H), 7.56-7.45 (m, 2H), 7.40-7.28 (m, 2H), 4.43-4.20 (m, 3H), 3.77-3.62 (m, 3H), 3.62-3.44 (m, 3H), 3.28-3.24 (m, 1H), 3.23-3.11 (m, 2H), 3.10-3.03 (m, 1H), 2.79-2.61 (m, 2H), 2.49 (s, 3H), 2.34 (q, J=9.2 Hz, 1H), 2.17-1.60 (m, 9H); LCMS (ESI, M+1): m/z=562.2

Example 211

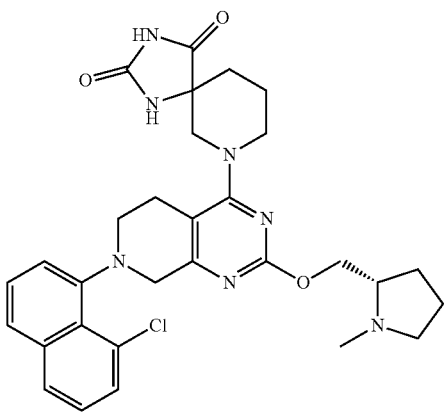 [SMILES: CN1CCC[C@H]1COc1nc2c(c(N3CCCC4(C3)NC(=O)NC4=O)n1)CCN(c1cccc3cccc(Cl)c13)C2]

9-[7-(8-chloro-1-naphthyl)-2-[[(2S)-1-methylpyrrolidin-2-yl]methoxy]-6,8-dihydro-5H-pyrido[3,4-d]pyrimidin-4-yl]-1,3,9-triazaspiro[4.5]decane-2,4-dione Synthesized according to Example 205. The title compound was obtained as white solid. $^1$H NMR (400 MHz, METHANOL-d4) δ=8.56 (s, 1H), 7.84 (d, J=8.0 Hz, 1H), 7.70 (dd, J=3.6, 7.4 Hz, 1H), 7.56-7.53 (m, 1H), 7.51 (td, J=3.6, 8.0 Hz, 1H), 7.42-7.37 (m, 1H), 7.34 (dd, J=7.6, 11.2 Hz, 1H), 4.63 (br s, 1H), 4.53-4.37 (m, 2H), 4.37-4.29 (m, 1H), 4.28-3.98 (m, 2H), 3.70 (br d, J=17.6 Hz, 1H), 3.65-3.56 (m, 1H), 3.43 (td, J=2.4, 13.2 Hz, 1H), 3.31-3.24 (m, 1H), 3.24-3.13 (m, 2H), 3.12-2.99 (m, 1H), 2.78 (br d, J=14.0 Hz, 1H), 2.71 (br d, J=4.0 Hz, 2H), 2.67 (d, J=3.2 Hz, 2H), 2.24-2.06 (m, 2H), 2.03-1.77 (m, 6H); LCMS (ESI, M+1): m/z=576.3.

Example 212

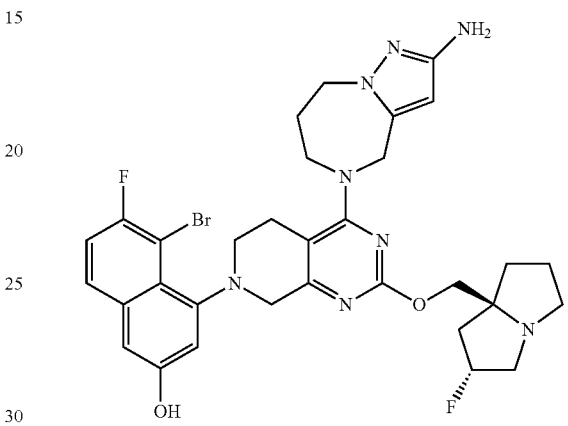

4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-bromo-6-fluoronaphthalen-2-ol

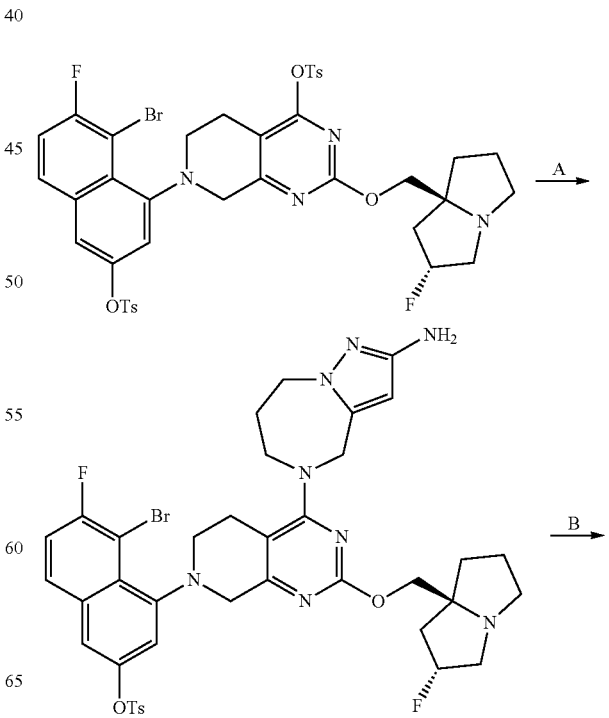

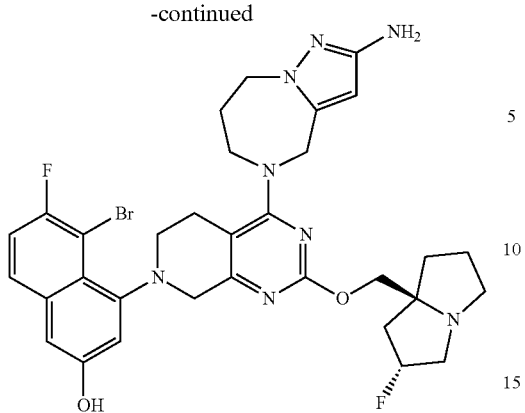

Step A. 4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-bromo-6-fluoronaphthalen-2-yl 4-methylbenzenesulfonate: To a mixture of 5-bromo-6-fluoro-4-(2-(((2R,7aS)-2-fluorohexahydro-1H-pyrrolizin-7a-yl)methoxy)-4-(tosyloxy)-5,6-dihydropyrido[3,4-d]pyrimidin-7(8H)-yl)naphthalen-2-yl 4-methylbenzenesulfonate (50 mg, 1 equiv), 5,6,7,8-tetrahydro-4H-pyrazolo[1,5-a][1,4]diazepin-2-amine (17.8 mg, 2 equiv) and 4 Å molecular sieve (20 mg) in DMF (0.5 mL) was added N-ethyl-N-isopropylpropan-2-amine (37.8 mg, 5 equiv). The mixture was stirred at 40° C. for 12 hours. The reaction mixture was filtered and purified with HPLC [0.1% FA condition] to afford the title compound (45 mg, 87% yield) as yellow solid. LCMS (ESI, M+1,): m/z=835.2.

Step B. 4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-bromo-6-fluoronaphthalen-2-ol: To a solution of 4-(4-(2-amino-7,8-dihydro-4H-pyrazolo[1,5-a][1,4]diazepin-5(6H)-yl)-2-(((2R,7aS)-2-fluorohexahydro-1H-pyrrolizin-7a-yl)methoxy)-5,6-dihydropyrido[3,4-d]pyrimidin-7(8H)-yl)-5-bromo-6-fluoronaphthalen-2-yl 4-methylbenzenesulfonate (20 mg, 1.0 equiv) in MeOH (0.5 mL) was added NaOH (19.0 mg, 20 equiv). The mixture was stirred at 25° C. for 0.5 hour. The reaction mixture was diluted with $H_2O$ (1.5 mL) and extracted with ethyl acetate (3×1.5 mL). The combined organic layers were concentrated and purified by prep-HPLC [Phenomenex luna C18 150×25 mm×10 μm; mobile phase: [water (FA)-ACN]; B %: 10%-40%, 10 min] to afford the title compound (16.5 mg, 45% yield) as pink solid. $^1$H NMR (400 MHz, METHANOL-d4) δ=7.68 (dd, J=5.6, 9.2 Hz, 1H), 7.25 (t, J=8.4 Hz, 1H), 6.97 (dd, J=2.4, 15.2 Hz, 2H), 5.38 (s, 1H), 4.79 (br d, J=4.4 Hz, 1H), 4.72-4.63 (m, 1H), 4.30-4.16 (m, 5H), 4.13-4.03 (m, 1H), 4.01-3.91 (m, 1H), 3.65 (br d, J=17.6 Hz, 1H), 3.56-3.41 (m, 4H), 3.30-3.11 (m, 4H), 2.72-2.62 (m, 1H), 2.49-2.29 (m, 2H), 2.27-2.16 (m, 2H), 2.14-1.94 (m, 4H); LCMS (ESI, M+1): m/z=681.2.

Example 213 and Example 214

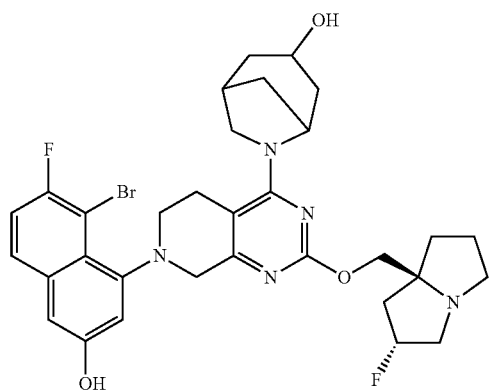 [SMILES: Oc1cc(N2CCc3c(nc(OC[C@@]45CCCN4C[C@H](F)C5)nc3N3CC4CC(O)CC3C4)C2)c2c(Br)c(F)ccc2c1]

6-(7-(8-bromo-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-6-azabicyclo[3.2.1]octan-3-ol

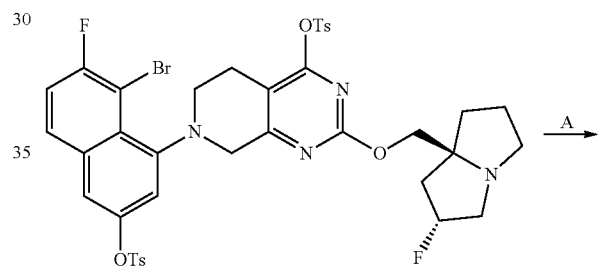

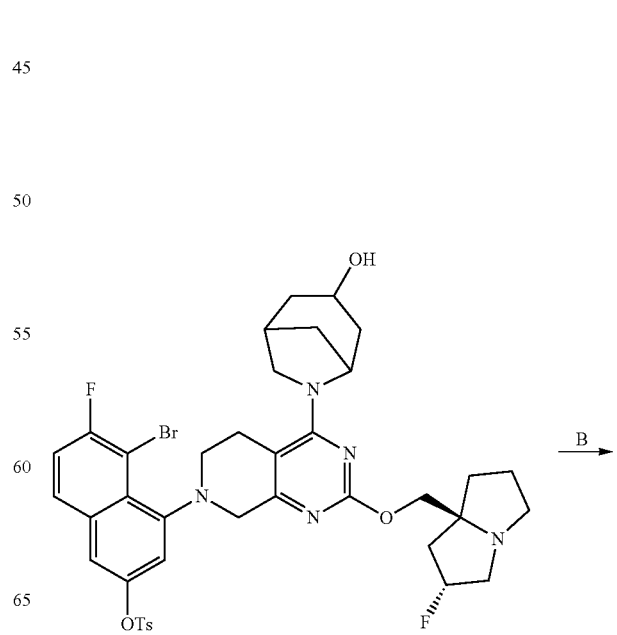

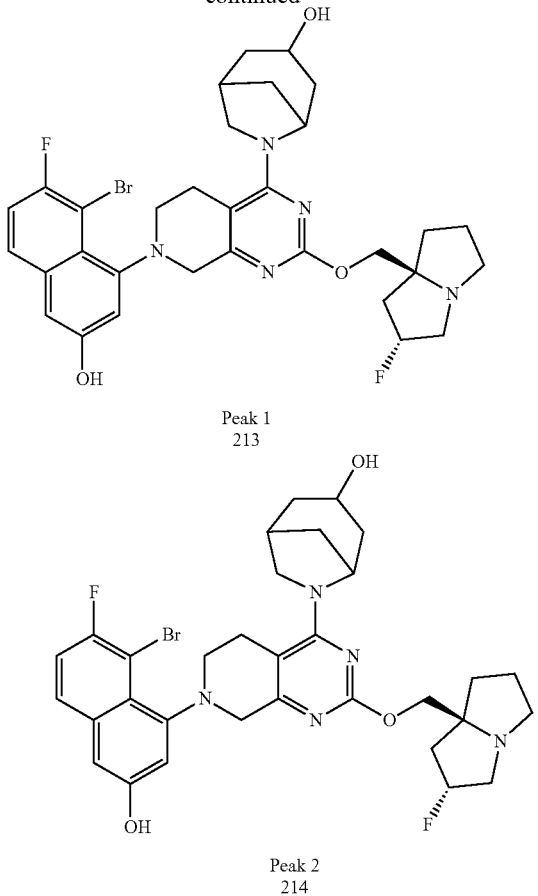

Peak 1
213

Peak 2
214

Step A. 5-bromo-6-fluoro-4-(2-(((2R,7aS)-2-fluorohexahydro-1H-pyrrolizin-7a-yl)methoxy)-4-(3-hydroxy-6-azabicyclo[3.2.1]octan-6-yl)-5,6-dihydropyrido[3,4-d]pyrimidin-7(8H)-yl)naphthalen-2-yl 4-methylbenzenesulfonate: To a solution of 5-bromo-6-fluoro-4-(2-(((2R,7aS)-2-fluorohexahydro-1H-pyrrolizin-7a-yl)methoxy)-4-(tosyloxy)-5,6-dihydropyrido[3,4-d]pyrimidin-7(8H)-yl)naphthalen-2-yl 4-methylbenzenesulfonate (40 mg, 1.0 equiv) in DMF (0.5 mL) were added N-ethyl-N-isopropylpropan-2-amine (48 mg, 8.0 equiv), 4 Å molecular sieve (5.0 mg) and 6-azabicyclo[3.2.1]octan-3-ol (8.92 mg, 1.5 equiv). The mixture was stirred at 40° C. for 12 hours. The mixture was filtered and purified by reversed phase flash chromatography [C18, 0.1% formic acid condition] to afford the title compound (45 mg) as yellow solid. LCMS (ESI, M+1): m/z=810.1.

Step B. 6-(7-(8-bromo-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-6-azabicyclo[3.2.1]octan-3-ol: To a solution of 5-bromo-6-fluoro-4-(2-(((2R,7aS)-2-fluorohexahydro-1H-pyrrolizin-7a-yl)methoxy)-4-(3-hydroxy-6-azabicyclo[3.2.1]octan-6-yl)-5,6-dihydropyrido[3,4-d]pyrimidin-7(8H)-yl) naphthalen-2-yl 4-methylbenzenesulfonate (37 mg, crude) in MeOH (0.5 mL) was added NaOH (4.0 M, 20.0 equiv). The mixture was stirred at 22° C. for 0.5 hour. The mixture was filtered and purified with reversed phase flash chromatography [C18, 0.1% formic acid condition] and prep-HPLC [Welch Xtimate C18 150×25 mm×5 μm; mobile phase: water (NH₃H₂O)-ACN; B %: 27%-57%, 8 min] to afford two peaks: peak 1/Example 213 (3.16 mg, 10% yield) as yellow solid. ¹H NMR (400 MHz, METHANOL-d₄) δ=7.69-7.60 (m, 1H), 7.22 (t, J=8.8 Hz, 1H), 7.05-6.90 (m, 2H), 5.39-5.17 (m, 1H), 4.65-4.55 (m, 1H), 4.13-3.95 (m, 4H), 4.37-3.92 (m, 2H), 3.70-3.37 (m, 3H), 3.25-3.13 (m, 4H), 3.05-2.93 (m, 2H), 2.44-2.27 (m, 1H), 2.22-2.08 (m, 2H), 2.71-2.08 (m, 1H), 2.06-1.83 (m, 6H), 1.80-1.63 (m, 2H); LCMS (ESI, M+1): m/z=656.3. Peak 2/Example 214 (3.65 mg, 12% yield) as yellow solid. ¹H NMR (400 MHz, METHANOL-d4) δ=7.66 (dd, J=5.6, 8.8 Hz, 1H), 7.23 (t, J=8.8 Hz, 1H), 7.02-6.92 (m, 2H), 5.39-5.16 (m, 1H), 4.64 (br s, 1H), 4.19-3.89 (m, 4H), 3.81-3.36 (m, 5H), 3.23-3.09 (m, 5H), 3.02-2.89 (m, 2H), 2.60 (br s, 2H), 2.22-2.07 (m, 3H), 1.95 (br d, J=7.6 Hz, 4H), 1.75-1.68 (m, 1H), 1.56-1.45 (m, 1H), 1.43-1.34 (m, 1H); LCMS (ESI, M+1): m/z=656.2.

Example 215

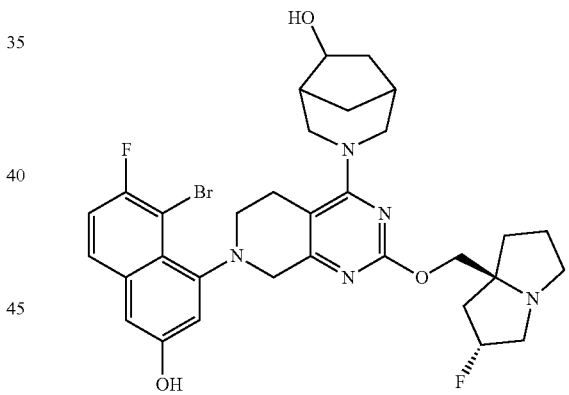

3-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.2.1]octan-6-ol Synthesized according to Example 212. The title compound was obtained as pink solid. ¹H NMR (400 MHz, METHANOL-d4) δ=7.69-7.64 (m, 1H), 7.24 (dt, J=2.4, 8.8 Hz, 1H), 7.02-6.95 (m, 2H), 5.45-5.25 (m, 1H), 4.66-4.56 (m, 1H), 4.36-4.29 (m, 1H), 4.28-4.19 (m, 3H), 4.18-4.11 (m, 1H), 3.62-3.43 (m, 3H), 3.43-3.34 (m, 3H), 3.23-3.07 (m, 3H), 3.07-2.99 (m, 1H), 2.68 (br d, J=14.4 Hz, 1H), 2.55-2.35 (m, 1H), 2.34-2.23 (m, 3H), 2.22-2.11 (m, 3H), 2.09-2.00 (m, 2H), 1.99-1.89 (m, 1H), 1.82-1.68 (m, 2H); LCMS (ESI, M+1): m/z=656.

Example 216

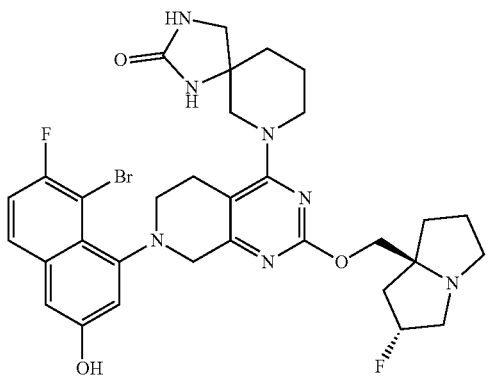 [SMILES: O=C1NCC2(CCCN(c3nc(OC[C@@]45CCCN4C[C@H](F)C5)nc4c3CCN(c3cc(O)cc5ccc(F)c(Br)c35)C4)C2)N1]

7-(7-(8-bromo-7-fluoro-3-hydroxynaphthalen-1-yl)-
2-(((2R,7aS)-2-fluorohexahydro-1H-pyrrolizin-7a-
yl)methoxy)-5,6,7,8-tetrahydropyrido[3,4-d]pyrimi-
din-4-yl)-1,3,7-triazaspiro[4.5]decan-2-one Synthesized according to Example 212. The title compound was obtained as white solid. $^1$H NMR (400 MHz, METHANOL-d4) δ=7.68 (ddd, J=3.2, 5.6, 9.0 Hz, 1H), 7.37-7.18 (m, 1H), 7.08-6.92 (m, 2H), 5.73-5.42 (m, 1H), 4.69-4.44 (m, 2H), 4.33-3.97 (m, 2H), 3.92-3.34 (m, 10H), 3.28-3.12 (m, 3H), 2.77-2.51 (m, 3H), 2.44-2.12 (m, 4H), 2.03-1.67 (m, 4H). LCMS (ESI, M+1): m/z=684.1.

Example 217

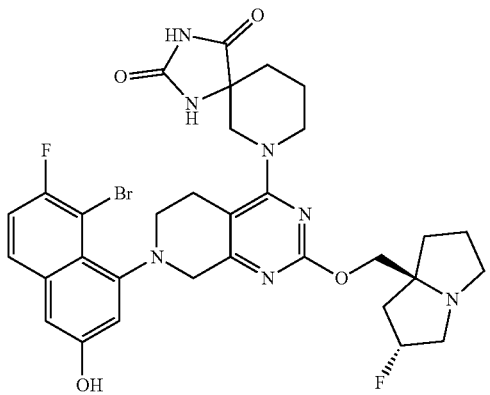 [SMILES: O=C1NC(=O)C2(CCCN(c3nc(OC[C@@]45CCCN4C[C@H](F)C5)nc4c3CCN(c3cc(O)cc5ccc(F)c(Br)c35)C4)C2)N1]

7-(7-(8-bromo-7-fluoro-3-hydroxynaphthalen-1-yl)-
2-(((2R,7aS)-2-fluorohexahydro-1H-pyrrolizin-7a-
yl)methoxy)-5,6,7,8-tetrahydropyrido[3,4-d]pyrimi-
din-4-yl)-1,3,7-triazaspiro[4.5]decane-2,4-dione Synthesized according to Example 212. The title compound was obtained as white solid. $^1$H NMR (400 MHz, METHANOL-d4) δ=7.67 (dd, J=5.6, 9.2 Hz, 1H), 7.24 (t, J 8.8 Hz, 1H), 7.05-6.94 (m, 2H), 5.52-5.25 (m, 1H), 4.40-4.22 (m, 3H), 4.17-3.95 (m, 2H), 3.67-3.48 (m, 3H), 3.45-3.37 (m, 3H), 3.20-2.98 (m, 3H), 2.79-2.65 (m, 1H), 2.49-2.27 (m, 2H), 2.26-2.01 (m, 5H), 2.01-1.76 (m, 4H); LCMS (ESI, M+1): m/z=698.1.

Example 218

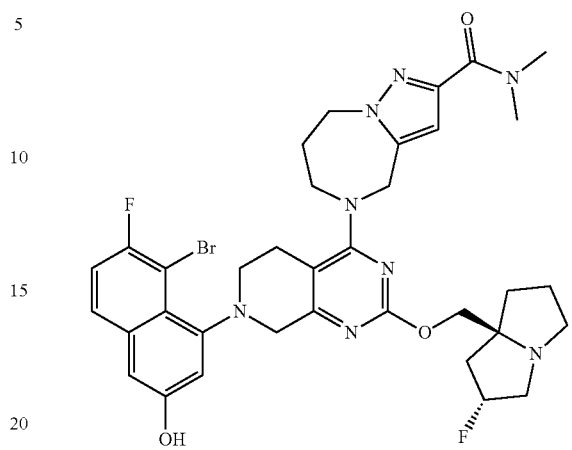

5-(7-(8-bromo-7-fluoro-3-hydroxynaphthalen-1-yl)-
2-(((2R,7aS)-2-fluorohexahydro-1H-pyrrolizin-7a-
yl)methoxy)-5,6,7,8-tetrahydropyrido[3,4-d]pyrimi-
din-4-yl)-N,N-dimethyl-5,6,7,8-tetrahydro-4H-
pyrazolo[1,5-a][1,4]diazepine-2-carboxamide Synthesized according to Example 212. The title compound was obtained as yellow solid. $^1$H NMR (400 MHz, METHANOL-d4) δ=7.67 (dd, J=5.6, 9.2 Hz, 1H), 7.31-7.15 (m, 1H), 6.98 (br d, J=3.2 Hz, 2H), 6.61 (d, J=2.4 Hz, 1H), 5.53-5.28 (m, 1H), 5.04-4.93 (m, 1H), 4.57-4.47 (m, 2H), 4.32-4.14 (m, 4H), 4.10-3.99 (m, 1H), 3.65-3.44 (m, 5H), 3.37 (br s, 4H), 3.23-3.12 (m, 3H), 3.08 (s, 3H), 2.75-2.63 (m, 1H), 2.51-1.90 (m, 5H), 2.15-1.90 (m, 4H); LCMS (ESI, M+1): m/z=737.1.

Example 219

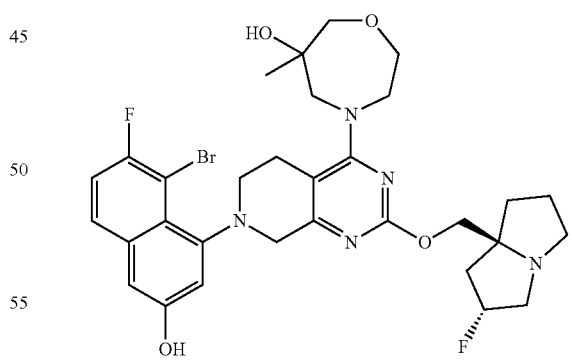

4-(7-(8-bromo-7-fluoro-3-hydroxynaphthalen-1-yl)-
2-(((2R,7aS)-2-fluorohexahydro-1H-pyrrolizin-7a-
yl)methoxy)-5,6,7,8-tetrahydropyrido[3,4-d]pyrimi-
din-4-yl)-6-methyl-1,4-oxazepan-6-ol Synthesized according to Example 212. The title compound was obtained as white solid. $^1$H NMR (400 MHz, METHANOL-d4) δ=8.54 (s, 5H), 7.74-7.60 (m, 1H), 7.24

(dt, J=5.6, 8.6 Hz, 1H), 7.05-6.86 (m, 2H), 5.48-5.20 (m, 1H), 4.33-4.19 (m, 2H), 4.19-4.10 (m, 2H), 4.09-3.92 (m, 2H), 3.91-3.70 (m, 3H), 3.69-3.59 (m, 1H), 3.59-3.49 (m, 3H), 3.49-3.43 (m, 1H), 3.42-3.34 (m, 2H), 3.26-3.02 (m, 3H), 2.75-2.56 (m, 1H), 2.43-2.29 (m, 1H), 2.29-2.21 (m, 1H), 2.17-2.09 (m, 1H), 2.08-1.97 (m, 2H), 1.96-1.84 (m, 1H), 1.18 (dd, J=2.0, 5.9 Hz, 3H); LCMS (ESI, M+1): m/z=660.

Example 220

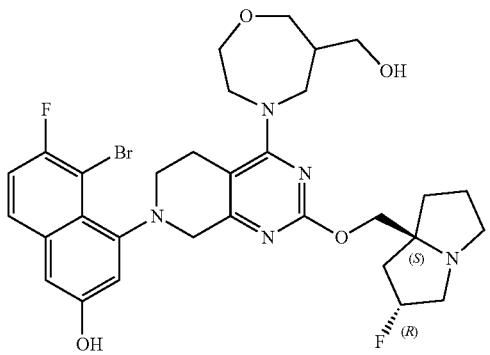

5-bromo-6-fluoro-4-(2-(((2R,7aS)-2-fluorohexahydro-1H-pyrrolizin-7a-yl)methoxy)-4-(6-(hydroxymethyl)-1,4-oxazepan-4-yl)-5,6-dihydropyrido[3,4-d]pyrimidin-7(8H)-yl)naphthalen-2-ol Synthesized according to Example 212. The title compound was obtained as yellow solid. $^1$H NMR (400 MHz, METHANOL-d4) δ=7.73-7.63 (m, 1H), 7.24 (t, J=8.8 Hz, 1H), 7.02-6.95 (m, 2H), 5.59-5.18 (m, 1H), 4.55-4.01 (m, 6H), 3.97-3.88 (m, 1H), 3.84-3.75 (m, 2H), 3.73-3.62 (m, 2H), 3.59-3.48 (m, 4H), 3.46-3.37 (m, 3H), 3.24-3.08 (m, 3H), 2.70 (br d, J=13.6 Hz, 1H), 2.50-2.39 (m, 1H), 2.35-2.29 (m, 1H), 2.22 (br s, 2H), 2.12-1.92 (m, 3H); LCMS (ESI, M+1): m/z=660.3.

Example 221

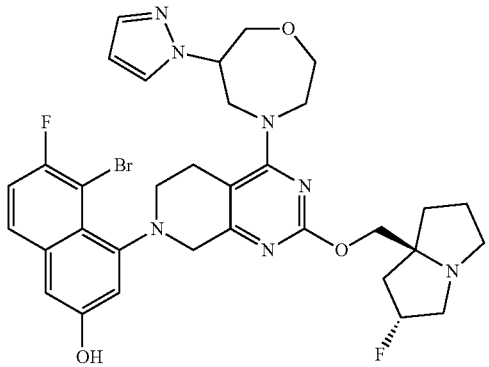 [SMILES: Oc1cc(N2CCc3c(nc(OC[C@@]45CCCN4C[C@H](F)C5)nc3N3CCOCC(n4cccn4)C3)C2)c2c(Br)c(F)ccc2c1]

4-(4-(6-(1H-pyrazol-1-yl)-1,4-oxazepan-4-yl)-2-(((2R,7aS)-2-fluorotetrahydro-1H-pyrrolizin-7a(5H)-yl)methoxy)-5,8-dihydropyrido[3,4-d]pyrimidin-7(6H)-yl)-5-bromo-6-fluoronaphthalen-2-ol Synthesized according to Example 212. The title compound was obtained as yellow solid. $^1$H NMR (400 MHz, METHANOL-d$_4$) δ=7.88-7.80 (m, 1H), 7.73-7.64 (m, 1H), 7.54 (s, 1H), 7.26 (t, J=8.4 Hz, 1H), 7.07-6.92 (m, 2H), 6.36 (s, 1H), 5.68-5.46 (m, 1H), 5.22-5.06 (m, 1H), 4.67-4.42 (m, 3H), 4.35-4.20 (m, 2H), 4.20-4.09 (m, 2H), 4.07-3.97 (m, 2H), 3.97-3.91 (m, 2H), 3.91-3.84 (m, 3H), 3.83-3.73 (m, 1H), 3.64-3.57 (m, 1H), 3.51-3.42 (m, 1H), 3.30-3.20 (m, 1H), 3.20-3.10 (m, 1H), 2.83-2.69 (m, 1H), 2.68-2.47 (m, 2H), 2.45-2.29 (m, 3H), 2.27-2.07 (m, 1H); LCMS (ESI, M+1): m/z=696.1.

Example 222

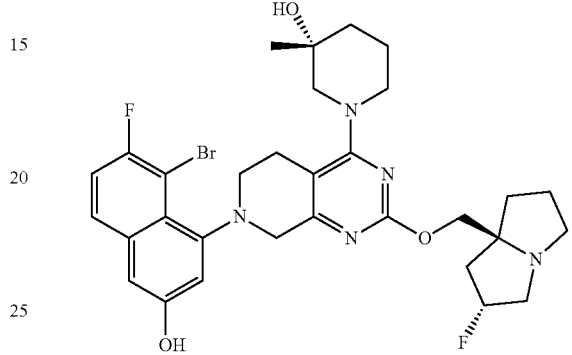

(R)-1-(7-(8-bromo-7-fluoro-3-hydroxynaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3-methylpiperidin-3-ol Synthesized according to Example 212. The title compound was obtained as yellow solid. $^1$H NMR (400 MHz, METHANOL-d4) δ=7.73-7.64 (m, 1H), 7.26 (t, J=8.4 Hz, 1H), 7.04-6.97 (m, 2H), 5.53-5.31 (m, 1H), 4.41-4.22 (m, 3H), 3.76-3.39 (m, 8H), 3.13 (br d, J=0.8 Hz, 3H), 2.78-2.61 (m, 1H), 2.52-2.31 (m, 2H), 2.27-1.96 (m, 5H), 1.93-1.60 (m, 4H), 1.30-1.21 (m, 3H); LCMS (ESI, M+1): m/z=644.1.

Example 223

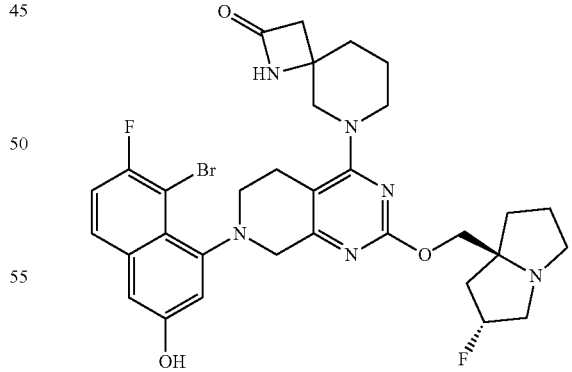

6-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,6-diazaspiro[3.5]nonan-2-one Synthesized according to Example 212. The title compound was obtained as white solid. $^1$H NMR (400 MHz, METHANOL-d4) δ=7.71-7.66 (m, 1H), 7.26 (t, J=8.8 Hz, 1H), 7.06-6.95 (m, 2H), 5.40-5.19 (m, 1H), 4.32-4.04 (m, 3H), 3.99-3.47 (m, 6H), 3.27-3.13 (m, 5H), 3.04-2.97 (m, 1H), 2.89-2.63 (m, 3H), 2.36-2.07 (m, 3H), 2.05-1.78 (m, 7H). LCMS (ESI, M+1): m/z=669.

Example 224

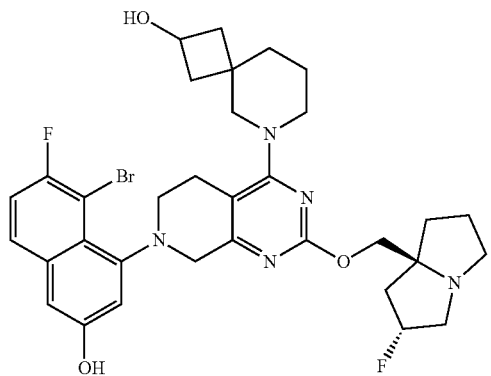 [SMILES: Oc1cc(N2CCc3c(nc(OC[C@@]45CCCN4C[C@H](F)C5)nc3N3CCCC4(CC(O)C4)C3)C2)c2c(Br)c(F)ccc2c1]

6-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-6-azaspiro[3.5]nonan-2-ol Synthesized according to Example 212. $^1$H NMR (400 MHz, METHANOL-d4) δ=7.69 (dd, J=5.6, 8.8 Hz, 1H), 7.31-7.22 (m, 1H), 7.01 (s, 2H), 5.61-5.25 (m, 1H), 4.43-4.23 (m, 4H), 3.88-3.76 (m, 1H), 3.71-3.65 (m, 2H), 3.60-3.45 (m, 5H), 3.27-3.16 (m, 3H), 2.68-2.33 (m, 4H), 2.29-1.98 (m, 6H), 1.89-1.61 (m, 6H); LCMS (ESI, M+1): m/z=670.2.

Example 225

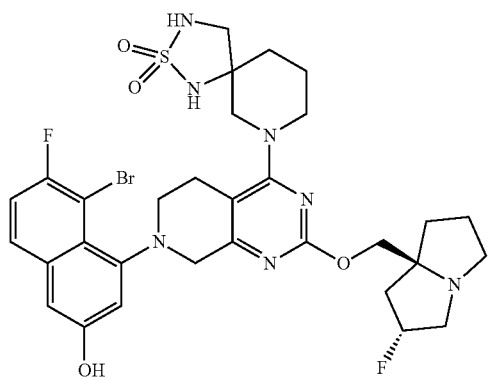 [SMILES: O=S1(=O)NCC2(CCCN(c3nc(OC[C@@]45CCCN4C[C@H](F)C5)nc4c3CCN(c3cc(O)cc5ccc(F)c(Br)c35)C4)C2)N1]

7-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-2-thia-1,3,7-triazaspiro[4.5]decane 2,2-dioxide Synthesized according to Example 212. The title compound was obtained as yellow solid. $^1$H NMR (400 MHz, METHANOL-d$_4$) δ=7.64 (td, J=5.6, 9.2 Hz, 1H), 7.22 (dt, J=4.0, 8.8 Hz, 1H), 7.05-6.88 (m, 2H), 5.39-5.17 (m, 1H), 4.25 (br d, J=17.6 Hz, 1H), 4.18-4.02 (m, 2H), 4.00-3.77 (m, 1H), 3.59 (br d, J=10.0 Hz, 1H), 3.54 (br dd, J=7.2, 11.6 Hz, 2H), 3.51-3.44 (m, 1H), 3.44-3.33 (m, 2H), 3.29-3.19 (m, 3H), 3.18-3.08 (m, 3H), 3.04-2.94 (m, 1H), 2.71-2.57 (m, 1H), 2.40-2.07 (m, 3H), 2.06-1.64 (m, 7H); LCMS (ESI, M+1): m/z=720.3.

Example 226

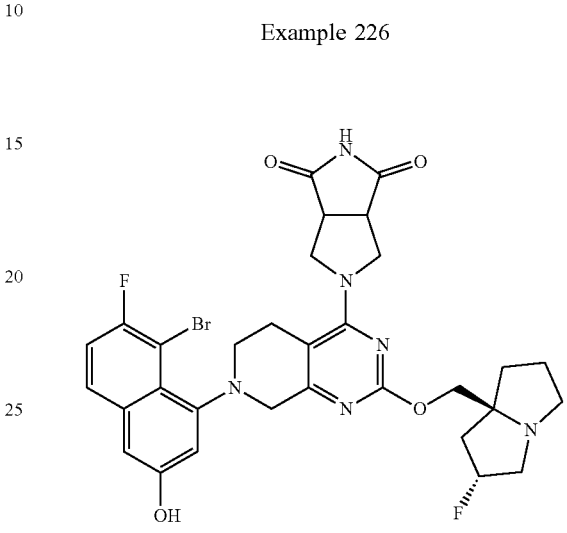

5-(7-(8-bromo-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione Synthesized according to Example 212. The title compound was obtained as yellow solid. $^1$H NMR (400 MHz, METHANOL-d4) δ=7.73-7.62 (m, 1H), 7.24 (br t, J=8.4 Hz, 1H), 6.99 (s, 2H), 5.60-5.21 (m, 1H), 4.66-4.60 (m, 1H), 4.41-4.14 (m, 4H), 3.81-3.72 (m, 1H), 3.70-3.46 (m, 8H), 3.27-3.11 (m, 3H), 2.70 (br d, J=14.5 Hz, 1H), 2.56-2.30 (m, 2H), 2.28-1.95 (m, 4H); LCMS (ESI, M+1): m/z=669.

Example 227

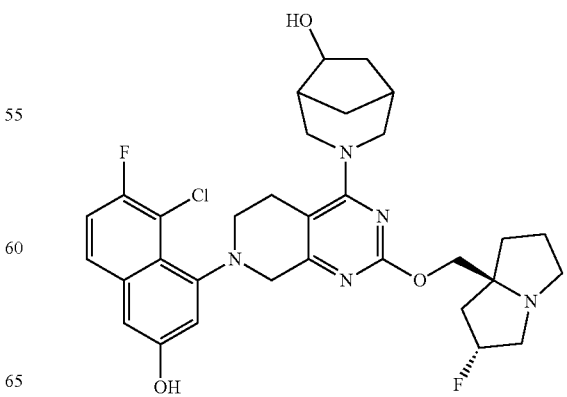

3-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.2.1]octan-6-ol

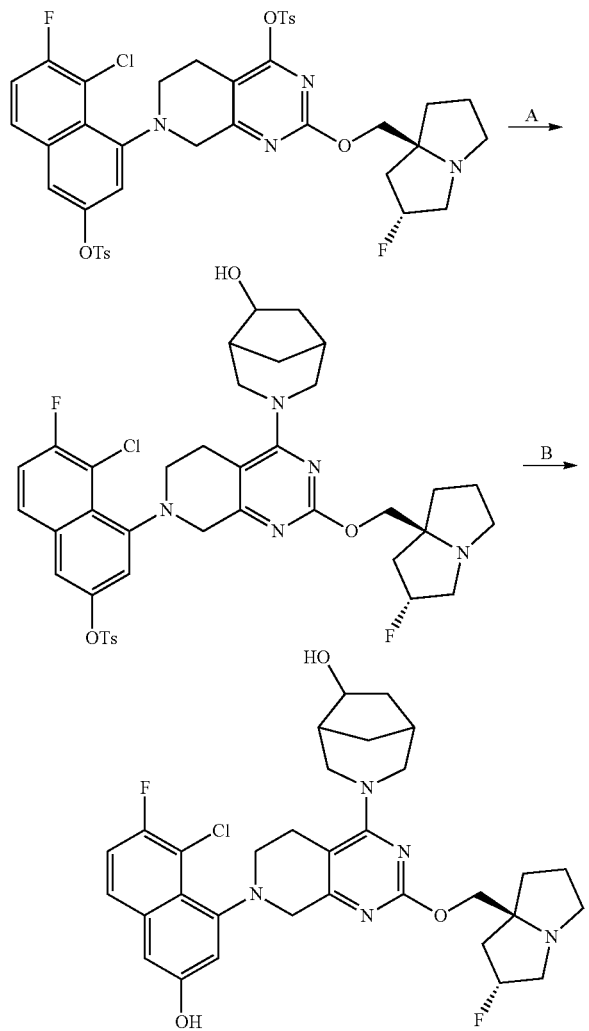

Step A. 5-chloro-6-fluoro-4-(2-(((2R,7aS)-2-fluorotetrahydro-1H-pyrrolizin-7a(5H)-yl)methoxy)-4-(6-hydroxy-3-azabicyclo[3.2.1]octan-3-yl)-5,8-dihydropyrido[3,4-d]pyrimidin-7(6H)-yl)naphthalen-2-yl 4-methylbenzenesulfonate: To a solution of 5-chloro-6-fluoro-4-(2-(((2R,7aS)-2-fluorotetrahydro-1H-pyrrolizin-7a(5H)-yl)methoxy)-4-(tosyloxy)-5,8-dihydropyrido[3,4-d]pyrimidin-7(6H)-yl)naphthalen-2-yl 4-methylbenzenesulfonate (110 mg, 1 equiv) and 3-azabicyclo[3.2.1]octan-6-ol (66.6 mg, crude, HCl) in DMF (0.5 mL) were added N-ethyl-N-isopropylpropan-2-amine (175 mg, 10 equiv) and 4 Å molecular sieve (5 mg). The mixture was stirred at 40° C. until reaction was completed. The residue was purified by reversed phase flash chromatography [C18, 0.1% formic acid] to afford the title compound (80 mg, 77% yield) as white solid. LCMS (ESI, M+1): m/z=766.2.

Step B 3-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3-azabicyclo[3.2.1]octan-6-ol: To a solution of 5-chloro-6-fluoro-4-(2-(((2R,7aS)-2-fluorotetrahydro-1H-pyrrolizin-7a(5H)-yl)methoxy)-4-(6-hydroxy-3-azabicyclo[3.2.1]octan-3-yl)-5,8-dihydropyrido[3,4-d]pyrimidin-7(6H)-yl)naphthalen-2-yl 4-methylbenzenesulfonate (50 mg, 1 equiv) in MeOH (0.5 mL) was added NaOH (26.1 mg, 10 equiv). The mixture was stirred at 25° C. for 20 minutes. The mixture was purified by prep-HPLC (column: Phenomenex luna C18 150×25 mm×10 μm; mobile phase A: water (FA), B: ACN; B %: 15%-45%, 10 min) afford the title compound (5.58 mg, 13% yield) as a yellow solid. $^1$H NMR (400 MHz, METHANOL-d4) δ=7.64 (br dd, J=6.0, 7.6 Hz, 1H), 7.29 (br t, J=8.8 Hz, 1H), 6.97 (br s, 2H), 5.56-5.36 (m, 1H), 4.69-4.48 (m, 1H), 4.44-3.84 (m, 5H), 3.74-3.48 (m, 5H), 3.45-3.36 (m, 1H), 3.30-3.18 (m, 2H), 3.16-3.01 (m, 2H), 2.97-2.67 (m, 1H), 2.60-2.35 (m, 2H), 2.34-2.12 (m, 6H), 2.11-1.99 (m, 1H), 1.86-1.69 (m, 2H), 1.62-1.29 (m, 1H). LCMS (ESI, M+1): m/z=612.3.

Example 228

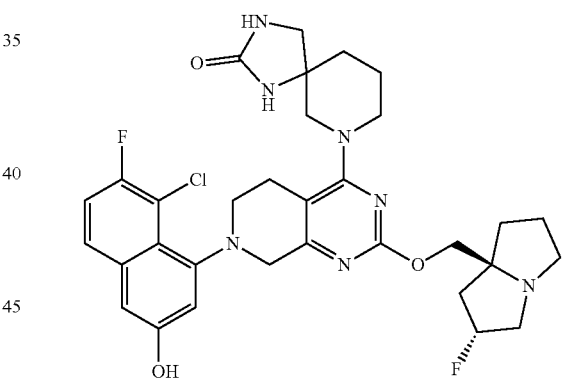

7-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-1,3,7-triazaspiro[4.5]decan-2-one Synthesized according to Example 212. The title compound was obtained as yellow solid. $^1$H NMR (400 MHz, METHANOL-d4) δ=7.62 (dd, J=5.6, 9.1 Hz, 1H), 7.27 (t, J=8.8 Hz, 1H), 6.97-6.88 (m, 2H), 5.40-5.15 (m, 1H), 4.27 (dd, J=8.8, 17.3 Hz, 1H), 4.22-4.02 (m, 2H), 3.76-3.58 (m, 3H), 3.57-3.48 (m, 2H), 3.44-3.33 (m, 1H), 3.29-3.07 (m, 7H), 3.03-2.95 (m, 1H), 2.72-2.61 (m, 1H), 2.35-2.14 (m, 2H), 2.14-2.06 (m, 1H), 2.01-1.69 (m, 7H); LCMS (ESI, M+1): m/z=640.2.

Example 229

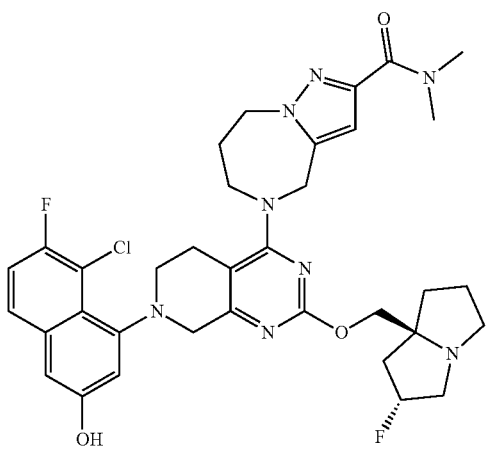 [SMILES: CN(C)C(=O)c1cc2n(n1)CCCN(c1nc(OC[C@@]34CCCN3C[C@H](F)C4)nc3c1CCN(c1cc(O)cc4ccc(F)c(Cl)c14)C3)C2]

5-(7-(8-chloro-7-fluoro-3-hydroxynaphthalen-1-yl)-
2-(((2R,7aS)-2-fluorohexahydro-1H-pyrrolizin-7a-
yl)methoxy)-5,6,7,8-tetrahydropyrido[3,4-d]pyrimi-
din-4-yl)-N,N-dimethyl-5,6,7,8-tetrahydro-4H-
pyrazolo[1,5-a][1,4]diazepine-2-carboxamide Synthesized according to Example 212. The title compound was obtained as yellow solid. $^1$H NMR (400 MHz, METHANOL-d4) δ=7.64 (dd, J=5.6, 9.2 Hz, 1H), 7.29 (t, J=8.8 Hz, 1H), 7.01-6.91 (m, 2H), 6.60 (d, J=1.6 Hz, 1H), 5.53-5.15 (m, 1H), 5.03-4.93 (m, 1H), 4.60-4.49 (m, 2H), 4.29-4.10 (m, 4H), 4.09-3.98 (m, 1H), 3.76-3.34 (m, 5H), 3.33-3.27 (m, 4H), 3.18-3.06 (m, 5H), 2.69 (br d, J=14.8 Hz, 1H), 2.43-1.82 (m, 9H). LCMS (ESI, M+1): m/z=693.3.

Example 230

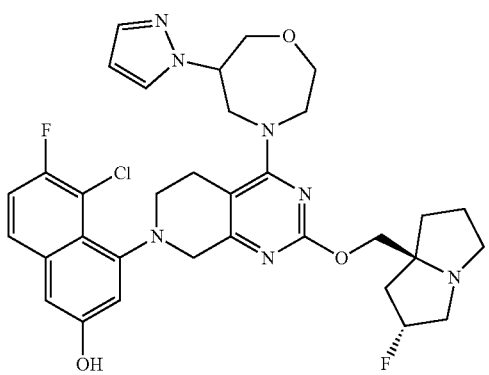 [SMILES: Oc1cc(N2CCc3c(nc(OC[C@@]45CCCN4C[C@H](F)C5)nc3N3CCOCC(n4cccn4)C3)C2)c2c(Cl)c(F)ccc2c1]

4-(4-(6-(1H-pyrazol-1-yl)-1,4-oxazepan-4-yl)-2-
(((2R,7aS)-2-fluorohexahydro-1H-pyrrolizin-7a-yl)
methoxy)-5,6-dihydropyrido[3,4-d]pyrimidin-7(8H)-
yl)-5-chloro-6-fluoronaphthalen-2-ol Synthesized according to Example 212. The title compound was obtained as yellow solid. $^1$H NMR (400 MHz, METHANOL-d$_4$) δ=7.87-7.80 (m, 1H), 7.69-7.60 (m, 1H), 7.57-7.50 (m, 1H), 7.30 (t, J=8.8 Hz, 1H), 7.05-6.91 (m, 2H), 6.42-6.31 (m, 1H), 5.69-5.47 (m, 1H), 5.21-5.03 (m, 1H), 4.70-4.46 (m, 3H), 4.37-4.21 (m, 2H), 4.20-4.08 (m, 2H), 4.08-3.92 (m, 4H), 3.91-3.65 (m, 4H), 3.64-3.51 (m, 1H), 3.50-3.40 (m, 1H), 3.29-3.19 (m, 1H), 3.18-3.06 (m, 1H), 2.81-2.71 (m, 1H), 2.71-2.61 (m, 1H), 2.61-2.52 (m, 1H), 2.43-2.28 (m, 3H), 2.27-2.09 (m, 1H); LCMS (ESI, M+1): m/z=652.4.

Example 231

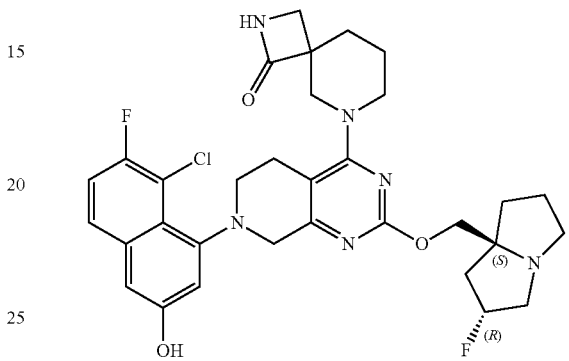

6-(7-(8-chloro-7-fluoro-3-hydroxynaphthalen-1-yl)-
2-(((2R,7aS)-2-fluorotetrahydro-1H-pyrrolizin-7a
(5H)-yl)methoxy)-5,6,7,8-tetrahydropyrido[3,4-d]
pyrimidin-4-yl)-2,6-diazaspiro[3.5]nonan-1-one Synthesized according to Example 212. The title compound was obtained as white solid. $^1$H NMR (400 MHz, METHANOL-d4) δ=7.71-7.63 (m, 1H), 7.31 (t, J=8.8 Hz, 1H), 7.06-6.92 (m, 2H), 5.69-5.46 (m, 1H), 4.67-4.51 (m, 2H), 4.32 (br d, J=17.6 Hz, 1H), 4.21-3.83 (m, 6H), 3.83-3.72 (m, 1H), 3.71-3.40 (m, 4H), 3.25-3.11 (m, 3H), 2.79-2.56 (m, 3H), 2.47-2.28 (m, 3H), 2.26-1.82 (m, 5H); LCMS (ESI, M+1): m/z=625.3.

Example 232

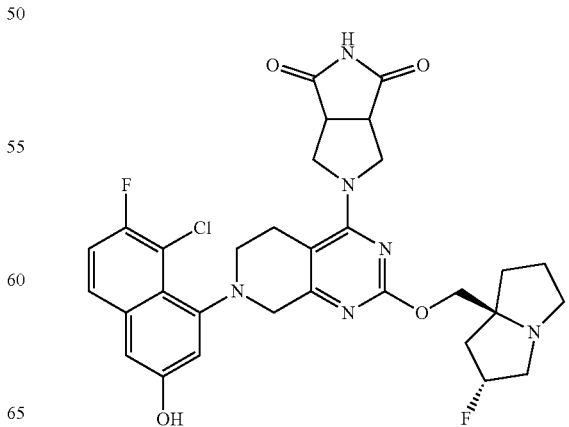

5-(7-(8-chloro-7-fluoro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)tetrahydropyrrolo[3,4-c]pyrrole-1,3(2H,3aH)-dione Synthesized according to Example 212. The title compound was obtained as white solid. $^1$H NMR (400 MHz, METHANOL-d4) δ=7.65 (dd, J=5.6, 8.8 Hz, 1H), 7.30 (t, J=8.8 Hz, 1H), 6.99 (s, 2H), 5.69-5.46 (m, 1H), 4.68-4.50 (m, 3H), 4.37-4.20 (m, 2H), 4.02-3.93 (m, 1H), 3.95-3.85 (m, 3H), 3.78-3.66 (m, 2H), 3.65-3.53 (m, 3H), 3.47 (dt, J=5.6, 10.4 Hz, 1H), 3.28 (br d, J=1.6 Hz, 1H), 3.24-3.11 (m, 1H), 2.80 (br d, J=14.4 Hz, 1H), 2.69 (br t, J=4.4 Hz, 2H), 2.47-2.30 (m, 3H), 2.26-2.12 (m, 1H); LCMS (ESI, M+1): m/z=625.1.

Example A

KRas Binding Assay

This Example illustrates that exemplary compounds of the present invention bind to KRas and are capable of displacing a labeled tracer ligand occupying the KRas binding site. KRaS$^{WT}$, KRas$^{G12A}$, KRas$^{G12C}$, KRas$^{G12D}$, KRas$^{G12R}$, KRas$^{G12S}$, KRas$^{G12V}$, KRas$^{G13D}$, or KRas$^{Q61H}$ was used in the assay.

The ability of a compound to bind to KRas was measured using a TR-FRET displacement assay. Biotinylated KRas (corresponding to amino acids 1-169, produced at Accelegan Inc.) was incubated with custom made Cy5 labelled tracer, terbium streptavidin (Cisbio Inc.) and compound (1% DMSO final) in buffer (50 mM HEPES, pH 7.5, 5 mM MgCl$_2$, 0.005% Tween-20 and 1 mM DTT). After a 60-minute incubation at room temperature, the reaction was measured using a BMG LABTECH CLARIO star Plus via TR-FRET. 100 percent of control (POC) is determined by using a DMSO control and 0 POC is determined using a concentration of control compound that completely inhibits binding of the tracer to KRas. The POC values were fit to a 4-parameter IC$_{50}$ equation and the IC$_{50}$ value reported.

TABLE 2

Binding to KRas (IC$_{50}$ nM) by Exemplary Compounds of Formula (I)

| Ex. No. | G12D | G12V | G12R | G12A | G12S | G12C | WT | G13D | Q61H |
|---|---|---|---|---|---|---|---|---|---|
| 1 | ≤2 | ≤2 | ≤2 | ≤2 | ≤2 | ≤2 | ≤2 | ≤2 | ≤2 |
| 2 | ≤2 | ≤2 | ≤2 | ≤2 | ≤2 | ≤2 | ≤2 | ≤2 | ≤2 |
| 3 | 16 | 17 | 25 | | | | | | |
| 4 | 97 | 90 | 127 | | | | | | |
| 5 | 19070 | 7652 | 8070 | | | | | | |
| 6 | 310 | 118 | 71 | 86 | 100 | 88 | 104 | 159 | 132 |
| 7 | 121 | 68 | 50 | 92 | 107 | 89 | 143 | 143 | 173 |
| 8 | 43 | 137 | 102 | 316 | 175 | 139 | 271 | 628 | 567 |
| 9 | 192 | 165 | 168 | 128 | 154 | 115 | 54 | 66 | 76 |
| 10 | 67 | 81 | 74 | 169 | 101 | 81 | 171 | 375 | 291 |
| 11 | 22 | 18 | 42 | 45 | 15 | 41 | 51 | 42 | 50 |
| 12 | 3 | ≤2 | ≤2 | ≤2 | ≤2 | ≤2 | ≤2 | ≤2 | ≤2 |
| 13 | 290 | 73 | 99 | 51 | 70 | 82 | 41 | 40 | 57 |
| 14 | 256 | 112 | 233 | 145 | 171 | 173 | 119 | 118 | 135 |
| 15 | 126 | 103 | 144 | | | | | | |
| 16 | 63 | 18 | 28 | 45 | 45 | 37 | 66 | 65 | 55 |
| 17 | 26 | ≤2 | ≤2 | | | | | | |
| 18 | ≤2 | ≤2 | ≤2 | | | | | | |
| 19 | 26 | 6 | 4 | 4 | 9 | 5 | 8 | 11 | 9 |
| 20 | ≤2 | ≤2 | ≤2 | | | | | | |
| 21 | ≤2 | ≤2 | ≤2 | | | | | | |
| 22 | 68 | 71 | 123 | 93 | 89 | 72 | 105 | 101 | 95 |
| 23 | 69 | 5 | 4 | 9 | 12 | 7 | 36 | 42 | 38 |
| 24 | ≤2 | ≤2 | ≤2 | | | | | | |
| 25 | 3 | 3 | 4 | | | | | | |
| 26 | 110 | 4 | 5 | 7 | 10 | 7 | 24 | 34 | 22 |
| 27 | ≤2 | ≤2 | ≤2 | | | | | | |
| 28 | ≤2 | ≤2 | ≤2 | | | | | | |
| 29 | ≤2 | ≤2 | ≤2 | | | | | | |
| 30 | ≤2 | ≤2 | ≤2 | | | | | | |
| 31 | 31 | ≤2 | ≤2 | | | | | | |
| 32 | ≤2 | ≤2 | 3 | | | | | | |
| 33 | 5 | ≤2 | ≤2 | | | | | | |
| 34 | ≤2 | ≤2 | ≤2 | | | | | | |
| 35 | 7 | ≤2 | ≤2 | | | | | | |
| 36 | 5 | ≤2 | 5 | | | | | | |
| 37 | 479 | 221 | 168 | | | | 214 | | |
| 38 | ≤2 | 204 | 485 | | | | 445 | | |
| 39 | 7110 | 221 | 239 | 425 | 592 | 317 | 1366 | 1530 | 1637 |
| 40 | 2371 | 155 | 51 | 115 | 158 | 63 | 566 | 1030 | 854 |
| 41 | 1300 | 206 | 245 | 452 | 255 | 520 | 543 | 583 | 685 |
| 42 | 223 | 160 | 276 | 175 | 190 | 263 | 127 | 128 | 157 |
| 43 | 552 | 271 | 198 | | | 271 | | | |
| 44 | 162 | 200 | 308 | 202 | 202 | 232 | 191 | 163 | 226 |
| 45 | 7870 | 394 | 354 | 922 | 1128 | 328 | 7538 | 3967 | 4409 |
| 46 | 6753 | 232 | 277 | 448 | 611 | 401 | 1822 | 2857 | 2231 |
| 47 | 222 | 87 | 61 | 82 | 86 | 65 | 137 | 179 | 172 |
| 48 | 192 | 94 | 141 | 101 | 124 | 82 | 159 | 80 | 214 |
| 49 | 465 | 184 | 167 | 317 | 364 | 273 | 579 | 662 | 703 |
| 50 | 219 | 342 | 284 | 569 | 330 | 299 | 613 | 800 | 808 |
| 51 | 309 | 652 | 492 | 1257 | 669 | 564 | 1373 | 2030 | 1930 |
| 52 | 1234 | 348 | 723 | 1275 | 584 | 662 | 2217 | 1153 | 1418 |
| 53 | 2720 | 937 | 397 | 548 | 854 | 741 | 894 | 1184 | 1150 |
| 54 | 1463 | 707 | 663 | 767 | 924 | 755 | 943 | 1075 | 1232 |
| 55 | 1155 | 1095 | 744 | 2080 | 1155 | 893 | 2902 | 3861 | 4546 |
| 56 | 874 | 1617 | 1808 | 3009 | 2028 | 1647 | 5122 | 5722 | 5563 |
| 57 | 4798 | 3609 | 1288 | 2034 | 2294 | 2100 | 2977 | 3315 | 3451 |
| 58 | 19970 | 2858 | 7914 | | | 6572 | | | |
| 59 | ≤2 | ≤2 | ≤2 | | | | | | |
| 60 | ≤2 | ≤2 | ≤2 | | | | | | |
| 61 | 4 | 4 | 9 | | | | | | |
| 62 | ≤2 | ≤2 | ≤2 | | | | | | |
| 63 | 8 | ≤2 | ≤2 | | | | | | |
| 64 | ≤2 | ≤2 | ≤2 | | | | | | |
| 65 | 3 | ≤2 | ≤2 | | | | | | |
| 66 | ≤2 | ≤2 | ≤2 | | | | | | |
| 67 | 11 | 7 | ≤2 | | | | | | |
| 68 | ≤2 | ≤2 | 3 | | | | | | |
| 69 | ≤2 | ≤2 | ≤2 | | | | | | |
| 70 | ≤2 | ≤2 | ≤2 | | | | | | |
| 71 | 4 | ≤2 | ≤2 | | | | | | |
| 72 | ≤2 | ≤2 | ≤2 | | | | | | |
| 73 | 5 | 3 | 3 | | | | | | |
| 74 | ≤2 | 3 | 4 | | | | | | |
| 75 | ≤2 | 3 | ≤2 | | | | | | |
| 76 | 37 | 7 | 7 | | | | | | |
| 77 | 740 | 188 | 165 | | | | | | |
| 78 | 30 | 41 | 81 | 59 | 22 | 80 | 73 | 67 | 112 |
| 79 | 53 | 67 | 135 | 128 | 35 | 116 | 109 | 111 | 151 |
| 80 | 121 | 130 | 285 | 428 | 68 | 211 | 200 | 213 | 260 |
| 81 | 5404 | 3398 | 4022 | 4047 | 1159 | 3557 | 3606 | 3716 | 5329 |
| 82 | 1121 | 958 | 291 | 628 | 696 | 475 | 712 | 552 | 606 |
| 83 | 929 | 427 | 311 | 206 | 240 | 190 | 83 | 139 | 189 |
| 84 | 2106 | 291 | 104 | 215 | 351 | 161 | 838 | 696 | 734 |
| 85 | 1028 | 491 | 399 | 223 | 263 | 274 | 140 | 186 | 213 |
| 86 | 1320 | 498 | 465 | 225 | 304 | 576 | 158 | 151 | 194 |
| 87 | 4876 | 1875 | 165 | 1136 | 1149 | 470 | 1007 | 1470 | 844 |
| 88 | 1114 | 403 | 470 | 475 | 505 | 482 | 215 | 176 | 228 |
| 89 | 7108 | 593 | 219 | 427 | 721 | 465 | 959 | 1133 | 929 |
| 90 | 6278 | 2123 | 1071 | 1028 | 1872 | 1164 | 225 | 440 | 321 |
| 91 | 1040 | 435 | 229 | 292 | 459 | 382 | 765 | 919 | 963 |
| 92 | 532 | 295 | 279 | 303 | 342 | 348 | 232 | 247 | 325 |
| 93 | 2617 | 701 | 234 | 427 | 698 | 256 | 678 | 1099 | 1235 |
| 94 | 2124 | 1293 | 244 | 793 | 883 | 525 | 860 | 699 | 757 |
| 95 | 4696 | 990 | 724 | 655 | 953 | 656 | 255 | 254 | 343 |
| 96 | 3283 | 357 | 1159 | 304 | 348 | 304 | 747 | 1326 | 1275 |
| 97 | 1161 | 567 | 499 | 484 | 520 | 558 | 321 | 336 | 400 |

TABLE 2-continued

Binding to KRas (IC$_{50}$ nM) by Exemplary Compounds of Formula (I)

| Ex. No. | G12D | G12V | G12R | G12A | G12S | G12C | WT | G13D | Q61H |
|---|---|---|---|---|---|---|---|---|---|
| 98 | 1072 | 341 | 514 | 453 | 482 | 330 | 444 | 629 | 537 |
| 99 | 3012 | 958 | 338 | 1251 | 1252 | 1004 | 1236 | 1561 | 1125 |
| 100 | 4424 | 2032 | 339 | 1006 | 1427 | 828 | 1145 | 1366 | 1397 |
| 101 | 1215 | 546 | 400 | 487 | 383 | 355 | 515 | 673 | 740 |
| 102 | 15040 | 6447 | 3076 | 805 | 3092 | 2988 | 357 | 363 | 424 |
| 103 | 2581 | 1390 | 364 | 785 | 791 | 427 | 718 | 691 | 690 |
| 104 | 4203 | 852 | 365 | 755 | 1123 | 894 | 1589 | 1795 | 1978 |
| 105 | 607 | 368 | 461 | 382 | 385 | 457 | 469 | 566 | 600 |
| 106 | 2232 | 1303 | 1786 | 628 | 752 | 369 | 1418 | 1073 | 1457 |
| 107 | 1448 | 406 | 638 | 423 | 535 | 487 | 369 | 465 | 528 |
| 108 | 4087 | 948 | 381 | 656 | 975 | 485 | 1548 | 1292 | 1596 |
| 109 | 1765 | 690 | 387 | 735 | 612 | 456 | 519 | 893 | 898 |
| 110 | 726 | 566 | 788 | 595 | 551 | 639 | 400 | 412 | 491 |
| 111 | 602 | 404 | 546 | 440 | 486 | 417 | 411 | 544 | 513 |
| 112 | 7286 | 1581 | 2094 | 1339 | 1329 | 1566 | 412 | 581 | 647 |
| 113 | 843 | 450 | 756 | 464 | 601 | 418 | 509 | 654 | 523 |
| 114 | 3729 | 997 | 455 | 1924 | 704 | 1307 | 1094 | 1206 | 1184 |
| 115 | 3036 | 1805 | 460 | 1107 | 1351 | 928 | 1152 | 1396 | 1215 |
| 116 | 3295 | 1788 | 462 | 1160 | 1495 | 1112 | 2097 | 1674 | 1642 |
| 117 | 2270 | 495 | 3979 | 5283 | 3417 | 2365 | 6165 | 7027 | 9679 |
| 118 | 1797 | 948 | 558 | 880 | 917 | 652 | 1947 | 1574 | 1494 |
| 119 | 1050 | 564 | 836 | 644 | 797 | 811 | 967 | 735 | 778 |
| 120 | 6382 | 4209 | 1315 | 1532 | 2475 | 573 | 1810 | 2008 | 2100 |
| 121 | 2298 | 612 | 2368 | 4551 | 3416 | 2339 | 3617 | 5146 | 6355 |
| 122 | 1903 | 613 | 689 | 1415 | 1200 | 941 | 1748 | 2574 | 2088 |
| 123 | 4231 | 639 | 1524 | 1930 | 1667 | 884 | 2484 | 6144 | 4626 |
| 124 | 30770 | 5019 | 645 | 5236 | 3432 | 4129 | 5876 | 7464 | 7700 |
| 125 | 1027 | 1410 | 1490 | 1324 | 665 | 1198 | 651 | 720 | 1045 |
| 126 | 720 | 2747 | 3291 | 5901 | 2909 | 2741 | 4255 | 5681 | 5449 |
| 127 | 2039 | 739 | 1355 | 2072 | 1402 | 1151 | 1543 | 1826 | 1747 |
| 128 | 10550 | 744 | 1041 | 2076 | 1670 | 1512 | 3588 | 4575 | 3833 |
| 129 | 16010 | 2410 | 760 | 2968 | 2140 | 1296 | 2210 | 3216 | 2428 |
| 130 | 5071 | 1258 | 1227 | 1457 | 1300 | 1096 | 772 | 1156 | 950 |
| 131 | 2123 | 1256 | 774 | 1197 | 1352 | 1067 | 1415 | 1358 | 1480 |
| 132 | 3901 | 1643 | 775 | 1184 | 1656 | 1316 | 1432 | 1454 | 1716 |
| 133 | 945 | 936 | 781 | 1025 | 1018 | 871 | 1338 | 1503 | 1438 |
| 134 | 1546 | 828 | 3219 | 4629 | 3342 | 2592 | 6361 | 9181 | 8678 |
| 135 | 4096 | 2853 | 850 | 2671 | 2423 | 1933 | 2833 | 2811 | 2848 |
| 136 | 3393 | 868 | 1628 | 1537 | 1987 | 969 | 1564 | 3278 | 2300 |
| 137 | 3236 | 1472 | 1142 | 948 | 1076 | 1034 | 1664 | 1349 | 1471 |
| 138 | 7755 | 1009 | 1842 | 2739 | 4146 | 1372 | 6052 | 7305 | 7302 |
| 139 | 12400 | 1173 | 1408 | 2536 | 2833 | 1491 | 3479 | 5443 | 4575 |
| 140 | 5214 | 2385 | 1437 | 1655 | 2002 | 1179 | 1922 | 1763 | 2234 |
| 141 | 8519 | 1260 | 1636 | 2953 | 2490 | 2299 | 1615 | 1198 | 1610 |
| 142 | 10540 | 1381 | 1721 | 2325 | 1873 | 1250 | 7522 | 13130 | 7246 |
| 143 | 5925 | 4146 | 2014 | 2227 | 2472 | 1915 | 2048 | 1324 | 1251 |
| 144 | 1261 | 6276 | 11100 | 8494 | 5681 | 4975 | 7514 | 10150 | 10630 |
| 145 | 11550 | 1271 | 1593 | 2528 | 2695 | 1857 | 4723 | 7071 | 10710 |
| 146 | 1324 | 6012 | 8206 | 9311 | 5253 | 4463 | 8417 | 10550 | 6450 |
| 147 | 1325 | 1449 | 1487 | 2707 | 2154 | 1653 | 2451 | 3631 | 3213 |
| 148 | 7622 | 1353 | 4351 | 3245 | 2895 | 3071 | 7312 | 7152 | 7799 |
| 149 | 43040 | 1422 | 1816 | 2535 | 3349 | 1846 | 4755 | 6889 | 6314 |
| 150 | 5528 | 2552 | 1556 | 5031 | 4866 | 1953 | 4731 | 5980 | 5160 |
| 151 | 30860 | 5410 | 1613 | 2689 | 4715 | 3473 | 3649 | 2700 | 4575 |
| 152 | 16860 | 5221 | 17800 | 6423 | 10060 | 1729 | 6202 | 9414 | 10990 |
| 153 | 1734 | 3364 | 4661 | 7284 | 4170 | 3507 | 8434 | 6440 | 8150 |
| 154 | 35690 | 3073 | 2372 | 4041 | 7122 | 1794 | 6788 | 8229 | 6912 |
| 155 | 22420 | 7306 | 4916 | 1856 | 3401 | 4419 | 3169 | 4863 | 4673 |
| 156 | 14670 | 2861 | 2099 | 2744 | 2679 | 1902 | 3572 | 4233 | 5546 |
| 157 | 6300 | 1949 | 9035 | 24250 | 10570 | 7016 | 17340 | 15500 | 19910 |
| 158 | 24760 | 3483 | 2209 | 5035 | 4720 | 2679 | 8254 | 10410 | 10410 |
| 159 | 13830 | 6748 | 7634 | 10010 | 8845 | 7575 | 7338 | 9818 | 2358 |
| 160 | 4445 | 2564 | 7653 | 9262 | 6739 | 4236 | 8741 | 10020 | 11020 |
| 161 | 7688 | 2744 | 14610 | 21680 | 14990 | 6788 | 27380 | 25160 | 21280 |
| 162 | 7513 | 8353 | 2788 | 5218 | 3429 | 3793 | 4081 | 3413 | 3984 |
| 163 | 7111 | 5166 | 3465 | | | | | | |
| 164 | 11240 | 6272 | 10890 | 7494 | 7320 | 3803 | 9409 | 14500 | 15480 |
| 165 | 14170 | 4344 | 7468 | 8672 | 8075 | 3870 | 5920 | 6712 | 6550 |
| 166 | 9853 | 7319 | 4652 | 5509 | 5134 | 4153 | 4815 | 4796 | 4581 |
| 167 | 25200 | 4211 | 5543 | 8097 | 7345 | 5409 | 5856 | 5195 | 7330 |
| 168 | 26360 | 7121 | 4948 | 11050 | 9628 | 5391 | 15050 | 21940 | 14620 |
| 169 | 8483 | 8172 | 5122 | | | | | | |
| 170 | 25030 | 5872 | 11870 | 27860 | 16450 | 15070 | 16990 | 16370 | 17040 |
| 171 | 16630 | 8802 | 8276 | | | | | | |
| 172 | 224 | 153 | 153 | | | | | | |
| 173 | 1155 | 535 | 307 | | | | | | |
| 174 | 287 | 38 | 24 | | | | | | |
| 175 | ≤2 | ≤2 | ≤2 | | | | | | |
| 176 | 78 | 11 | ≤2 | | | | | | |
| 177 | 19 | 9 | 15 | | | | | | |
| 178 | ≤2 | ≤2 | ≤2 | | | | | | |
| 179 | 207 | 101 | 80 | | | | | | |
| 180 | 4 | 8 | 6 | | | | | | |
| 181 | ≤2 | ≤2 | ≤2 | | | | | | |
| 182 | 209 | 75 | 118 | | | | | | |
| 183 | 150 | 54 | 23 | | | | | | |
| 184 | 23 | 12 | 11 | | | | | | |
| 185 | 143 | 52 | 46 | | | | | | |
| 186 | ≤2 | ≤2 | ≤2 | | | | | | |
| 187 | 4 | ≤2 | ≤2 | | | | | | |
| 188 | ≤2 | ≤2 | ≤2 | | | | | | |
| 189 | ≤2 | ≤2 | ≤2 | | | | | | |
| 190 | ≤2 | ≤2 | ≤2 | | | | | | |
| 191 | ≤2 | ≤2 | ≤2 | | | | | | |
| 192 | ≤2 | ≤2 | 3 | | | | | | |
| 193 | ≤2 | ≤2 | ≤2 | | | | | | |
| 194 | ≤2 | ≤2 | ≤2 | | | | | | |
| 195 | 17 | 8 | 20 | | | | | | |
| 196 | ≤2 | ≤2 | ≤2 | | | | | | |
| 197 | ≤2 | ≤2 | ≤2 | | | | | | |
| 198 | ≤2 | ≤2 | 5 | | | | | | |
| 199 | ≤2 | ≤2 | ≤2 | | | | | | |
| 200 | ≤2 | ≤2 | ≤2 | | | | | | |
| 201 | ≤2 | ≤2 | 4 | | | | | | |
| 202 | ≤2 | ≤2 | 7 | | | | | | |
| 203 | ≤2 | ≤2 | 3 | | | | | | |
| 204 | 6 | 6 | 9 | | | | | | |
| 205 | 4688 | 4696 | 6430 | | | | | | |
| 206 | 932 | 833 | 1625 | | | | | | |
| 207 | 765 | 404 | 553 | | | | | | |
| 208 | 136 | 197 | 350 | | | | | | |
| 209 | 1123 | 1903 | 4139 | | | | | | |
| 210 | 579 | 497 | 699 | | | | | | |
| 211 | 101 | 38 | 34 | | | | | | |
| 212 | ≤2 | ≤2 | ≤2 | | | | | | |
| 213 | 11 | 3 | 3 | | | | | | |
| 214 | 558 | 118 | 54 | | | | | | |
| 215 | 10 | 3 | 3 | | | | | | |
| 216 | ≤2 | ≤2 | 3 | | | | | | |
| 217 | ≤2 | ≤2 | ≤2 | | | | | | |
| 218 | ≤2 | ≤2 | ≤2 | | | | | | |
| 219 | 3 | 3 | 4 | | | | | | |
| 220 | ≤2 | ≤2 | ≤2 | | | | | | |
| 221 | 4 | 3 | 5 | | | | | | |
| 222 | ≤2 | ≤2 | ≤2 | | | | | | |
| 223 | ≤2 | ≤2 | ≤2 | | | | | | |
| 224 | ≤2 | ≤2 | ≤2 | | | | | | |
| 225 | ≤2 | ≤2 | ≤2 | | | | | | |
| 226 | ≤2 | ≤2 | ≤2 | | | | | | |
| 227 | 20 | 4 | 6 | | | | | | |
| 228 | ≤2 | ≤2 | ≤2 | | | | | | |
| 229 | ≤2 | ≤2 | ≤2 | | | | | | |
| 230 | 5 | 3 | 5 | | | | | | |
| 231 | 12 | 15 | 26 | | | | | | |
| 232 | ≤2 | ≤2 | ≤2 | | | | | | |

Example B

Inhibition of KRas Phosphorylation of ERK by Exemplary Compounds of Formula (I)

This Example illustrates that exemplary compounds of the present invention inhibit the phosphorylation of ERK downstream of KRas WT, G12C, G12D, G12R, G12S, G12V, G13D, Q61H.

AsPC-1 (G12D, ATCC CRL-1682), A549 (G12S, ATCC CCL-185), HCT116 (G13D, ATCC CCL-247) cells were grown in DMEM medium supplemented with 10% fetal bovine serum and Penicillin/Streptomycin. NCI-H358 (G12C, ATCC CRL-5807), NCI-H460 (Q61H, ATCC HTB-117), NCI-H727 (G12V, ATCC CRL-5815), MKN1 (WT-dep, JCRB JCRB0252), PSN-1 (G12R, ATCC CRM-CRL-3211) cells were grown in RPMI medium supplemented with 10% fetal bovine serum, 10 mM HEPES, 10 mM Sodium Pyruvate, and Penicillin/Streptomycin. Cells were plated in black well clear bottom tissue culture treated 96 well plates (Corning, 3904) at a density of 20,000 cells/well and allowed to attach for 12-14 hours. Diluted compounds were then added in a final concentration of 0.5% DMSO. After 3 hours, 50 µL of 4.0% formaldehyde was added and the plates incubated at room temperature for 20 minutes. The plates were then dumped and permeabilized with 150 µL of ice cold 100% methanol for 10 minutes. Non-specific antibody binding to the plates was blocked using 100 µL Odyssey blocking buffer (LI-COR Biosciences, 927-60010) for 1 hour at room temperature.

The amount of phospho-ERK was determined using an antibody specific for the phosphorylated form of ERK and compared to the amount of GAPDH. Primary antibodies used for the detection were added as follows: Phospho-ERK (Cell Signaling CS-9101) diluted 1:500 and GAPDH (Millipore MAB374) diluted 1:5000 in Odyssey blocking buffer+0.05% Tween 20. The plates were incubated overnight at 4 C. The plates were washed 3× with 150 uL PBS+0.1% Tween 20.

Secondary antibodies used to visualize primary antibodies were added as follows: Goat Anti-Rabbit-800 (LI-COR, 926-32211) and Goat Anti-Mouse-680 (LI-COR, 926-68070) diluted 1:800 both in Odyssey blocking buffer+ 0.05% Tween 20 and were incubated for 1 hour at room temperature. The plates were washed 3× with 150 uL PBS+0.100 Tween 20. Plates were imaged dry on a Li-COR Odyssey CLX plate reader.

The phospho-ERK (Thr202/Tyr204) signal was normalized to the GAPDH signal for each well and percent of DMSO control values were calculated. IC50 values were generated using a 4-parameter fit of the dose response curve.

TABLE 3

Inhibition ($IC_{50}$ nM) of KRas-mediated Phosphorylation of ERK by Exemplary Compounds of Formula (I)

| Ex. No. | AsPC-1 | H727 | H358 | HCT116 | H460 | A549 | PSN1 |
|---|---|---|---|---|---|---|---|
| 1 | 398 | 1262 | 236 | 601 | 357 | 1020 | 1396 |
| 2 | 280 | 798 | 252 | 863 | 184 | 241 | 3529 |
| 17 | | 1127 | 232 | 10000 | | 189 | >10000 |
| 18 | 182 | 503 | | | 317 | | |
| 19 | 2685 | 2929 | | | 1290 | | |
| 20 | | 747 | 314 | 860 | | 446 | >10000 |
| 21 | 204 | 466 | | | 202 | | |
| 23 | 3851 | 2418 | | | 1769 | | |
| 24 | 25 | 134 | | | 65 | | |
| 25 | 448 | 540 | | | 171 | | |
| 26 | 10000 | 3125 | | | 3263 | | |
| 27 | 808 | 549 | | | 282 | | |
| 28 | 1007 | 987 | | | 494 | | |
| 29 | 509 | 542 | | | 285 | | |
| 30 | 447 | 399 | | | 309 | | |
| 31 | 3544 | 3320 | | | >10000 | | |
| 32 | 624 | 1094 | | | 381 | | |
| 33 | 1360 | 1862 | | | 398 | | |
| 34 | 258 | 1041 | | | 774 | | |
| 35 | 2361 | 1616 | | | 1428 | | |
| 36 | 1764 | 1734 | | | 731 | | |
| 59 | 44 | 181 | | | 17 | | |
| 67 | 1568 | 876 | | | 225 | | |

Example C

Inhibition of KRas Phosphorylation of ERK (HTRF) by Exemplary Compounds of Formula (I)

Cisbio HTRF Advanced pERK Assay Catalog #64AER-PEH
Cells: MKN1, PSN1
Procedure:
Day 1: Seed 6,000 cells/well-25 µl/well in 384-well white solid bottom plate; RPM1_10% FBS. Incubate overnight at 37° C./5% CO2.
Day 2: Echo transfer 25 nl of 10 mM compound 10 point dilution at 1:3 (Cf=10 uM) and incubate for 3 hour at 37° C./5% CO2.
Add 8.5 µl/well of 4× Lysis Buffer/25× Blocking reagent (do not dump media) and incubate for 30 min at room temperature on shaker.
Add conjugate mixture of 4.25 ul/well 1×-pERK-D2 and 1×-pERK-K diluted in Detection Buffer for a total of 8.5 µl/well.
Incubate for 4 hours at room temperature covered.
Read HTRF using ClarioStar
Cells: ASPC1, H727, A549, H460, HCT116, H358
Culture/Assay media: RPMI-1640+10% FBS
Procedure:
Cell Seeding
1. To harvest cells from flask using 0.05% Trypsin/EDTA solution. Add 10 mL of media to stop trypsinizing. Pipette the cells into a conical bottom 50 mL centrifuge tube and centrifuge 5 min×1000 rpm.
2. Re-suspend the cell pellet in media, take a cell count, and then adjust the cell density using fresh media.
3. Seed 6,000 cells into cell culture plate with 50 µL media. The
4. Incubate cell plate overnight in a 37° C., 5% CO2 incubator.
Compound Titrations
1. Use Tecan to complete the compound addition. Compounds start from 10 uM top, 3-fold dilution, and 10 doses. The final DMSO concentration is 0.8%. Dispensed 0.2 uM Trametinib as Min control.
2. Incubate cell plate for 3 hrs in the incubator.
Detection with Cisbio pERK HTRF Kit
1. Dilute 1 volume of 4× lysis buffer with 3 volumes of deionized water. Then, add 100× the blocking reagent. Keep lysis buffer on the ice.
2. At the end of the compound treatment, flick-off the media.
3. Add 35 µL of lysis buffer per well using a Multidrop Combi. Then place on a plate agitator shaking at 300 rpm at 4° C. for 40 mins.
4. Make up the HTRF antibody buffer. For each assay plate, mix 50 µL of d2-conjugate antibody with 950 µL of detection buffer. Similarly, mix 50 µL of Cryptate antibody with 950 µL of detection buffer. Then mix the two diluted antibodies together.
5. Dispense 3.4 µL the antibody buffer to wells of an empty assay plate. Seal the plate and centrifuge plate 30 sec×1000 rpm.
6. At the end of the 4° C. lysis, centrifuge the lysate plates 3 mins×1500 rpm.
7. Use the Bravo to transfer 13.6 µL of lysate from cell culture plate to assay plate. Then incubate assay plate for 2 hrs at room temperature.
8. At the end of incubation, read plate on the Envision after centrifuging plate 30 sec×1000 rpm.

TABLE 4

Inhibition (HTRF $IC_{50}$ nM) of KRas-mediated Phosphorylation of ERK by Exemplary Compounds of Formula (I)

| Ex. No. | AsPC-1 | H727 | MKN1 | PSN1 | A549 | H460 | HCT116 | H358 |
|---|---|---|---|---|---|---|---|---|
| 2 | 29 | 315 | | | 144 | 146 | 426 | |
| 15 | 1114 | 3186 | | | | | | |
| 18 | | | 22 | ≥10000 | | | | |
| 19 | | | 389 | ≥10000 | | | | |
| 21 | | | 9 | 645.5 | | | | |
| 23 | | | 53 | ≥10000 | | | | |
| 24 | 10 | 35 | 6 | 2952 | 17 | 59 | 148 | |
| 25 | 180 | 767 | 51 | 8319 | | | 521 | |
| 27 | | | 9 | 2718 | | | | |
| 28 | | | 36 | ≥10000 | | | | |
| 29 | 318 | 906 | 20 | 5809 | | | 1313 | |
| 30 | 86 | 227 | 16 | 3511 | | 203 | 480 | 83 |
| 31 | | | 637 | ≥10000 | | | | |
| 32 | | | 31 | 1545 | | | | |
| 33 | | | 11 | ≥10000 | | | | |
| 34 | 31 | 217 | 134 | ≥10000 | 351 | 784 | 1270 | 38 |
| 35 | | | 159 | 5722 | | | | |
| 36 | | | 37 | ≥10000 | | | | |
| 59 | 8 | 40 | 5 | 25.32 | 3 | 9 | 16 | 4 |
| 60 | 556 | 258 | 29 | 6607 | | | 1116 | |
| 61 | 211 | 1200 | 51 | 3651 | | | 2377 | |
| 62 | 15 | 81 | 4 | 324.8 | 25 | 69 | 125 | 11 |
| 63 | 457 | 608 | 33 | 6956 | | | 1174 | |
| 64 | 595 | 778 | 83 | 2629 | | | 891 | |
| 65 | 1293 | 739 | 26 | 4423 | | | 1214 | |
| 66 | 1 | 5 | 1 | | 5 | 36 | 62 | 2 |
| 67 | | | 112 | ≥10000 | | | | |
| 68 | 112 | 423 | 71 | 2259 | | 421 | 1167 | |
| 69 | 122 | 194 | 41 | 578.3 | 59 | 68 | 164 | |
| 70 | 705 | 471 | 40 | 749.8 | | | 1490 | |
| 71 | 1169 | 848 | 211 | 6042 | | | | |
| 72 | 10 | 59 | 7 | 148.4 | 32 | 59 | 126 | 8 |
| 73 | 661 | 871 | 85 | 6383 | | | | |
| 74 | 253 | 790 | 78 | 4054 | | | 1449 | |
| 75 | 128 | 242 | 128 | ≥10000 | | | 2162 | |
| 76 | 2074 | 1782 | 468 | 5629 | | | | |
| 175 | 53 | 85 | 58 | 7861 | 326 | 750 | 1115 | 50 |
| 176 | 5940 | 984 | | | | | | |
| 177 | 1307 | 1385 | 479 | ≥10000 | | | | |
| 178 | 17 | 68 | 20 | 7625 | | | | |
| 179 | 5171 | 4794 | 1206 | ≥10000 | | | | |
| 180 | 383 | 600 | 462 | ≥10000 | | 1563 | | |
| 181 | 228 | 191 | 90 | ≥10000 | | | | |
| 182 | 3921 | 4664 | 1298 | ≥10000 | | | | |
| 183 | 1545 | 2924 | 498 | ≥10000 | | | | |
| 184 | 770 | 796 | 652 | ≥10000 | | | | |
| 185 | 5120 | 3722 | 1545 | ≥10000 | | | | |
| 186 | 4361 | 2667 | | | | | | |
| 187 | 5327 | 1319 | | | | | | |
| 188 | 2 | 4 | 7 | 2876 | | 49 | | 3 |
| 189 | 2 | 3 | 4 | 2676 | | 39 | | 1 |
| 190 | 2 | 6 | 6 | 5450 | | 49 | | 3 |
| 191 | 3 | 3 | 10 | 2965 | | 33 | | 3 |
| 192 | 24 | 29 | 11 | ≥10000 | | | | |
| 193 | 3 | 5 | 4 | 2101 | | 38 | 74 | 2 |
| 194 | 71 | 115 | 100 | ≥10000 | | 426 | | 63 |
| 195 | 1110 | 373 | 1515 | ≥10000 | | | | |
| 196 | 6 | 11 | 5 | 18 | 2 | 2 | 5 | 1 |
| 197 | 136 | 313 | 12 | 1690 | | 285 | 499 | |
| 198 | 185 | 344 | 185 | ≥10000 | 671 | 1242 | 1953 | |
| 199 | 43 | 262 | 31 | 2503 | 201 | 242 | 441 | 65 |
| 200 | 62 | 264 | 27 | 9113 | 142 | 578 | 832 | 77 |
| 201 | 49 | 176 | 49 | 80.45 | 14 | 26 | 49 | 12 |
| 202 | 543 | 1346 | 101 | 3905 | | | | |
| 203 | 132 | 283 | 181 | ≥10000 | 524 | 1102 | 1699 | |
| 204 | 1528 | 1667 | | | | | | |
| 205 | ≥10000 | ≥10000 | | | | | | |
| 206 | ≥10000 | ≥10000 | | | | | | |
| 207 | ≥10000 | ≥10000 | | | | | | |
| 208 | 4053 | 6941 | | | | | | |
| 209 | 7196 | 8520 | | | | | | |
| 210 | ≥10000 | ≥10000 | | | | | | |
| 211 | 4891 | 2877 | | | | | | |
| 212 | 111 | 268 | 61 | ≥10000 | | 545 | 1108 | |
| 213 | 1743 | 1171 | 148 | 6504 | | | | |
| 214 | ≥10000 | 7428 | 1705 | ≥10000 | | | | |
| 215 | 1295 | 957 | 203 | 7584 | | | | |
| 216 | 92 | 300 | 19 | 1264 | 206 | 293 | 531 | 27 |
| 217 | 234 | 390 | 21 | 269 | 160 | 132 | 227 | |
| 218 | 46 | 86 | 85 | 6067 | 294 | 845 | 1338 | 61 |
| 219 | 448 | 1581 | 97 | 6116 | | 1022 | | |
| 220 | 668 | 616 | 29 | 4102 | | | | |
| 221 | 1363 | 1465 | 145 | ≥10000 | | | | |
| 222 | 179 | 530 | 37 | 2823 | | 352 | 672 | |
| 223 | 320 | 234 | 19 | 606.6 | | 325 | | |
| 224 | 976 | 651 | 62 | ≥10000 | | | | |
| 225 | 23 | 82 | 3 | 327.9 | | 56 | 158 | 9 |
| 226 | 45 | 43 | 7 | 2788 | | 169 | | 22 |
| 227 | 4047 | 1301 | 524 | 7048 | | | | |
| 228 | 108 | 197 | 24 | 696.4 | 146 | 253 | 405 | |
| 229 | 220 | 260 | 317 | 2141 | 705 | 1402 | 1981 | |
| 230 | 1092 | 1751 | 112 | ≥10000 | | | | |
| 231 | 2364 | 4376 | 929 | ≥10000 | | | | |
| 232 | 125 | 114 | 34 | 2772 | 98 | 331 | 709 | |

Example D: Anti-Proliferative Activity of Pan-KRas Inhibitors Against Mutations that Confer Resistance to Adagrasib To test the anti-proliferative activity of a prototype pan KRas inhibitor against mutations that confer resistance to adagrasib, mouse 3T3 fibroblasts were transduced with retroviruses that expressed various engineered human KRas mutant constructs. Cells were selected with puromycin to select for cells that were successfully transduced by the retrovirus and plated in ultra-low attachment plates where cells grew as 3 dimensional cultures. Cells were treated with a serial dilution of MRTX849 or Example 5 of co-pending patent application 63/125,776 and 50% inhibitory concentration (IC50) values were calculated (Table 5). Example 5 of 63/125,776 demonstrated activity against numerous codon 12 mutations including the G12W mutation predicted to result from a single nucleotide substitution from the cysteine 12 codon.

TABLE 5

IC50 Values of the KRas G12C Inhibitor MRTX849 and the Pan KRas Inhibitor Example 5 of 63/125,776 in a 5-day Viability Assay in 3T3 Cells Engineered to Express MRTX849 Resistance Mutations

| | MRTX849 (nM) | Example 5 (of 63/125,776) (nM) |
|---|---|---|
| G12A | >3000 | 32 |
| G12C | 16.62 | 28.1 |
| G12D | >3000 | 20.25 |
| G12R | >3000 | 1742 |
| G12V | >3000 | 94 |
| G12W | >3000 | 50 |
| G13D | >3000 | 610 |
| Q61H | >3000 | 58 |

While the invention has been described in connection with specific embodiments thereof, it will be understood that it is capable of further modifications and this application is intended to cover any variations, uses, or adaptations of the invention following, in general, the principles of the invention and including such departures from the present disclo-

The invention claimed is:
1. A compound selected from:
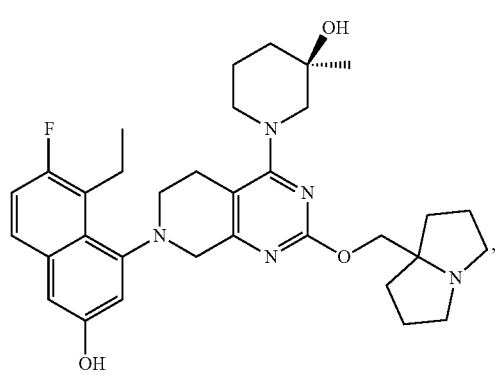
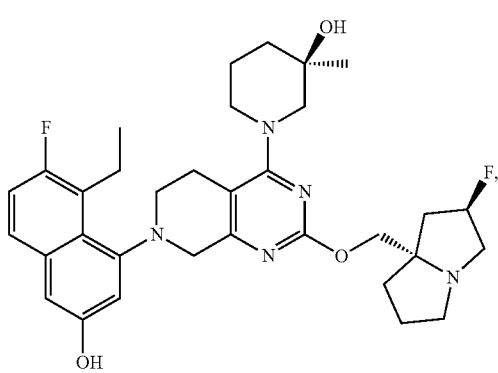
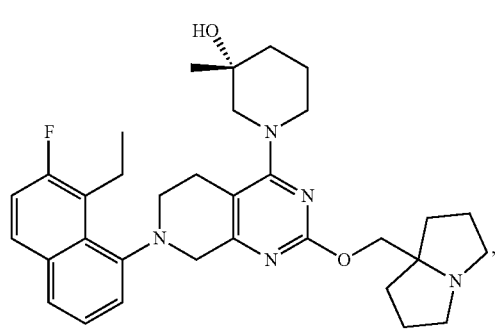
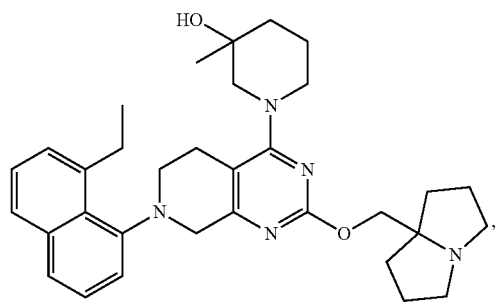
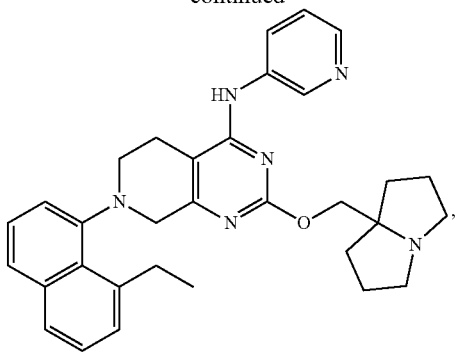
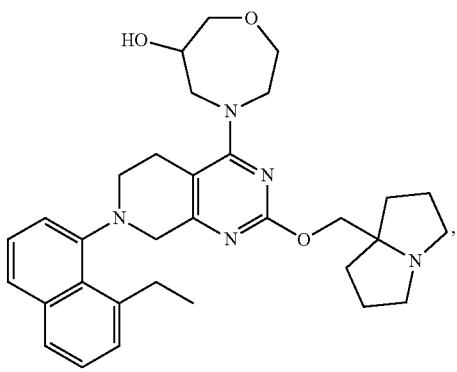
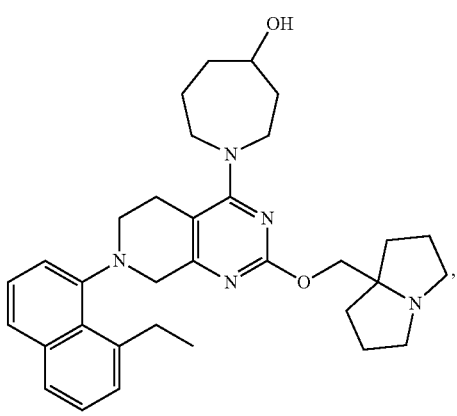
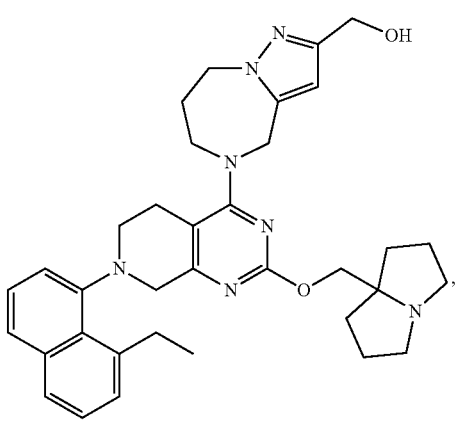

287
-continued
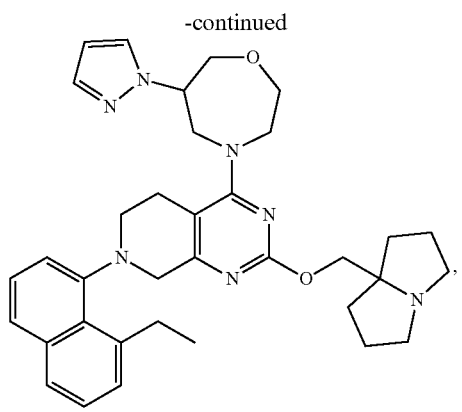
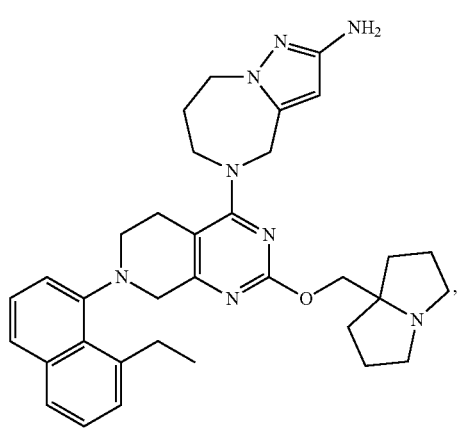
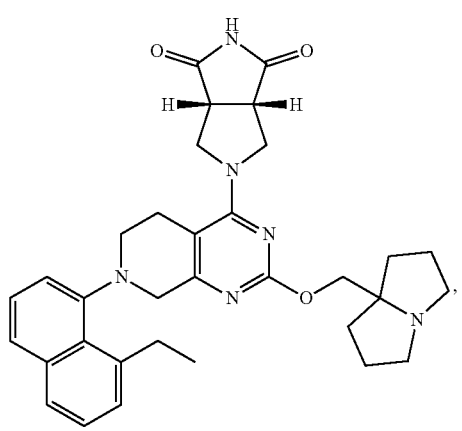
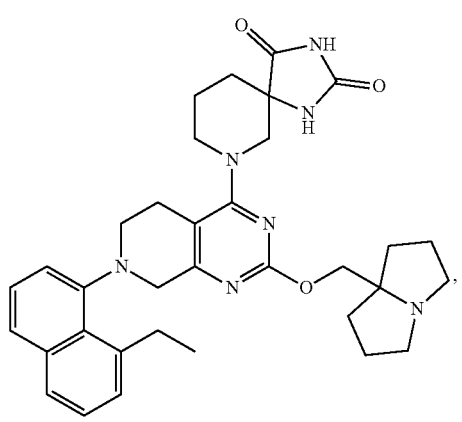
288
-continued
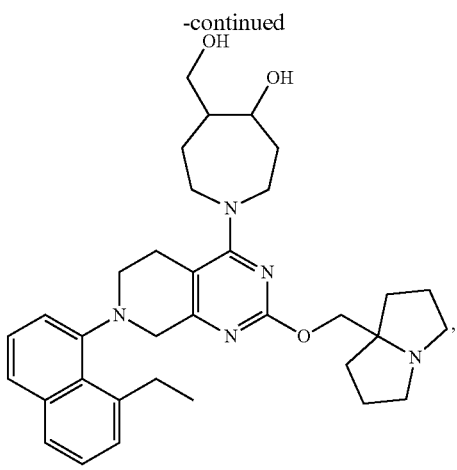
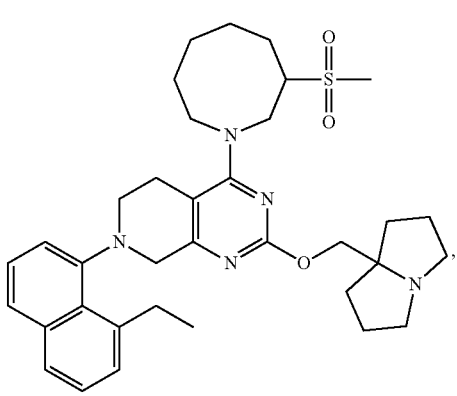
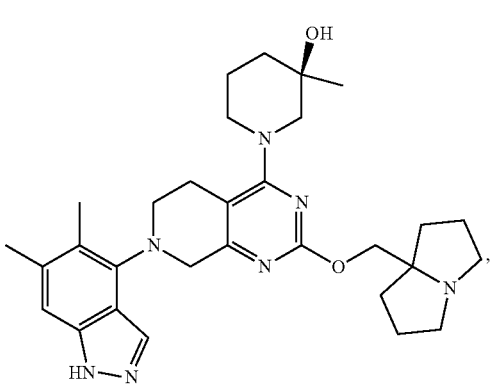
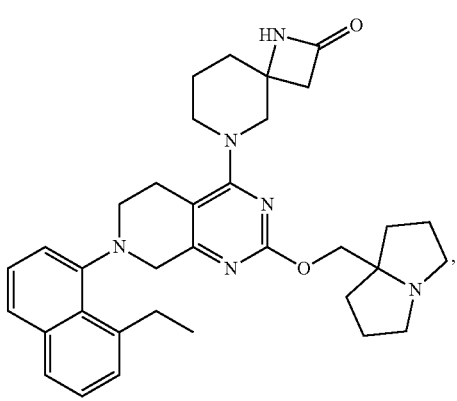

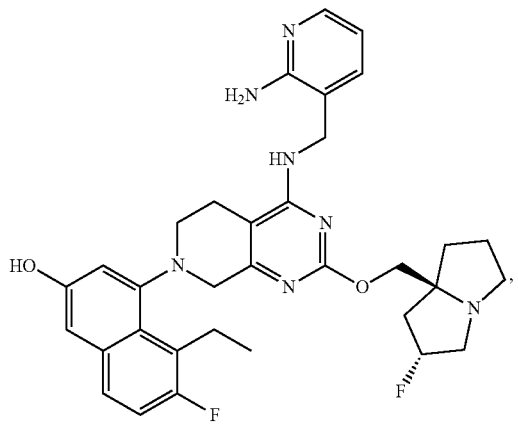
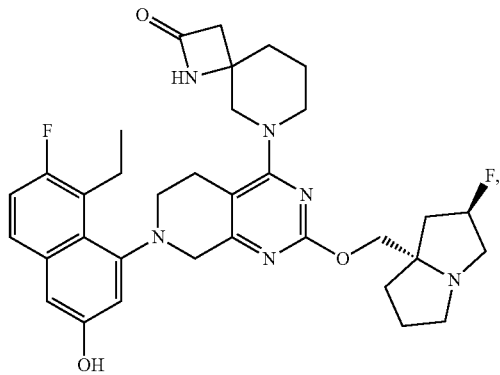
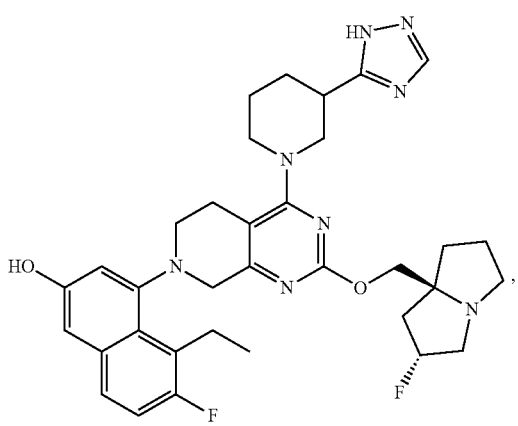
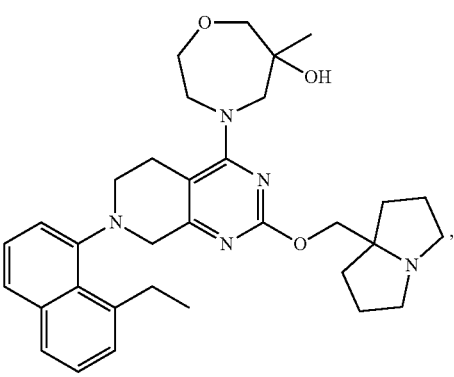
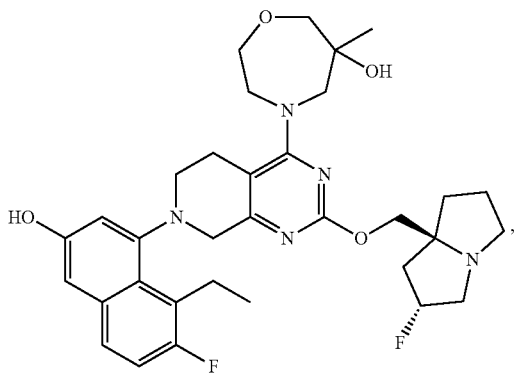

291
-continued
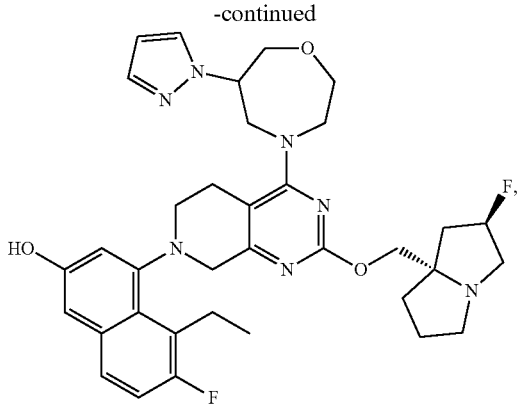
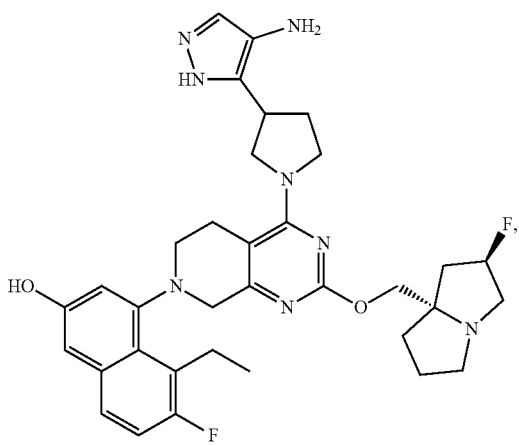
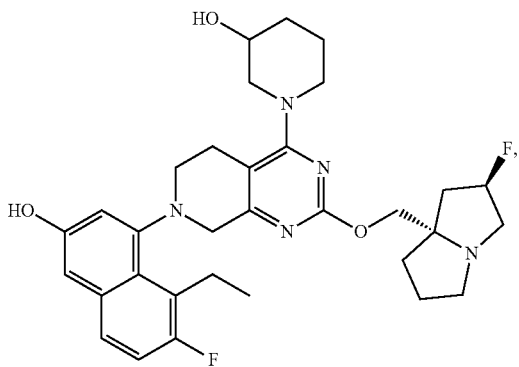
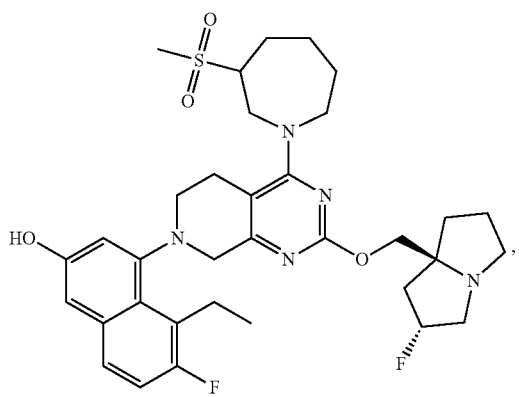
292
-continued
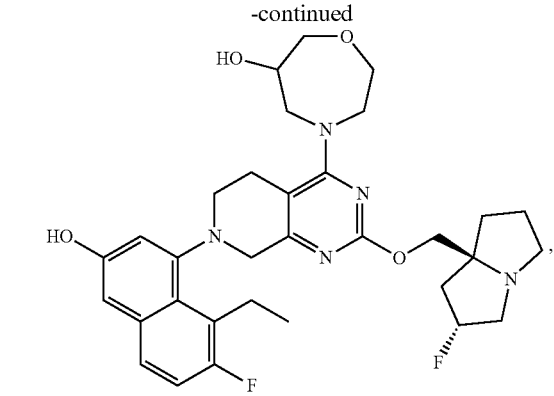
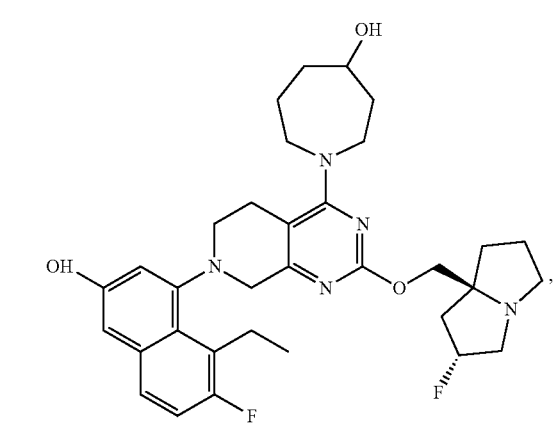
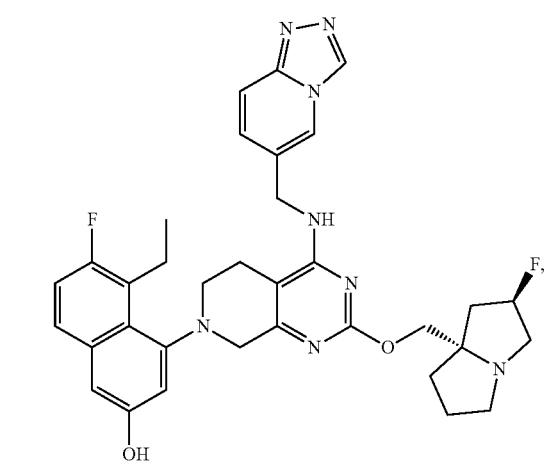
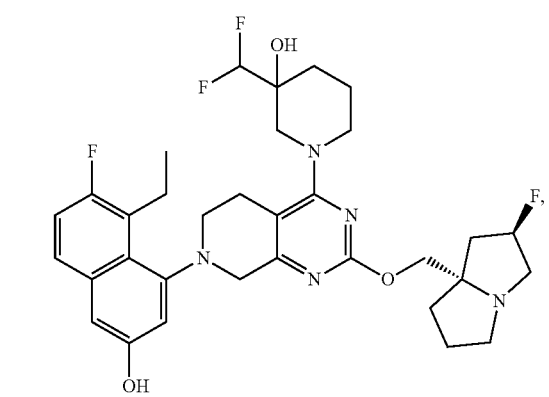

293
-continued
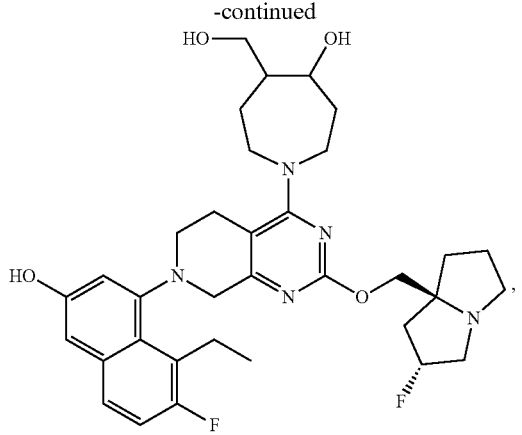
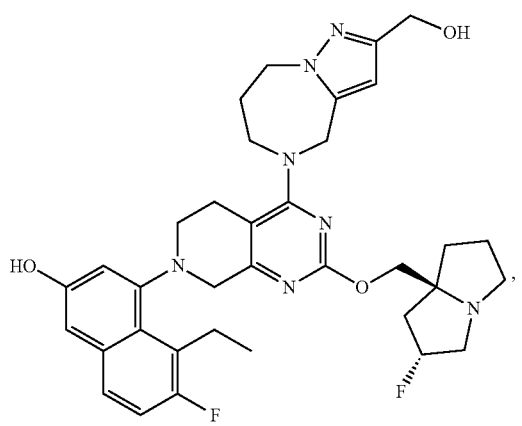
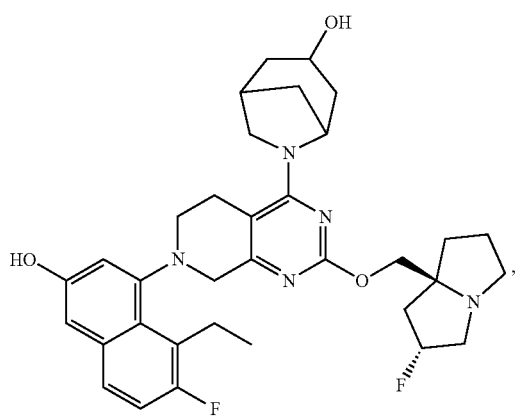
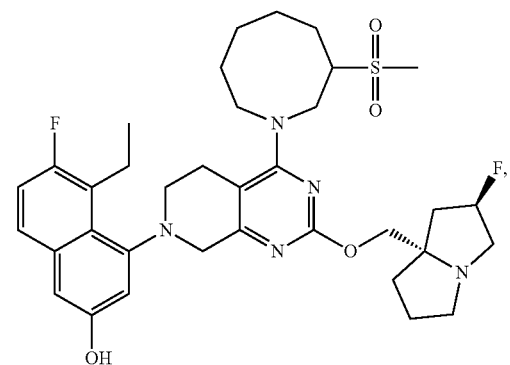
294
-continued
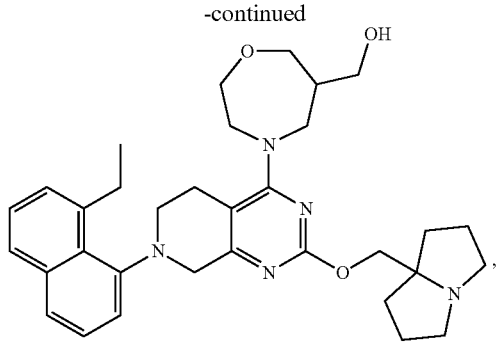
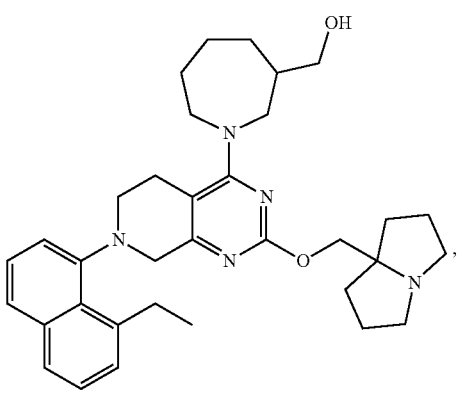
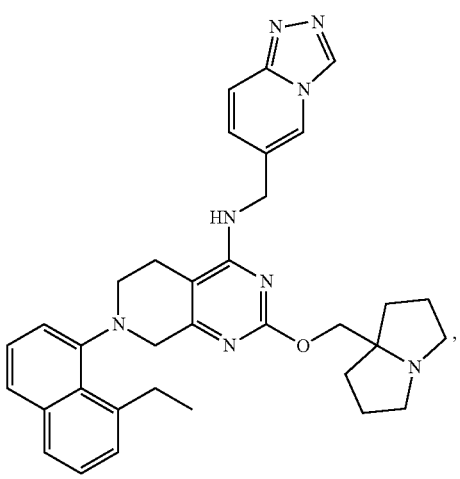
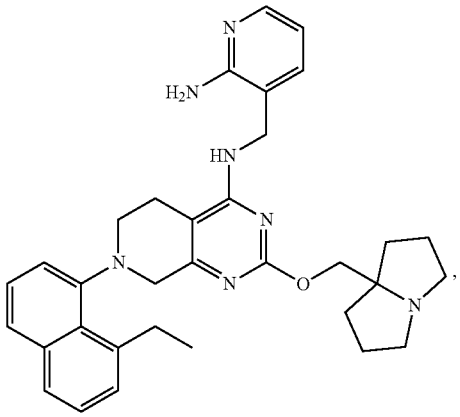

295
-continued
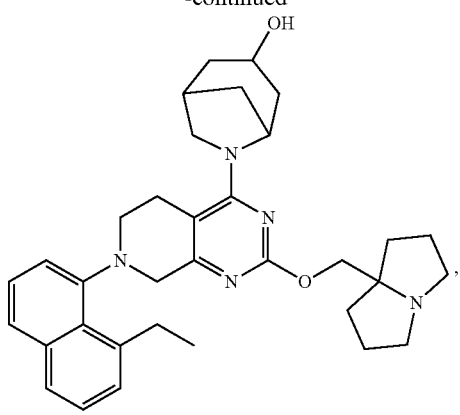
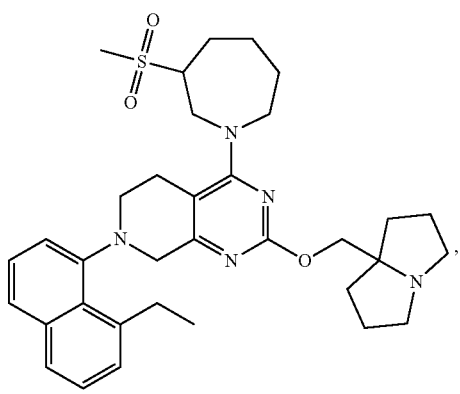
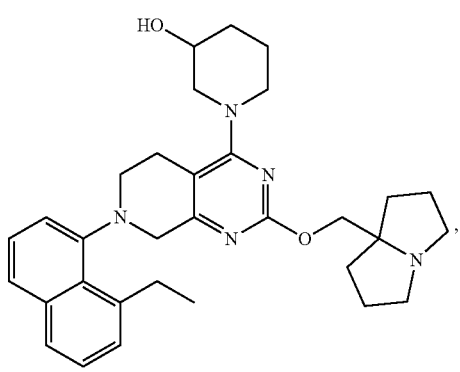
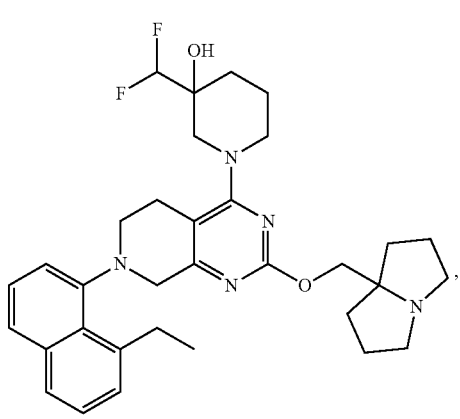
296
-continued
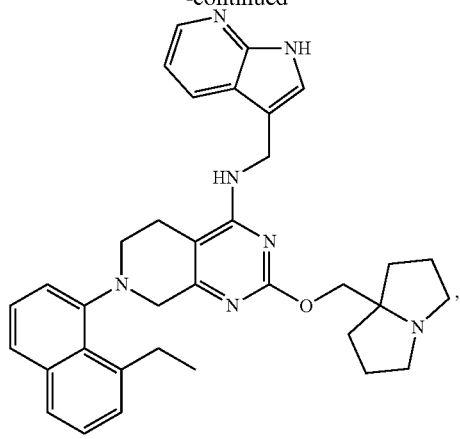
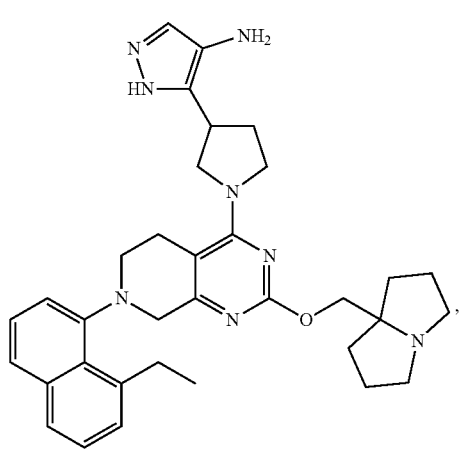
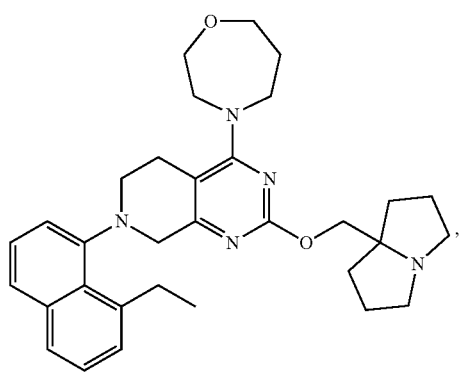
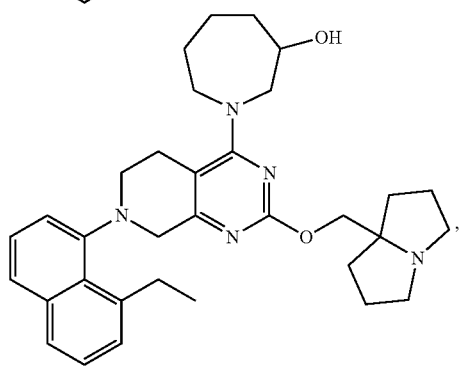

297
-continued
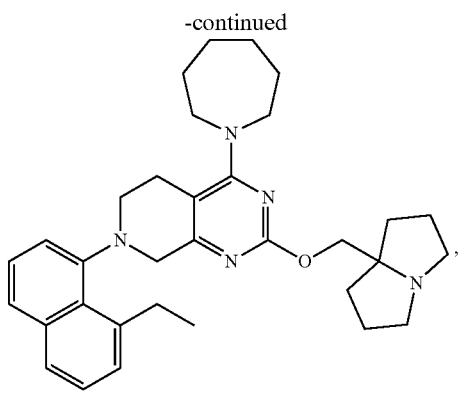
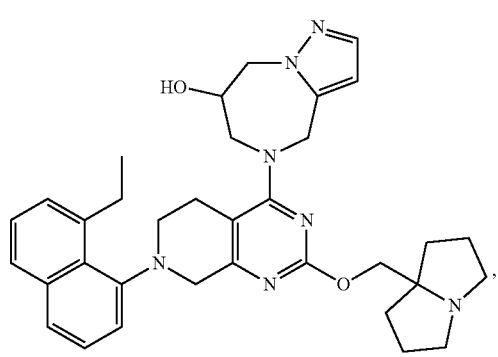
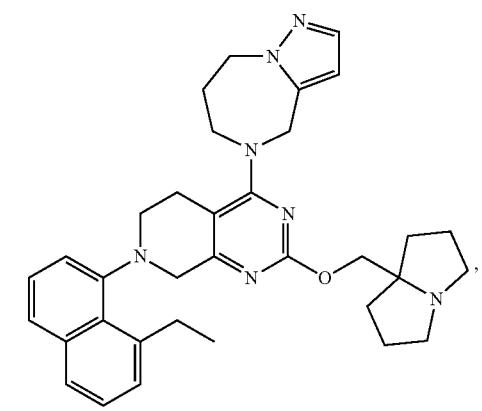
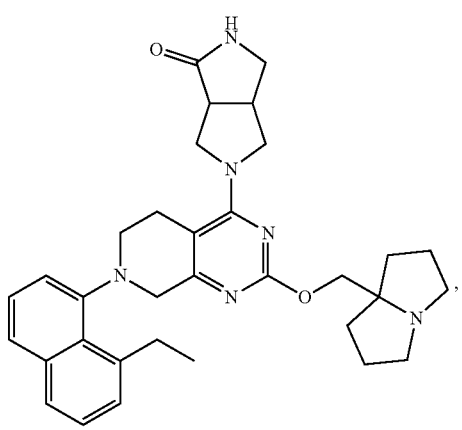
298
-continued
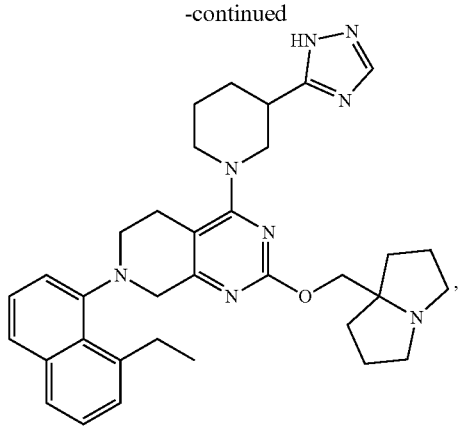
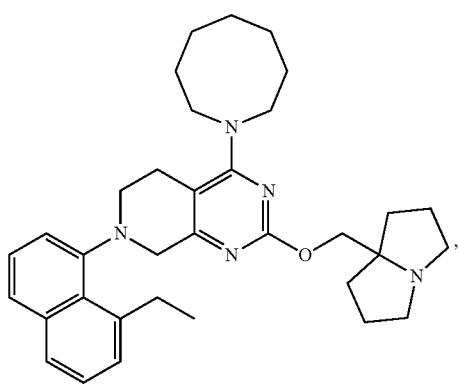
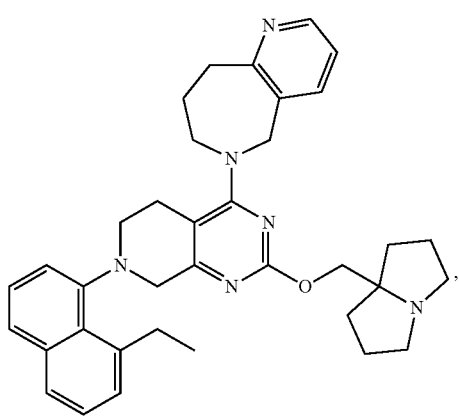
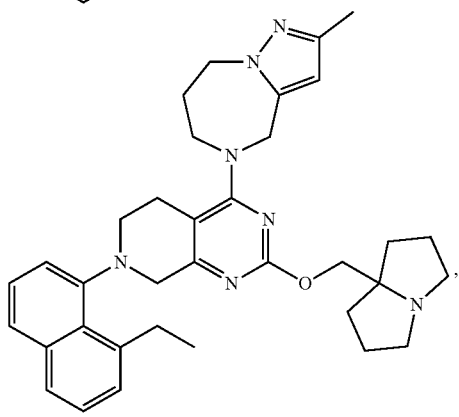

299
-continued
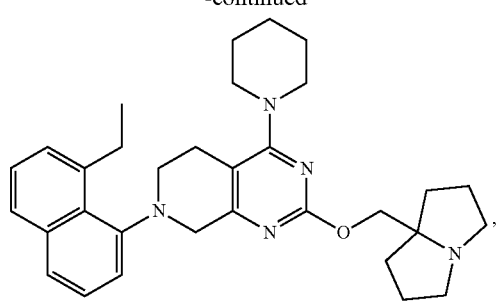
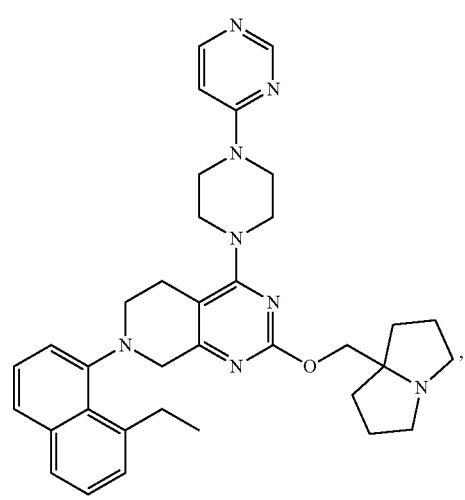
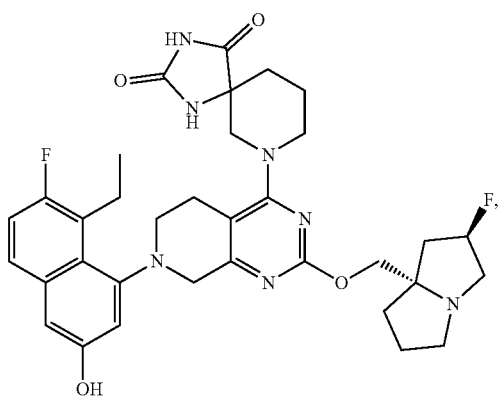
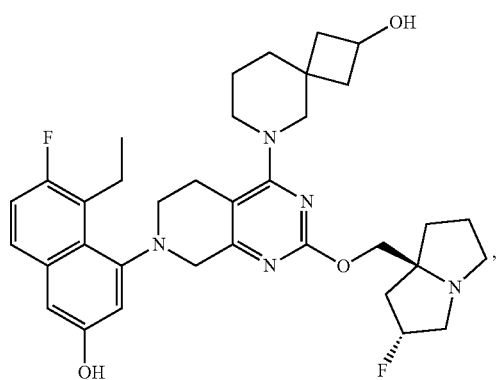
300
-continued
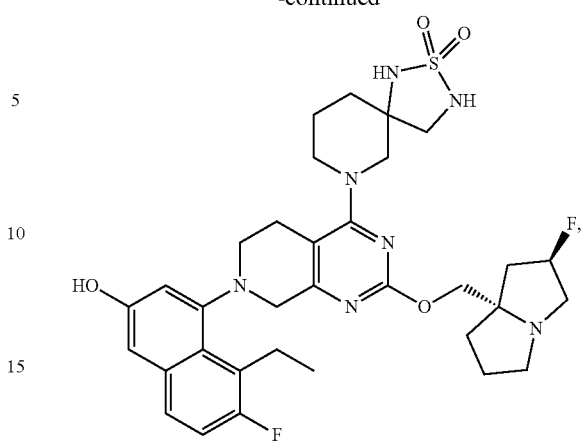
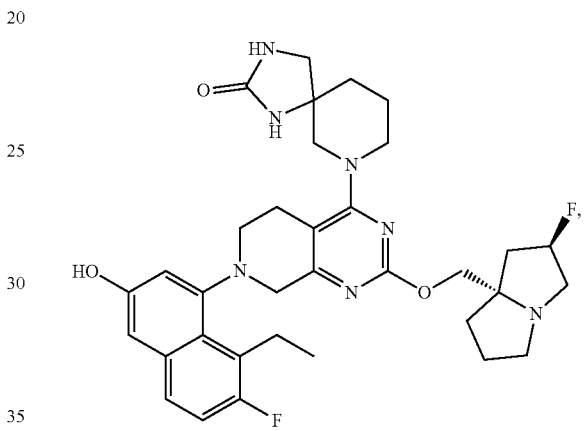
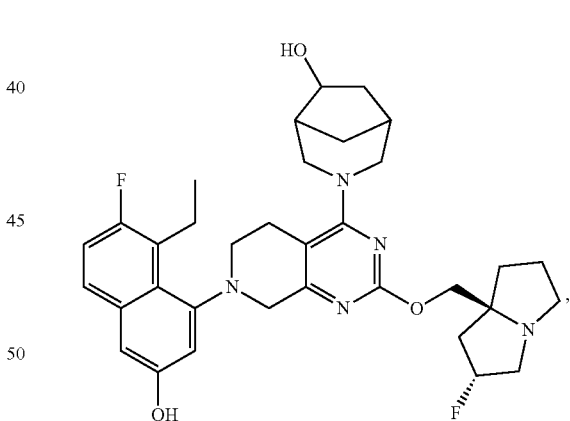
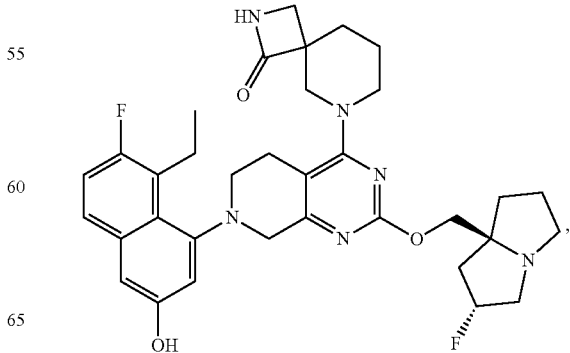

301
-continued
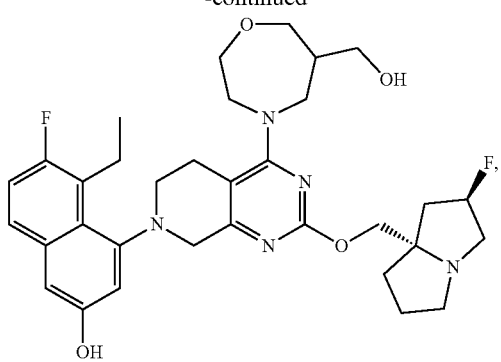
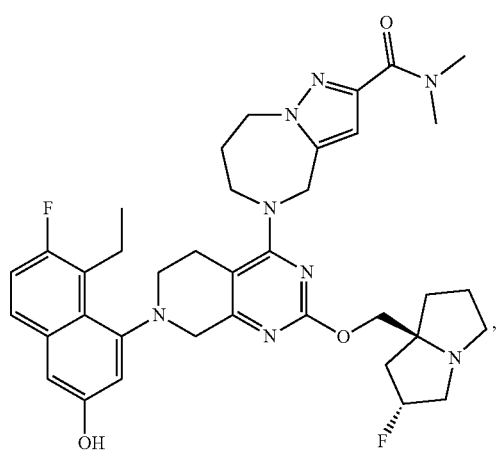
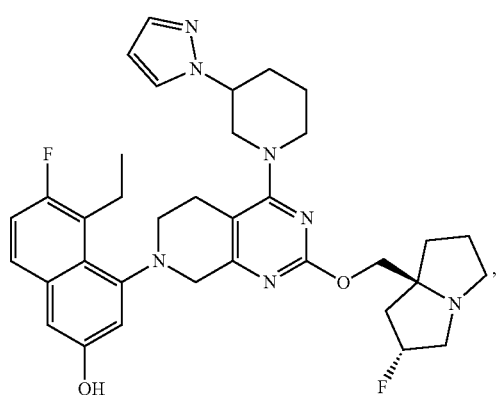
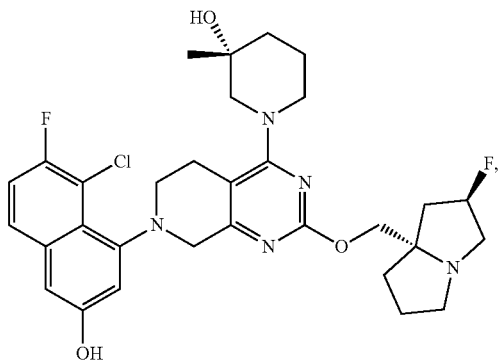
302
-continued
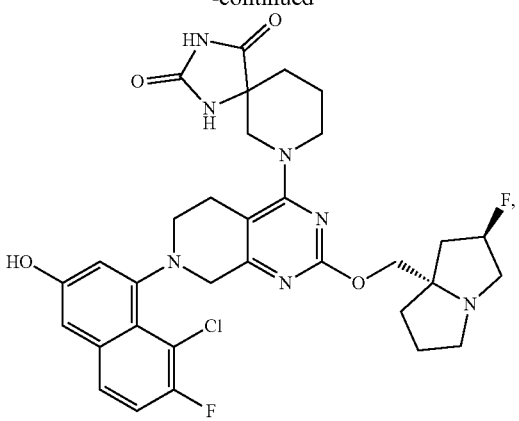
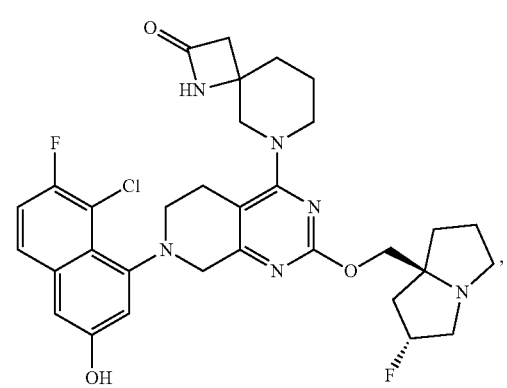
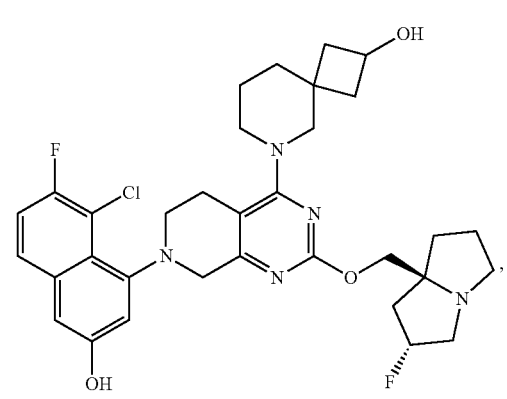
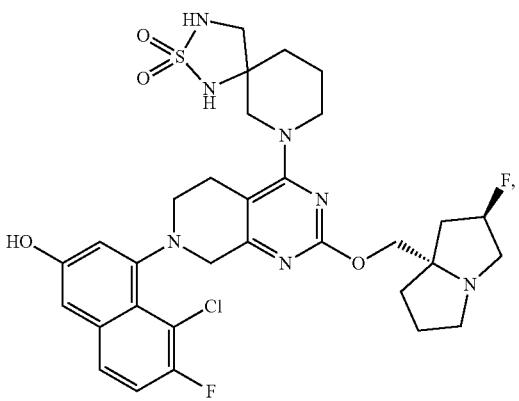

303
-continued
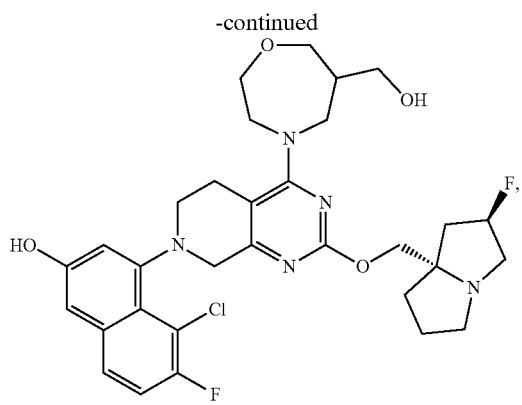
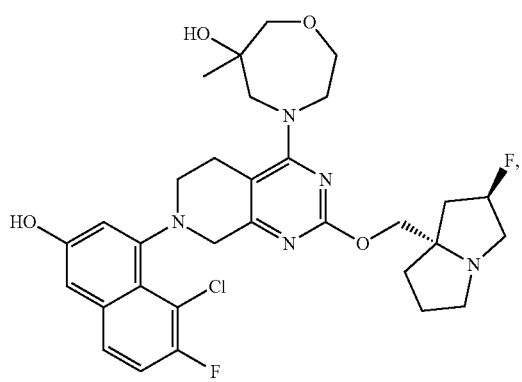
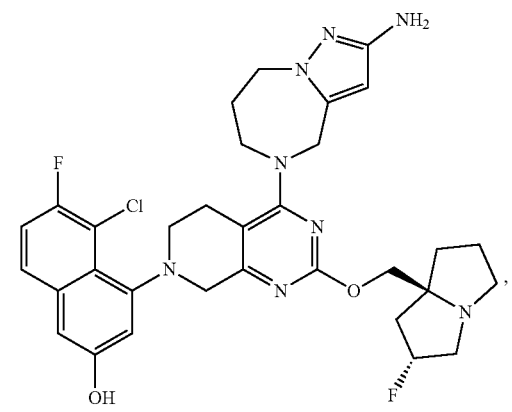
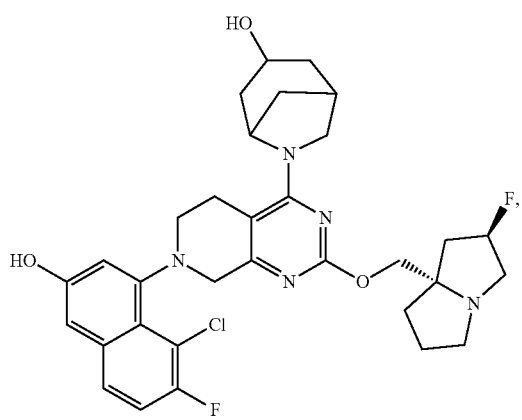
304
-continued
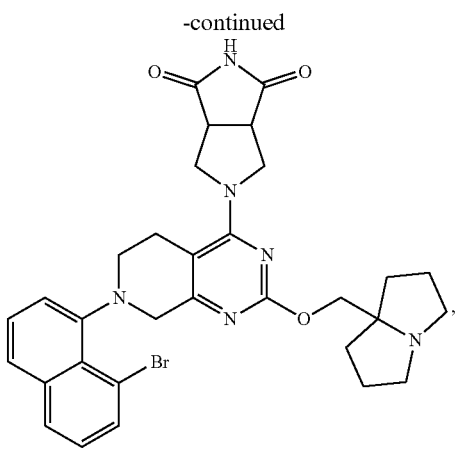
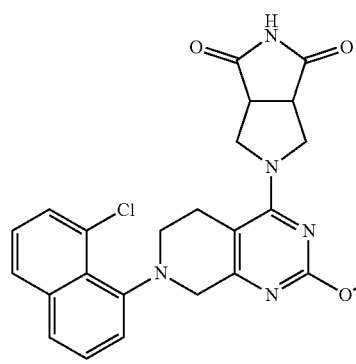
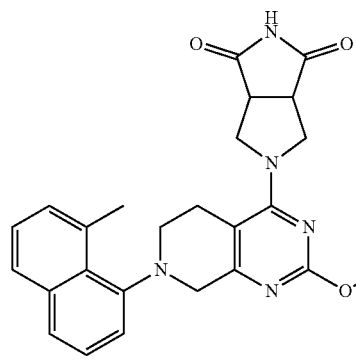
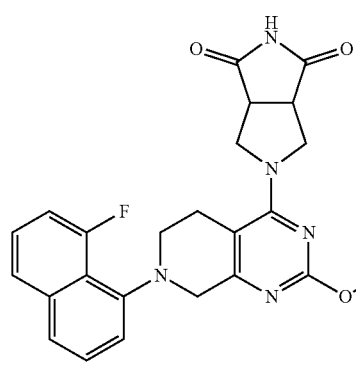

305
-continued
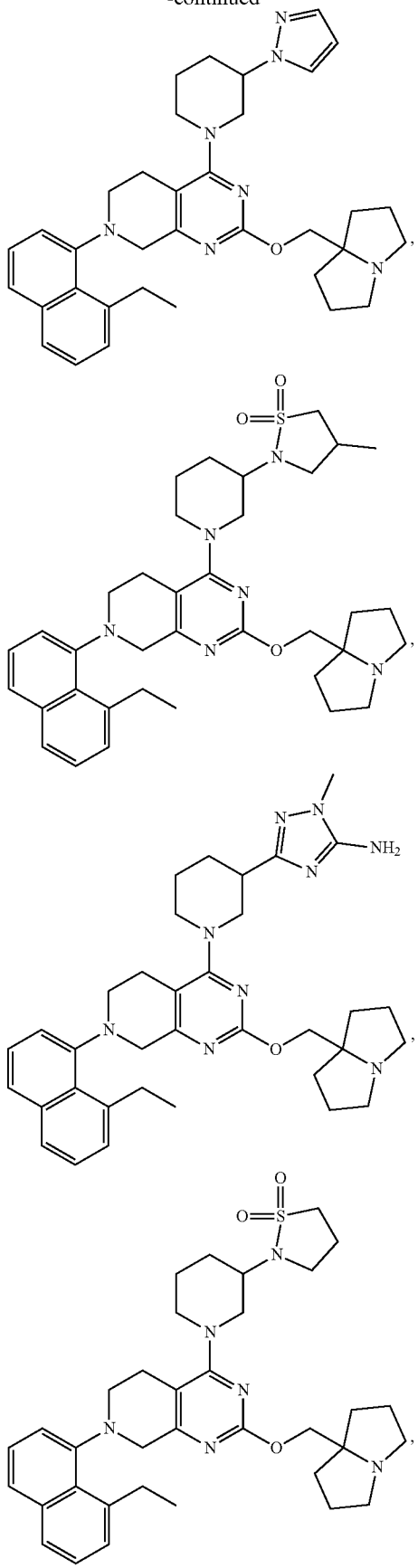
306
-continued
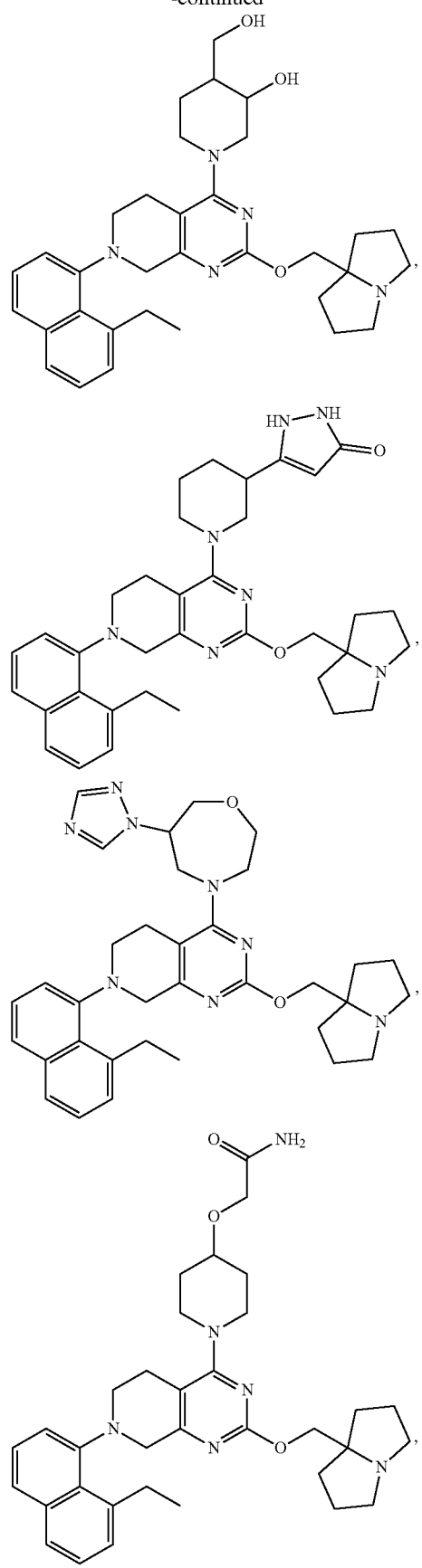

307
-continued
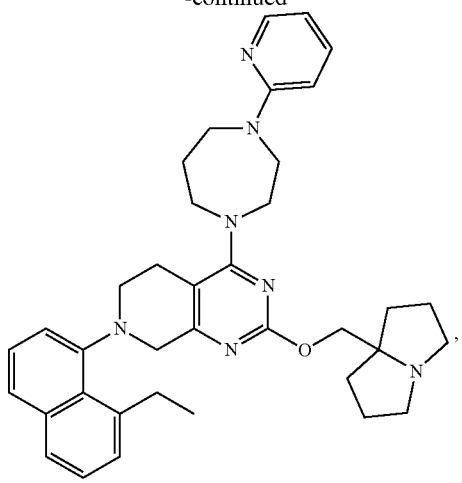
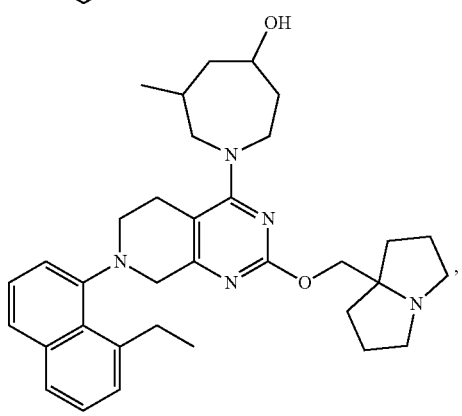
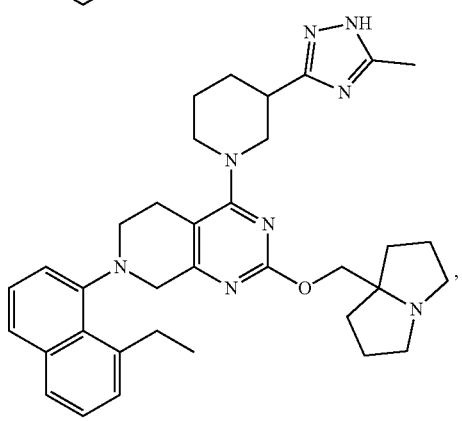
308
-continued
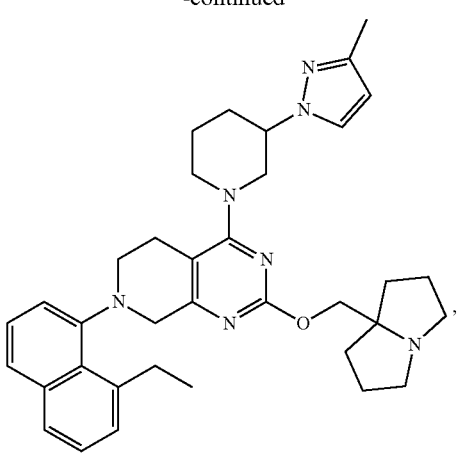

309
-continued
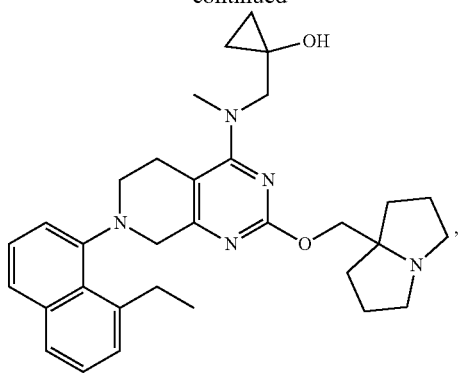
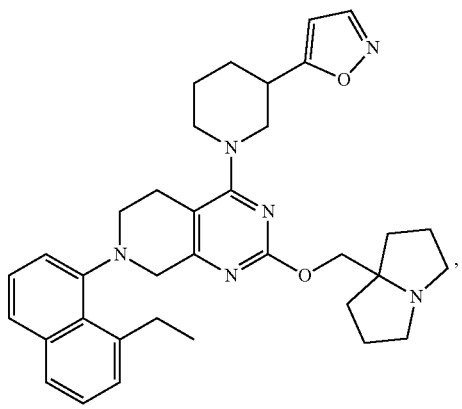
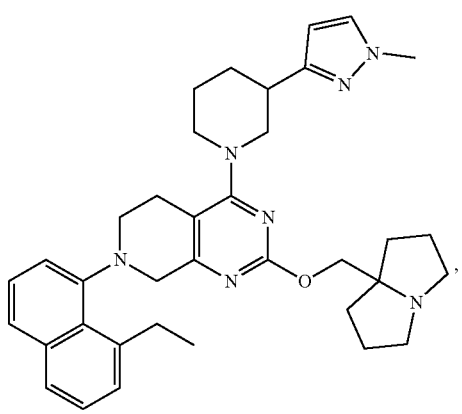
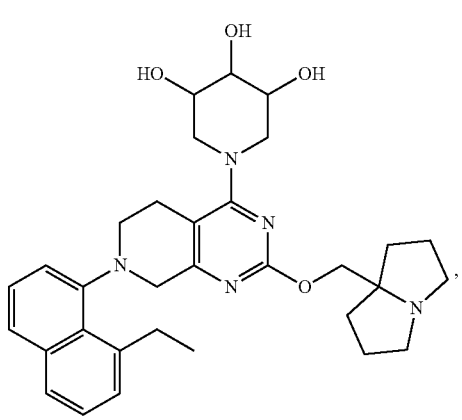
310
-continued
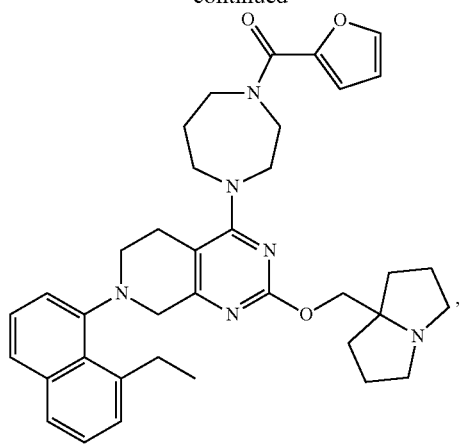
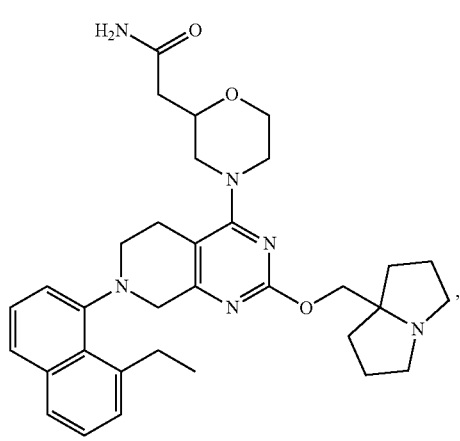
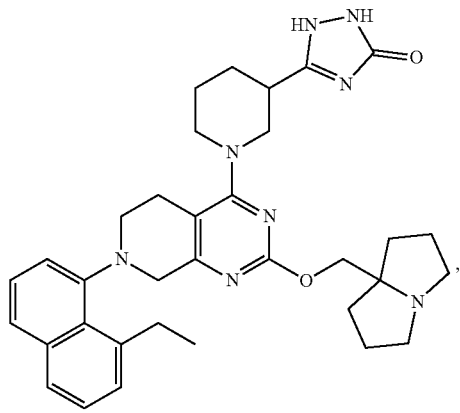
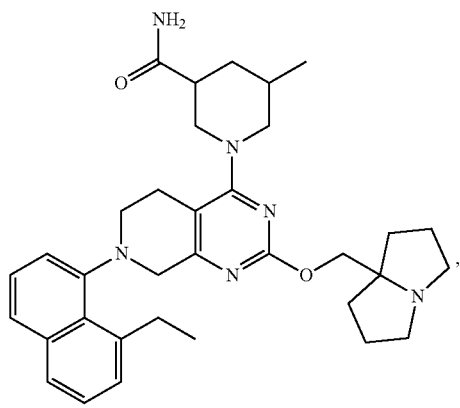

311
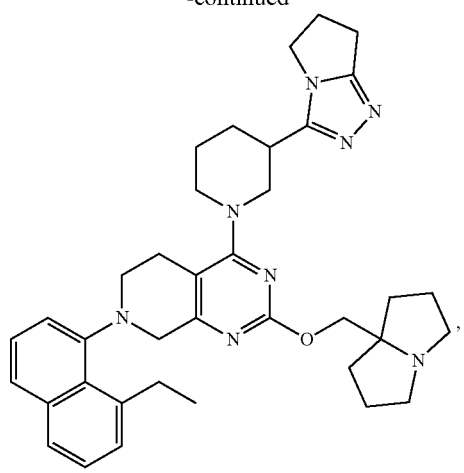
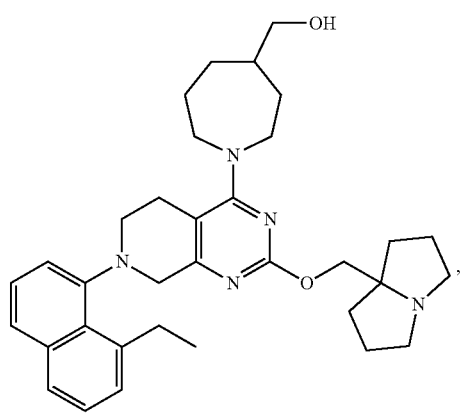
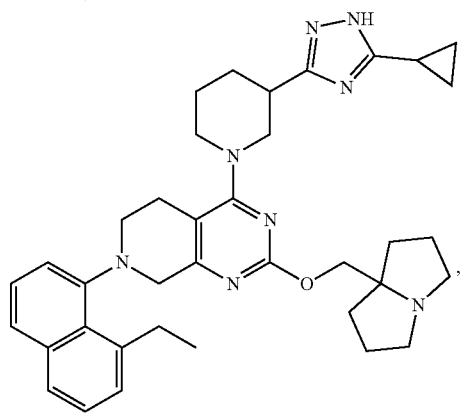
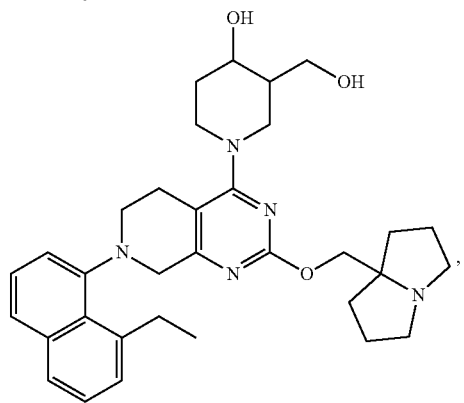
312
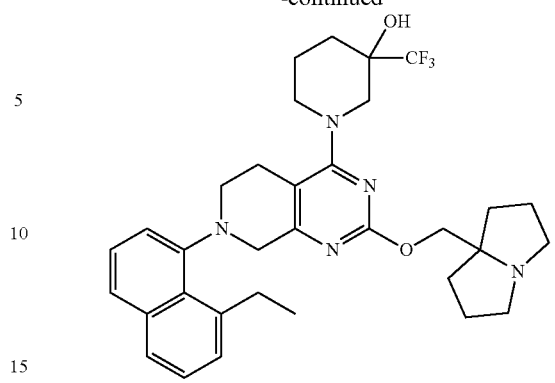
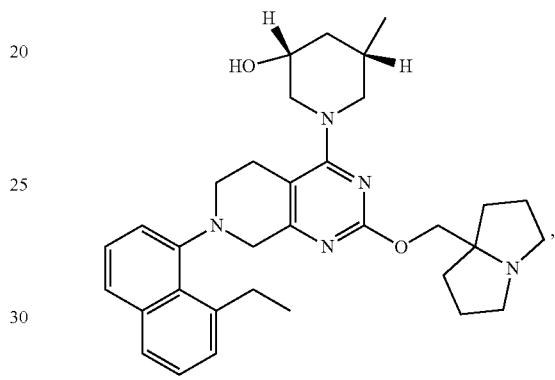
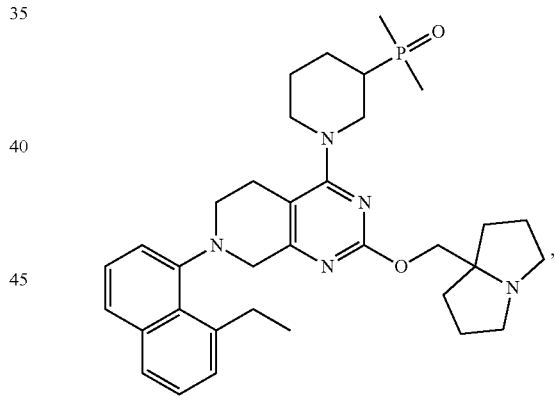
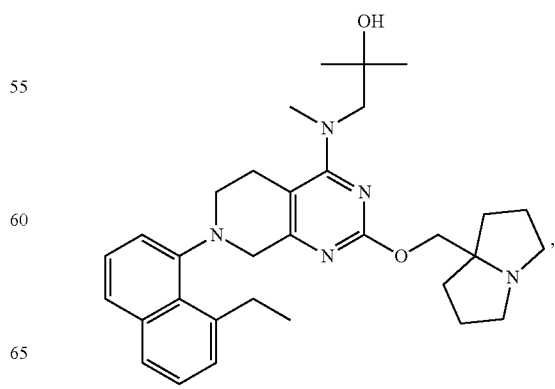

313
-continued
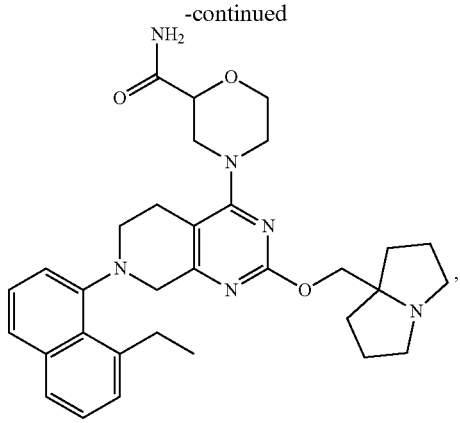
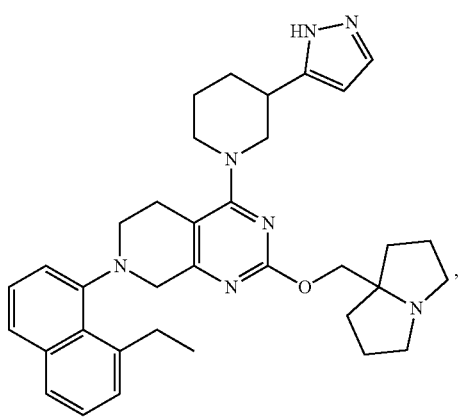
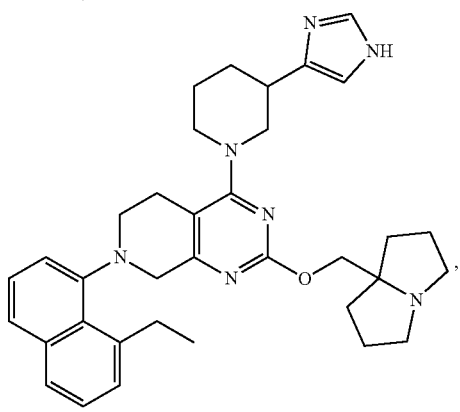
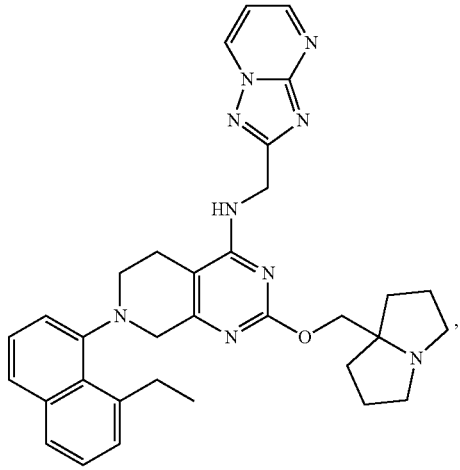
314
-continued
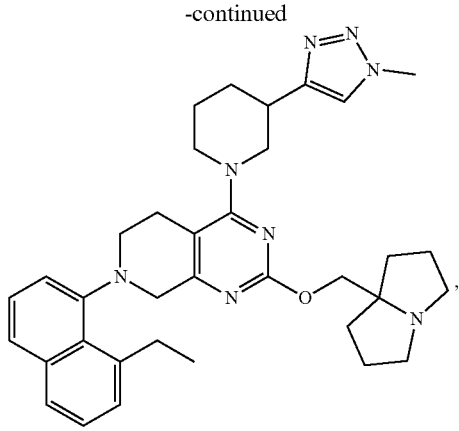
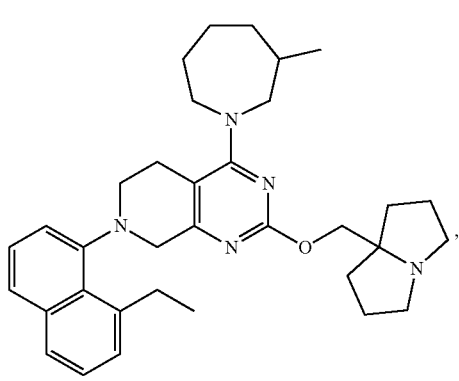
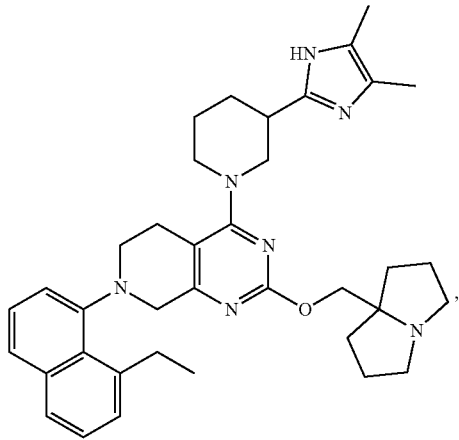
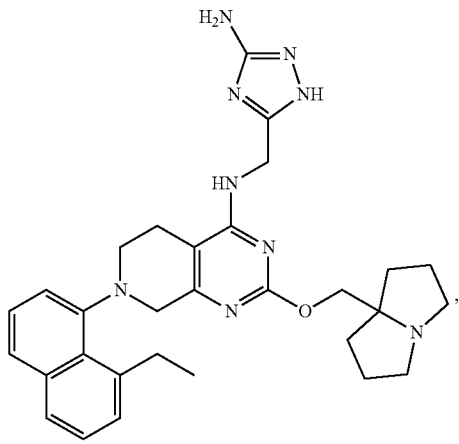

315
-continued
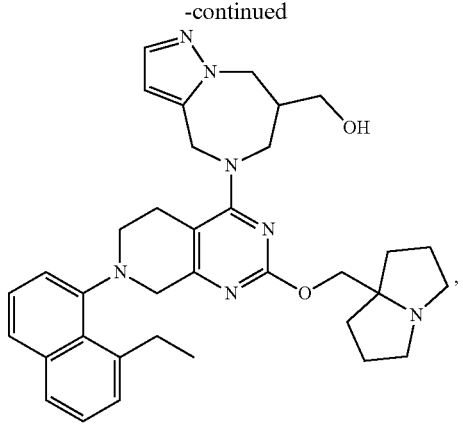
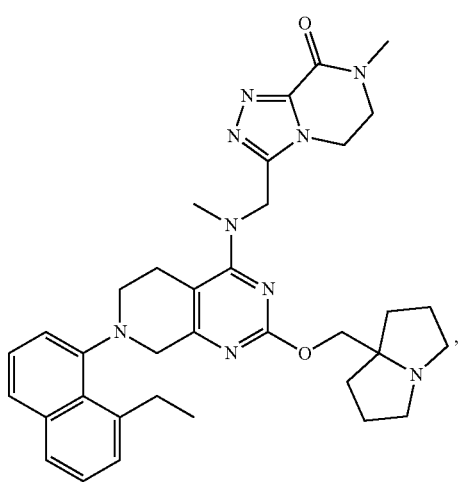
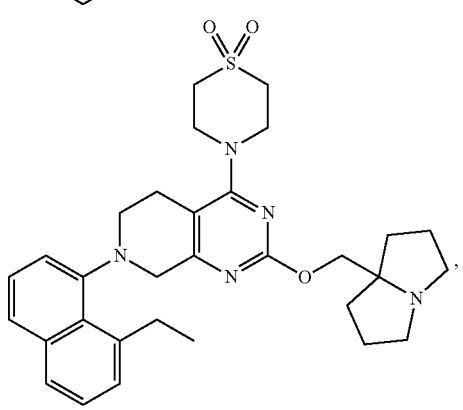
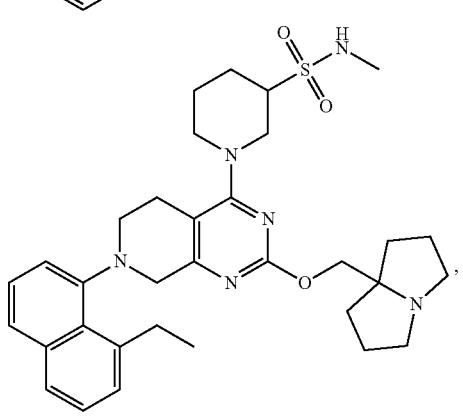
316
-continued
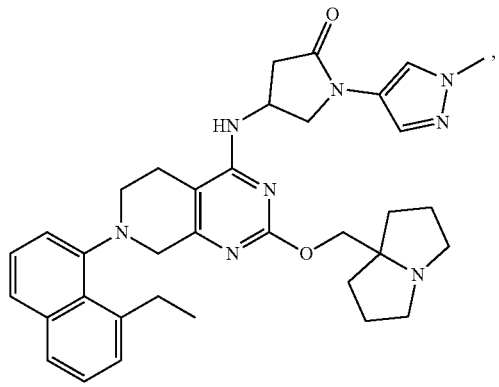
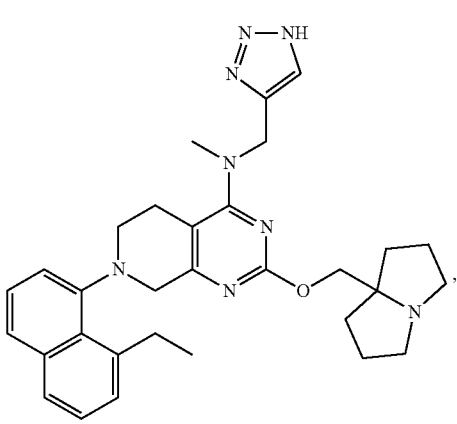
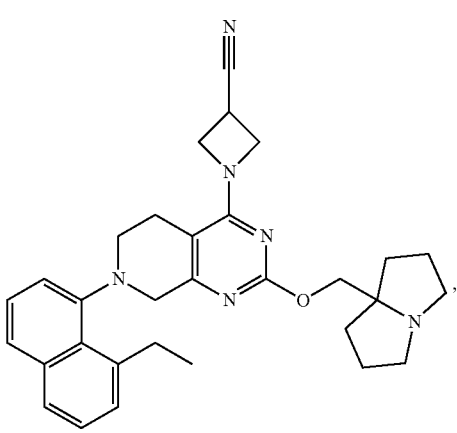
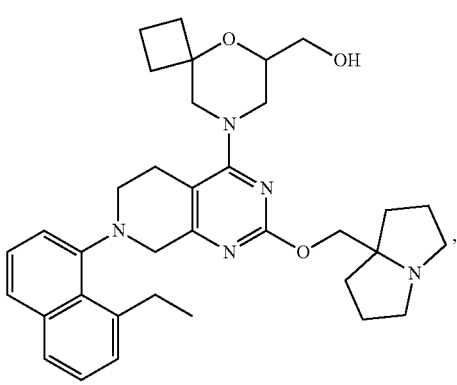

317
-continued
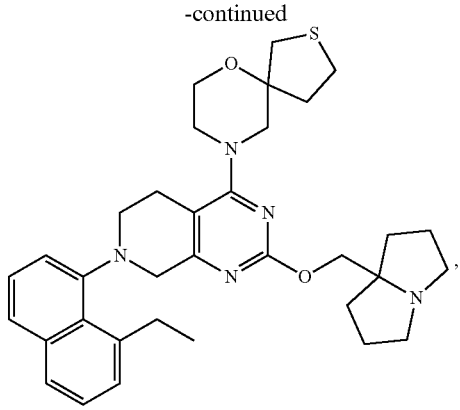
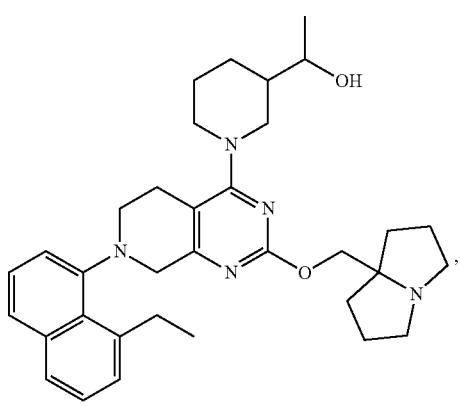
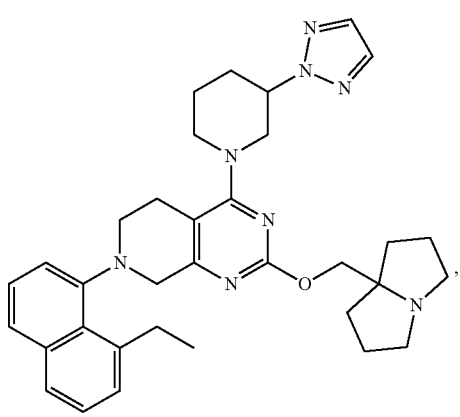
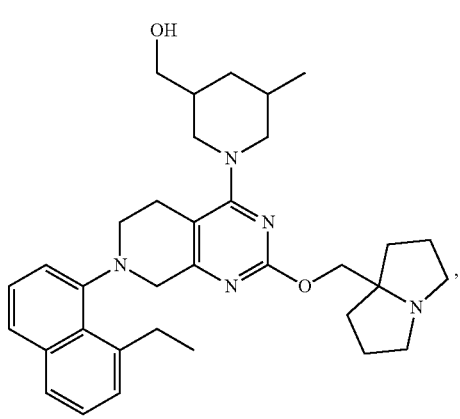
318
-continued
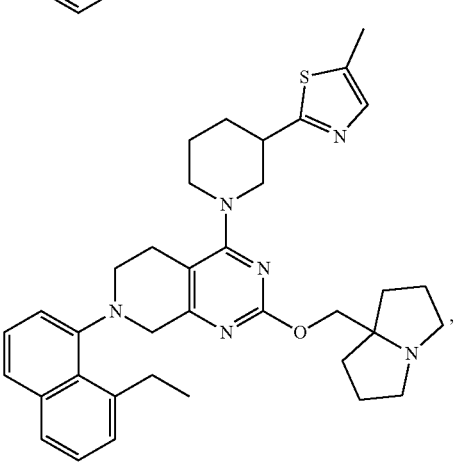
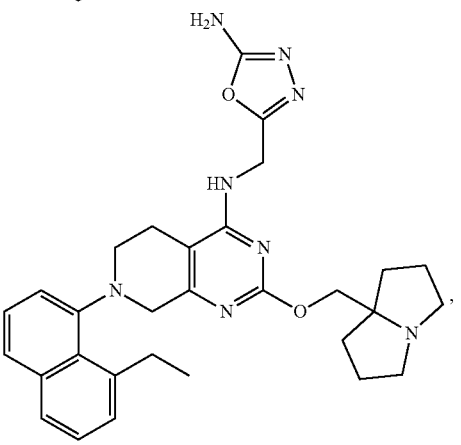
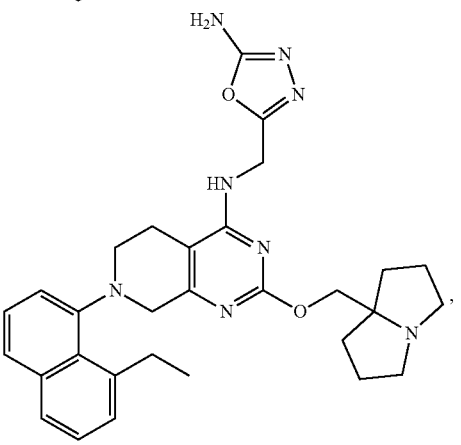
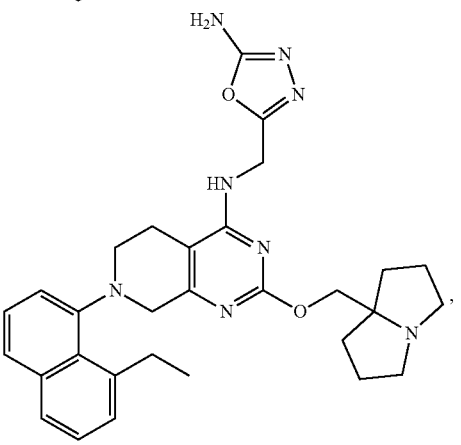

319
-continued
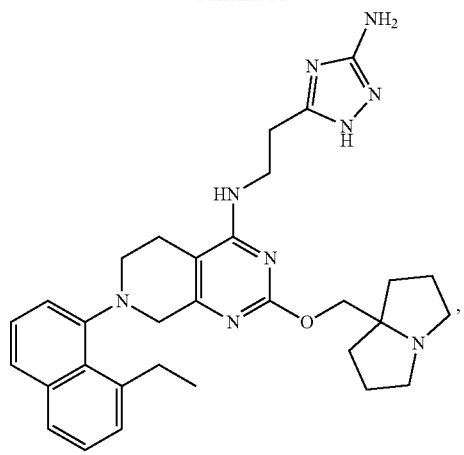
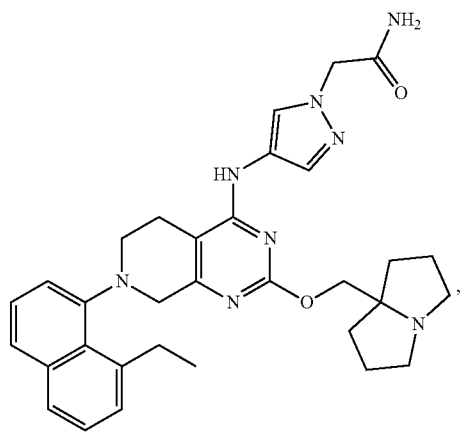
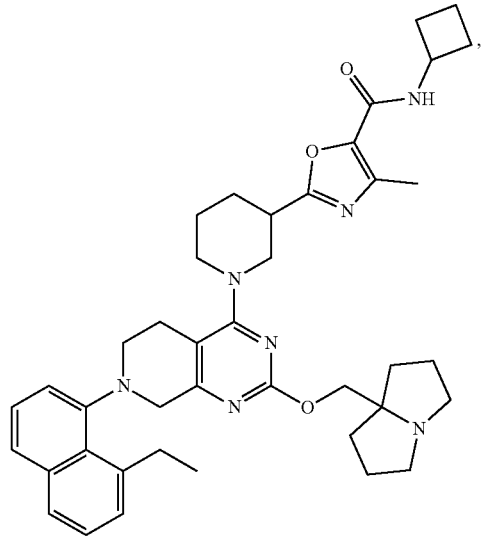
320
-continued
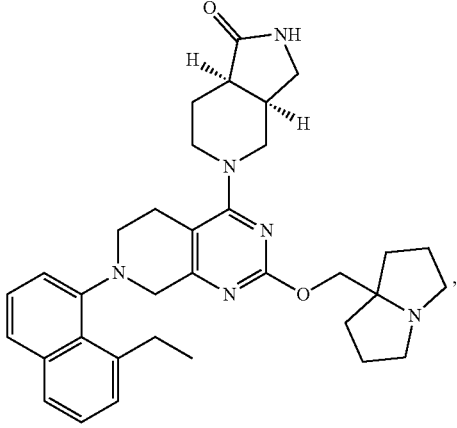
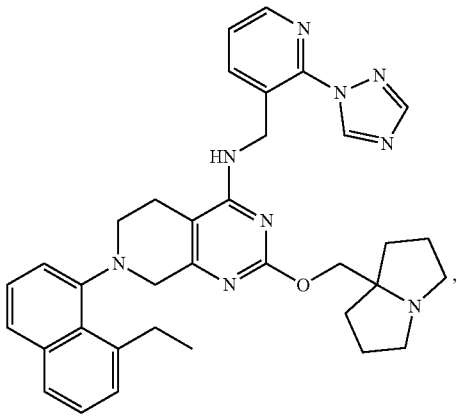
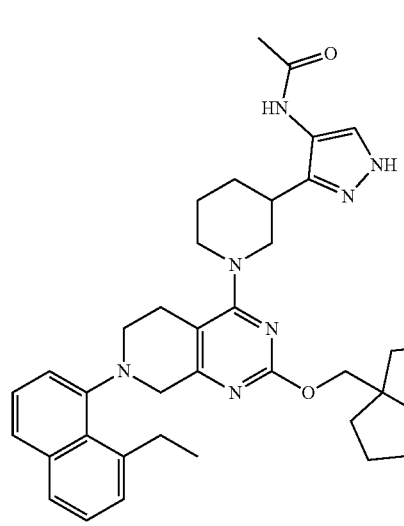

321
-continued
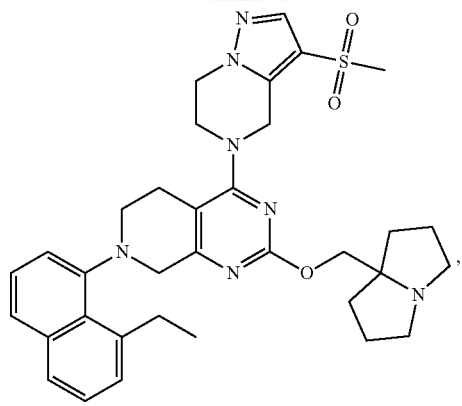
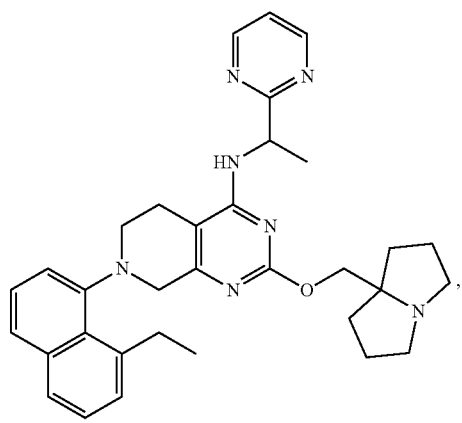
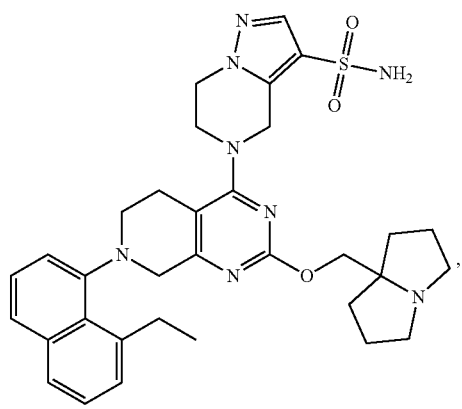
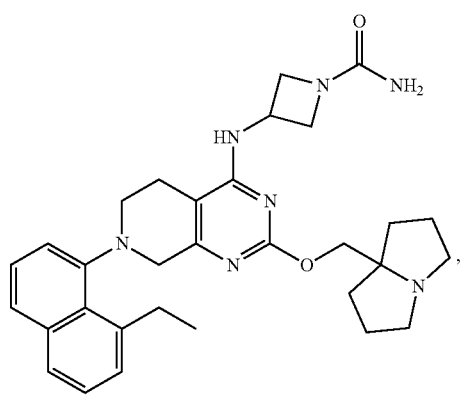
322
-continued
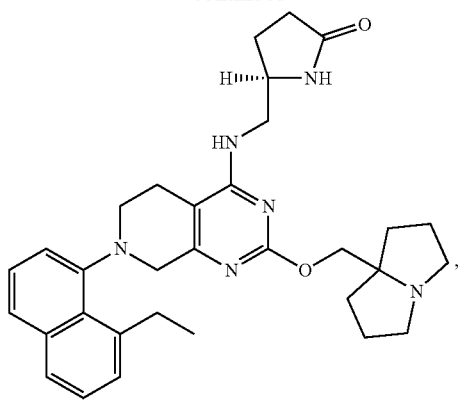
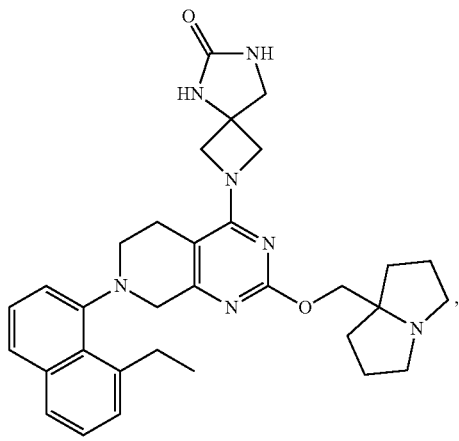
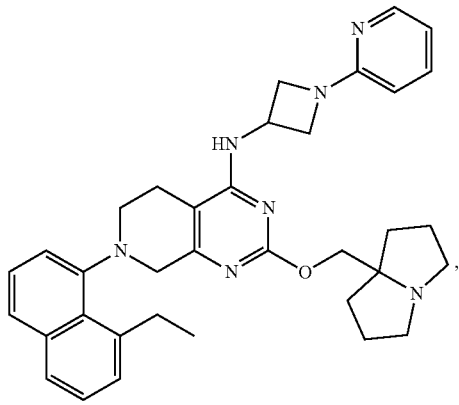
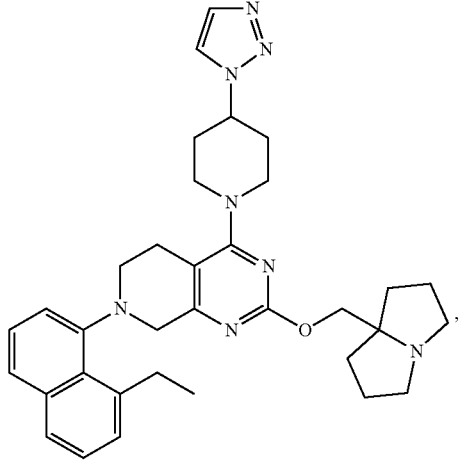

323
-continued
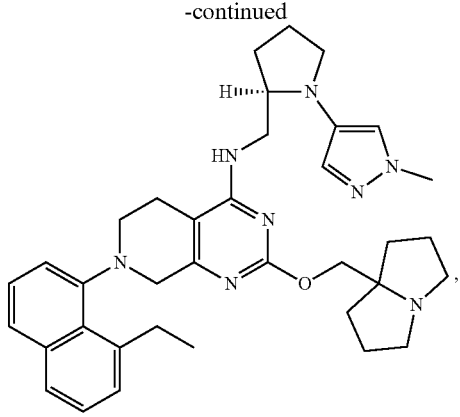
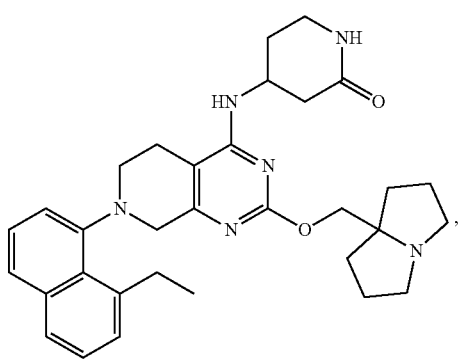
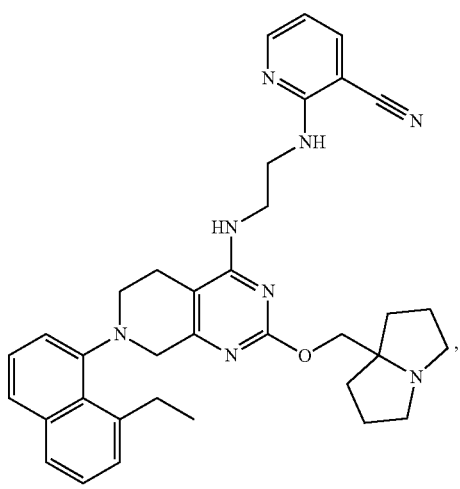
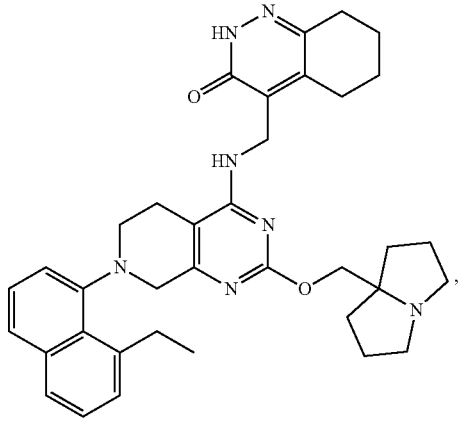
324
-continued
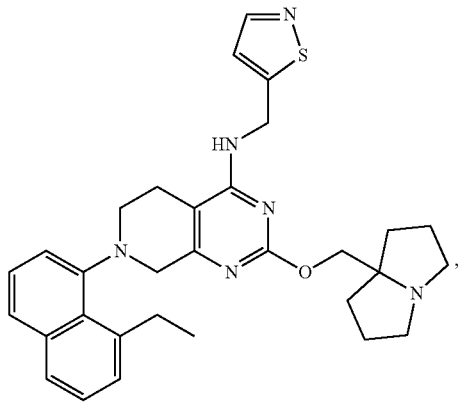
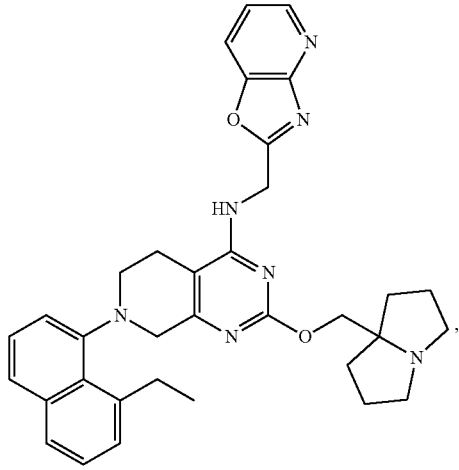
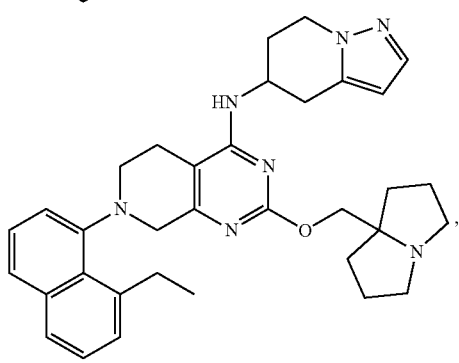
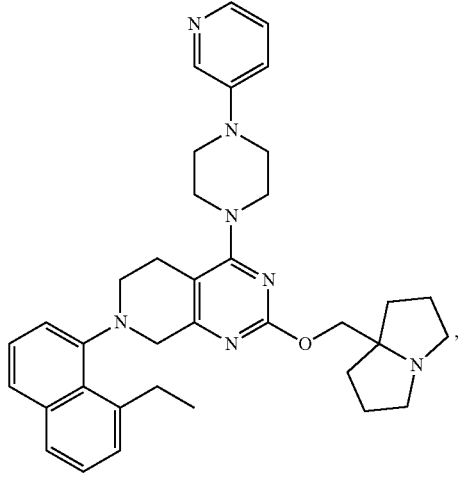

325
-continued
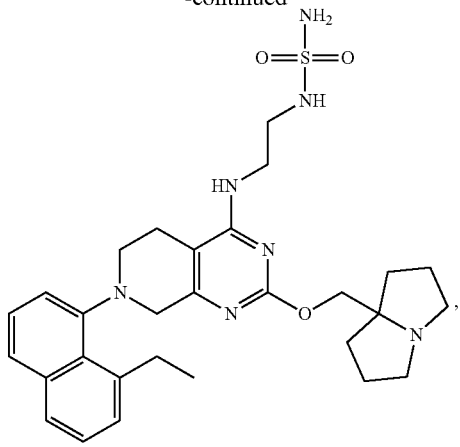
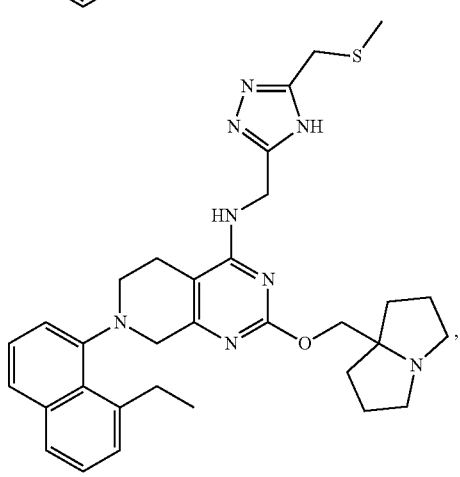
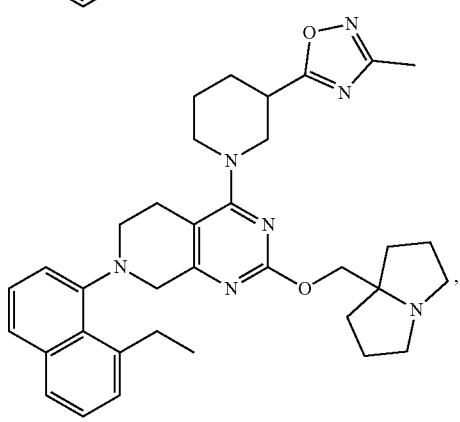
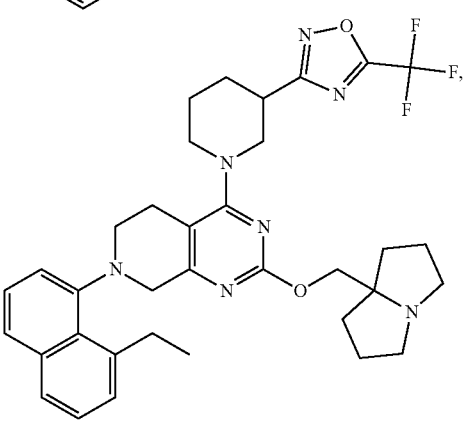
326
-continued
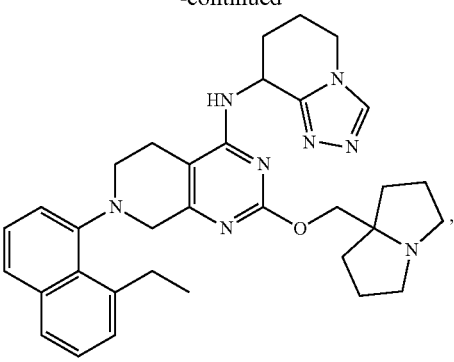
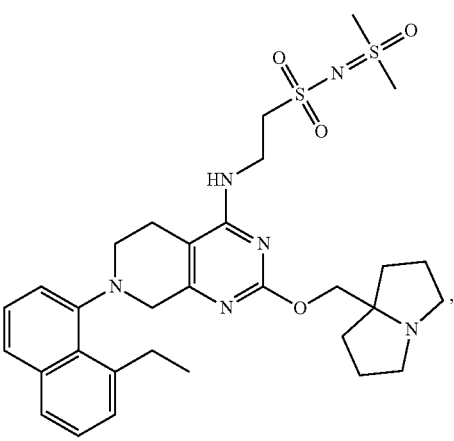 [SMILES: CCc1cccc2cccc(N3CCc4c(nc(OCC56CCCN5CCC6)nc4NCCS(=O)(=O)N=S(C)(C)=O)C3)c12]
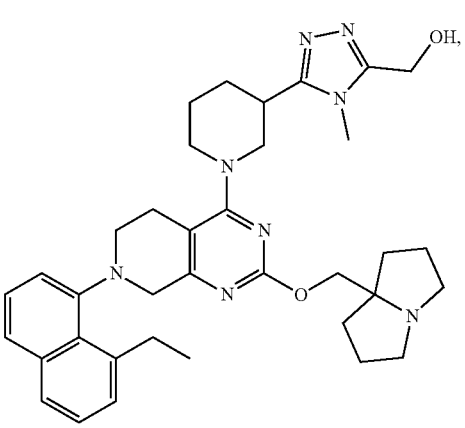
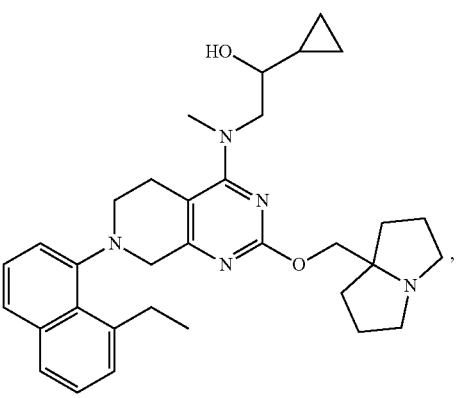

327
-continued
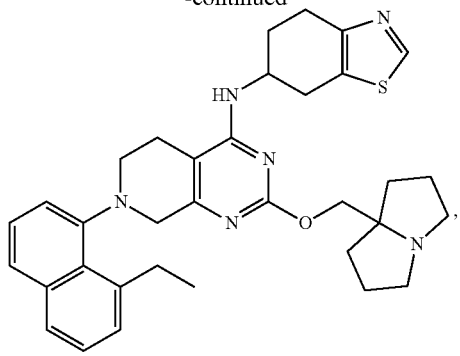
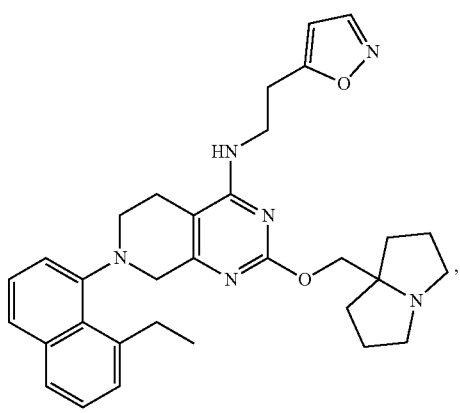
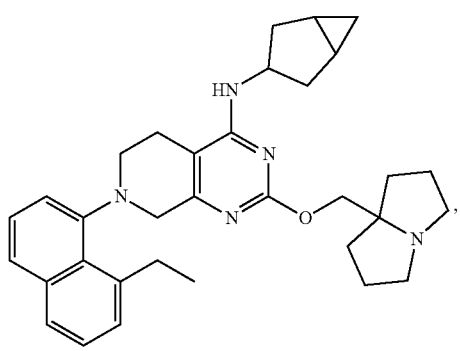
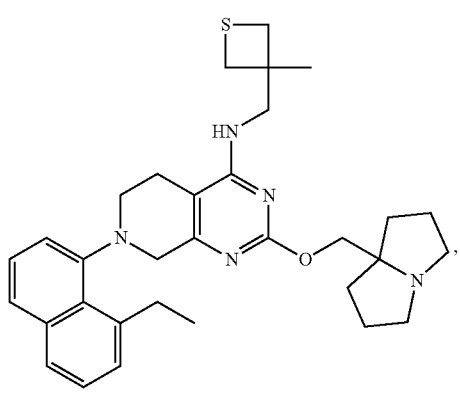
328
-continued
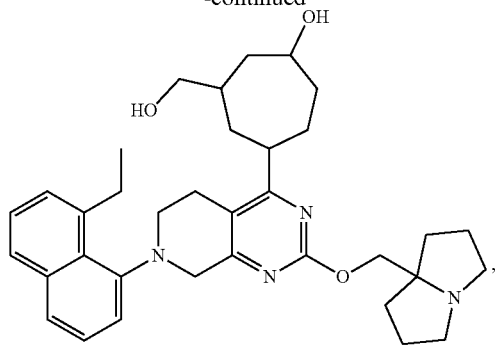
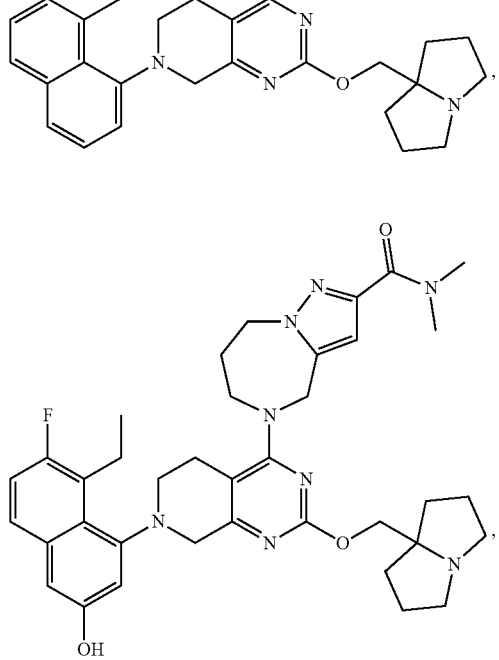
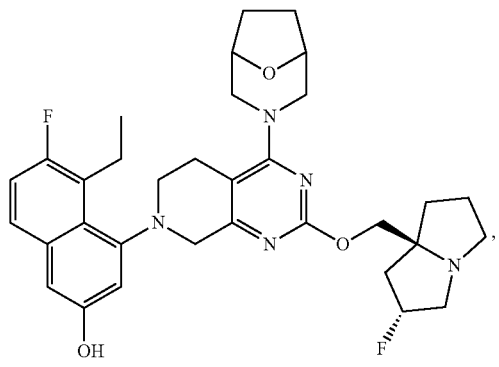
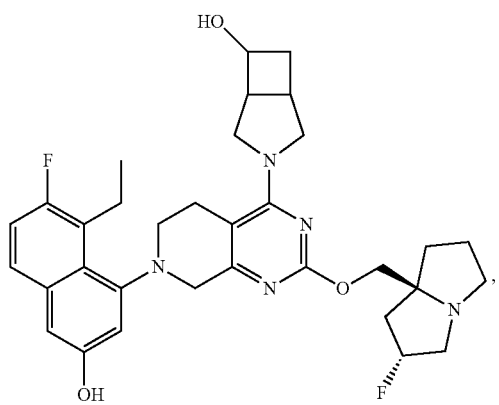

329
-continued
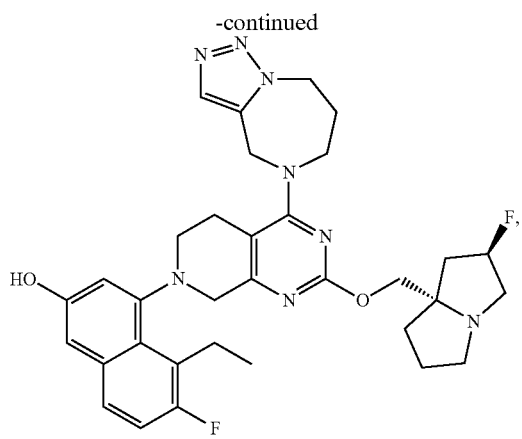
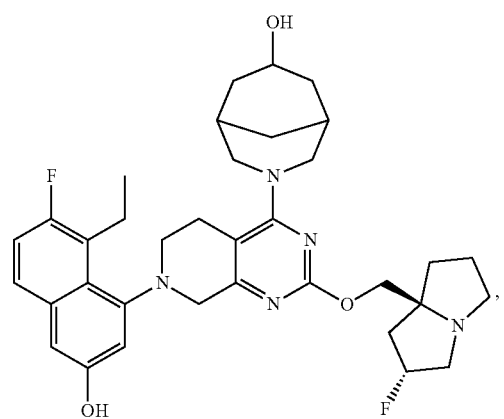
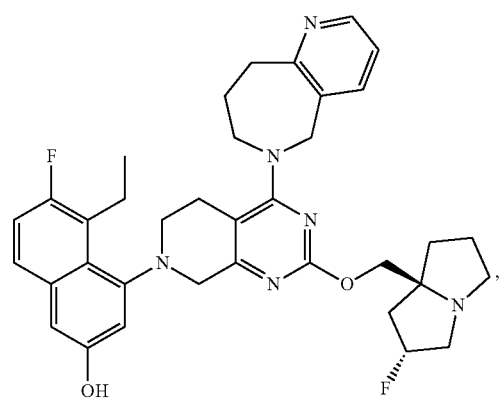
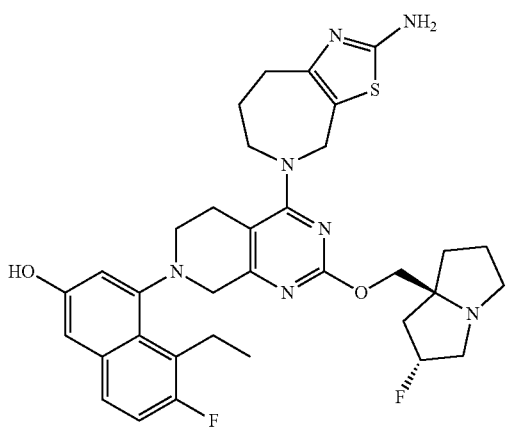
330
-continued
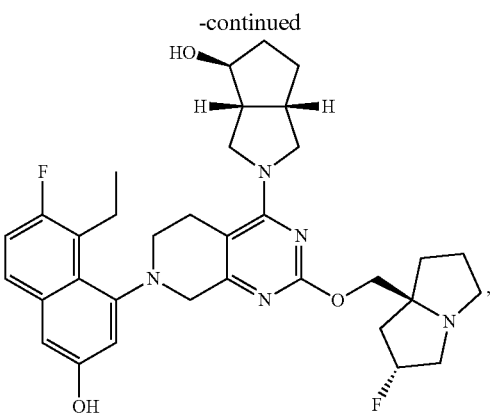
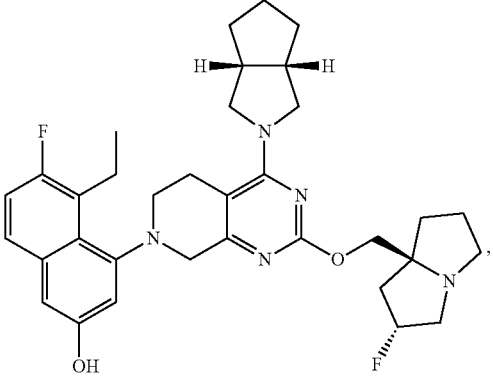
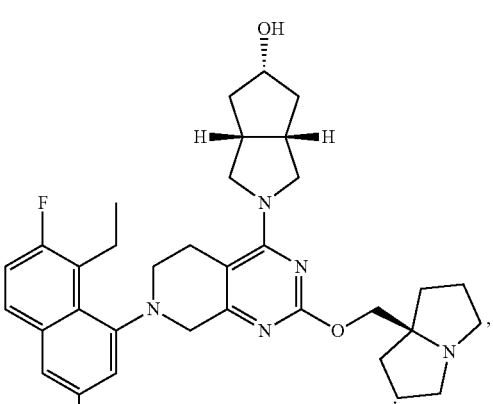
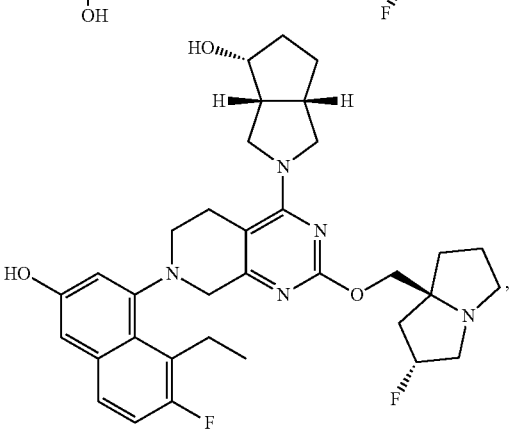

331
-continued
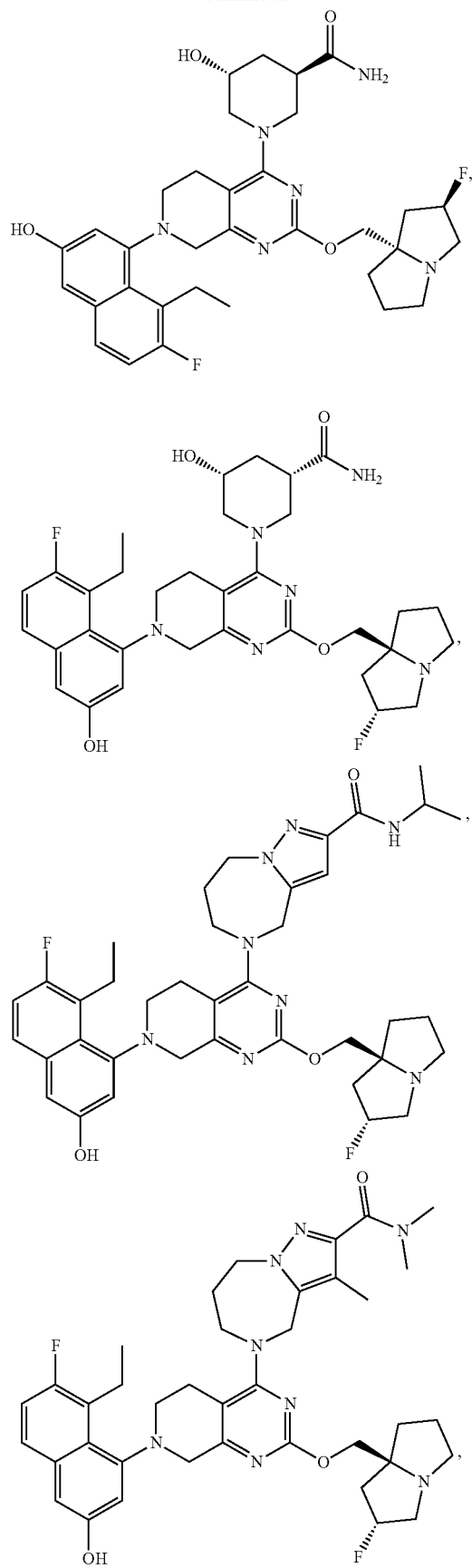
332
-continued
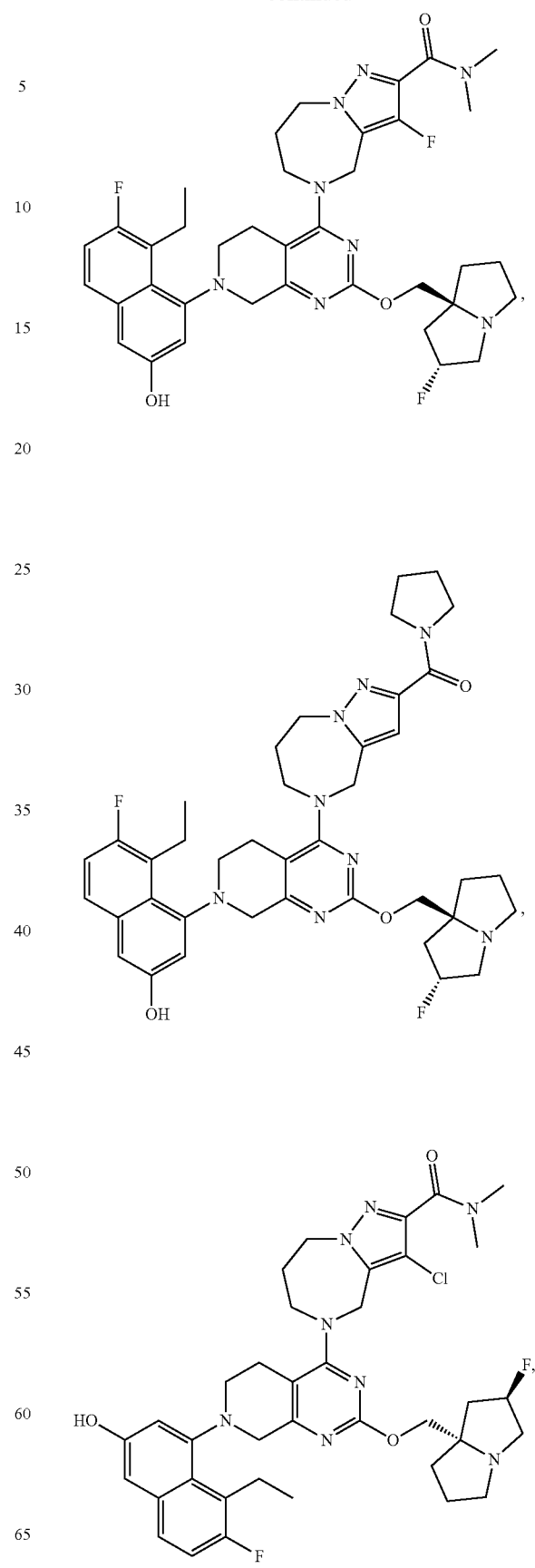

333
-continued
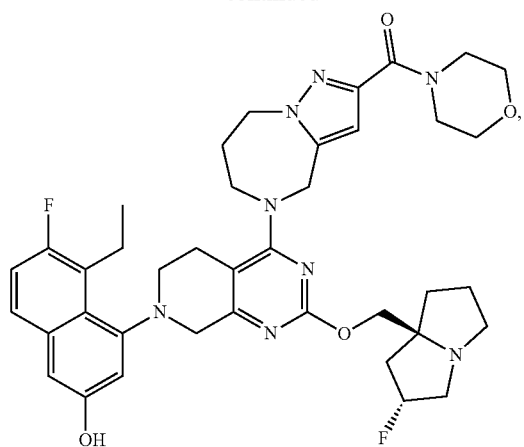
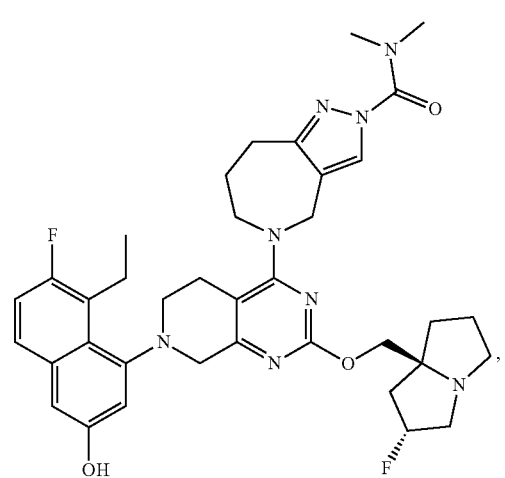
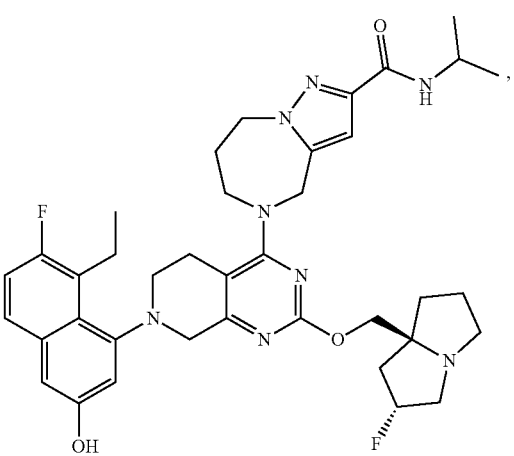
334
-continued
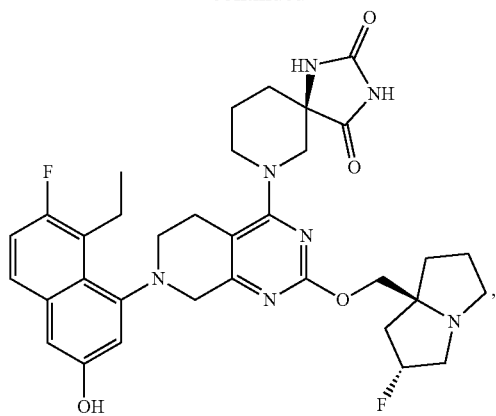
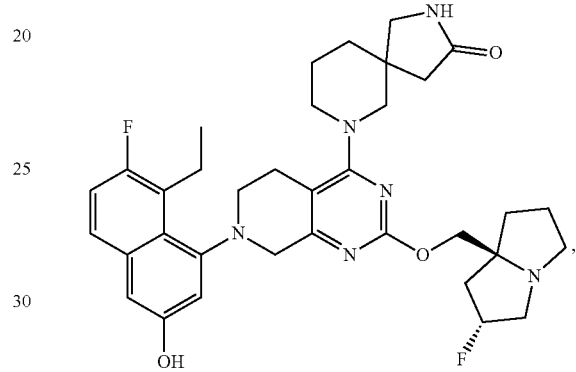
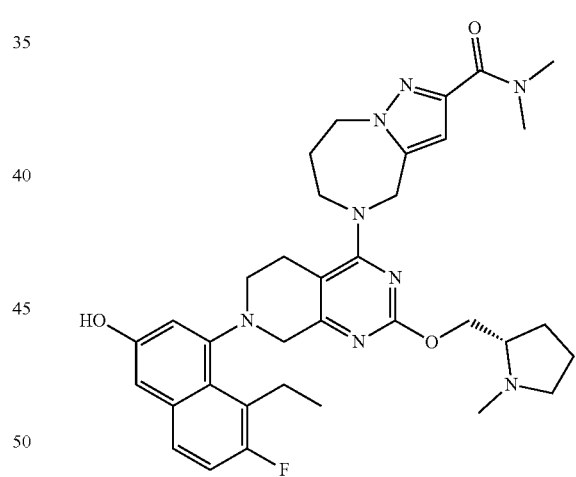
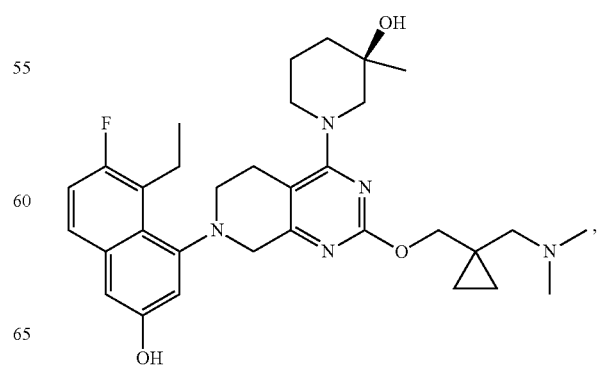

335
-continued
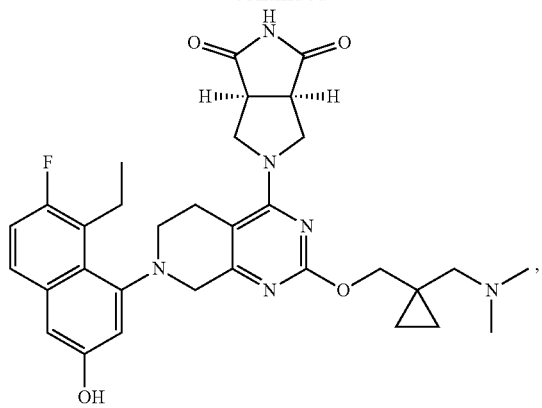
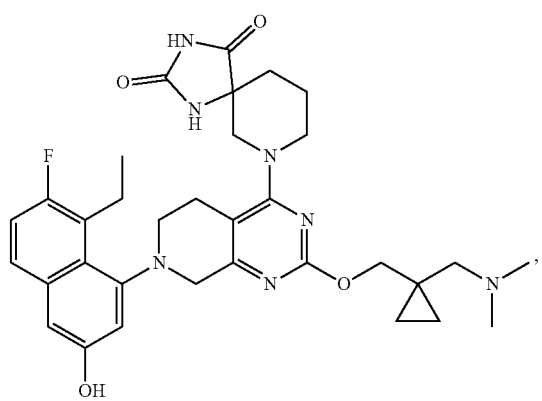
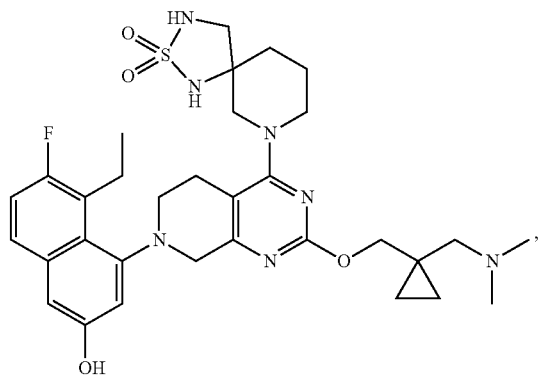
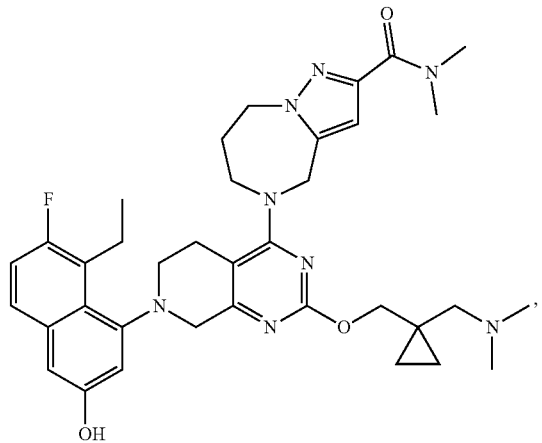
336
-continued
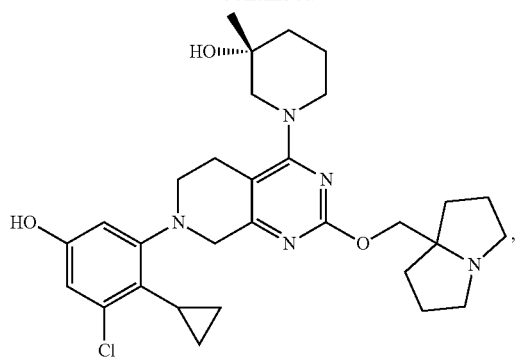
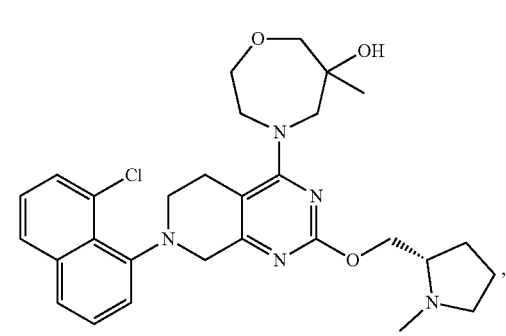
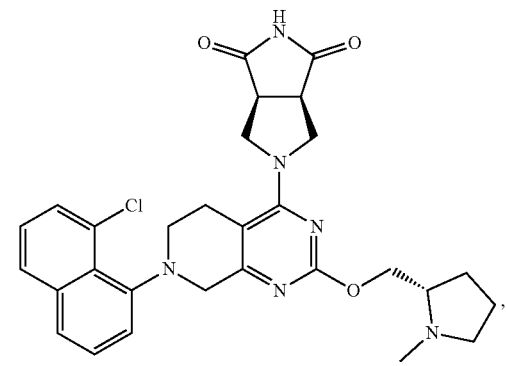
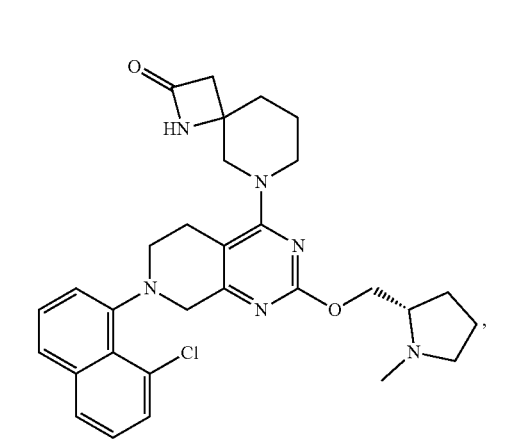

337
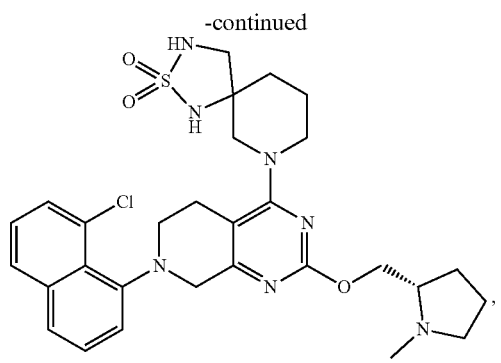
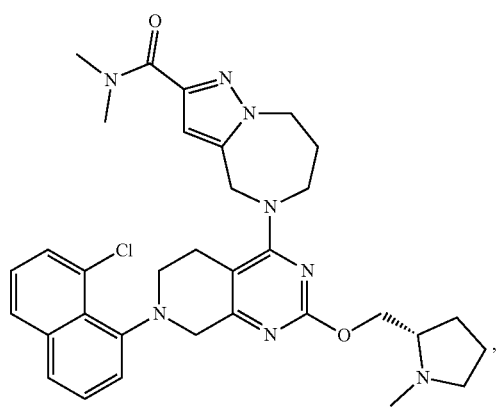
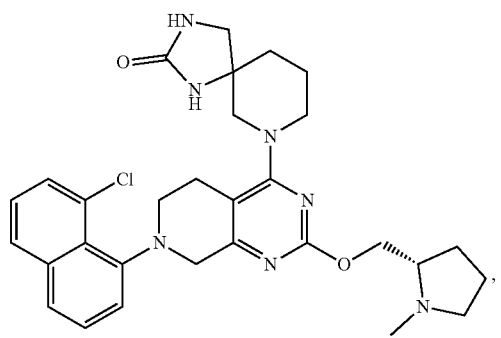
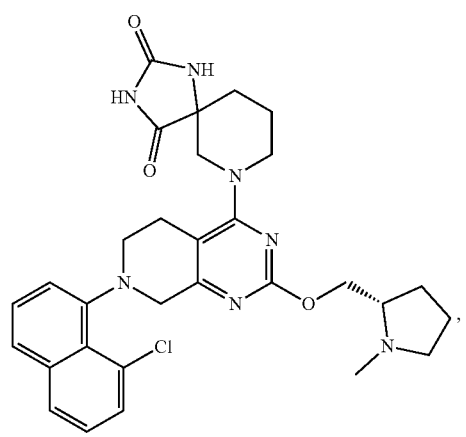
338
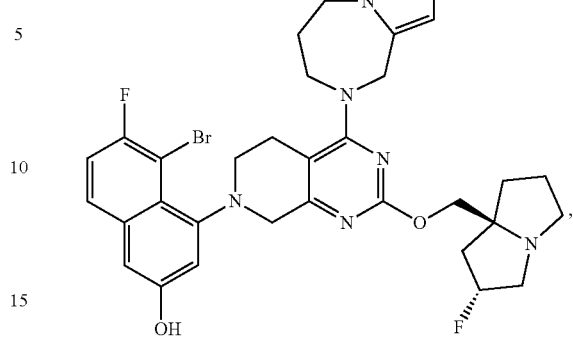
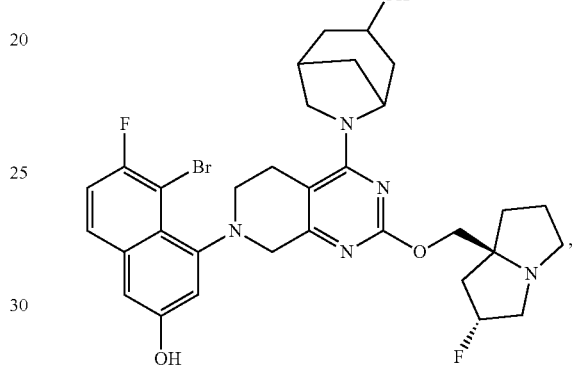
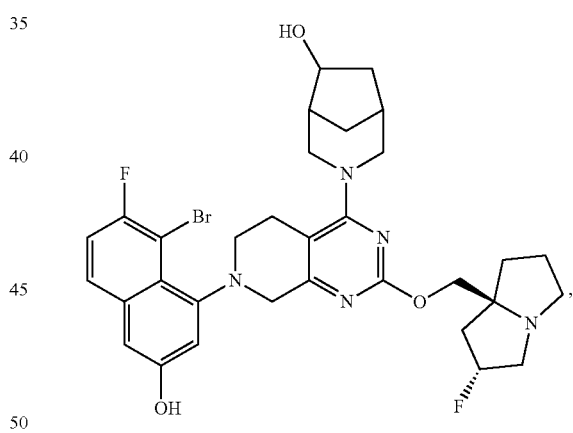
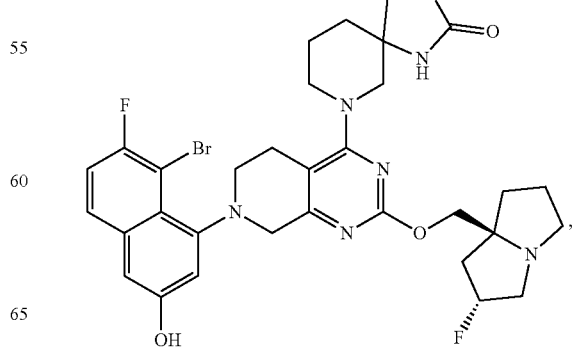

339
-continued
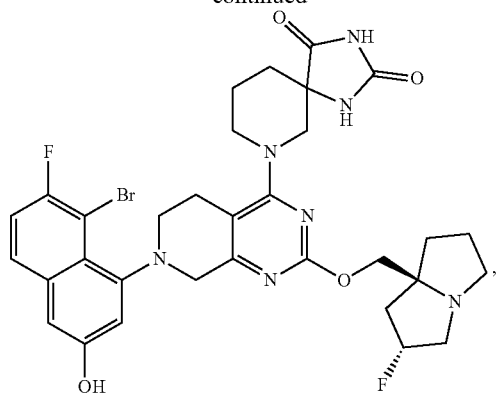
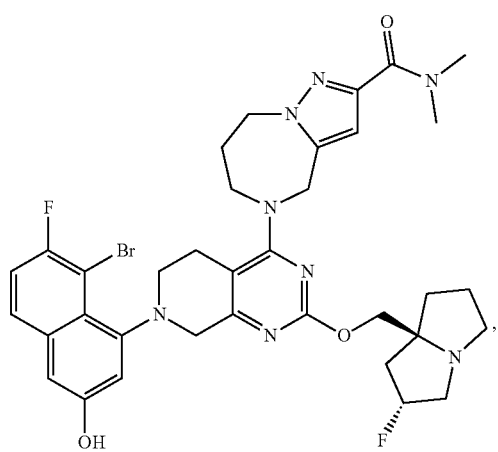
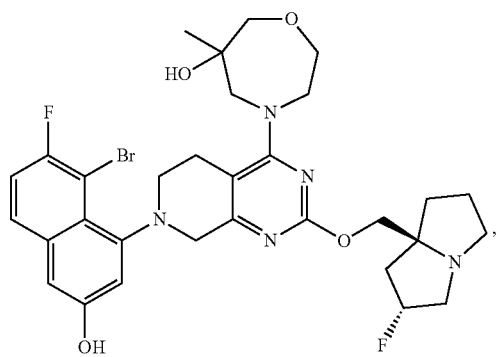
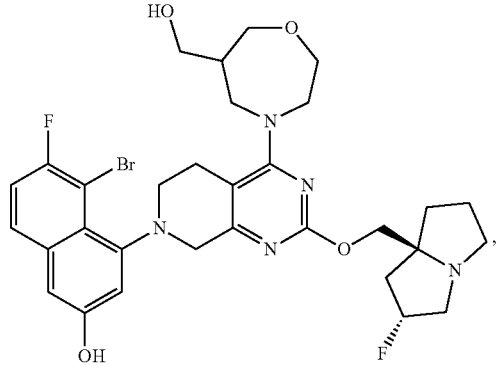
340
-continued
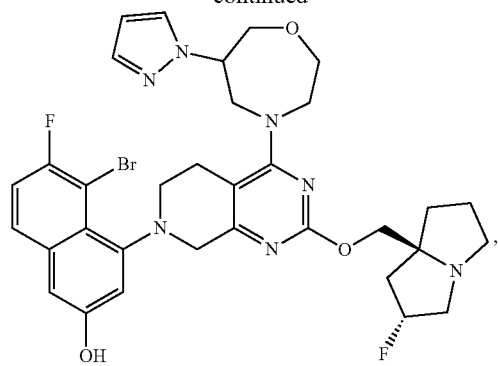
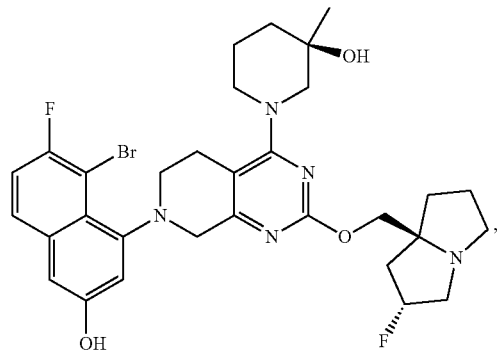
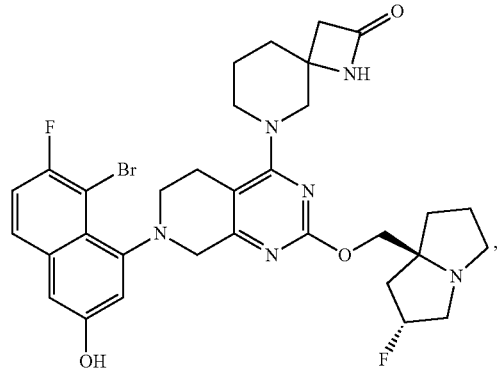
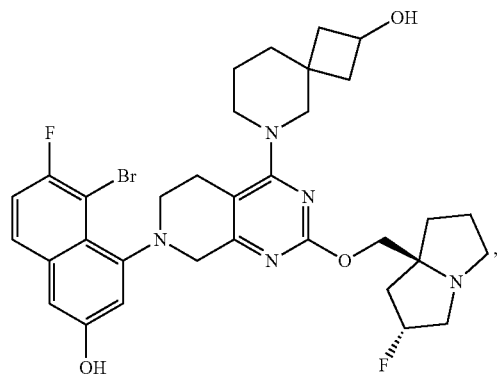

341
-continued
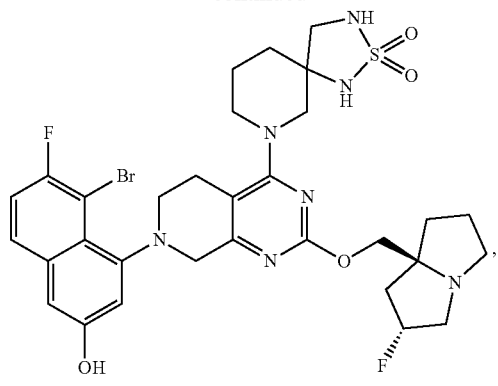
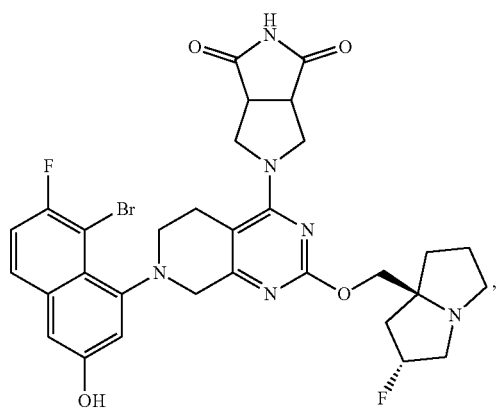
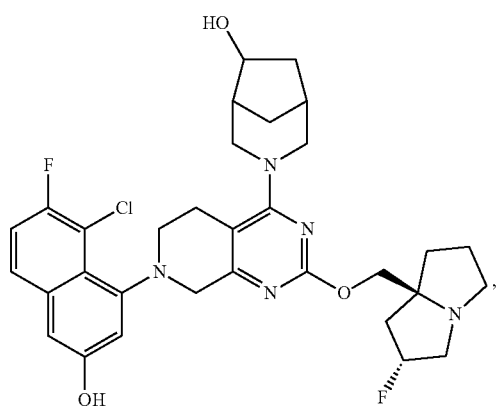
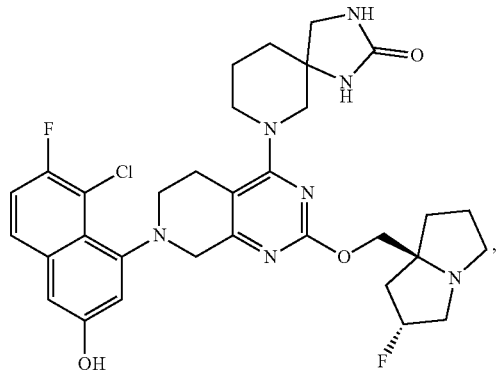
342
-continued
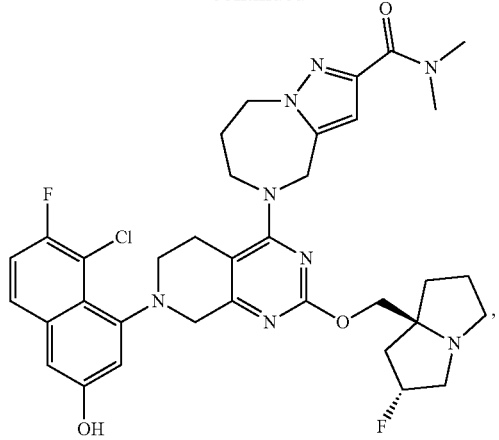
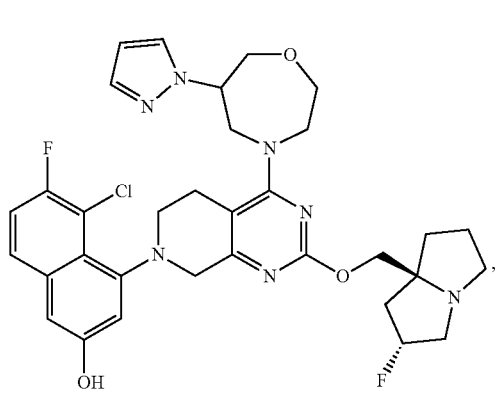
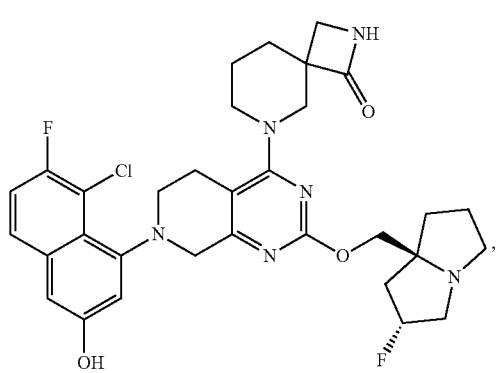
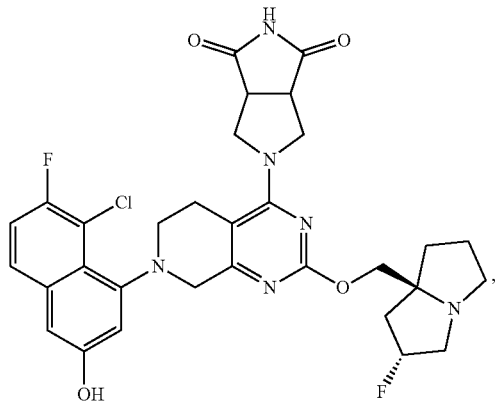
and a pharmaceutically acceptable salt thereof.

2. The compound of claim 1, wherein the compound is

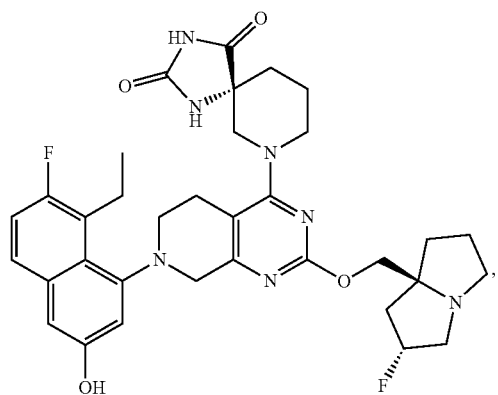 [SMILES: CCc1c(F)ccc2cc(O)cc(N3CCc4c(nc(OC[C@@]56CCCN5C[C@H](F)C6)nc4N4CCC[C@]5(C4)NC(=O)NC5=O)C3)c12]

or a pharmaceutically acceptable salt thereof.

3. The compound of claim 1, wherein the compound is

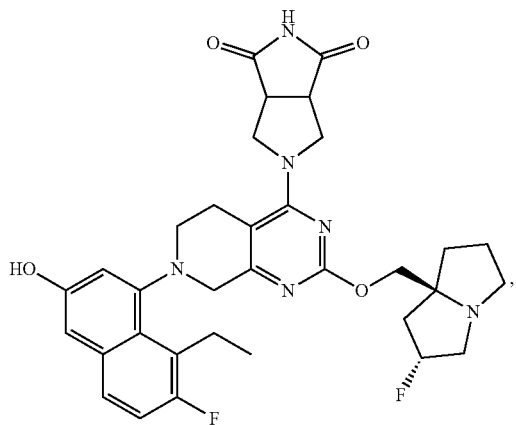 [SMILES: CCc1c(F)ccc2cc(O)cc(N3CCc4c(nc(OC[C@@]56CCCN5C[C@H](F)C6)nc4N4CC5C(=O)NC(=O)C5C4)C3)c12]

or a pharmaceutically acceptable salt thereof.

4. The compound of claim 1, wherein the compound is

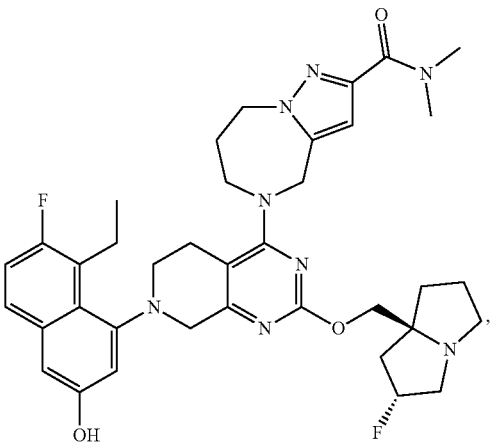 [SMILES: CCc1c(F)ccc2cc(O)cc(N3CCc4c(nc(OC[C@@]56CCCN5C[C@H](F)C6)nc4N4CCCn5nc(C(=O)N(C)C)cc5C4)C3)c12]

or a pharmaceutically acceptable salt thereof.

5. A pharmaceutical composition comprising a therapeutically effective amount of a compound of any one of claim 1, 3, 4, or 2 or a pharmaceutically acceptable salt thereof, and a pharmaceutically acceptable excipient.

* * * * *

UNITED STATES PATENT AND TRADEMARK OFFICE
CERTIFICATE OF CORRECTION

PATENT NO. : 11,999,753 B2
APPLICATION NO. : 17/553224
DATED : June 4, 2024
INVENTOR(S) : Xiaolun Wang et al.

Page 1 of 3

It is certified that error appears in the above-identified patent and that said Letters Patent is hereby corrected as shown below:

In the Claims

In Column 312, Claim 60, Line 2, delete " 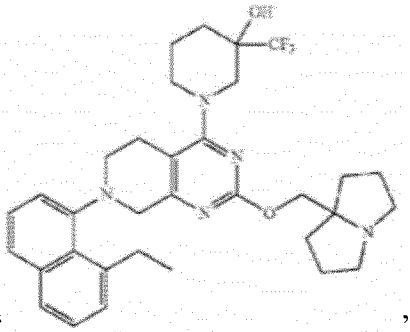 " and insert

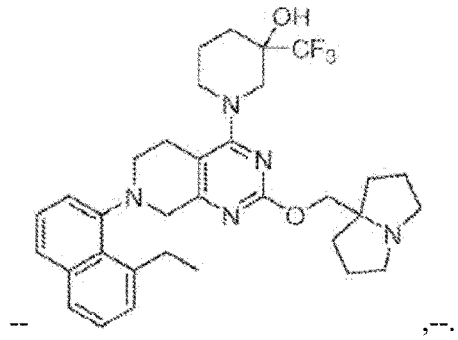 ,--.

Signed and Sealed this
Twentieth Day of May, 2025

Coke Morgan Stewart
*Acting Director of the United States Patent and Trademark Office*

CERTIFICATE OF CORRECTION (continued)
U.S. Pat. No. 11,999,753 B2

Page 2 of 3

In Column 328, Claim 60, Line 4, delete " 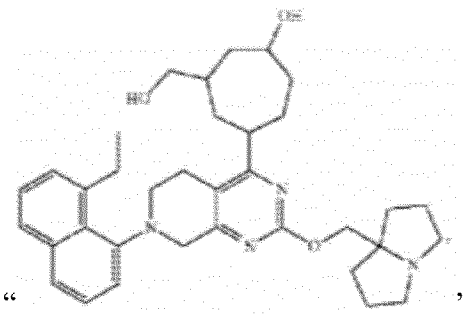 " and insert 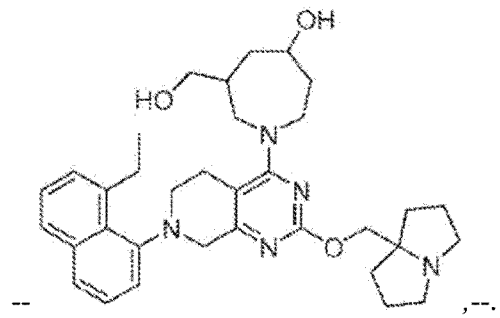 ,--.

In Column 329, Claim 60, Line 4, delete " 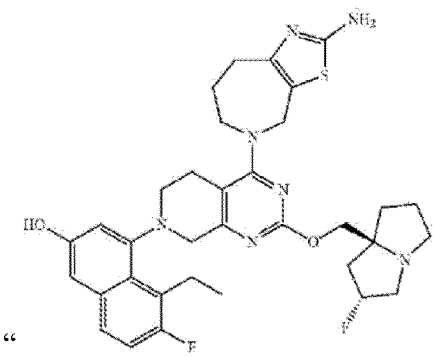 " and insert 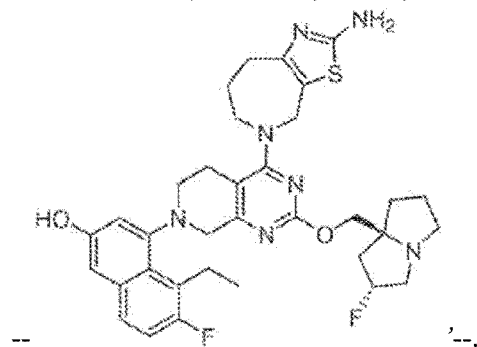 ,--.

CERTIFICATE OF CORRECTION (continued)
U.S. Pat. No. 11,999,753 B2

In Column 333, Claim 60, Line 3, delete " 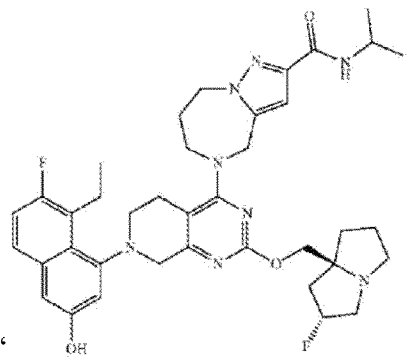 " and insert

-- 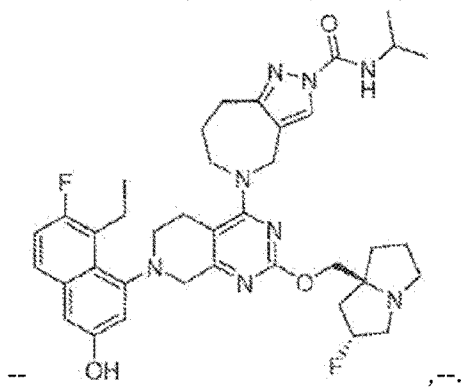 ,--.